US012454701B2

(12) United States Patent
Miller et al.

(10) Patent No.: US 12,454,701 B2
(45) Date of Patent: Oct. 28, 2025

(54) RECOMBINANT ADENO-ASSOCIATED VIRAL VECTOR FOR GENE DELIVERY

(71) Applicant: Abeona Therapeutics Inc., New York, NY (US)

(72) Inventors: Timothy J. Miller, New York, NY (US); Linas Padegimas, Mayfield, OH (US)

(73) Assignee: Abeona Therapeutics Inc., Cleveland, OH (US)

( * ) Notice: Subject to any disclaimer, the term of this patent is extended or adjusted under 35 U.S.C. 154(b) by 1179 days.

(21) Appl. No.: 17/299,434

(22) PCT Filed: Dec. 4, 2019

(86) PCT No.: PCT/US2019/064396

§ 371 (c)(1),
(2) Date: Jun. 3, 2021

(87) PCT Pub. No.: WO2020/117898

PCT Pub. Date: Jun. 11, 2020

(65) Prior Publication Data

US 2022/0090129 A1 Mar. 24, 2022

Related U.S. Application Data

(60) Provisional application No. 62/914,856, filed on Oct. 14, 2019, provisional application No. 62/863,126, filed on Jun. 18, 2019, provisional application No. 62/801,195, filed on Feb. 5, 2019, provisional application No. 62/775,871, filed on Dec. 5, 2018.

(51) Int. Cl.

| | |
|---|---|
| ***C12N 15/86*** | (2006.01) |
| ***A61K 48/00*** | (2006.01) |
| ***C07K 14/005*** | (2006.01) |
| ***C07K 14/47*** | (2006.01) |
| ***C07K 14/705*** | (2006.01) |
| ***C12N 9/26*** | (2006.01) |
| ***C12N 9/40*** | (2006.01) |

(52) U.S. Cl.

CPC .......... *C12N 15/86* (2013.01); *A61K 48/0058* (2013.01); *C07K 14/005* (2013.01); *C07K 14/4712* (2013.01); *C07K 14/705* (2013.01); *C12N 9/2411* (2013.01); *C12N 9/2465* (2013.01); *C12Y 302/0102* (2013.01); *C12Y 302/01022* (2013.01); *C12N 2750/14122* (2013.01); *C12N 2750/14143* (2013.01); *C12N 2750/14171* (2013.01)

(58) Field of Classification Search

CPC .......... C12N 15/86; C12N 2750/14122; C12N 2750/14111; C12N 2750/14143; C12N 2750/14171; A61K 48/0058; C07K 14/4712; C07K 14/705

See application file for complete search history.

(56) References Cited

U.S. PATENT DOCUMENTS

| | | | | |
|---|---|---|---|---|
| 5,958,736 | A | 9/1999 | Ståhl et al. | |
| 6,582,692 | B1 | 6/2003 | Podsakoff et al. | |
| 7,906,111 | B2 | 3/2011 | Wilson et al. | |
| 8,795,965 | B2 | 8/2014 | Zhang | |
| 8,853,381 | B2 | 10/2014 | Matsui et al. | |
| 9,434,928 | B2 | 9/2016 | Mendell et al. | |
| 9,670,507 | B2 | 6/2017 | Xiao et al. | |
| 9,926,574 | B2 | 3/2018 | Barkats | |
| 10,208,318 | B2 | 2/2019 | Barkats | |
| 10,301,648 | B2 | 5/2019 | Vandenberghe et al. | |
| 10,532,110 | B2 | 1/2020 | Gray et al. | |
| 10,561,743 | B2 | 2/2020 | Gray et al. | |
| 2003/0083299 | A1 | 5/2003 | Ferguson | |
| 2004/0101514 | A1 | 5/2004 | Liu et al. | |
| 2004/0235174 | A1 | 11/2004 | Grimm et al. | |
| 2005/0014262 | A1 | 1/2005 | Gao et al. | |
| 2009/0202490 | A1 | 8/2009 | Schaffer et al. | |
| 2011/0035819 | A1 * | 2/2011 | Cooper | A61K 48/005 435/375 |
| 2012/0164106 | A1 | 6/2012 | Schaffer et al. | |
| 2013/0195801 | A1 | 8/2013 | Gao et al. | |
| 2013/0225666 | A1 | 8/2013 | Kaspar et al. | |
| 2017/0130245 | A1 * | 5/2017 | Kotin | C12N 15/86 |
| 2017/0360960 | A1 * | 12/2017 | Gray | A61P 25/00 |
| 2019/0048343 | A1 | 2/2019 | Gao et al. | |
| 2019/0365925 | A1 | 12/2019 | Gray et al. | |
| 2020/0206363 | A1 | 7/2020 | Gray et al. | |
| 2024/0269326 | A1 | 8/2024 | Padegimas | |

FOREIGN PATENT DOCUMENTS

| | | |
|---|---|---|
| EP | 1620133 | 2/2006 |
| JP | 2013531471 A | 8/2013 |
| JP | 2021097675 A | 7/2021 |
| RU | 2457252 | 7/2012 |

(Continued)

OTHER PUBLICATIONS

Kingdoms of Life, waynesword.palomar.edu/trfeb98.htm, last visited Apr. 8, 2021 (Year: 2021).*

Daya et al Gene Therapy Using Adeno-Associated Virus Vectors, Clin. Microbiol. Rev. 21(4): 583-593, 2008 (Year: 2008).*

Mouse Study Used in Research, Multiple Sclerosis News Today, multiplesclerosisnewstoday.com/news-posts/2023/09/08/lets-not-get-overexcited-about-any-mice-study-used-research/; Sep. 8, 2023; last visited Sep. 27, 2024 (Year: 2024).*

(Continued)

*Primary Examiner* — Kevin K Hill

*Assistant Examiner* — Allison Marie Johnson

(74) *Attorney, Agent, or Firm* — COOLEY LLP

(57) ABSTRACT

Provided herein are recombinant AAV vectors, AAV viral vectors, and capsid proteins for improved gene therapy, and methods for their manufacture and use.

25 Claims, 63 Drawing Sheets

Specification includes a Sequence Listing.

(56) References Cited

FOREIGN PATENT DOCUMENTS

| | | | | |
|---|---|---|---|---|
| WO | WO-2001/083692 | | 11/2001 | |
| WO | WO-2005/033321 | | 4/2005 | |
| WO | WO-2007/089632 | | 8/2007 | |
| WO | WO-2009137006 | A2 | 11/2009 | |
| WO | WO-2011/133890 | | 10/2011 | |
| WO | WO-2012057363 | A1 | 5/2012 | |
| WO | WO-2012/145601 | | 10/2012 | |
| WO | WO-2012145601 | A2 * | 10/2012 | ......... A61K 38/1709 |
| WO | WO-2011133890 | A8 | 3/2013 | |
| WO | WO-2013174760 | A1 | 11/2013 | |
| WO | WO-2014/052789 | | 4/2014 | |
| WO | WO-2015/191508 | | 12/2015 | |
| WO | WO-2015191508 | A1 * | 12/2015 | ........... C07K 14/005 |
| WO | WO-2016/081811 | | 5/2016 | |
| WO | WO-2016081811 | A1 * | 5/2016 | ......... A61K 31/7088 |
| WO | WO-2018022608 | A2 * | 2/2018 | ............. A61K 48/00 |
| WO | WO-2018178067 | A1 | 10/2018 | |
| WO | WO-2020018766 | A1 | 1/2020 | |
| WO | WO-2020/117898 | | 6/2020 | |

OTHER PUBLICATIONS

Maguire et al Viral vectors for gene delivery to the inner ear, Hearing Research 394: e107927, 13 pages, doi.org/10.1016/j.heares.2020.107927, 2020 (Year: 2020).*

Greenberg ,Gene Therapy for heart failure, Trends in Cardiovascular Medicine 27: 216-222, 2017 (Year: 2017).*

Perrin, Make mouse studies work, Nature (507): 423-425, 2014 (Year: 2014).*

Ferdowsian et al, Primates in Medical Research: A Matter of Convenience, not Sound Science, The Hastings Center, www.thehastingscenter.org/primates-in-medical-research-convenience-not-sound-science/; Jul. 8, 2022; last visited Sep. 27, 2024 (Year: 2022).*

Kattenhorn et al, Adeno-Associated Virus Gene Therapy for Liver Disease, Human Gene Therapy 27(12): 947-961, Nov. 28, 2016 (Year: 2016).*

Mingozzi and High, Immune responses to AAV vectors: overcoming barriers to successful gene therapy, Blood 122(1): 23-36, 2013 (Year: 2013).*

Bosch, Megan E., et al. "Self-complementary AAV9 gene delivery partially corrects pathology associated with juvenile neuronal ceroid lipofuscinosis (CLN3)." Journal of Neuroscience 36.37 (2016): 9669-9682. (Year: 2016).*

Boukharov, Natalia, et al. "Developing gene therapy for mitigating multisystemic pathology in Fabry disease: proof of concept in an aggravated mouse model." Human Gene Therapy 35.17-18 (2024): 680-694. (Year: 2024).*

Kevany, Brian M., et al. "AAV gene therapy for the treatment of Fabry disease: A novel capsid with improved tropism to heart, kidney and CNS and improved GLA expression." Molecular Genetics and Metabolism 126.2 (2019): S83. (Year: 2019).*

Kevany, Brian M., Linas Padegimas, and Timothy J. Miller. "A novel AAV capsid with improved CNS tropism for treating Pompe disease by intravenous administration." Molecular Genetics and Metabolism 126.2 (2019): S83. (Year: 2019).*

Kerns, Scott, et al. "An improved, novel, systemically administered AAV gene therapy for treatment of CLN3 juvenile neuronal ceroid lipofuscinosis." Molecular Genetics and Metabolism 126.2 (2019): S82-S83. (Year: 2019).*

Wiley, Luke A., et al. "The degree of adeno-associated virus-induced retinal inflammation varies based on serotype and route of delivery: intravitreal, subretinal, or suprachoroidal." Human gene therapy 34.11-12 (2023): 530-539. (Year: 2023).*

Ng et al (Predicting the Effects of Amino Acid Substitutions on Protein Function, Annual Review Genomics Human Genetics 7: 61-80, 2006) (Year: 2006).*

Becerra et al. (1985). "Direct mapping of adeno-associated virus capsid proteins B and C: a possible ACG initiation codon." PNAS. 82(23): 7919-23.

Cassinotti et al. (1988). "Organization of the adeno-associated virus (AAV) capsid gene: mapping of a minor spliced mRNA coding for virus capsid protein 1." Virology. 167(1): 176-84.

Chao et al. (2000). "Several log increase in therapeutic transgene delivery by distinct adeno-associated viral serotype vectors." Mol. Ther. 2(6): 619-623.

Chao et al. (2001). "Sustained and complete phenotype correction of hemophilia B mice following intramuscular injection of AAV1 serotype vectors." Molecular Therapy. 4(3): 217-22.

Clark et al. (1997). "Recombinant adeno-associated viral vectors mediate long-term transgene expression in muscle." Hum. Gene Ther. 8(6): 659-669.

Dalkara et al. (2013). "In Vivo-Directed Evolution of a New Adeno-Associated Virus for Therapeutic Outer Retinal Gene Delivery from the Vitreous", Science Transl. Med. 5(189): 1-11.

De et al. (2006). "High levels of persistent expression of a1-antitrypsin mediated by the nonhuman primate serotype rh. 10 adeno-associated virus despite preexisting immunity to common human adeno-associated viruses." Mol. Ther. 13(1): 67-76.

Dimattia et al. (2012). "Structural insight into the unique properties of adeno-associated virus serotype 9." Journal of Virology. 86(12): 6947-6958.

Gao et al. (2000). "Purification of recombinant adeno-associated virus vectors by column chromatography and its performance in vivo." Human Gene Ther. Methods, 11(15): 2079-91.

Gao et al. (2004). "Clades of Adeno-associated viruses are widely disseminated in human tissues." J. Virol. 78(12): 6381-6388.

Gray et al. (2010). "Directed evolution of a novel adeno-associated virus (AAV) vector that crosses the seizure-compromised blood-brain barrier (BBB)." Mol. Ther. 18(3): 570-578.

Gray, SJ. (2013). "Gene therapy and neurodevelopmental disorders." Neuropharm. 68: 136-142.

Guo et al. (2019). "Rapid AAV-Neutralizing Antibody Determination with a Cell-Binding Assay." Mol. Ther. Methods Clin. Dev. 13: 40-46.

Herzog et al. (1997). "Stable gene transfer and expression of human blood coagulation factor IX after intramuscular injection of recombinant adeno-associated virus." Proc Natl Acad Sci USA, 94(11): 5804-5809.

Hutson et al. (2012). "Corticospinal tract transduction: a comparison of seven adeno-associated viral vector serotypes and a non-integrating lentiviral vector." Gene Ther. 19(1): 49-60.

Kessler et al. (1996). "Gene delivery to skeletal muscle results in sustained expression and systemic delivery of a therapeutic protein." Proc Nat. Acad Sc. USA, 93: 14082-14087.

Koerber et al. (2009). "Molecular evolution of adeno-associated virus for enhanced glial gene delivery." Mol. Ther. 17(12): 2088-2095.

Lewis et al. (2002). "Generation of neutralizing activity against human immunodeficiency virus type 1 in serum by antibody gene transfer." J Virol, 76(17): 8769-8775.

Li et al. (2004). "Transepithelial electrical measurements with the Ussing chamber." J. Cystic Fibrosis. 3:123-126.

Maguire et al. (2010). J. "Directed evolution of adeno-associated virus for glioma cell transduction." Neuro-Onc. 96(3): 337-347.

Marsic et al. (2014). "Vector design Tour de Force: integrating combinatorial and rational approaches to derive novel adeno-associated virus variants." Molecular Therapy, 22(11): 1900-1909.

Mori et al. (2004). "Two novel adeno-associated viruses from cynomolgus monkey: pseudotyping characterization of capsid protein." Virology, 330(2): 375-383.

Muralidhar et al. (1994). "Site-directed mutagenesis of adeno-associated virus type 2 structural protein initiation codons: effects on regulation of synthesis and biological activity." Journal of Virology. 68(1): 170-6.

Murphy et al. (1997). "Long-term correction of obesity and diabetes in genetically obese mice by a single intramuscular injection of recombinant adeno-associated virus encoding mouse leptin." Proc. Natl. Acad. Sci. 94(25): 13921-13926.

Muzyczka, N. (1992). "Use of adeno-associated virus as a general transduction vector for mammalian cells." Curr. Topics Microbiol. Immunol. 158: 97-129.

(56) References Cited

OTHER PUBLICATIONS

Ostedgaard et al. (2005). "A shortened adeno-associated virus expression cassette for CFTR gene transfer to cystic fibrosis airway epithelia." Proc. Natl. Acad. Sci. 102(8): 2952-2957.
Park et al. (2016). "Potentiation of AF508-and G551D-CFTR-mediated CI-current by novel hydroxypyrazolines." PLoS One. 11(2): e0149131.
Perabo et al (2006). "Combinatorial engineering of a gene therapy vector: directed evolution of adeno-associated virus." The Journal of Gene Medicine. 8:155-162.
Powell et al. (2016). "Characterization of a novel adeno-associated viral vector with preferential oligodendrocyte tropism." Gene Therapy. 23(11): 807-814.
PCT/US2019/064396, International Search Report and Written Opinion mailed Mar. 19, 2020, 9 pages.
PCT/US2019/064396, International Preliminary Report on Patentability mailed Jun. 8, 2021, 6 pages.
Rabinowitz et al. (2000). "Building a better vector: the manipulation of AAV virions." Virology. 278(2): 301-8.
Schlesinger et al. (1999). "Alphavirus vectors for gene expression and vaccines." Curr. Opin. Biotechnol. 10(5): 434-439.
Sonntag et al. (2010). "A viral assembly factor promotes AAV2 capsid formation in the nucleolus." PNAS. 107(22): 10220-5.
Srivastava et al. (1983). "Nucleotide sequence and organization of the adeno-associated virus 2 genome." J. Virol. 45(2): 555-64.
Trempe et al (1988). "Alternate mRNA splicing is required for synthesis of adeno-associated virus VP1 capsid protein." Journal of Virology. 62(9): 3356-63.
Wang et al. (2014). "Efficient Production of Dual Recombinant Adeno-Associated Viral Vectors for Factor VIII Delivery." Human Gene Ther. Methods, 25: 261-68.
Wu et al. (2006). "Single amino acid changes can influence titer, heparin binding, and tissue tropism in different adeno-associated virus serotypes." J. Virol. 80(22): 11393-7.
Xiao et al. (1996). "Efficient long-term gene transfer into muscle tissue of immunocompetent mice by adeno-associated virus vector." J. Virol. 70(11): 8098-8108.
Xiao et al. (1999). "Gene therapy vectors based on adeno-associated virus type 1." J. Virol. 73(5): 3994-4003.
Yang et al. (2014). "Global CNS transduction of adult mice by intravenously delivered rAAVrh. 8 and rAAVrh. 10 and nonhuman primates by rAAVrh. 10." Mol. Ther. 22(7): 1299-1309.
Ying et al. (1999). "Cancer therapy using a self-replicating RNA vaccine." Nat. Med. 5(7): 823-827.
Zhang et al. (1996). "An enhanced green fluorescent protein allows sensitive detection of gene transfer in mammalian cells." Biochem. Biophys. Res. Commun. 227(3): 707-11.
Gao. Z., et al., A Single HI Promoter Can Drive Both Guide RNA and Endonuclease Expression in the CRISPR-Cas9 System, Molecular Therapy: Nucleic Acids, 2019, vol. 14, pp. 32-40.
Hartman et al. (2018). "Intravitreal, subretinal, and suprachoroidal injections: evolution of microneedles for drug delivery." Journal of Ocular Pharmacology and Therapeutics. 34(1-2): 141-53.
International Preliminary Report on Patentability for International Application No. PCT/US2022/029797 dated Nov. 30, 2023, 8 pages.
International Search Report and Written Opinion for International Application No. PCT/US2022/029797 dated Oct. 5, 2022, 16 pages.
Klimczak et al. (2009). "A novel adeno-associated viral variant for efficient and selective intravitreal transduction of rat Muller cells." PloS one. vol. 4, No. 10, pp. E7467.
Peng et al., "Subretinal injection: a review on the novel route of therapeutic delivery for vitreoretinal diseases,". Ophthalmic research. 2017; 58(4): 217-26.
Yiu et al., 2020, "Suprachoroidal and Subretinal Injections of AA V Using Transscleral Micro needles for Retinal Gene Delivery in Nonhuman Primates," Molecular Therapy—Methods & Clinical Development, 16: 179-191.
Zeng et al. (2020). "'Para-retinal' vector administration into the deep vitreous enhances retinal transgene expression." Molecular Therapy—Methods & Clinical Development. 18: 422-7.
Decision of Rejection for Japanese Application No. 2023-108201 mailed Oct. 9, 2024, 15 pages.
Office Action for Australian Application No. 20220201540 dated Oct. 18, 2024, 3 pages.
Office Action for Canadian Application No. 3121177 mailed Jan. 16, 2025, 13 pages.

* cited by examiner

Comparison of transduction efficiency in Lec2 cells treated with the same amount of AAV9-GFP or AAV214-GFP virus.

- Serum from AAV9 treated subject 60 Days Post-Treatment
- Total antibodies against AAV9 titered > 1:1E+6 by ELISA Controls = anti-AAV9 antibodies from commercial source added to virus preps at 5 or 0.5 μg (expected result for AAV9 is no signal)

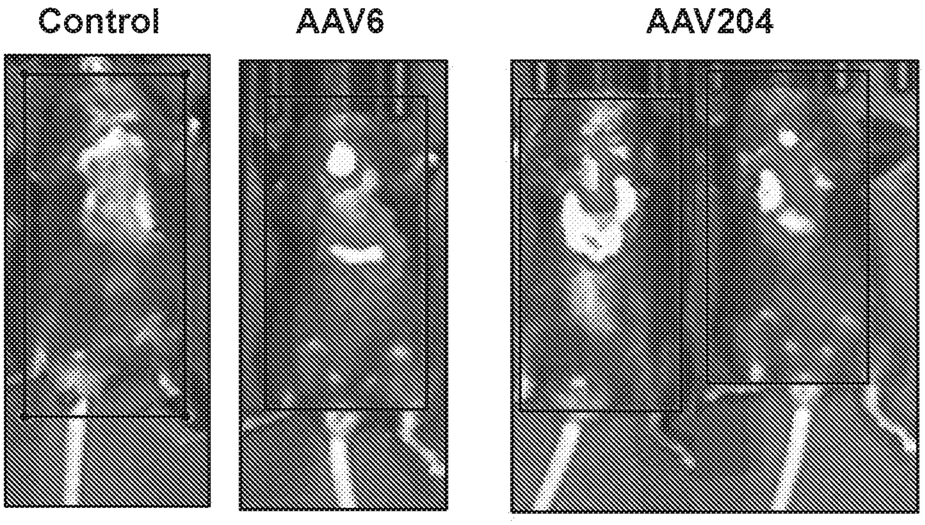
AAV204 demonstrates ~3-5x higher expression in lung after delivery compared to AAV6
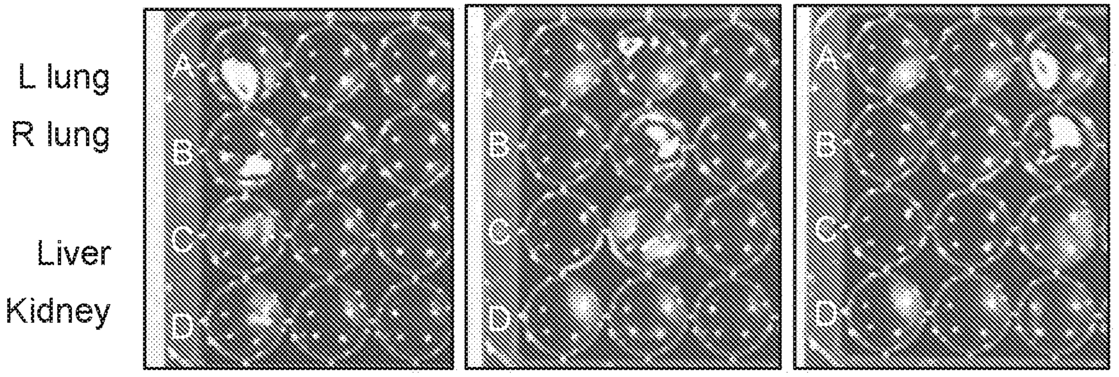
*Ex vivo* organ imaging
FIG. 9

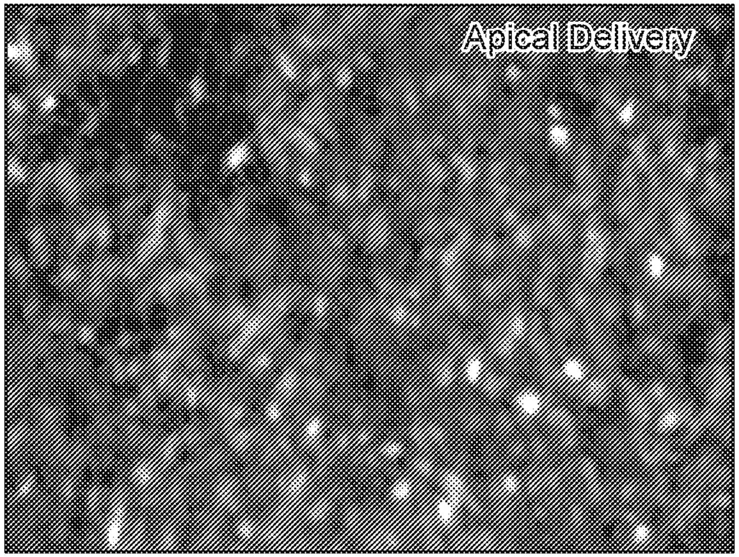
Human delta508 CF bronchial cells polarized airway cultures with AAV204-GFP
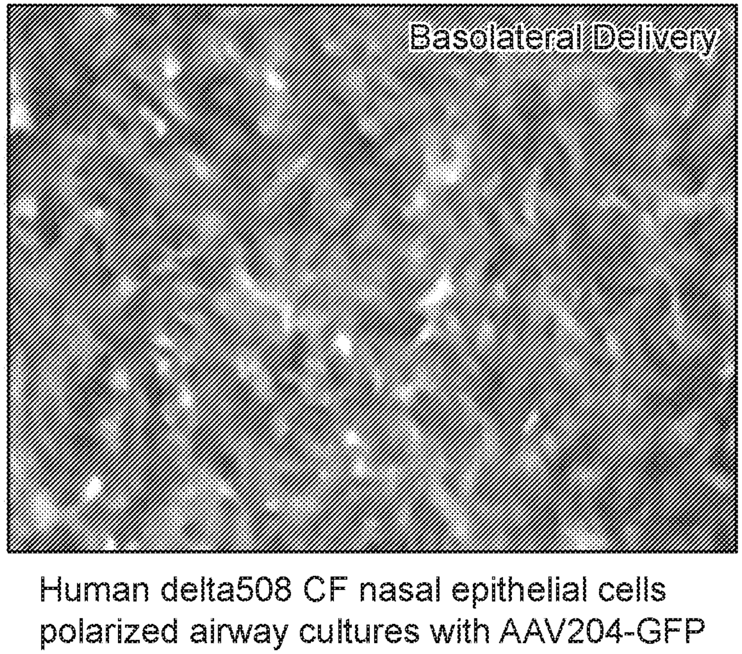
Human delta508 CF nasal epithelial cells polarized airway cultures with AAV204-GFP
FIG. 11A

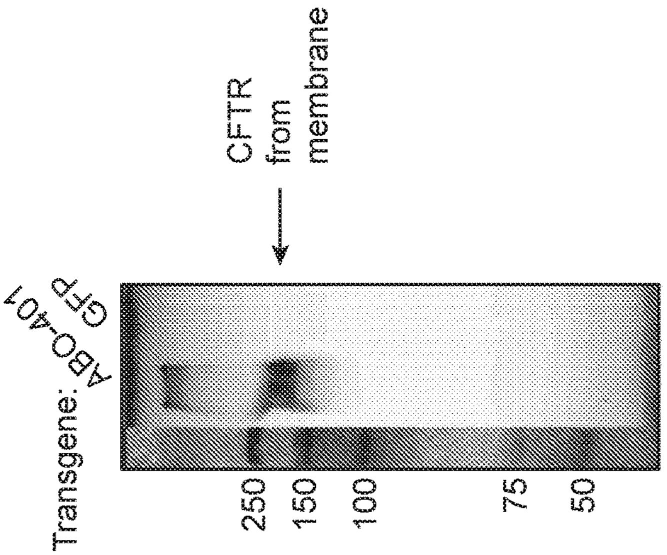
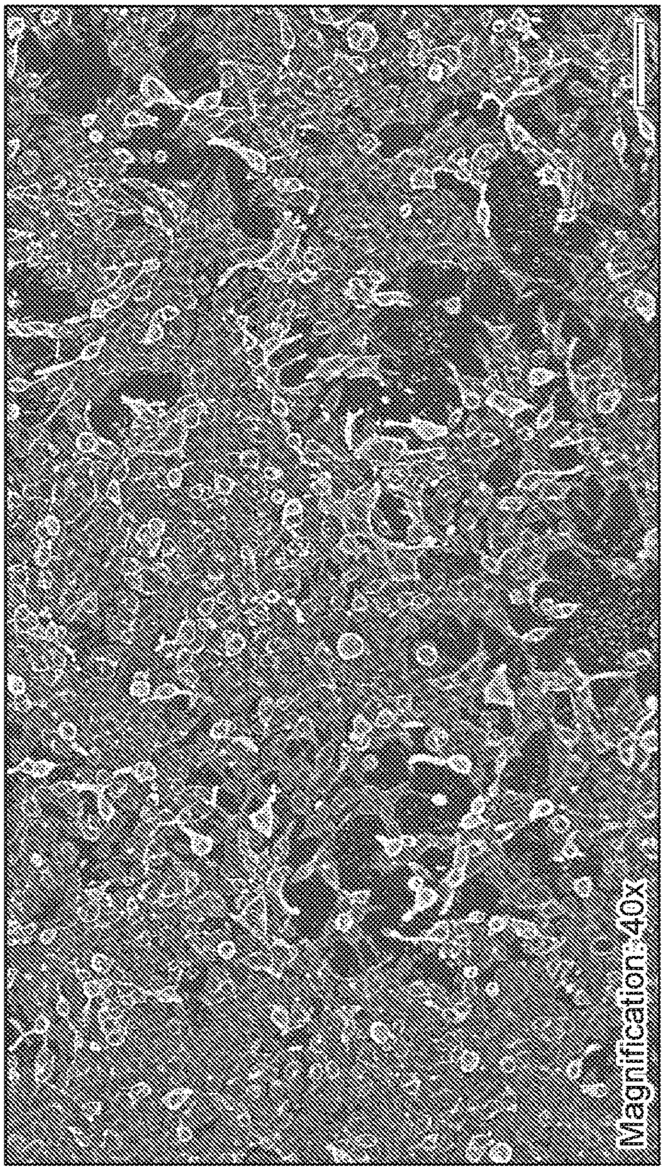
ABO-401 produces CFTR that is membrane localized in human CF cells
FIG. 11B AAV204 delivered CFTR transgene restores chloride channel current

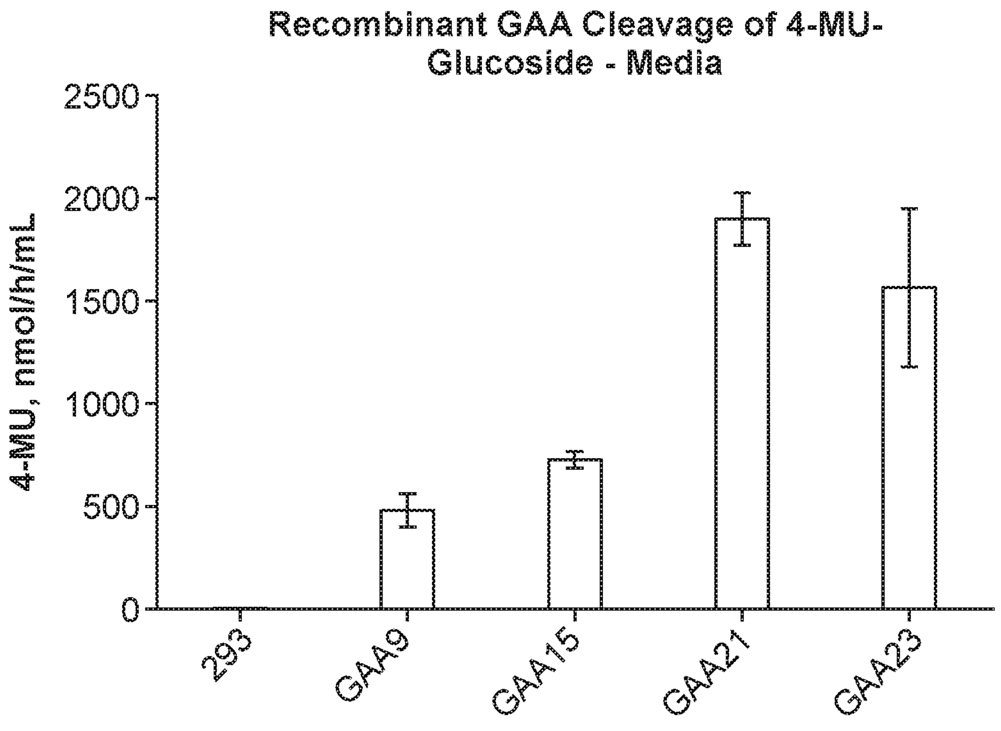
293 = non-transfected control
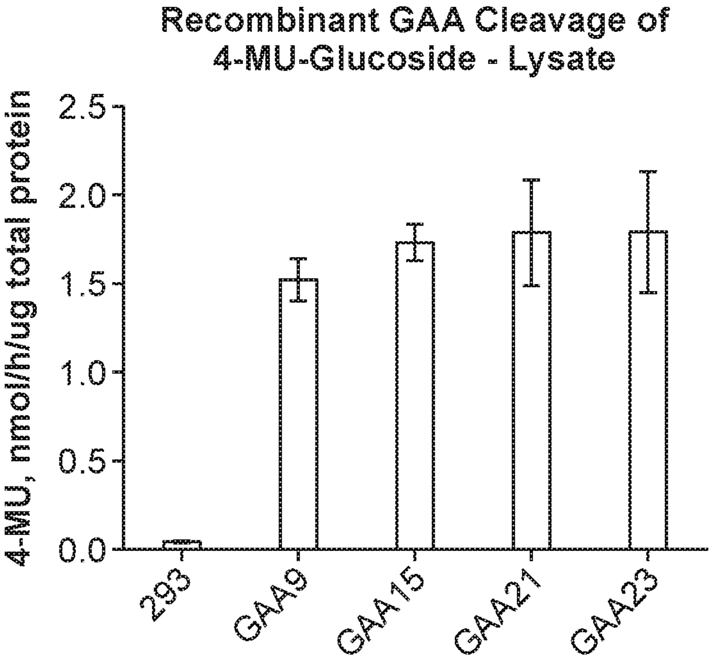
293 = non-transfected control
FIG. 18B

Alignment of VP1 protein sequence of AAV204 and AAV6 pos.129, F to L, (Phe to Leu)
pos.586, S to N, (Ser to Asn)

```
Majority            MAADGYLPDWLEDNLSEGIREWWDLKPGAPKPKANQQKQDDGRGLVLPGYKYLGPFNGLDKGEPVNAADAAALEHDKAYD
                                   10        20        30        40        50        60        70        80
AAV6_VP1.pro        MAADGYLPDWLEDNLSEGIREWWDLKPGAPKPKANQQKQDDGRGLVLPGYKYLGPFNGLDKGEPVNAADAAALEHDKAYD 80
AAV204(ITcord_2-04) MAADGYLPDWLEDNLSEGIREWWDLKPGAPKPKANQQKQDDGRGLVLPGYKYLGPFNGLDKGEPVNAADAAALEHDKAYD 80
Majority            QQLKAGDNPYLRYNHADAEFQERLQEDTSFGGNLGRAVFQAKKRVLEPXGLVEEGAKTAPGKKRPVEQSPQEPDSSSGIG
                                   90       100       110       120       130      1400       150       160
AAV6_VP1.pro        QQLKAGDNPYLRYNHADAEFQERLQEDTSFGGNLGRAVFQAKKRVLEPFGLVEEGAKTAPGKKRPVEQSPQEPDSSSGIG 160
AAV204(ITcord_2-04) QQLKAGDNPYLRYNHADAEFQERLQEDTSFGGNLGRAVFQAKKRVLEPLGLVEEGAKTAPGKKRPVEQSPQEPDSSSGIG 160
Majority            KTGQQPAKKRLNFGQTGDSESVPDPQPLGEPPATPAAVGPTTMASGGGAPMADNNEGADGVGNASGNWHCDSTWLGDRVI
                                  170       180       190       200       210       220       230       240
AAV6_VP1.pro        KTGQQPAKKRLNFGQTGDSESVPDPQPLGEPPATPAAVGPTTMASGGGAPMADNNEGADGVGNASGNWHCDSTWLGDRVI 240
AAV204(ITcord_2-04) KTGQQPAKKRLNFGQTGDSESVPDPQPLGEPPATPAAVGPTTMASGGGAPMADNNEGADGVGNASGNWHCDSTWLGDRVI 240
Majority            TTSTRTWALPTYNNHLYKQISSASTGASNDNHYFGYSTPWGYFDFNRFHCHFSPRDWQRLINNNWGFRPKRLNFKLFNIQ
                                  250       260       270       280       290       300       310       320
AAV6_VP1.pro        TTSTRTWALPTYNNHLYKQISSASTGASNDNHYFGYSTPWGYFDFNRFHCHFSPRDWQRLINNNWGFRPKRLNFKLFNIQ 320
AAV204(ITcord_2-04) TTSTRTWALPTYNNHLYKQISSASTGASNDNHYFGYSTPWGYFDFNRFHCHFSPRDWQRLINNNWGFRPKRLNFKLFNIQ 320
Majority            VKEVTTNDGVTTIANNLTSTVQVFSDSEYQLPYVLGSAHQGCLPPFPADVFMIPQYGYLTLNNGSQAVGRSSFYCLEYFP
                                  330       340       350       360       370       380       390       400
AAV6_VP1.pro        VKEVTTNDGVTTIANNLTSTVQVFSDSEYQLPYVLGSAHQGCLPPFPADVFMIPQYGYLTLNNGSQAVGRSSFYCLEYFP 400
AAV204(ITcord_2-04) VKEVTTNDGVTTIANNLTSTVQVFSDSEYQLPYVLGSAHQGCLPPFPADVFMIPQYGYLTLNNGSQAVGRSSFYCLEYFP 400
```

FIG. 20

```
Majority              SQMLRTGNNFTFSYTFEDVPFHSSYAHSQSLDRLMNPLIDQYLYYLNRTQNQSGSAQNKDLLFSRGSPAGMSVQPKNWLP
                                410       420       430       440       450       460       470       480
AAV6_VP1.pro          SQMLRTGNNFTFSYTFEDVPFHSSYAHSQSLDRLMNPLIDQYLYYLNRTQNQSGSAQNKDLLFSRGSPAGMSVQPKNWLP 480
AAV204(ITcord_2-04)   SQMLRTGNNFTFSYTFEDVPFHSSYAHSQSLDRLMNPLIDQYLYYLNRTQNQSGSAQNKDLLFSRGSPAGMSVQPKNWLP 480
Majority              GPCYRQQRVSKTKTDNNNSNFTWTGASKYNLNGRESIINPGTAMASHKDDKDKFFPMSGVMIFGKESAGASNTALDNVMI
                                490       500       510       520       530       540       550       560
AAV6_VP1.pro          GPCYRQQRVSKTKTDNNNSNFTWTGASKYNLNGRESIINPGTAMASHKDDKDKFFPMSGVMIFGKESAGASNTALDNVMI 560
AAV204(ITcord_2-04)   GPCYRQQRVSKTKTDNNNSNFTWTGASKYNLNGRESIINPGTAMASHKDDKDKFFPMSGVMIFGKESAGASNTALDNVMI 560
Majority              TDEEEIKATNPVATERFGTVAVNLQXSSTDPATGDVHVMGALPGMVWQDRDVYLQGPIWAKIPHTDGHFHPSPLMGGFGL
                                570       580       590       600       610       620       630       640
AAV6_VP1.pro          TDEEEIKATNPVATERFGTVAVNLQSSSTDPATGDVHVMGALPGMVWQDRDVYLQGPIWAKIPHTDGHFHPSPLMGGFGL 640
AAV204(ITcord_2-04)   TDEEEIKATNPVATERFGTVAVNLQNSSTDPATGDVHVMGALPGMVWQDRDVYLQGPIWAKIPHTDGHFHPSPLMGGFGL 640
Majority              KHPPPQILIKNTPVPANPPAEFSATKFASFITQYSTGQVSVEIEWELQKENSKRWNPEVQYTSNYAKSANVDFTVDNNGL
                                650       660       670       680       690       700       710       720
AAV6_VP1.pro          KHPPPQILIKNTPVPANPPAEFSATKFASFITQYSTGQVSVEIEWELQKENSKRWNPEVQYTSNYAKSANVDFTVDNNGL 720
AAV204(ITcord_2-04)   KHPPPQILIKNTPVPANPPAEFSATKFASFITQYSTGQVSVEIEWELQKENSKRWNPEVQYTSNYAKSANVDFTVDNNGL 720
Majority              YTEPRPIGTRYLTRPL
                                730
AAV6_VP1.pro          YTEPRPIGTRYLTRPL                                                                 736
AAV204(ITcord_2-04)   YTEPRPIGTRYLTRPL                                                                 736
```

Decoration 'Decoration #2' : Box residues that differ from AAV6_VP1.pro

FIG. 20 (Cont.)

```
clustalw.aln

CLUSTAL 2.1 multiple sequence alignment of VP1 protein sequences

ITB102_45_VP1       MAADGYLPDWLEDNLSEGIREWWALKPGAPKPKANQQKQDDGRGLVLPGYKYLGPFNGLD
AAV214_VP1          MAADGYLPDWLEDNLSEGIREWWALKPGAPKPKANQQKQDDGRGLVLPGYKYLGPFNGLD
AAV214A_VP1         MAADGYLPDWLEDNLSEGIREWWALKPGAPKPKANQQKQDDGRGLVLPGYKYLGPFNGLD
AAV214-AB_VP1       MAADGYLPDWLEDNLSEGIREWWALKPGAPKPKANQQKQDDGRGLVLPGYKYLGPFNGLD
AAV214e_VP1         MAADGYLPDWLEDNLSEGIREWWDLKPGAPKPKANQQKQDDGRGLVLPGYKYLGPFNGLD
AAV214e8_VP1        MAADGYLPDWLEDNLSEGIREWWALKPGAPKPKANQQKQDDGRGLVLPGYKYLGPFNGLD
AAV214e9_VP1        MAADGYLPDWLEDNLSEGIREWWALKPGAPQPKANQQHQDNARGLVLPGYKYLGPGNGLD
AAV214e10_VP1       MAADGYLPDWLEDNLSEGIREWWDLKPGAPKPKANQQKQDDGRGLVLPGYKYLGPFNGLD
AAV8_VP1            MAADGYLPDWLEDNLSEGIREWWALKPGAPKPKANQQKQDDGRGLVLPGYKYLGPFNGLD 60
AAV9_VP1            MAADGYLPDWLEDNLSEGIREWWALKPGAPQPKANQQHQDNARGLVLPGYKYLGPGNGLD
                    *********************** ******:******:**:.************* ****

ITB102_45_VP1       KGEPVNAADAAALEHDKAYDQQLKAGDNPYLRYNHADAEFQERLQEDTSFGGNLGRAVFQ
AAV214_VP1          KGEPVNAADAAALEHDKAYDQQLKAGDNPYLRYNHADAEFQERLQEDTSFGGNLGRAVFQ
AAV214A_VP1         KGEPVNAADAAALEHDKAYDQQLKAGDNPYLRYNHADAEFQERLQEDTSFGGNLGRAVFQ
AAV214-AB_VP1       KGEPVNAADAAALEHDKAYDQQLKAGDNPYLRYNHADAEFQERLQEDTSFGGNLGRAVFQ
AAV214e_VP1         KGEPVNAADAAALEHDKAYDQQLKAGDNPYLRYNHADAEFQERLQEDTSFGGNLGRAVFQ
AAV214e8_VP1        KGEPVNAADAAALEHDKAYDQQLQAGDNPYLRYNHADAEFQERLQEDTSFGGNLGRAVFQ
AAV214e9_VP1        KGEPVNAADAAALEHDKAYDQQLKAGDNPYLKYNHADAEFQERLKEDTSFGGNLGRAVFQ
AAV214e10_VP1       KGEPVNAADAAALEHDKAYDQQLKAGDNPYLRYNHADAEFQERLQEDTSFGGNLGRAVFQ
AAV8_VP1            KGEPVNAADAAALEHDKAYDQQLQAGDNPYLRYNHADAEFQERLQEDTSFGGNLGRAVFQ 120
AAV9_VP1            KGEPVNAADAAALEHDKAYDQQLKAGDNPYLKYNHADAEFQERLKEDTSFGGNLGRAVFQ
                    ***********************:*******:************:***************

ITB102_45_VP1       AKKRVLEPFGLVEEGAKTAPGKKRPVEQSPQ-EPDSSSGIGKTGQQPAKKRLNFGQTGDS
AAV214_VP1          AKKRVLEPFGLVEEGAKTAPGKKRPVEQSPQ-EPDSSSGIGKTGQQPAKKRLNFGQTGDS
AAV214A_VP1         AKKRVLEPFGLVEEGAKTAPGKKRPVEQSPQ-EPDSSSGIGKTGQQPAKKRLNFGQTGDS
AAV214-AB_VP1       AKKRVLEPFGLVEEGAKTAPGKKRPVEQSPQ-EPDSSSGIGKTGQQPAKKRLNFGQTGDS
AAV214e_VP1         AKKRVLEPLGLVEEGAKTAPGKKRPVEPSPQRSPDSSTGIGKKGQQPARKRLNFGQTGDS
AAV214e8_VP1        AKKRVLEPLGLVEEGAKTAPGKKRPVEPSPQRSPDSSTGIGKKGQQPARKRLNFGQTGDS
AAV214e9_VP1        AKKRLLEPLGLVEEAAKTAPGKKRPVEQSPQ-EPDSSAGIGKSGAQPAKKRLNFGQTGDT
AAV214e10_VP1       AKKRVLEPLGLVEEGAKTAPGKKRPVEPSPQRSPDSSTGIGKKGQQPAKKRLNFGQTGDS
AAV8_VP1            AKKRVLEPLGLVEEGAKTAPGKKRPVEPSPQRSPDSSTGIGKKGQQPARKRLNFGQTGDS 180
AAV9_VP1            AKKRLLEPLGLVEEAAKTAPGKKRPVEQSPQ-EPDSSAGIGKSGAQPAKKRLNFGQTGDT
                    ****:***:*****.************ *** .****:****.* ***:**********:

ITB102_45_VP1       ESVPDPQPLGEPPATPAAVGPTTMASGGGAPMADNNEGADGVGNASGNWHCDSTWLGDRV
AAV214_VP1          ESVPDPQPLGEPPATPAAVGPTTMASGGGAPMADNNEGADGVGNASGNWHCDSTWLGDRV
AAV214A_VP1         ESVPDPQPLGEPPATPAAVGPTTMASGGGAPMADNNEGADGVGNASGNWHCDSTWLGDRV
AAV214-AB_VP1       ESVPDPQPLGEPPATPAAVGPTTMASGGGAPMADNNEGADGVGNASGNWHCDSTWLGDRV
AAV214e_VP1         ESVPDPQPLGEPPATPAAVGPTTMASGGGAPMADNNEGADGVGNASGNWHCDSTWLGDRV
AAV214e8_VP1        ESVPDPQPLGEPPAAPSGVGPNTMASGGGAPMADNNEGADGVGNASGNWHCDSTWLGDRV
AAV214e9_VP1        ESVPDPQPIGEPPAAPSGVGSLTMASGGGAPMADNNEGADGVGNASGNWHCDSTWLGDRV
AAV214e10_VP1       ESVPDPQPIGEPPAGPSGLGSGTMASGGGAPMADNNEGADGVGNASGNWHCDSTWLGDRV
AAV8_VP1            ESVPDPQPLGEPPAAPSGVGPNTMAAGGGAPMADNNEGADGVGSSSGNWHCDSTWLGDRV 240
AAV9_VP1            ESVPDPQPIGEPPAAPSGVGSLTMASGGGAPVADNNEGADGVGSSSGNWHCDSQWLGDRV
                    ********:***** *:.:*. ***:*****:***********.:******** ******
```

FIG. 21

```
ITB102_45_VP1      ITTSTRTWALPTYNNHLYKQISSASTG-ASNDNHYFGYSTPWGYFDFNRFHCHFSPRDWQ
AAV214_VP1         ITTSTRTWALPTYNNHLYKQISSASTG-ASNDNHYFGYSTPWGYFDFNRFHCHFSPRDWQ
AAV214A_VP1        ITTSTRTWALPTYNNHLYKQISNSTSGGSSNDNAYFGYSTPWGYFDFNRFHCHFSPRDWQ
AAV214-AB_VP1      ITTSTRTWALPTYNNHLYKQISSSTSGGSSNDNAYFGYSTPWGYFDFNRFHCHFSPRDWQ
AAV214e_VP1        ITTSTRTWALPTYNNHLYKQISSASTG-ASNDNHYFGYSTPWGYFDFNRFHCHFSPRDWQ
AAV214e8_VP1       ITTSTRTWALPTYNNHLYKQISSASTG-ASNDNHYFGYSTPWGYFDFNRFHCHFSPRDWQ
AAV214e9_VP1       ITTSTRTWALPTYNNHLYKQISSASTG-ASNDNHYFGYSTPWGYFDFNRFHCHFSPRDWQ
AAV214e10_VP1      ITTSTRTWALPTYNNHLYKQISSASTG-ASNDNHYFGYSTPWGYFDFNRFHCHFSPRDWQ
AAV8_VP1           ITTSTRTWALPTYNNHLYKQISNGTSGGATNDNTYFGYSTPWGYFDFNRFHCHFSPRDWQ 300
AAV9_VP1           ITTSTRTWALPTYNNHLYKQISNSTSGGSSNDNAYFGYSTPWGYFDFNRFHCHFSPRDWQ
                   **********************..:.* ::*** **************************

ITB102_45_VP1      RLINNNWGFRPKRLNFKLFNIQVKEVTDNNGVKTIANNLTSTVQVFTDSDYQLPYVLGSA
AAV214_VP1         RLINNNWGFRPKRLNFKLFNIQVKEVTDNNGVKTIANNLTSTVQVFTDSDYQLPYVLGSA
AAV214A_VP1        RLINNNWGFRPKRLNFKLFNIQVKEVTDNNGVKTIANNLTSTVQVFTDSDYQLPYVLGSA
AAV214-AB_VP1      RLINNNWGFRPKRLNFKLFNIQVKEVTDNNGVKTIANNLTSTVQVFTDSDYQLPYVLGSA
AAV214e_VP1        RLINNNWGFRPKRLNFKLFNIQVKEVTDNNGVKTIANNLTSTVQVFTDSDYQLPYVLGSA
AAV214e8_VP1       RLINNNWGFRPKRLNFKLFNIQVKEVTDNNGVKTIANNLTSTVQVFTDSDYQLPYVLGSA
AAV214e9_VP1       RLINNNWGFRPKRLNFKLFNIQVKEVTDNNGVKTIANNLTSTVQVFTDSDYQLPYVLGSA
AAV214e10_VP1      RLINNNWGFRPKRLNFKLFNIQVKEVTDNNGVKTIANNLTSTVQVFTDSDYQLPYVLGSA
AAV8_VP1           RLINNNWGFRPKRLSFKLFNIQVKEVTQNEGTKTIANNLTSTIQVFTDSEYQLPYVLGSA 360
AAV9_VP1           RLINNNWGFRPKRLNFKLFNIQVKEVTDNNGVKTIANNLTSTVQVFTDSDYQLPYVLGSA
                   **************.************:*:*.**********:******:**********

ITB102_45_VP1      HEGCLPPFPADVFMIPQYGYLTLNNGSQAVGRSSFYCLEYFPSQMLRTGNNFTFSYTFED
AAV214_VP1         HQGCLPPFPADVFMIPQYGYLTLNDGSQAVGRSSFYCLEYFPSQMLRTGNNFTFSYTFED
AAV214A_VP1        HQGCLPPFPADVFMIPQYGYLTLNDGSQAVGRSSFYCLEYFPSQMLRTGNNFTFSYTFED
AAV214-AB_VP1      HQGCLPPFPADVFMIPQYGYLTLNDGSQAVGRSSFYCLEYFPSQMLRTGNNFTFSYTFED
AAV214e_VP1        HQGCLPPFPADVFMIPQYGYLTLNDGSQAVGRSSFYCLEYFPSQMLRTGNNFTFSYTFED
AAV214e8_VP1       HQGCLPPFPADVFMIPQYGYLTLNDGSQAVGRSSFYCLEYFPSQMLRTGNNFTFSYTFED
AAV214e9_VP1       HQGCLPPFPADVFMIPQYGYLTLNDGSQAVGRSSFYCLEYFPSQMLRTGNNFTFSYTFED
AAV214e10_VP1      HQGCLPPFPADVFMIPQYGYLTLNDGSQAVGRSSFYCLEYFPSQMLRTGNNFTFSYTFED
AAV8_VP1           HQGCLPPFPADVFMIPQYGYLTLNNGSQAVGRSSFYCLEYFPSQMLRTGNNFQFTYTFED 420
AAV9_VP1           HEGCLPPFPADVFMIPQYGYLTLNDGSQAVGRSSFYCLEYFPSQMLRTGNNFQFSYEFEN
                   *:**********************:*************************** *:* **:

ITB102_45_VP1      VPFHSSYAHSQSLDRLMNPLIDQYLYYLSRTQTTGGTANTQTLGFSQGGPNTMANQAKNW
AAV214_VP1         VPFHSSYAHSQSLDRLMNPLIDQYLYYLSKTINGSG-QNQQTLKFSQGGPNTMANQAKNW
AAV214A_VP1        VPFHSSYAHSQSLDRLMNPLIDQYLYYLSKTINGSG-QNQQTLKFSQGGPNTMANQAKNW
AAV214-AB_VP1      VPFHSSYAHSQSLDRLMNPLIDQYLYYLSKTINGSG-QNQQTLKFSQGGPNTMANQAKNW
AAV214e_VP1        VPFHSSYAHSQSLDRLMNPLIDQYLYYLSKTINGSG-QNQQTLKFSQGGPNTMANQAKNW
AAV214e8_VP1       VPFHSSYAHSQSLDRLMNPLIDQYLYYLSKTINGSG-QNQQTLKFSQGGPNTMANQAKNW
AAV214e9_VP1       VPFHSSYAHSQSLDRLMNPLIDQYLYYLSKTINGSG-QNQQTLKFSQGGPNTMANQAKNW
AAV214e10_VP1      VPFHSSYAHSQSLDRLMNPLIDQYLYYLSKTINGSG-QNQQTLKFSQGGPNTMANQAKNW
AAV8_VP1           VPFHSSYAHSQSLDRLMNPLIDQYLYYLSRTQTTGGTANTQTLGFSQGGPNTMANQAKNW 480
AAV9_VP1           VPFHSSYAHSQSLDRLMNPLIDQYLYYLSKTINGSG-QNQQTLKFSVAGPSNMAVQGRNY
                   *****************************:* . .*  * *** ** .**..** *.:*:

ITB102_45_VP1      LPGPCYRQQRVSTTTGQNNNSNFAWTAGTKYHLNGRNSLMNPGPAMASHKEGEDRFFPLS
AAV214_VP1         LPGPCYRQQRVSTTTGQNNNSNFAWTAGTKYHLNGRNSLMNPGPAMASHKEGEDRFFPLS
AAV214A_VP1        LPGPCYRQQRVSTTTGQNNNSNFAWTAGTKYHLNGRNSLMNPGPAMASHKEGEDRFFPLS
AAV214-AB_VP1      LPGPCYRQQRVSTTTGQNNNSNFAWTAGTKYHLNGRNSLMNPGPAMASHKEGEDRFFPLS
AAV214e_VP1        LPGPCYRQQRVSTTTGQNNNSNFAWTAGTKYHLNGRNSLMNPGPAMASHKEGEDRFFPLS
AAV214e8_VP1       LPGPCYRQQRVSTTTGQNNNSNFAWTAGTKYHLNGRNSLMNPGPAMASHKEGEDRFFPLS
AAV214e9_VP1       LPGPCYRQQRVSTTTGQNNNSNFAWTAGTKYHLNGRNSLMNPGPAMASHKEGEDRFFPLS
AAV214e10_VP1      LPGPCYRQQRVSTTTGQNNNSNFAWTAGTKYHLNGRNSLMNPGPAMASHKEGEDRFFPLS
AAV8_VP1           LPGPCYRQQRVSTTTGQNNNSNFAWTAGTKYHLNGRNSLANPGIAMATHKDDEERFFPSN 540
AAV9_VP1           IPGPSYRQQRVSTTVTQNNNSEFAWPGASSWALNGRNSLMNPGPAMASHKEGEDRFFPLS
                   :***.*********. *****:***...:.: ******* *** ***:**:.*:**** .
```

FIG. 21 (Cont. 1)

```
ITB102_45_VP1     GSLIFGKQGTGRDNVDADKVMITNEEEIKTTNPVATEEYGIVADNLQQNTAPQIGTVNS
AAV214_VP1        GSLIFGKQNAARDNADYSDVMLTSEEEIKTTNPVATEEYGIVADNLQQNTAPQIGTVNS
AAV214A_VP1       GSLIFGKQNAARDNADYSDVMLTSEEEIKTTNPVATEEYGIVADNLQQNTAPQIGTVNS
AAV214-AB_VP1     GSLIFGKQNAARDNADYSDVMLTSEEEIKTTNPVATEEYGIVADNLQQNTAPQIGTVNS
AAV214e_VP1       GSLIFGKQNAARDNADYSDVMLTSEEEIKTTNPVATEEYGIVADNLQQNTAPQIGTVNS
AAV214e8_VP1      GSLIFGKQNAARDNADYSDVMLTSEEEIKTTNPVATEEYGIVADNLQQNTAPQIGTVNS
AAV214e9_VP1      GSLIFGKQNAARDNADYSDVMLTSEEEIKTTNPVATEEYGIVADNLQQNTAPQIGTVNS
AAV214e10_VP1     GSLIFGKQNAARDNADYSDVMLTSEEEIKTTNPVATEEYGIVADNLQQNTAPQIGTVNS
AAV8_VP1          GILIFGKQNAARDNADYSDVMLTSEEEIKTTNPVATEEYGIVADNLQQNTAPQIGTVNS 600
AAV9_VP1          GSLIFGKQGTGRDNVDADKVMITNEEEIKTTNPVATESYGQVATNHQSAQAQAQTGWVQN
                  * ******.:.***.* ..**:*.*************.** ** * *. :: .* * *:.

ITB102_45_VP1     QGALPGMVWQNRDVYLQGPIWAKIPHTDGNFHPSPLMGGFGLKHPPPQILIKNTPVPADP
AAV214_VP1        QGALPGMVWQNRDVYLQGPIWAKIPHTDGNFHPSPLMGGFGLKHPPPQILIKNTPVPADP
AAV214A_VP1       QGALPGMVWQNRDVYLQGPIWAKIPHTDGNFHPSPLMGGFGLKHPPPQILIKNTPVPADP
AAV214-AB_VP1     QGALPGMVWQNRDVYLQGPIWAKIPHTDGNFHPSPLMGGFGLKHPPPQILIKNTPVPADP
AAV214e_VP1       QGALPGMVWQNRDVYLQGPIWAKIPHTDGNFHPSPLMGGFGLKHPPPQILIKNTPVPADP
AAV214e8_VP1      QGALPGMVWQNRDVYLQGPIWAKIPHTDGNFHPSPLMGGFGLKHPPPQILIKNTPVPADP
AAV214e9_VP1      QGALPGMVWQNRDVYLQGPIWAKIPHTDGNFHPSPLMGGFGLKHPPPQILIKNTPVPADP
AAV214e10_VP1     QGALPGMVWQNRDVYLQGPIWAKIPHTDGNFHPSPLMGGFGLKHPPPQILIKNTPVPADP
AAV8_VP1          QGALPGMVWQNRDVYLQGPIWAKIPHTDGNFHPSPLMGGFGLKHPPPQILIKNTPVPADP 660
AAV9_VP1          QGILPGMVWQDRDVYLQGPIWAKIPHTDGNFHPSPLMGGFGMKHPPPQILIKNTPVPADP
                  ** *******:******************************:******************

ITB102_45_VP1     PTTFNQSKLNSFITQYSTGQVSVEIEWELQKENSKRWNPEIQYTSNYYKSTSVDFAVNTE
AAV214_VP1        PTTFNQSKLNSFITQYSTGQVSVEIEWELQKENSKRWNPEIQYTSNYYKSTSVDFAVNTE
AAV214A_VP1       PTTFNQSKLNSFITQYSTGQVSVEIEWELQKENSKRWNPEIQYTSNYYKSTSVDFAVNTE
AAV214-AB_VP1     PTTFNQSKLNSFITQYSTGQVSVEIEWELQKENSKRWNPEIQYTSNYYKSTSVDFAVNTE
AAV214e_VP1       PTTFNQSKLNSFITQYSTGQVSVEIEWELQKENSKRWNPEIQYTSNYYKSTSVDFAVNTE
AAV214e8_VP1      PTTFNQSKLNSFITQYSTGQVSVEIEWELQKENSKRWNPEIQYTSNYYKSTSVDFAVNTE
AAV214e9_VP1      PTTFNQSKLNSFITQYSTGQVSVEIEWELQKENSKRWNPEIQYTSNYYKSTSVDFAVNTE
AAV214e10_VP1     PTTFNQSKLNSFITQYSTGQVSVEIEWELQKENSKRWNPEIQYTSNYYKSTSVDFAVNTE
AAV8_VP1          PTTFNQSKLNSFITQYSTGQVSVEIEWELQKENSKRWNPEIQYTSNYYKSTSVDFAVNTE 720
AAV9_VP1          PTAFNKDKLNSFITQYSTGQVSVEIEWELQKENSKRWNPEIQYTSNYYKSNNVEFAVNTE
                  **:**:.*****************************************..*:******

ITB102_45_VP1     GVYSEPHPIGTRYLTRPL 736
AAV214_VP1        GVYSEPHPIGTRYLTRPL 735
AAV214A_VP1       GVYSEPHPIGTRYLTRPL 736
AAV214-AB_VP1     GVYSEPHPIGTRYLTRPL 736
AAV214e_VP1       GVYSEPHPIGTRYLTRPL 736
AAV214e8_VP1      GVYSEPHPIGTRYLTRPL 736
AAV214e9_VP1      GVYSEPHPIGTRYLTRPL 735
AAV214e10_VP1     GVYSEPHPIGTRYLTRPL 736
AAV8_VP1          GVYSEPRPIGTRYLTRNL 738
AAV9_VP1          GVYSEPRPIGTRYLTRNL 736
                  ******:********* *
```

FIG. 21 (Cont. 2)

```
clustalw.aln

CLUSTAL 2.1 multiple sequence alignment of VP2 protein sequences

ITB102_45_VP2      MAPGKKRPVEQSPQ-EPDSSSGIGKTGQQPAKKRLNFGQTGDSESVPDPQPLGEPPATPA
AAV214_VP2         MAPGKKRPVEQSPQ-EPDSSSGIGKTGQQPAKKRLNFGQTGDSESVPDPQPLGEPPATPA
AAV214A_VP2        MAPGKKRPVEQSPQ-EPDSSSGIGKTGQQPAKKRLNFGQTGDSESVPDPQPLGEPPATPA
AAV214AB_VP2       MAPGKKRPVEQSPQ-EPDSSSGIGKTGQQPAKKRLNFGQTGDSESVPDPQPLGEPPATPA
AAV214e_VP2        MAPGKKRPVEPSPQRSPDSSTGIGKKGQQPARKRLNFGQTGDSESVPDPQPLGEPPATPA
AAV214e8_VP2       MAPGKKRPVEPSPQRSPDSSTGIGKKGQQPARKRLNFGQTGDSESVPDPQPLGEPPAAPS
AAV214e9_VP2       MAPGKKRPVEQSPQ-EPDSSAGIGKSGAQPAKKRLNFGQTGDTESVPDPQPIGEPPAAPS
AAV214e10_VP2      MAPGKKRPVEPSPQRSPDSSTGIGKKGQQPAKKRLNFGQTGDSESVPDPQPIGEPPAGPS
AAV8_VP2           MAPGKKRPVEPSPQRSPDSSTGIGKKGQQPARKRLNFGQTGDSESVPDPQPLGEPPAAPS 60
AAV9_VP2           MAPGKKRPVEQSPQ-EPDSSAGIGKSGAQPAKKRLNFGQTGDTESVPDPQPIGEPPAAPS
                   ********** *** .****:****.* ***:**********:********:***** *:

ITB102_45_VP2      AVGPTTMASGGGAPMADNNEGADGVGNASGNWHCDSTWLGDRVITTSTRTWALPTYNNHL
AAV214_VP2         AVGPTTMASGGGAPMADNNEGADGVGNASGNWHCDSTWLGDRVITTSTRTWALPTYNNHL
AAV214A_VP2        AVGPTTMASGGGAPMADNNEGADGVGNASGNWHCDSTWLGDRVITTSTRTWALPTYNNHL
AAV214AB_VP2       AVGPTTMASGGGAPMADNNEGADGVGNASGNWHCDSTWLGDRVITTSTRTWALPTYNNHL
AAV214e_VP2        AVGPTTMASGGGAPMADNNEGADGVGNASGNWHCDSTWLGDRVITTSTRTWALPTYNNHL
AAV214e8_VP2       GVGPNTMASGGGAPMADNNEGADGVGNASGNWHCDSTWLGDRVITTSTRTWALPTYNNHL
AAV214e9_VP2       GVGSLTMASGGGAPMADNNEGADGVGNASGNWHCDSTWLGDRVITTSTRTWALPTYNNHL
AAV214e10_VP2      GLGSGTMASGGGAPMADNNEGADGVGNASGNWHCDSTWLGDRVITTSTRTWALPTYNNHL
AAV8_VP2           GVGPNTMAAGGGAPMADNNEGADGVGSSSGNWHCDSTWLGDRVITTSTRTWALPTYNNHL 120
AAV9_VP2           GVGSLTMASGGGAPVADNNEGADGVGSSSGNWHCDSQWLGDRVITTSTRTWALPTYNNHL
                   .:*. ***:*****:***********.:******** ***********************

ITB102_45_VP2      YKQISSASTG-ASNDNHYFGYSTPWGYFDFNRFHCHFSPRDWQRLINNNWGFRPKRLNFK
AAV214_VP2         YKQISSASTG-ASNDNHYFGYSTPWGYFDFNRFHCHFSPRDWQRLINNNWGFRPKRLNFK
AAV214A_VP2        YKQISNSTSGGSSNDNAYFGYSTPWGYFDFNRFHCHFSPRDWQRLINNNWGFRPKRLNFK
AAV214AB_VP2       YKQISSSTSGGSSNDNAYFGYSTPWGYFDFNRFHCHFSPRDWQRLINNNWGFRPKRLNFK
AAV214e_VP2        YKQISSASTG-ASNDNHYFGYSTPWGYFDFNRFHCHFSPRDWQRLINNNWGFRPKRLNFK
AAV214e8_VP2       YKQISSASTG-ASNDNHYFGYSTPWGYFDFNRFHCHFSPRDWQRLINNNWGFRPKRLNFK
AAV214e9_VP2       YKQISSASTG-ASNDNHYFGYSTPWGYFDFNRFHCHFSPRDWQRLINNNWGFRPKRLNFK
AAV214e10_VP2      YKQISSASTG-ASNDNHYFGYSTPWGYFDFNRFHCHFSPRDWQRLINNNWGFRPKRLNFK
AAV8_VP2           YKQISNGTSGGATNDNTYFGYSTPWGYFDFNRFHCHFSPRDWQRLINNNWGFRPKRLSFK 180
AAV9_VP2           YKQISNSTSGGSSNDNAYFGYSTPWGYFDFNRFHCHFSPRDWQRLINNNWGFRPKRLNFK
                   *****..::* ::*** ****************************************.**

ITB102_45_VP2      LFNIQVKEVTDNNGVKTIANNLTSTVQVFTDSDYQLPYVLGSAHEGCLPPFPADVFMIPQ
AAV214_VP2         LFNIQVKEVTDNNGVKTIANNLTSTVQVFTDSDYQLPYVLGSAHQGCLPPFPADVFMIPQ
AAV214A_VP2        LFNIQVKEVTDNNGVKTIANNLTSTVQVFTDSDYQLPYVLGSAHQGCLPPFPADVFMIPQ
AAV214AB_VP2       LFNIQVKEVTDNNGVKTIANNLTSTVQVFTDSDYQLPYVLGSAHQGCLPPFPADVFMIPQ
AAV214e_VP2        LFNIQVKEVTDNNGVKTIANNLTSTVQVFTDSDYQLPYVLGSAHQGCLPPFPADVFMIPQ
AAV214e8_VP2       LFNIQVKEVTDNNGVKTIANNLTSTVQVFTDSDYQLPYVLGSAHQGCLPPFPADVFMIPQ
AAV214e9_VP2       LFNIQVKEVTDNNGVKTIANNLTSTVQVFTDSDYQLPYVLGSAHQGCLPPFPADVFMIPQ
AAV214e10_VP2      LFNIQVKEVTDNNGVKTIANNLTSTVQVFTDSDYQLPYVLGSAHQGCLPPFPADVFMIPQ
AAV8_VP2           LFNIQVKEVTQNEGTKTIANNLTSTIQVFTDSEYQLPYVLGSAHQGCLPPFPADVFMIPQ 240
AAV9_VP2           LFNIQVKEVTDNNGVKTIANNLTSTVQVFTDSDYQLPYVLGSAHEGCLPPFPADVFMIPQ
                   **********:*:*.**********:******:***********:***************
```

FIG. 22

```
ITB102_45_VP2     YGYLTLNNGSQAVGRSSFYCLEYFPSQMLRTGNNFTFSYTFEDVPFHSSYAHSQSLDRLM
AAV214_VP2        YGYLTLNDGSQAVGRSSFYCLEYFPSQMLRTGNNFTFSYTFEDVPFHSSYAHSQSLDRLM
AAV214A_VP2       YGYLTLNDGSQAVGRSSFYCLEYFPSQMLRTGNNFTFSYTFEDVPFHSSYAHSQSLDRLM
AAV214AB_VP2      YGYLTLNDGSQAVGRSSFYCLEYFPSQMLRTGNNFTFSYTFEDVPFHSSYAHSQSLDRLM
AAV214e_VP2       YGYLTLNDGSQAVGRSSFYCLEYFPSQMLRTGNNFTFSYTFEDVPFHSSYAHSQSLDRLM
AAV214e8_VP2      YGYLTLNDGSQAVGRSSFYCLEYFPSQMLRTGNNFTFSYTFEDVPFHSSYAHSQSLDRLM
AAV214e9_VP2      YGYLTLNDGSQAVGRSSFYCLEYFPSQMLRTGNNFTFSYTFEDVPFHSSYAHSQSLDRLM
AAV214e10_VP2     YGYLTLNDGSQAVGRSSFYCLEYFPSQMLRTGNNFTFSYTFEDVPFHSSYAHSQSLDRLM
AAV8_VP2          YGYLTLNNGSQAVGRSSFYCLEYFPSQMLRTGNNFQFTYTFEDVPFHSSYAHSQSLDRLM 300
AAV9_VP2          YGYLTLNDGSQAVGRSSFYCLEYFPSQMLRTGNNFQFSYEFENVPFHSSYAHSQSLDRLM
                  *******:*************************** *:* **:*****************

ITB102_45_VP2     NPLIDQYLYYLSRTQTTGGTANTQTLGFSQGGPNTMANQAKNWLPGPCYRQQRVSTTTGQ
AAV214_VP2        NPLIDQYLYYLSKTINGSG-QNQQTLKFSQGGPNTMANQAKNWLPGPCYRQQRVSTTTGQ
AAV214A_VP2       NPLIDQYLYYLSKTINGSG-QNQQTLKFSQGGPNTMANQAKNWLPGPCYRQQRVSTTTGQ
AAV214AB_VP2      NPLIDQYLYYLSKTINGSG-QNQQTLKFSQGGPNTMANQAKNWLPGPCYRQQRVSTTTGQ
AAV214e_VP2       NPLIDQYLYYLSKTINGSG-QNQQTLKFSQGGPNTMANQAKNWLPGPCYRQQRVSTTTGQ
AAV214e8_VP2      NPLIDQYLYYLSKTINGSG-QNQQTLKFSQGGPNTMANQAKNWLPGPCYRQQRVSTTTGQ
AAV214e9_VP2      NPLIDQYLYYLSKTINGSG-QNQQTLKFSQGGPNTMANQAKNWLPGPCYRQQRVSTTTGQ
AAV214e10_VP2     NPLIDQYLYYLSKTINGSG-QNQQTLKFSQGGPNTMANQAKNWLPGPCYRQQRVSTTTGQ
AAV8_VP2          NPLIDQYLYYLSRTQTTGGTANTQTLGFSQGGPNTMANQAKNWLPGPCYRQQRVSTTTGQ 360
AAV9_VP2          NPLIDQYLYYLSKTINGSG-QNQQTLKFSVAGPSNMAVQGRNYIPGPSYRQQRVSTTVTQ
                  ************:* . .*  * *** ** .**..** *.:*::***.*********. *

ITB102_45_VP2     NNNSNFAWTAGTKYHLNGRNSLMNPGPAMASHKEGEDRFFPLSGSLIFGKQGTGRDNVDA
AAV214_VP2        NNNSNFAWTAGTKYHLNGRNSLMNPGPAMASHKEGEDRFFPLSGSLIFGKQNAARDNADY
AAV214A_VP2       NNNSNFAWTAGTKYHLNGRNSLMNPGPAMASHKEGEDRFFPLSGSLIFGKQNAARDNADY
AAV214AB_VP2      NNNSNFAWTAGTKYHLNGRNSLMNPGPAMASHKEGEDRFFPLSGSLIFGKQNAARDNADY
AAV214e_VP2       NNNSNFAWTAGTKYHLNGRNSLMNPGPAMASHKEGEDRFFPLSGSLIFGKQNAARDNADY
AAV214e8_VP2      NNNSNFAWTAGTKYHLNGRNSLMNPGPAMASHKEGEDRFFPLSGSLIFGKQNAARDNADY
AAV214e9_VP2      NNNSNFAWTAGTKYHLNGRNSLMNPGPAMASHKEGEDRFFPLSGSLIFGKQNAARDNADY
AAV214e10_VP2     NNNSNFAWTAGTKYHLNGRNSLMNPGPAMASHKEGEDRFFPLSGSLIFGKQNAARDNADY
AAV8_VP2          NNNSNFAWTAGTKYHLNGRNSLANPGIAMATHKDDEERFFPSNGILIFGKQNAARDNADY 420
AAV9_VP2          NNNSEFAWPGASSWALNGRNSLMNPGPAMASHKEGEDRFFPLSGSLIFGKQGTGRDNVDA
                  ****:***...:.: ******* *** ***:**:.*:**** .* ******.:.***.*

ITB102_45_VP2     DKVMITNEEEIKTTNPVATEEYGIVADNLQQQNTAPQIGTVNSQGALPGMVWQNRDVYLQ
AAV214_VP2        SDVMLTSEEEIKTTNPVATEEYGIVADNLQQQNTAPQIGTVNSQGALPGMVWQNRDVYLQ
AAV214A_VP2       SDVMLTSEEEIKTTNPVATEEYGIVADNLQQQNTAPQIGTVNSQGALPGMVWQNRDVYLQ
AAV214AB_VP2      SDVMLTSEEEIKTTNPVATEEYGIVADNLQQQNTAPQIGTVNSQGALPGMVWQNRDVYLQ
AAV214e_VP2       SDVMLTSEEEIKTTNPVATEEYGIVADNLQQQNTAPQIGTVNSQGALPGMVWQNRDVYLQ
AAV214e8_VP2      SDVMLTSEEEIKTTNPVATEEYGIVADNLQQQNTAPQIGTVNSQGALPGMVWQNRDVYLQ
AAV214e9_VP2      SDVMLTSEEEIKTTNPVATEEYGIVADNLQQQNTAPQIGTVNSQGALPGMVWQNRDVYLQ
AAV214e10_VP2     SDVMLTSEEEIKTTNPVATEEYGIVADNLQQQNTAPQIGTVNSQGALPGMVWQNRDVYLQ
AAV8_VP2          SDVMLTSEEEIKTTNPVATEEYGIVADNLQQQNTAPQIGTVNSQGALPGMVWQNRDVYLQ 480
AAV9_VP2          DKVMITNEEEIKTTNPVATESYGQVATNHQSAQAQAQTGWVQNQGILPGMVWQDRDVYLQ
                  ..**:*.*************.** ** * *. ::. * * *:.** *******:******

ITB102_45_VP2     GPIWAKIPHTDGNFHPSPLMGGFGLKHPPPQILIKNTPVPADPPTTFNQSKLNSFITQYS
AAV214_VP2        GPIWAKIPHTDGNFHPSPLMGGFGLKHPPPQILIKNTPVPADPPTTFNQSKLNSFITQYS
AAV214A_VP2       GPIWAKIPHTDGNFHPSPLMGGFGLKHPPPQILIKNTPVPADPPTTFNQSKLNSFITQYS
AAV214AB_VP2      GPIWAKIPHTDGNFHPSPLMGGFGLKHPPPQILIKNTPVPADPPTTFNQSKLNSFITQYS
AAV214e_VP2       GPIWAKIPHTDGNFHPSPLMGGFGLKHPPPQILIKNTPVPADPPTTFNQSKLNSFITQYS
AAV214e8_VP2      GPIWAKIPHTDGNFHPSPLMGGFGLKHPPPQILIKNTPVPADPPTTFNQSKLNSFITQYS
AAV214e9_VP2      GPIWAKIPHTDGNFHPSPLMGGFGLKHPPPQILIKNTPVPADPPTTFNQSKLNSFITQYS
AAV214e10_VP2     GPIWAKIPHTDGNFHPSPLMGGFGLKHPPPQILIKNTPVPADPPTTFNQSKLNSFITQYS
AAV8_VP2          GPIWAKIPHTDGNFHPSPLMGGFGLKHPPPQILIKNTPVPADPPTTFNQSKLNSFITQYS 540
AAV9_VP2          GPIWAKIPHTDGNFHPSPLMGGFGMKHPPPQILIKNTPVPADPPTAFNKDKLNSFITQYS
                  ************************:********************:**:.**********
```

FIG. 22 (Cont. 1)

```
ITB102_45_VP2      TGQVSVEIEWELQKENSKRWNPEIQYTSNYYKSTSVDFAVNTEGVYSEPHPIGTRYLTRP
AAV214_VP2         TGQVSVEIEWELQKENSKRWNPEIQYTSNYYKSTSVDFAVNTEGVYSEPHPIGTRYLTRP
AAV214A_VP2        TGQVSVEIEWELQKENSKRWNPEIQYTSNYYKSTSVDFAVNTEGVYSEPHPIGTRYLTRP
AAV214AB_VP2       TGQVSVEIEWELQKENSKRWNPEIQYTSNYYKSTSVDFAVNTEGVYSEPHPIGTRYLTRP
AAV214e_VP2        TGQVSVEIEWELQKENSKRWNPEIQYTSNYYKSTSVDFAVNTEGVYSEPHPIGTRYLTRP
AAV214e8_VP2       TGQVSVEIEWELQKENSKRWNPEIQYTSNYYKSTSVDFAVNTEGVYSEPHPIGTRYLTRP
AAV214e9_VP2       TGQVSVEIEWELQKENSKRWNPEIQYTSNYYKSTSVDFAVNTEGVYSEPHPIGTRYLTRP
AAV214e10_VP2      TGQVSVEIEWELQKENSKRWNPEIQYTSNYYKSTSVDFAVNTEGVYSEPHPIGTRYLTRP
AAV8_VP2           TGQVSVEIEWELQKENSKRWNPEIQYTSNYYKSTSVDFAVNTEGVYSEPRPIGTRYLTRN 600
AAV9_VP2           TGQVSVEIEWELQKENSKRWNPEIQYTSNYYKSNNVEFAVNTEGVYSEPRPIGTRYLTRN
                   *********************************..*:************:*********

ITB102_45_VP2      L 599
AAV214_VP2         L 598
AAV214A_VP2        L 599
AAV214AB_VP2       L 599
AAV214e_VP2        L 599
AAV214e8_VP2       L 599
AAV214e9_VP2       L 598
AAV214e10_VP2      L 599
AAV8_VP2           L 601
AAV9_VP2           L 599
                   *
```

FIG. 22 (Cont. 2)

```
clustalw.aln

CLUSTAL 2.1 multiple sequence alignment of VP3 protein sequences

ITB102_45_VP3      MASGGGAPMADNNEGADGVGNASGNWHCDSTWLGDRVITTSTRTWALPTYNNHLYKQISS
AAV214_VP3         MASGGGAPMADNNEGADGVGNASGNWHCDSTWLGDRVITTSTRTWALPTYNNHLYKQISS
AAV214A¬_VP3       MASGGGAPMADNNEGADGVGNASGNWHCDSTWLGDRVITTSTRTWALPTYNNHLYKQISN
AAV214AB_VP3       MASGGGAPMADNNEGADGVGNASGNWHCDSTWLGDRVITTSTRTWALPTYNNHLYKQISS
AAV214E¬_VP3       MASGGGAPMADNNEGADGVGNASGNWHCDSTWLGDRVITTSTRTWALPTYNNHLYKQISS
AAV214E8¬_VP3      MASGGGAPMADNNEGADGVGNASGNWHCDSTWLGDRVITTSTRTWALPTYNNHLYKQISS
AAV214E9¬_VP3      MASGGGAPMADNNEGADGVGNASGNWHCDSTWLGDRVITTSTRTWALPTYNNHLYKQISS
AAV214E10_VP3      MASGGGAPMADNNEGADGVGNASGNWHCDSTWLGDRVITTSTRTWALPTYNNHLYKQISS
AAV8_VP3           MAAGGGAPMADNNEGADGVGSSSGNWHCDSTWLGDRVITTSTRTWALPTYNNHLYKQISN 60
AAV9_VP3           MASGGGAPVADNNEGADGVGSSSGNWHCDSQWLGDRVITTSTRTWALPTYNNHLYKQISN
                   **:*****:***********.:******** ****************************.

ITB102_45_VP3      ASTG-ASNDNHYFGYSTPWGYFDFNRFHCHFSPRDWQRLINNNWGFRPKRLNFKLFNIQV
AAV214_VP3         ASTG-ASNDNHYFGYSTPWGYFDFNRFHCHFSPRDWQRLINNNWGFRPKRLNFKLFNIQV
AAV214A¬_VP3       STSGGSSNDNAYFGYSTPWGYFDFNRFHCHFSPRDWQRLINNNWGFRPKRLNFKLFNIQV
AAV214AB_VP3       STSGGSSNDNAYFGYSTPWGYFDFNRFHCHFSPRDWQRLINNNWGFRPKRLNFKLFNIQV
AAV214E¬_VP3       ASTG-ASNDNHYFGYSTPWGYFDFNRFHCHFSPRDWQRLINNNWGFRPKRLNFKLFNIQV
AAV214E8¬_VP3      ASTG-ASNDNHYFGYSTPWGYFDFNRFHCHFSPRDWQRLINNNWGFRPKRLNFKLFNIQV
AAV214E9¬_VP3      ASTG-ASNDNHYFGYSTPWGYFDFNRFHCHFSPRDWQRLINNNWGFRPKRLNFKLFNIQV
AAV214E10_VP3      ASTG-ASNDNHYFGYSTPWGYFDFNRFHCHFSPRDWQRLINNNWGFRPKRLNFKLFNIQV
AAV8_VP3           GTSGGATNDNTYFGYSTPWGYFDFNRFHCHFSPRDWQRLINNNWGFRPKRLSFKLFNIQV 120
AAV9_VP3           STSGGSSNDNAYFGYSTPWGYFDFNRFHCHFSPRDWQRLINNNWGFRPKRLNFKLFNIQV
                   .::* ::*** ****************************************.********

ITB102_45_VP3      KEVTDNNGVKTIANNLTSTVQVFTDSDYQLPYVLGSAHEGCLPPFPADVFMIPQYGYLTL
AAV214_VP3         KEVTDNNGVKTIANNLTSTVQVFTDSDYQLPYVLGSAHQGCLPPFPADVFMIPQYGYLTL
AAV214A¬_VP3       KEVTDNNGVKTIANNLTSTVQVFTDSDYQLPYVLGSAHQGCLPPFPADVFMIPQYGYLTL
AAV214AB_VP3       KEVTDNNGVKTIANNLTSTVQVFTDSDYQLPYVLGSAHQGCLPPFPADVFMIPQYGYLTL
AAV214E¬_VP3       KEVTDNNGVKTIANNLTSTVQVFTDSDYQLPYVLGSAHQGCLPPFPADVFMIPQYGYLTL
AAV214E8¬_VP3      KEVTDNNGVKTIANNLTSTVQVFTDSDYQLPYVLGSAHQGCLPPFPADVFMIPQYGYLTL
AAV214E9¬_VP3      KEVTDNNGVKTIANNLTSTVQVFTDSDYQLPYVLGSAHQGCLPPFPADVFMIPQYGYLTL
AAV214E10_VP3      KEVTDNNGVKTIANNLTSTVQVFTDSDYQLPYVLGSAHQGCLPPFPADVFMIPQYGYLTL
AAV8_VP3           KEVTQNEGTKTIANNLTSTIQVFTDSEYQLPYVLGSAHQGCLPPFPADVFMIPQYGYLTL 180
AAV9_VP3           KEVTDNNGVKTIANNLTSTVQVFTDSDYQLPYVLGSAHEGCLPPFPADVFMIPQYGYLTL
                   ****:*:*.**********:******:***********:*********************

ITB102_45_VP3      NNGSQAVGRSSFYCLEYFPSQMLRTGNNFTFSYTFEDVPFHSSYAHSQSLDRLMNPLIDQ
AAV214_VP3         NDGSQAVGRSSFYCLEYFPSQMLRTGNNFTFSYTFEDVPFHSSYAHSQSLDRLMNPLIDQ
AAV214A¬_VP3       NDGSQAVGRSSFYCLEYFPSQMLRTGNNFTFSYTFEDVPFHSSYAHSQSLDRLMNPLIDQ
AAV214AB_VP3       NDGSQAVGRSSFYCLEYFPSQMLRTGNNFTFSYTFEDVPFHSSYAHSQSLDRLMNPLIDQ
AAV214E¬_VP3       NDGSQAVGRSSFYCLEYFPSQMLRTGNNFTFSYTFEDVPFHSSYAHSQSLDRLMNPLIDQ
AAV214E8¬_VP3      NDGSQAVGRSSFYCLEYFPSQMLRTGNNFTFSYTFEDVPFHSSYAHSQSLDRLMNPLIDQ
AAV214E9¬_VP3      NDGSQAVGRSSFYCLEYFPSQMLRTGNNFTFSYTFEDVPFHSSYAHSQSLDRLMNPLIDQ
AAV214E10_VP3      NDGSQAVGRSSFYCLEYFPSQMLRTGNNFTFSYTFEDVPFHSSYAHSQSLDRLMNPLIDQ
AAV8_VP3           NNGSQAVGRSSFYCLEYFPSQMLRTGNNFQFTYTFEDVPFHSSYAHSQSLDRLMNPLIDQ 240
AAV9_VP3           NDGSQAVGRSSFYCLEYFPSQMLRTGNNFQFSYEFENVPFHSSYAHSQSLDRLMNPLIDQ
                   *:*************************** *:* **:***********************
```

FIG. 23

```
ITB102_45_VP3      YLYYLSRTQTTGGTANTQTLGFSQGGPNTMANQAKNWLPGPCYRQQRVSTTTGQNNNSNF
AAV214_VP3         YLYYLSKTINGSG-QNQQTLKFSQGGPNTMANQAKNWLPGPCYRQQRVSTTTGQNNNSNF
AAV214A¬_VP3       YLYYLSKTINGSG-QNQQTLKFSQGGPNTMANQAKNWLPGPCYRQQRVSTTTGQNNNSNF
AAV214AB_VP3       YLYYLSKTINGSG-QNQQTLKFSQGGPNTMANQAKNWLPGPCYRQQRVSTTTGQNNNSNF
AAV214E¬_VP3       YLYYLSKTINGSG-QNQQTLKFSQGGPNTMANQAKNWLPGPCYRQQRVSTTTGQNNNSNF
AAV214E8¬_VP3      YLYYLSKTINGSG-QNQQTLKFSQGGPNTMANQAKNWLPGPCYRQQRVSTTTGQNNNSNF
AAV214E9¬_VP3      YLYYLSKTINGSG-QNQQTLKFSQGGPNTMANQAKNWLPGPCYRQQRVSTTTGQNNNSNF
AAV214E10_VP3      YLYYLSKTINGSG-QNQQTLKFSQGGPNTMANQAKNWLPGPCYRQQRVSTTTGQNNNSNF
AAV8_VP3           YLYYLSRTQTTGGTANTQTLGFSQGGPNTMANQAKNWLPGPCYRQQRVSTTTGQNNNSNF 300
AAV9_VP3           YLYYLSKTINGSG-QNQQTLKFSVAGPSNMAVQGRNYIPGPSYRQQRVSTTVTQNNNSEF
                   ******:* . .*  * *** ** .**..** *.:*::***.*********. *****:*

ITB102_45_VP3      AWTAGTKYHLNGRNSLMNPGPAMASHKEGEDRFFPLSGSLIFGKQGTGRDNVDADKVMIT
AAV214_VP3         AWTAGTKYHLNGRNSLMNPGPAMASHKEGEDRFFPLSGSLIFGKQNAARDNADYSDVMLT
AAV214A¬_VP3       AWTAGTKYHLNGRNSLMNPGPAMASHKEGEDRFFPLSGSLIFGKQNAARDNADYSDVMLT
AAV214AB_VP3       AWTAGTKYHLNGRNSLMNPGPAMASHKEGEDRFFPLSGSLIFGKQNAARDNADYSDVMLT
AAV214E¬_VP3       AWTAGTKYHLNGRNSLMNPGPAMASHKEGEDRFFPLSGSLIFGKQNAARDNADYSDVMLT
AAV214E8¬_VP3      AWTAGTKYHLNGRNSLMNPGPAMASHKEGEDRFFPLSGSLIFGKQNAARDNADYSDVMLT
AAV214E9¬_VP3      AWTAGTKYHLNGRNSLMNPGPAMASHKEGEDRFFPLSGSLIFGKQNAARDNADYSDVMLT
AAV214E10_VP3      AWTAGTKYHLNGRNSLMNPGPAMASHKEGEDRFFPLSGSLIFGKQNAARDNADYSDVMLT
AAV8_VP3           AWTAGTKYHLNGRNSLANPGIAMATHKDDEERFFPSNGILIFGKQNAARDNADYSDVMLT 360
AAV9_VP3           AWPGASSWALNGRNSLMNPGPAMASHKEGEDRFFPLSGSLIFGKQGTGRDNVDADKVMIT
                   **...:.: ******* *** ***:**:.*:**** .* ******.:.***.* ..**:*

ITB102_45_VP3      NEEEIKTTNPVATEEYGIVADNLQQQNTAPQIGTVNSQGALPGMVWQNRDVYLQGPIWAK
AAV214_VP3         SEEEIKTTNPVATEEYGIVADNLQQQNTAPQIGTVNSQGALPGMVWQNRDVYLQGPIWAK
AAV214A¬_VP3       SEEEIKTTNPVATEEYGIVADNLQQQNTAPQIGTVNSQGALPGMVWQNRDVYLQGPIWAK
AAV214AB_VP3       SEEEIKTTNPVATEEYGIVADNLQQQNTAPQIGTVNSQGALPGMVWQNRDVYLQGPIWAK
AAV214E¬_VP3       SEEEIKTTNPVATEEYGIVADNLQQQNTAPQIGTVNSQGALPGMVWQNRDVYLQGPIWAK
AAV214E8¬_VP3      SEEEIKTTNPVATEEYGIVADNLQQQNTAPQIGTVNSQGALPGMVWQNRDVYLQGPIWAK
AAV214E9¬_VP3      SEEEIKTTNPVATEEYGIVADNLQQQNTAPQIGTVNSQGALPGMVWQNRDVYLQGPIWAK
AAV214E10_VP3      SEEEIKTTNPVATEEYGIVADNLQQQNTAPQIGTVNSQGALPGMVWQNRDVYLQGPIWAK
AAV8_VP3           SEEEIKTTNPVATEEYGIVADNLQQQNTAPQIGTVNSQGALPGMVWQNRDVYLQGPIWAK 420
AAV9_VP3           NEEEIKTTNPVATESYGQVATNHQSAQAQAQTGWVQNQGILPGMVWQDRDVYLQGPIWAK
                   .*************.** ** * *. :: .* * *:.** *******:************
```

FIG. 23 (Cont. 1)

```
ITB102_45_VP3       IPHTDGNFHPSPLMGGFGLKHPPPQILIKNTPVPADPPTTFNQSKLNSFITQYSTGQVSV
AAV214_VP3          IPHTDGNFHPSPLMGGFGLKHPPPQILIKNTPVPADPPTTFNQSKLNSFITQYSTGQVSV
AAV214Ā¬_VP3        IPHTDGNFHPSPLMGGFGLKHPPPQILIKNTPVPADPPTTFNQSKLNSFITQYSTGQVSV
AAV214AB_VP3        IPHTDGNFHPSPLMGGFGLKHPPPQILIKNTPVPADPPTTFNQSKLNSFITQYSTGQVSV
AAV214E¬_VP3        IPHTDGNFHPSPLMGGFGLKHPPPQILIKNTPVPADPPTTFNQSKLNSFITQYSTGQVSV
AAV214E8¬_VP3       IPHTDGNFHPSPLMGGFGLKHPPPQILIKNTPVPADPPTTFNQSKLNSFITQYSTGQVSV
AAV214E9¬_VP3       IPHTDGNFHPSPLMGGFGLKHPPPQILIKNTPVPADPPTTFNQSKLNSFITQYSTGQVSV
AAV214E10_VP3       IPHTDGNFHPSPLMGGFGLKHPPPQILIKNTPVPADPPTTFNQSKLNSFITQYSTGQVSV
AAV8_VP3            IPHTDGNFHPSPLMGGFGLKHPPPQILIKNTPVPADPPTTFNQSKLNSFITQYSTGQVSV 480
AAV9_VP3            IPHTDGNFHPSPLMGGFGMKHPPPQILIKNTPVPADPPTAFNKDKLNSFITQYSTGQVSV
                    ******************:********************:**:.****************

ITB102_45_VP3       EIEWELQKENSKRWNPEIQYTSNYYKSTSVDFAVNTEGVYSEPHPIGTRYLTRPL 534
AAV214_VP3          EIEWELQKENSKRWNPEIQYTSNYYKSTSVDFAVNTEGVYSEPHPIGTRYLTRPL 533
AAV214Ā¬_VP3        EIEWELQKENSKRWNPEIQYTSNYYKSTSVDFAVNTEGVYSEPHPIGTRYLTRPL 534
AAV214AB_VP3        EIEWELQKENSKRWNPEIQYTSNYYKSTSVDFAVNTEGVYSEPHPIGTRYLTRPL 534
AAV214E¬_VP3        EIEWELQKENSKRWNPEIQYTSNYYKSTSVDFAVNTEGVYSEPHPIGTRYLTRPL 533
AAV214E8¬_VP3       EIEWELQKENSKRWNPEIQYTSNYYKSTSVDFAVNTEGVYSEPHPIGTRYLTRPL 533
AAV214E9¬_VP3       EIEWELQKENSKRWNPEIQYTSNYYKSTSVDFAVNTEGVYSEPHPIGTRYLTRPL 533
AAV214E10_VP3       EIEWELQKENSKRWNPEIQYTSNYYKSTSVDFAVNTEGVYSEPHPIGTRYLTRPL 533
AAV8_VP3            EIEWELQKENSKRWNPEIQYTSNYYKSTSVDFAVNTEGVYSEPRPIGTRYLTRNL 535
AAV9_VP3            EIEWELQKENSKRWNPEIQYTSNYYKSNNVEFAVNTEGVYSEPRPIGTRYLTRNL 534
                    ***************************..*:************:********* *
```

FIG. 23 (Cont. 2)

AAV viral particles with the AAV110 VP1 capsid protein expressed GFP in muscle following IM administration IM administration of AV110 shows highly specific muscle tropism.

IHC analysis of IM administered AAV110- vs AAV9-delivered transgene in muscle

Fluorescent analysis of IM administered AAV110- vs AAV9-delivered transgene in muscle Intramuscular Administration of AAV214 Shows High Expression after 28 days

Variable Regions I-IX of VP3 protein for AAV214 (SEQ ID NO:41)

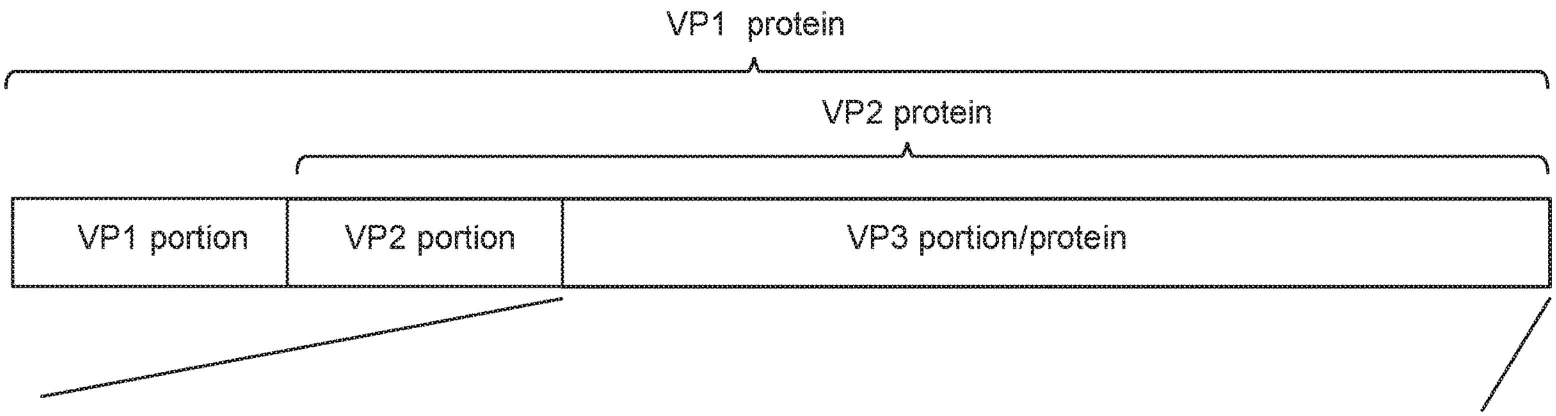

1 MASGGGAPMA DNNEGADGVG NASGNWHCDS TWLGDRVITT STRTWALPTY NNHLYKQISS

61 ASTGASNDNH YFGYSTPWGY FDFNRFHCHF SPRDWQRLIN NNWGFRPKRL NFKLFNIQVK (I: ASTGAS)

121 EVTDNNGVKT IANNLTSTVQ VFTDSDYQLP YVLGSAHQGC LPPFPADVFM IPQYGYLTLN (II: DNNGVK)

181 DGSQAVGRSS FYCLEYFPSQ MLRTGNNFTF SYTFEDVPFH SSYAHSQSLD RLMNPLIDQY (III: NDGS)

241 LYYLSKTING SGQNQQTLKF SQGGPNTMAN QAKNWLPGPC YRQQRVSTTT GQNNNSNFAW (IV: INGSGQNQQT; V: RVSTTTGQNNNSNFAW)

301 TAGTKYHLNG RNSLMNPGPA MASHKEGEDR FFPLSGSLIF GKQNAARDNA DYSDVMLTSE (VI: HKEGEDRFFPLSG; VII: KQNAARDNADYSDV)

361 EEIKTTNPVA TEEYGIVADN LQQQNTAPQI GTVNSQGALP GMVWQNRDVY LQGPIWAKIP (VIII: ADNLQQQNTAPQI)

421 HTDGNFHPSP LMGGFGLKHP PPQILIKNTP VPADPPTTFN QSKLNSFITQ YSTGQVSVEI

481 EWELQKENSK RWNPEIQYTS NYYKSTSVDF AVNTEGVYSE PHPIGTRYLT RPL (IX: NYYKSTSVDF)

FIG. 30

RECOMBINANT ADENO-ASSOCIATED VIRAL VECTOR FOR GENE DELIVERY

CROSS REFERENCE TO RELATED APPLICATIONS

This application is a U.S. National Phase application, filed under 35 U.S.C. § 371(c), of International Application No. PCT/US2019/064396, filed Dec. 4, 2019, which claims priority to U.S. Provisional Application Nos. 62/775,871, filed Dec. 5, 2018; 62/801,195, filed Feb. 5, 2019; 62/863,126 filed Jun. 18, 2019, and 62/914,856 filed Oct. 14, 2019, each of which is incorporated by reference herein in its entirety for all purposes.

INCORPORATION BY REFERENCE OF SEQUENCE LISTING

The contents of the text file submitted electronically herewith are incorporated herein by reference in their entirety: A computer readable format copy of the Sequence Listing (filename: ABEO_002_04US_SeqList_ST25.txt, date created: Jun. 2, 2021, file size: about 556 kb).

BACKGROUND

Adeno-associated viral vectors are promising delivery vectors for gene therapy. However, their therapeutic efficacy is undermined by the vectors' delivery efficiency or limited tissue tropisms. Therefore, there is an urgent need for new AAV vectors with a better therapeutic potential.

SUMMARY

The present disclosure relates generally to the field of gene therapy and in particular, to recombinant adeno-associated viral (AAV) vector particles (also known as AAV viral vectors) with novel capsid proteins, their manufacture, and their use to deliver transgenes to treat or prevent a disease or disorder.

BRIEF DESCRIPTION OF THE DRAWINGS

FIG. 5A shows transduction spread mediated by intravitreal injection of AAV204, mostly peripheral and some foveal. FIG. 5B shows (by GFP expression) transduction of a variety of retinal cells including photoreceptors and RPE cells in primates after intravitreal injection of AAV204 virus. FIG. 5C shows massive photoreceptor and RPE transduction in the macula where most cones (photoreceptors responsible for color vision) were concentrated. FIGS. 5D-5F show expression of GFP from AAV204 driven by the VMD2 (vitelliform macular degeneration-2 promoters), which is a cell-specific promoter for the RPE. SLO imaging was performed at Day 14 (FIG. 5D) and Day 28 (FIG. 5E) after intra-vitreal injection of the $2.5\times10^{12}$ viral genomes (vg) vector. FIG. 5F shows GFP expression and nuclei (DAPI) in the periphery at Day 28.

FIG. 9 shows comparison of lung transduction using AAV204 or AAV6 (benchmark of AAV lung transduction) via intratracheal delivery.

FIG. 10C shows a comparison of CFTRΔR versus full-length codon-optimized CFTR expression with respect to membrane potential assayed by FLIPR. 293 cells were transduced with AAV204 expressing the proteins were monitored for changes in fluorescence. Baseline was read for 1 minute and then 50 μM forskolin was added to the cells.

FIGS. 11A-11C shows AAV204 ability to transduce cultivated CF patient cells (FIG. 11A), CFTRΔR expression and proper localization in cell membrane (FIG. 11B), and CFTRΔR expression restores CFTR current in human CF patient cells (FIG. 11C).

FIGS. 18A-18B shows the immunoblot (FIG. 18A) and enzymatic (FIG. 18B) analysis of recombinant hGAA expressed in HEK293 cells by transfection.

FIG. 20 shows an alignment of the VP1 amino acid sequences from AAV204 (SEQ ID NO: 2) and AAV6 (SEQ ID NO: 63).

FIG. 21 shows an alignment of the VP1 protein amino acid sequences from AAV214 (SEQ ID NO: 3); AAV214A (SEQ ID NO: 30), AAV214AB (SEQ ID NO: 84), AAV214e (SEQ ID NO: 31), AAV214e8 (SEQ ID NO: 32), AAV214e9 (SEQ ID NO: 33), AAV214e10 (SEQ ID NO: 34), ITB204_45 (SEQ ID NO: 49), AAV9 (SEQ ID NO: 71) and AAV8 (SEQ ID NO: 67).

FIG. 22 shows an alignment of the VP2 protein amino acid sequences from AAV214 (SEQ ID NO: 35); AAV214A (SEQ ID NO: 36), AAV214AB (SEQ ID NO: 85), AAV214e (SEQ ID NO: 37), AAV214e8 (SEQ ID NO: 38), AAV214e9 (SEQ ID NO: 39), AAV214e10 (SEQ ID NO: 40), ITB204_45 (SEQ ID NO: 50), AAV9 (SEQ ID NO: 72) and AAV8 (SEQ ID NO: 68).

FIG. 23 shows an alignment of VP3 protein amino acid sequences from AAV214 (SEQ ID NO: 41); AAV214A (SEQ ID NO: 42), AAV214AB (SEQ ID NO: 86), AAV214e (SEQ ID NO: 43), AAV214e8 (SEQ ID NO: 44), AAV214e9 (SEQ ID NO: 45), AAV214e10 (SEQ ID NO: 46), ITB204_45 (SEQ ID NO: 51), AAV9 (SEQ ID NO: 73) and AAV8 (SEQ ID NO: 69).

FIG. 30 shows a diagram of the VP1, VP2, and VP3 capsid proteins. The VP1- and VP2-specific portions are indicated along with the VP3 portion, which is identical to the VP3 protein produced. The amino acid sequence of AAV214 VP3 (SEQ ID NO:41) is shown and variable regions I-IX are indicated. The full VP1 protein amino acid sequence for AAV214 is provided as SEQ ID NO:3.

FIG. 31A shows Animals dosed by IM with either AAV9 or AAV214 were assayed for neutralizing antibodies against AAV9. Analysis was performed by measuring the ability of animal serum to inhibit the transduction of an AAV9.luciferase vector into the permissive cell type, Lec2. Three days post-transduction, cells were assayed for luciferase activity. Each group consisted of 2 or 3 rats for either control, AAV9 or AAV214. FIGS. 31B and 31C show cross-reactivity to AAV9 and AAV204. FIG. 31B shows the development of various AAV neutralizing antibodies after AAV9 challenge. FIG. 31C shows the development of various AAV neutralizing antibodies after AAV204 challenge.

DETAILED DESCRIPTION

Figure 1:
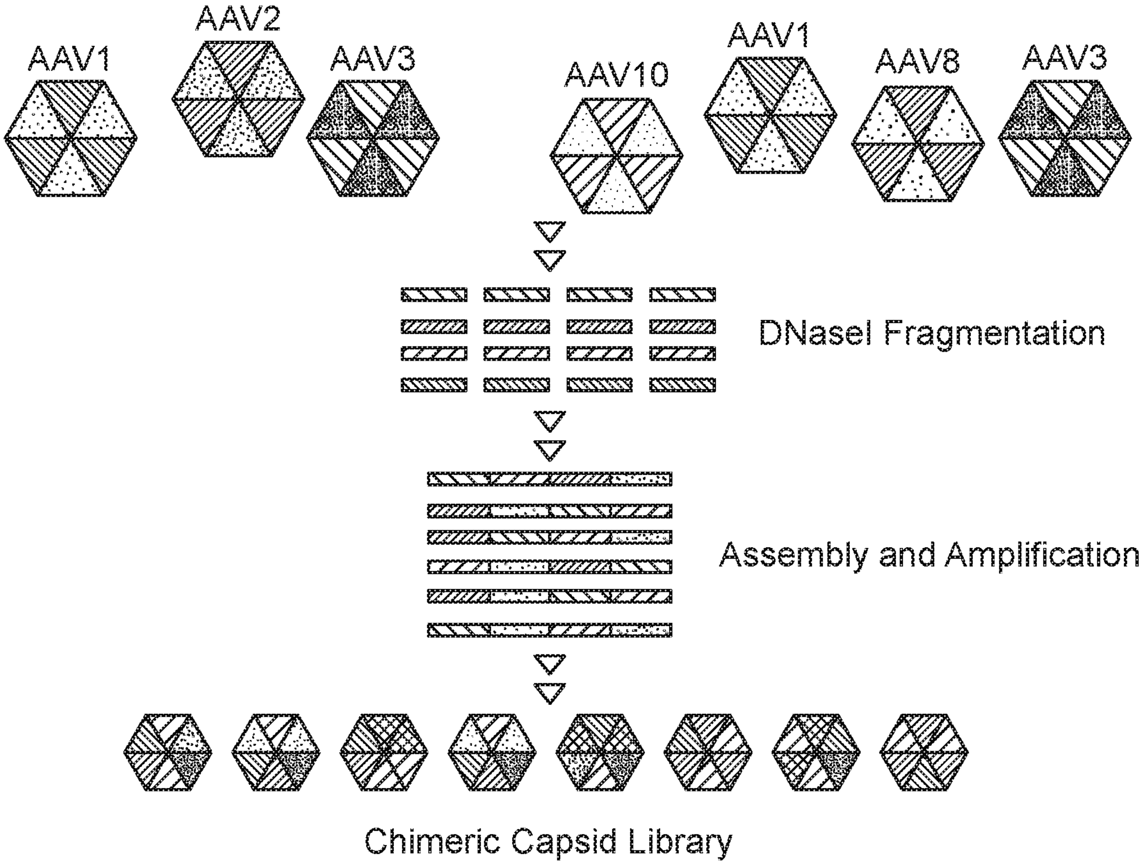
FIG. 1 Strategy for AIM capsid library construction.

Some embodiments according to the present disclosure will be described more fully hereinafter. Aspects of the disclosure may, however, be embodied in different forms and should not be construed as limited to the embodiments set forth herein. Rather, these embodiments are provided so that this disclosure will be thorough and complete, and will fully convey the scope of the invention to those skilled in the art. The terminology used in the description herein is for the purpose of describing particular embodiments only and is not intended to be limiting.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein.

Unless the context indicates otherwise, it is specifically intended that the various features of the invention described herein can be used in any combination. Moreover, the disclosure also contemplates that In embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless explicitly indicated otherwise, all specified some embodiments, features, and terms intend to include both the recited embodiment, feature, or term and biological equivalents thereof.

Incorporation by Reference

All references, articles, publications, patents, patent publications, and patent applications cited herein are incorporated by reference in their entireties for all purposes. However, mention of any reference, article, publication, patent, patent publication, and patent application cited herein is not, and should not, be taken as an acknowledgment or any form of suggestion that they constitute valid prior art or form part of the common general knowledge in any country in the world.

Definitions

The practice of the present technology will employ, unless otherwise indicated, conventional techniques of organic chemistry, pharmacology, immunology, molecular biology, microbiology, cell biology and recombinant DNA, which are within the skill of the art. See, e.g., Sambrook, Fritsch and Maniatis, Molecular Cloning: A Laboratory Manual, 2nd edition (1989); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, a Laboratory Manual, and Animal Cell Culture (RI. Freshney, ed. (1987)).

As used in the description of the invention and the appended claims, the singular forms "a," "an" and "the" are intended to include the plural forms as well, unless the context clearly indicates otherwise.

As used herein, the term "comprising" is intended to mean that the compositions and methods include the recited elements, but do not exclude others. As used herein, the transitional phrase "consisting essentially of" (and grammatical variants) is to be interpreted as encompassing the recited materials or steps and those that do not materially affect the basic and novel characteristic(s) of the recited embodiment. Thus, the term "consisting essentially of" as used herein should not be interpreted as equivalent to "comprising." "Consisting of" shall mean excluding more than trace elements of other ingredients and substantial method steps for administering the compositions disclosed herein. Aspects defined by each of these transition terms are within the scope of the present disclosure.

All numerical designations, e.g., pH, temperature, time, concentration, and molecular weight, including ranges, are approximations which are varied (+) or (−) by increments of 1.0 or 0.1, as appropriate, or, alternatively, by a variation of +/−15%, 10%, 5%, 2%. It is to be understood, although not always explicitly stated, that all numerical designations are preceded by the term "about". It also is to be understood, although not always explicitly stated, that the reagents described herein are merely exemplary and that equivalents of such are known in the art. The term "about," as used herein when referring to a measurable value such as an amount or concentration and the like, is meant to encompass variations of 20%, 10%, 5%, 1%, 0.5%, or even 0.1% of the specified amount.

The terms "acceptable," "effective," or "sufficient" when used to describe the selection of any components, ranges, dose forms, etc. disclosed herein intend that said component, range, dose form, etc. is suitable for the disclosed purpose.

Also, as used herein, "and/or" refers to and encompasses any and all possible combinations of one or more of the associated listed items, as well as the lack of combinations when interpreted in the alternative ("or").

Unless specifically recited, the term "host cell" includes a eukaryotic host cell, including, for example, fungal cells, yeast cells, higher plant cells, insect cells and mammalian cells. Non-limiting examples of eukaryotic host cells include simian, bovine, porcine, murine, rat, avian, reptilian and human, e.g., HEK293 cells and 293T cells.

The term "isolated" as used herein refers to molecules or biologicals or cellular materials being substantially free from other materials.

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising, consisting essentially of, or consisting of purine and pyrimidine bases or other natural, chemically or biochemically modified, non-natural, or derivatized nucleotide bases.

A "gene" refers to a polynucleotide containing at least one open reading frame (ORF) that is capable of encoding a particular polypeptide or protein. A "gene product" or, alternatively, a "gene expression product" refers to the amino acid sequence (e.g., peptide or polypeptide) generated when a gene is transcribed and translated.

As used herein, "expression" refers to the two-step process by which polynucleotides are transcribed into mRNA and/or the process by which the transcribed mRNA is subsequently translated into peptides, polypeptides, or proteins. If the polynucleotide is derived from genomic DNA, expression may include splicing of the mRNA in a eukaryotic cell.

"Under transcriptional control" is a term well understood in the art and indicates that transcription of a polynucleotide sequence, usually a DNA sequence, depends on its being operatively linked to an element that contributes to the initiation of, or promotes, transcription. "Operatively linked" intends that the polynucleotides are arranged in a manner that allows them to function in a cell. In one aspect, this invention provides promoters operatively linked to the downstream sequences.

The term "encode" as it is applied to polynucleotides refers to a polynucleotide which is said to "encode" a polypeptide if, in its native state or when manipulated by methods well known to those skilled in the art, it can be transcribed to produce the mRNA for the polypeptide and/or a fragment thereof. The antisense strand is the complement of such a nucleic acid, and the encoding sequence can be deduced therefrom.

The term "promoter" as used herein means a control sequence that is a region of a polynucleotide sequence at which the initiation and rate of transcription of a coding sequence, such as a gene or a transgene, are controlled. Promoters may be constitutive, inducible, repressible, or tissue-specific, for example. Promoters may contain genetic elements at which regulatory proteins and molecules such as RNA polymerase and transcription factors may bind. Non-limiting exemplary promoters include Rous sarcoma virus (RSV) LTR promoter (optionally with the RSV enhancer), a cytomegalovirus (CMV) promoter, an SV40 promoter, a dihydrofolate reductase promoter, a β-actin promoter, a phosphoglycerol kinase (PGK) promoter, a U6 promoter, an H1 promoter, a ubiquitous chicken β-actin hybrid (CBh)

promoter, a small nuclear RNA (U1a or U1b) promoter, an MeCP2 promoter, an MeP418 promoter, an MeP426 promoter, a minimal MeCP2 promoter, a VMD2 promoter, an mRho promoter or an EFI promoter.

Additional non-limiting exemplary promoters provided herein include, but are not limited to EF1a, Ubc, human β-actin, CAG, TRE, Ac5, Polyhedrin, CaMKIIa, Gal1, TEF1, GDS, ADH1, Ubi, and α-1-antitrypsin (hAAT). It is known in the art that the nucleotide sequences of such promoters may be modified in order to increase or decrease the efficiency of mRNA transcription. See, e.g., Gao et al. (2018) Mol. Ther.: Nucleic Acids 12:135-145 (modifying TATA box of 7SK, U6 and H1 promoters to abolish RNA polymerase III transcription and stimulate RNA polymerase II-dependent mRNA transcription). Synthetically-derived promoters may be used for ubiquitous or tissue specific expression. Further, virus-derived promoters, some of which are noted above, may be useful in the methods disclosed herein, e.g., CMV, HIV, adenovirus, and AAV promoters. In embodiments, the promoter is used together with an enhancer to increase the transcription efficiency. Non-limiting examples of enhancers include an interstitial retinoid-binding protein (IRBP) enhancer, an RSV enhancer or a CMV enhancer.

An enhancer is a regulatory element that increases the expression of a target sequence. A "promoter/enhancer" is a polynucleotide that contains sequences capable of providing both promoter and enhancer functions. For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter. Non-limiting examples of linked enhancer/promoter for use in the methods, compositions and constructs provided herein include a PDE promoter plus IRBP enhancer or a CMV enhancer plus U1a promoter. It is understood in the art that enhancers can operate from a distance and irrespective of their orientation relative to the location of an endogenous or heterologous promoter. It is thus further understood that an enhancer operating at a distance from a promoter is thus "operably linked" to that promoter irrespective of its location in the vector or its orientation relative to the location of the promoter.

The term "protein", "peptide" and "polypeptide" are used interchangeably and in their broadest sense to refer to a compound of two or more subunits of amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise, consist essentially of, or consist of a protein's or peptide's sequence. As used herein the term "amino acid" refers to either natural and/or unnatural or synthetic amino acids, including glycine and both the D and L optical isomers, amino acid analogs and peptidomimetics.

As used herein, the term "signal peptide" or "signal polypeptide" intends an amino acid sequence usually present at the N-terminal end of newly synthesized secretory or membrane polypeptides or proteins. It acts to direct the polypeptide to a specific cellular location, e.g. across a cell membrane, into a cell membrane, or into the nucleus. In embodiments, the signal peptide is removed following localization. Examples of signal peptides are well known in the art. Non-limiting examples are those described in U.S. Pat. Nos. 8,853,381, 5,958,736, and 8,795,965. In embodiments, the signal peptide can be an IDUA signal peptide.

The terms "equivalent" or "biological equivalent" are used interchangeably when referring to a particular molecule, biological material, or cellular material and intend those having minimal homology while still maintaining desired structure or functionality. Non-limiting examples of equivalent polypeptides include a polypeptide having at least about 60%, at least about 65%, at least about 70%, at least about 75%, at least about 80%, at least about 85%, at least about 90%, at least about 95% identity or at least about 99% identity to a reference polypeptide (for instance, a wild-type polypeptide); or a polypeptide which is encoded by a polynucleotide having at least about 70%, at least about 75%, at least about 80%, at least about 85%, at least about 90%, at least about 95% identity, at least about 97% sequence identity or at least about 99% sequence identity to the reference polynucleotide (for instance, a wild-type polynucleotide).

"Homology" or "identity" or "similarity" refers to sequence similarity between two peptides or between two nucleic acid molecules. Percent identity can be determined by comparing a position in each sequence that may be aligned for purposes of comparison. When a position in the compared sequence is occupied by the same base or amino acid, then the molecules are identical at that position. A degree of identity between sequences is a function of the number of matching positions shared by the sequences. "Unrelated" or "non-homologous" sequences share less than 40% identity, less than 25% identity, with one of the sequences of the present disclosure. Alignment and percent sequence identity may be determined for the nucleic acid or amino acid sequences provided herein by importing said nucleic acid or amino acid sequences into and using ClustalW (available at https://genome.jp/tools-bin/clustalw/). For example, the ClustalW parameters used for performing the protein sequence alignments found herein (e.g., FIGS. 20-23) were generated using the Gonnet (for protein) weight matrix. In embodiments, the ClustalW parameters used for performing nucleic acid sequence alignments using the nucleic acid sequences found herein are generated using the ClustalW (for DNA) weight matrix.

As used herein, amino acid modifications may be amino acid substitutions, amino acid deletions or amino acid insertions. Amino acid substitutions may be conservative amino acid substitutions or non-conservative amino acid substitutions. A conservative replacement (also called a conservative mutation, a conservative substitution or a conservative variation) is an amino acid replacement in a protein that changes a given amino acid to a different amino acid with similar biochemical properties (e.g., charge, hydrophobicity or size). As used herein, "conservative variations" refer to the replacement of an amino acid residue by another, biologically similar residue. Examples of conservative variations include the substitution of one hydrophobic residue such as isoleucine, valine, leucine or methionine for another; or the substitution of one charged or polar residue for another, such as the substitution of arginine for lysine, glutamic acid for aspartic acid, glutamine for asparagine, and the like. Other illustrative examples of conservative substitutions include the changes of: alanine to serine; asparagine to glutamine or histidine; aspartate to glutamate; cysteine to serine; glycine to proline; histidine to asparagine or glutamine; lysine to arginine, glutamine, or glutamate;

phenylalanine to tyrosine, serine to threonine; threonine to serine; tryptophan to tyrosine; tyrosine to tryptophan or phenylalanine; and the like.

As used herein, the term "vector" refers to a nucleic acid comprising, consisting essentially of, or consisting of an intact replicon such that the vector may be replicated when placed within a cell, for example by a process of transfection, infection, or transformation. It is understood in the art that once inside a cell, a vector may replicate as an extrachromosomal (episomal) element or may be integrated into a host cell chromosome. Vectors may include nucleic acids derived from retroviruses, adenoviruses, herpesvirus, baculoviruses, modified baculoviruses, papovaviruses, or otherwise modified naturally-occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising, consisting essentially of, or consisting of DNA condensed with cationic polymers such as heterogeneous polylysine, defined-length oligopeptides, and polyethyleneimine, in some cases contained in liposomes; and the use of ternary complexes comprising, consisting essentially of, or consisting of a virus and polylysine-DNA.

With respect to general recombinant techniques, vectors that contain both a promoter and a cloning site into which a polynucleotide can be operatively linked are well known in the art. Such vectors are capable of transcribing RNA in vitro or in vivo, and are commercially available from sources such as Agilent Technologies (Santa Clara, Calif) and Promega Biotech (Madison, Wis.). In order to optimize expression and/or in vitro transcription, it may be necessary to remove, add or alter 5' and/or 3' untranslated portions of cloned transgenes to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

A "viral vector" is defined as a recombinantly produced virus or viral particle that contains a polynucleotide to be delivered into a host cell, either in vivo, ex vivo or in vitro. Examples of viral vectors include retroviral vectors, AAV vectors, lentiviral vectors, adenovirus vectors, alphavirus vectors and the like. Alphavirus vectors, such as Semliki Forest virus-based vectors and Sindbis virus-based vectors, have also been developed for use in gene therapy and immunotherapy. See, e.g., Schlesinger and Dubensky (1999) Curr. Opin. Biotechnol. 5:434-439 and Ying, et al. (1999) Nat. Med. 5(7):823-827.

As used herein, the term "recombinant expression system" or "recombinant vector" refers to a genetic construct or constructs for the expression of certain genetic material formed by recombination.

A "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; polypeptides; polysaccharides; lipopolysaccharides; artificial viral envelopes; metal particles; bacteria; viruses, such as baculoviruses, adenoviruses and retroviruses; bacteriophage, cosmid, plasmid, and fungal vectors; and other recombination vehicles typically used in the art which have been described for expression in a variety of eukaryotic and prokaryotic hosts, and may be used for gene therapy as well as for simple protein expression. Liposomes that also comprise, consist essentially of, or consist of a targeting antibody or fragment thereof can be used in the methods disclosed herein. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins disclosed herein are other non-limiting techniques.

A polynucleotide disclosed herein can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "plasmid" is a DNA molecule that is typically separate from and capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or, alternatively, the proteins produced may act as toxins under similar circumstances. It is known in the art that while plasmid vectors often exist as extrachromosomal circular DNA molecules, plasmid vectors may also be designed to be stably integrated into a host chromosome either randomly or in a targeted manner, and such integration may be accomplished using either a circular plasmid or a plasmid that has been linearized prior to introduction into the host cell.

"Plasmids" used in genetic engineering are called "plasmid vectors". Many plasmids are commercially available for such uses. The gene to be replicated is inserted into copies of a plasmid containing genes that make cells resistant to particular antibiotics, and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria or eukaryotic cells containing a plasmid harboring the gene of interest, which can be induced to produce large amounts of proteins from the inserted gene.

In aspects where gene transfer is mediated by a DNA viral vector, such as an adenovirus (Ad) or adeno-associated virus (AAV), a vector construct refers to the polynucleotide comprising, consisting essentially of, or consisting of the viral genome or part thereof, and a transgene.

The term "adeno-associated virus" or "AAV" as used herein refers to a member of the class of viruses associated with this name and belonging to the genus Dependoparvovirus, family Parvoviridae. Adeno-associated virus is a single-stranded DNA virus that grows only in cells in which certain functions are provided by a co-infecting helper virus. General information and reviews of AAV can be found in, for example, Carter, 1989, Handbook of Parvoviruses, Vol. 1, pp. 169-228, and Berns, 1990, Virology, pp. 1743-1764, Raven Press, (New York). It is fully expected that the same principles described in these reviews will be applicable to additional AAV serotypes characterized after the publication dates of the reviews because it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3: 1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control. Multiple serotypes of this virus are known to be suitable for gene delivery; all known serotypes can infect cells from various tissue types. At least 11 sequentially numbered AAV serotypes are known in the art. Non-limiting exemplary serotypes useful in the methods disclosed herein include any of the 11 serotypes, e.g., AAV2, AAV8, AAV9, or variant serotypes, e.g., AAV-DJ and AAV PHP.B. The AAV particle comprises, consists essentially of, or consists of three major viral proteins: VP1, VP2 and VP3. In embodiments, the AAV refers to the serotype AAV1, AAV2, AAV4, AAV5, AAV6, AAV7, AAV8, AAV9, AAV10, AAV11, AAV12, AAV13, AAVPHP.B, or AAVrh74.

An "AAV vector" as used herein refers to a vector comprising, consisting essentially of, or consisting of one or more heterologous nucleic acid (HNA) sequences and one or more AAV inverted terminal repeat sequences (ITRs). Such AAV vectors can be replicated and packaged into infectious viral particles when present in a host cell that provides the functionality of rep and cap gene products; for example, by transfection of the host cell. In embodiments, AAV vectors contain a promoter, at least one nucleic acid that may encode at least one protein or RNA, and/or an enhancer and/or a terminator within the flanking ITRs that is packaged into the infectious AAV particle. The encapsidated nucleic acid portion may be referred to as the AAV vector genome. Plasmids containing AAV vector may also contain elements for manufacturing purposes, e.g., antibiotic resistance genes, etc., but these are not encapsidated and thus do not form part of the AAV particle.

As used herein, the term "viral capsid" or "capsid" refers to the proteinaceous shell or coat of a viral particle. Capsids function to encapsidate, protect, transport, and release into the host cell a viral genome. Capsids are generally comprised of oligomeric structural subunits of protein ("capsid proteins"). As used herein, the term "encapsidated" means enclosed within a viral capsid. The viral capsid of AAV is composed of a mixture of three viral capsid proteins: VP1, VP2, and VP3. The mixture of VP1, VP2 and VP3 contains 60 monomers that are arranged in a T=1 icosahedral symmetry in a ratio of 1:1:10 (VP1:VP2:VP3) or 1:1:20 (VP1:VP2:VP3) as described in Sonntag F et al., (June 2010). "A viral assembly factor promotes AAV2 capsid formation in the nucleolus". Proceedings of the National Academy of Sciences of the United States of America. 107 (22): 10220-5, and Rabinowitz J E, Samulski R J (December 2000). "Building a better vector: the manipulation of AAV virions". Virology. 278 (2): 301-8, each of which is incorporated herein by reference in its entirety.

An "AAV virion" or "AAV viral particle" or "AAV viral vector" or "AAV vector particle" or "AAV particle" refers to a viral particle composed of at least one AAV capsid protein and an encapsidated polynucleotide AAV vector. Thus, production of AAV vector particle necessarily includes production of AAV vector, as such a vector is contained within an AAV vector particle.

As used herein, the term "helper" in reference to a virus or plasmid refers to a virus or plasmid used to provide the additional components necessary for replication and packaging of any one of the AAV vectors disclosed herein. The components encoded by a helper virus may include any genes required for virion assembly, encapsidation, genome replication, and/or packaging. For example, the helper virus or plasmid may encode necessary enzymes for the replication of the viral genome. Non-limiting examples of helper viruses and plasmids suitable for use with AAV constructs include pHELP (plasmid), adenovirus (virus), or herpesvirus (virus). In embodiments, the pHELP plasmid may be the pHELPK plasmid, wherein the ampicillin expression cassette is exchanged with a kanamycin expression cassette; pHELPK has the sequence shown in SEQ ID NO: 92.

As used herein, a packaging cell (or a helper cell) is a cell used to produce viral vectors. Producing recombinant AAV viral vectors requires Rep and Cap proteins provided in trans as well as gene sequences from Adenovirus that help AAV replicate. In some aspects, Packaging/helper cells contain a plasmid is stably incorporated into the genome of the cell. In other aspects, the packaging cell may be transiently transfected. Typically, a packaging cell is a eukaryotic cell, such as a mammalian cell or an insect cell.

As used herein, a reporter protein is a detectable protein that is operably linked to a promoter to assay the expression (for example, tissue specificity and/or strength) of the promoter. In aspects, a reporter protein may be operably linked to a polypeptide. In aspects, reporter proteins may be used in monitoring DNA delivery methods, functional identification and characterization of promoter and enhancer elements, translation and transcription regulation, mRNA processing and protein:protein interactions. Non-limiting examples of a reporter protein are β-galactosidase; a fluorescent protein, such as, Green Fluorescent Protein (GFP) or Red Fluorescent Protein (RFP); luciferase; glutathione S-transferase; and maltose binding protein.

A "composition" is intended to mean a combination of active polypeptide, polynucleotide or antibody, and another compound or composition, inert (e.g., a detectable label) or active (e.g., a gene delivery vehicle).

A "pharmaceutical composition" is intended to include the combination of an active polypeptide, polynucleotide or antibody with a carrier, inert or active such as a solid support, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

A "subject" of diagnosis or treatment is a cell or an animal such as a mammal, or a human. A subject is not limited to a specific species and includes non-human animals subject to diagnosis or treatment and those subject to infections or animal models, including, without limitation, simian, murine, rat, canine, or leporid species, as well as other livestock, sport animals, or pets. In embodiments, the subject is a human.

The term "tissue" is used herein to refer to tissue of a living or deceased organism or any tissue derived from or designed to mimic a living or deceased organism. The tissue may be healthy, diseased, and/or have genetic mutations. The biological tissue may include any single tissue (e.g., a collection of cells that may be interconnected), or a group of tissues making up an organ or part or region of the body of an organism. The tissue may comprise, consist essentially of, or consist of a homogeneous cellular material or it may be a composite structure such as that found in regions of the body including the thorax which for instance can include lung tissue, skeletal tissue, and/or muscle tissue. Exemplary tissues include, but are not limited to those derived from liver, lung, thyroid, skin, pancreas, blood vessels, bladder, kidneys, brain, biliary tree, duodenum, abdominal aorta, iliac vein, heart and intestines, including any combination thereof.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

As used herein the term "effective amount" intends to mean a quantity sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of gene therapy, In embodiments the effective amount is the amount sufficient to result in regaining part or full function of a gene that is deficient in a subject. In other some embodiments, the effective amount of an AAV viral particle is the amount sufficient to result in expression of a gene in a subject. In embodiments, the effective amount is the amount required to increase galactose metabolism in a subject in need thereof. The skilled artisan will be able to determine appropriate amounts depending on these and other factors.

In embodiments, the effective amount will depend on the size and nature of the application in question. It will also depend on the nature and sensitivity of the target subject and the methods in use. The skilled artisan will be able to determine the effective amount based on these and other considerations. The effective amount may comprise, consist essentially of, or consist of one or more administrations of a composition depending on the embodiment.

As used herein, the term "administer" or "administration" intends to mean delivery of a substance to a subject such as an animal or human. Administration can be effected in one dose, continuously or intermittently throughout the course of treatment. Methods of determining the most effective means and dosage of administration are known to those of skill in the art and will vary with the composition used for therapy, the purpose of the therapy, as well as the age, health or gender of the subject being treated. Single or multiple administrations can be carried out with the dose level and pattern being selected by the treating physician or in the case of pets and other animals, treating veterinarian.

AAV Structure and Function

AAV is a replication-deficient parvovirus, the single-stranded DNA genome of which is about 4.7 kb in length, including two 145-nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_001862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). The sequence of the AAV rh.74 genome is provided in U.S. Pat. No. 9,434,928, incorporated herein by reference in its entirety. U.S. Pat. No. 9,434,928 also provide the sequences of the capsid proteins and a self-complementary genome. In one aspect, the genome is a self-complementary genome. Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome.

The cap gene is expressed from the p40 promoter and encodes the three capsid proteins, VP1, VP2, and VP3. Alternative splicing and non-consensus translational start sites are responsible for the production of the three related capsid proteins. More specifically, after the single mRNA from which each of the VP1, VP2 and VP3 proteins are translated is transcribed, it can be spliced in two different manners: either a longer or shorter intron can be excised, resulting in the formation of two pools of mRNAs: a 2.3 kb- and a 2.6 kb-long mRNA pool. The longer intron is often preferred and thus the 2.3-kb-long mRNA can be called the major splice variant. This form lacks the first AUG codon, from which the synthesis of VP1 protein starts, resulting in a reduced overall level of VP1 protein synthesis. The first AUG codon that remains in the major splice variant is the initiation codon for the VP3 protein. However, upstream of that codon in the same open reading frame lies an ACG sequence (encoding threonine) which is surrounded by an optimal Kozak (translation initiation) context. This contributes to a low level of synthesis of the VP2 protein, which is actually the VP3 protein with additional N terminal residues, as is VP1, as described in Becerra S P et al., (December 1985). "Direct mapping of adeno-associated virus capsid proteins B and C: a possible ACG initiation codon". Proceedings of the National Academy of Sciences of the United States of America. 82 (23): 7919-23, Cassinotti P et al., (November 1988). "Organization of the adeno-associated virus (AAV) capsid gene: mapping of a minor spliced mRNA coding for virus capsid protein 1". Virology. 167 (1): 176-84, Muralidhar S et al., (January 1994). "Site-directed mutagenesis of adeno-associated virus type 2 structural protein initiation codons: effects on regulation of synthesis and biological activity". Journal of Virology. 68 (1): 170-6, and Trempe J P, Carter B J (September 1988). "Alternate mRNA splicing is required for synthesis of adeno-associated virus VP1 capsid protein". Journal of Virology. 62 (9): 3356-63, each of which is herein incorporated by reference. A single consensus poly-A site is located at map position 95 of the AAV genome. The life cycle and genetics of AAV are reviewed in Muzyczka, Current Topics in Microbiology and Immunology, 158: 97-129 (1992).

Each VP1 protein contains a VP1 portion, a VP2 portion and a VP3 portion. The VP1 portion is the N-terminal portion of the VP1 protein that is unique to the VP1 protein. The VP2 portion is the amino acid sequence present within the VP1 protein that is also found in the N-terminal portion of the VP2 protein. The VP3 portion and the VP3 protein have the same sequence. The VP3 portion is the C-terminal portion of the VP1 protein that is shared with the VP1 and VP2 proteins. See FIG. 30.

The VP3 protein can be further divided into discrete variable surface regions I-IX (VR-I-IX). Each of the variable surface regions (VRs) can comprise or contain specific amino acid sequences that either alone or in combination with the specific amino acid sequences of each of the other VRs can confer unique infection phenotypes (e.g., decreased antigenicity, improved transduction and/or tissue-specific tropism relative to other AAV serotypes) to a particular serotype as described in DiMatta et al., "Structural Insight into the Unique Properties of Adeno-Associated Virus Serotype 9" J. Virol., Vol. 86 (12): 6947-6958, June 2012, the contents of which are incorporated herein by reference.

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA to generate AAV vectors. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., Hum Gene Ther, 8: 659-669 (1997); Kessler et al., Proc Nat. Acad Sc. USA, 93: 14082-14087 (1996); and Xiao et al., J Virol, 70: 8098-8108 (1996). See also, Chao et al., Mol Ther, 2:619-623 (2000) and Chao et al., Mol Ther, 4:217-222 (2001). Moreover, because muscle is highly vascularized, recombinant AAV transduction has resulted in the appearance of transgene products in the systemic circulation following intramuscular injection as described in Herzog et al., Proc Natl Acad Sci USA, 94: 5804-5809 (1997) and Murphy et al., Proc Natl Acad Sci USA, 94: 13921-13926 (1997). Moreover, Lewis et al., J Virol, 76: 8769-8775 (2002) demonstrated that skeletal myofibers possess the necessary cellular factors for correct antibody glycosylation, folding, and secretion, indicating that muscle is capable of stable expression of secreted protein therapeutics. Recombinant AAV (rAAV) genomes of the invention comprise, consist essentially of, or consist of a nucleic acid molecule encoding a therapeutic protein (e.g., CFTR) and one or more AAV ITRs flanking the nucleic acid molecule. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13, AAV PHP.B and AAV rh74. Production of pseudotyped rAAV is disclosed in, for example, WO2001083692. Other types of rAAV variants, for example rAAV with capsid mutations, are also contemplated. See, e.g., Marsic et al., Molecular Therapy, 22(11): 1900-1909 (2014). The nucleotide sequences of the genomes of various AAV serotypes are known in the art.

AAV Vector Particles, Capsid Proteins, and AAV Vectors

Provided herein are AAV vector particles, AAV Vectors, and capsid proteins that have desirable tissue specificity and find use in delivering a variety of therapeutic payloads, including nucleic acids, and proteins useful in the treatment of disease.

AAV Capsid Proteins

The disclosure provides AAV particles possessing properties of high gene transfer efficiency and increased tissue tropism. AAV vector delivery currently relies on the use of serotype selection for tissue targeting based on the natural tropism of the virus or by the direct injection into target tissues. If systemic delivery is required to achieve maximal therapeutic benefit, then serotype selection is the only available option for tissue targeting combined with tissue specific promoters. Many currently available AAV vectors are thus suboptimal for gene therapy.

The present disclosure provides AAV capsid protein sequences that confer high gene transfer efficiency and increased tissue specificity on the AAV capsids comprising them. In embodiments, the AAV capsid sequences provided herein were generated using the AAV capsid generating platform shown in FIG. 1.

In embodiments, the VP1 capsid protein comprises any one of the amino acid sequences listed in Table 1, or a sequence having up to 1, 2, 3, 4, 5, 6, 7, 8, 9, or 10 amino acids mutated, deleted or added as compared to, any one of the amino acid sequence listed in Table 1. In aspects, up to 20 amino acids, up to 30 amino acids, or up to 40 amino acids may be mutated, deleted or added compared to these sequences, In embodiments, the VP1 capsid protein is encoded by any one of the nucleic acid sequences listed in Table 1, or a sequence having up to 5, up to 10, up to 30, or up to 60 nucleotide changes to any one of the nucleic acid sequences listed in Table 1.

TABLE 1

VP1 Capsid Proteins

| Amino Acid SEQ ID NO: | NA SEQ ID NO: | AAV Capsid Name |
|---|---|---|
| 1 | 98 | AAV 110 |
| 2 | 15 | AAV 204 |
| 3 | 18 | AAV 214 |
| 30 | 19 | AAV 214A |
| 31 | 20 | AAV 214e |
| 32 | 21 | AAV 214e8 |
| 33 | 22 | AAV 214e9 |
| 34 | 23 | AAV 214e0 |
| 49 | 47 | AAV ITB102_45 |
| 84 | 82 | AAV 214AB |

In embodiments, the AAV VP1 protein comprises, consists essentially of, or consists of an amino acid sequence of SEQ ID NOs: 1-3, 30-34, 49 or 84, or a sequence having up to 1, 2, 3, 4, 5, 6, 7, 8, 9, or 10 amino acids different from SEQ ID NOs: 1-3, 30-34, 49 or 84. Also provided are polynucleotides encoding these VP1 proteins. In embodiments, the polynucleotides encoding the VP1 proteins comprise, consist essentially of, or consist of the sequence of SEQ ID NOs: 15, 18-23, 47, 82, and 98 or a sequence having up to 5, up to 10, or up to 30 nucleotide changes to SEQ ID NOs: 15, 18-23, 47, 82, and 98.

In embodiments, the AAV capsid sequence is an AAV-110 capsid protein (SEQ ID NO: 1), AAV204 capsid protein (SEQ ID NO: 2), AAV214 capsid protein (SEQ ID NO: 3) or AAV ITB102_45 capsid protein (SEQ ID NO: 49). In embodiments, the AAV capsid protein is a variant of the AAV214 capsid protein. In embodiments, the AAV capsid protein is AAV214A (SEQ ID NO: 30), AAV-214-AB (SEQ ID NO: 84), AAV214e (SEQ ID NO: 31), AAV214e8 (SEQ ID NO: 32), AAV214e9 (SEQ ID NO: 33) or AAV214e10 (SEQ ID NO: 34).

Sequences for exemplary VP2 and VP3 proteins are provided in Table 2 and Table 3. Given the VP2 and VP3 sequences, the VP1 portions may be determined by alignment with the full, VP1 protein sequence.

TABLE 2

VP2 Capsid Proteins

| Amino Acid SEQ ID NO: | Name |
|---|---|
| 35 | 214 |
| 36 | 214A |
| 37 | 214e |
| 38 | 214e8 |
| 39 | 214e9 |
| 40 | 214e10 |
| 85 | 214AB |
| 50 | ITB102_45 |

An exemplary nucleic acid for ITB102_45 is SEQ ID NO:47. Exemplary nucleic acids for the other capsid VP2 portions may be derived from the corresponding portions of the VP1 capsid protein nucleic acids.

TABLE 3

VP3 Capsid proteins

| Amino Acid SEQ ID NO: | NA SEQ ID NO: | AAV Capsid Name |
|---|---|---|
| 17 | 16 | 204 |
| 41 | 24 | 214 |
| 42 | 25 | 214A |
| 43 | 26 | 214e |
| 44 | 27 | 214e8 |
| 45 | 28 | 214e9 |
| 46 | 29 | 214e10 |
| 86 | 83 | 214AB |
| 51 | 48 | ITB102_45 |

The VP3 proteins of AAV214, AAV214e, AAV214e8, AAV214e9, AAV214e10 have the same amino acid (SEQ ID NO:41) and nucleic acid (SEQ ID NO: 24) sequences.

In embodiments, the AAV VP2 proteins comprise, consist essentially of, or consist of an amino acid sequence of any one of SEQ ID NOs: 35-40, 50 or 85, or a sequence having up to 1, 2, 3, 4, 5, 6, 7, 8, 9, or 10 amino acids different from SEQ ID NOs: 35-40, 50 or 85. Also provided are polynucleotides encoding these VP2 proteins. In embodiments, the polynucleotide encoding the VP2 protein comprises, consists essentially of, or consists of the sequence of SEQ ID NO: 47, or a sequence having up to 5, up to 10, or up to 30 nucleotide changes to SEQ ID NOs: 47.

In embodiments, the AAV VP3 proteins comprise, consist essentially of, or consist of an amino acid sequence of SEQ ID NOs: 17, 41-46, 51, or 86, or a sequence having up to 1, 2, 3, 4, 5, 6, 7, 8, 9, or 10 amino acids different from SEQ ID NOs: 17, 41-46, 51, or 86. Also provided are polynucleotides encoding these VP3 proteins. In embodiments, the polynucleotides encoding the proteins that comprise, consist essentially of, or consist of the sequence of SEQ ID NOs: 16, 24-29, 48 and 83, or a sequence having up to 5, up to 10, or up to 30 nucleotide changes to SEQ ID NOs: 16, 24-29, 48 and 83.

In embodiments, the AAV capsid protein is a chimeric protein. In embodiments, a VP1, VP2, or VP3 portion of the AAV capsid protein disclosed herein may be replaced with a VP1, VP2, or VP3 portion from a different AAV capsid protein disclosed herein.

In embodiments, provided herein is an AAV capsid protein comprising a leucine residue at amino acid 129, an asparagine residue at amino acid 586 and a glutamic acid residue at amino acid 723, wherein amino acid positions in the AAV capsid protein are numbered with respect to amino acid positions in the amino acid sequence of SEQ ID NO: 2. In some cases, the protein comprises the amino acid sequence of SEQ ID NO: 2. In other cases, these amino acids may be introduced into other capsid proteins.

In embodiments, provided herein is an AAV VP1 capsid protein comprising a VP1 portion, a VP2 portion and a VP3 portion, wherein the VP1 portion comprises a leucine (L) residue at amino acid 129, wherein the VP2 portion comprises a threonine (T) or asparagine (N) residue at amino acid 157 and a lysine (K) or serine (S) residue at amino acid 162, and wherein the VP3 portion comprises asparagine (N) residue at amino acid 223, an alanine (A) residue at amino acid 224, a histidine (H) residue at amino acid 272, a threonine (T) residue at amino acid 410, a histidine (H) residue at amino acid 724 and a proline (P) residue at amino acid 734, wherein amino acid positions in the AAV capsid protein are numbered with respect to amino acid positions in the amino acid sequence of SEQ ID NO: 3 (i.e., VP1 capsid subunit numbering).

In embodiments, the VP1 portion further comprises an aspartic acid (D) or alanine (A) residue at amino acid 24, wherein amino acid positions in the AAV capsid protein are numbered with respect to amino acid positions in the amino acid sequence of SEQ ID NO: 3. In embodiments, the VP2 portion further comprises one or more of (i) a proline (P) residue at amino acid 148; (ii) an arginine (R) residue inserted at amino acid 152; (iii) an arginine (R) residue at amino acid 168; (iv) an isoleucine (I) residue at amino acid 189; and (v) a serine (S) residue at amino acid 200, wherein amino acid positions in the AAV capsid protein are numbered with respect to amino acid positions in the amino acid sequence of SEQ ID NO: 3.

In embodiments, one or more variable regions I through IX (see FIG. 30) in the disclosed VP3 portion capsid proteins may be removed and replaced with alternative regions. Suitable alternatives are identified in the table below. The location for these, as well as the identity of additional alternatives may be identified by alignment to SEQ ID NO:41 as shown in FIG. 30. In embodiments, one or more VRs may have an insertion of 1, 2 or 3 amino acids. In embodiments, one or more VRs may have a deletion of 1, 2 or 3 amino acids.

| VR | Sequence |
|---|---|
| I | SASTGAS (SEQ ID NO. 52);<br>NSTSGGSS (SEQ ID NO. 53);<br>SSTSGGSS (SEQ ID NO: 87) |
| II | DNNGVK (SEQ ID NO. 54) |
| III | NDGS (SEQ ID NO. 55) |
| IV | INGSGQNQQT (SEQ ID NO. 56) |
| VI | RVSTTTGQNNNSNFAWTA (SEQ ID NO. 57) |
| VII | HKEGEDRFFPLSG (SEQ ID NO. 58); |
| VIII | ADNLQQQNTAPQI (SEQ ID NO. 60); |
| IX | NYYKSTSVDF (SEQ ID NO. 61). |

The disclosure provides nucleic acids encoding any one of the AAV capsid proteins disclosed herein. The disclosure also provides vectors comprising any one of the nucleic acids disclosed herein.

In embodiments, AAV is an AAV9 serotype. Alternative serotypes or modified capsid viruses can be used to optimize neuronal tropism. Alternative vectors include: a modified AAV9 serotype vector for higher neuronal tropism than standard AAV9, e.g., PHP.B that uses a Cre-lox recombination system to identify neuronally targeted vectors. Alternatively, the AAV9 PHP.B has a modified amino acid 498 of VP1 from asparagine to lysine to reduce the liver tropism. Further variants of AAVrh74 that have mutated several amino acids can be used for very broad tissue tropism including the brain.

AA V Vectors

The AAV vectors supply the nucleic acid that becomes encapsidated into the AAV vector particle including element (s) involved in controlling expression of the nucleic acids in the subject, as well as the ITRs to facilitate encapsidation. In embodiments, the AAV vectors disclosed herein comprise at least one heterologous nucleic acid (HNA) sequence, which, when expressed in a cell of a subject, is effective to treat a disease or disorder. In embodiments, the HNA sequence comprises a transgene. In embodiments, the AAV vectors comprise at least one ITR sequence and at least one transgene. In embodiments, the transgene encodes a therapeutic protein or a therapeutic RNA.

In embodiments, control of transgene expression in the host cell may be regulated by regulatory elements contained within the AAV vector, including promoter sequences, and poly-A sites. In embodiments, the AAV vector may also encode a signal peptide. In embodiments, the AAV vectors have 5' and 3' inverted terminal repeats (ITRs). The 5' ITR is located upstream of a promoter, which in turn is upstream of the transgene. In embodiments, the 5' and 3' ITR have the same sequence. In embodiments, they have a different sequence. In embodiments, an AAV vector of the disclosure may comprise, in 5' to 3' orientation, a first (5') ITR, a promoter, a transgene, a poly-A site, and a second (3') ITR.

In embodiments, the AAV vector has the nucleotide sequence shown in SEQ ID NO: 88 (pA_CF1), SEQ ID NO: 89 (pA_CF3), SEQ ID NO: 90 (pA_CF5), or SEQ ID NO: 91 (pA_CF7). These vectors contain the following components:

| Plasmid name | Promoter | Intron | Kozak | Signal Peptide | CFTRΔR |
|---|---|---|---|---|---|
| pA-CF1 | U1a | none | Full | none | CFTRΔR Codon optimized |
| pA-CF3 | U1a | none | Full | none | CFTRΔR codon optimized |
| pA-CF5 | H1 mut. | none | Full | none | CFTRΔR Codon optimized |
| pA-CF7 | H1 mut. | none | Full | none | CFTR Codon optimized (full size) |

In embodiments, the HNA (for example, an HNA comprising a transgene) is operably linked to a constitutive promoter. The constitutive promoter can be any constitutive promoter known in the art and/or provided herein. In embodiments, the constitutive promoter comprises, consists essentially of, or consists of a Rous sarcoma virus (RSV) LTR promoter (optionally with the RSV enhancer), a cytomegalovirus (CMV) promoter, an SV40 promoter, a dihydrofolate reductase promoter, a beta-actin promoter, a phosphoglycerol kinase (PGK) promoter, a U6 promoter, an H1 promoter, a hybrid chicken beta actin promoter, a MeCP2 promotor, an H1 promoter, a U1a promoter, a mMeP418 promoter, a mMeP426 promoter, a minimal MeCP2 promoter, a CAG promoter, or an EF1 promoter. It is known in the art that the nucleotide sequences of such promoters may be modified in order to increase or decrease the efficiency of mRNA transcription. See, e.g., Gao et al. (2018) Mol. Ther.: Nucleic Acids 12:135-145 (modifying TATA box of 7SK, U6 and H1 promoters to abolish RNA polymerase III transcription and stimulate RNA polymerase II-dependent mRNA transcription). In embodiments, the HNA sequence is operably linked to a tissue-specific control promoter, or an inducible promoter. In embodiments, the tissue-specific control promoter is a central nervous system (CNS) cell-specific promoter, a lung-specific promoter, a skin-specific promoter, a muscle-specific promoter, a liver-specific promoter, an eye-specific promoter (e.g., a VMD2, or mRho promoter).

In embodiments, the promoter may comprise, consist essentially of or consist of a polynucleotide having the sequence of SEQ ID NO: 96 (mouse U1 promoter) or a SEQ ID NO: 97 (a H1 promoter). In embodiments, the promoter is an U1a or U1b promoter, EF1 promoter, or CBA (chicken beta-actin). In embodiments, the promoter may comprise, consist essentially of or consist of any one of the nucleic acid sequences listed in Table 5, or a sequence having up to 5, up to 10, or up to 30 nucleotide changes to any one of the nucleic acid sequences listed in Table 5.

TABLE 5

| Promoter name | Nucleic acid SEQ ID No. |
|---|---|
| Mouse U1a promoter | 152 |
| Polymerase III H1 mutant promoter | 153 |
| Chicken β-actin hybrid promoter CBh (CBh promoter consists of CMV enhancer, CBA promoter, first CBA exon and partial intron) | 154 |
| MeCP2 min promoter sequence | 155 |
| MeCP2 promoter sequence | 156 |
| MeCP418 promoter sequence | 157 |
| MeCP426 promoter sequence | 158 |
| VMD2 promoter | 159 |
| PDE6b promoter | 160 |
| mRho promoter | 161 |
| CMV promoter | 162 |
| UbC promoter | 163 |

In embodiments, the HNA sequence is operably liked to an additional regulatory element. The additional regulatory element can be a woodchuck hepatitis virus post-transcriptional regulatory element ("WPRE"). In embodiments, AAV vectors may comprise regulatory components suitable for growth and culture of the vector in a bacterial host for vector production purposes. For example, the vector may comprise genes for antibiotic resistance, and maintenance of the plasmid in bacteria, as well as associated regulatory elements to control protein expression in bacteria.

In embodiments, the HNA sequence is operably linked to a poly-A site. The polyadenylation site comprises, consists essentially of or consists of an MeCP2 poly-A site, a retinol dehydrogenase 1 (RDH1) poly-A site, a bovine growth hormone (BGH) poly-A site, an SV40 poly-A site, a SPA49 poly-A site, a sNRP-TK65 poly-A site, a sNRP poly-A site, or a TK65 poly-A site. An exemplary SPA49 poly-A sequence is described in Ostedgaard et al., Proc. Nat'l Acad. Sci. USA (Feb. 22, 2005) 102:2952-2957, incorporated herein by reference.

Heterologous Nucleic Acids (HNA)

The AAV vectors disclosed herein infect and deliver one or more heterologous nucleic acids (HNA) to target tissues. In embodiments, the HNA sequences are transcribed and optionally, translated in the cells of the target tissue.

In some cases, the HNA encodes an antisense RNA, microRNA, siRNA, or guide RNA (gRNA). CRISPR technology has been used to target the genome of living cells for modification. Cas9 protein is a large enzyme that must be delivered efficiently to target tissues and cells to mediate gene repair through the CRISPR system and current CRISPR/Cas9 gene correction protocols suffer from a number of drawbacks. Long-term expression of Cas9 can elicit host immune responses. An additional guide RNA may be delivered via a separate vector due to packaging constraints. In embodiments, the HNA encodes a Cas9 protein or an equivalent thereof.

In embodiments, the HNA comprises a transgene encoding a protein, which may be expressed in cells of a subject to treat a disease or a disorder, resulting from reduced or eliminated activity of the native protein. Thus, in embodiments, the transgene may encode a protein selected from cystic fibrosis transmembrane conductance regulator (CFTR), N-acetyl-alpha-glucosaminidase (NAGLU), N-sulfoglucosamine sulfohydrolase (SGSH), palmitoyl-protein thioesterase 1 (PPT1), survival of motor neuron 1, telomeric (SMN1), alkaline phosphatase, biomineralization associated (ALPL, also known as TNALP), glial cell derived neurotrophic factor (GDNF), glucosylceramidase beta (GBA1), iduronidase alpha-L-(IDUA), cytochrome P450 family 4 subfamily V member 2 (CYP4V2), retinoschisin 1 (RS1), phosphodiesterase 6B (PDE6B), methyl-CpG binding protein 2 (MeCP2), rhodopsin (Rho), or ceroid lipofuscinosis, neuronal, 1 (CLN1).

In embodiments, the transgene encodes a CFTR. In embodiments, the CFTR comprises a mutant sequence, a codon-optimized sequence, and/or a truncated sequence of CFTR. Exemplary suitable CFTR sequences are disclosed in U.S. Patent Pub. No. 20110035819, which is incorporated herein by reference in its entirety. In embodiments, the CFTR comprises a deletion of amino acids 708-759 ("CFTRΔR"). See Ostedgaard et al., Proc. Nat'l Acad. Sci. USA (Feb. 22, 2005) 102:2952-2957, incorporated herein by reference in its entirety.

In embodiments, a transgene comprises, consists essentially of, or consists of a nucleic acid having the sequence of SEQ ID NO: 4 (a codon-optimized CFTRΔR) or SEQ ID NO: 93 (full-length codon optimized CFTR), or a sequence having up to 5, up to 10, or up to 30 nucleotide changes to SEQ ID No. 4 or 93. In embodiments, the transgene encodes a protein that comprises, consists essentially of, or consists of an amino acid having the sequence of SEQ ID NO: 95 (a CFTRΔR) or SEQ IS NO: 94 (full-length CFTR), or a sequence having up to 1, 2, 3, 4, 5, 6, 7, 8, 9, or 10 amino acids different from SEQ ID NO: 94 or 95.

In embodiments, the transgene encodes a CLN3 lysosomal/endosomal transmembrane protein, battenin (CLN3) protein, alpha-galactosidase A (GLA), or acid alpha-glucosidase (GAA).

In embodiments, the GAA protein is encoded by a nucleotide sequence of SEQ ID NOs: 5, 6 or 7, or a sequence having up to 5, up to 10, or up to 30 nucleotide changes to SEQ ID Nos. 5, 6, or 7. In embodiments, the GAA protein comprises an amino acid sequence of SEQ ID NO: 8, or a sequence having up to 1, 2, 3, 4, 5, 6, 7, 8, 9, or 10 amino acids different from SEQ ID NO. 8.

In embodiments, the GLA protein is encoded by a nucleotide sequence SEQ ID NO: 9 or 10, or a sequence having up to 5, up to 10, or up to 30 nucleotide changes to SEQ ID No. 9 or 10. In embodiments, the GLA protein comprises an amino acid sequence of SEQ ID NO: 11, or a sequence having up to 1, 2, 3, 4, 5, 6, 7, 8, 9, or 10 amino acids different from SEQ ID No. 11.

In embodiments, the CLN3 protein is encoded by a nucleotide sequence of SEQ ID NO: 12 or 13, or a sequence having up to 5, up to 10, or up to 30 nucleotide changes to SEQ ID No. 12 or 13. In embodiments, the CLN3 protein comprises an amino acid sequence of SEQ ID NO: 14, or a sequence having up to 1, 2, 3, 4, 5, 6, 7, 8, 9, or 10 amino acids different from SEQ ID No. 14.

In embodiments, the transgene comprises any one of the nucleic acid sequences listed in Table 4, or a sequence having up to 5, up to 10, or up to 30 nucleotide changes to any one of the DNA sequences in Table 4. In embodiments, the transgene encodes any one of the amino acid sequences listed in Table 4, or a sequence having up to 1, 2, 3, 4, 5, 6, 7, 8, 9, or 10 amino acids different from any one of the amino acid sequences listed in Table 4.

TABLE 4

| Name of transgene | Nucleic acid SEQ ID Nos. | Amino acid SEQ ID Nos. encoded by transgene | Features |
|---|---|---|---|
| Sulfoglucosamine sulfohydrolase (SGSH) | 99 | 134 | Natural |
| CO1-SGSH | 100 | 134 | Codon optimized |
| CO1-SGSH-GET | 101 | 135 | Codon optimized + GET |
| CO2-SGSH | 102 | 134 | Codon optimized |
| Ceroid Lipofuscinosis, Neuronal, 1 (CLN1) | 103 | 136 | Codon optimized |
| Survival Motor Neuron 1 (SMN1) | 104 | 137 | Natural |
| CO1-SMN1 | 105 | 137 | Codon optimized |
| CO2-SMN1 | 106 | 137 | Codon optimized |
| Tissue Non-specific Alkaline Phosphatase (TNALP) | 107 | 138 | Natural, Contains D10 tag at C end |
| CO1-TNALP | 108 | 138 | Codon optimized, Contains D10 tag at C end |
| CO2-TNALP | 109 | 138 | Codon optimized, Contains D10 tag at C end |
| Glial Cell Derived Neurotrophic Factor (GDNF) | 110 | 139 | Natural, splice variant 1 |
| Tissue Glucosyl Ceramidase beta (GBA1) | 111 | 140 | Natural |
| CO1-GBA1 | 112 | 140 | Codon optimized |
| CO2-GBA1 | 113 | 140 | Codon optimized |
| Iduronidase alpha-L- (IDUA) | 114 | 141 | Natural |
| CO1-IDUA | 115 | 141 | Codon optimized |
| Cytochrome P450 family 4 subfamily V member 2 (CYP4V2) | 116 | 142 | Natural |
| Retinoschisin 1 (RS1) | 117 | 143 | Natural |
| Phosphodiesterase 6B (PDE6B) | 118 | 144 | Natural |
| Methyl-CpG Binding Protein (MeCP2) | 119 | 145 | Natural |
| N-acetyl-alpha-glucosaminidase (NAGLU) | 120 | 146 | Natural |
| Ceroid Lipofuscinosis, Neuronal 3 (CLN3) | 121 | 14 | Natural |
| CO1-CLN3 | 122 | 14 | Codon optimized |
| Acid Alpha-Glucosidase (GAA) | 123 | 8 | Natural |
| CO1-GAA | 124 | 8 | Codon optimized |
| CO2-GAA | 125 | 8 | Codon optimized |
| CO3-GAA | 126 | 8 | Codon optimized |
| Alpha-Galactosidase A (GLA) | 127 | 148 | Natural |
| CO1-GLA | 128 | 148 | Codon optimized |
| CO1-GLA-GET | 129 | 149 | Codon optimized + GET |
| CO2-GLA | 130 | 148 | Codon optimized |
| CO3-GLA | 131 | 148 | Codon optimized |
| Cystic Fibrosis Transmembrane Regulator ΔR (CFTRΔR) | 132 | 150 | Codon optimized, Contains R domain deletion |
| Cystic Fibrosis Transmembrane Regulator (CFTR) | 133 | 151 | Codon optimized, full length |

In embodiments, the transgene comprises a nucleic acid sequence set forth in any one of SEQ ID Nos. 99-133, or a sequence having up to 5, up to 10, or up to 30 nucleotide changes to any one of SEQ ID Nos. 99-133. In embodiments, the transgene encodes an amino acid sequence set forth in any one of SEQ ID Nos. 134-151, or a sequence having up to 1, 2, 3, 4, 5, 6, 7, 8, 9, or 10 amino acids different from any one of the amino acid sequences SEQ ID Nos. 134-151.

In embodiments, the heterologous nucleic acid encodes a reporter protein; for example, a fluorescent protein.

Methods of Producing AAV Viral Vectors

A variety of approaches may be used to produce AAV viral vectors. In embodiments, packaging is achieved by using a helper virus or helper plasmid and a cell line. The helper virus or helper plasmid contains elements and sequences that facilitate viral vector production. In another aspect, the helper plasmid is stably incorporated into the genome of a packaging cell line, such that the packaging cell line does not require additional transfection with a helper plasmid.

In embodiments, the cell is a packaging or helper cell line. In embodiments In aspects, the helper cell line is eukaryotic cell; for example, an HEK 293 cell or 293T cell. In embodiments, the helper cell is a yeast cell or an insect cell.

In embodiments, the cell comprises a nucleic acid encoding a tetracycline activator protein; and a promoter that regulates expression of the tetracycline activator protein. In embodiments, the promoter that regulates expression of the tetracycline activator protein is a constitutive promoter. In embodiments, the promoter is a phosphoglycerate kinase promoter (PGK) or a CMV promoter.

A helper plasmid may comprise, for example, at least one viral helper DNA sequence derived from a replication-incompetent viral genome encoding in trans all virion proteins required to package a replication incompetent AAV, and for producing virion proteins capable of packaging the replication-incompetent AAV at high titer, without the production of replication-competent AAV.

Helper plasmids for packaging AAV are known in the art, see, e.g., U.S. Patent Pub. No. 2004/0235174 A1, incorporated herein by reference. As stated therein, an AAV helper plasmid may contain as helper virus DNA sequences, by way of non-limiting example, the Ad5 genes E2A, E4 and VA, controlled by their respective original promoters or by heterologous promoters. AAV helper plasmids may additionally contain an expression cassette for the expression of a marker protein such as a fluorescent protein to permit the simple detection of transfection of a desired target cell.

The disclosure provides methods of producing AAV particles comprising transfecting a packaging cell line with any one of the AAV helper plasmids disclosed herein; and any one of the AAV vectors disclosed herein. In embodiments, the AAV helper plasmid and AAV vector are co-transfected into the packaging cell line. In embodiments, the cell line is a mammalian cell line, for example, human embryonic kidney (HEK) 293 cell line. The disclosure provides cells comprising any one of the AAV vectors and/or AAV particles disclosed herein.

Pharmaceutical Compositions

The disclosure provides pharmaceutical compositions comprising any one of the AAV vectors, AAV capsids and/or AAV particles described herein. Typically, the AAV particles are administered for therapy.

The pharmaceutical composition, as described herein, may be formulated by any methods known or developed in the art of pharmacology, which include but are not limited to contacting the active ingredients (e.g., viral particles or recombinant vectors) with an excipient or other accessory ingredient, dividing or packaging the product to a dose unit. The viral particles of this disclosure may be formulated with desirable features, e.g., increased stability, increased cell transfection, sustained or delayed release, biodistributions or tropisms, modulated or enhanced translation of encoded protein in vivo, and the release profile of encoded protein in vivo.

As such, the pharmaceutical composition may further comprise saline, lipidoids, liposomes, lipid nanoparticles, polymers, lipoplexes, core-shell nanoparticles, peptides, proteins, cells transfected with viral vectors (e.g., for transplantation into a subject), nanoparticle mimics or combinations thereof. In embodiments, the pharmaceutical composition is formulated as a nanoparticle. In embodiments, the nanoparticle is a self-assembled nucleic acid nanoparticle.

A pharmaceutical composition in accordance with the present disclosure may be prepared, packaged, and/or sold in bulk, as a single unit dose, and/or as a plurality of single unit doses. The amount of the active ingredient is generally equal to the dosage of the active ingredient which would be administered to a subject and/or a convenient fraction of such a dosage such as, for example, one-half or one-third of such a dosage. The formulations of the invention can include one or more excipients, each in an amount that together increases the stability of the viral vector, increases cell transfection or transduction by the viral vector, increases the expression of viral vector encoded protein, and/or alters the release profile of viral vector encoded proteins. In embodiments, the pharmaceutical composition comprises an excipient. Non limiting examples of excipients include solvents, dispersion media, diluents, or other liquid vehicles, dispersion or suspension aids, surface active agents, isotonic agents, thickening or emulsifying agents, preservatives, or combination thereof.

In embodiments, the pharmaceutical composition comprises a cryoprotectant. The term “cryoprotectant” refers to an agent capable of reducing or eliminating damage to a substance during freezing. Non-limiting examples of cryoprotectants include sucrose, trehalose, lactose, glycerol, dextrose, raffinose and/or mannitol.

Therapeutic Methods

This disclosure provides methods of preventing or treating a disorder, comprising, consisting essentially of, or consisting of administering to a subject a therapeutically effective amount of any one of the pharmaceutical compositions disclosed herein.

In embodiments, the disorder is a CNS disorder, a skin disorder, a lung disorder, a muscle disorder, a liver disorder, or an ophthalmic disease (or a retinal disease). In embodiments, the disorder is cystic fibrosis.

In embodiments, the disorder is hypophosphatasia, amyotrophic lateral sclerosis (ALS), spinal muscular atrophy (SMA), recessive dystrophic epidermolysis bullosa (RDEB), lysosomal storage disorder (including Duchenne's Muscular Dystrophy, and Becker muscular dystrophy), juvenile Batten disease, infantile Batten disease, autosomal dominant disorders, muscular dystrophy, Bietti's Crystalline Dystrophy, retinoschisis (e.g., degenerative, hereditary, tractional, exudative), hemophilia A, hemophilia B, multiple sclerosis, diabetes mellitus, Fabry disease, Pompe disease, neuronal ceroid lipofuscinosis 1 (CLN1), CLN3 disease (or Juvenile Neuronal Ceroid Lipofuscinosis), Gaucher disease, cancer, arthritis, muscle wasting, heart disease, intimal hyperplasia, Rett syndrome, epilepsy, Huntington's disease, Parkinson's disease, Alzheimer's disease, an autoimmune disease, cystic fibrosis, thalassemia, Hurler's Syndrome (MPS IH), Sly syndrome, Scheie Syndrome, Hurler-Scheie Syndrome, Hunter's Syndrome, Sanfilippo Syndrome A (mucopolysaccharidosis IIIA or MPS IIIA), Sanfilippo Syndrome B (mucopolysaccharidosis IIIB or MPS IIIB), Sanfilippo Syndrome C, Sanfilippo Syndrome D, Morquio Syndrome, Maroteaux-Lamy Syndrome, Krabbe's disease, phenylketonuria, spinal cerebral ataxia, LDL receptor deficiency, hyperammonemia, anemia, arthritis, or adenosine deaminase deficiency.

In addition to specific transgenes disclosed herein, known active enzyme sequences may be used as transgenes to deliver functional enzyme activity.

One of the challenges for treating cystic fibrosis is the size restriction in packaging a CFTR gene in a viral particle and the difficulty of delivery of viral particles to lung cells. The AAV particles of this disclosure solve these problems by providing CFTR transgene constructs that are efficiently packaged and have better lung tropism. Therefore, in embodiments, the disclosure provides compositions and methods for treating cystic fibrosis.

In embodiments, the disorder is CLN3 disease. CLN3 disease or Juvenile Neuronal Ceroid Lipofuscinosis is a lysosomal storage disease caused by an autosomal recessively inherited mutation in the CLN3 gene. CLN3 disease is a progressive neurodegenerative disorder in which the central nervous system (CNS) is greatly affected resulting in behavioral issues, vision loss, and other cognitive disabilities.

In embodiments, the disorder is Fabry disease. Fabry disease is an X-linked lysosomal storage disorder caused by a deficiency in alpha-galactosidase A (GLA) activity that results in the accumulation of the glycolipid products, globotriaosylceramide (Gb3) and lyso-Gb3 in the lysosome. Disease presentation is highly heterogeneous but usually includes frequent bouts of peripheral neurotrophic pain, angiokeratomas, reduced sweat production, corneal dystrophy, and gastrointestinal complications. As the disease progresses patients suffer from cardiomyopathy, renal insufficiency and cerebrovascular disease, all of which are the primary causes of reduced life-span in Fabry patients. While males are the most severely affected population of patients with mutations in the GLA gene, it has become increasingly clear that female patients are also frequently symptomatic but are often misdiagnosed. Enzyme replacement therapy (ERT) is currently the only FDA-approved therapy to treat Fabry and requires bi-weekly injections of relatively large quantities of recombinant protein. While ERT reduces the accumulation of Gb3 in the heart, kidney and vasculature it fails to completely treat all symptoms of Fabry, primarily due to its inability to efficiently enter the CNS. Gene therapy strategies have been investigated and while many show great promise in correcting the glycolipid accumulation, most have failed to efficiently enter the CNS and also suffered from an immune response often seen during GLA replacement.

In embodiments, the AAV viral vectors disclosed herein are used to treat Fabry disease in patients, who are unresponsive to ERT, or when ERT fails to address all symptoms. In embodiments, the AAV viral vectors disclosed herein are used to treat Fabry disease in patients who have already been administered ERT.

In embodiments, the disorder is Pompe disease. Pompe disease is a lysosomal storage disorder caused by a deficiency in acid α-glucosidase (GAA) activity that results in the accumulation of glycogen in the lysosome. The disease presents as a form of muscular dystrophy which primarily affects both smooth and striated musculature as well as the central nervous system (CNS), with early mortality. Enzyme replacement therapy (ERT) is currently the only FDA-approved therapy to treat Pompe and requires bi-weekly injections of relatively large quantities of recombinant protein. While ERT significantly reduces the mortality rate of infantile Pompe patients, who typically die by the age of two without therapy, it fails to completely ameliorate all symptoms of Pompe, primarily due to its inability to efficiently enter the CNS and resulting immune responses to the GAA protein. Gene therapy strategies have been investigated and while many show great promise in correcting the glycogen accumulation and other symptoms of Pompe. Most have suffered from the severe immune response seen during GAA replacement. Previous work has demonstrated that hepatic-specific expression can make animals tolerate to the GAA protein and significantly reduce the humoral response.

In embodiments, the AAV viral vectors disclosed herein are used to treat Pompe disease in patients who have already been administered ERT; for example those who are unresponsive to ERT, or when ERT fails to address all their symptoms.

In embodiments, the cancer is a solid cancer; for example, bladder, breast, cervical, colon, rectal, endometrial, kidney, lip, oral, liver, melanoma, mesothelioma, non-small cell lung, non-melanoma skin, ovarian, pancreatic, prostate, sarcoma, small cell lung tumor, or thyroid.

In embodiments, the disorder is an ophthalmic disease. The eye is immune privileged tissue. Only a very small number of viruses is necessary for therapeutic benefit. In embodiments, the ophthalmic disease affects photoreceptor and RPE cells. In some embodiments, the ophthalmic disease comprises, consists essentially of, or consists of retinitis pigmentosa (e.g., autosomal recessive (SPATA7 gene; LRAT gene; TULP1 gene), autosomal dominant (AIPL1 gene), and X-linked (RPGR gene)), eye disorders related to mutations in the bestrophin-1 (BEST-1) gene (e.g., vitelliform macular dystrophy, age-related macular degeneration, autosomal dominant vitreoretinochoroidopathy, glaucoma, cataracts), Leber congenital amaurosis (LCA; aryl-hydrocarbon interacting protein-like 1 (AIPL1) gene), cone-rod dystrophy (CRD; ABCA4 gene), Stargardt's (ABCA4 gene), choroideremia (CHM gene), Usher Syndrome (MYO7A gene; CDH23 gene; USH2A gene; CLRN1 gene), retinoschisis (RS1 gene), Bietti's Crystalline Dystrophy (CYP4V2 gene) or Achromatopsia (CNGA3 gene, CNGB3 gene, GNAT2 gene, PDE6C gene, or PDE6H gene).

In embodiments, the subject is a mammal; for example, a human. In particular aspects, the human is an infant human; for example, under 3 years old, 2 years old, or under 1 year old.

The methods of treatment and prevention disclosed herein may be combined with appropriate diagnostic techniques to identify and select patients for the therapy or prevention. For example, the method of treating or preventing a disorder, for example, cystic fibrosis, disclosed herein may further comprise steps of performing a genetic test to identify a gene mutation or deletion related to the disorder in the subject. In embodiments, the method of treating or preventing a disorder, for example, cystic fibrosis, comprises administering to a subject who has been previously identified as carrying a mutation related to the disorder, or as being at high risk for developing the disorder (for example, based on hereditary factors).

The disclosure provides methods of increasing the level of a protein in a host cell, comprising contacting the host cell with any one of the AAV particles disclosed herein, wherein the AAV particle comprises any one of the AAV vectors disclosed herein, comprising an HNA sequence encoding the protein. In embodiments, the protein is a therapeutic protein. In embodiments, the host cell is in vitro, in vivo, or ex vivo. In embodiments, the host cell is derived from a subject. In embodiments, the subject suffers from a disorder, which results in a reduced level and/or functionality of the protein, as compared to the level and/or functionality of the protein in a normal subject.

In embodiments, the level of the protein is increased to level of about $1\times10^{-7}$ ng, about $3\times10^{-7}$ ng, about $5\times10^{-7}$ ng, about $7\times10^{-7}$ ng, about $9\times10^{-7}$ ng, about $1\times10^{-6}$ ng, about $2\times10^{-6}$ ng, about $3\times10^{-6}$ ng, about $4\times10^{-6}$ ng, about $6\times10^{-6}$ ng, about $7\times10^{-6}$ ng, about $8\times10^{-6}$ ng, about $9\times10^{-6}$ ng, about $10\times10^{-6}$ ng, about $12\times10^{-6}$ ng, about $14\times10^{-6}$ ng, about $16\times10^{-6}$ ng, about $18\times10^{-6}$ ng, about $20\times10^{-6}$ ng, about $25\times10^{-6}$ ng, about $30\times10^{-6}$ ng, about $35\times10^{-6}$ ng, about $40\times10^{-6}$ ng, about $45\times10^{-6}$ ng, about $50\times10^{-6}$ ng, about $55\times10^{-6}$ ng, about $60\times10^{-6}$ ng, about $65\times10^{-6}$ ng, about $70\times10^{-6}$ ng, about $75\times10^{-6}$ ng, about $80\times10^{-6}$ ng, about $85\times10^{-6}$ ng, about $90\times10^{-6}$ ng, about $95\times10^{-6}$ ng, about $10\times10^{-5}$ ng, about $20\times10^{-5}$ ng, about $30\times10^{-5}$ ng, about $40\times10^{-5}$ ng, about $50\times10^{-5}$ ng, about $60\times10^{-5}$ ng, about $70\times10^{-5}$ ng, about $80\times10^{-5}$ ng, or about $90\times10^{-5}$ ng in the host cell.

The disclosure provides methods of introducing a gene of interest to a cell in a subject comprising contacting the cell with an effective amount of any one of the AAV viral vector particles disclosed herein, wherein the particle contains any one of the AAV vectors disclosed herein, comprising the gene of interest.

Dosage and Administration

Methods of determining the most effective means and dosage of administration are known to those of skill in the art and will vary with the composition used for therapy, the purpose of the therapy and the subject being treated. Single or multiple administrations can be carried out with the dose level and pattern being selected by the treating physician. It is noted that dosage may be impacted by the route of administration. Suitable dosage formulations and methods of administering the agents are known in the art. Non-limiting examples of such suitable dosages may be as low as $10^9$ vector genomes to as much as $10^{17}$ vector genomes per administration.

In embodiments of the methods described herein, the number of viral particles (e.g., AAV) administered to the subject ranges from about $10^9$ to about $10^{17}$. In particular some embodiments, about $10^{10}$ to about $10^{12}$, about $10^{11}$ to about $10^{13}$, about $10^{11}$ to about $10^{12}$, about $10^{11}$ to about $10^{14}$, about $5\times10^{11}$ to about $5\times10^{12}$, or about $10^{12}$ to about $10^{13}$ viral particles are administered to the subject. For administration to a human eye, a total dose of about $1\times10^{10}$ vg/eye may be used, and a total dose of $5\times10^9$ vg/eye may be used for a mouse eye. Non-invasive, in vivo imaging techniques can be used to monitor efficacy/safety in animals, which include but are not limited to scanning laser ophthalmoscopy (SLO), optical coherence tomography (OCT), multi-photon microscopy, fluorescein angiography.

In embodiments, the AAV particles repair the gene deficiency in a subject. In embodiments, the ratio of repaired target polynucleotide or polypeptide to unrepaired target polynucleotide or polypeptide in a successfully treated cell, tissue, organ or subject is at least about 1.5:1, about 2:1, about 3:1, about 4:1, about 5:1, about 6:1, about 7:1, about 8:1, about 9:1, about 10:1, about 20:1, about 50:1, about 100:1, about 1000:1, about 10,000:1, about 100,000:1, or about 1,000,000:1. The amount or ratio of repaired target polynucleotide or polypeptide can be determined by any method known in the art, including but not limited to Western blot, Northern blot, Southern blot, PCR, sequencing, mass spectrometry, flow cytometry, immunohistochemistry, immunofluorescence, fluorescence in situ hybridization, next generation sequencing, immunoblot, and ELISA.

In embodiments, the viral particle is introduced to the subject intravenously, intrathecally, intracerebrally, intraventricularly, intranasally, intratracheally, intra-aurally, intra-ocularly, or peri-ocularly, orally, rectally, transmucosally, inhalationally, transdermally, parenterally, subcutaneously, intradermally, intramuscularly, intrapleurally, topically, intralymphatically, intracisternally; such introduction may also be intra-arterial, intracardiac, subventricular, epidural, intracerebral, intracerebroventricular, sub-retinal, intravitreal, intraarticular, intraperitoneal, intrauterine, or any combination thereof. In embodiments, the viral particles are delivered to a desired target tissue, e.g., to the lung, eye, or CNS, as non-limiting examples. In embodiments, delivery of viral particles is systemic. The intracisternal route of administration involves administration of a drug directly into the cerebrospinal fluid of the brain ventricles. It could be performed by direct injection into the cisterna *magna* or via a permanently positioned tube.

For treating an ophthalmic disease (or an eye disorder) intraocularly, there are multiple modes of administration known to those skilled in the art, including but not limited to: lacrimal gland (LG) administration, topical eye drop, intra-stromal administration to the cornea, intra-cameral administration (anterior chamber), intravitreal administration, sub-retinal administration, systemic administration, or a combination thereof. 80% of genetic eye disorders occur in the photoreceptors. Intravitreal delivery of small volume gene therapies can occur in an out-patient clinic.

Administration of the AAV vector, AAV particle or compositions of this disclosure can be effected in one dose, continuously or intermittently throughout the course of treatment. In embodiments, the AAV vector, AAV particle or compositions of this disclosure are parenterally administered by injection, infusion or implantation.

In embodiments, the AAV particles of this disclosure show enhanced tropism for brain and cervical spine. In embodiments, the viral particles of the disclosure can cross the blood-brain-barrier (BBB). In embodiments, the AAV particles of this disclosure show high retinal tropism by subretinal and intravitreal injections. In embodiments, the AAV particles of this disclosure target multiple eye cell types, such as, for example, cones, rods, and retinal pigment epithelium (RPE). In embodiments, AAV particles of this disclosure escape neutralizing antibodies against natural serotypes, and thus enable potential redosing. In a further aspect, the AAV particles and compositions of the disclosure may be administered in combination with other known treatments for the disorder being treated.

Kits

The agents, vectors, or compositions described herein may, In embodiments, be assembled into pharmaceutical or diagnostic or research kits to facilitate their use in therapeutic, diagnostic or research applications. In embodiments, the kits of the present disclosure include any one of the modified AAV capsid proteins, AAV vectors, AAV particles, host cells, isolated tissues, compositions, or pharmaceutical compositions as described herein.

In embodiments, a kit further comprises instructions for use. Specifically, such kits may include one or more agents described herein, along with instructions describing the intended application and the proper use of these agents. As an example, In embodiments, the kit may include instructions for mixing one or more components of the kit and/or isolating and mixing a sample and applying to a subject. In embodiments, agents in a kit are in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. In embodiments, the compositions may be provided in a preservation solution (e.g., cryopreservation solution). Non-limiting examples of preservation solutions include DMSO, paraformaldehyde, and CryoStor® (Stem Cell Technologies, Vancouver, Canada). In embodiments, the preservation solution contains an amount of metalloprotease inhibitors.

In embodiments, the kit contains any one or more of the components described herein in one or more containers. Thus, In embodiments, the kit may include a container housing agents described herein. The agents may be in the form of a liquid, gel or solid (powder). The agents may be prepared sterilely, packaged in a syringe and shipped refrigerated. Alternatively, they may be housed in a vial or other container for storage. A second container may have other agents prepared sterilely. Alternatively, the kit may include the active agents premixed and shipped in a syringe, vial, tube, or other container. The kit may have one or more or all of the components required to administer the agents to a subject, such as a syringe, topical application devices, or IV needle tubing and bag.

It is to be understood that while the invention has been described in conjunction with the above embodiments, the foregoing description and examples are intended to illustrate and not limit the scope of the invention. Other aspects, advantages and modifications within the scope of the invention will be apparent to those skilled in the art to which the invention pertains.

In addition, where features or aspects of the invention are described in terms of Markush groups, those skilled in the art will recognize that the invention is also thereby described in terms of any individual member or subgroup of members of the Markush group.

EXAMPLES

Example 1

Capsid Generating Platform

Some AAV capsid sequences provided herein (e.g., AAV204, AAV110) were generated using the AAV capsid generating platform shown in FIG. 1. Briefly, the platform comprises a DNase I fragmentation step, and an assembly and amplification step, which finally result in the formation of a chimeric capsid library. Other AAV capsid sequences provided herein (e.g., AAV214) were generated by rational design.

Capsid proteins generated using these methodologies were analyzed by alignment with the amino acid sequences of known AAV capsid proteins. Sequence alignment of VP1 protein sequence from AAV204 (SEQ ID NO: 2) and AAV6 (SEQ ID NO: 63) is shown in FIG. 20. Sequence alignment of VP1 amino acid sequences of AAV 214, AAV 214A, AAV 214e, AAV 214e8, AAV 214e9, AAV 214e10, AAV 214AB, and AAV ITB102_45 is provided in FIG. 21. Sequence alignment of VP2 amino acid sequences of AAV 214, AAV 214A, AAV 214e, AAV 214e8, AAV 214e9, AAV 214e10, AAV 214AB, and AAV ITB102_45 is provided in FIG. 22. Sequence alignment of VP1 amino acid sequences of AAV 214, AAV 214A, AAV 214e, AAV 214e8, AAV 214e9, AAV 214e10, AAV 214AB, and AAV ITB102_45 is provided in FIG. 23.

Viral vectors may be made using a standard triple-transfection method known in the art. Briefly, three separate plasmids expressing, respectively, the viral capsid protein, helper proteins (e.g., the essential viral Rep and Cap proteins), and the transgene of interest are transfected into adherent or suspension 293 cells, and viral particles are later harvested using ultracentrifugation or chromatography followed by diafiltration/ultrafiltration and terminal sterile filtration. See, e.g., Guo et al., Mol. Ther. Methods Clin. Dev., Vol. 13, pp. 40-46 at 44 (November 2018); Wang et al., Human Gene Ther. Methods, Vol. 25, pp. 261-68 at 262; and Gao et al., Human Gene Ther. Methods, Vol. 11, pp. 2079-91, each of which is incorporated herein by reference in their entireties for all purposes.

Example 2

Characterization of AAV214 and AAV204 Viral Vectors

The efficiency of transduction of AAV214 or AAV204 vectors in different target tissues was assessed as described below.

Figure 2A:
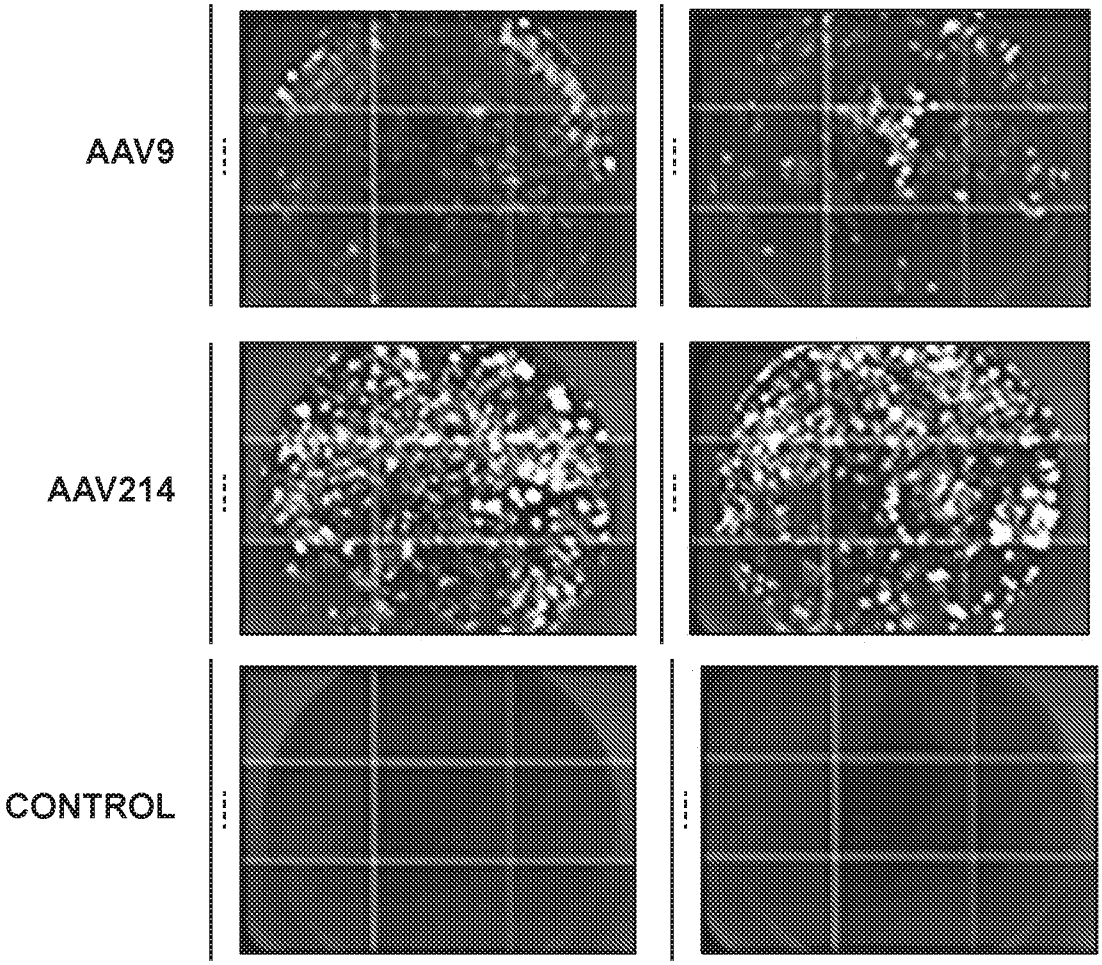
FIG. 2A Comparison of transduction efficiency in tissue culture. HEK 293 cells were plated in a 96-well plate at 50,000 cells per well. Cells were transduced with capsids containing AAV9-GFP or AAV214-GFP virus at an MOI of 5E+5. Images were taken 45 hours post transduction.

The transduction efficiency of an AAV214 viral vector comprising an EGFP transgene (AAV214-GFP) and an AAV9 viral vector comprising an EGFP transgene (AAV9-GFP) were evaluated in vitro. HEK 293 cells were seeded in a 96-well plate at 50,000 cells per well. Cells were transduced with AAV214-GFP or AAV9-GFP at an MOI of 5E+5. Images taken 45 hours post transduction revealed that transduction efficiency was higher for AAV214-GFP in HEK 293 cells (FIG. 2A). It is noted that "GFP" as used herein refers to EGFP (see, e.g., Zhang et al. (1996) Biochem. Biophys. Res. Commc'n. 227(3):707-11) unless otherwise specified.

Figure 2B:
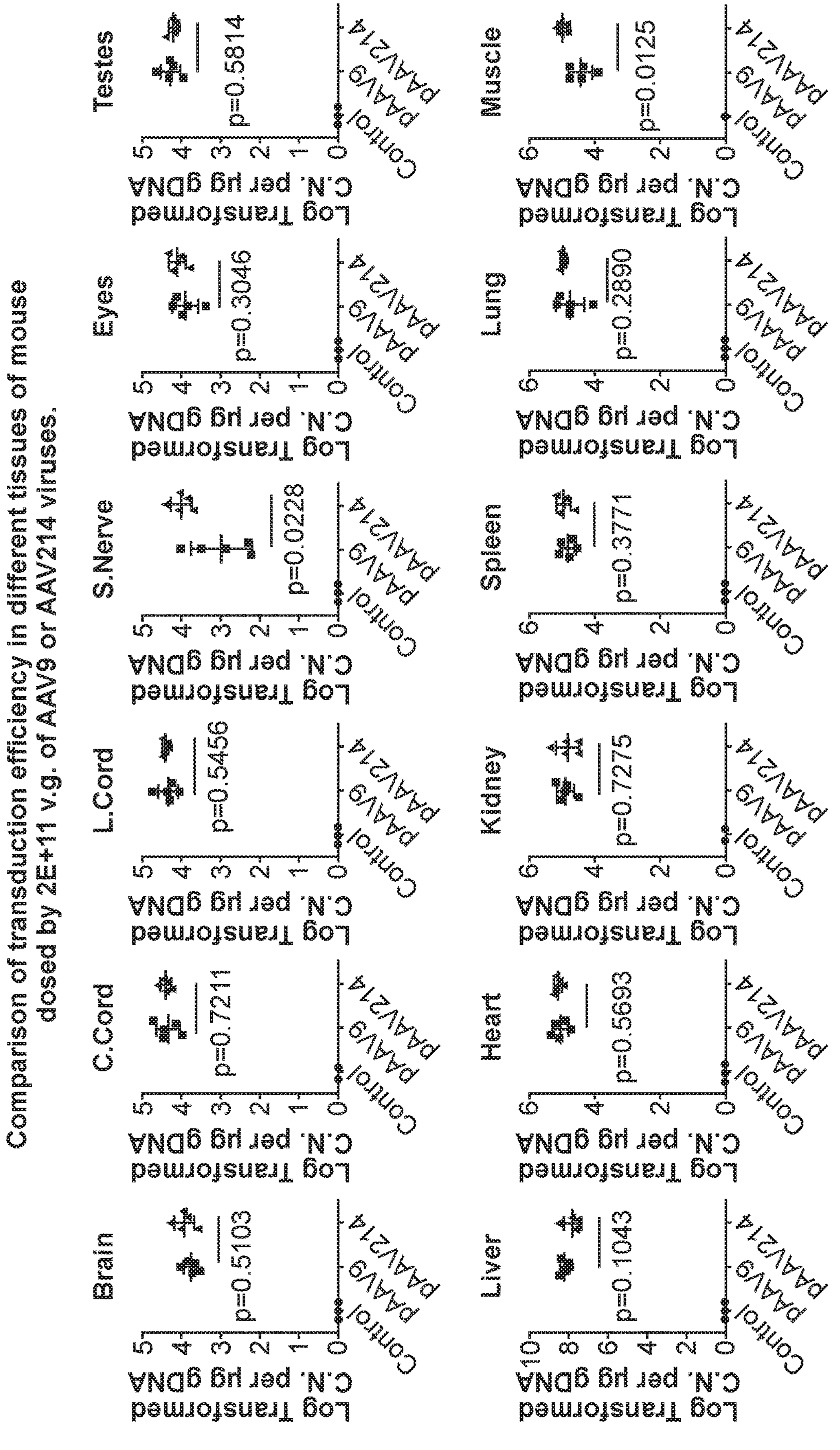
FIG. 2B Comparison of transduction efficiency in different tissues of mouse dosed with 2E+11 viral genomes (vg) of AAV9 or AAV214 viruses.

To test transduction efficiency in vivo, 10-week old C57BL/6 mice were dosed by intravenous (IV) injection of 2E+11 vg of AAV214-GFP or AAV9-GFP in 200 μL of TMN200 (200 mM Tris-HCl, 1 mM MgCl2, 200 mM NaCl and 0.001% Pluronic F68). Thirteen days later, mice were euthanized, tissue samples of internal organs (brain, spinal cord (cervical and lumbar), sciatic nerve, eyes, heart, kidney, liver, lung, testes, spleen and muscle) were collected, and total DNA was isolated and analyzed using an absolute qPCR approach for GFP gene copy number estimation. Obtained AAV biodistribution data were plotted using Prism software for statistical analysis (GraphPad Software). An unpaired t-test performed on log-transformed data did not reveal a statistically significant difference between AAV9-GFP and AAV214-GFP transduction efficiencies in most tissues tested ($p<0.05$). However, in the case of sciatic nerve and muscle, the mean value of detected viral DNA copy number per microgram of total DNA isolated from AAV214-GFP dosed animals was higher and statistically significantly different from AAV9-GFP dosed animals (sciatic nerve: 4.1-fold, $p=0.0228$; muscle: 3-fold, $p=0.0125$) (FIG. 2B).

Figure 2C:
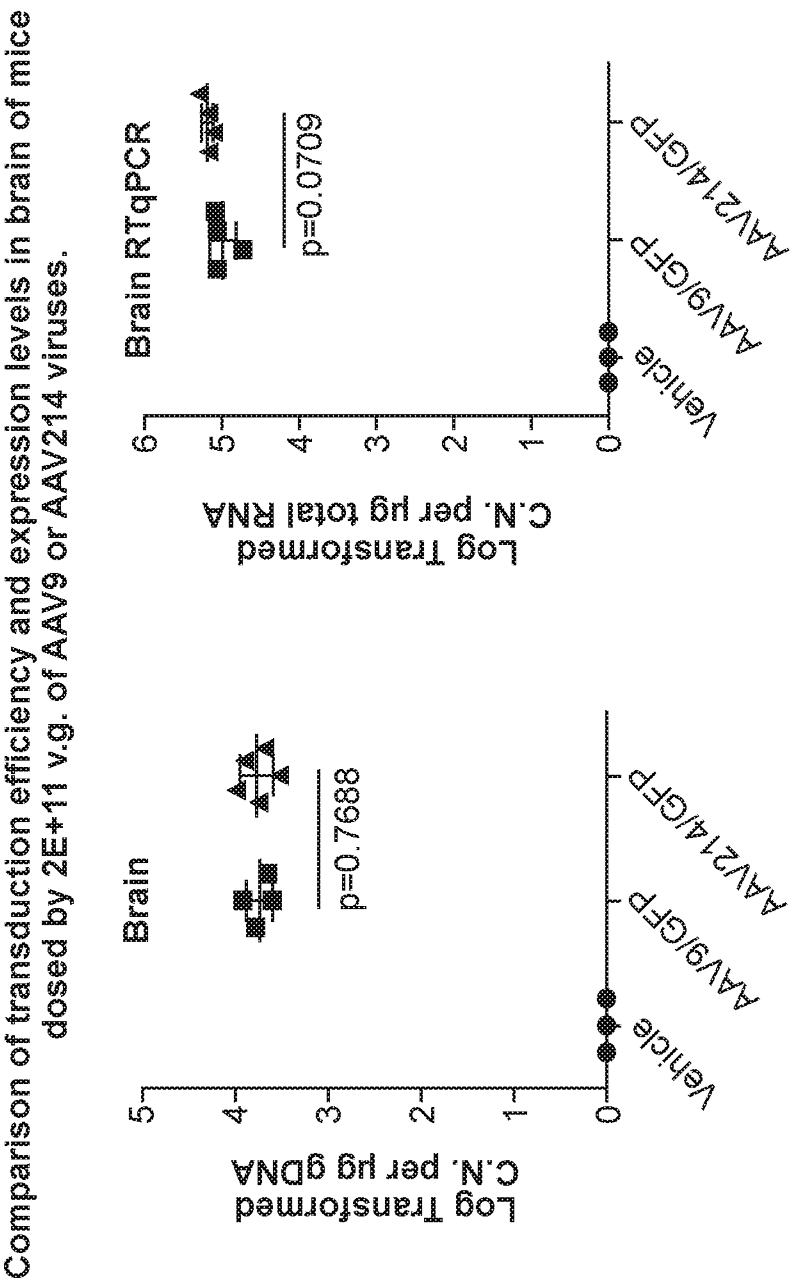
FIG. 2C Comparison of transduction efficiency and expression levels in brain of mice dosed with 2E+11 vg of AAV9 or AAV214 viruses.

The same experiment was repeated with the brain sample split into two halves. One half was used for total DNA isolation and followed by biodistribution analysis using absolute qPCR. The other half was used for total RNA isolation, DNase treatment, conversion into cDNA, and qPCR analysis to quantify EGFP gene expression levels. Obtained AAV biodistribution and transgene expression data were plotted using Prism software for statistical analysis. An unpaired t-test performed on log-transformed data did not reveal a statistically significant difference between AAV9-GFP and AAV214-GFP transduction efficiencies (p=0.7668) or expression levels (p=0.0709) in brain tissue (FIG. 2C).

Figure 3A:
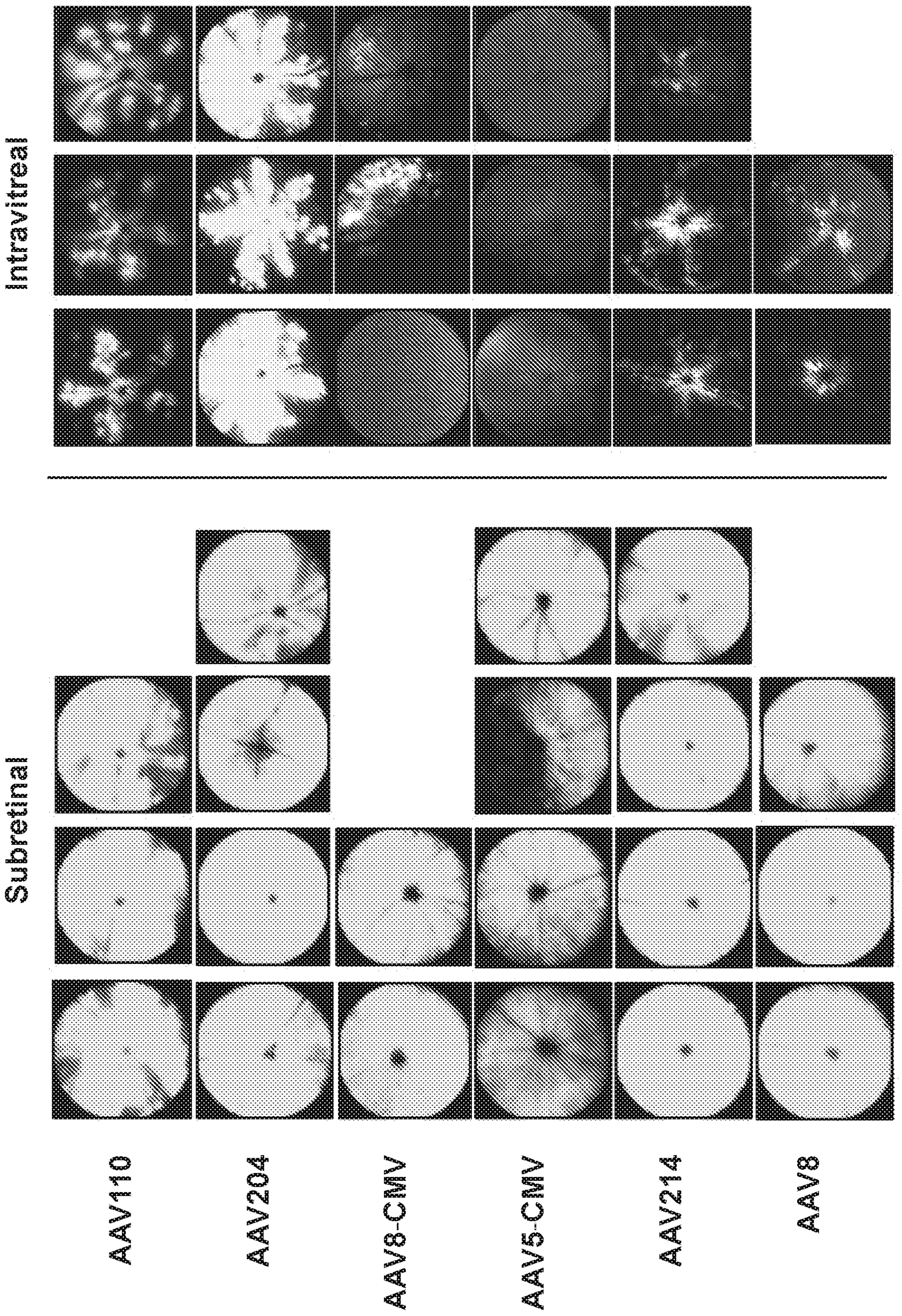
FIG. 3A Scanning laser ophthalmoscopy imaging of mouse retinas after AAV administration. Wild-type C57BL/6J mice were administered the labeled AAV serotype by both subretinal (right eye) and intravitreal (left eye) injection. 1 μL of AAV vector at 5E+12 vg/mL (5E+9 vg/eye) was injected for both methods of administration and animals were imaged after 10 days with a HRA2 Spectralis Scanning Laser Ophthalmoscope (Heidelberg Engineering, Carlsbad, CA). Images where cataract prevented sufficient observation were omitted from figure.
Figure 3B:
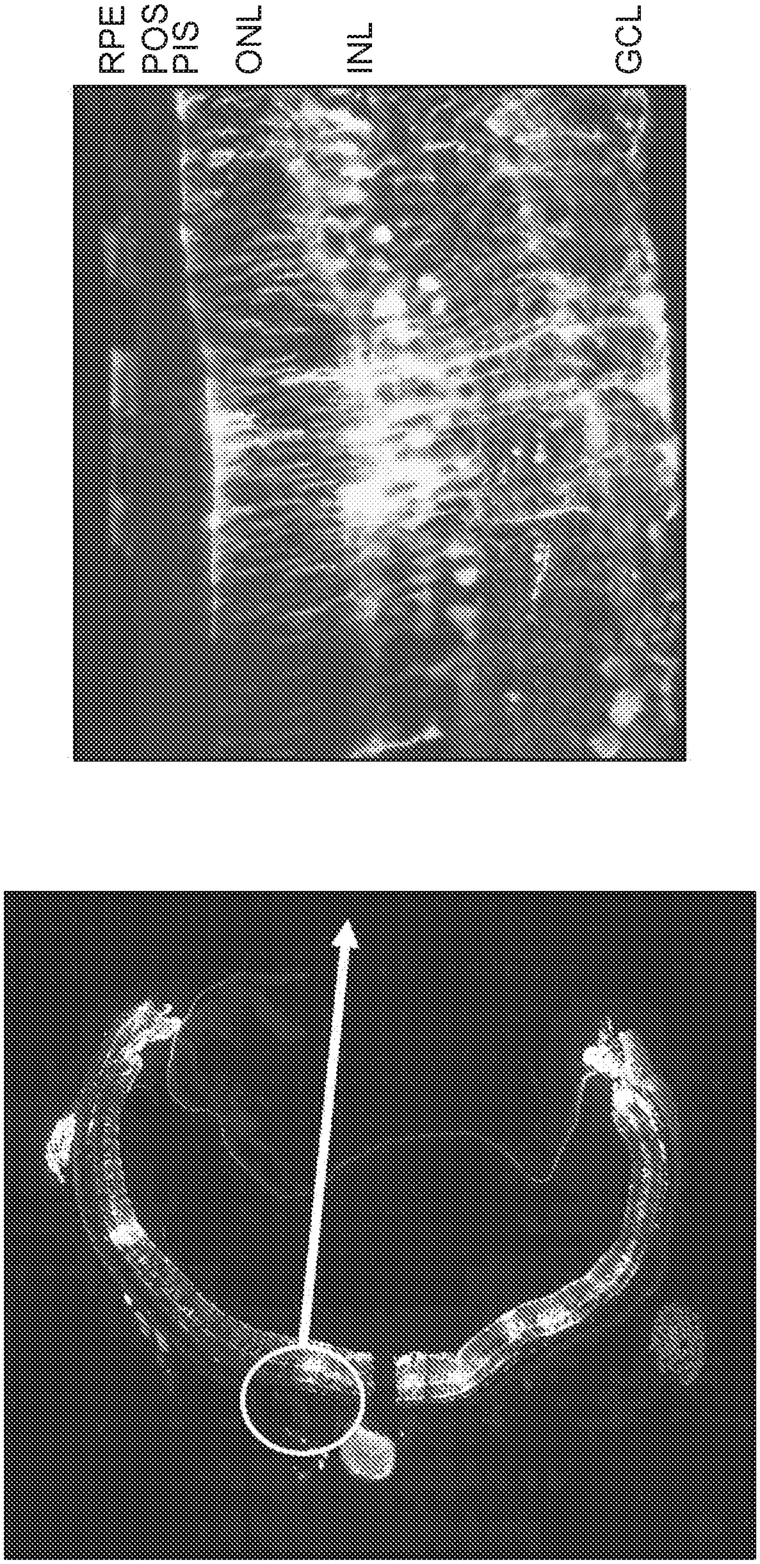
FIG. 3B IHC analysis of mouse eye dosed with AAV204-GFP intravitreally.

Wild-type C57BL/6J mice were administered a set of AAV viral vectors including AAV204-GFP, AAV110-GFP, and AAV214-GFP by both subretinal (right eye) and intravitreal (left eye) injection. 1 μL of AAV vector at 5E+12 vg/mL (5E+9 vg/eye) was injected for both methods of administration and animals were imaged after 10 days with an HRA2 Spectralis Scanning Laser Ophthalmoscope (Heidelberg Engineering, Carlsbad, CA). Images where cataract prevented sufficient observation were omitted from the analysis. Ophthalmoscopy imaging revealed that all tested viruses were capable of transfecting retinal cells if dosed into the subretinal cavity. However, only AAV204 and AAV110 showed enhanced transduction of retinal cells mediated by intravitreal delivery (FIG. 3A). Immunohistochemistry analysis of AAV204-GFP intravitreally dosed mouse eyes demonstrated GFP expression in various types of retinal cells including photoreceptors, RPE, Müller glia cells, retinal ganglion cells and bipolar cells (FIG. 3B).

Figure 4:
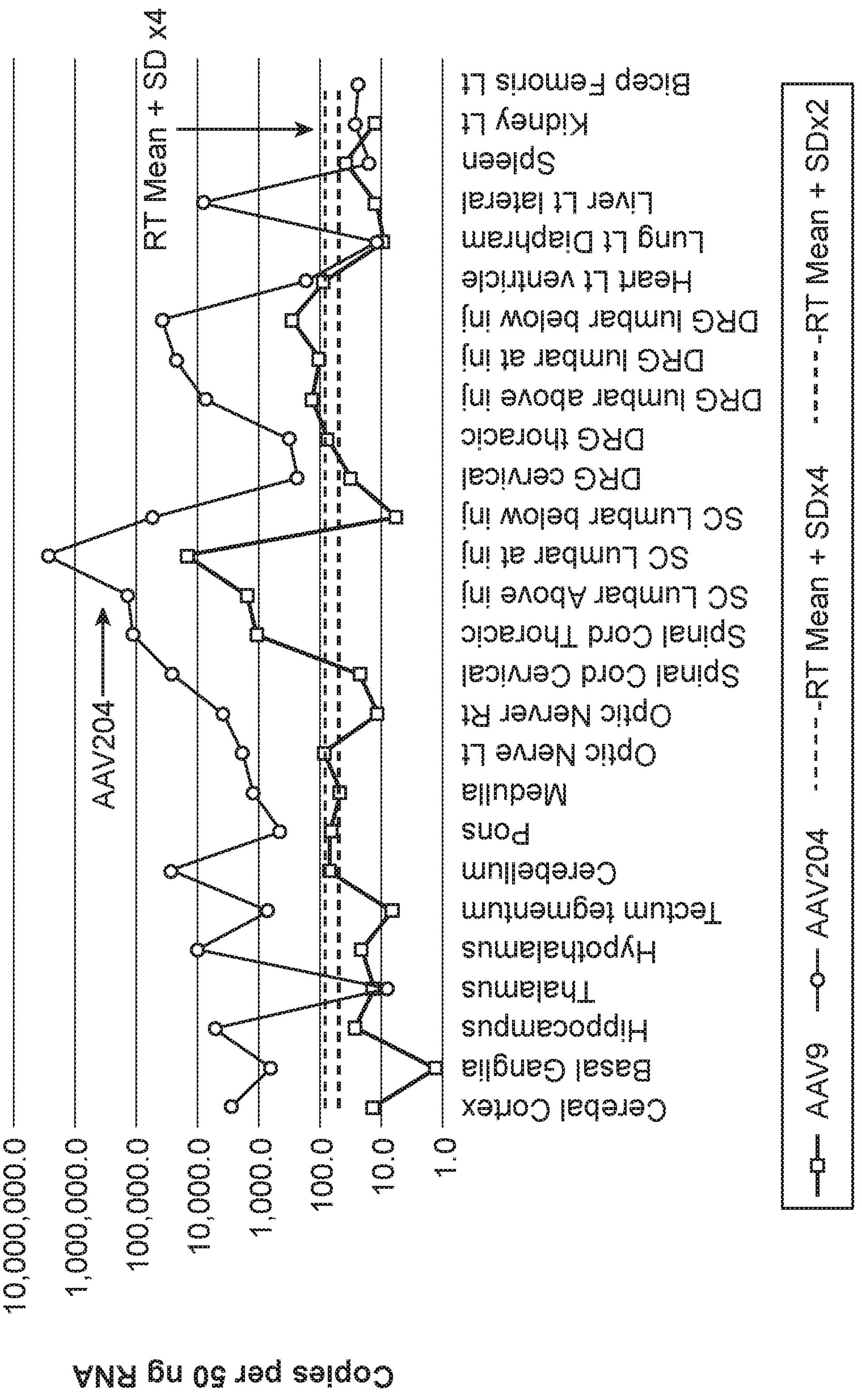
FIG. 4 compares GFP expression mediated by AAV204 or AAV9 transduction in primates by RT-qPCR. The dotted line corresponds to background calculated as −RT mean plus 2 or 4 standard deviations.
Figure 5A:
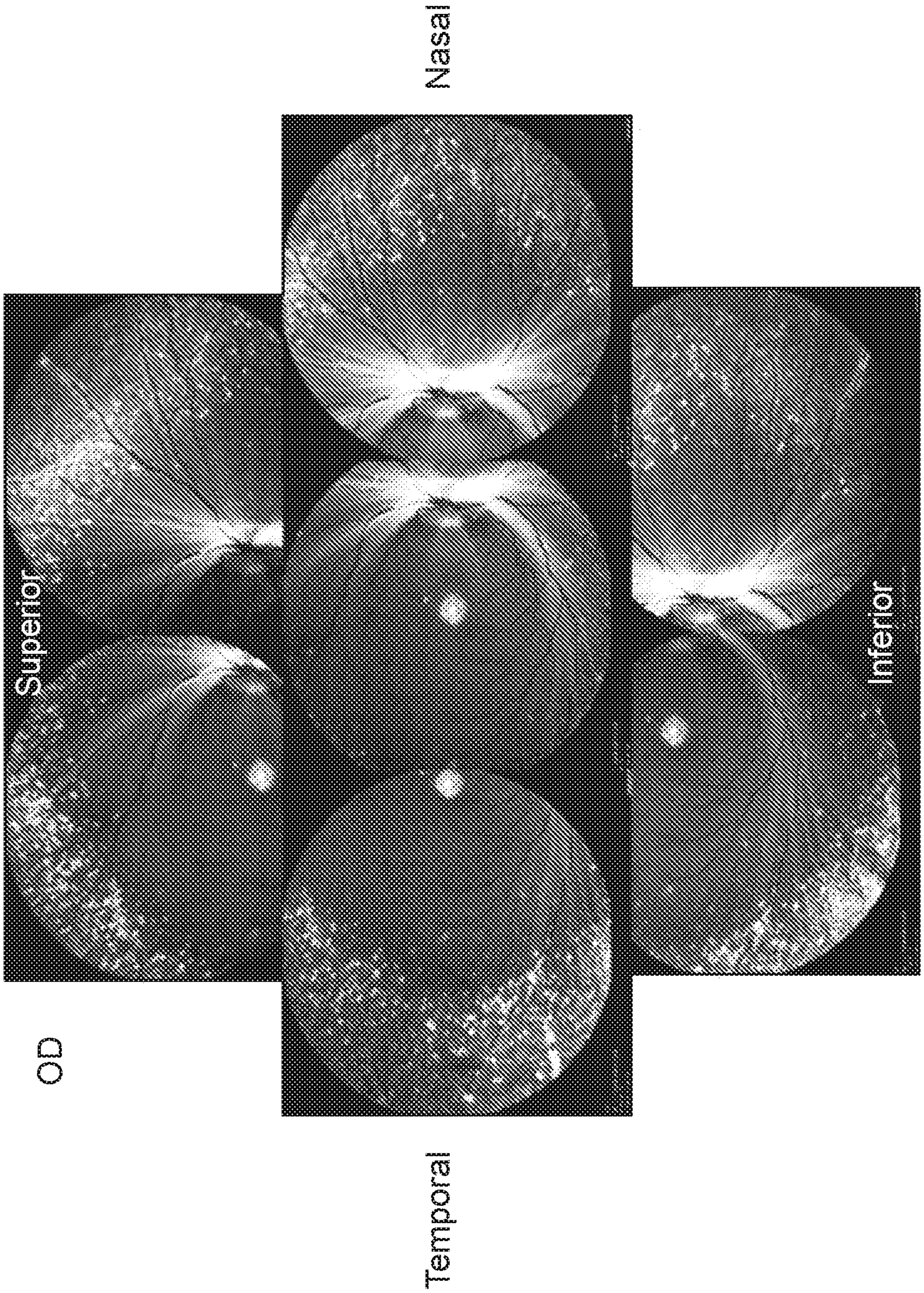
FIGS. 5A-5F shows AAV204-mediated eye expression.
Figure 5B:
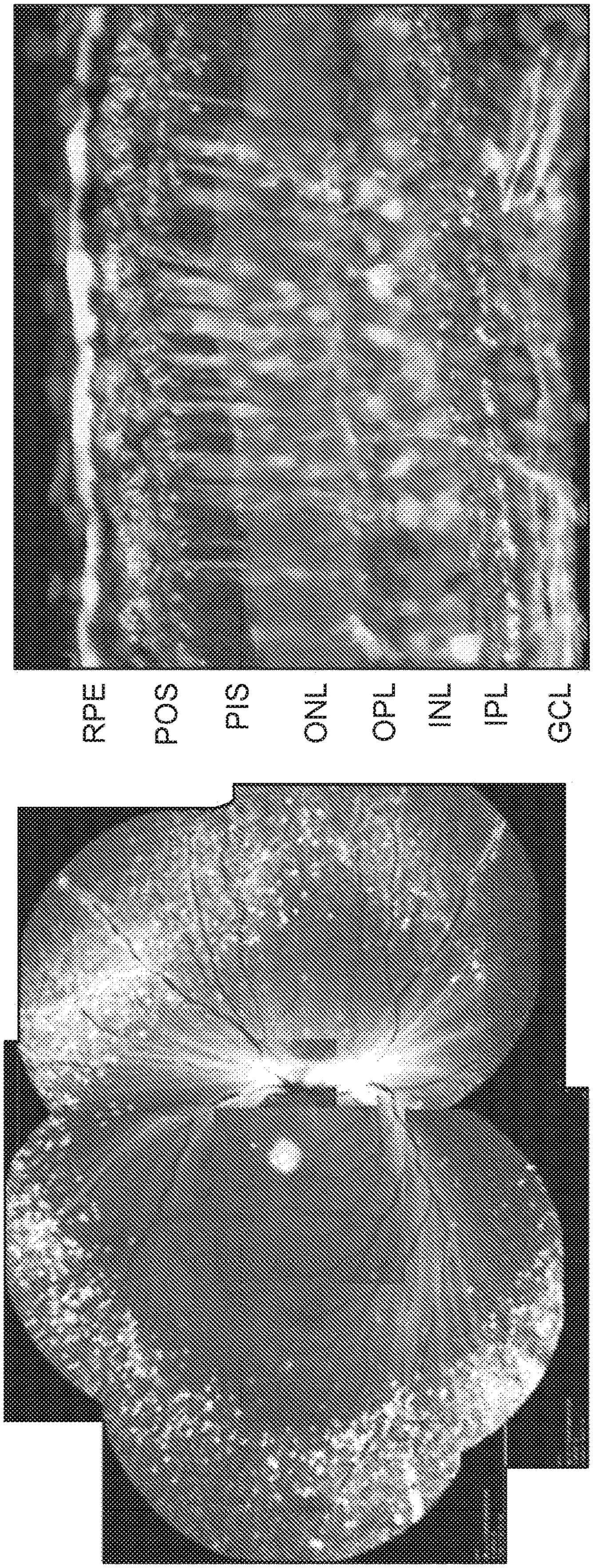
Figure 5C:
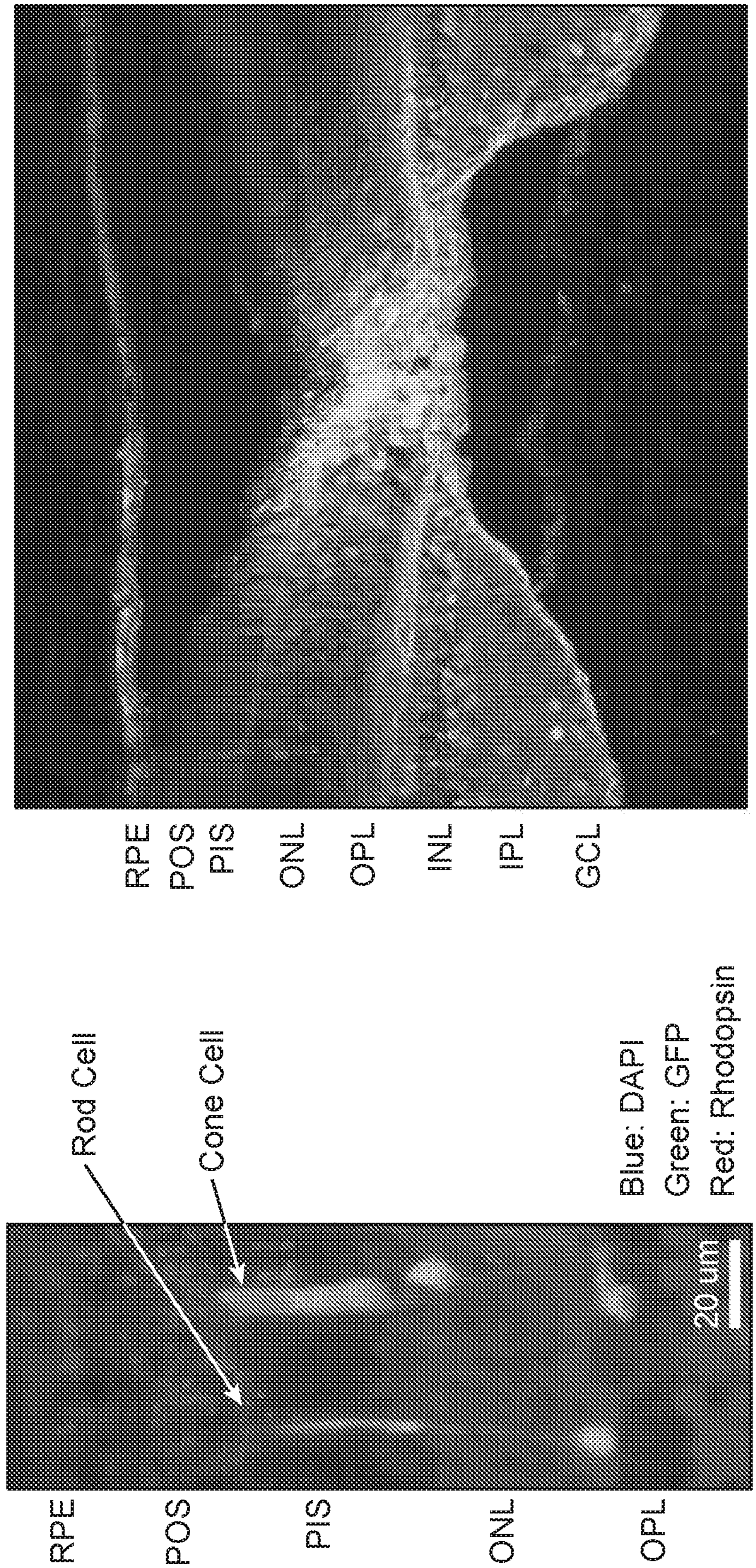

AAV204-GFP and AAV9-GFP were administered by intrathecal (1E+13 vg) and/or intravitreal injection (1.5E+12 vg) to 2.5- to 3-year-old cynomolgus monkeys (*Macaca fascicularis*) each weighing about 2 kg. After four weeks, animals were euthanized and GFP expression was evaluated by RT-qPCR. Data analysis showed that AAV204-GFP mediated delivery resulted in enhanced GFP expression in most of the tissues that were assayed, including specific areas of the brain and spinal cord. See FIG. 4. The eyes of the intravitreally dosed (1.5E+12 vg of AAV204-GFP per eye) cynomolgus monkeys were evaluated by scanning laser ophthalmoscopy (SLO), sectioned and analyzed for GFP, rhodopsin and genomic DNA using conventional immunochemistry staining methods. As shown in FIGS. 5A and 5B, the administration of AAV204-GFP resulted in significant transduction of the vector in the peripheral retina and the foveal region of the eye. Enhanced expression of GFP delivered by AAV204 was seen in retinal cells including photoreceptors, RPE, bipolar cells and ganglion cells (FIG. 5B). A significant number of rods and cones were transduced in the macula (FIG. 5C).

Figure 5D:
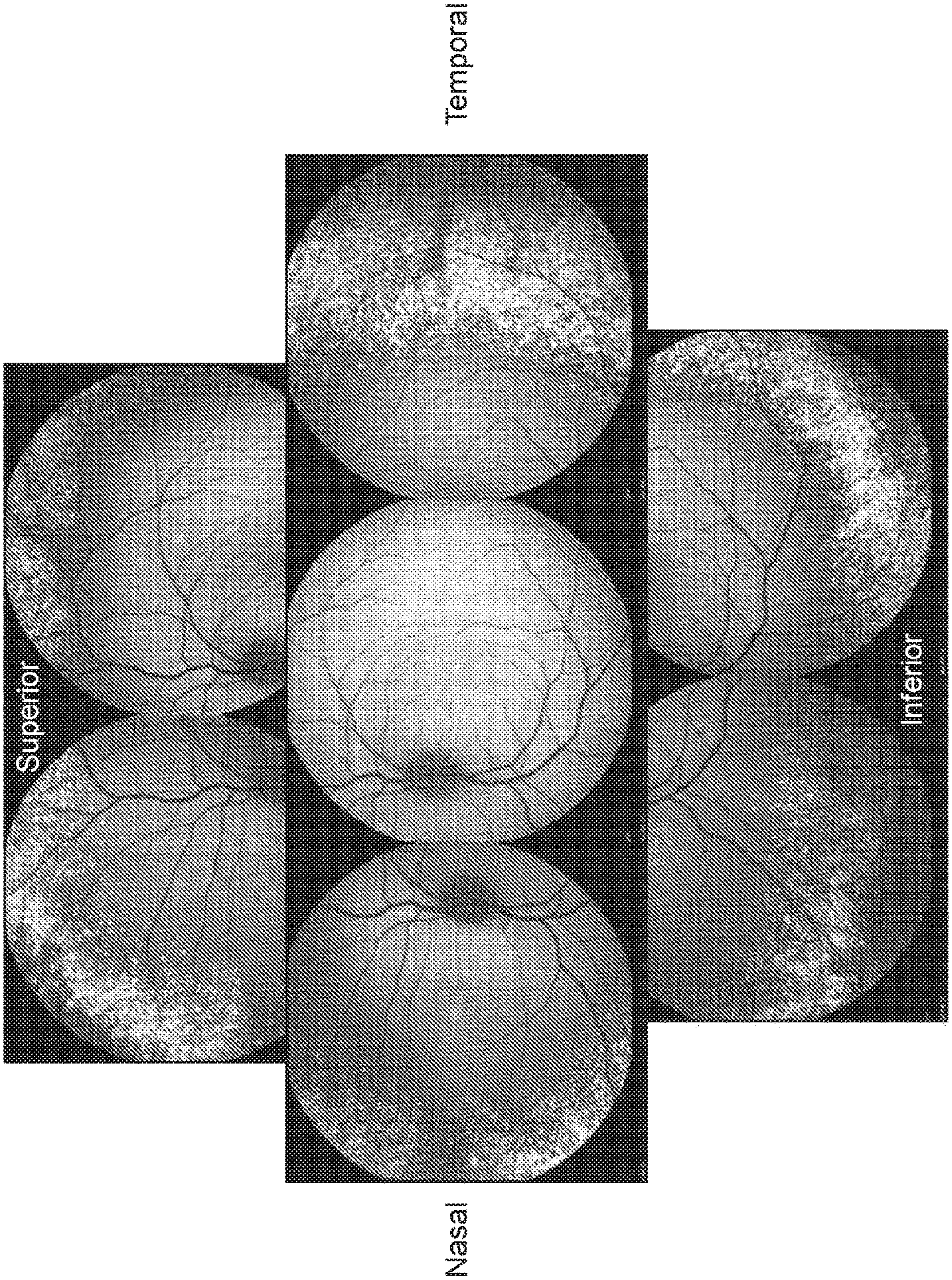
Figure 5E:
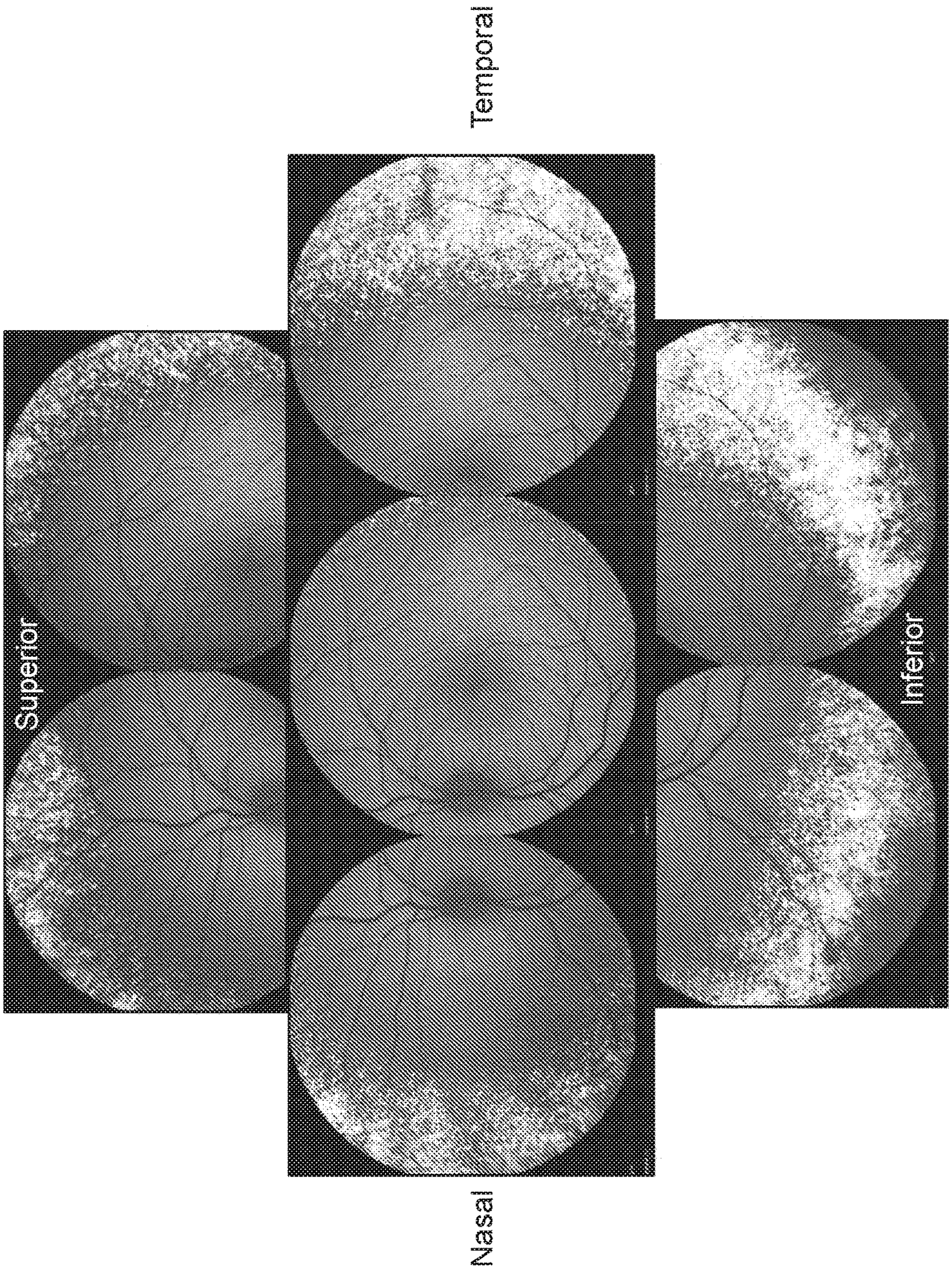
Figure 5F:
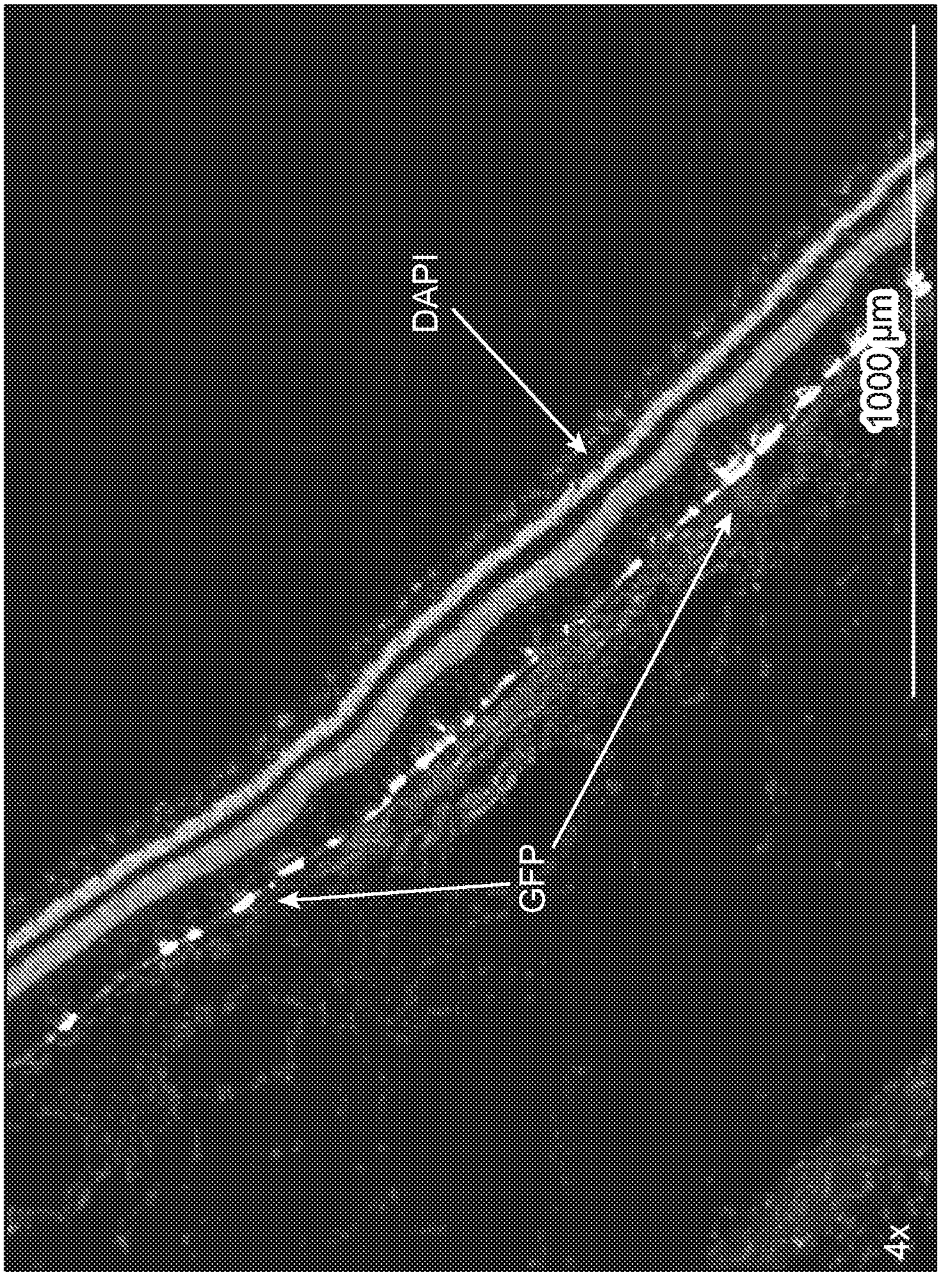

The AAV204 vector can also be combined with RPE-specific promoters to express proteins specifically. FIGS. 5D-5F show expression of GFP from AAV204 driven by the VMD2 (vitelliform macular degeneration-2) promoter (SEQ ID NO:159). $2.5\times10^{12}$ viral genomes (vg) vector were administered intravitreally and expression was monitored at 14 days and at 28 days (sacrifice). Scanning laser ophthalmoscopy (SLO) imaging was performed at Day 14 (FIG. 5D) and Day 28 (FIG. 5E). FIG. 5F shows GFP expression and nuclei (DAPI) in the periphery at Day 28.

Figure 6:
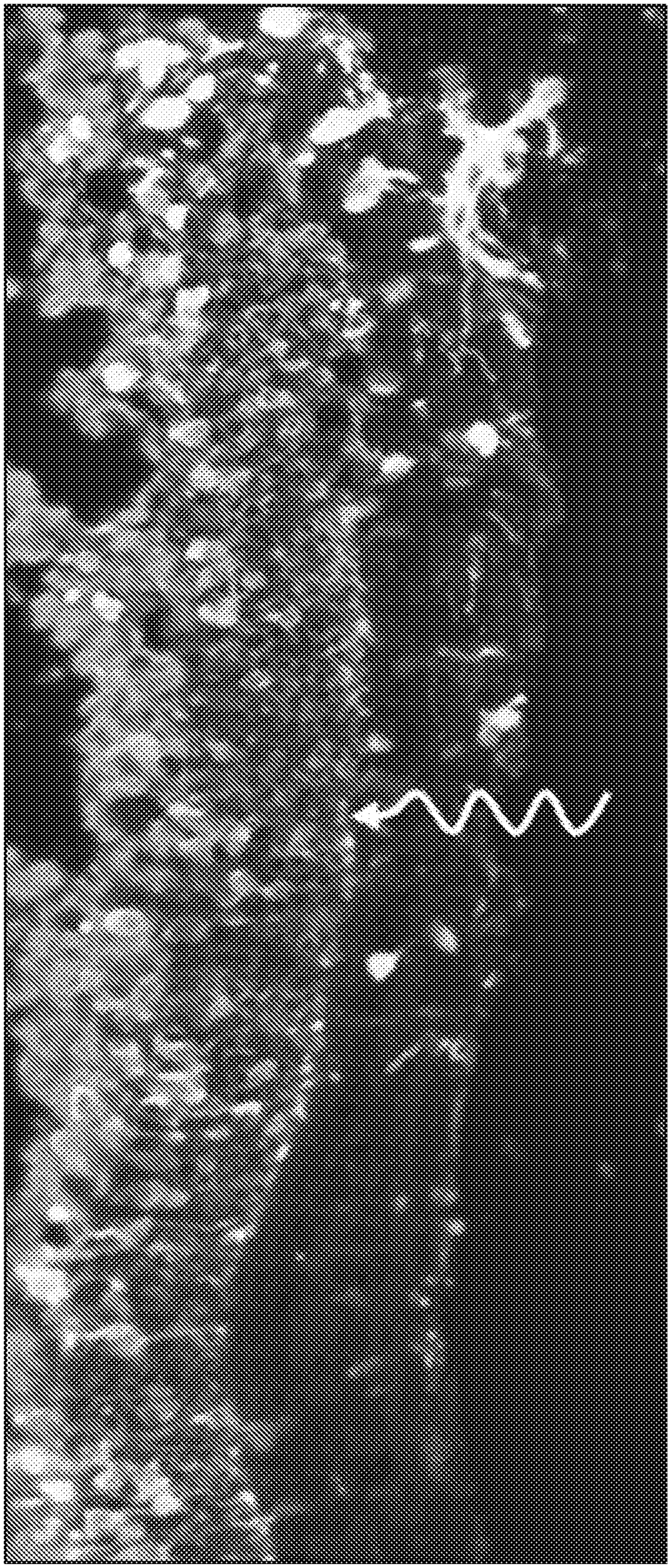
FIG. 6 shows IHC analysis of NHP eye explant transduction performed ex vivo.

AAV204-GFP was also evaluated in non-human primate explant cultures. Cynomolgus monkey retinas were isolated from eyes within 1 h of the animal being humanely euthanized. Retinas were dissected into ~5×5 mm sections and cultured in transwell insert culture dishes. One day post-isolation, explants were transduced with AAV204-GFP in culture media and incubated for one-week post-transduction. Explants were fixed, embedded and sectioned for standard immunohistochemistry. Sections were stained for GFP (green) and rhodopsin (red) and imaged using fluorescence microscopy. Sections showed significant GFP expression in the photoreceptor layer after AAV204-GFP transduction (FIG. 6).

Figure 7:
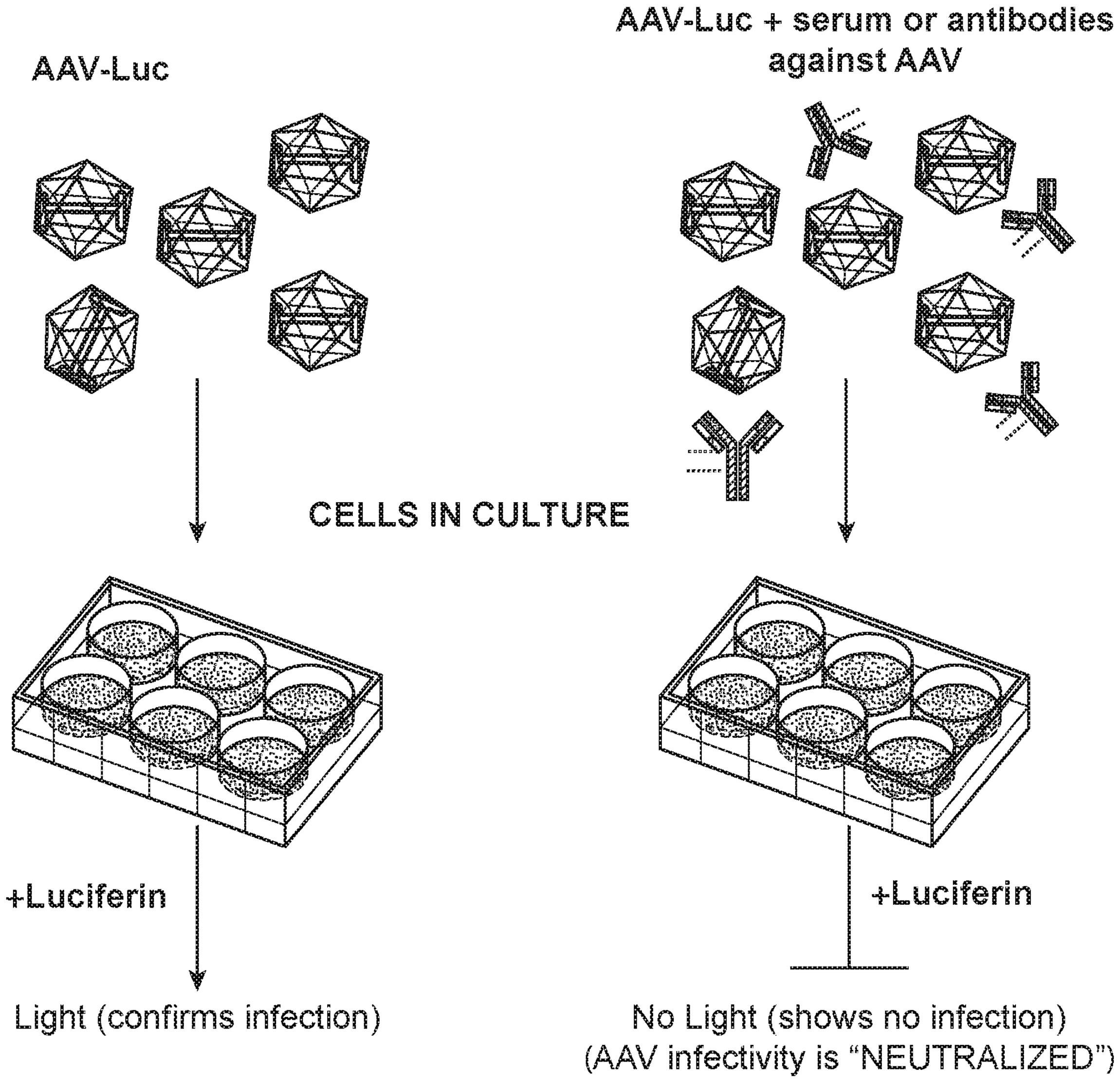
FIG. 7 Neutralizing antibody quantitation strategy. Absence of luminescence indicated that target AAV was bound by neutralizing antibodies.
Figure 8:
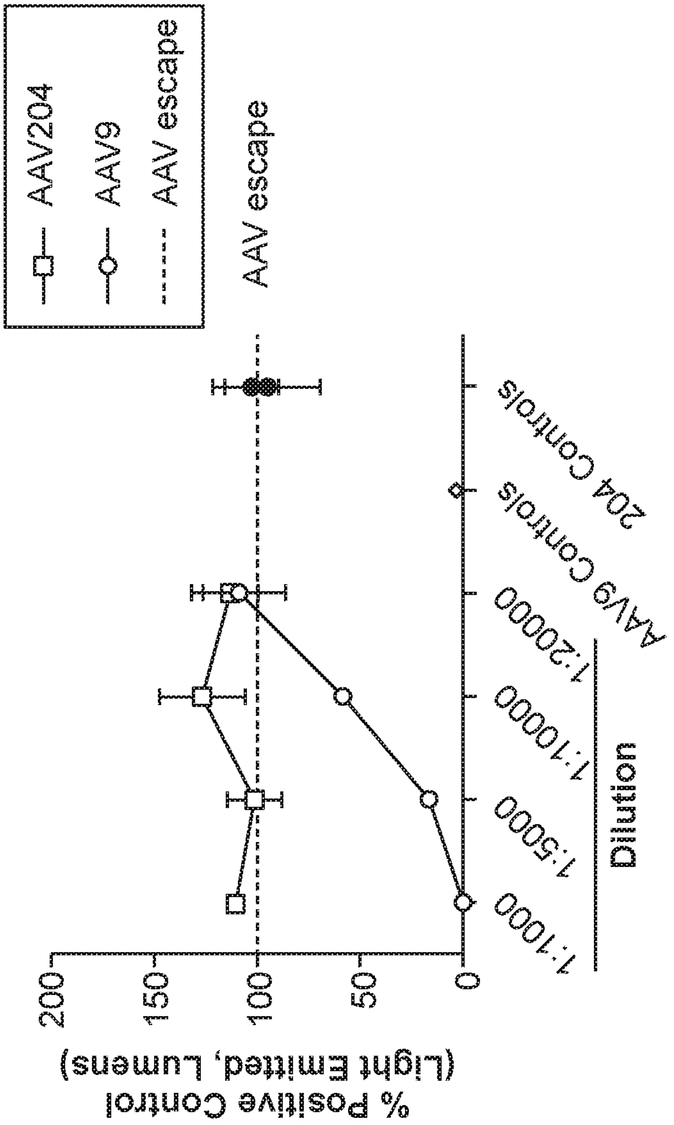
FIG. 8 demonstrates different immunogenicity of AAV204 and AAV9. Neutralizing antibody titer was obtained using an in-house developed process. Either AAV9-Luc or pA-AAV204-Luc was incubated with various dilutions of serum at an MOI of 25,000. After incubation, the virus/serum mixture was transferred to wells containing 20,000 Lec2 cells and incubated with the cells for 24 hours, after which time luminescence was measured and compared to a control value from cells transduced with only virus at the same MOI.

Immunogenicity of the AAV204 vector was evaluated using the neutralizing antibody assay (FIG. 7). Either AAV9-Luc virus comprised of AAV9 capsid and a firefly luciferase expression cassette or AAV204-Luc virus comprised of AAV204 capsid and a firefly luciferase expression cassette was incubated with various dilutions of serum from an AAV9-treated human subject (60 days post-treatment) at MOI of 25,000. After incubation the virus/serum mixture was transferred to wells containing 20,000 Lec2 cells. Serum-treated cells were incubated for 24 hours and then emitted luminescence was measured and compared to a control value from cells transduced with untreated virus at the same MOI. The results showed that AAV204 vector particles had reduced immunogenicity compared to AAV9 vector particles (see FIG. 8).

Example 3

Amelioration of Defects Caused by Mutations in the Cystic Fibrosis Transmembrane Conductance Regulator (CFTR) Gene Using a CFTR Transgene Delivered by AAV204 Viral Vector AAV204 vector particles containing a nucleic acid encoding a codon-optimized CFTR transgene (that is, a CFTRΔR gene comprising nucleic acid sequence set forth in SEQ ID NO: 4, and encoding a protein lacks amino acids 708-759 of full length CFTR) were prepared using an pA-CF3 plasmid (SEQ ID NO: 89) having, from 5' to 3', a 5' ITR, a mouse U1a promoter (SEQ ID NO: 96), the CFTRΔR transgene, a synthetic poly-A sequence (49 bp) and a 3' ITR. The resulting particles were used to deliver the CFTRΔR transgene into either cells or mice, as described below.

Figure 10A:
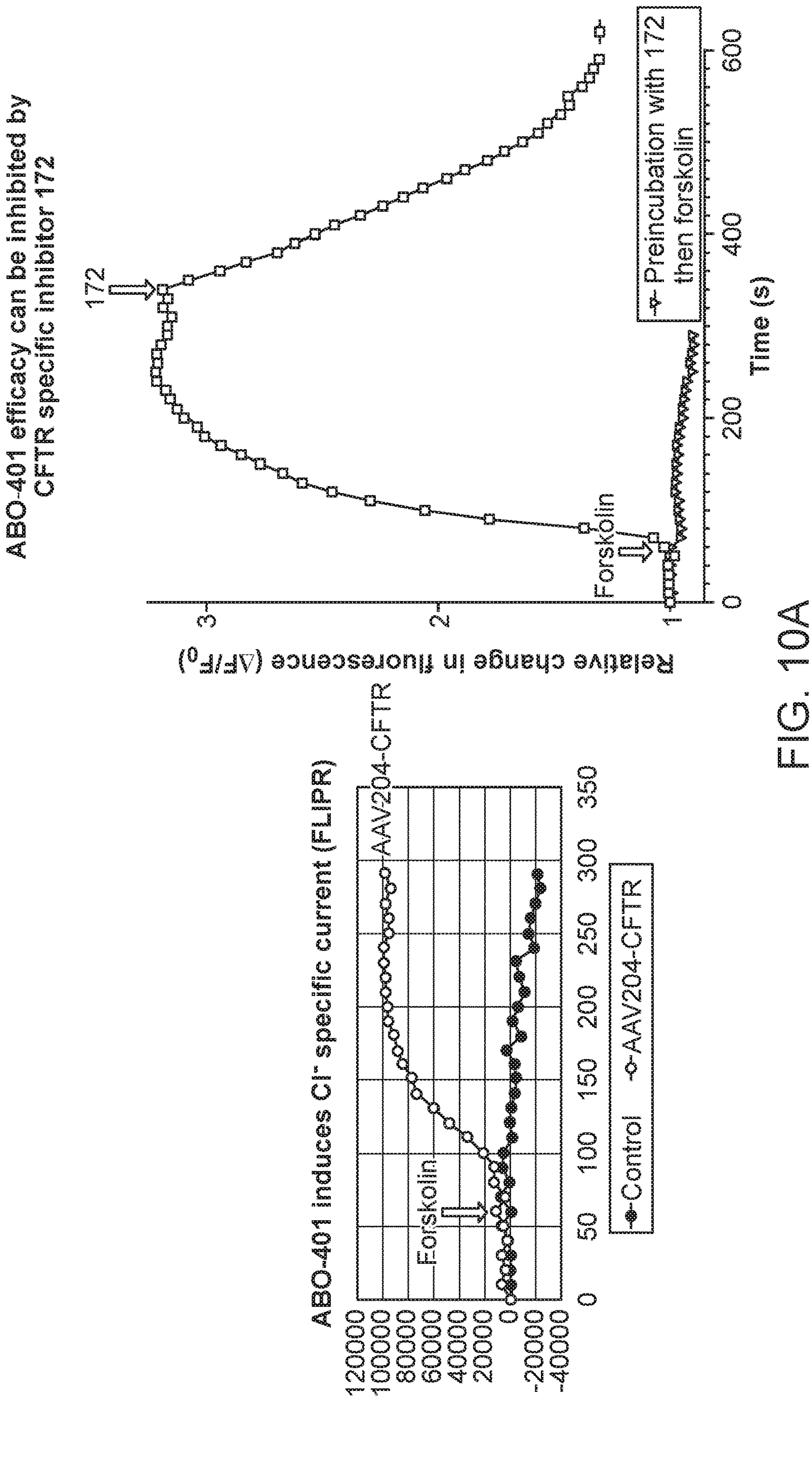
FIGS. 10A-10C shows functionality of CFTRΔR and full-length expression cassette by FLIPR assay (FIG. 10A) and dose response (FIG. 10B) to AAV204 packed CFTRΔR expression cassette treatment.
Figure 10B:
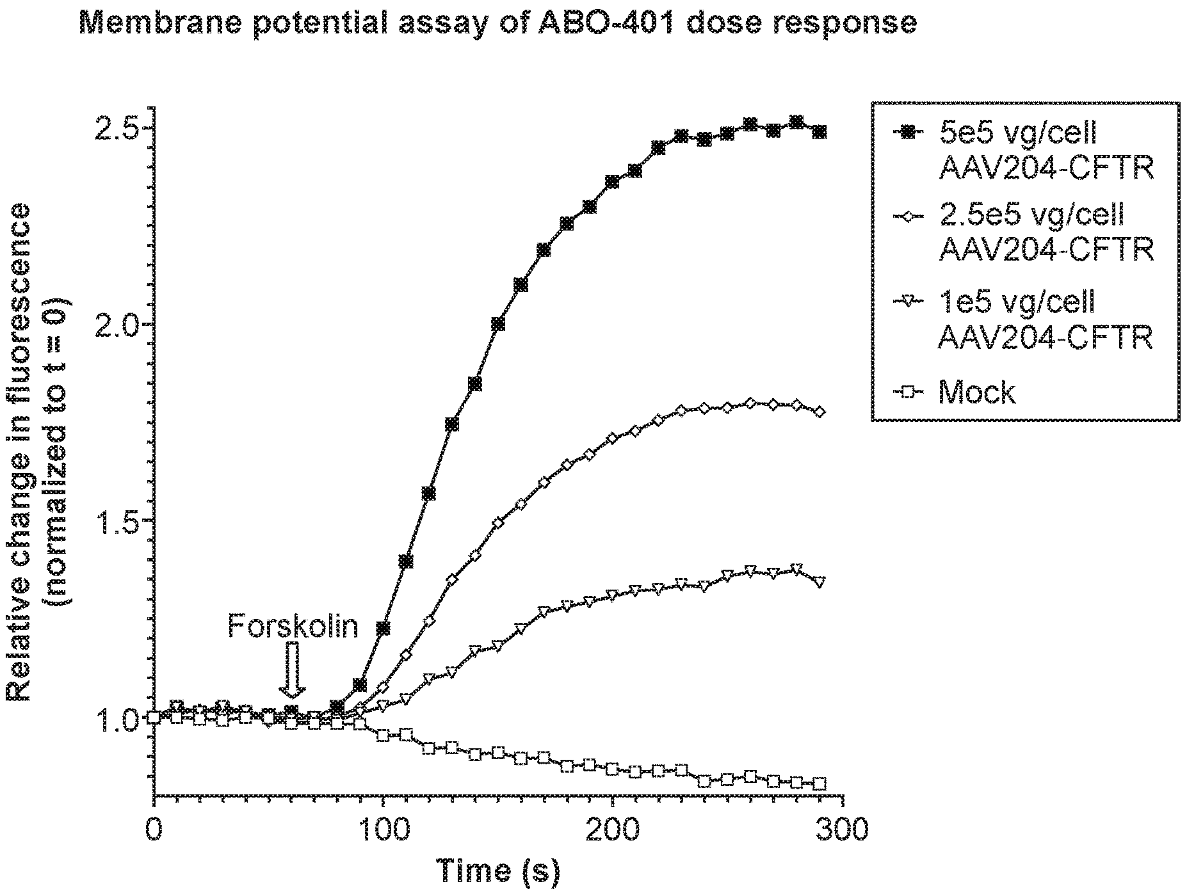

In vitro assays: An AAV204 viral vector comprising the CFTRΔR transgene was used to transduce Lec2 cells. The FLIPR assay was used to measure the functionality of the CFTRΔR transgene delivered by the AAV204-CFTRΔR viral vector. The results showed that human CFTR (hCFTR) ion channel function was restored by stimulation with forskolin, a known opener of the CFTR chloride channel, when the cells were transduced using the AAV204-CFTRΔR viral vector, as compared to cells transfected with a control AAV204 viral vector lacking a transgene. Further, chloride-specific current signal was increased by 3.5-fold compared to baseline in cells transduced using the AAV204-CFTRΔR viral vector as compared to the control. See FIG. 10A, left panel. Pre-incubation with a selective inhibitor of CFTR, CFTRinh-172 (4-[[4-Oxo-2-thioxo-3-[3-trifluoromethyl) phenyl]-5-thiazolidinylidene] methyl]benzoic acid) (Tocris Bioscience) (available at http://tocris.com/products/cftrinh-172_3430) prevented forskolin-induced membrane potential changes in the presence of CFTRΔR. See FIG. 10B. These results demonstrate the functionality of the CFTRΔR expression cassette.

Figure 10C:
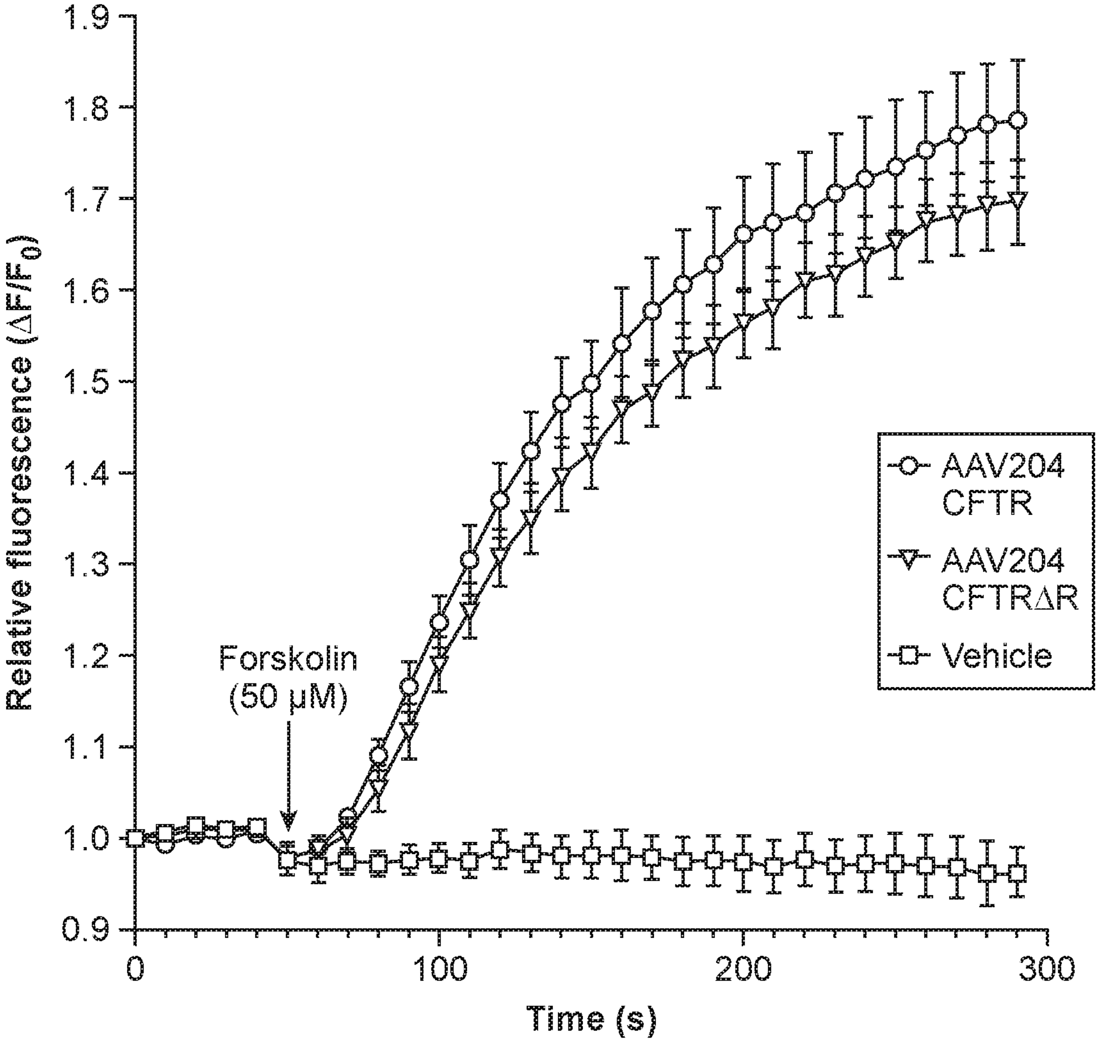

A membrane potential assay was performed to evaluate whether the functionality of the CFTRΔR expression cassette was dependent on the amount of the AAV204-CFTRΔR virus used for transfection. See FIG. 10B. The results showed that the membrane potential changes in the presence of CFTRΔR were indeed dependent on the dose of the virus particle delivering the transgene. We also expressed the full-length CFTR using AAV204 and obtained increased fluorescence in response to forskolin. (FIG. 10C). We also confirmed by western blot that expression from AAV204 results in fully-processed full-length CFTR and CFTRΔR (data not shown). These data confirm that that AAV204 delivery of either protein restores chloride channel function in vitro.

In vivo assays using mouse model: An AAV204 viral vector comprising a luciferase transgene was administered to mice intratracheally. Bioluminescence imaging (BLI) was used to assess the ability of an AAV204 viral vector to transduce lung cells, as reflected by luciferase expression, in comparison to AAV6. FIG. 9, upper panel, shows that luciferase expression mediated by the AAV204 viral vector was about 3.5-fold higher compared to the AAV6 viral vector. FIG. 9, lower panel illustrates expression, shown by ex vivo BLI, in the left and right lungs with little or no expression in the liver or kidney. These results demonstrate that an AAV204 viral vector is capable of promoting enhanced expression of a reporter transgene in specific tissues in mice.

Figure 12A:
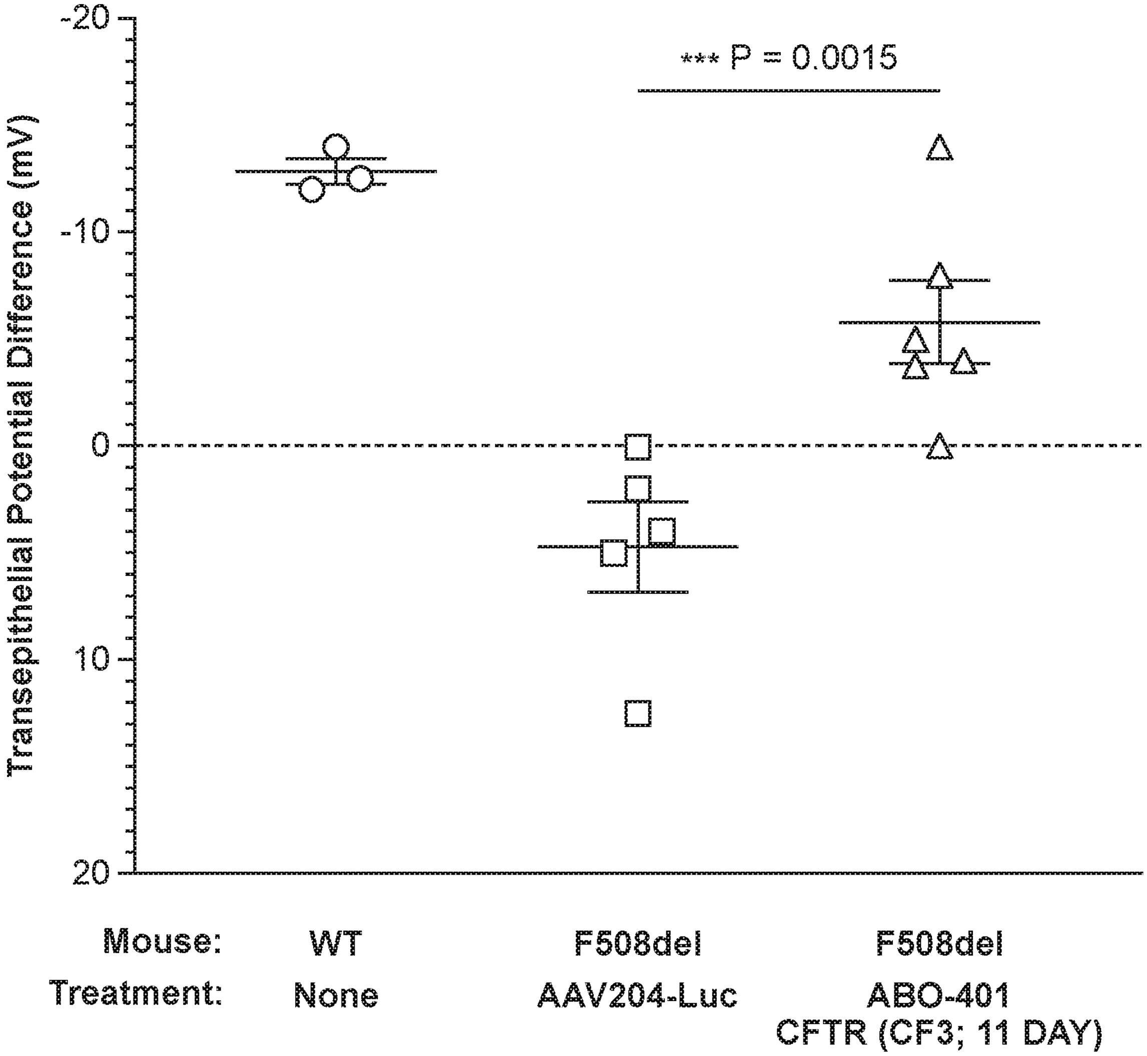
FIG. 12A shows the in vivo effect of administering AAV204 particles comprising CFTR transgene nasal to mouse models of cystic fibrosis.

The efficacy of AAV204 vector particles comprising the CFTRΔR transgene was tested in a mouse model of cystic fibrosis referred to as "F508del". These mice carry a mutant CFTR gene comprising a deletion of a single amino acid, F508, which is the most common CFTR mutation in humans, affecting approximately 90% of CF patients (see, e.g., Park et al., PLoS One (Feb. 10, 2016) 11(2): e0149131). AAV204 vector particles comprising the CFTRΔR transgene or the luciferase transgene were intranasally administered to wild-type and F508del mice. Nasal potential difference (NPD) was measured to determine the functionality of the CFTRΔR transgene. As shown in FIG. 12A, mice that were administered the AAV204-CFTR vector particles showed corrected forskolin-stimulated current, as compared to mice administered the control vector containing a luciferase transgene (AAV204-Luc).

Figure 11C:
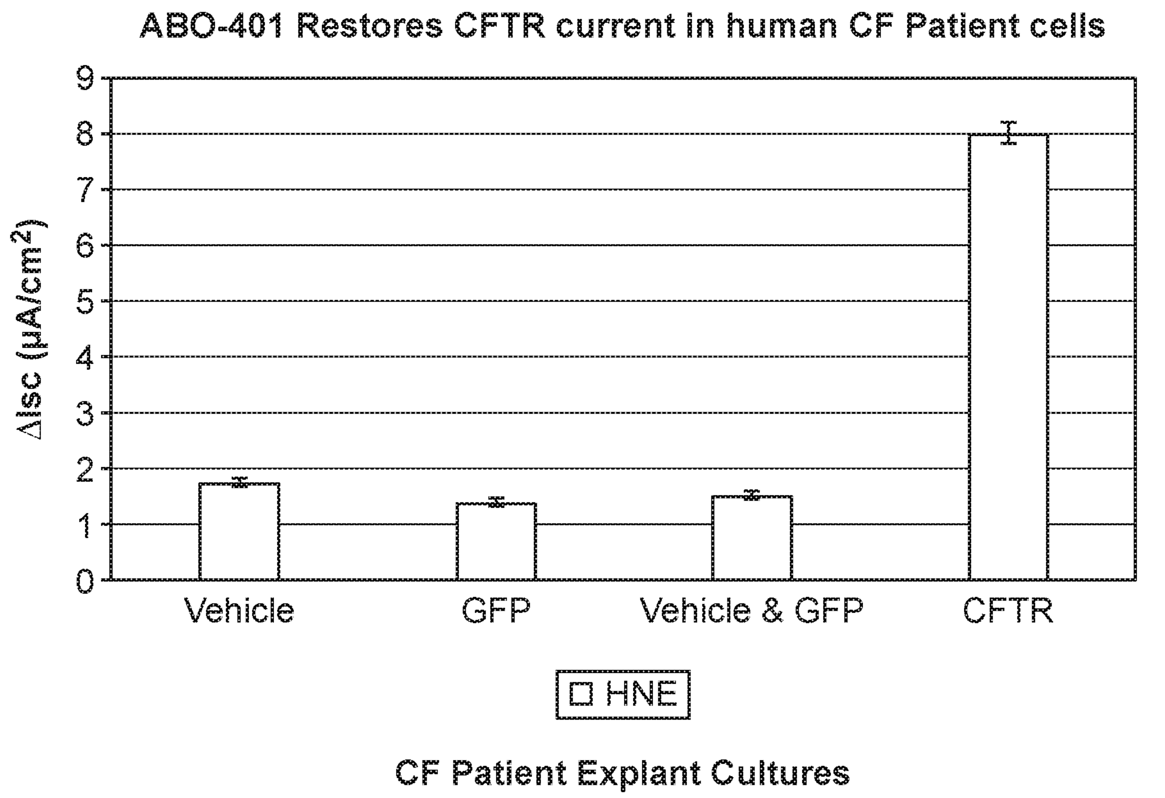

Assays using human patient cells: The ability of AAV204 vector particles comprising the CFTRΔR transgene to mediate delivery of hCFTR into human airway cells isolated from patients suffering from cystic fibrosis, and to correct chloride transport in these cells was evaluated. When AAV204 vector particles comprising GFP transgene were applied to the apical and basolateral compartments, AAV204 transduced human nasal and bronchial epithelial (HNE and HBE) cells isolated from cystic fibrosis patients, and maintained in air-liquid interface cultures. See FIG. 11A. The CFTRΔR protein was membrane-localized in these cells; see FIG. 11B, left panel. FIG. 11B, right panel shows a western blot illustrating membrane localization.

Figure 12B:
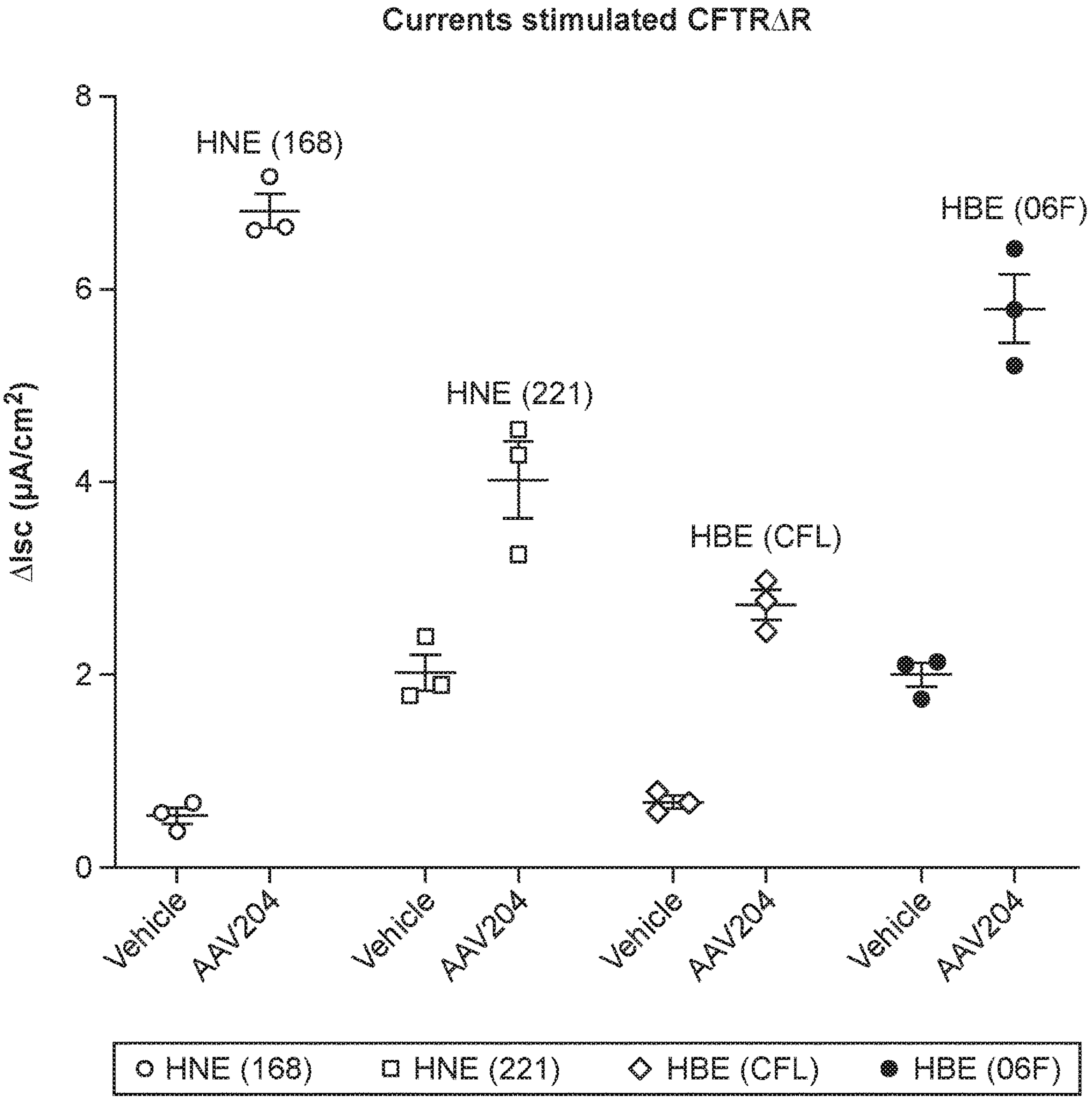
FIG. 12B shows effect of AAV204/CFTRΔR treatment (by increase of nasal membrane potential) in different CF patient cells.

The functionality of AAV204 vector particles comprising the CFTRΔR transgene was evaluated as described below. The results show that CFTR current was restored in explant cultures of human nasal epithelial cells derived from cystic fibrosis patients following transduction of the AAV204 vector comprising the CFTRΔR transgene. See FIG. 11C. It was also tested whether the AAV particles could restore CFTR function in nasal and bronchial cells isolated from human cystic fibrosis patients by measuring changes in transmembrane conductance using an Ussing chamber, which is known to those skilled in the art to measure the movement of ions between the surfaces of polarized epithelium. Briefly, in an Ussing chamber the apical and basolateral surfaces of the epithelium face two separate chambers containing symmetrical salt solutions. Ion transport across the epithelium produces a potential difference between the two chambers. Diffusion forces that would otherwise create a potential difference are actively cancelled out by applying a short-circuit current ($I_{sc}$) across the epithelium. This allows for the movement of ions by active transport following stimulation, to be measured by changes in this current ($\Delta I_{sc}$) and calculation of cystic fibrosis transmembrane conductance, as is well-known in the art. See, e.g., Li et al., J. Cystic Fibrosis (July 2004) 3:123-126; Park et al., PLoS One (Feb. 10, 2016) 11(2): e0149131. As shown in FIG. 12B, when CFTRΔR was transduced, forskolin-stimulated, CFTRinh-172-inhibited current was restored to 6-7 $\mu A/cm^2$ as compared to vehicle.

In sum, our results show that AAV204 mediates efficient delivery of highly-expressed, functional CFTR, and further, restores CFTR function in cells in vitro, in mouse models and in explant cultures of human patient cells. These results demonstrate the therapeutic potential in cystic fibrosis of AAV204 particles comprising the CFTRΔR transgene.

Example 4

Amelioration of Defects Caused by CLN3 Disease Using Optimized CLN3 Transgenes Delivered by AAV214 Vector An AAV capsid (AAV214) with enhanced tropism for CNS tissue after systemic administration, and an optimized CLN3 (comprising a nucleic acid sequence of SEQ ID NO: 122) transgene cassette to improve biodistribution and expression in CNS and somatic tissues, were developed and tested for functionality. AAV9 was used as a benchmark to assess the tropism of AAV214 and the biodistribution of the optimized CLN3 transgene cassette in a mouse model of juvenile neuronal ceroid lipofuscinosis, which lacks a 1.02 kb segment spanning exons 7 and 8 of CLN3 (CLN3Δex7/8) in a C57BL/6 background. This CLN3 deletion is one that occurs in approximately 85% of mutated CLN3 alleles and recapitulates many disease phenotypes associated with human disease, including motor deficits, glial activation, and progressive accumulation of lysosomal storage material.

TABLE 6

Study design with CLN3$^{\Delta ex7/8}$ mice model

| Group | Strain | Treatment | Route | No. Animals | Dose amount (vg/kg) | Dose volume (ul/animal) |
|---|---|---|---|---|---|---|
| 1 | CLN3$^{\Delta ex7/8}$ | vehicle | IV | 3 male<br>6 female | 0 | 200 |
| 2 | CLN3$^{\Delta ex7/8}$ | AAV9-CLN3 | IV | 5 male<br>5 female | $2 \times 10^{13}$ | 200 |
| 3 | CLN3$^{\Delta ex7/8}$ | AAV214-CLN3 | IV | 5 male<br>5 female | $2 \times 10^{13}$ | 200 |

Figure 13:
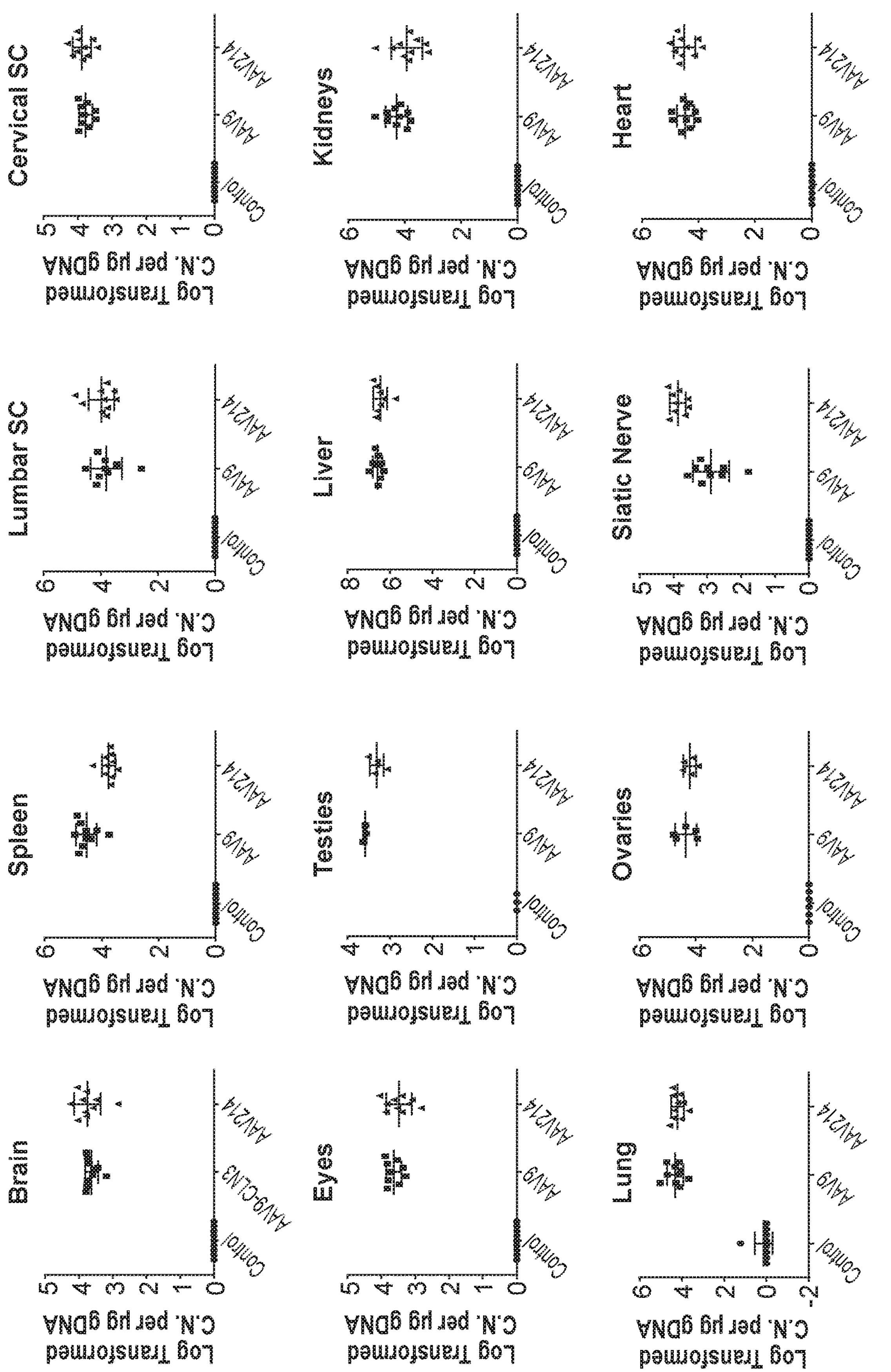
FIG. 13 shows the bio distribution of the AAV9-CLN3 and AAV214-CLN3 vectors in CLN3Δex7/8 mice model 30 days after intravenous administration of viral particles.

AAV9 and AAV214 viral vectors each comprising the CLN3 transgene (AAV9-CLN3 and AAV214-CLN3, respectively) were intravenously administered to wild type mice at a dosage of $2.0\times10^{13}$ vg/kg (viral vector genomes/kilogram). See Table 6. After 30 days, the animals were humanely sacrificed and tissues were harvested for biodistribution analysis, which evaluates the delivery of the vector particles to several different organs, including the primary regions of the CNS and the spinal cord (cervical and lumbar). A t-test analysis of log-transformed data did not reveal a statistically significant difference between AAV214-CLN3 and AAV9-CLN3 in biodistribution values for most tissues that were tested (see FIG. 13). However, the sciatic nerve demonstrated statistically significantly (p=0.0001) higher (744%) biodistribution using AAV214-CLN3 compared to AAV9, while spleen was better transduced with AAV9-CLN3 (p<0.0001). Current studies assessing expression and dose response over a longer duration indicate that AAV214-CLN3 can be used for effectively delivering the CLN3 expression cassette to CNS tissues via systemic administration.

Figure 14:
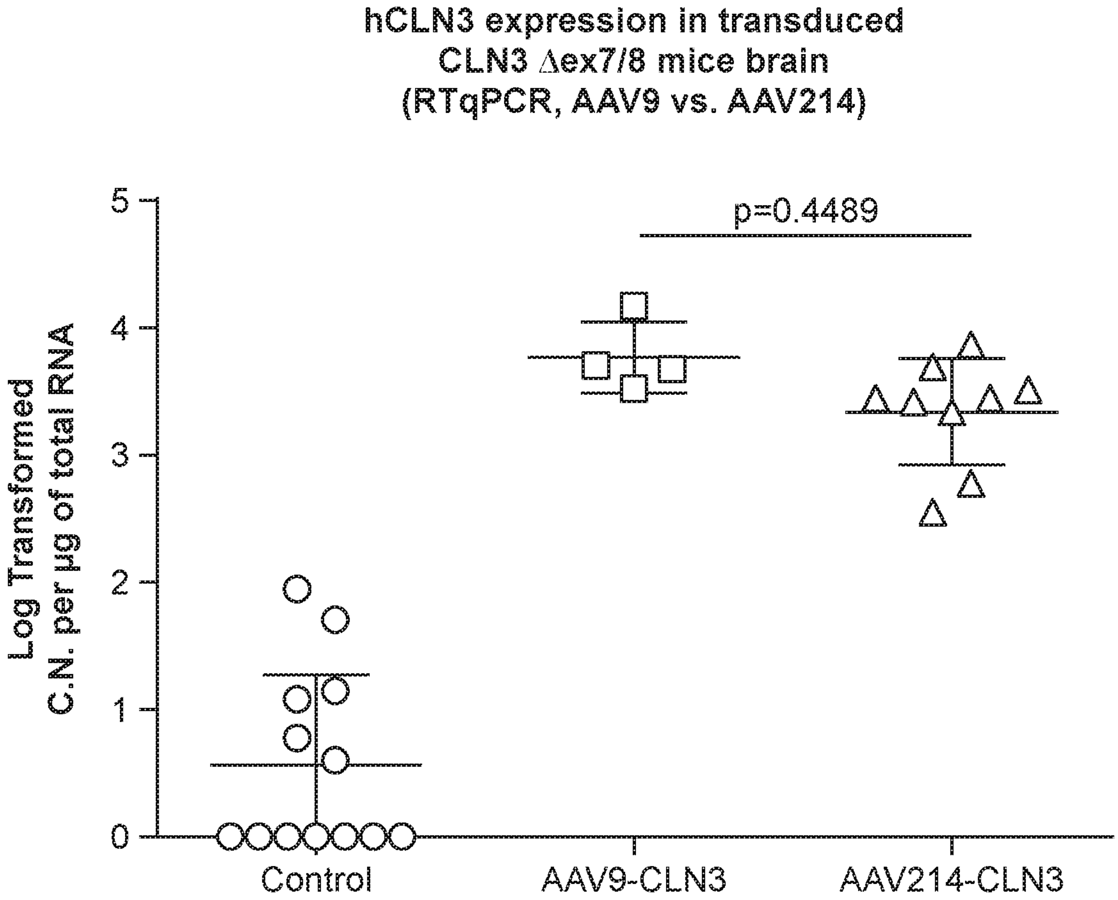
FIG. 14 shows the expression of AAV9-CLN3 and AAV214-CLN3 vectors in CLN3Δex7/8 mice brain tissues as measured by RT-qPCR.

Expression of the CLN3 transgene was assessed by RTqPCR using total RNA isolated from left hemispheres of the brain. One-way ANOVA analysis of log-transformed data revealed no statistically significant difference in mean CLN3 expression values for AAV9-CLN3 versus AAV214-CLN3 dosed animals (p=0.4489). However, both tested viral vectors produced higher CLN3 expression levels than control (p<0.0001; FIG. 14).

In summary, these results showed that the novel AAV214 viral vector comprising an optimized CLN3 expression cassette demonstrates equivalent tropism to AAV9 in the most tissues including CNS if dosed via systemic administration in mouse model of CLN3 disease. These results indicate that the AAV214 vector comprising the optimized CLN3 transgene described herein can be used in prevention and treatment of CLN3 disease.

Example 5

Figure 15:
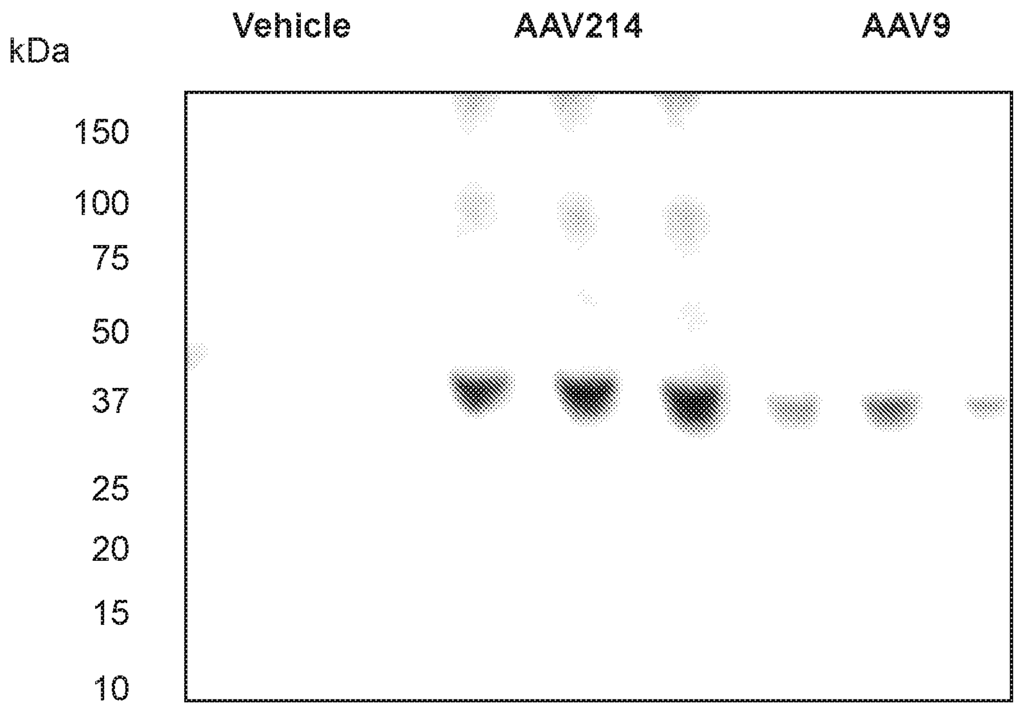
FIG. 15 shows the immunoblot of GLA expression in transduced HEK293 cells.
Figure 16:
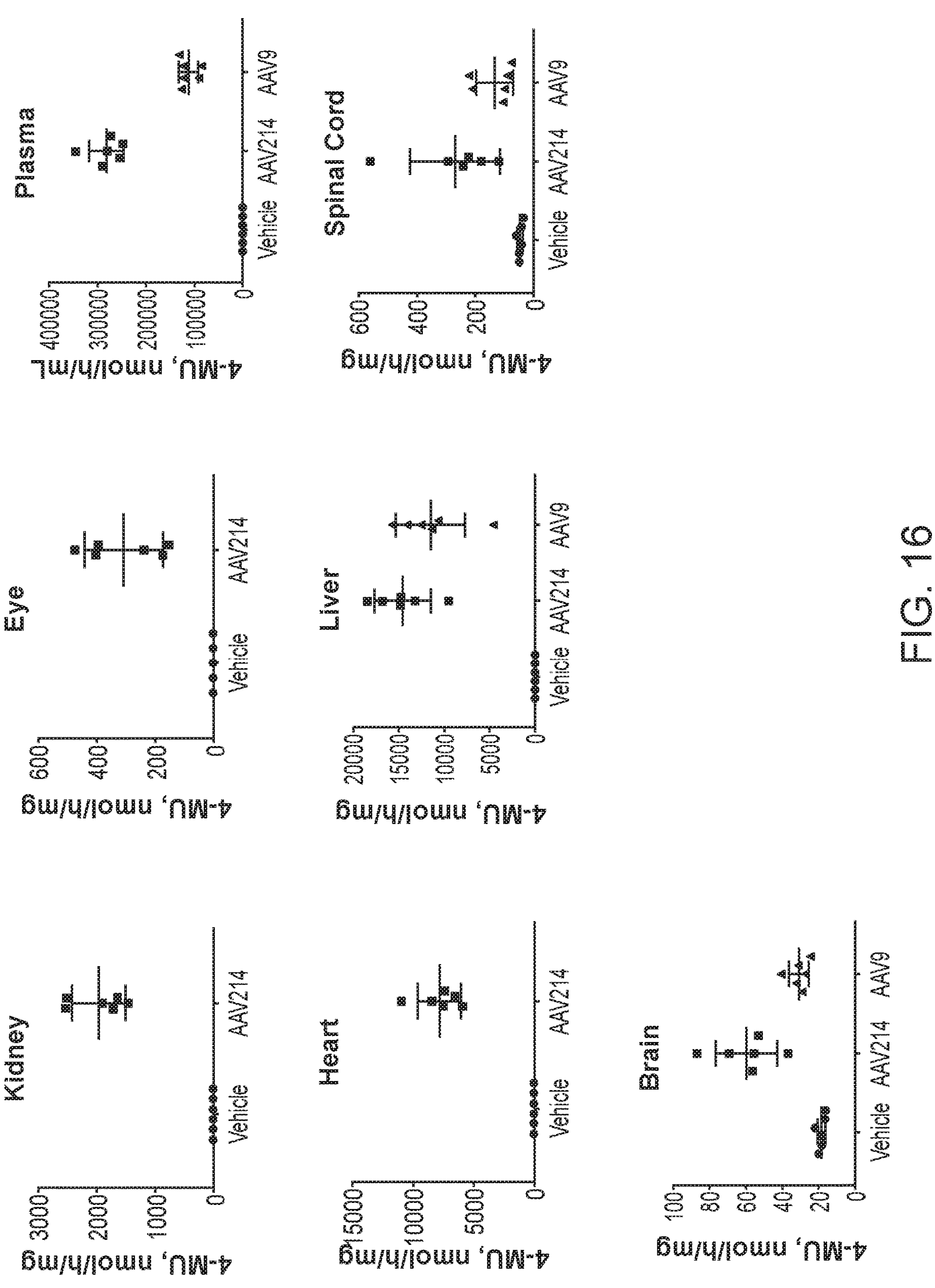
FIG. 16 shows the enzymatic activities (supraphysiological) of GLA in plasma, brain, liver, spinal cord, heart, kidney, and eye in C57BL/6 mice after AAV administration.
Figure 17:
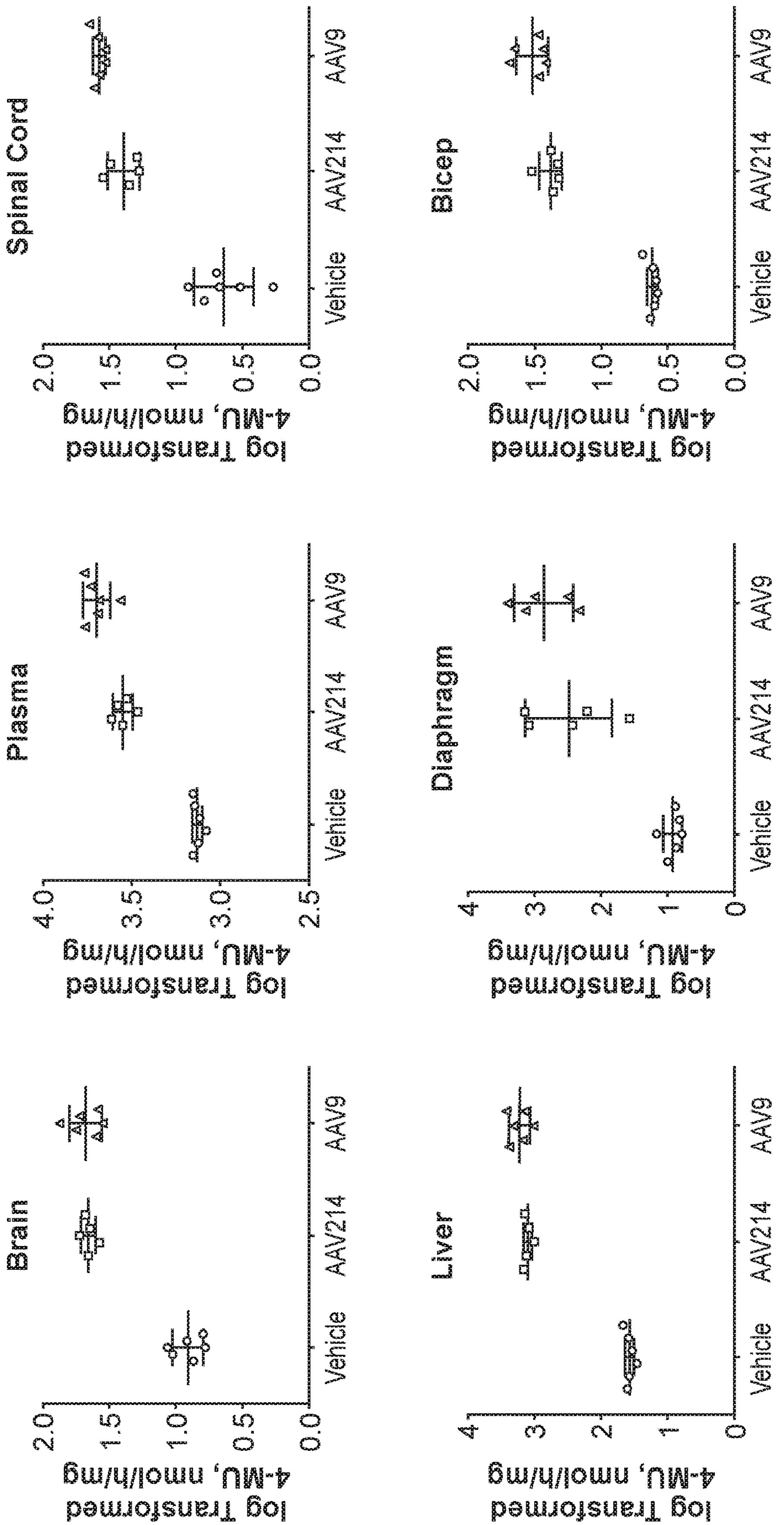
FIG. 17 shows the enzymatic activities of GAA in brain, bicep, diaphragm and liver in C57BL/6 mice after AAV administration by intravenous injection.
Figure 18A:
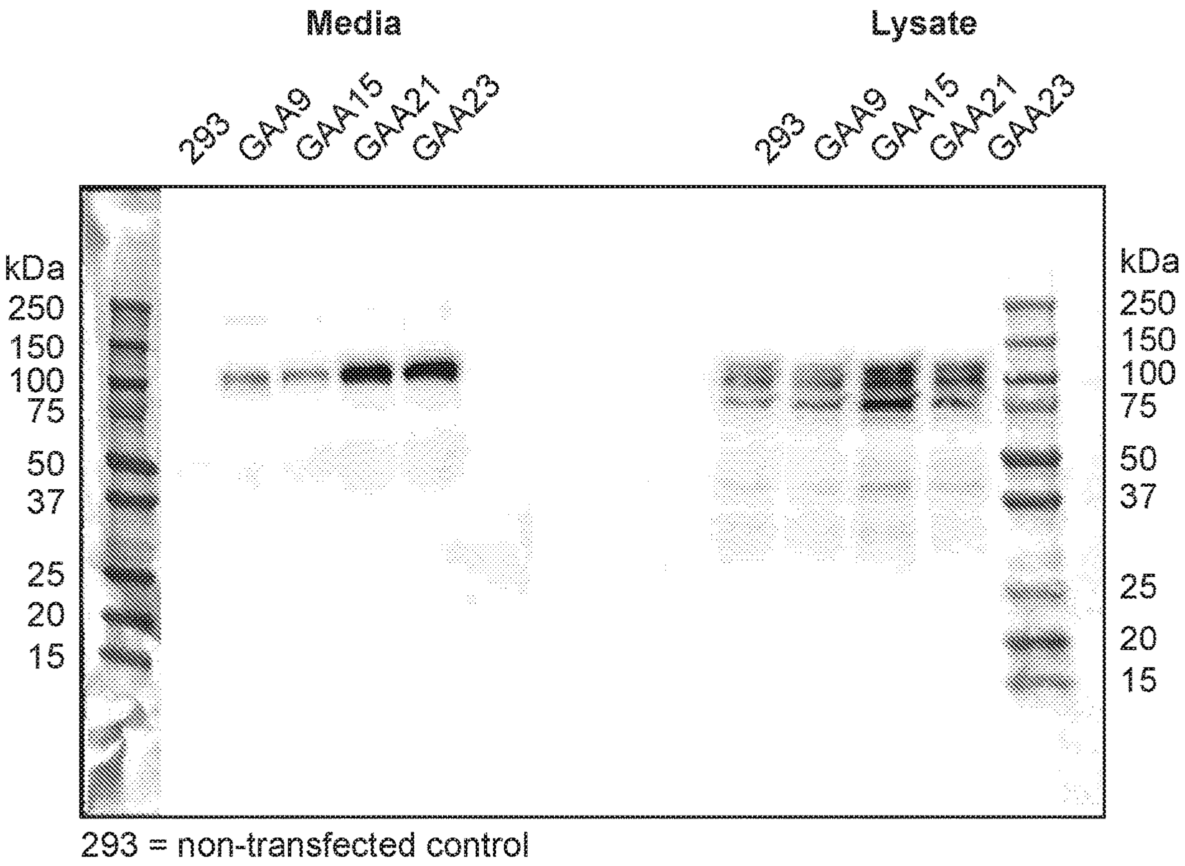

Amelioration of Defects Caused by Fabry Disease Using Optimized GLA Transgenes Delivered by AAV214 Vector AAV9 and AAV214 viral vectors comprising a CBh promoter, CBA-MVM hybrid intron, natural GLA transgene sequence, and TK65 poly-A site were administered to wild type C57BL/6 mice by IV injection (see Table 7). Expected transgenic GLA protein size in plasma samples was confirmed by immunoblotting (FIG. 15). GLA enzymatic activity was assessed in plasma, brain, spinal cord, heart, kidney, liver and eye. Statistical analysis performed on log-transformed GLA enzyme activity values showed that all AAV214-GLA transduced samples had statistically significantly higher GLA activity compared to control (p<0.0001). GLA enzyme activity was also statistically significantly higher in AAV214-GLA transduced plasma, brain and spinal cord tissues compared to AAV9-GLA (FIG. 16). In summary, analysis of GLA enzymatic activity shows effective transduction of AAV214 constructs into multiple target tissues, particularly CNS tissues, demonstrating therapeutic benefit of the AAV214 vector in subjects with Fabry disease.

TABLE 7

Animal Study Design

| Group | Mouse Strain | Vector | Dose (vg/kg) | Dose Volume (microliter) | Animals |
|---|---|---|---|---|---|
| 1 | C57BL6 | Vehicle | 0 | 0 | 6 |
| 2 | C57BL6 | AAV9-hGLA | $1\times10^{13}$ | 200 | 6 |
| 3 | C57BL6 | AAV214-hGLA | $1\times10^{13}$ | 200 | 6 |

No acute toxic effects from systemic administration of the GLA transgene via an AAV9 or AAV214 viral vector were observed after the 10-day study in wild type animals. No animals treated in this experiment exhibited any adverse effects due to treatment. The effective delivery of AAV9 and AAV214 to target tissues, notably to the CNS, heart and kidney, after systemic administration demonstrates the ability to safely transduce key target tissues associated with Fabry disease.

Example 6

Amelioration of Defects Caused by Pompe Disease Using Optimized GAA Transgenes Delivered by AAV214 Vector AAV9-GAA and AAV214-GAA vectors comprising a CBh promoter, CBA-MVM hybrid intron, codon optimized GAA transgene sequence, and BGH poly-A site were intravenously dosed by into wild-type C57BL/6 mice (see Table 8). In order to determine whether the transgenes were effectively delivered to the target tissues, GAA enzymatic activity protein was tested in brain, spinal cord, diaphragm, bicep, liver and plasma from the treated mice. One-way ANOVA analysis of log-transformed values of GAA enzymatic activity revealed that all tested tissues of dosed animals had statistically significantly (p<0.002) higher GAA activity compared to control animals. No statistically significant difference in enzyme activity was shown between AAV214 and AAV9 dosed tissues, except for in plasma, where AAV9 had slight advantage (p=0.0018) (FIGS. 19A-E). Analysis of GAA enzymatic activity confirmed effective transduction of AAV214 constructs into multiple target tissues, including an ability to cross the blood brain barrier, and transduction to tissues important for treating Pompe disease, such as, biceps and diaphragm (FIG. 19). These results suggest that a single intravenous injection of an AAV214 viral vector comprising an optimized GAA expression cassette as described herein may be sufficient to achieve delivery of the corrected GAA transgene to the target tissues. No acute toxic effects from the systemic administration of the GAA transgene via the AAV9 or AAV214 vector were observed after the 10-day study in wild type animals.

Figure 19A:
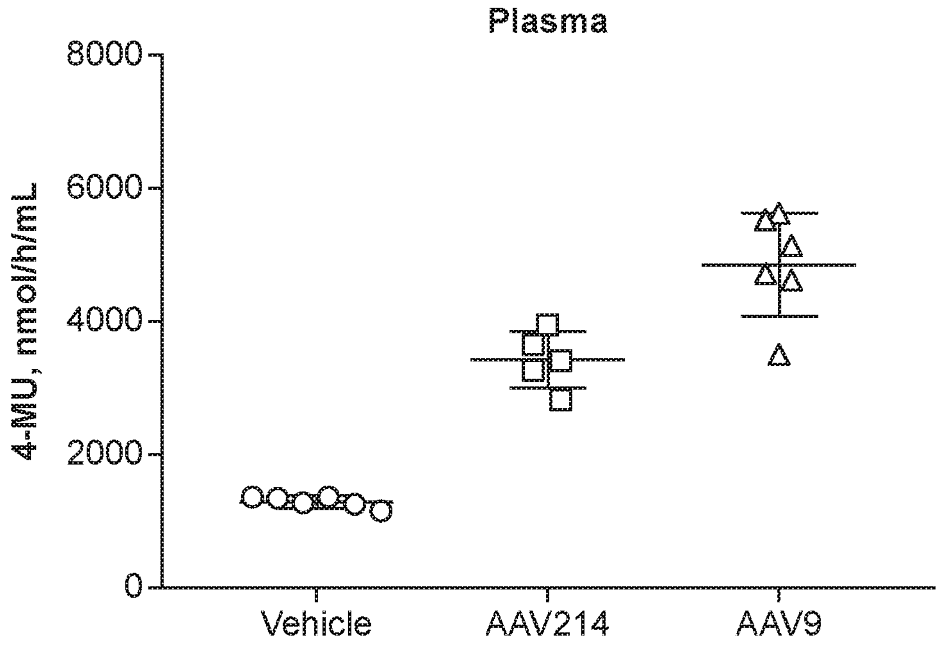
FIGS. 19A-19E shows the enzymatic activities of GAA in plasma (FIG. 19A), brain (FIG. 19B), bicep (FIG. 19C), diaphragm (FIG. 19D) or liver (FIG. 19E) in C57BL/6 mice after AAV administration.
Figure 19B:
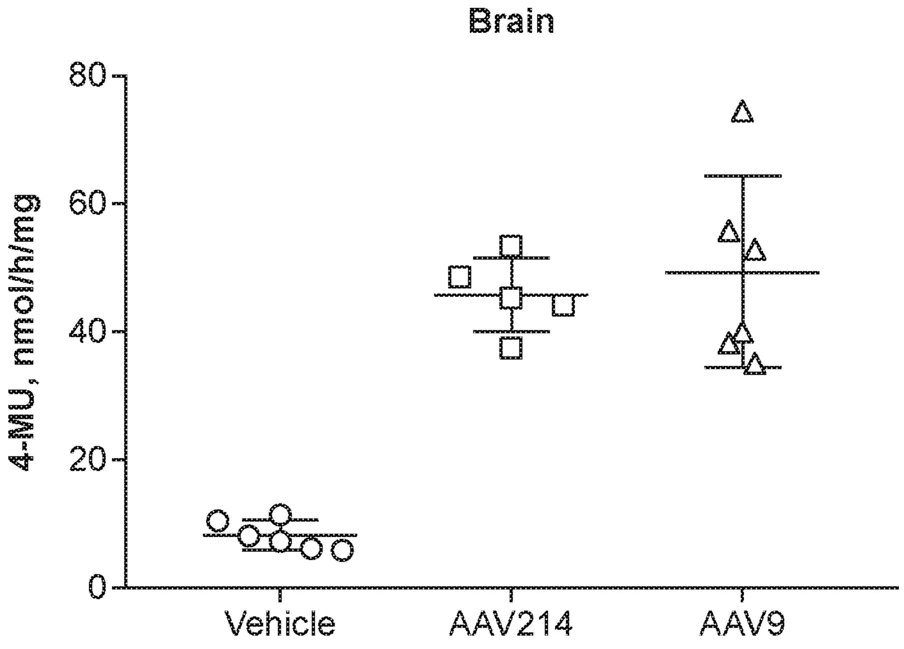
Figure 19C:
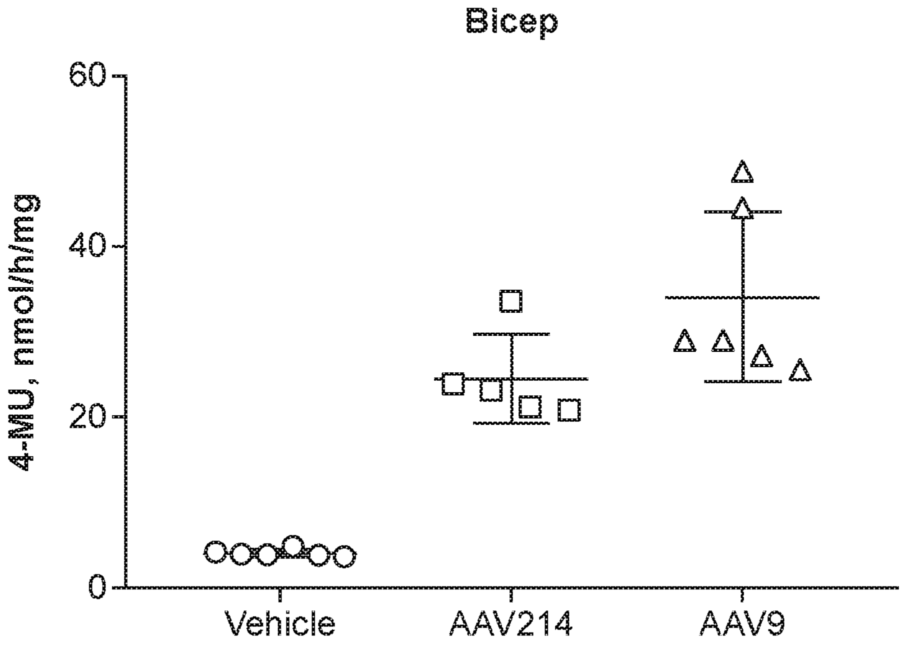
Figure 19D:
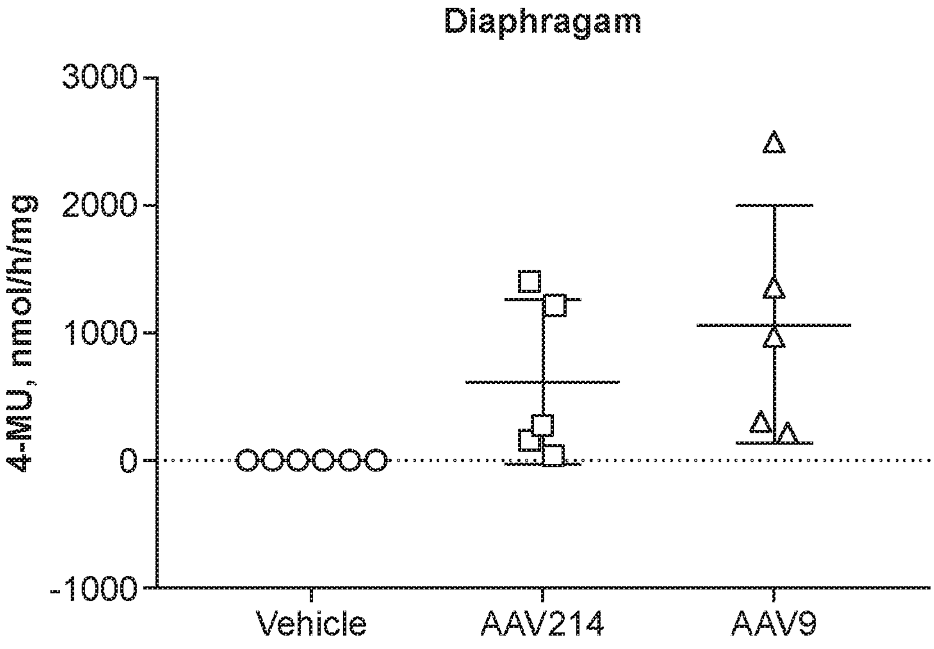
Figure 19E:
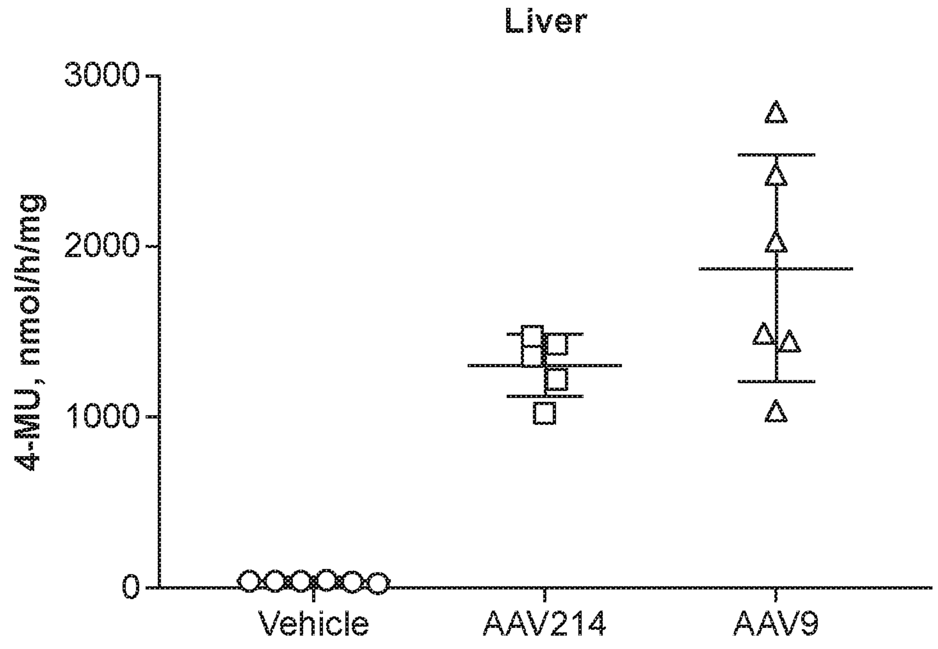
Figure 19F:
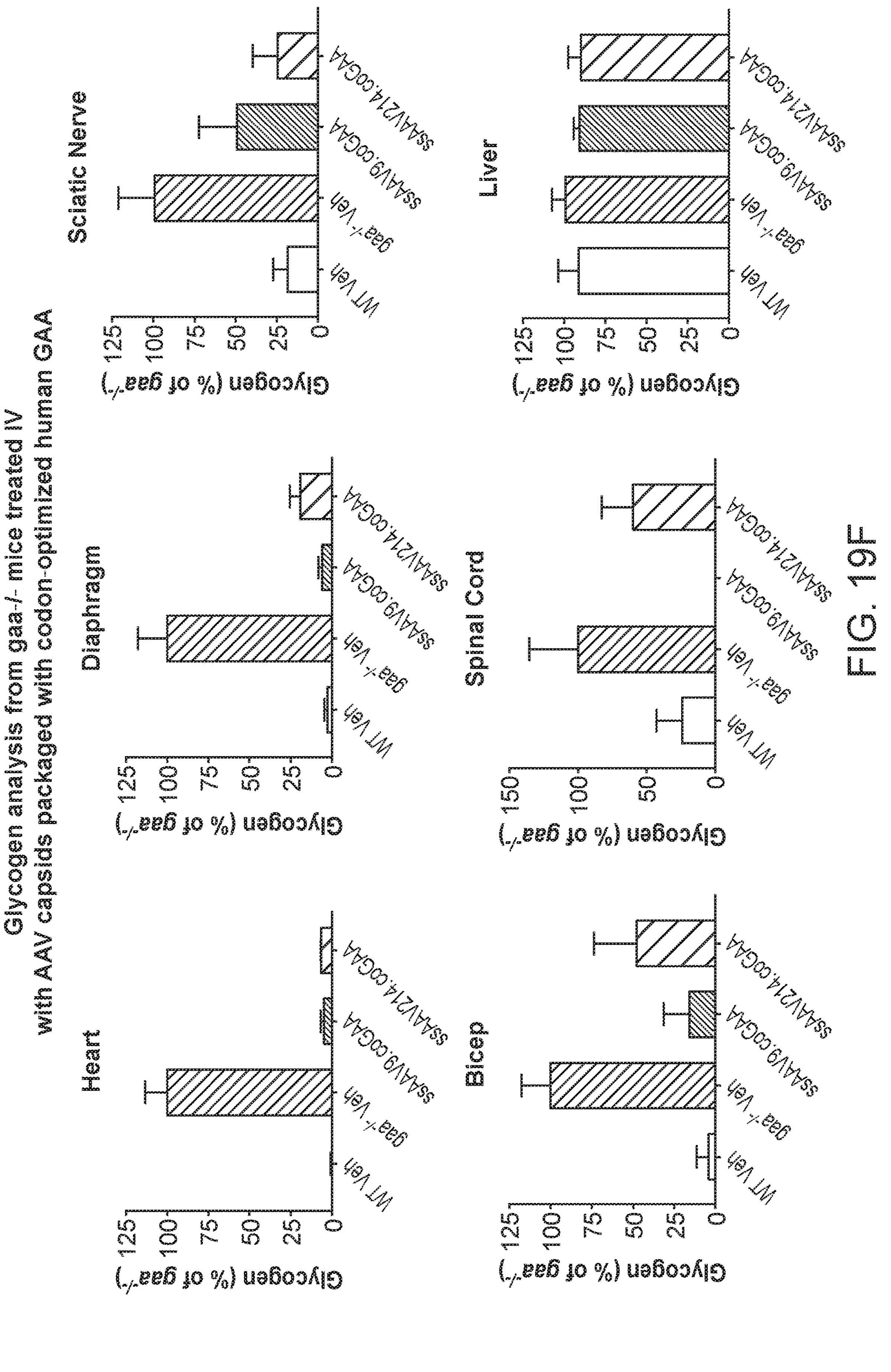
FIG. 19F shows glycogen levels in GAA−/− mice treated IV with AAV capsid. Data is presented as % of glycogen found in the GAA−/− mice. Decreased glycogen shows restoration of GAA functionality by AAV9- and AAV214-mediated expression of codon-optimized GAA enzyme.

FIG. 19F shows repair of the underlying molecular pathology by AAV-delivered GAA. Glycogen analysis from gaa−/− mice treated intravenously with AAV capsids packaged with codon-optimized human GAA. Glycogen content was measured indirectly by release of glucose following amyloglucosidase treatment. Free glucose was measured with Infinity Glucose Reagent and analyzed on a SpectraMax i3×. Data is presented as % of gaa−/− vehicle control treated animals. The data shows the reduction in glycogen levels obtained by AAV-delivered GAA. Glycogen clearance was observed in all target tissues with AAV214 performing as effectively as AAV9.

These data confirm that systemic delivery of AAV9 and AAV214, notably with muscle and peripheral nervous system (PNS) expression, demonstrates the ability to both safely transduce key target tissues associated with Pompe disease and to restore GAA functionality.

TABLE 8

| Animal Study Design | | | | | |
|---|---|---|---|---|---|
| Group | Mouse Strain | Vector | Dose (vg/kg) | Dose Vol. (microliters) | Animals |
| 1 | C57BL6 | Vehicle | 0 | 0 | 6 |
| 2 | C57BL6 | AAV9-hGAA | $1 \times 10^{13}$ | 200 | 6 |
| 3 | C57BL6 | AAV214-hGAA | $1 \times 10^{13}$ | 200 | 5 |

Example 7

AAV110 Vector Particles Show Highly Specific Muscle Tropism

AAV110 particles were prepared using the pAAV110 plasmid (also referred as ITCord1.10 plasmid) encoding the AAV110 capsid proteins. An AAV110-GFP viral vector comprising a CBh promoter, CBA-MVM hybrid intron, EGFP transgene sequence, and BGH poly-A site were administered ($1\times10^{11}$ vg total, equivalent to $5\times10^{12}$ vg/kg) into each leg (biceps femoris) in a single injection in C57Bl/6 wild type mice. Another group of animals was administered an equivalent amount of AAV9-GFP viral vector for comparison.

Figure 24A:
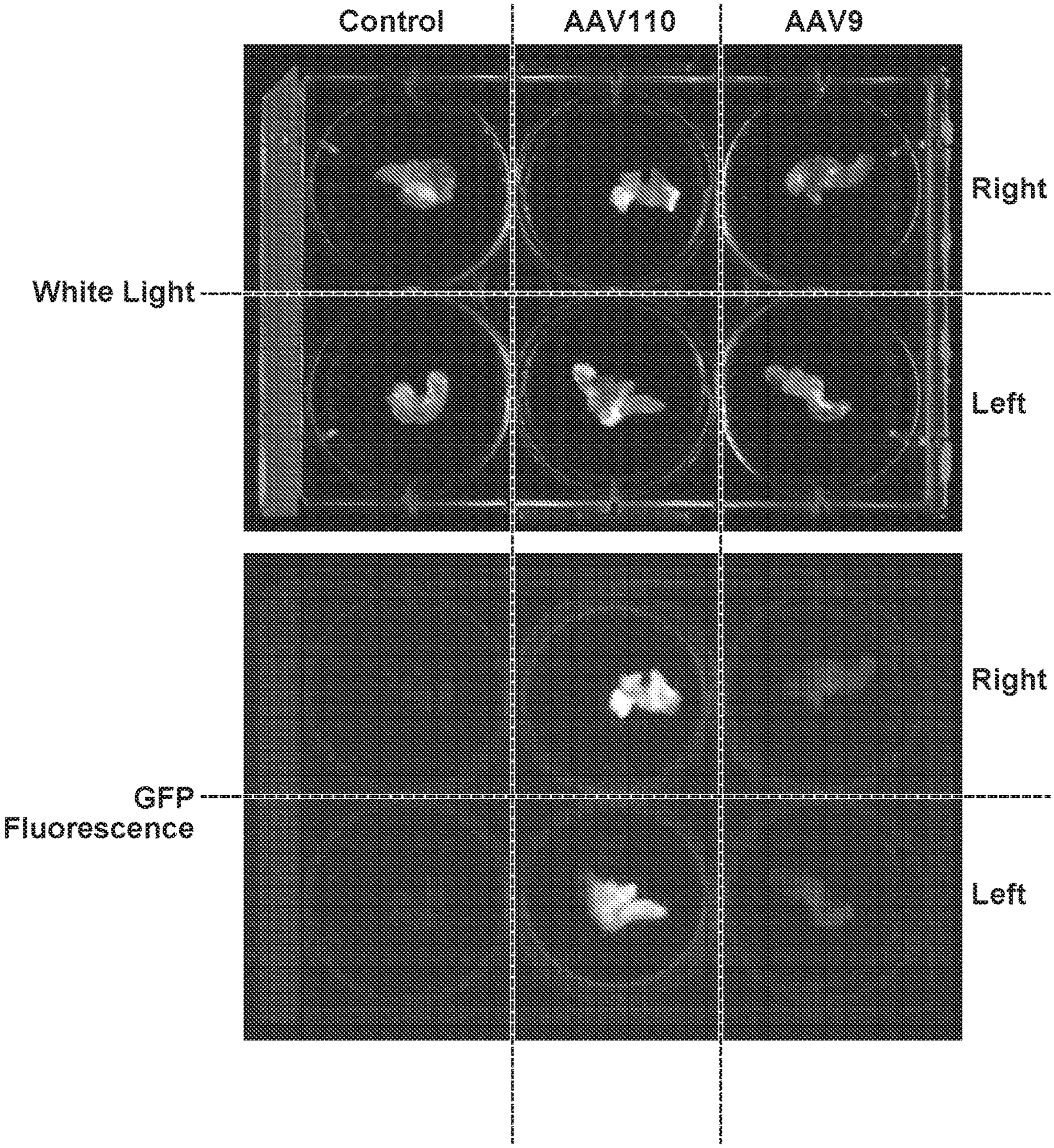
FIG. 24A shows expression of a GFP transgene delivered by an AAV110 vector particle and an AAV9 vector particle in muscle following intramuscular administration. The upper panel shows left and right legs in white light showing the overall tissue structure. The lower panel shows GFP fluorescence.
Figure 24B:
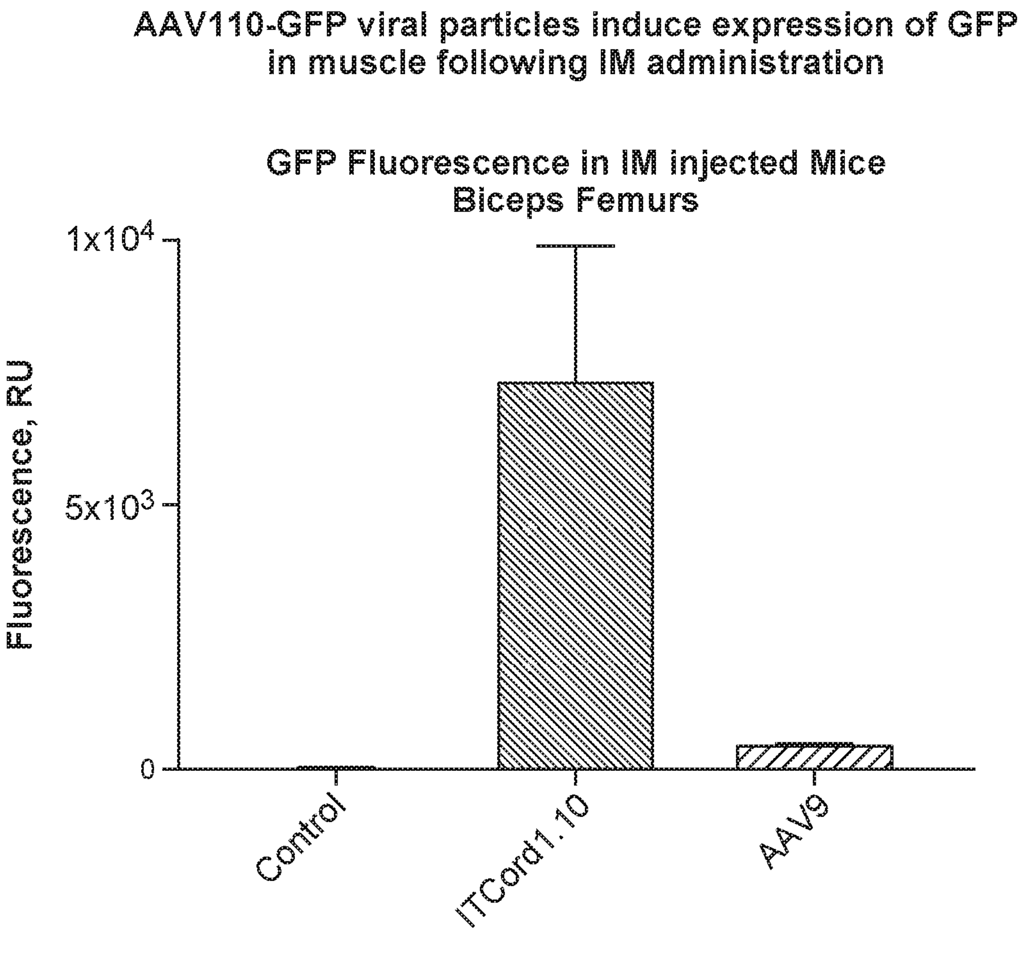
FIG. 24B provides a quantitative analysis of the fluorescence obtained in FIG. 24A for the AAV110 particle (ITCord1.10) compared to AAV9.

GFP expression was evaluated by imaging the leg muscle for fluorescence. FIG. 24A. The data showed the both right and left legs administered the AAV110-GFP viral vector expressed a high level of GFP, establishing muscle tropism for the AAV110 capsid. In contrast, AAV9-GFP vector particles provided substantially less muscle expression (FIG. 24B).

Figure 25A:
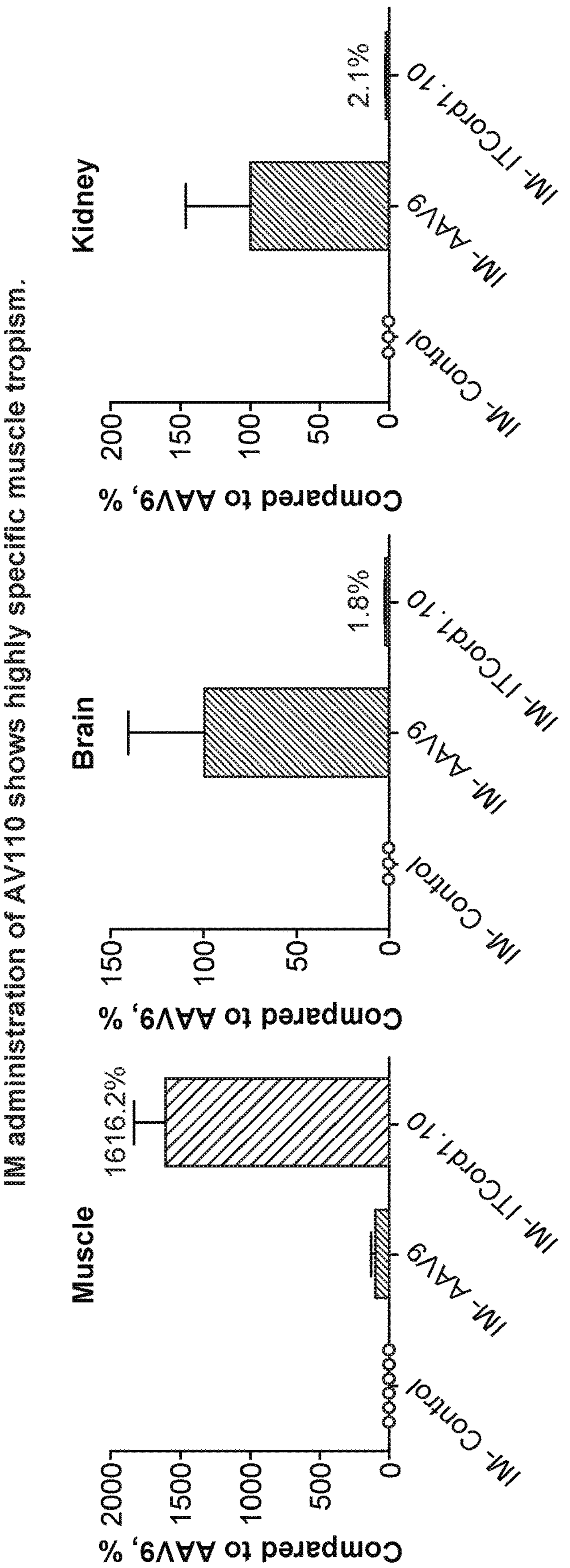
FIG. 25A-25C illustrates expression, relative to AAV9, of a transgene delivered by the AAV110 particle (ITCord1.10) following intramuscular administration. The data shows that AAV110 expression in muscle is particularly high.
Figure 25B:
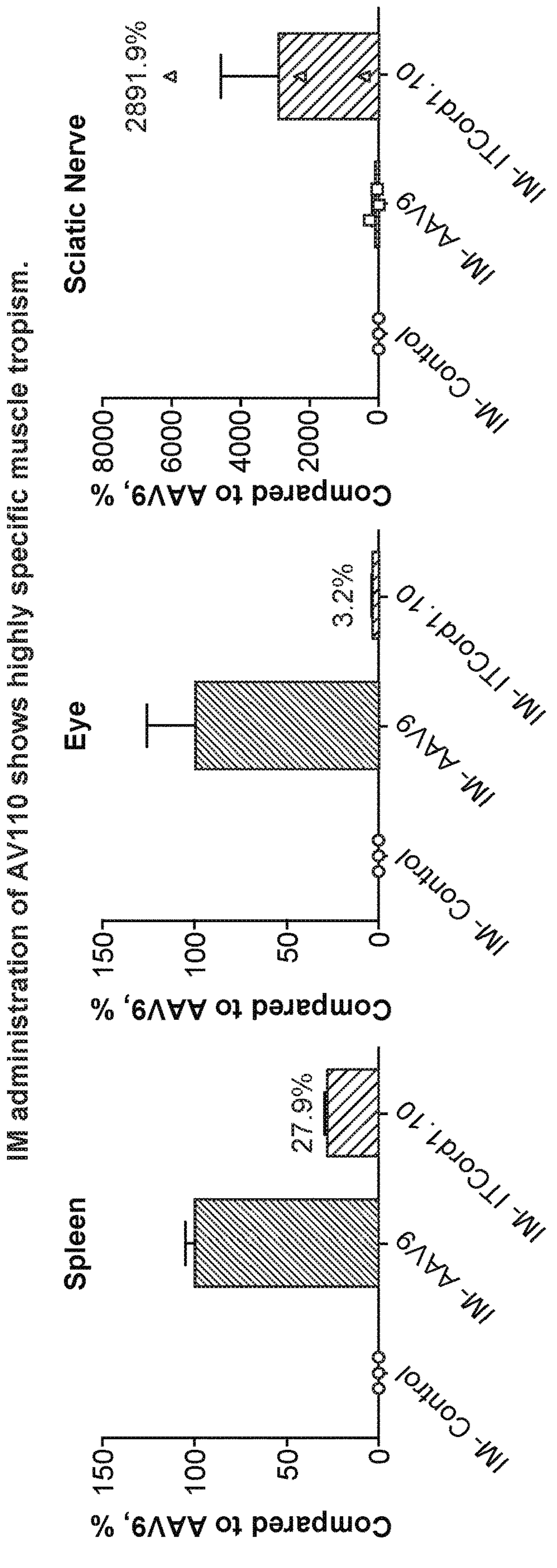
Figure 25C:
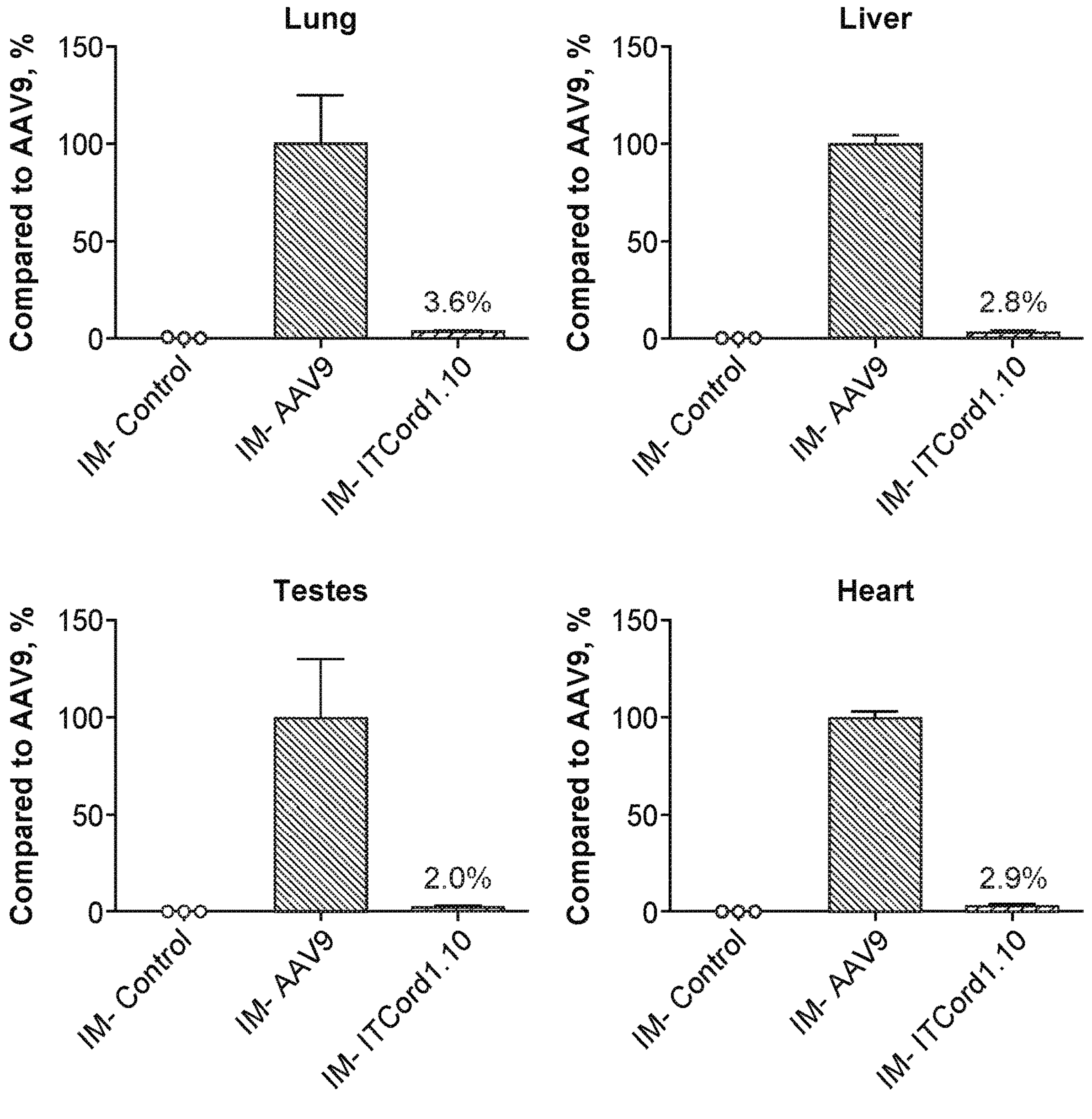

To assess the GFP transgene distribution in other tissues induced by intramuscular dosing of AAV110-GFP or AAV9-GFP we examined transgene biodistribution (BD) in a panel of organs. See FIG. 25. The data confirms that AAV110 transduction mostly happens in muscle, as well as in the sciatic nerve and spleen. In contrast to AAV9, AAV110 shows little to no biodistribution in brain, kidney, eye, lung, heart, liver and testes. In each case, BD was about 3% or less than that obtained with AAV9 intramuscular delivery of transgene.

Figure 26A:
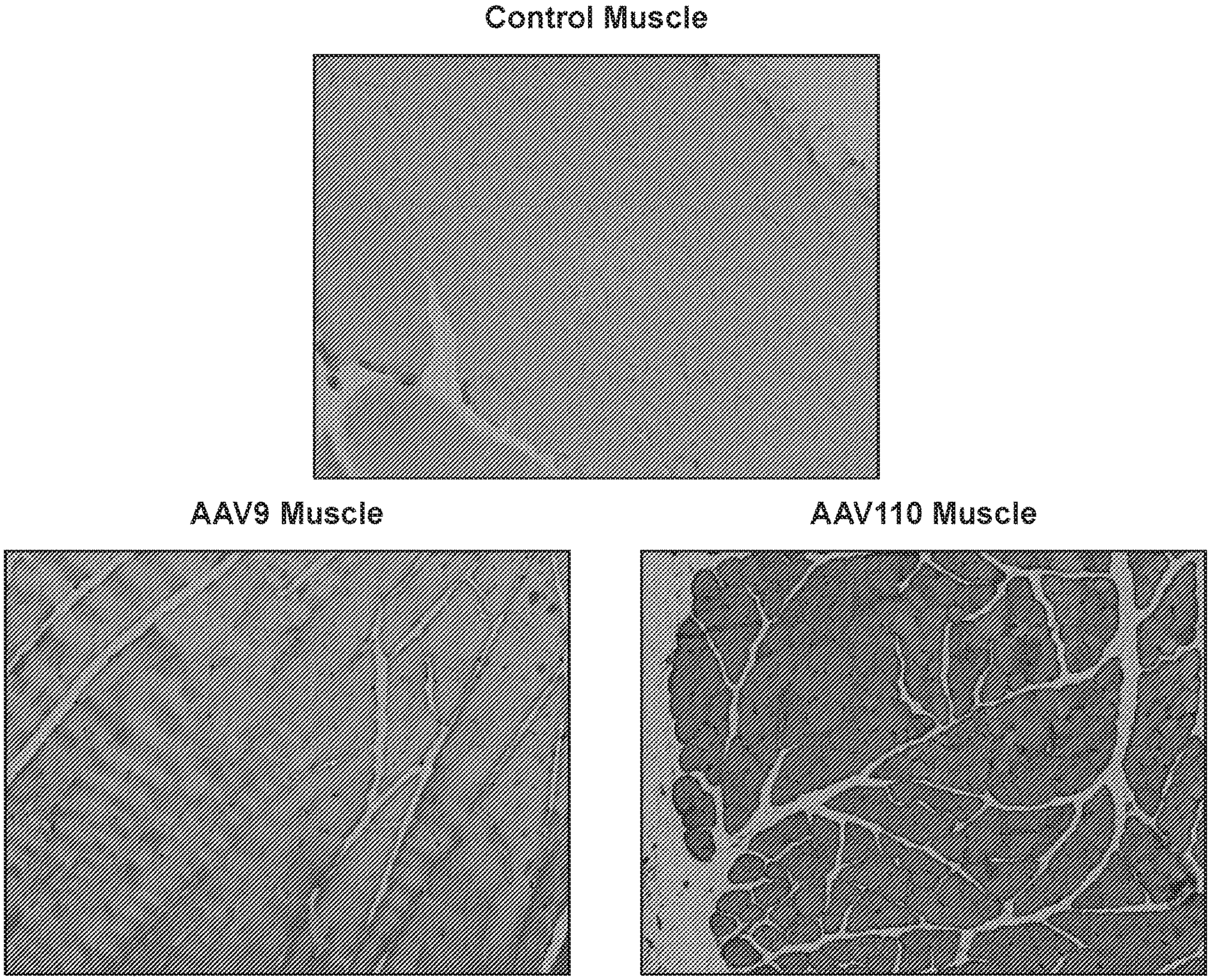
FIG. 26A shows immunohistochemistry of muscle tissue to detect GFP expression following intramuscular administration of AAV110 and AAV9 particles expressing GFP. The FIG. shows GFP expressed from AAV9 vector particles (lower left panel), GFP expressed from AAV110 particles (lower right panel) and control muscle (upper panel). Tissue was stained with anti-GFP antibody.

Immunohistochemistry analysis of muscle tissue confirmed high levels of GFP expression in muscle with AAV110 and less with AAV9 (FIG. 26). This data confirms superior muscle tropism and expression by AAV110.

Example 8

Figure 27:
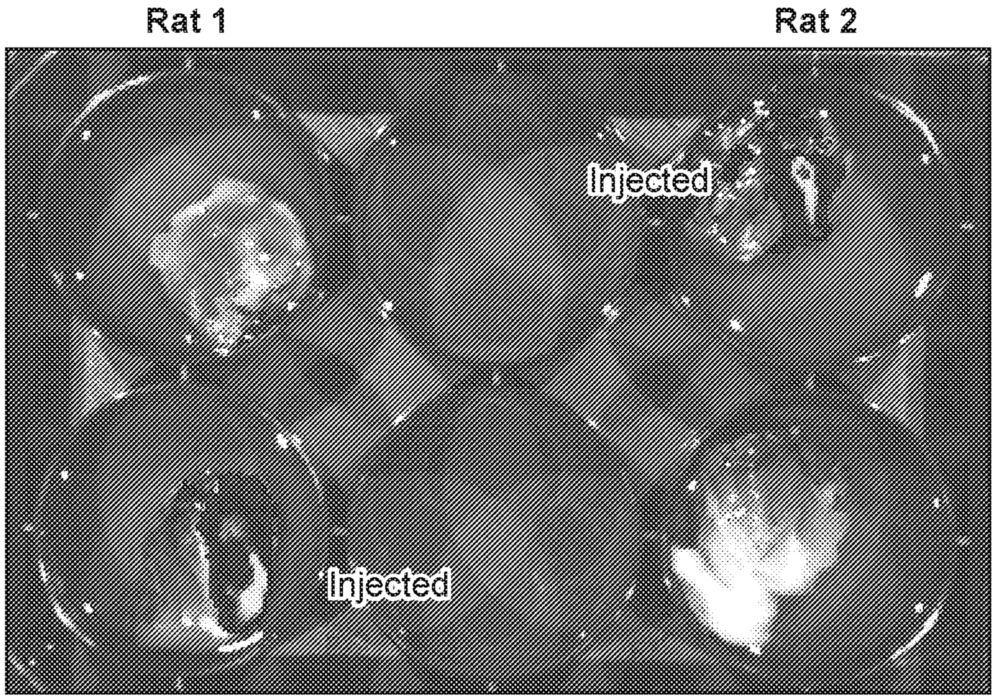
FIG. 27 shows a bioluminescence image showing luciferase, expressed as a transgene and exposed to luciferin. The data was obtained 28 days following AAV214 administration.

AAV214 Vector Particles Provide High Level Expression in Muscle after IM and IV Administration An AAV viral vector comprising the AAV214 capsid proteins and a luciferase expression cassette driven by U1a promoter (AAV214-Luc) was generated. We administered AAV214-Luc to the right leg of adult wild-type rats at a dose of $5\times10^{12}$ vg/kg in each muscle in a total volume of 0.1 mL per muscle. The left leg was untreated. To measure expression, we exposed the muscles to luciferin and measured emitted light. The data in the table below shows that injected muscle but not untreated muscle shows high expression 28 days after administration. FIG. 27 shows luciferase activity in the tissue, indicating activity of the expressed enzyme.

| ID | Total Flux [photons/second] | | |
|---|---|---|---|
| | pre-luciferin | 0 min post-luciferin | 5 min post-luciferin |
| Rat 1-left | $8.95 \times 10^4$ | $5.21 \times 10^4$ | $6.06 \times 10^4$ |
| Rat 1-right | $1.75 \times 10^6$ | $6.52 \times 10^6$ | $1.24 \times 10^7$ |
| Rat 2-right | $5.65 \times 10^6$ | $9.12 \times 10^6$ | $1.11 \times 10^7$ |
| Rat 2-left | $1.32 \times 10^5$ | $9.34 \times 10^6$ | $1.46 \times 10^7$ |

Figure 28:
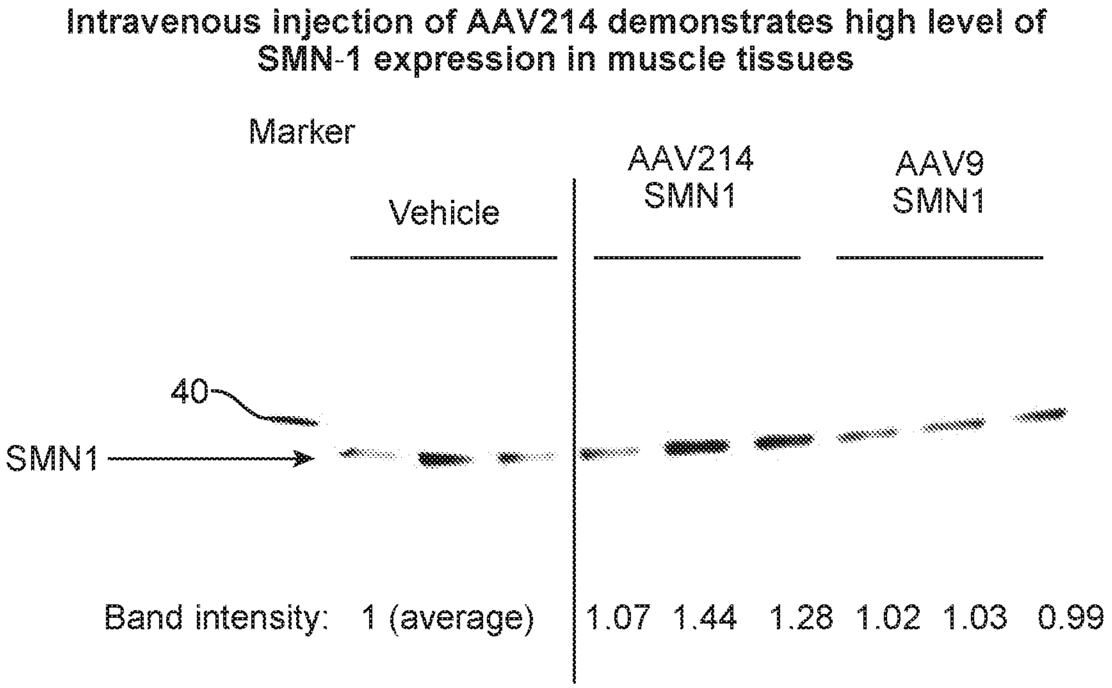
FIG. 28 compares muscle expression of SMN-1 protein delivered intravenously in AAV214 and AAV9.

Similar results were obtained with a different transgene, codon optimized SMN-1 (survival of motor neuron 1) (which is defective in spinal muscle atrophy (SMA)) driven by a CBh promoter. We compared the ability of intravenously-administered AAV214-SMN1 viral vector particles with AAV9-SMN1 vector particles to express SMN-1 when administered intravenously. FIG. 28 shows expression of SMN1 in Tibialis anterior muscle tissue following infection of juvenile wild-type mice. The data illustrate that AAV214 vector particles provide improved expression with an increase from at least 10 to 30%, relative to vehicle and suitable for muscle transduction when delivered intravenously.

Figure 26B:
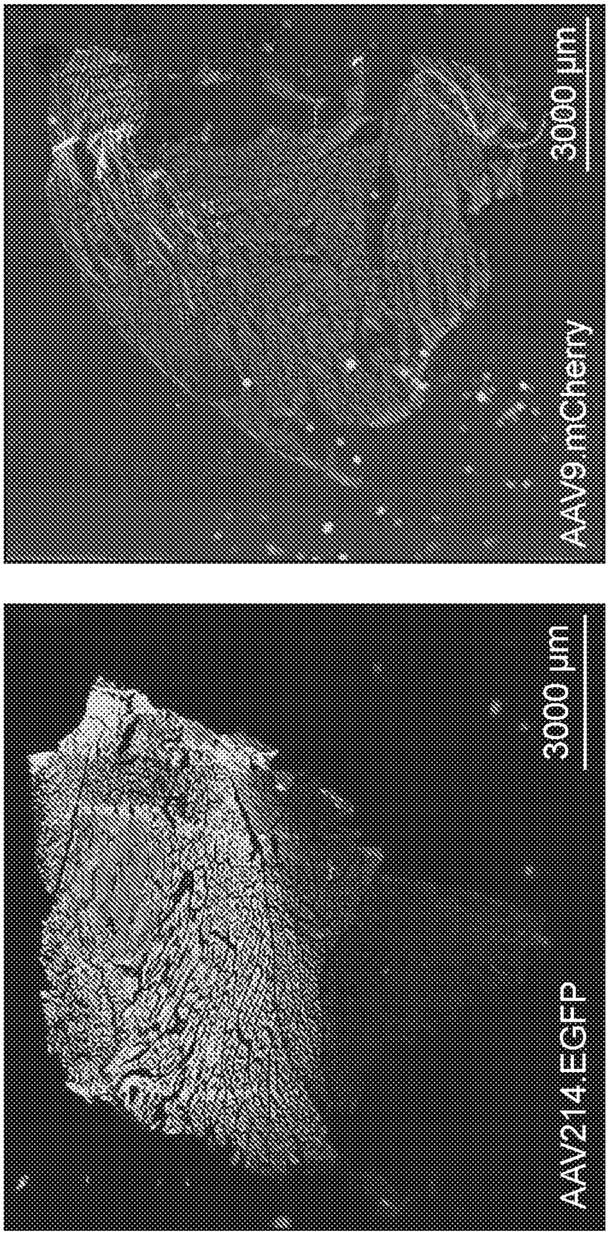
FIG. 26B. IM Delivered AAV214 Transduces a Larger Muscle Area Than AAV9. Whole rat muscle (biceps femoris) was analyzed for GFP or mCherry expression by immunohistochemistry 10 days post-IM injection. Fixed and frozen sections were probed with GFP and mCherry pAb. AAV214 displayed a significantly larger transduction area in comparison to AAV9 which was largely confined to the upper portion of the muscle consistent with the injection site.

Comparison of AAV214 and AAV9 viral vectors to transduce muscle tissue showed that IM delivered AAV214 is able to transduce a larger muscle area than AAV9. Whole rat muscle (biceps femoris) was analyzed for GFP or mCherry expression by immunohistochemistry 10 days post-IM injection. Fixed and frozen sections were probed with GFP and mCherry pAb. AAV214 displayed a significantly larger transduction area in comparison to AAV9, which was largely confined to the upper portion of the muscle consistent with the injection site. (FIG. 26B).

Example 9

Figure 29:
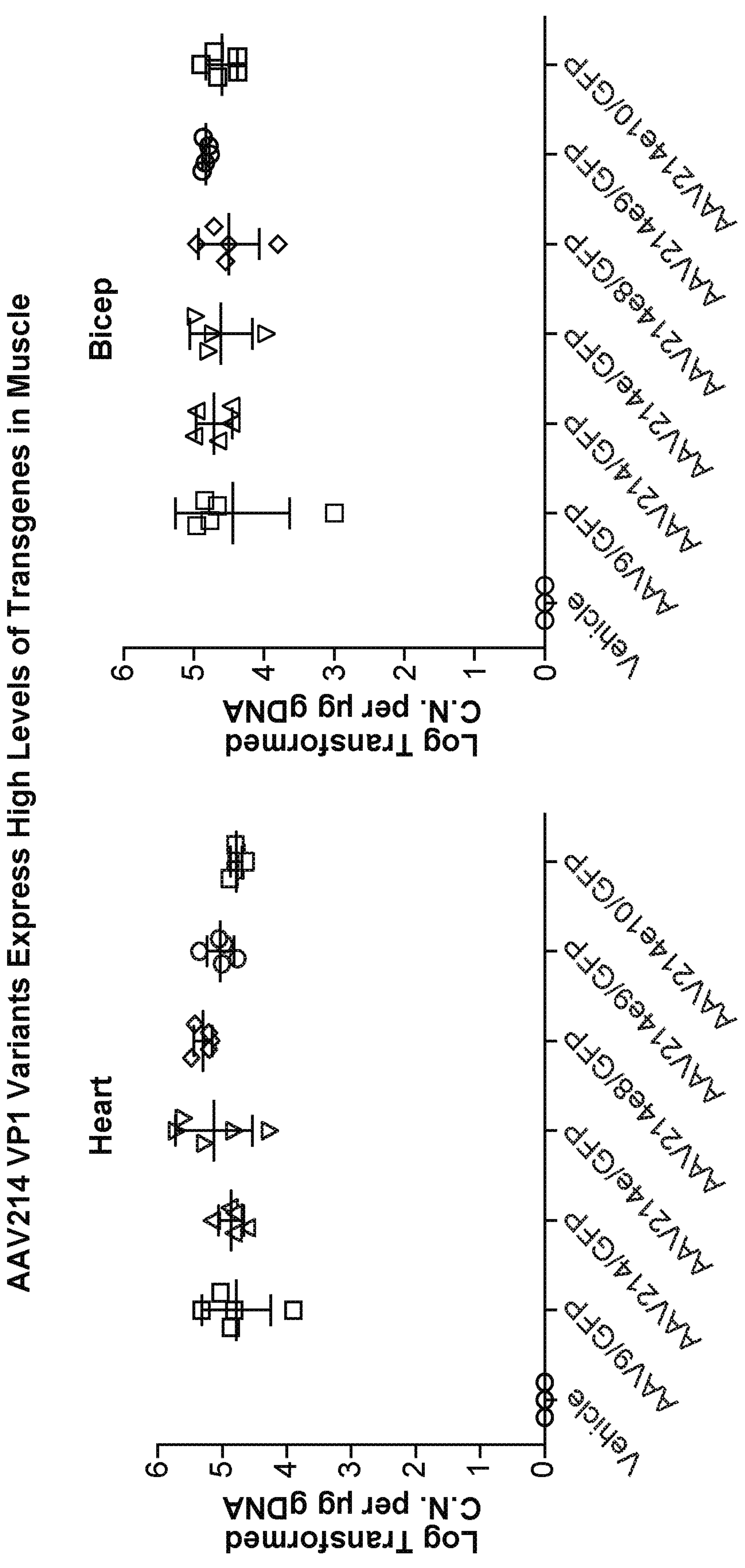
FIG. 29 shows expression of GFP in heart and in bicep as a transgene mediated by variants of the AAV214 versus AAV9. The y-axis shows the log 10 value of virus copy number per microgram of genomic DNA.

AAV Vector Particles Containing Capsid Proteins Derived from AAV214 Exhibit High Expression in Muscle after IV Dosing AAV214 VP1 proteins were modified by exchanging their N-terminus with amino acid sequences from known AAV serotypes (AAV8, AAV9, AAVrh10), thereby producing the variants shown in the table below. AAV viral vector particles were then prepared with each of newly-derived capsid proteins, essentially as described in Example 1, and their ability to transduce muscle following intravenous administration was assessed. We found that each viral vector conferred good muscle transduction in leg and heart (FIG. 29). One-way ANOVA analysis of log transformed biodistribution data did not reveal a statistically significant difference ($p>0.05$) in mean biodistribution values for the viral vectors tested.

| VP1 Amino Acid SEQ ID NO: | VP1 Nucleic Acid SEQ ID NO: | AAV Capsid Name |
|---|---|---|
| 31 | 20 | AAV 214e |
| 32 | 21 | AAV 214e8 |
| 33 | 22 | AAV 214e9 |
| 34 | 23 | AAV 214e10 |

Example 10

Capsid-Induced Cross-Neutralizing Antibody Production

AAV204 and AAV214 have limited or very low cross-reactivity with AAV9 nAbs and low possibility of inducing nAbs production cross-reacting with AAV9.

Figure 31A:
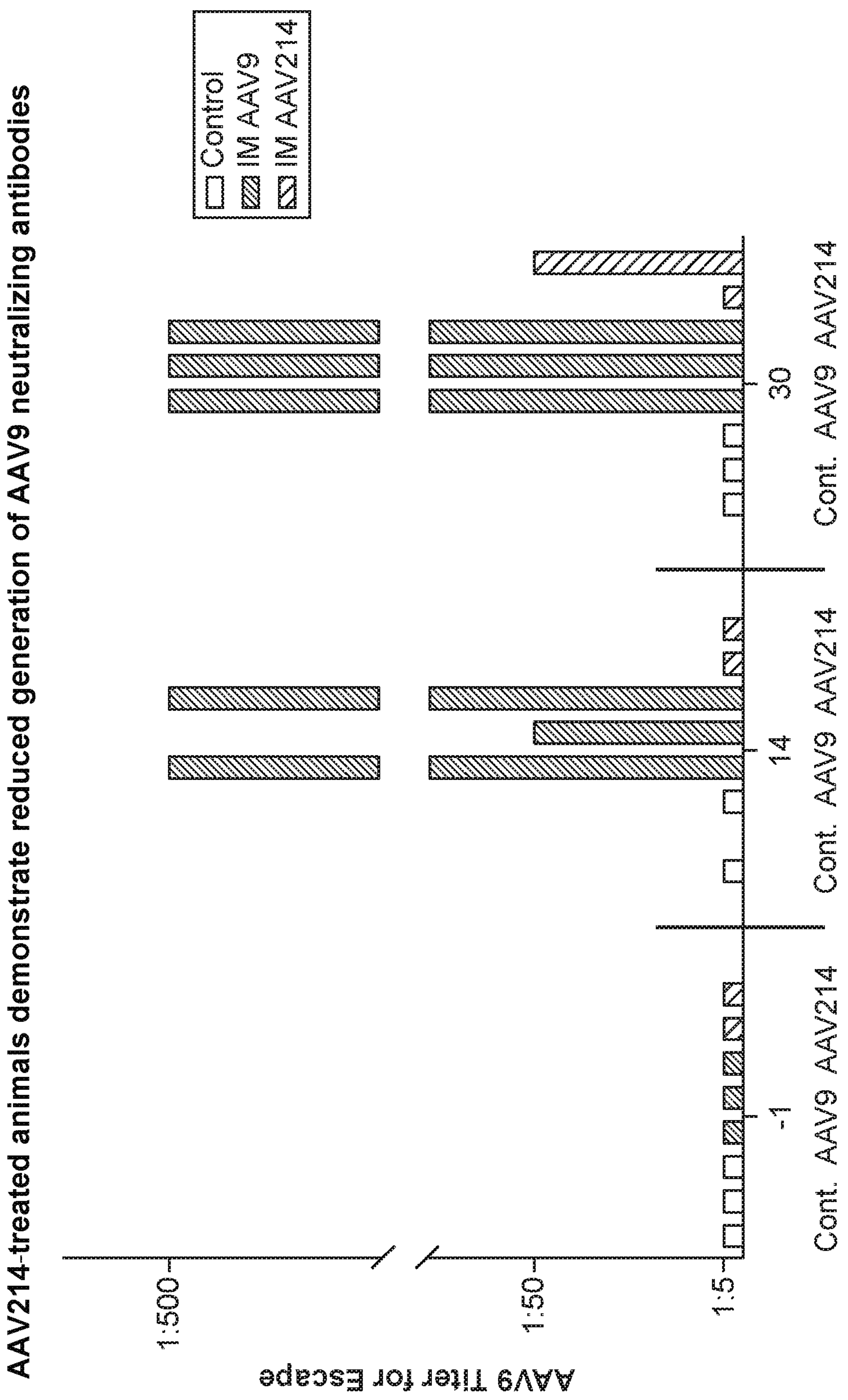
FIGS. 31A-31C illustrate AAV214-treated animals demonstrate reduced generation of AAV9 neutralizing antibodies.

We tested the ability of animals dosed by IM with either AAV9 or AAV214 to produce neutralizing antibodies against AAV9. (FIG. 31A). Analysis was performed by measuring the ability of animal serum to inhibit the transduction of an AAV9.luciferase vector into the permissive cell type, Lec2. Three days post-transduction cells were assayed for luciferase activity. Each group consisted of 2 or 3 rats for either control, AAV9 or AAV214. Advantageously, animals injected with AAV214 by IM do not show a cross-reactive immune response to AAV9, which could allow for a larger patient population due to inclusion of patients with pre-existing immunity to AAV9, either naturally occurring or due to previous dosing.

Figure 31B:
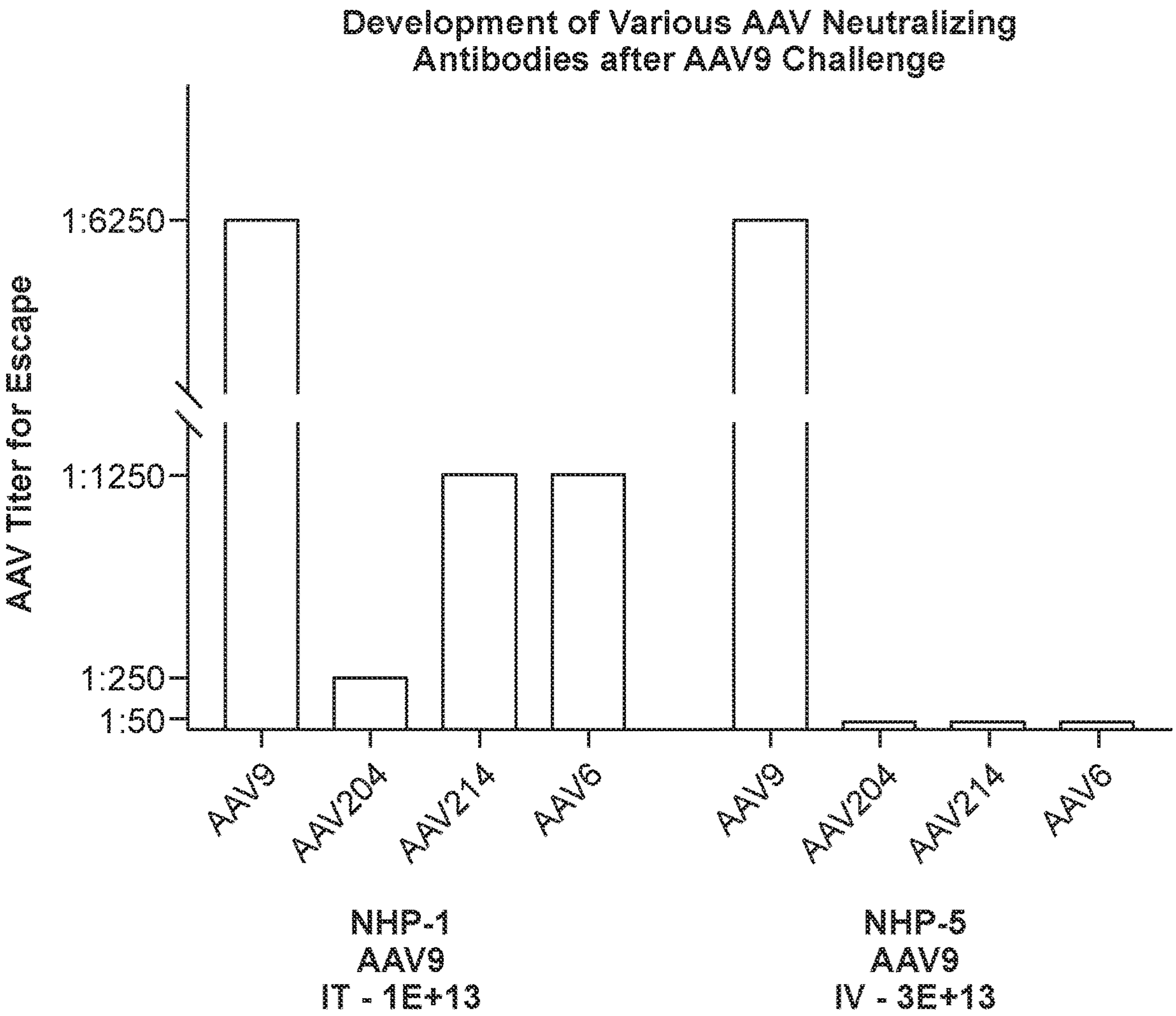
Figure 31C:
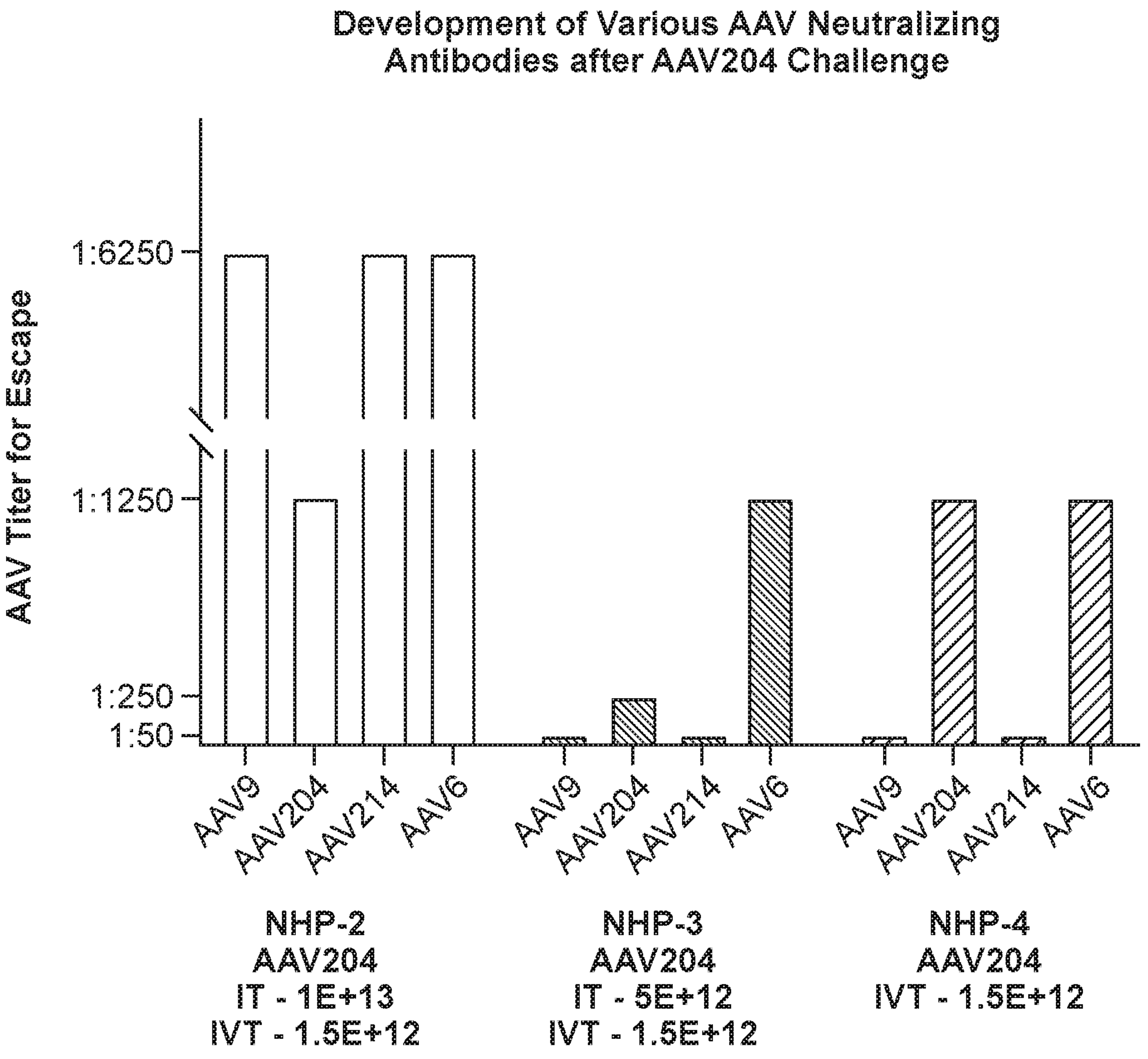

Similar data were obtained in non-human primates (NHPs). Both AAV9 intrathecally (IT) and intravenously (IV) dosed NHPs developed nAbs against AAV9 (FIG. 31B). The IT dosed animal serum showed much higher cross-reactivity to other tested viruses (AAV204, AAV214 and AAV6). However, we believe that dosing route doesn't have significant impact on nAbs development differences because two animals dosed with AAV204 by intrathecal plus intravitreal route (IT+IV) also revealed similar differences in cross reactivity (FIG. 31C; see NHP-2 and NHP-3). Moreover, intravitreally (IVT) only AAV204 dosed animal (FIG. 31C; see NHP-4) showed similar cross reactivity as IT+IVT treated animal (NHP-3). The differences in the developed cross reactivity might be explained by the identity of the AAV capsid protein epitope against of which nAbs were produced. Both AAV9 dosed animal serum samples showed low reactivity to AAV204 (FIG. 31B), and two of three AAV204 treated animals demonstrated very low reactivity to AAV9 and AAV214 suggesting high chance of compatibility (FIG. 31C). In contrast, AAV6 revealed high cross reactivity in all AAV204 dosed animals (FIGS. 31B and C).

ALTERNATIVE EMBODIMENTS

1. A polynucleotide encoding an adeno-associated viral (AAV) capsid protein that comprises an amino acid sequence with at least 70% identity to SEQ ID NO: 3, 30-34, 49 or 84 or the use of a polynucleotide encoding an adeno-associated viral (AAV) capsid protein that comprises an amino acid sequence with at least 70% identity to SEQ ID NO: 1.
2. The polynucleotide of embodiment 1, wherein the amino acid sequence has at least 80% identity to SEQ ID NO: 3, 30-34, 49 or 84.
3. The polynucleotide of embodiment 1, wherein the amino acid sequence has at least 90% identity to SEQ ID NO: 3, 30-34, 49 or 84.
4. The polynucleotide of embodiment 1, wherein the amino acid sequence has at least 95% identity to SEQ ID NO: 3, 30-34, 49 or 84.
5. The polynucleotide of embodiment 1, wherein the amino acid sequence has at least 99% identity to SEQ ID NO: 3, 30-34, 49 or 84.
6. The polynucleotide of embodiment 1, wherein the amino acid sequence comprises SEQ ID NO: 3, 30-34, 49 or 84.
7. The polynucleotide of any one of embodiments 1-6, wherein the amino acid sequence comprises a VP1, VP2, and VP3 portion of the AAV capsid protein and wherein the VP3 portion has the sequence of SEQ ID NO:41.
8. The polynucleotide of embodiment 7, wherein the AAV capsid protein is at least 70%, 80%, 90%, or 99% identical to SEQ ID NO: 3, 30-34, 49 or 84.
9. The polynucleotide of any one of embodiments 1-8, wherein the polynucleotide is contained within a plasmid, a bacterial artificial chromosome, a yeast artificial chromosome a phage, or a viral vector.
10. A host cell comprising the polynucleotide of any one of embodiments 1-8.
11. An AAV capsid protein comprising an amino acid sequence with at least 70%, 80%, 90%, or 99% identity with SEQ ID NO: 3, 30-34, 49 or 84.
12. An AAV capsid protein comprising an amino acid sequence having the sequence of SEQ ID NO:2, 3, 30-34, 49 or 84.
13. An AAV viral vector comprising
    (i) an AAV capsid protein of embodiment 11 or 12, and
    (ii) an AAV vector.
14. The AAV viral vector of embodiment 13, wherein the AAV vector comprises a heterologous nucleic acid.
15. The AAV viral vector of embodiment 14, wherein the heterologous nucleic acid is a transgene.
16. The AAV viral vector of embodiment 13 to 15, wherein the transgene encodes a cystic fibrosis transmembrane conductance regulator (CFTR), a CLN3 protein, an alpha-galactosidase A (GLA), or an acid alpha-glucosidase (GAA).
17. The AAV viral vector of embodiment 15, wherein the transgene comprises a sequence with at least 70%, 80%, 90%, or 99% identity with any one of SEQ ID NOs: 5, 6, 7, 9, 10, 12, and 13.
18. The AAV viral vector of embodiment 15, wherein the transgene encodes a protein comprising an amino acid sequence with at least 70%, 80%, 90%, or 99% identity with any one of SEQ ID NOs: 4, 5, 8, 11, and 14.
19. The AAV viral vector of embodiment 13 to 18, wherein the heterologous nucleic acid is operably linked to a promoter.
20. The AAV viral vector of embodiment 19, wherein the promoter is a tissue-specific control promoter, or a constitutive promoter.
21. The AAV viral vector of embodiment 20, wherein the promoter is a constitutive promoter which is a Rous sarcoma virus (RSV) LTR promoter (optionally with the RSV enhancer), a cytomegalovirus (CMV) promoter, an SV40 promoter, a dihydrofolate reductase promoter, a beta-actin promoter, a phosphoglycerol kinase (PGK) promoter, a U6 promoter, an H1 promoter, a CAG promoter, a hybrid chicken beta-actin promoter, an MeCP2 promoter, an EF1 promoter, a ubiquitous chicken β-actin hybrid (CBh) promoter, a U1a promoter, a U1b promoter, an MeCP2 promoter, an MeP418 promoter, an MeP426 promoter, a minimal MeCP2 promoter, a VMD2 promoter, an mRho promoter, EF1a promoter, Ubc promoter, human β-actin promoter, TRE promoter, Ac5 promoter, Polyhedrin promoter, CaMKIIa promoter, Gal1 promoter, TEF1 promoter, GDS promoter, ADH1 promoter, Ubi promoter, or α-1-antitrypsin (hAAT) promoter.

22. The AAV viral vector of embodiment 10, wherein the promoter is a tissue-specific control promoter, which is a central nervous system (CNS) cell-specific promoter, a lung-specific promoter, a skin-specific promoter, a muscle-specific promoter, a liver-specific promoter, or an eye-specific promoter.

23. The AAV viral vector of embodiment 14, wherein the heterologous nucleic acid encodes an mRNA, siRNA, gRNA, or microRNA.

24. The AAV viral vector of embodiment 14, wherein the heterologous nucleic acid encodes a polypeptide.

25. The AAV viral vector of embodiment 14, wherein the heterologous nucleic acid encodes a cystic fibrosis transmembrane conductance regulator (CFTR), a CLN3 protein, an alpha-galactosidase A (GLA), or an acid alpha-glucosidase (GAA).

26. The AAV viral vector of embodiment 25, wherein the heterologous nucleic acid encodes a CFTR.

27. The AAV viral vector of embodiment 26, wherein the CFTR comprises or consists of an amino acid sequence encoded by SEQ ID NO: 4.

28. The AAV viral vector of embodiment 15, wherein the heterologous nucleic acid encodes a protein comprising an amino acid sequence with at least 70%, 80%, 90%, or 99% identity with any one of SEQ ID NOs; 5, 8, 11, and 14.

29. The AAV viral vector of embodiment 15, wherein the heterologous nucleic acid comprises a sequence with at least 70%, 80%, 90%, or 99% identity with any one of SEQ ID NOs: 4, 5, 6, 7, 9, 10, 12, and 13.

30. The AAV viral vector of embodiment 18, wherein the heterologous nucleic acid encodes a reporter protein.

31. A method of introducing a gene of interest to a cell in a subject, comprising contacting the cell with an effective amount of an AAV viral vectors of any one of embodiments 13-30.

32. The method of embodiment 31, wherein the AAV viral vector is introduced to the subject orally, rectally, transmucosally, inhalationally, transdermally, parenterally, intravenously, subcutaneously, intradermally, intramuscularly, intrapleurally, intracerebrally, intrathecally, intracerebrally, intraventricularly, intranasally, intra-aurally, intra-ocularly, peri-ocularly, topically, intralymphatically, intracistemally, intrathecally, or intra-vitreally.

33. The method of embodiment 31 or 32, wherein the subject is a mammal.

34. The method of embodiments 31 to 33, wherein the subject is human.

35. The method of embodiment 31 to 34, wherein the cell is a somatic cell.

36. The method of embodiment 35, wherein the somatic cell is a nerve cell, a retinal cell, a muscle cell, an epithelial cell, a lung cell, a liver cell, a stem cell, or a skin cell.

37. A pharmaceutical composition comprising the polynucleotide of any one of embodiments 1-8, the AAV capsid protein of embodiment 11 or 12, or the AAV viral vector of any one of embodiments 13-30.

38. A method of treating a disorder, comprising administering to a subject a therapeutically effective amount of the pharmaceutical composition of embodiment 37.

39. The method of embodiment 38, wherein the disorder is a CNS disorder, a skin disorder, a lung disorder, a muscle disorder, a liver disorder, or a retinal disorder.

40. The method of embodiment 38 or 39, wherein the disorder is amyotrophic lateral sclerosis (ALS), spinal muscular atrophy (SMA), Fabry disease, Pompe disease, CLN3 disease (or Juvenile Neuronal Ceroid Lipofuscinosis), recessive dystrophic epidermolysis bullosa (RDEB), juvenile Batten disease, autosomal dominant disorder, muscular dystrophy, hemophilia A, hemophilia B, multiple sclerosis, diabetes mellitus, Gaucher disease, cancer, arthritis, muscle wasting, heart disease, intimal hyperplasia, epilepsy, Huntington's disease, Parkinson's disease, Alzheimer's disease, cystic fibrosis, thalassemia, Hurler's Syndrome, Sly syndrome, Scheie Syndrome, Hurler-Scheie Syndrome, Hunter's Syndrome, Sanfilippo Syndrome A (mucopolysaccharidosis IIIA or MPS IIIA), Sanfilippo Syndrome B (mucopolysaccharidosis IIIB or MPS IIIB), Sanfilippo Syndrome C, Sanfilippo Syndrome D, Morquio Syndrome, Maroteaux-Lamy Syndrome, Krabbe's disease, phenylketonuria, Batten's disease, spinal cerebral ataxia, LDL receptor deficiency, hyperammonemia, arthritis, macular degeneration, retinitis pigmentosa, ceroid lipofuscinosis, neuronal, 1 (CLN1), or adenosine deaminase deficiency.

41. The method of embodiment 38, wherein the disorder is spinal muscular atrophy (SMA), recessive dystrophic epidermolysis bullosa (RDEB), Fabry disease, Pompe disease, CLN3 disease (or Juvenile Neuronal Ceroid Lipofuscinosis), MPS IIIA, MPS TIM, juvenile Batten disease, and Duchenne muscular dystrophy (DMD), or Becker muscular dystrophy.

42. The method of embodiment 38, wherein disorder is cancer and the cancer is bladder cancer, breast cancer, cervical cancer, colon cancer, rectal cancer, endometrial cancer, kidney cancer, lip cancer, oral cancer, liver cancer, melanoma, mesothelioma, non-small cell lung cancer, nonmelanoma skin cancer, oral cancer, ovarian cancer, pancreatic cancer, prostate cancer, sarcoma, small cell lung cancer, or thyroid cancer.

43. The method of embodiment 37 to 42, wherein the subject is a mammal.

44. The method of embodiment 43, wherein the subject is human.

45. A kit comprising the polynucleotide of any one of embodiments 1-8, the cell of embodiment 10, the AAV capsid protein of embodiment 12 or 13, and/or the AAV viral vector of any one of embodiments 13-30.

46. An AAV packaging system, comprising the polynucleotide of any one of embodiments 1-8 and a helper cell.

47. The AAV package system of embodiment 46, wherein the helper cell is a yeast cell, a mammalian cell, or an insect cell 48. A nucleic acid encoding an AAV capsid protein, the AAV capsid protein comprising a leucine residue at amino acid 129, an asparagine residue at amino acid 586 and a glutamic acid residue at amino acid 723, wherein amino acid positions in the AAV capsid protein are numbered with respect to amino acid positions in the amino acid sequence of SEQ ID NO: 2.

49. The nucleic acid of embodiment 48, wherein the encoded AAV capsid amino acid sequence is at least 95% identical to the amino acid sequence of SEQ ID NO: 2.

50. The nucleic acid of embodiment 48, wherein the encoded AAV capsid amino acid sequence is at least 99% identical to the amino acid sequence of SEQ ID NO: 2

51. The nucleic acid of embodiment 48, wherein the nucleic acid sequence is at least 99% identical to the nucleotide sequence of SEQ ID NO: 15.

52. The nucleic acid of embodiment 48, wherein the nucleic acid sequence is 100% identical to the nucleotide sequence of SEQ ID NO: 15.

53. A vector comprising the nucleic acid of embodiment 48 to 52.

54. An AAV capsid protein encoded by the nucleic acid of embodiment 48 to 52.

55. The AAV capsid protein of embodiment 54, wherein the protein comprises the amino acid sequence of SEQ ID NO: 2.

56. An AAV viral vector comprising the AAV capsid protein encoded by the nucleic acid of embodiment 54 or 55 and an AAV vector, wherein the AAV vector comprises a heterologous nucleic acid.

57. The AAV viral vector of embodiment 56, wherein the heterologous nucleic acid is operably linked to a constitutive promoter.

58. The AAV viral vector of embodiment 56 or 57, wherein the heterologous nucleic acid encodes a polypeptide.

59. The AAV viral vector of embodiment 56 or 57, wherein heterologous nucleic acid encodes an antisense RNA, microRNA, or RNAi.

60. The AAV viral vector of embodiment 56, wherein the AAV capsid protein comprises the amino acid sequence of SEQ ID NO: 2.

61. A nucleic acid encoding an AAV capsid protein comprising a VP1 portion, a VP2 portion and a VP3 portion, wherein the VP3 portion comprises variable regions (VR) I to IX wherein:

```
                                        (SEQ ID NO. 54)
(a) VR-II comprises amino acid sequence DNNGVK;

                                        (SEQ ID NO. 55)
(b) VR-III comprises amino acid sequence NDGS;

                                        (SEQ ID NO. 56)
(c) VR-IV comprises amino acid sequence
INGSGQNQQT;

                                        (SEQ ID NO. 57)
(d) VR-V comprises amino acid sequence
RVSTTTGQNNNSNFAWTA;

                                        (SEQ ID NO. 58)
(e)VR-VI comprises amino acid sequence
HKEGEDRFFPLSG;

                                        (SEQ ID NO. 59)
(f) VR-VII comprises amino acid sequence
KQNAARDNADYSDV;
```

-continued

```
                                        (SEQ ID NO. 60)
(g) VR-VIII comprises amino acid sequence
ADNLQQQNTAPQI; and

                                        (SEQ ID NO. 61)
(h) VR-IX comprises amino acid sequence
NYYKSTSVDF.
```

62. The nucleic acid of embodiment 61, wherein the VR-I region comprises SASTGAS (SEQ ID NO. 52).

63. The nucleic acid of embodiment 61, wherein the VR-I region comprises NSTSGGSS (SEQ ID NO. 53) or SSTSGGSS (SEQ ID NO. 87).

64. The nucleic acid of embodiment 61 to 63, wherein the VP3 portion further comprises one or more of:

(i) an asparagine (N) at amino acid 223;

(ii) an alanine (A) residue at amino acid 224;

(iii) a threonine (T) residue at amino acid 410;

(iv) a histidine residue at amino acid 724; and (v) a proline (P) residue at amino acid 734, wherein amino acid positions in the AAV capsid protein are numbered with respect to amino acid positions in the amino acid sequence of SEQ ID NO: 3.

65. The nucleic acid of embodiment 61 to 64, wherein the encoded AAV capsid amino acid sequence is at least 95% identical to the amino acid sequence of SEQ ID NO: 3, 30, 31, 32, 33, 34, 49 or 84.

66. The nucleic acid of embodiment 61 to 65, wherein the encoded AAV capsid amino acid sequence is at least 99% identical to the amino acid sequence of SEQ ID NO: 3, 30, 31, 32, 33, 34, 49 or 84.

67. The nucleic acid of embodiment 61 to 66, wherein the nucleic acid sequence is at least 99% identical to the nucleotide sequence selected from SEQ ID NO: 18, 19, 20, 21, 22, 23, 47, 82 or 98.

68. The nucleic acid of embodiment 61, wherein the nucleic acid sequence is 100% identical to the nucleotide sequence selected from SEQ ID NO: 18, 19, 20, 21, 22, 23, 47, 82 or 98.

69. A vector comprising the nucleic acid of embodiment 61 to 68.

70. An AAV capsid protein encoded by the nucleic acid of embodiment 61 to 68.

71. The AAV capsid protein of embodiment 70, wherein the protein comprises the amino acid sequence of SEQ ID NO: 3, 30, 31, 32, 33, 34, 49 or 84.

72. An AAV viral vector comprising the AAV capsid protein encoded by the nucleic acid of embodiment 61 to 68 and an AAV vector, wherein the AAV vector comprises a heterologous nucleic acid.

73. The AAV viral vector of embodiment 72, wherein the heterologous nucleic acid is operably linked to a constitutive promoter.

74. The AAV viral vector of embodiment 72 or 73, wherein the heterologous nucleic acid encodes a polypeptide.

75. The AAV viral vector of embodiment 72 or 73, wherein the heterologous nucleic acid encodes an antisense RNA, microRNA, or RNAi.

76. The AAV viral vector of embodiment 72 to 75, wherein the AAV capsid protein comprises the amino acid sequence of SEQ ID NO: 3, 30, 31, 32, 33, 34, 49 or 84.

77. A nucleic acid encoding an AAV capsid protein comprising a VP1 portion, a VP2 portion and a VP3 portion, wherein the VP3 portion comprises variable regions (VR) I to IX wherein:

(a) VR-I comprises amino acid sequence SASTGAS (SEQ ID NO: 52)

(b) VR-II comprises amino acid sequence DNNGVK; (SEQ ID NO. 54)

(c) VR-III comprises amino acid sequence NDGS; (SEQ ID NO. 55)

(d) VR-IV comprises amino acid sequence INGSGQNQQT; (SEQ ID NO. 56)

(e) VR-V comprises amino acid sequence RVSTTTGQNNNSNFAWTA; (SEQ ID NO. 57)

(f) VR-VI comprises amino acid sequence HKEGEDRFFPLSG; (SEQ ID NO. 58)

(g) VR-VII comprises amino acid sequence KQNAARDNADYSDV; (SEQ ID NO. 59)

(h) VR-VIII comprises amino acid sequence ADNLQQQNTAPQI; and (SEQ ID NO. 60)

(i) VR-IX comprises amino acid sequence NYYKSTSVDF. (SEQ ID NO. 61)

78. The nucleic acid of embodiment 77, wherein the VP3 portion further comprises one or more of:
(i) an asparagine (N) at amino acid 223;
(ii) an alanine (A) residue at amino acid 224;
(iii) a threonine (T) residue at amino acid 410;
(iv) a histidine residue at amino acid 724; and
(v) a proline (P) residue at amino acid 734,
wherein amino acid positions in the AAV capsid protein are numbered with respect to amino acid positions in the amino acid sequence of SEQ ID NO: 3.

79. The nucleic acid of embodiment 77 or 78, wherein the VP3 portion has the sequence of SEQ ID NO: 41.

80. The nucleic acid of embodiment 77 to 79, wherein the VP1 and VP2 portion of the encoded AAV capsid amino acid sequence is at least 95% identical to the amino acid sequence of the VP1 and VP2 portion of SEQ ID NO: 3, 31, 32, 33 or 34.

81. The nucleic acid of embodiment 77 to 80, wherein the encoded AAV capsid amino acid sequence is at least 99% identical to the amino acid sequence of SEQ ID NO: 3, 31, 32, 33 or 34.

82. The nucleic acid of embodiment 77 to 81, wherein the nucleic acid sequence is at least 99% identical to the nucleotide sequence selected from SEQ ID NO: 18, 20, 21, 22 or 23.

83. The nucleic acid of embodiment 77 to 82, wherein the nucleic acid sequence is 100% identical to the nucleotide sequence selected from SEQ ID NO: 18, 20, 21, 22 or 23.

84. A vector comprising the nucleic acid of embodiments 57 to 83.

85. An AAV capsid protein encoded by the nucleic acid of embodiments 77 to 83.

86. The AAV capsid protein of embodiment 85, wherein the protein comprises the amino acid sequence of SEQ ID NO: 3, 31, 32, 33 or 34.

87. An AAV viral vector comprising the AAV capsid protein encoded by the nucleic acid of embodiment 88 and an AAV vector, wherein the AAV vector comprises a heterologous nucleic acid.

88. The AAV viral vector of embodiment 87, wherein the heterologous nucleic acid is operably linked to a constitutive promoter.

89. The AAV viral vector of embodiment 87 or 88, wherein the heterologous nucleic acid encodes a polypeptide.

90. The AAV viral vector of embodiment 87 or 88, wherein the heterologous nucleic acid encodes an antisense RNA, microRNA, or RNAi.

91. The AAV viral vector of embodiment 87 to 90, wherein the AAV capsid protein comprises the amino acid sequence of SEQ ID NO: 3, 31, 32, 33 or 34.

92. A nucleic acid encoding an AAV capsid protein comprising a VP1 portion, a VP2 portion and a VP3 portion, wherein the VP1 portion comprises a leucine (L) residue at amino acid 129, wherein the VP2 portion comprises a threonine (T) or asparagine (N) residue at amino acid 157 and a lysine (K) or serine (S) residue at amino acid 162, and wherein the VP3 portion comprises asparagine (N) residue at amino acid 223, an alanine (A) residue at amino acid 224, a histidine (H) residue at amino acid 272, a threonine (T) residue at amino acid 410, a histidine (H) residue at amino acid 724 and a proline (P) residue at amino acid 734, wherein amino acid positions in the AAV capsid protein are numbered with respect to amino acid positions in the amino acid sequence of SEQ ID NO: 3.

93. The nucleic acid of embodiment 92, wherein the VP3 portion comprises variable regions (VR) I to IX wherein:

(a) VR-I comprises amino acid sequence SASTGAS; (SEQ ID NO: 52)

(b) VR-II comprises amino acid sequence DNNGVK; (SEQ ID NO. 54)

(c) VR-III comprises amino acid sequence NDGS; (SEQ ID NO. 55)

(d) VR-IV comprises amino acid sequence INGSGQNQQT; (SEQ ID NO. 56)

(e) VR-V comprises amino acid sequence RVSTTTGQNNNSNFAWTA; (SEQ ID NO. 57)

(f)VR-VI comprises amino acid sequence HKEGEDRFFPLSG; (SEQ ID NO. 58)

(g) VR-VII comprises amino acid sequence KQNAARDNADYSDV; (SEQ ID NO. 59)

-continued (SEQ ID NO. 60)
(h) VR-VIII comprises amino acid sequence

ADNLQQQNTAPQI; and (SEQ ID NO. 61)
(i) VR-IX comprises amino acid sequence

NYYKSTSVDF.

94. The nucleic acid of embodiment 92 or 93, wherein the VP1 portion further comprises an aspartic acid (D) or alanine (A) residue at amino acid 24, wherein amino acid positions in the AAV capsid protein are numbered with respect to amino acid positions in the amino acid sequence of SEQ ID NO: 3.

95. The nucleic acid of embodiment 92 to 94, wherein the VP2 portion further comprises one or more of (i) a proline (P) residue at amino acid 148;

(ii) an arginine (R) residue inserted at amino acid 152;

(iii) an arginine (R) residue at amino acid 168;

(iv) an isoleucine (I) residue at amino acid 189; and (v) a serine (S) residue at amino acid 200, wherein amino acid positions in the AAV capsid protein are numbered with respect to amino acid positions in the amino acid sequence of SEQ ID NO: 3.

96. The nucleic acid of embodiment 92 to 96, wherein the encoded AAV capsid amino acid sequence is at least 95% identical to the amino acid sequence of SEQ ID NO: 31, 32, 33 or 34.

97. The nucleic acid of embodiment 92, wherein the encoded AAV capsid amino acid sequence is at least 99% identical to the amino acid sequence of SEQ ID NO: 31, 32, 33 or 34.

98. The nucleic acid of embodiment 92, wherein the nucleic acid sequence is at least 99% identical to the nucleotide sequence selected from SEQ ID NO: 20, 21, 22 or 23.

99. The nucleic acid of embodiment 98, wherein the nucleic acid sequence is 100% identical to the nucleotide sequence selected from SEQ ID NO: 20, 21, 22 or 23.

100. A vector comprising the nucleic acid of embodiment 92 to 99.

101. An AAV capsid protein encoded by the nucleic acid of embodiment 92 to 99.

102. The AAV capsid protein of embodiment 101, wherein the protein comprises the amino acid sequence of SEQ ID NO: 31, 32, 33 or 34.

103. An AAV viral vector comprising the AAV capsid protein encoded by the nucleic acid of embodiment 101 or 102 and an AAV vector, wherein the AAV vector comprises a heterologous nucleic acid.

104. The AAV viral vector of embodiment 103, wherein the heterologous nucleic acid is operably linked to a constitutive promoter.

105. The AAV viral vector of embodiment 103 or 104, wherein the heterologous nucleic acid encodes a polypeptide, an antisense RNA, microRNA, or RNAi.

What is claimed is:

1. A nucleic acid encoding an AAV capsid protein comprising a VP1 portion, a VP2 portion, and a VP3 portion, wherein the VP3 portion comprises the amino acid sequence of SEQ ID NO: 41.

2. The nucleic acid of claim 1, wherein the encoded AAV capsid protein comprises the amino acid sequence of SEQ ID NO: 3, SEQ ID NO: 31, SEQ ID NO: 32, SEQ ID NO: 33, or SEQ ID NO: 34.

3. The nucleic acid of claim 1, wherein the nucleic acid comprises a sequence at least 95% identical to the nucleotide sequence selected from SEQ ID NOS: 18 and 20-23.

4. The nucleic acid of claim 3, wherein the nucleic acid sequence is 100% identical to the nucleotide sequence selected from SEQ ID NOS: 18 and 20-23.

5. A vector comprising the nucleic acid of claim 1.

6. An AAV capsid protein encoded by the nucleic acid of claim 1.

7. The AAV capsid protein of claim 6, wherein the protein comprises the amino acid sequence of SEQ ID NO: 3, SEQ ID NO: 31, SEQ ID NO: 32, SEQ ID NO: 33, or SEQ ID NO: 34.

8. An AAV viral vector comprising an AAV capsid protein and an AAV vector genome, wherein the AAV capsid protein comprises a VP1 portion, a VP2 portion, and a VP3 portion, wherein the VP3 portion comprises the amino acid sequence of SEQ ID NO: 41, and wherein the AAV vector genome comprises in 5' to 3' orientation, (a) a first AAV inverted terminal repeat, (b) a promoter, (c) a heterologous nucleic acid, (d) a poly-A tail, and (e) a second AAV inverted terminal repeat, wherein the heterologous nucleic acid is operably linked to the promoter.

9. The AAV viral vector of claim 8, wherein the promoter is a constitutive promoter.

10. The AAV viral vector of claim 8, wherein the heterologous nucleic acid encodes a polypeptide.

11. The AAV viral vector of claim 8, wherein the heterologous nucleic acid encodes an mRNA, antisense RNA, microRNA, or RNAi.

12. The AAV viral vector of claim 8, wherein the AAV capsid protein comprises the amino acid sequence of SEQ ID NO: 3, SEQ ID NO: 31, SEQ ID NO: 32, SEQ ID NO: 33, or SEQ ID NO: 34.

13. An AAV viral vector comprising:

(i) an AAV capsid protein having the amino acid sequence of SEQ ID NO: 3, SEQ ID NO: 31, SEQ ID NO: 32, SEQ ID NO: 33, or SEQ ID NO: 34, and (ii) an AAV vector genome, wherein the AAV vector genome comprises in 5' to 3' orientation, (a) a first AAV inverted terminal repeat, (b) a promoter, (c) a heterologous nucleic acid, (d) a poly-A tail, and (e) a second AAV inverted terminal repeat.

14. The AAV viral vector of claim 13, wherein the heterologous nucleic acid encodes an mRNA, siRNA, gRNA, or microRNA.

15. The AAV viral vector of claim 13, wherein the heterologous nucleic acid encodes a polypeptide.

16. The AAV viral vector of claim 15, wherein the heterologous nucleic acid encodes a cystic fibrosis transmembrane conductance regulator (CFTR), a CLN3 protein, an alpha-galactosidase A (GLA), or an acid alpha-glucosidase (GAA).

17. The AAV viral vector of claim 16, wherein the heterologous nucleic acid encodes a CFTR.

18. The AAV viral vector of claim 17, wherein the CFTR comprises an amino acid sequence encoded by SEQ ID NO: 4.

19. The AAV viral vector of claim 15, wherein the heterologous nucleic acid encodes a protein comprising an amino acid sequence with at least 70%, 80%, 90%, or 99% identity with any one of SEQ ID NOs: 8, 11, and 14.

20. The AAV viral vector of claim 15, wherein the heterologous nucleic acid comprises a sequence with at least 70%, 80%, 90%, or 99% identity with any one of SEQ ID NOs: 4, 5, 6, 7, 9, 10, 12, and 13.

21. The AAV viral vector of claim 8, wherein the promoter is a Rous sarcoma virus (RSV) LTR promoter, a cytomegalovirus (CMV) promoter, an SV40 promoter, a dihydrofolate reductase promoter, a beta-actin promoter, a phosphoglycerol kinase (PGK) promoter, a U6 promoter, an H1 promoter, a CAG promoter, a hybrid chicken beta-actin promoter, an MeCP2 promoter, an EF1 promoter, a ubiquitous chicken β-actin hybrid (CBh) promoter, a U1a promoter, a U1b promoter, an MeCP2 promoter, an MeP418 promoter, an MeP426 promoter, a minimal MeCP2 promoter, a VMD2 promoter, an mRho promoter, EF1a promoter, Ubc promoter, human β-actin promoter, TRE promoter, Ac5 promoter, Polyhedrin promoter, CaMKIIa promoter, Gal1 promoter, TEF1 promoter, GDS promoter, ADH1 promoter, Ubi promoter, or α-1-antitrypsin (hAAT) promoter.

22. A method of introducing a heterologous nucleic acid to a cell in a subject, comprising administering the AAV viral vector of claim 8 to the subject, wherein the AAV viral vector comprises the heterologous nucleic acid.

23. The method of claim 22, wherein the AAV viral vector is administered to the subject orally, rectally, transmucosally, inhalationally, transdermally, parenterally, intravenously, subcutaneously, intradermally, intramuscularly, intrapleurally, intracerebrally, intrathecally, intracerebrally, intraventricularly, intranasally, intra-aurally, intra-ocularly, peri-ocularly, topically, intralymphatically, intracistemally, subretinally, or intravitreally.

24. The method of claim 22, wherein the subject has Stargardt disease, amyotrophic lateral sclerosis (ALS), spinal muscular atrophy (SMA), Fabry disease, Pompe disease, CLN3 disease (or Juvenile Neuronal Ceroid Lipofuscinosis), recessive dystrophic epidermolysis bullosa (RDEB), juvenile Batten disease, autosomal dominant disorder, muscular dystrophy, hemophilia A, hemophilia B, multiple sclerosis, diabetes mellitus, Gaucher disease cancer, arthritis, muscle wasting, heart disease, intimal hyperplasia, epilepsy, Huntington's disease, Parkinson's disease, Alzheimer's disease, cystic fibrosis, thalassemia, Hurler's Syndrome, Sly syndrome, Scheie Syndrome, Hurler-Scheie Syndrome, Hunter's Syndrome, Sanfilippo Syndrome A (mucopolysaccharidosis IIIA or MPS IIIA), Sanfilippo Syndrome B (mucopolysaccharidosis IIIB or MPS IIIB), Sanfilippo Syndrome C, Sanfilippo Syndrome D, Morquio Syndrome, Maroteaux-Lamy Syndrome, Krabbe's disease, phenylketonuria, Batten's disease, spinal cerebral ataxia, LDL receptor deficiency, hyperammonemia, arthritis, macular degeneration, retinitis pigmentosa, ceroid lipofuscinosis, neuronal, 1 (CLN1), or adenosine deaminase deficiency.

25. The method of claim 22, wherein the subject is a mammal.

* * * * *

SEQUENCE LISTING

```
<160> NUMBER OF SEQ ID NOS: 163

<210> SEQ ID NO 1
<211> LENGTH: 737
<212> TYPE: PRT
<213> ORGANISM: Artificial Sequence
<220> FEATURE:
<223> OTHER INFORMATION: AAV110 VP1

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160
```

-continued

```
Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Thr Pro Ala Ala Val Gly Pro Thr Thr Met Ala Ser Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Ala Ser Thr Gly Ala Ser Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Asn
        435                 440                 445

Arg Thr Gln Asn Gln Ser Gly Ser Ala Gln Asn Lys Asp Leu Leu Phe
    450                 455                 460

Ser Arg Gly Ser Pro Ala Gly Met Ser Val Gln Pro Lys Asn Trp Leu
465                 470                 475                 480

Pro Gly Pro Cys Tyr Arg Gln Gln Arg Val Ser Lys Thr Lys Thr Asp
                485                 490                 495

Asn Asn Asn Ser Asn Phe Thr Trp Thr Gly Ala Ser Lys Tyr Asn Leu
            500                 505                 510

Asn Gly Arg Glu Ser Ile Ile Asn Pro Gly Thr Ala Met Ala Ser His
        515                 520                 525

Lys Asp Asp Lys Asp Lys Phe Phe Pro Met Ser Gly Val Met Ile Phe
    530                 535                 540

Gly Lys Glu Ser Ala Gly Ala Ser Asn Thr Ala Leu Asp Asn Val Met
545                 550                 555                 560

Ile Thr Asp Glu Glu Glu Ile Lys Ala Thr Asn Pro Val Ala Thr Glu
                565                 570                 575
```

-continued

```
Arg Phe Gly Thr Val Ala Val Asn Leu Gln Ser Ser Ser Thr Asp Pro
            580                 585                 590

Ala Thr Gly Asp Val His Val Met Gly Ala Leu Pro Gly Met Val Trp
        595                 600                 605

Gln Asp Arg Asp Val Tyr Leu Gln Gly Pro Ile Trp Ala Lys Ile Pro
    610                 615                 620

His Thr Asp Gly His Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Ala Glu Phe Ser Ala Thr Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Val Gln Tyr Thr Ser
    690                 695                 700

Asn Tyr Ala Lys Ser Ala Asn Val Asp Phe Thr Val Asp Asn Asn Gly
705                 710                 715                 720

Leu Tyr Thr Glu Pro Arg Pro Ile Gly Thr Arg Tyr Leu Thr Arg Pro
                725                 730                 735

Leu


<210> SEQ ID NO 2
<211> LENGTH: 736
<212> TYPE: PRT
<213> ORGANISM: Artificial Sequence
<220> FEATURE:
<223> OTHER INFORMATION: AAV204 VP1

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
```

```
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Asn Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620
```

Thr Asp Gly His Phe His Pro Ser Pro Leu Met Gly Gly Phe Gly Leu
625 630 635 640

Lys His Pro Pro Pro Gln Ile Leu Ile Lys Asn Thr Pro Val Pro Ala
645 650 655

Asn Pro Pro Ala Glu Phe Ser Ala Thr Lys Phe Ala Ser Phe Ile Thr
660 665 670

Gln Tyr Ser Thr Gly Gln Val Ser Val Glu Ile Glu Trp Glu Leu Gln
675 680 685

Lys Glu Asn Ser Lys Arg Trp Asn Pro Glu Val Gln Tyr Thr Ser Asn
690 695 700

Tyr Ala Lys Ser Ala Asn Val Asp Phe Thr Val Asp Asn Asn Gly Leu
705 710 715 720

Tyr Thr Glu Pro Arg Pro Ile Gly Thr Arg Tyr Leu Thr Arg Pro Leu
725 730 735

<210> SEQ ID NO 3
<211> LENGTH: 735
<212> TYPE: PRT
<213> ORGANISM: Artificial Sequence
<220> FEATURE:
<223> OTHER INFORMATION: AAV214 VP1

<400> SEQUENCE: 3

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Phe Gly Leu Val Glu Glu Gly Ala Lys Thr Ala Pro Gly Lys Lys Arg
130 135 140

Pro Val Glu Gln Ser Pro Gln Glu Pro Asp Ser Ser Ser Gly Ile Gly
145 150 155 160

Lys Thr Gly Gln Gln Pro Ala Lys Lys Arg Leu Asn Phe Gly Gln Thr
165 170 175

Gly Asp Ser Glu Ser Val Pro Asp Pro Gln Pro Leu Gly Glu Pro Pro
180 185 190

Ala Thr Pro Ala Ala Val Gly Pro Thr Thr Met Ala Ser Gly Gly Gly
195 200 205

Ala Pro Met Ala Asp Asn Asn Glu Gly Ala Asp Gly Val Gly Asn Ala
210 215 220

Ser Gly Asn Trp His Cys Asp Ser Thr Trp Leu Gly Asp Arg Val Ile
225 230 235 240

Thr Thr Ser Thr Arg Thr Trp Ala Leu Pro Thr Tyr Asn Asn His Leu
245 250 255

```
Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Asp Asn Asn Gly Val Lys Thr Ile Ala Asn Asn
                325                 330                 335

Leu Thr Ser Thr Val Gln Val Phe Thr Asp Ser Asp Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asp Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Lys
        435                 440                 445

Thr Ile Asn Gly Ser Gly Gln Asn Gln Gln Thr Leu Lys Phe Ser Gln
    450                 455                 460

Gly Gly Pro Asn Thr Met Ala Asn Gln Ala Lys Asn Trp Leu Pro Gly
465                 470                 475                 480

Pro Cys Tyr Arg Gln Gln Arg Val Ser Thr Thr Thr Gly Gln Asn Asn
                485                 490                 495

Asn Ser Asn Phe Ala Trp Thr Ala Gly Thr Lys Tyr His Leu Asn Gly
            500                 505                 510

Arg Asn Ser Leu Met Asn Pro Gly Pro Ala Met Ala Ser His Lys Glu
        515                 520                 525

Gly Glu Asp Arg Phe Phe Pro Leu Ser Gly Ser Leu Ile Phe Gly Lys
    530                 535                 540

Gln Asn Ala Ala Arg Asp Asn Ala Asp Tyr Ser Asp Val Met Leu Thr
545                 550                 555                 560

Ser Glu Glu Glu Ile Lys Thr Thr Asn Pro Val Ala Thr Glu Glu Tyr
                565                 570                 575

Gly Ile Val Ala Asp Asn Leu Gln Gln Gln Asn Thr Ala Pro Gln Ile
            580                 585                 590

Gly Thr Val Asn Ser Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asp
                645                 650                 655

Pro Pro Thr Thr Phe Asn Gln Ser Lys Leu Asn Ser Phe Ile Thr Gln
            660                 665                 670
```

-continued

```
Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Tyr Lys Ser Thr Ser Val Asp Phe Ala Val Asn Thr Glu Gly Val Tyr
705                 710                 715                 720

Ser Glu Pro His Pro Ile Gly Thr Arg Tyr Leu Thr Arg Pro Leu
                725                 730                 735


<210> SEQ ID NO 4
<211> LENGTH: 4287
<212> TYPE: DNA
<213> ORGANISM: Artificial Sequence
<220> FEATURE:
<223> OTHER INFORMATION: CFTRdeltaR

<400> SEQUENCE: 4

atgcagagaa gccccctgga gaaggcctct gtggtgagca agctgttctt cagctggacc     60

agacccatcc tgagaaaggg ctacagacag agactggagc tgtctgacat ctaccagatc    120

ccctctgtgg actctgctga caacctgtct gagaagctgg agagagagtg ggacagagag    180

ctggccagca agaagaaccc caagctgatc aatgccctga gaagatgctt cttctggaga    240

ttcatgttct atggcatctt cctgtacctg gggggaggtga ccaaggctgt gcagcccctg    300

ctgctgggca gaatcattgc cagctatgac cctgacaaca aggaggagag aagcattgcc    360

atctacctgg gcattggcct gtgcctgctg ttcattgtga gaaccctgct gctgcaccct    420

gccatctttg gcctgcacca cattggcatg cagatgagaa ttgccatgtt cagcctgatc    480

tacaagaaga ccctgaagct gagcagcaga gtgctggaca agatcagcat tggccagctg    540

gtgagcctgc tgagcaacaa cctgaacaag tttgatgagg gcctggccct ggcccacttt    600

gtgtggattg ccccctgca ggtggccctg ctgatgggcc tgatctggga gctgctgcag    660

gcctctgcct tctgtggcct gggcttcctg attgtgctgg ccctgttcca ggctggcctg    720

ggcagaatga tgatgaagta cagagaccag agagctggca agatctctga gagactggtg    780

atcacctctg agatgattga gaacatccag tctgtgaagg cctactgctg ggaggaggcc    840

atggagaaga tgattgagaa cctgagacag acagagctga agctgaccag aaaggctgcc    900

tatgtgagat acttcaacag ctctgccttc ttcttctctg gcttctttgt ggtgttcctg    960

tctgtgctgc cctatgccct gatcaagggc atcatcctga gaaagatctt caccaccatc   1020

agcttctgca ttgtgctgag aatggctgtg accagacagt tcccctgggc tgtgcagacc   1080

tggtatgaca gcctgggggc catcaacaag atccaggact tcctgcagaa gcaggagtac   1140

aagaccctgg agtacaacct gaccaccaca gaggtggtga tggagaatgt gacagccttc   1200

tgggaggagg gctttgggga gctgtttgag aaggccaagc agaacaacaa caacagaaag   1260

accagcaatg gggatgacag cctgttcttc agcaacttca gcctgctggg cacccctgtg   1320

ctgaaggaca tcaacttcaa gattgagaga ggccagctgc tggctgtggc tggcagcaca   1380

ggggctggca agaccagcct gctgatgatg atcatggggg agctggagcc ctctgagggc   1440

aagatcaagc actctggcag aatcagcttc tgcagccagt tcagctggat catgcctggc   1500

accatcaagg agaacatcat ctttggggtg agctatgatg agtacagata cagatctgtg   1560

atcaaggcct gccagctgga ggaggacatc agcaagtttg ctgagaagga caacattgtg   1620

ctgggggagg ggggcatcac cctgtctggg ggccagagag ccagaatcag cctggccaga   1680

gctgtgtaca aggatgctga cctgtacctg ctggacagcc cctttggcta cctggatgtg   1740
```

-continued

```
ctgacagaga aggagatctt tgagagctgt gtgtgcaagc tgatggccaa caagaccaga   1800
atcctggtga ccagcaagat ggagcacctg aagaaggctg acaagatcct gatcctgcat   1860
gagggcagca gctacttcta tggcaccttc tctgagctgc agaacctgca gcctgacttc   1920
agcagcaagc tgatgggctg tgacagcttt gaccagttct ctgctgagag aagaaacagc   1980
atcctgacag agaccctgca cagattcagc ctggaggggg atgcccctgt gagctggaca   2040
gagaccaaga agcagagctt caagcagaca ggggagtttg gggagaagag aaagaacagc   2100
atcctgaacc ccatcaacag caccctgcag gccagaagaa gacagtctgt gctgaacctg   2160
atgacccact ctgtgaacca gggccagaac atccacagaa agaccacagc cagcaccaga   2220
aaggtgagcc tggcccccca ggccaacctg acagagctgg acatctacag cagaagactg   2280
agccaggaga caggcctgga gatctctgag gagatcaatg aggaggacct gaaggagtgc   2340
ttctttgatg acatggagag catccctgct gtgaccacct ggaacaccta cctgagatac   2400
atcacagtgc acaagagcct gatctttgtg ctgatctggt gcctggtgat cttcctggct   2460
gaggtggctg ccagcctggt ggtgctgtgg ctgctgggca acacccccct gcaggacaag   2520
ggcaacagca cccacagcag aaacaacagc tatgctgtga tcatcaccag caccagcagc   2580
tactatgtgt tctacatcta tgtgggggtg gctgacaccc tgctggccat gggcttcttc   2640
agaggcctgc ccctggtgca caccctgatc acagtgagca agatcctgca ccacaagatg   2700
ctgcactctg tgctgcaggc ccccatgagc accctgaaca ccctgaaggc tgggggcatc   2760
ctgaacagat tcagcaagga cattgccatc ctggatgacc tgctgcccct gaccatcttt   2820
gacttcatcc agctgctgct gattgtgatt ggggccattg ctgtggtggc tgtgctgcag   2880
ccctacatct ttgtggccac agtgcctgtg attgtggcct tcatcatgct gagagcctac   2940
ttcctgcaga ccagccagca gctgaagcag ctggagtctg agggcagaag ccccatcttc   3000
acccacctgg tgaccagcct gaagggcctg tggaccctga gagcctttgg cagacagccc   3060
tactttgaga ccctgttcca caaggccctg aacctgcaca cagccaactg gttcctgtac   3120
ctgagcaccc tgagatggtt ccagatgaga attgagatga tctttgtgat cttcttcatt   3180
gctgtgacct tcatcagcat cctgaccaca ggggaggggg agggcagagt gggcatcatc   3240
ctgaccctgg ccatgaacat catgagcacc ctgcagtggg ctgtgaacag cagcattgat   3300
gtggacagcc tgatgagatc tgtgagcaga gtgttcaagt tcattgacat gcccacagag   3360
ggcaagccca ccaagagcac caagccctac aagaatggcc agctgagcaa ggtgatgatc   3420
attgagaaca gccatgtgaa gaaggatgac atctggccct ctgggggcca gatgacagtg   3480
aaggacctga cagccaagta cacagagggg ggcaatgcca tcctggagaa catcagcttc   3540
agcatcagcc ctggccagag agtgggcctg ctgggcagaa caggctctgg caagagcacc   3600
ctgctgtctg ccttcctgag actgctgaac acagaggggg agatccagat tgatggggtg   3660
agctgggaca gcatcaccct gcagcagtgg agaaaggcct ttggggtgat cccccagaag   3720
gtgttcatct tctctggcac cttcagaaag aacctggacc cctatgagca gtggtctgac   3780
caggagatct ggaaggtggc tgatgaggtg ggcctgagat ctgtgattga gcagttccct   3840
ggcaagctgg actttgtgct ggtggatggg ggctgtgtgc tgagccatgg ccacaagcag   3900
ctgatgtgcc tggccagatc tgtgctgagc aaggccaaga tcctgctgct ggatgagccc   3960
tctgcccacc tggaccctgt gacctaccag atcatcagaa gaaccctgaa gcaggccttt   4020
gctgactgca cagtgatcct gtgtgagcac agaattgagg ccatgctgga gtgccagcag   4080
```

ttcctggtga ttgaggagaa caaggtgaga cagtatgaca gcatccagaa gctgctgaat 4140
gagagaagcc tgttcagaca ggccatcagc ccctctgaca gagtgaagct gttcccccac 4200
agaaacagca gcaagtgcaa gagcaagccc cagattgctg ccctgaagga ggagaccgag 4260
gaggaggtgc aggacaccag actgtaa 4287

<210> SEQ ID NO 5
<211> LENGTH: 2859
<212> TYPE: DNA
<213> ORGANISM: Artificial Sequence
<220> FEATURE:
<223> OTHER INFORMATION: GAA

<400> SEQUENCE: 5
atgggagtcc gccacccgcc ctgctcacat cgcctgcttg ctgtctgtgc cctcgtgtca 60
cttgctaccg ccgcgctgct tggtcacatt ctgctgcacg actttttact agttccgagg 120
gaactgtcgg gatccagccc cgtgctcgag gaaactcacc ccgcgcacca acagggggcg 180
tccaggccgg gaccgcgcga cgcccaggcc cacccgggcc ggcctcgggc cgtgccaact 240
cagtgcgatg tgccgccgaa ctcccgcttc gactgtgcgc ctgacaaggc cataacccag 300
gaacagtgcg aagcacgcgg ctgctgctat attccggcga agcagggctt gcagggtgcc 360
caaatgggtc agccttggtg cttctttccc ccgtcgtacc cctcgtacaa gctggagaac 420
ctgagcagca gcgaaatggg gtacaccgcc actctgaccc ggacgacccc gaccttcttc 480
ccgaaagaca tcctgaccct gcggctggat gtgatgatgg aaactgagaa cagactgcac 540
ttcactatca aggaccccgc gaaccgcaga tatgaggtgc cactggaaac ccctcatgtg 600
cattcccggg ccccatcccc tctgtactcg gtggaattct ccgaagaacc cttcggggtc 660
attgtgcgcc ggcagcttga tggccgggtc ctgctcaaca ccaccgtggc accccttttc 720
ttcgctgacc agttcctcca gctgagcacc tcgctgccga gccagtacat caccggactg 780
gccgagcacc tctcccctct gatgctgtcc actagctgga ctaggatcac tctgtggaac 840
cgggatctgg cccctacccc gggcgcgaac ctgtacggat cgcacccctt ctacctggcc 900
ctcgaggacg gaggctccgc ccacggagtg ttcctgctga actccaacgc tatggacgtg 960
gtgctccagc cgtcccctgc actgtcctgg cggagcacag gggtattctt ggatgtctac 1020
atcttcctcg gcccggagcc aaagtccgtg gtgcaacagt atctggatgt cgtgggttac 1080
ccattcatgc cgccatactg gggccttggc ttccacctgt gccgctgggg atacagctcc 1140
accgccatca ctagacaggt cgtggaaaac atgactagag cccacttccc cctcgatgtc 1200
cagtggaatg acctggacta catggattcc agacgcgact tcactttcaa caaggatgga 1260
ttcagagatt tccccgctat ggtccaagaa ctgcaccagg gtggccggcg gtacatgatg 1320
attgtggacc ccgccatttc aagctccgga ccagcgggct cgtaccggcc ctacgacgaa 1380
ggtttgcgcc gcggcgtgtt catcactaac gaaaccggcc agccactgat tgggaaggtc 1440
tggcctggaa gcaccgcgtt cccggacttc actaacccaa cggccttggc gtggtgggag 1500
gacatggtgg ccgaattcca cgaccaagtc ccattcgacg gaatgtggat cgacatgaac 1560
gagcccagca acttcatccg aggctccgag gacggctgcc ctaacaacga acttgagaac 1620
cctccgtacg tgcctggcgt cgtcggcgga acactgcagg ccgctacgat ctgtgcctca 1680
tcgcatcagt tcctgtcaac ccactacaac ctccataatc tgtacggcct caccgaagcc 1740
atcgcctccc accgggccct ggtcaaggcc cgggggacta ggcccttcgt gattagccgg 1800
agcactttcg ccggacacgg aagatacgcc ggacattgga ccggcgacgt gtggtcatcg 1860

```
tgggagcagc tcgcctcctc cgtccccgaa atcctgcagt tcaatctcct gggagtcccc   1920

ctcgtgggcg cggacgtgtg cggattcctg ggcaatacct ctgaggagct gtgcgtgaga   1980

tggacccagc tgggggcgtt ctaccccttc atgcggaacc acaactcact gctgtccctg   2040

cctcaagagc cgtactcatt ctccgagccg gcacaacagg ccatgcgaaa ggctctgacc   2100

ctccgctatg cgctcttgcc ccacctctac actctgtttc accaagccca tgtcgcgggc   2160

gaaacagtgg ccagaccact ctttctggaa ttcccaaagg actcctcaac ctggactgtg   2220

gatcatcagc tgctctgggg agaggcactg ctgatcaccc cggtgctcca agccggaaag   2280

gcggaagtga ccggatactt ccctctcggt acttggtacg acctccaaac cgtgccggtc   2340

gaggccctgg gcagcttgcc tccgccgccg gctgccccgc gggagcctgc aatccactcc   2400

gaggggcaat gggtgaccct ccctgcacca ctggacacca tcaacgtgca cctccgggcc   2460

ggctacatca tcccgctgca aggaccgggt ctgactacca ccgaatcccg gcagcagccc   2520

atggcactgg ccgtggccct gaccaaggga ggggaagcac ggggagaact cttttgggac   2580

gatggagaat ccctggaagt gctcgagcgg ggagcctaca ctcaagtcat ctttcttgcc   2640

cgcaacaaca ccatcgtgaa cgaattggtc cgcgtgacct ccgagggggc cggactccag   2700

ctgcaaaaag tgaccgtgct gggggtggca accgccccgc aacaagtgtt gtctaacgga   2760

gtgccggtgt ccaacttcac ctactcccct gataccaaag ttctagatat ttgcgtgagc   2820

ctgctgatgg gagaacagtt cctggtgtcc tggtgctga                          2859
```

```
<210> SEQ ID NO 6
<211> LENGTH: 2859
<212> TYPE: DNA
<213> ORGANISM: Artificial Sequence
<220> FEATURE:
<223> OTHER INFORMATION: GAA codon-optimized nucleotide sequence 1 (GAA
      15)

<400> SEQUENCE: 6
```

```
atgggagtcc gccacccgcc ctgctcacat cgcctgcttg ctgtctgtgc cctcgtgtca     60

cttgctaccg ccgcgctgct tggtcacatt ctgctgcacg actttttact agttccgagg    120

gaactgtcgg gatccagccc cgtgctcgag gaaactcacc ccgcgcacca acagggggcg    180

tccaggccgg gaccgcgcga cgcccaggcc cacccgggcc ggcctcgggc cgtgccaact    240

cagtgcgatg tgccgccgaa ctcccgcttc gactgtgcgc ctgacaaggc cataacccag    300

gaacagtgcg aagcacgcgg ctgctgctat attccggcga agcagggctt gcagggtgcc    360

caaatgggtc agccttggtg cttctttccc ccgtcgtacc cctcgtacaa gctggagaac    420

ctgagcagca gcgaaatggg gtacaccgcc actctgaccc ggacgacccc gaccttcttc    480

ccgaaagaca tcctgaccct gcggctggat gtgatgatgg aaactgagaa cagactgcac    540

ttcactatca aggaccccgc gaaccgcaga tatgaggtgc cactggaaac ccctcatgtg    600

cattcccggg ccccatcccc tctgtactcg gtggaattct ccgaagaacc cttcggggtc    660

attgtgcgcc ggcagcttga tggccgggtc ctgctcaaca ccaccgtggc accccttttc    720

ttcgctgacc agttcctcca gctgagcacc tcgctgccga gccagtacat caccggactg    780

gccgagcacc tctcccctct gatgctgtcc actagctgga ctaggatcac tctgtggaac    840

cgggatctgg cccctacccc gggcgcgaac ctgtacggat cgcacccctt ctacctggcc    900

ctcgaggacg gaggctccgc ccacggagtg ttcctgctga actccaacgc tatggacgtg    960

gtgctccagc cgtcccctgc actgtcctgg cggagcacag gggtattctg ggatgtctac   1020
```

atcttcctcg gcccggagcc aaagtccgtg gtgcaacagt atctggatgt cgtgggttac 1080
ccattcatgc cgccatactg ggccttggc ttccacctgt gccgctgggg atacagctcc 1140
accgccatca ctagacaggt cgtggaaaac atgactagag cccacttccc cctcgatgtc 1200
cagtggaatg acctggacta catggattcc agacgcgact tcactttcaa caaggatgga 1260
ttcagagatt tccccgctat ggtccaagaa ctgcaccagg gtggccggcg gtacatgatg 1320
attgtggacc ccgccatttc aagctccgga ccagcgggct cgtaccggcc ctacgacgaa 1380
ggtttgcgcc gcggcgtgtt catcactaac gaaaccggcc agccactgat tgggaaggtc 1440
tggcctggaa gcaccgcgtt cccggacttc actaacccaa cggccttggc gtggtgggag 1500
gacatggtgg ccgaattcca cgaccaagtc ccattcgacg gaatgtggat cgacatgaac 1560
gagcccagca acttcatccg aggctccgag gacggctgcc ctaacaacga acttgagaac 1620
cctccgtacg tgcctggcgt cgtcggcgga acactgcagg ccgctacgat ctgtgcctca 1680
tcgcatcagt tcctgtcaac ccactacaac ctccataatc tgtacggcct caccgaagcc 1740
atcgcctccc accgggccct ggtcaaggcc cgggggacta ggcccttcgt gattagccgg 1800
agcactttcg ccggacacgg aagatacgcc ggacattgga ccggcgacgt gtggtcatcg 1860
tgggagcagc tcgcctcctc cgtccccgaa atcctgcagt tcaatctcct gggagtcccc 1920
ctcgtgggcg cggacgtgtg cggattcctg ggcaatacct ctgaggagct gtgcgtgaga 1980
tggacccagc tgggggcgtt ctaccccttc atgcggaacc acaactcact gctgtccctg 2040
cctcaagagc cgtactcatt ctccgagccg gcacaacagg ccatgcgaaa ggctctgacc 2100
ctccgctatg cgctcttgcc ccacctctac actctgtttc accaagccca tgtcgcgggc 2160
gaaacagtgg ccagaccact ctttctggaa ttcccaaagg actcctcaac ctggactgtg 2220
gatcatcagc tgctctgggg agaggcactg ctgatcaccc cggtgctcca agccggaaag 2280
gcggaagtga ccggatactt ccctctcggt acttggtacg acctccaaac cgtgccggtc 2340
gaggccctgg gcagcttgcc tccgccgccg gctgccccgc gggagcctgc aatccactcc 2400
gaggggcaat gggtgaccct ccctgcacca ctggacacca tcaacgtgca cctccgggcc 2460
ggctacatca tcccgctgca aggaccgggt ctgactacca ccgaatcccg gcagcagccc 2520
atggcactgg ccgtggccct gaccaaggga ggggaagcac ggggagaact cttttgggac 2580
gatggagaat ccctggaagt gctcgagcgg ggagcctaca ctcaagtcat ctttcttgcc 2640
cgcaacaaca ccatcgtgaa cgaattggtc cgcgtgacct ccgagggggc cggactccag 2700
ctgcaaaaag tgaccgtgct gggggtggca accgccccgc aacaagtgtt gtctaacgga 2760
gtgccggtgt ccaacttcac ctactcccct gataccaaag ttctagatat ttgcgtgagc 2820
ctgctgatgg gagaacagtt cctggtgtcc tggtgctga 2859

<210> SEQ ID NO 7
<211> LENGTH: 2859
<212> TYPE: DNA
<213> ORGANISM: Artificial Sequence
<220> FEATURE:
<223> OTHER INFORMATION: GAA Codon-optimized 2 (GAA21)

<400> SEQUENCE: 7
atgggagtta gacaccctcc atgtagccac agactgctgg ccgtgtgtgc tctggtgtct 60
ctggctacag ctgccctgct gggacatatc ctgctgcacg acttcttact agttcccaga 120
gagctgtccg gcagcagccc tgtgctggaa gaaacacacc ctgcacatca gcagggcgcc 180

-continued

```
tctagacctg gacctagaga tgctcaggcc catcctggca gacctagagc tgtgcccaca    240
cagtgtgacg tgccacctaa cagcagattc gactgcgccc ctgacaaggc catcacacaa    300
gagcagtgtg aagccagagg ctgctgctac atccctgcca aacaaggact gcagggcgct    360
cagatgggac agccctggtg cttcttccca ccatcttacc ccagctacaa gctggaaaac    420
ctgagcagca gcgagatggg ctacaccgcc acactgacca gaaccacacc tacattcttc    480
ccgaaggaca tcctgacact gcggctggac gtgatgatgg aaaccgagaa ccggctgcac    540
ttcaccatca aggaccccgc caatcggaga tacgaggtgc cactggaaac ccctcacgtg    600
cactctagag ccccatctcc actgtacagc gtggaattca gcgaggaacc cttcggcgtg    660
atcgtgcgga gacagctgga tggaagagtg ctgctgaaca ccacagtggc ccctctgttc    720
ttcgccgacc agtttctgca gctgtccacc agcctgccta gccagtatat cacaggcctg    780
gccgagcacc tgtctccact gatgctgtct accagctgga cccggatcac cctgtggaac    840
agggatcttg ctcctacacc tggcgccaac ctgtacggct ctcacccttt ttatctggcc    900
ctggaagatg gcggatctgc ccacggtgtc tttctgctga actccaacgc catggacgtg    960
gtgctgcagc catctcctgc tctgtcttgg agaagcacag gcggcatcct ggacgtgtac   1020
atctttctgg gccccgagcc taagagcgtg gtgcagcagt atctggacgt cgtgggctac   1080
cccttcatgc ctccttattg ggggcctgggc ttccacctgt gcagatgggg atacagcagc   1140
accgccatca ccagacaggt ggtggaaaac atgacccggg ctcacttccc actggatgtg   1200
cagtggaacg acctggacta catggacagc agacgggact tcaccttcaa caaggacggc   1260
ttcagagact tccccgccat ggtgcaagaa ctgcaccaag gcggcagacg gtacatgatg   1320
atcgtggatc cagccatcag ctctagcggc cctgccggct cttacagacc ttacgatgag   1380
ggcctgagaa gaggcgtgtt catcaccaac gagacaggcc agcctctgat cggcaaagtg   1440
tggcctggca gcacagcctt tccagacttc acaaaccccca ccgctctggc ttggtgggaa   1500
gatatggtgg ccgagtttca cgatcaggtg ccccttcgacg gcatgtggat cgacatgaac   1560
gagcccagca acttcatccg ggcagcgag gatggctgcc ccaacaacga actggaaaat   1620
cctccttacg tgcccggcgt tgtcggcgga acacttcagg ccgctacaat ctgtgccagc   1680
agccaccagt tcctcagcac ccactacaac ctgcacaatc tgtatggcct gaccgaggcc   1740
attgccagcc atagagccct ggttaaggcc aggggcacca gacctttcgt gatcagcaga   1800
agcaccttcg ccggccacgg cagatatgcc ggacattgga caggcgacgt gtggtctagt   1860
tgggagcagc tggctagcag cgtgccagag atcctgcagt tcaatctgct gggcgtgcca   1920
ctcgtgggag ccgatgtttg tggcttcctg ggcaacacct ccgaggaact gtgtgtgcgt   1980
tggacacagc tgggcgcctt ctatcccttc atgagaaacc acaacagcct tctcagcctg   2040
ccacaagagc cctacagctt ctctgagcct gcacagcagg ccatgagaaa ggccctgact   2100
ctgagatacg ctctgctgcc ccacctgtac accctgtttc accaggctca tgtggccggg   2160
gagacagtgg ctagacctct gttcctggaa ttccccaagg acagctccac ctggaccgtg   2220
gatcatcagc tgctgtgggg agaagccctg ctcatcacac ctgttctgca ggccggaaag   2280
gccgaagtga ccggctattt tcctctcggc acttggtacg acctgcagac cgtgcctgtt   2340
gaggctctgg gatctcttcc tccacctcct gccgctccta gagagcctgc cattcactct   2400
gaaggccagt gggttaccct gcctgctcct ctggacacca tcaacgtgca cctgagagct   2460
ggctacatca tccctctgca aggccctggc ctgacaacca ccgaatctag acagcagccc   2520
atggctctgg ccgtggcttt gacaaaaggc ggagaggcta gaggcgagct gttctgggat   2580
```

```
gatggcgaga gcctggaagt gctggaacgg ggcgcttata cccaagtgat cttcctggcc   2640

agaaacaaca ccatcgtgaa cgaactcgtg cgcgtgacca gtgaaggtgc tggactgcaa   2700

ctgcagaaag tgaccgtgct cggagtggcc acagcacctc agcaggttct gtctaatggc   2760

gtgcccgtgt ccaacttcac atacagcccc gacaccaagg tcctggacat ctgtgtgtca   2820

ctgctgatgg gcgagcagtt cctggtgtcc tggtgttga                          2859
```

<210> SEQ ID NO 8
<211> LENGTH: 952
<212> TYPE: PRT
<213> ORGANISM: Homo sapiens
<220> FEATURE:
<221> NAME/KEY: MISC_FEATURE
<222> LOCATION: (1)..(952)
<223> OTHER INFORMATION: Acid Alpha-Glucosidase (GAA)

<400> SEQUENCE: 8

```
Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300
```

```
Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
    370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
    450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
    530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
    610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
        675                 680                 685

Glu Pro Ala Gln Gln Ala Met Arg Lys Ala Leu Thr Leu Arg Tyr Ala
    690                 695                 700

Leu Leu Pro His Leu Tyr Thr Leu Phe His Gln Ala His Val Ala Gly
705                 710                 715                 720
```

```
Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Val Glu Ala Leu Gly
    770                 775                 780

Ser Leu Pro Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
    850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
        915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950
```

<210> SEQ ID NO 9
<211> LENGTH: 1290
<212> TYPE: DNA
<213> ORGANISM: Artificial Sequence
<220> FEATURE:
<223> OTHER INFORMATION: GLA

<400> SEQUENCE: 9

```
atgcagctga ggaacccaga actacatctg ggctgcgcgc ttgcgcttcg cttcctggcc      60

ctcgtttcct gggacatccc tggggctaga gcactggaca atggattggc aaggacgcct     120

accatgggct ggctgcactg ggagcgcttc atgtgcaacc ttgactgcca ggaagagcca     180

gattcctgca tcagtgagaa gctcttcatg gagatggcag agctcatggt ctcagaaggc     240

tggaaggatg caggttatga gtacctctgc attgatgact gttggatggc tccccaaaga     300

gattcagaag gcagacttca ggcagaccct cagcgctttc ctcatgggat tcgccagcta     360

gctaattatg ttcacagcaa aggactgaag ctagggattt atgcagatgt tggaaataaa     420

acctgcgcag gcttccctgg gagttttgga tactacgaca ttgatgccca gacctttgct     480

gactggggag tagatctgct aaaatttgat ggttgttact gtgacagttt ggaaaatttg     540

gcagatggtt ataagcacat gtccttggcc ctgaatagga ctggcagaag cattgtgtac     600

tcctgtgagt ggcctcttta tatgtggccc tttcaaaagc ccaattatac agaaatccga     660

cagtactgca atcactggcg aaattttgct gacattgatg attcctggaa aagtataaag     720
```

agtatcttgg actggacatc ttttaaccag gagagaattg ttgatgttgc tggaccaggg 780
ggttggaatg acccagatat gttagtgatt ggcaactttg gcctcagctg gaatcagcaa 840
gtaactcaga tggccctctg ggctatcatg gctgctcctt tattcatgtc taatgacctc 900
cgacacatca gccctcaagc caaagctctc cttcaggata aggacgtaat tgccatcaat 960
caggacccct tgggcaagca agggtaccag cttagacagg gagacaactt tgaagtgtgg 1020
gaacgacctc tctcaggctt agcctgggct gtagctatga taaaccggca ggagattggt 1080
ggacctcgct cttataccat cgcagttgct tccctgggta aaggagtggc ctgtaatcct 1140
gcctgcttca tcacacagct cctccctgtg aaaaggaagc tagggttcta tgaatggact 1200
tcaaggttaa gaagtcacat aaatcccaca ggcactgttt tgcttcagct agaaaataca 1260
atgcagatgt cattaaaaga cttactttaa 1290

<210> SEQ ID NO 10
<211> LENGTH: 1290
<212> TYPE: DNA
<213> ORGANISM: Artificial Sequence
<220> FEATURE:
<223> OTHER INFORMATION: GLA codon-optimized

<400> SEQUENCE: 10
atgcagctga gaaatcctga actgcacctg ggctgtgccc tggctctgag atttctggct 60
ctggtgtcct gggacattcc tggcgctaga gccctggata atggcctggc cagaacacct 120
acaatgggct ggctgcactg ggagagattc atgtgcaacc tggactgcca agaggaaccc 180
gacagctgca tcagcgagaa gctgttcatg gaaatggccg agctgatggt gtccgaaggc 240
tggaaggatg ccggctacga gtacctgtgc atcgacgatt gctggatggc ccctcagaga 300
gattctgagg gcagactgca ggccgatcct cagagatttc ctcacggaat ccggcagctg 360
gccaactacg tgcactctaa gggactgaag ctgggcatct acgccgacgt gggcaacaag 420
acatgtgccg gctttccagg cagcttcggc tactacgata tcgacgccca gacctttgcc 480
gattggggcg tcgacctgct gaagttcgat ggctgctact gcgacagcct ggaaaacctg 540
gccgacggct acaaacacat gtctctggcc ctgaaccgga ccggcagatc tatcgtgtac 600
tcttgcgagt ggcccctgta catgtggccc ttccagaagc ctaactacac cgagatcaga 660
cagtactgca accactggcg gaacttcgcc gacatcgatg acagctggaa gtccatcaag 720
agcatcctgg actggaccag cttcaatcaa gagcggatcg tggatgtggc tggcccaggc 780
ggatggaacg atcctgatat gctggtcatc ggcaacttcg gcctgagctg gaatcagcaa 840
gtgacccaga tggccctgtg ggccattatg gccgctcctc tgttcatgag caacgacctg 900
agacacatca gccctcaggc caaggctctg ctgcaggata aggacgtgat cgccatcaac 960
caggatcctc tgggcaagca gggctatcag ctgagacagg gcgacaattt cgaagtgtgg 1020
gaaagacctc tgagcggcct ggcttgggcc gtcgccatga tcaatagaca agagatcggc 1080
ggaccccggt cctatacaat tgccgtggct tctctcggaa aaggcgtggc ctgcaatcct 1140
gcctgcttta tcacacagct gctccccgtg aagagaaagc tgggctttta cgagtggacc 1200
agcagactga gatcccacat caaccccaca ggcactgttc tgctgcaact ggaaaacaca 1260
atgcagatga gcctgaagga cctgctgtag 1290

<210> SEQ ID NO 11
<211> LENGTH: 429
<212> TYPE: PRT
<213> ORGANISM: Artificial Sequence

<220> FEATURE:
<223> OTHER INFORMATION: GLA

<400> SEQUENCE: 11

```
Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400
```

```
Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
            420                 425


<210> SEQ ID NO 12
<211> LENGTH: 1317
<212> TYPE: DNA
<213> ORGANISM: Artificial Sequence
<220> FEATURE:
<223> OTHER INFORMATION: CLN3

<400> SEQUENCE: 12

atgggaggct gtgcaggctc gcggcggcgc ttttcggatt ccgaggggga ggagaccgtc     60

ccggagcccc ggctccctct gttggaccat cagggcgcgc attggaagaa cgcggtgggc    120

ttctggctgc tgggcctttg caacaacttc tcttatgtgg tgatgctgag tgccgcccac    180

gacatcctta gccacaagag gacatcggga aaccagagcc atgtggaccc aggcccaacg    240

ccgatccccc acaacagctc atcacgattt gactgcaact ctgtctctac ggctgctgtg    300

ctcctggcgg acatcctccc cacactcgtc atcaaattgt tggctcctct tggccttcac    360

ctgctgccct acagcccccg ggttctcgtc agtgggattt gtgctgctgg aagcttcgtc    420

ctggttgcct tttctcattc tgtggggacc agcctgtgtg gtgtggtctt cgctagcatc    480

tcatcaggcc ttggggaggt caccttcctc tccctcactg ccttctaccc cagggccgtg    540

atctcctggt ggtcctcagg gactgggggga gctgggctgc tgggggccct gtcctacctg    600

ggcctcaccc aggccggcct ctcccctcag cagaccctgc tgtccatgct gggtatccct    660

gccctgctgc tggccagcta tttcttgttg ctcacatctc ctgaggccca ggaccctgga    720

ggggaagaag aagcagagag cgcagcccgg cagcccctca taagaaccga ggccccggag    780

tcgaagccag gctccagctc cagcctctcc cttcgggaaa ggtggacagt gttcaagggt    840

ctgctgtggt acattgttcc cttggtcgta gtttactttg ccgagtattt cattaaccag    900

ggactttttg aactcctctt tttctggaac acttccctga gtcacgctca gcaataccgc    960

tggtaccaga tgctgtacca ggctggcgtc tttgcctccc gctcttctct ccgctgctgt   1020

cgcatccgtt tcacctgggc cctggccctg ctgcagtgcc tcaacctggt gttcctgctg   1080

gcagacgtgt ggttcggctt tctgccaagc atctacctcg tcttcctgat cattctgtat   1140

gaggggctcc tgggaggcgc agcctacgtg aacaccttcc acaacatcgc cctggagacc   1200

agtgatgagc accgggagtt tgcaatggcg gccacctgca tctctgacac actggggatc   1260

tccctgtcgg ggctcctggc tttgcctctg catgacttcc tctgccagct ctcctga      1317


<210> SEQ ID NO 13
<211> LENGTH: 1318
<212> TYPE: DNA
<213> ORGANISM: Artificial Sequence
<220> FEATURE:
<223> OTHER INFORMATION: CLN3 codon-optimized

<400> SEQUENCE: 13

atgggaggat gtgctgggtc aagaagacgg tttagcgatt ccgaaggaga ggagactgtg     60

cctgagccaa gactgcccct gctggatcac cagggagcac actggaagaa cgcagtggga    120

ttctggctgc tgggcctgtg caacaacttc agctacgtgg tcatgctgtc cgccgcccac    180

gacatcctgt cccacaagcg gacctccggc aatcagtctc acgtggaccc cggccctaca    240
```

```
ccaatccccc acaacagcag cagccggttc gactgtaatt ccgtgtctac cgcagccgtg    300

ctgctggcag acatcctgcc caccctggtc atcaagctgc tggcaccact gggcctgcac    360

ctgctgcctt attctccaag ggtgctggtg agcggcatct gcgcagcagg cagcttcgtg    420

ctggtggcct ttagccactc cgtgggcacc tctctgtgcg gagtggtgtt tgcaagcatc    480

agctccggcc tgggagaggt gaccttcctg agcctgacag ccttttaccc tcgcgccgtg    540

atctcctggt ggtctagcgg cacaggagga gcaggcctgc tgggcgccct gtcctatctg    600

ggcctgaccc aggcaggcct gtccccacag cagacactgc tgtctatgct gggcatccct    660

gccctgctgc tggcaagcta cttcctgctg ctgacctccc cagaggcaca ggaccccgga    720

ggagaggagg aggccgagag cgccgcaagg cagccactga tcaggaccga ggcaccagag    780

tccaagcctg gctcctctag ctccctgtct ctgcgggaga gatggacagt gttcaagggc    840

ctgctgtggt acatcgtgcc cctggtggtg gtgtacttcg ccgagtactt catcaaccag    900

ggcctgtttg agctgctgtt cttttggaat acctctctga gccacgccca gcagtaccgg    960

tggtatcaga tgctgtatca ggcaggcgtg ttcgcctccc ggtctagcct gagatgctgt   1020

cggatcagat tcacctgggc actggccctg ctgcagtgcc tgaacctggt gttcctgctg   1080

gccgacgtgt ggttcggctt tctgccctct atctacctgg tgtttctgat catcctgtat   1140

gagggcctgc tgggaggagc agcctatgtg aacaccttcc acaatatcgc cctggagaca   1200

tctgacgagc acagagagtt tgctatggcc gccacctgta tcagcgatac actgggcatc   1260

tctctgagcg gactgctggc tctgcctctg catgactttc tgtgccagct gagttaat    1318
```

```
<210> SEQ ID NO 14
<211> LENGTH: 438
<212> TYPE: PRT
<213> ORGANISM: Homo sapiens
<220> FEATURE:
<221> NAME/KEY: MISC_FEATURE
<222> LOCATION: (1)..(438)
<223> OTHER INFORMATION: Ceroid Lipofuscinosis, Neuronal 3 (CLN3)

<400> SEQUENCE: 14

Met Gly Gly Cys Ala Gly Ser Arg Arg Arg Phe Ser Asp Ser Glu Gly
1               5                   10                  15

Glu Glu Thr Val Pro Glu Pro Arg Leu Pro Leu Leu Asp His Gln Gly
            20                  25                  30

Ala His Trp Lys Asn Ala Val Gly Phe Trp Leu Leu Gly Leu Cys Asn
        35                  40                  45

Asn Phe Ser Tyr Val Val Met Leu Ser Ala Ala His Asp Ile Leu Ser
    50                  55                  60

His Lys Arg Thr Ser Gly Asn Gln Ser His Val Asp Pro Gly Pro Thr
65                  70                  75                  80

Pro Ile Pro His Asn Ser Ser Ser Arg Phe Asp Cys Asn Ser Val Ser
                85                  90                  95

Thr Ala Ala Val Leu Leu Ala Asp Ile Leu Pro Thr Leu Val Ile Lys
            100                 105                 110

Leu Leu Ala Pro Leu Gly Leu His Leu Leu Pro Tyr Ser Pro Arg Val
        115                 120                 125

Leu Val Ser Gly Ile Cys Ala Ala Gly Ser Phe Val Leu Val Ala Phe
    130                 135                 140

Ser His Ser Val Gly Thr Ser Leu Cys Gly Val Val Phe Ala Ser Ile
145                 150                 155                 160

Ser Ser Gly Leu Gly Glu Val Thr Phe Leu Ser Leu Thr Ala Phe Tyr
```

```
                165                 170                 175

Pro Arg Ala Val Ile Ser Trp Trp Ser Ser Gly Thr Gly Gly Ala Gly
            180                 185                 190

Leu Leu Gly Ala Leu Ser Tyr Leu Gly Leu Thr Gln Ala Gly Leu Ser
        195                 200                 205

Pro Gln Gln Thr Leu Leu Ser Met Leu Gly Ile Pro Ala Leu Leu Leu
    210                 215                 220

Ala Ser Tyr Phe Leu Leu Leu Thr Ser Pro Glu Ala Gln Asp Pro Gly
225                 230                 235                 240

Gly Glu Glu Glu Ala Glu Ser Ala Ala Arg Gln Pro Leu Ile Arg Thr
                245                 250                 255

Glu Ala Pro Glu Ser Lys Pro Gly Ser Ser Ser Ser Leu Ser Leu Arg
            260                 265                 270

Glu Arg Trp Thr Val Phe Lys Gly Leu Leu Trp Tyr Ile Val Pro Leu
        275                 280                 285

Val Val Val Tyr Phe Ala Glu Tyr Phe Ile Asn Gln Gly Leu Phe Glu
    290                 295                 300

Leu Leu Phe Phe Trp Asn Thr Ser Leu Ser His Ala Gln Gln Tyr Arg
305                 310                 315                 320

Trp Tyr Gln Met Leu Tyr Gln Ala Gly Val Phe Ala Ser Arg Ser Ser
                325                 330                 335

Leu Arg Cys Cys Arg Ile Arg Phe Thr Trp Ala Leu Ala Leu Leu Gln
            340                 345                 350

Cys Leu Asn Leu Val Phe Leu Leu Ala Asp Val Trp Phe Gly Phe Leu
        355                 360                 365

Pro Ser Ile Tyr Leu Val Phe Leu Ile Ile Leu Tyr Glu Gly Leu Leu
    370                 375                 380

Gly Gly Ala Ala Tyr Val Asn Thr Phe His Asn Ile Ala Leu Glu Thr
385                 390                 395                 400

Ser Asp Glu His Arg Glu Phe Ala Met Ala Ala Thr Cys Ile Ser Asp
                405                 410                 415

Thr Leu Gly Ile Ser Leu Ser Gly Leu Leu Ala Leu Pro Leu His Asp
            420                 425                 430

Phe Leu Cys Gln Leu Ser
        435


<210> SEQ ID NO 15
<211> LENGTH: 2211
<212> TYPE: DNA
<213> ORGANISM: Artificial Sequence
<220> FEATURE:
<223> OTHER INFORMATION: AAV204 VP1

<400> SEQUENCE: 15

atggctgccg atggttatct tccagattgg ctcgaggaca acctctctga gggcattcgc      60

gagtggtggg acttgaaacc tggagccccg aagcccaaag ccaaccagca aaagcaggac     120

gacggccggg gtctggtgct tcctggctac aagtacctcg gacccttcaa cggactcgac     180

aagggggagc ccgtcaacgc ggcggacgca gcggccctcg agcacgacaa ggcctacgac     240

cagcagctca aagcgggtga caatccgtac ctgcggtata accacgccga cgccgagttt     300

caggagcgtc tgcaagaaga tacgtctttt gggggcaacc tcgggcgagc agtcttccag     360

gccaagaagc gggttctcga acctctcggt ctggttgagg aaggcgctaa gacggctcct     420

ggaaagaaac gtccggtaga gcagtcacca caagagccag actcctcctc gggcatcggc     480
```

aagacaggcc agcagcccgc taaaaagaga ctcaattttg gtcagactgg cgactcagag 540
tcagtccccg acccacaacc tctcggagaa cctccagcaa cccccgctgc tgtgggacct 600
actacaatgg cttcaggcgg tggcgcacca atggcggaca ataacgaagg cgccgacgga 660
gtgggtaatg cctcaggaaa ttggcattgc gattccacat ggctgggcga cagagtcatc 720
accaccagca cccgaacatg ggccttgccc acctataaca accacctcta caagcaaatc 780
tccagtgctt caacgggggc cagcaacgac aaccactact tcggctacag caccccctgg 840
gggtattttg atttcaacag attccactgc catttctcac cacgtgactg gcagcgactc 900
atcaacaaca attggggatt ccggcccaag agactcaact tcaagctctt caacatccaa 960
gtcaaggagg tcacgacgaa tgatggcgtc acgaccatcg ctaataacct taccagcacg 1020
gttcaagtct tctcggactc ggagtaccag ttgccgtacg tcctcggctc tgcgcaccag 1080
ggctgcctcc ctccgttccc ggcggacgtg ttcatgattc cgcagtacgg ctacctaacg 1140
ctcaacaatg gcagccaggc agtgggacgg tcatcctttt actgcctgga atatttccca 1200
tcgcagatgc tgagaacggg caataacttt accttcagct acaccttcga ggacgtgcct 1260
ttccacagca gctacgcgca cagccagagc ctggaccggc tgatgaatcc tctcatcgac 1320
cagtacctgt attacctgaa cagaactcag aatcagtccg gaagtgccca aaacaaggac 1380
ttgctgttta gccgggggtc tccagctggc atgtctgttc agcccaaaaa ctggctacct 1440
ggaccctgtt accggcagca gcgcgtttct aaaacaaaaa cagacaacaa caacagcaac 1500
tttacctgga caggtgcttc aaaatataac cttaatgggc gtgaatctat aatcaaccct 1560
ggcactgcta tggcctcaca caaagacgac aaagacaagt tctttcccat gagcggtgtc 1620
atgatttttg gaaaggagag cgccggagct tcaaacactg cattggacaa tgtcatgatc 1680
acagacgaag aggaaatcaa agccactaac cccgtggcca ccgaaagatt tgggactgtg 1740
gcagtcaatc tccagaacag cagcacagac cctgcgaccg gagatgtgca tgttatggga 1800
gccttacctg gaatggtgtg gcaagacaga gacgtatacc tgcagggtcc tatttgggcc 1860
aaaattcctc acacggatgg acactttcac ccgtctcctc tcatgggcgg ctttggactt 1920
aagcacccgc ctcctcagat cctcatcaaa aacacgcctg ttcctgcgaa tcctccggca 1980
gagttttcgg ctacaaagtt tgcttcattc atcacccagt attccacagg acaagtgagc 2040
gtggagattg aatgggagct gcagaaagaa aacagcaaac gctggaatcc cgaagtgcag 2100
tatacatcta actatgcaaa atctgccaac gttgatttca ctgtagacaa caatggactt 2160
tatactgagc ctcgccccat tggcacccgt tacctcaccc gtcccctgta a 2211

<210> SEQ ID NO 16
<211> LENGTH: 1605
<212> TYPE: DNA
<213> ORGANISM: Artificial Sequence
<220> FEATURE:
<223> OTHER INFORMATION: AAV204 VP3

<400> SEQUENCE: 16
atggcttcag gcggtggcgc accaatggcg gacaataacg aaggcgccga cggagtgggt 60
aatgcctcag gaaattggca ttgcgattcc acatggctgg gcgacagagt catcaccacc 120
agcacccgaa catgggcctt gcccacctat aacaaccacc tctacaagca aatctccagt 180
gcttcaacgg gggccagcaa cgacaaccac tacttcggct acagcacccc ctgggggtat 240
tttgatttca acagattcca ctgccatttc tcaccacgtg actggcagcg actcatcaac 300
aacaattggg gattccggcc caagagactc aacttcaagc tcttcaacat ccaagtcaag 360

```
gaggtcacga cgaatgatgg cgtcacgacc atcgctaata accttaccag cacggttcaa    420

gtcttctcgg actcggagta ccagttgccg tacgtcctcg gctctgcgca ccagggctgc    480

ctccctccgt tcccggcgga cgtgttcatg attccgcagt acggctacct aacgctcaac    540

aatggcagcc aggcagtggg acggtcatcc ttttactgcc tggaatattt cccatcgcag    600

atgctgagaa cgggcaataa ctttaccttc agctacacct tcgaggacgt gcctttccac    660

agcagctacg cgcacagcca gagcctggac cggctgatga atcctctcat cgaccagtac    720

ctgtattacc tgaacagaac tcagaatcag tccggaagtg cccaaaacaa ggacttgctg    780

tttagccggg ggtctccagc tggcatgtct gttcagccca aaaactggct acctggaccc    840

tgttaccggc agcagcgcgt ttctaaaaca aaaacagaca acaacaacag caactttacc    900

tggacaggtg cttcaaaata taaccttaat gggcgtgaat ctataatcaa ccctggcact    960

gctatggcct cacacaaaga cgacaaagac aagttctttc ccatgagcgg tgtcatgatt   1020

tttggaaagg agagcgccgg agcttcaaac actgcattgg acaatgtcat gatcacagac   1080

gaagaggaaa tcaaagccac taaccccgtg gccaccgaaa gatttgggac tgtggcagtc   1140

aatctccaga acagcagcac agaccctgcg accggagatg tgcatgttat gggagcctta   1200

cctggaatgg tgtggcaaga cagagacgta tacctgcagg gtcctatttg ggccaaaatt   1260

cctcacacgg atggacactt tcacccgtct cctctcatgg gcggctttgg acttaagcac   1320

ccgcctcctc agatcctcat caaaaacacg cctgttcctg cgaatcctcc ggcagagttt   1380

tcggctacaa agtttgcttc attcatcacc cagtattcca caggacaagt gagcgtggag   1440

attgaatggg agctgcagaa agaaaacagc aaacgctgga atcccgaagt gcagtataca   1500

tctaactatg caaaatctgc caacgttgat ttcactgtag acaacaatgg actttatact   1560

gagcctcgcc ccattggcac ccgttacctc acccgtcccc tgtaa                   1605
```

<210> SEQ ID NO 17
<211> LENGTH: 534
<212> TYPE: PRT
<213> ORGANISM: Artificial Sequence
<220> FEATURE:
<223> OTHER INFORMATION: AAV204 VP3

<400> SEQUENCE: 17

```
Met Ala Ser Gly Gly Gly Ala Pro Met Ala Asp Asn Asn Glu Gly Ala
1               5                   10                  15

Asp Gly Val Gly Asn Ala Ser Gly Asn Trp His Cys Asp Ser Thr Trp
            20                  25                  30

Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Ala Ser Thr Gly
    50                  55                  60

Ala Ser Asn Asp Asn His Tyr Phe Gly Tyr Ser Thr Pro Trp Gly Tyr
65                  70                  75                  80

Phe Asp Phe Asn Arg Phe His Cys His Phe Ser Pro Arg Asp Trp Gln
                85                  90                  95

Arg Leu Ile Asn Asn Asn Trp Gly Phe Arg Pro Lys Arg Leu Asn Phe
            100                 105                 110

Lys Leu Phe Asn Ile Gln Val Lys Glu Val Thr Thr Asn Asp Gly Val
        115                 120                 125

Thr Thr Ile Ala Asn Asn Leu Thr Ser Thr Val Gln Val Phe Ser Asp
    130                 135                 140
```

```
Ser Glu Tyr Gln Leu Pro Tyr Val Leu Gly Ser Ala His Gln Gly Cys
145                 150                 155                 160

Leu Pro Pro Phe Pro Ala Asp Val Phe Met Ile Pro Gln Tyr Gly Tyr
                165                 170                 175

Leu Thr Leu Asn Asn Gly Ser Gln Ala Val Gly Arg Ser Ser Phe Tyr
            180                 185                 190

Cys Leu Glu Tyr Phe Pro Ser Gln Met Leu Arg Thr Gly Asn Asn Phe
        195                 200                 205

Thr Phe Ser Tyr Thr Phe Glu Asp Val Pro Phe His Ser Ser Tyr Ala
    210                 215                 220

His Ser Gln Ser Leu Asp Arg Leu Met Asn Pro Leu Ile Asp Gln Tyr
225                 230                 235                 240

Leu Tyr Tyr Leu Asn Arg Thr Gln Asn Gln Ser Gly Ser Ala Gln Asn
                245                 250                 255

Lys Asp Leu Leu Phe Ser Arg Gly Ser Pro Ala Gly Met Ser Val Gln
            260                 265                 270

Pro Lys Asn Trp Leu Pro Gly Pro Cys Tyr Arg Gln Gln Arg Val Ser
        275                 280                 285

Lys Thr Lys Thr Asp Asn Asn Asn Ser Asn Phe Thr Trp Thr Gly Ala
    290                 295                 300

Ser Lys Tyr Asn Leu Asn Gly Arg Glu Ser Ile Ile Asn Pro Gly Thr
305                 310                 315                 320

Ala Met Ala Ser His Lys Asp Asp Lys Asp Lys Phe Phe Pro Met Ser
                325                 330                 335

Gly Val Met Ile Phe Gly Lys Glu Ser Ala Gly Ala Ser Asn Thr Ala
            340                 345                 350

Leu Asp Asn Val Met Ile Thr Asp Glu Glu Glu Ile Lys Ala Thr Asn
        355                 360                 365

Pro Val Ala Thr Glu Arg Phe Gly Thr Val Ala Val Asn Leu Gln Asn
    370                 375                 380

Ser Ser Thr Asp Pro Ala Thr Gly Asp Val His Val Met Gly Ala Leu
385                 390                 395                 400

Pro Gly Met Val Trp Gln Asp Arg Asp Val Tyr Leu Gln Gly Pro Ile
                405                 410                 415

Trp Ala Lys Ile Pro His Thr Asp Gly His Phe His Pro Ser Pro Leu
            420                 425                 430

Met Gly Gly Phe Gly Leu Lys His Pro Pro Pro Gln Ile Leu Ile Lys
        435                 440                 445

Asn Thr Pro Val Pro Ala Asn Pro Pro Ala Glu Phe Ser Ala Thr Lys
    450                 455                 460

Phe Ala Ser Phe Ile Thr Gln Tyr Ser Thr Gly Gln Val Ser Val Glu
465                 470                 475                 480

Ile Glu Trp Glu Leu Gln Lys Glu Asn Ser Lys Arg Trp Asn Pro Glu
                485                 490                 495

Val Gln Tyr Thr Ser Asn Tyr Ala Lys Ser Ala Asn Val Asp Phe Thr
            500                 505                 510

Val Asp Asn Asn Gly Leu Tyr Thr Glu Pro Arg Pro Ile Gly Thr Arg
        515                 520                 525

Tyr Leu Thr Arg Pro Leu
    530
```

<210> SEQ ID NO 18
<211> LENGTH: 2208

<212> TYPE: DNA
<213> ORGANISM: Artificial Sequence
<220> FEATURE:
<223> OTHER INFORMATION: ITB102 214 (AAV214) VP1

<400> SEQUENCE: 18
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctca aagcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctttggt ctggttgagg aaggtgctaa gacggctcct 420
ggaaagaaac gtccggtaga gcagtcgcca caagagccag actcctcctc gggcatcggc 480
aagacaggcc agcagcccgc taaaaagaga ctcaattttg gtcagactgg cgactcagag 540
tcagtccccg acccacaacc tctcggagaa cctccagcaa cccccgctgc tgtgggacct 600
actacaatgg cttcaggcgg tggcgcacca atggcggaca ataacgaagg cgccgacgga 660
gtgggtaatg cctcaggaaa ttggcattgc gattccacat ggctgggcga cagagtcatc 720
accaccagca cccgcacctg ggccttgccc acctacaata accacctcta caagcaaatc 780
tccagtgctt caacgggggc cagcaacgac aaccactact tcggctacag cacccccctgg 840 gggtattttg acttcaacag attccactgc cacttttcac cacgtgactg gcaaagactc 900
atcaacaaca actggggatt ccgacccaag agactcaact tcaagctctt taacattcaa 960
gtcaaagagg ttacggacaa caatggagtc aagaccatcg ccaataacct taccagcacg 1020
gtccaggtct tcacggactc agactatcag ctcccgtacg tcctcggctc tgcgcaccag 1080
ggctgcctcc ctccgttccc ggcggacgtg ttcatgattc cgcagtacgg ctacctaacg 1140
ctcaacgacg gcagccaggc agtgggacgg tcatcctttt actgcctgga atatttccca 1200
tcgcagatgc tgagaacggg caacaacttt accttcagct acacctttga ggacgttcct 1260
ttccacagca gctacgctca cagccagagt ctggaccgtc tcatgaatcc tctgattgac 1320
cagtacctgt actacttgtc taagactatc aacggatccg gccagaatca gcagactctg 1380
aagttcagcc aaggtgggcc taatacaatg gccaatcagg caaagaactg gctgccagga 1440
ccctgttacc gccaacaacg cgtctcaacg acaaccgggc aaaacaacaa tagcaacttt 1500
gcctggactg ctgggaccaa ataccatctg aatggaagaa attcattgat gaatcctggc 1560
cccgctatgg catcccacaa agagggcgag gaccgttttt ttcccctgtc cgggtccctg 1620
atttttggca aacaaaatgc tgccagagac aatgcggatt acagcgatgt catgctcacc 1680
agcgaggaag aaatcaaaac cactaaccct gtggctacag aggaatacgg tatcgtggca 1740
gataacttgc agcagcaaaa cacggctcct caaattggaa ctgtcaacag ccagggggcc 1800
ttacccggta tggtctggca gaaccgggac gtgtacctgc agggtcccat ctgggccaag 1860
attcctcaca cggacggcaa cttccacccg tctccgctga tgggcggctt tggcctgaaa 1920
catcctccgc ctcagatcct gatcaagaac acgcctgtac ctgcggatcc tccgaccacc 1980
ttcaaccagt caaagctgaa ctctttcatc acgcaataca gcaccggaca ggtcagcgtg 2040
gaaattgaat gggagctgca gaaggaaaac agcaagcgct ggaaccccga gatccagtac 2100
acctccaact actacaaatc tacaagtgtg gactttgctg ttaatacaga aggcgtgtac 2160
tctgaacccc accccattgg cacccgttac ctcacccgtc ccctgtaa 2208

<210> SEQ ID NO 19
<211> LENGTH: 2211
<212> TYPE: DNA
<213> ORGANISM: Artificial Sequence
<220> FEATURE:
<223> OTHER INFORMATION: AAV214-A VP1

<400> SEQUENCE: 19
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctca aagcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga accttttggt ctggttgagg aaggtgctaa gacggctcct 420
ggaaagaaac gtccggtaga gcagtcgcca caagagccag actcctcctc gggcatcggc 480
aagacaggcc agcagcccgc taaaaagaga ctcaattttg gtcagactgg cgactcagag 540
tcagtccccg acccacaacc tctcggagaa cctccagcaa cccccgctgc tgtgggacct 600
actacaatgg cttcaggcgg tggcgcacca atggcggaca ataacgaagg cgccgacgga 660
gtgggtaatg cctcaggaaa ttggcattgc gattccacat ggctgggcga cagagtcatc 720
accaccagca cccgcacctg ggccttgccc acctacaata accacctcta caagcaaatc 780
tccaacagca catctggagg atcttcaaat gacaacgcct acttcggcta cagcaccccc 840
tgggggtatt ttgacttcaa cagattccac tgccactttt caccacgtga ctggcaaaga 900
ctcatcaaca acaactgggg attccgaccc aagagactca acttcaagct ctttaacatt 960
caagtcaaag aggttacgga caacaatgga gtcaagacca tcgccaataa ccttaccagc 1020
acggtccagg tcttcacgga ctcagactat cagctcccgt acgtcctcgg ctctgcgcac 1080
cagggctgcc tccctccgtt cccggcggac gtgttcatga ttccgcagta cggctaccta 1140
acgctcaacg acggcagcca ggcagtggga cggtcatcct tttactgcct ggaatatttc 1200
ccatcgcaga tgctgagaac gggcaacaac tttaccttca gctacacctt tgaggacgtt 1260
cctttccaca gcagctacgc tcacagccag agtctggacc gtctcatgaa tcctctgatt 1320
gaccagtacc tgtactactt gtctaagact atcaacggat ccggccagaa tcagcagact 1380
ctgaagttca gccaaggtgg gcctaataca atggccaatc aggcaaagaa ctggctgcca 1440
ggaccctgtt accgccaaca acgcgtctca acgacaaccg ggcaaaacaa caatagcaac 1500
tttgcctgga ctgctgggac caaataccat ctgaatggaa gaaattcatt gatgaatcct 1560
ggccccgcta tggcatccca caaagagggc gaggaccgtt tttttcccct gtccgggtcc 1620
ctgatttttg gcaaacaaaa tgctgccaga gacaatgcgg attacagcga tgtcatgctc 1680
accagcgagg aagaaatcaa aaccactaac cctgtggcta cagaggaata cggtatcgtg 1740
gcagataact tgcagcagca aaacacggct cctcaaattg gaactgtcaa cagccagggg 1800
gccttacccg gtatggtctg gcagaaccgg gacgtgtacc tgcagggtcc catctgggcc 1860
aagattcctc acacggacgg caacttccac ccgtctccgc tgatgggcgg ctttggcctg 1920
aaacatcctc cgcctcagat cctgatcaag aacacgcctg tacctgcgga tcctccgacc 1980
accttcaacc agtcaaagct gaactctttc atcacgcaat acagcaccgg acaggtcagc 2040

```
gtggaaattg aatgggagct gcagaaggaa aacagcaagc gctggaaccc cgagatccag   2100

tacacctcca actactacaa atctacaagt gtggactttg ctgttaatac agaaggcgtg   2160

tactctgaac cccaccccat tggcacccgt tacctcaccc gtcccctgta a            2211


<210> SEQ ID NO 20
<211> LENGTH: 2211
<212> TYPE: DNA
<213> ORGANISM: Artificial Sequence
<220> FEATURE:
<223> OTHER INFORMATION: AAV214e VP1

<400> SEQUENCE: 20

atggctgccg atggttatct tccagattgg ctcgaggaca acctctctga gggcattcgc     60

gagtggtggg acttgaaacc tggagccccg aaacccaaag ccaaccagca aaagcaggac    120

gacggccggg gtctggtgct tcctggctac aagtacctcg gacccttcaa cggactcgac    180

aagggggagc ccgtcaacgc ggcggatgca gcggccctcg agcacgacaa ggcctacgac    240

cagcagctca aagcgggtga caatccgtac ctgcggtata accacgccga cgccgagttt    300

caggagcgtc tgcaagaaga tacgtctttt gggggcaacc tcgggcgagc agtcttccag    360

gccaagaagc gggttctcga acctctcggt ctggttgagg aaggcgctaa gacggctcct    420

ggaaagaaga gaccggtaga gccatcaccc cagcgttctc cagactcctc tacgggcatc    480

ggcaagaaag gccaacagcc cgccagaaaa agactcaatt ttggtcagac tggcgactca    540

gagtcagtcc ccgacccaca acctctcgga gaacctccag caacccccgc tgctgtggga    600

cctactacaa tggcttcagg cggtggcgca ccaatggcag acaataacga aggcgccgac    660

ggagtgggta atgcctcagg aaattggcat tgcgattcca catggctggg cgacagagtc    720

atcaccacca gcacccgcac ctgggccttg cccacctaca ataaccacct ctacaagcaa    780

atctccagtg cttcaacggg ggccagcaac gacaaccact acttcggcta cagcaccccc    840

tgggggtatt ttgacttcaa cagattccac tgccactttt caccacgtga ctggcaaaga    900

ctcatcaaca acaactgggg attccgaccc aagagactca acttcaagct ctttaacatt    960

caagtcaaag aggttacgga caacaatgga gtcaagacca tcgccaataa ccttaccagc   1020

acggtccagg tcttcacgga ctcagactat cagctcccgt acgtcctcgg ctctgcgcac   1080

cagggctgcc tccctccgtt cccggcggac gtgttcatga ttccgcagta cggctaccta   1140

acgctcaacg acggcagcca ggcagtggga cggtcatcct tttactgcct ggaatatttc   1200

ccatcgcaga tgctgagaac gggcaacaac tttaccttca gctacacctt tgaggacgtt   1260

cctttccaca gcagctacgc tcacagccag agtctggacc gtctcatgaa tcctctgatt   1320

gaccagtacc tgtactactt gtctaagact atcaacggat ccggccagaa tcagcagact   1380

ctgaagttca gccaaggtgg gcctaataca atggccaatc aggcaaagaa ctggctgcca   1440

ggaccctgtt accgccaaca acgcgtctca acgacaaccg ggcaaaacaa caatagcaac   1500

tttgcctgga ctgctgggac caaataccat ctgaatggaa gaaattcatt gatgaatcct   1560

ggccccgcta tggcatccca caaagagggc gaggaccgtt tttttcccct gtccgggtcc   1620

ctgatttttg gcaaacaaaa tgctgccaga gacaatgcgg attacagcga tgtcatgctc   1680

accagcgagg aagaaatcaa aaccactaac cctgtggcta cagaggaata cggtatcgtg   1740

gcagataact tgcagcagca aaacacggct cctcaaattg gaactgtcaa cagccagggg   1800

gccttacccg gtatggtctg gcagaaccgg gacgtgtacc tgcagggtcc catctgggcc   1860
```

aagattcctc acacggacgg caacttccac ccgtctccgc tgatgggcgg ctttggcctg 1920
aaacatcctc cgcctcagat cctgatcaag aacacgcctg tacctgcgga tcctccgacc 1980
accttcaacc agtcaaagct gaactctttc atcacgcaat acagcaccgg acaggtcagc 2040
gtggaaattg aatgggagct gcagaaggaa aacagcaagc gctggaaccc cgagatccag 2100
tacacctcca actactacaa atctacaagt gtggactttg ctgttaatac agaaggcgtg 2160
tactctgaac ccccaccccat tggcacccgt tacctcaccc gtcccctgta a 2211

<210> SEQ ID NO 21
<211> LENGTH: 2211
<212> TYPE: DNA
<213> ORGANISM: Artificial Sequence
<220> FEATURE:
<223> OTHER INFORMATION: AAV214e8 VP1

<400> SEQUENCE: 21
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540
gagtcagttc cagaccctca acctctcgga gaacctccag cagcgccctc tggtgtggga 600
cctaatacaa tggcttcagg cggtggcgca ccaatggcgg acaataacga aggcgccgac 660
ggagtgggta atgcctcagg aaattggcat tgcgattcca catggctggg cgacagagtc 720
atcaccacca gcacccgcac ctgggccttg cccacctaca ataaccacct ctacaagcaa 780
atctccagtg cttcaacggg ggccagcaac gacaaccact acttcggcta cagcaccccc 840
tgggggtatt ttgacttcaa cagattccac tgccactttt caccacgtga ctggcaaaga 900
ctcatcaaca acaactgggg attccgaccc aagagactca acttcaagct ctttaacatt 960
caagtcaaag aggttacgga caacaatgga gtcaagacca tcgccaataa ccttaccagc 1020
acggtccagg tcttcacgga ctcagactat cagctcccgt acgtcctcgg ctctgcgcac 1080
cagggctgcc tccctccgtt cccggcggac gtgttcatga ttccgcagta cggctaccta 1140
acgctcaacg acggcagcca ggcagtggga cggtcatcct tttactgcct ggaatatttc 1200
ccatcgcaga tgctgagaac gggcaacaac tttaccttca gctacacctt tgaggacgtt 1260
cctttccaca gcagctacgc tcacagccag agtctggacc gtctcatgaa tcctctgatt 1320
gaccagtacc tgtactactt gtctaagact atcaacggat ccggccagaa tcagcagact 1380
ctgaagttca gccaaggtgg gcctaataca atggccaatc aggcaaagaa ctggctgcca 1440
ggaccctgtt accgccaaca acgcgtctca acgacaaccg ggcaaaacaa caatagcaac 1500
tttgcctgga ctgctgggac caaataccat ctgaatggaa gaaattcatt gatgaatcct 1560
ggccccgcta tggcatccca caaagagggc gaggaccgtt tttttcccct gtccgggtcc 1620
ctgatttttg gcaaacaaaa tgctgccaga gacaatgcgg attacagcga tgtcatgctc 1680
accagcgagg aagaaatcaa aaccactaac cctgtggcta cagaggaata cggtatcgtg 1740

```
gcagataact tgcagcagca aaacacggct cctcaaattg gaactgtcaa cagccagggg   1800

gccttacccg gtatggtctg gcagaaccgg gacgtgtacc tgcagggtcc catctgggcc   1860

aagattcctc acacggacgg caacttccac ccgtctccgc tgatgggcgg ctttggcctg   1920

aaacatcctc cgcctcagat cctgatcaag aacacgcctg tacctgcgga tcctccgacc   1980

accttcaacc agtcaaagct gaactctttc atcacgcaat acagcaccgg acaggtcagc   2040

gtggaaattg aatgggagct gcagaaggaa aacagcaagc gctggaaccc cgagatccag   2100

tacacctcca actactacaa atctacaagt gtggactttg ctgttaatac agaaggcgtg   2160

tactctgaac cccaccccat tggcacccgt tacctcaccc gtcccctgta a            2211


<210> SEQ ID NO 22
<211> LENGTH: 2208
<212> TYPE: DNA
<213> ORGANISM: Artificial Sequence
<220> FEATURE:
<223> OTHER INFORMATION: AAV214e9 VP1

<400> SEQUENCE: 22

atggctgccg atggttatct tccagattgg ctcgaggaca accttagtga aggaattcgc     60

gagtggtggg ctttgaaacc tggagcccct caacccaagg caaatcaaca acatcaagac    120

aacgctcgag gtcttgtgct tccgggttac aaataccttg gacccggcaa cggactcgac    180

aagggggagc cggtcaacgc agcagacgcg gcggccctcg agcacgacaa ggcctacgac    240

cagcagctca aggccggaga caacccgtac ctcaagtaca accacgccga cgccgagttc    300

caggagcggc tcaaagaaga tacgtctttt gggggcaacc tcgggcgagc agtcttccag    360

gccaaaaaga ggcttcttga acctcttggt ctggttgagg aagcggctaa gacggctcct    420

ggaaagaaga ggcctgtaga gcagtctccc caggaaccgg actcctccgc gggtattggc    480

aaatcgggtg cacagcccgc taaaaagaga ctcaatttcg gtcagactgg cgacacagag    540

tcagtcccag accctcaacc aatcggagaa cctcccgcag ccccctctgg tgtgggatct    600

cttacaatgg cttcaggcgg tggcgcacca atggcggaca ataacgaagg cgccgacgga    660

gtgggtaatg cctcaggaaa ttggcattgc gattccacat ggctgggcga cagagtcatc    720

accaccagca cccgcacctg ggccttgccc acctacaata accacctcta caagcaaatc    780

tccagtgctt caacgggggc cagcaacgac aaccactact tcggctacag caccccctgg    840

gggtattttg acttcaacag attccactgc cacttttcac cacgtgactg gcaaagactc    900

atcaacaaca actggggatt ccgacccaag agactcaact tcaagctctt taacattcaa    960

gtcaaagagg ttacggacaa caatggagtc aagaccatcg ccaataacct taccagcacg   1020

gtccaggtct tcacggactc agactatcag ctcccgtacg tcctcggctc tgcgcaccag   1080

ggctgcctcc ctccgttccc ggcggacgtg ttcatgattc cgcagtacgg ctacctaacg   1140

ctcaacgacg gcagccaggc agtgggacgg tcatcctttt actgcctgga atatttccca   1200

tcgcagatgc tgagaacggg caacaacttt accttcagct acacctttga ggacgttcct   1260

ttccacagca gctacgctca cagccagagt ctggaccgtc tcatgaatcc tctgattgac   1320

cagtacctgt actacttgtc taagactatc aacggatccg gccagaatca gcagactctg   1380

aagttcagcc aaggtgggcc taatacaatg gccaatcagg caaagaactg gctgccagga   1440

ccctgttacc gccaacaacg cgtctcaacg acaaccgggc aaaacaacaa tagcaacttt   1500

gcctggactg ctgggaccaa ataccatctg aatggaagaa attcattgat gaatcctggc   1560
```

```
cccgctatgg catcccacaa agagggcgag gaccgttttt ttcccctgtc cgggtccctg   1620

atttttggca aacaaaatgc tgccagagac aatgcggatt acagcgatgt catgctcacc   1680

agcgaggaag aaatcaaaac cactaaccct gtggctacag aggaatacgg tatcgtggca   1740

gataacttgc agcagcaaaa cacggctcct caaattggaa ctgtcaacag ccagggggcc   1800

ttacccggta tggtctggca gaaccgggac gtgtacctgc agggtcccat ctgggccaag   1860

attcctcaca cggacggcaa cttccacccg tctccgctga tgggcggctt tggcctgaaa   1920

catcctccgc ctcagatcct gatcaagaac acgcctgtac ctgcggatcc tccgaccacc   1980

ttcaaccagt caaagctgaa ctctttcatc acgcaataca gcaccggaca ggtcagcgtg   2040

gaaattgaat gggagctgca gaaggaaaac agcaagcgct ggaaccccga gatccagtac   2100

acctccaact actacaaatc tacaagtgtg gactttgctg ttaatacaga aggcgtgtac   2160

tctgaacccc accccattgg cacccgttac ctcacccgtc cctgtaa                 2208
```

<210> SEQ ID NO 23
<211> LENGTH: 2211
<212> TYPE: DNA
<213> ORGANISM: Artificial Sequence
<220> FEATURE:
<223> OTHER INFORMATION: AAV214e10 VP1

<400> SEQUENCE: 23

```
atggctgccg atggttatct tccagattgg ctcgaggaca acctctctga gggcattcgc     60

gagtggtggg acttgaaacc tggagccccg aaacccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacgacaa ggcctacgac    240

cagcagctca aagcgggtga caatccgtac ctgcggtata accacgccga cgccgagttt    300

caggagcgtc tgcaagaaga tacgtctttt gggggcaacc tcgggcgagc agtcttccag    360

gccaagaagc gggttctcga acctctcggt ctggttgagg aaggcgctaa gacggctcct    420

ggaaagaaga gaccggtaga gccatcaccc cagcgttctc cagactcctc tacgggcatc    480

ggcaagaaag gccagcagcc cgcgaaaaag agactcaact ttgggcagac tggcgactca    540

gagtcagtgc ccgaccctca accaatcgga gaaccccccg caggcccctc tggtctggga    600

tctggtacaa tggcttcagg cggtggcgca ccaatggcgg acaataacga aggcgccgac    660

ggagtgggta atgcctcagg aaattggcat tgcgattcca catggctggg cgacagagtc    720

atcaccacca gcacccgcac ctgggccttg cccacctaca ataaccacct ctacaagcaa    780

atctccagtg cttcaacggg ggccagcaac gacaaccact acttcggcta cagcaccccc    840

tgggggtatt ttgacttcaa cagattccac tgccactttt caccacgtga ctggcaaaga    900

ctcatcaaca acaactgggg attccgaccc aagagactca acttcaagct ctttaacatt    960

caagtcaaag aggttacgga caacaatgga gtcaagacca tcgccaataa ccttaccagc   1020

acggtccagg tcttcacgga ctcagactat cagctcccgt acgtcctcgg ctctgcgcac   1080

cagggctgcc tccctccgtt cccggcggac gtgttcatga ttccgcagta cggctaccta   1140

acgctcaacg acggcagcca ggcagtggga cggtcatcct tttactgcct ggaatatttc   1200

ccatcgcaga tgctgagaac gggcaacaac tttaccttca gctacacctt tgaggacgtt   1260

cctttccaca gcagctacgc tcacagccag agtctggacc gtctcatgaa tcctctgatt   1320

gaccagtacc tgtactactt gtctaagact atcaacggat ccggccagaa tcagcagact   1380

ctgaagttca gccaaggtgg gcctaataca atggccaatc aggcaaagaa ctggctgcca   1440
```

```
ggaccctgtt accgccaaca acgcgtctca acgacaaccg ggcaaaacaa caatagcaac   1500

tttgcctgga ctgctgggac caaataccat ctgaatggaa gaaattcatt gatgaatcct   1560

ggccccgcta tggcatccca caaagagggc gaggaccgtt tttttcccct gtccgggtcc   1620

ctgatttttg gcaaacaaaa tgctgccaga gacaatgcgg attacagcga tgtcatgctc   1680

accagcgagg aagaaatcaa aaccactaac cctgtggcta cagaggaata cggtatcgtg   1740

gcagataact tgcagcagca aaacacggct cctcaaattg gaactgtcaa cagccagggg   1800

gccttacccg gtatggtctg gcagaaccgg gacgtgtacc tgcagggtcc catctgggcc   1860

aagattcctc acacggacgg caacttccac ccgtctccgc tgatgggcgg ctttggcctg   1920

aaacatcctc cgcctcagat cctgatcaag aacacgcctg tacctgcgga tcctccgacc   1980

accttcaacc agtcaaagct gaactctttc atcacgcaat acagcaccgg acaggtcagc   2040

gtggaaattg aatgggagct gcagaaggaa aacagcaagc gctggaaccc cgagatccag   2100

tacacctcca actactacaa atctacaagt gtggactttg ctgttaatac agaaggcgtg   2160

tactctgaac cccaccccat tggcacccgt tacctcaccc gtcccctgta a            2211
```

<210> SEQ ID NO 24
<211> LENGTH: 1602
<212> TYPE: DNA
<213> ORGANISM: Artificial Sequence
<220> FEATURE:
<223> OTHER INFORMATION: ITB102 214 (AAV214) VP3

<400> SEQUENCE: 24

```
atggcttcag gcggtggcgc accaatggcg gacaataacg aaggcgccga cggagtgggt     60

aatgcctcag gaaattggca ttgcgattcc acatggctgg gcgacagagt catcaccacc    120

agcacccgca cctgggcctt gcccacctac aataaccacc tctacaagca aatctccagt    180

gcttcaacgg gggccagcaa cgacaaccac tacttcggct acagcacccc ctgggggtat    240

tttgacttca acagattcca ctgccacttt tcaccacgtg actggcaaag actcatcaac    300

aacaactggg gattccgacc caagagactc aacttcaagc tctttaacat tcaagtcaaa    360

gaggttacgg acaacaatgg agtcaagacc atcgccaata accttaccag cacggtccag    420

gtcttcacgg actcagacta tcagctcccg tacgtcctcg gctctgcgca ccagggctgc    480

ctccctccgt tcccggcgga cgtgttcatg attccgcagt acggctacct aacgctcaac    540

gacggcagcc aggcagtggg acggtcatcc ttttactgcc tggaatattt cccatcgcag    600

atgctgagaa cgggcaacaa ctttaccttc agctacacct ttgaggacgt tcctttccac    660

agcagctacg ctcacagcca gagtctggac cgtctcatga atcctctgat tgaccagtac    720

ctgtactact tgtctaagac tatcaacgga tccggccaga atcagcagac tctgaagttc    780

agccaaggtg ggcctaatac aatggccaat caggcaaaga actggctgcc aggaccctgt    840

taccgccaac aacgcgtctc aacgacaacc gggcaaaaca acaatagcaa ctttgcctgg    900

actgctggga ccaaatacca tctgaatgga agaaattcat tgatgaatcc tggccccgct    960

atggcatccc acaaagaggg cgaggaccgt ttttttcccc tgtccgggtc cctgattttt   1020

ggcaaacaaa atgctgccag agacaatgcg gattacagcg atgtcatgct caccagcgag   1080

gaagaaatca aaaccactaa ccctgtggct acagaggaat acggtatcgt ggcagataac   1140

ttgcagcagc aaaacacggc tcctcaaatt ggaactgtca acagccaggg ggccttaccc   1200

ggtatggtct ggcagaaccg ggacgtgtac ctgcagggtc ccatctgggc caagattcct   1260
```

cacacggacg gcaacttcca cccgtctccg ctgatgggcg gctttggcct gaaacatcct 1320
ccgcctcaga tcctgatcaa gaacacgcct gtacctgcgg atcctccgac caccttcaac 1380
cagtcaaagc tgaactcttt catcacgcaa tacagcaccg gacaggtcag cgtggaaatt 1440
gaatgggagc tgcagaagga aaacagcaag cgctggaacc ccgagatcca gtacacctcc 1500
aactactaca aatctacaag tgtggacttt gctgttaata cagaaggcgt gtactctgaa 1560
ccccacccca ttggcacccg ttacctcacc cgtcccctgt aa 1602

<210> SEQ ID NO 25
<211> LENGTH: 1605
<212> TYPE: DNA
<213> ORGANISM: Artificial Sequence
<220> FEATURE:
<223> OTHER INFORMATION: AAV214-A VP3

<400> SEQUENCE: 25
atggcttcag gcggtggcgc accaatggcg gacaataacg aaggcgccga cggagtgggt 60
aatgcctcag gaaattggca ttgcgattcc acatggctgg gcgacagagt catcaccacc 120
agcacccgca cctgggcctt gcccacctac aataaccacc tctacaagca aatctccaac 180
agcacatctg gaggatcttc aaatgacaac gcctacttcg gctacagcac cccctggggg 240
tattttgact tcaacagatt ccactgccac ttttcaccac gtgactggca aagactcatc 300
aacaacaact ggggattccg acccaagaga ctcaacttca agctctttaa cattcaagtc 360
aaagaggtta cggacaacaa tggagtcaag accatcgcca ataaccttac cagcacggtc 420
caggtcttca cggactcaga ctatcagctc ccgtacgtcc tcggctctgc gcaccagggc 480
tgcctccctc cgttcccggc ggacgtgttc atgattccgc agtacggcta cctaacgctc 540
aacgacggca gccaggcagt gggacggtca tccttttact gcctggaata tttcccatcg 600
cagatgctga gaacgggcaa caactttacc ttcagctaca cctttgagga cgttcctttc 660
cacagcagct acgctcacag ccagagtctg gaccgtctca tgaatcctct gattgaccag 720
tacctgtact acttgtctaa gactatcaac ggatccggcc agaatcagca gactctgaag 780
ttcagccaag gtgggcctaa tacaatggcc aatcaggcaa agaactggct gccaggaccc 840
tgttaccgcc aacaacgcgt ctcaacgaca accgggcaaa acaacaatag caactttgcc 900
tggactgctg ggaccaaata ccatctgaat ggaagaaatt cattgatgaa tcctggcccc 960
gctatggcat cccacaaaga gggcgaggac cgtttttttc ccctgtccgg gtccctgatt 1020
tttggcaaac aaaatgctgc cagagacaat gcggattaca gcgatgtcat gctcaccagc 1080
gaggaagaaa tcaaaaccac taaccctgtg gctacagagg aatacggtat cgtggcagat 1140
aacttgcagc agcaaaacac ggctcctcaa attggaactg tcaacagcca gggggcctta 1200
cccggtatgg tctggcagaa ccgggacgtg tacctgcagg gtcccatctg ggccaagatt 1260
cctcacacgg acggcaactt ccacccgtct ccgctgatgg gcggctttgg cctgaaacat 1320
cctccgcctc agatcctgat caagaacacg cctgtacctg cggatcctcc gaccaccttc 1380
aaccagtcaa agctgaactc tttcatcacg caatacagca ccggacaggt cagcgtggaa 1440
attgaatggg agctgcagaa ggaaaacagc aagcgctgga accccgagat ccagtacacc 1500
tccaactact acaaatctac aagtgtggac tttgctgtta atacagaagg cgtgtactct 1560
gaaccccacc ccattggcac ccgttacctc acccgtcccc tgtaa 1605

<210> SEQ ID NO 26
<211> LENGTH: 1602

<212> TYPE: DNA
<213> ORGANISM: Artificial Sequence
<220> FEATURE:
<223> OTHER INFORMATION: AAV214e VP3

<400> SEQUENCE: 26

```
atggcttcag gcggtggcgc accaatggca gacaataacg aaggcgccga cggagtgggt     60

aatgcctcag gaaattggca ttgcgattcc acatggctgg gcgacagagt catcaccacc    120

agcacccgca cctgggcctt gcccacctac aataaccacc tctacaagca aatctccagt    180

gcttcaacgg gggccagcaa cgacaaccac tacttcggct acagcacccc ctgggggtat    240

tttgacttca acagattcca ctgccacttt tcaccacgtg actggcaaag actcatcaac    300

aacaactggg gattccgacc caagagactc aacttcaagc tctttaacat tcaagtcaaa    360

gaggttacgg acaacaatgg agtcaagacc atcgccaata accttaccag cacggtccag    420

gtcttcacgg actcagacta tcagctcccg tacgtcctcg gctctgcgca ccagggctgc    480

ctccctccgt tcccggcgga cgtgttcatg attccgcagt acggctacct aacgctcaac    540

gacggcagcc aggcagtggg acggtcatcc ttttactgcc tggaatattt cccatcgcag    600

atgctgagaa cgggcaacaa ctttaccttc agctacacct ttgaggacgt tcctttccac    660

agcagctacg ctcacagcca gagtctggac cgtctcatga atcctctgat tgaccagtac    720

ctgtactact tgtctaagac tatcaacgga tccggccaga atcagcagac tctgaagttc    780

agccaaggtg ggcctaatac aatggccaat caggcaaaga actggctgcc aggaccctgt    840

taccgccaac aacgcgtctc aacgacaacc gggcaaaaca acaatagcaa ctttgcctgg    900

actgctggga ccaaatacca tctgaatgga agaaattcat tgatgaatcc tggccccgct    960

atggcatccc acaaagaggg cgaggaccgt ttttttcccc tgtccgggtc cctgattttt   1020

ggcaaacaaa atgctgccag agacaatgcg gattacagcg atgtcatgct caccagcgag   1080

gaagaaatca aaaccactaa ccctgtggct acagaggaat acggtatcgt ggcagataac   1140

ttgcagcagc aaaacacggc tcctcaaatt ggaactgtca acagccaggg ggccttaccc   1200

ggtatggtct ggcagaaccg ggacgtgtac ctgcagggtc ccatctgggc caagattcct   1260

cacacggacg gcaacttcca cccgtctccg ctgatgggcg gctttggcct gaaacatcct   1320

ccgcctcaga tcctgatcaa gaacacgcct gtacctgcgg atcctccgac caccttcaac   1380

cagtcaaagc tgaactcttt catcacgcaa tacagcaccg gacaggtcag cgtggaaatt   1440

gaatgggagc tgcagaagga aaacagcaag cgctggaacc ccgagatcca gtacacctcc   1500

aactactaca aatctacaag tgtggacttt gctgttaata cagaaggcgt gtactctgaa   1560

ccccacccca ttggcacccg ttacctcacc cgtcccctgt aa                       1602
```

<210> SEQ ID NO 27
<211> LENGTH: 1602
<212> TYPE: DNA
<213> ORGANISM: Artificial Sequence
<220> FEATURE:
<223> OTHER INFORMATION: AAV214e8 VP3

<400> SEQUENCE: 27

```
atggcttcag gcggtggcgc accaatggcg gacaataacg aaggcgccga cggagtgggt     60

aatgcctcag gaaattggca ttgcgattcc acatggctgg gcgacagagt catcaccacc    120

agcacccgca cctgggcctt gcccacctac aataaccacc tctacaagca aatctccagt    180

gcttcaacgg gggccagcaa cgacaaccac tacttcggct acagcacccc ctgggggtat    240
```

tttgacttca acagattcca ctgccacttt tcaccacgtg actggcaaag actcatcaac 300
aacaactggg gattccgacc caagagactc aacttcaagc tctttaacat tcaagtcaaa 360
gaggttacgg acaacaatgg agtcaagacc atcgccaata accttaccag cacggtccag 420
gtcttcacgg actcagacta tcagctcccg tacgtcctcg gctctgcgca ccagggctgc 480
ctccctccgt tcccggcgga cgtgttcatg attccgcagt acggctacct aacgctcaac 540
gacggcagcc aggcagtggg acggtcatcc ttttactgcc tggaatattt cccatcgcag 600
atgctgagaa cgggcaacaa ctttaccttc agctacacct ttgaggacgt tcctttccac 660
agcagctacg ctcacagcca gagtctggac cgtctcatga atcctctgat tgaccagtac 720
ctgtactact tgtctaagac tatcaacgga tccggccaga atcagcagac tctgaagttc 780
agccaaggtg ggcctaatac aatggccaat caggcaaaga actggctgcc aggaccctgt 840
taccgccaac aacgcgtctc aacgacaacc gggcaaaaca acaatagcaa ctttgcctgg 900
actgctggga ccaaatacca tctgaatgga agaaattcat tgatgaatcc tggccccgct 960
atggcatccc acaaagaggg cgaggaccgt ttttttcccc tgtccgggtc cctgattttt 1020
ggcaaacaaa atgctgccag agacaatgcg gattacagcg atgtcatgct caccagcgag 1080
gaagaaatca aaaccactaa ccctgtggct acagaggaat acggtatcgt ggcagataac 1140
ttgcagcagc aaaacacggc tcctcaaatt ggaactgtca acagccaggg ggccttaccc 1200
ggtatggtct ggcagaaccg ggacgtgtac ctgcagggtc ccatctgggc caagattcct 1260
cacacggacg gcaacttcca cccgtctccg ctgatgggcg gctttggcct gaaacatcct 1320
ccgcctcaga tcctgatcaa gaacacgcct gtacctgcgg atcctccgac caccttcaac 1380
cagtcaaagc tgaactcttt catcacgcaa tacagcaccg gacaggtcag cgtggaaatt 1440
gaatgggagc tgcagaagga aaacagcaag cgctggaacc ccgagatcca gtacacctcc 1500
aactactaca aatctacaag tgtggacttt gctgttaata cagaaggcgt gtactctgaa 1560 ccccaccccca ttggcacccg ttacctcacc cgtcccctgt aa 1602

<210> SEQ ID NO 28
<211> LENGTH: 1602
<212> TYPE: DNA
<213> ORGANISM: Artificial Sequence
<220> FEATURE:
<223> OTHER INFORMATION: AAV214e9 VP3

<400> SEQUENCE: 28
atggcttcag gcggtggcgc accaatggcg gacaataacg aaggcgccga cggagtgggt 60
aatgcctcag gaaattggca ttgcgattcc acatggctgg gcgacagagt catcaccacc 120
agcacccgca cctgggcctt gcccacctac aataaccacc tctacaagca aatctccagt 180
gcttcaacgg gggccagcaa cgacaaccac tacttcggct acagcacccc ctgggggtat 240
tttgacttca acagattcca ctgccacttt tcaccacgtg actggcaaag actcatcaac 300
aacaactggg gattccgacc caagagactc aacttcaagc tctttaacat tcaagtcaaa 360
gaggttacgg acaacaatgg agtcaagacc atcgccaata accttaccag cacggtccag 420
gtcttcacgg actcagacta tcagctcccg tacgtcctcg gctctgcgca ccagggctgc 480
ctccctccgt tcccggcgga cgtgttcatg attccgcagt acggctacct aacgctcaac 540
gacggcagcc aggcagtggg acggtcatcc ttttactgcc tggaatattt cccatcgcag 600
atgctgagaa cgggcaacaa ctttaccttc agctacacct ttgaggacgt tcctttccac 660
agcagctacg ctcacagcca gagtctggac cgtctcatga atcctctgat tgaccagtac 720

```
ctgtactact tgtctaagac tatcaacgga tccggccaga atcagcagac tctgaagttc    780
agccaaggtg ggcctaatac aatggccaat caggcaaaga actggctgcc aggaccctgt    840
taccgccaac aacgcgtctc aacgacaacc gggcaaaaca acaatagcaa ctttgcctgg    900
actgctggga ccaaatacca tctgaatgga agaaattcat tgatgaatcc tggccccgct    960
atggcatccc acaaagaggg cgaggaccgt ttttttcccc tgtccgggtc cctgattttt   1020
ggcaaacaaa atgctgccag agacaatgcg gattacagcg atgtcatgct caccagcgag   1080
gaagaaatca aaaccactaa ccctgtggct acagaggaat acggtatcgt ggcagataac   1140
ttgcagcagc aaaacacggc tcctcaaatt ggaactgtca acagccaggg ggccttaccc   1200
ggtatggtct ggcagaaccg ggacgtgtac ctgcagggtc ccatctgggc caagattcct   1260
cacacggacg gcaacttcca cccgtctccg ctgatgggcg gctttggcct gaaacatcct   1320
ccgcctcaga tcctgatcaa gaacacgcct gtacctgcgg atcctccgac caccttcaac   1380
cagtcaaagc tgaactcttt catcacgcaa tacagcaccg gacaggtcag cgtggaaatt   1440
gaatgggagc tgcagaagga aaacagcaag cgctggaacc ccgagatcca gtacacctcc   1500
aactactaca aatctacaag tgtggacttt gctgttaata cagaaggcgt gtactctgaa   1560
ccccaccccca ttggcacccg ttacctcacc cgtcccctgt aa                      1602
```

```
<210> SEQ ID NO 29
<211> LENGTH: 1602
<212> TYPE: DNA
<213> ORGANISM: Artificial Sequence
<220> FEATURE:
<223> OTHER INFORMATION: AAV214e10 VP3

<400> SEQUENCE: 29
```

```
atggcttcag gcggtggcgc accaatggcg gacaataacg aaggcgccga cggagtgggt     60
aatgcctcag gaaattggca ttgcgattcc acatggctgg gcgacagagt catcaccacc    120
agcacccgca cctgggcctt gcccacctac aataaccacc tctacaagca aatctccagt    180
gcttcaacgg gggccagcaa cgacaaccac tacttcggct acagcacccc ctgggggtat    240
tttgacttca acagattcca ctgccacttt tcaccacgtg actggcaaag actcatcaac    300
aacaactggg gattccgacc caagagactc aacttcaagc tctttaacat tcaagtcaaa    360
gaggttacgg acaacaatgg agtcaagacc atcgccaata accttaccag cacggtccag    420
gtcttcacgg actcagacta tcagctcccg tacgtcctcg gctctgcgca ccagggctgc    480
ctccctccgt tcccggcgga cgtgttcatg attccgcagt acggctacct aacgctcaac    540
gacggcagcc aggcagtggg acggtcatcc ttttactgcc tggaatattt cccatcgcag    600
atgctgagaa cgggcaacaa ctttaccttc agctacacct ttgaggacgt tcctttccac    660
agcagctacg ctcacagcca gagtctggac cgtctcatga atcctctgat tgaccagtac    720
ctgtactact tgtctaagac tatcaacgga tccggccaga atcagcagac tctgaagttc    780
agccaaggtg ggcctaatac aatggccaat caggcaaaga actggctgcc aggaccctgt    840
taccgccaac aacgcgtctc aacgacaacc gggcaaaaca acaatagcaa ctttgcctgg    900
actgctggga ccaaatacca tctgaatgga agaaattcat tgatgaatcc tggccccgct    960
atggcatccc acaaagaggg cgaggaccgt ttttttcccc tgtccgggtc cctgattttt   1020
ggcaaacaaa atgctgccag agacaatgcg gattacagcg atgtcatgct caccagcgag   1080
gaagaaatca aaaccactaa ccctgtggct acagaggaat acggtatcgt ggcagataac   1140
```

```
ttgcagcagc aaaacacggc tcctcaaatt ggaactgtca acagccaggg ggccttaccc   1200

ggtatggtct ggcagaaccg ggacgtgtac ctgcagggtc ccatctgggc caagattcct   1260

cacacggacg gcaacttcca cccgtctccg ctgatgggcg gctttggcct gaaacatcct   1320

ccgcctcaga tcctgatcaa gaacacgcct gtacctgcgg atcctccgac caccttcaac   1380

cagtcaaagc tgaactcttt catcacgcaa tacagcaccg gacaggtcag cgtggaaatt   1440

gaatgggagc tgcagaagga aaacagcaag cgctggaacc ccgagatcca gtacacctcc   1500

aactactaca aatctacaag tgtggacttt gctgttaata cagaaggcgt gtactctgaa   1560

ccccacccca ttggcacccg ttacctcacc cgtcccctgt aa                      1602
```

```
<210> SEQ ID NO 30
<211> LENGTH: 736
<212> TYPE: PRT
<213> ORGANISM: Artificial Sequence
<220> FEATURE:
<223> OTHER INFORMATION: AAV214A VP1

<400> SEQUENCE: 30

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285
```

```
Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Gln Gly Gly Pro Asn Thr Met Ala Asn Gln Ala Lys Asn Trp Leu Pro
465                 470                 475                 480

Gly Pro Cys Tyr Arg Gln Gln Arg Val Ser Thr Thr Thr Gly Gln Asn
                485                 490                 495

Asn Asn Ser Asn Phe Ala Trp Thr Ala Gly Thr Lys Tyr His Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Asn Ala Ala Arg Asp Asn Ala Asp Tyr Ser Asp Val Met Leu
545                 550                 555                 560

Thr Ser Glu Glu Glu Ile Lys Thr Thr Asn Pro Val Ala Thr Glu Glu
                565                 570                 575

Tyr Gly Ile Val Ala Asp Asn Leu Gln Gln Gln Asn Thr Ala Pro Gln
            580                 585                 590

Ile Gly Thr Val Asn Ser Gln Gly Ala Leu Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Thr Thr Phe Asn Gln Ser Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700
```

```
Tyr Tyr Lys Ser Thr Ser Val Asp Phe Ala Val Asn Thr Glu Gly Val
705                 710                 715                 720

Tyr Ser Glu Pro His Pro Ile Gly Thr Arg Tyr Leu Thr Arg Pro Leu
                725                 730                 735


<210> SEQ ID NO 31
<211> LENGTH: 736
<212> TYPE: PRT
<213> ORGANISM: Artificial Sequence
<220> FEATURE:
<223> OTHER INFORMATION: AAV214e VP1

<400> SEQUENCE: 31

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Thr Pro Ala Ala Val Gly Pro Thr Thr Met Ala Ser Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Ala Ser Thr Gly Ala Ser Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335
```

```
Asn Leu Thr Ser Thr Val Gln Val Phe Thr Asp Ser Asp Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Gln Gly Gly Pro Asn Thr Met Ala Asn Gln Ala Lys Asn Trp Leu Pro
465                 470                 475                 480

Gly Pro Cys Tyr Arg Gln Gln Arg Val Ser Thr Thr Thr Gly Gln Asn
                485                 490                 495

Asn Asn Ser Asn Phe Ala Trp Thr Ala Gly Thr Lys Tyr His Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Asn Ala Ala Arg Asp Asn Ala Asp Tyr Ser Asp Val Met Leu
545                 550                 555                 560

Thr Ser Glu Glu Glu Ile Lys Thr Thr Asn Pro Val Ala Thr Glu Glu
                565                 570                 575

Tyr Gly Ile Val Ala Asp Asn Leu Gln Gln Gln Asn Thr Ala Pro Gln
            580                 585                 590

Ile Gly Thr Val Asn Ser Gln Gly Ala Leu Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Thr Thr Phe Asn Gln Ser Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Ser Val Asp Phe Ala Val Asn Thr Glu Gly Val
705                 710                 715                 720

Tyr Ser Glu Pro His Pro Ile Gly Thr Arg Tyr Leu Thr Arg Pro Leu
                725                 730                 735
```

<210> SEQ ID NO 32
<211> LENGTH: 736
<212> TYPE: PRT

```
<213> ORGANISM: Artificial Sequence
<220> FEATURE:
<223> OTHER INFORMATION: AAV214e8 VP1

<400> SEQUENCE: 32

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ser Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Ala Ser Thr Gly Ala Ser Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
```

```
385                 390                 395                 400

Pro Ser Gln Met Leu Arg Thr Gly Asn Asn Phe Thr Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Gln Gly Gly Pro Asn Thr Met Ala Asn Gln Ala Lys Asn Trp Leu Pro
465                 470                 475                 480

Gly Pro Cys Tyr Arg Gln Gln Arg Val Ser Thr Thr Thr Gly Gln Asn
                485                 490                 495

Asn Asn Ser Asn Phe Ala Trp Thr Ala Gly Thr Lys Tyr His Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Asn Ala Ala Arg Asp Asn Ala Asp Tyr Ser Asp Val Met Leu
545                 550                 555                 560

Thr Ser Glu Glu Glu Ile Lys Thr Thr Asn Pro Val Ala Thr Glu Glu
                565                 570                 575

Tyr Gly Ile Val Ala Asp Asn Leu Gln Gln Gln Asn Thr Ala Pro Gln
            580                 585                 590

Ile Gly Thr Val Asn Ser Gln Gly Ala Leu Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Thr Thr Phe Asn Gln Ser Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Ser Val Asp Phe Ala Val Asn Thr Glu Gly Val
705                 710                 715                 720

Tyr Ser Glu Pro His Pro Ile Gly Thr Arg Tyr Leu Thr Arg Pro Leu
                725                 730                 735


<210> SEQ ID NO 33
<211> LENGTH: 735
<212> TYPE: PRT
<213> ORGANISM: Artificial Sequence
<220> FEATURE:
<223> OTHER INFORMATION: AAV214e9 VP1

<400> SEQUENCE: 33

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
```

-continued

```
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Asp Asn Asn Gly Val Lys Thr Ile Ala Asn Asn
                325                 330                 335

Leu Thr Ser Thr Val Gln Val Phe Thr Asp Ser Asp Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asp Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Lys
        435                 440                 445
```

```
Thr Ile Asn Gly Ser Gly Gln Asn Gln Gln Thr Leu Lys Phe Ser Gln
    450                 455                 460

Gly Gly Pro Asn Thr Met Ala Asn Gln Ala Lys Asn Trp Leu Pro Gly
465                 470                 475                 480

Pro Cys Tyr Arg Gln Gln Arg Val Ser Thr Thr Thr Gly Gln Asn Asn
                485                 490                 495

Asn Ser Asn Phe Ala Trp Thr Ala Gly Thr Lys Tyr His Leu Asn Gly
            500                 505                 510

Arg Asn Ser Leu Met Asn Pro Gly Pro Ala Met Ala Ser His Lys Glu
        515                 520                 525

Gly Glu Asp Arg Phe Phe Pro Leu Ser Gly Ser Leu Ile Phe Gly Lys
    530                 535                 540

Gln Asn Ala Ala Arg Asp Asn Ala Asp Tyr Ser Asp Val Met Leu Thr
545                 550                 555                 560

Ser Glu Glu Glu Ile Lys Thr Thr Asn Pro Val Ala Thr Glu Glu Tyr
                565                 570                 575

Gly Ile Val Ala Asp Asn Leu Gln Gln Gln Asn Thr Ala Pro Gln Ile
            580                 585                 590

Gly Thr Val Asn Ser Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asp
                645                 650                 655

Pro Pro Thr Thr Phe Asn Gln Ser Lys Leu Asn Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Tyr Lys Ser Thr Ser Val Asp Phe Ala Val Asn Thr Glu Gly Val Tyr
705                 710                 715                 720

Ser Glu Pro His Pro Ile Gly Thr Arg Tyr Leu Thr Arg Pro Leu
                725                 730                 735


<210> SEQ ID NO 34
<211> LENGTH: 736
<212> TYPE: PRT
<213> ORGANISM: Artificial Sequence
<220> FEATURE:
<223> OTHER INFORMATION: AAV214e10 VP1

<400> SEQUENCE: 34

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80
```

```
Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ser Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Ala Ser Thr Gly Ala Ser Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Gln Gly Gly Pro Asn Thr Met Ala Asn Gln Ala Lys Asn Trp Leu Pro
465                 470                 475                 480

Gly Pro Cys Tyr Arg Gln Gln Arg Val Ser Thr Thr Thr Gly Gln Asn
                485                 490                 495
```

```
Asn Asn Ser Asn Phe Ala Trp Thr Ala Gly Thr Lys Tyr His Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Asn Ala Ala Arg Asp Asn Ala Asp Tyr Ser Asp Val Met Leu
545                 550                 555                 560

Thr Ser Glu Glu Glu Ile Lys Thr Thr Asn Pro Val Ala Thr Glu Glu
                565                 570                 575

Tyr Gly Ile Val Ala Asp Asn Leu Gln Gln Gln Asn Thr Ala Pro Gln
            580                 585                 590

Ile Gly Thr Val Asn Ser Gln Gly Ala Leu Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Thr Thr Phe Asn Gln Ser Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Ser Val Asp Phe Ala Val Asn Thr Glu Gly Val
705                 710                 715                 720

Tyr Ser Glu Pro His Pro Ile Gly Thr Arg Tyr Leu Thr Arg Pro Leu
                725                 730                 735


<210> SEQ ID NO 35
<211> LENGTH: 598
<212> TYPE: PRT
<213> ORGANISM: Artificial Sequence
<220> FEATURE:
<223> OTHER INFORMATION: AAV214 VP2

<400> SEQUENCE: 35

Met Ala Pro Gly Lys Lys Arg Pro Val Glu Gln Ser Pro Gln Glu Pro
1               5                   10                  15

Asp Ser Ser Ser Gly Ile Gly Lys Thr Gly Gln Gln Pro Ala Lys Lys
            20                  25                  30

Arg Leu Asn Phe Gly Gln Thr Gly Asp Ser Glu Ser Val Pro Asp Pro
        35                  40                  45

Gln Pro Leu Gly Glu Pro Pro Ala Thr Pro Ala Ala Val Gly Pro Thr
    50                  55                  60

Thr Met Ala Ser Gly Gly Gly Ala Pro Met Ala Asp Asn Asn Glu Gly
65                  70                  75                  80

Ala Asp Gly Val Gly Asn Ala Ser Gly Asn Trp His Cys Asp Ser Thr
                85                  90                  95

Trp Leu Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Ala Ser Thr
        115                 120                 125
```

-continued

```
Gly Ala Ser Asn Asp Asn His Tyr Phe Gly Tyr Ser Thr Pro Trp Gly
    130                 135                 140

Tyr Phe Asp Phe Asn Arg Phe His Cys His Phe Ser Pro Arg Asp Trp
145                 150                 155                 160

Gln Arg Leu Ile Asn Asn Asn Trp Gly Phe Arg Pro Lys Arg Leu Asn
                165                 170                 175

Phe Lys Leu Phe Asn Ile Gln Val Lys Glu Val Thr Asp Asn Asn Gly
            180                 185                 190

Val Lys Thr Ile Ala Asn Asn Leu Thr Ser Thr Val Gln Val Phe Thr
        195                 200                 205

Asp Ser Asp Tyr Gln Leu Pro Tyr Val Leu Gly Ser Ala His Gln Gly
    210                 215                 220

Cys Leu Pro Pro Phe Pro Ala Asp Val Phe Met Ile Pro Gln Tyr Gly
225                 230                 235                 240

Tyr Leu Thr Leu Asn Asp Gly Ser Gln Ala Val Gly Arg Ser Ser Phe
                245                 250                 255

Tyr Cys Leu Glu Tyr Phe Pro Ser Gln Met Leu Arg Thr Gly Asn Asn
            260                 265                 270

Phe Thr Phe Ser Tyr Thr Phe Glu Asp Val Pro Phe His Ser Ser Tyr
        275                 280                 285

Ala His Ser Gln Ser Leu Asp Arg Leu Met Asn Pro Leu Ile Asp Gln
    290                 295                 300

Tyr Leu Tyr Tyr Leu Ser Lys Thr Ile Asn Gly Ser Gly Gln Asn Gln
305                 310                 315                 320

Gln Thr Leu Lys Phe Ser Gln Gly Gly Pro Asn Thr Met Ala Asn Gln
                325                 330                 335

Ala Lys Asn Trp Leu Pro Gly Pro Cys Tyr Arg Gln Gln Arg Val Ser
            340                 345                 350

Thr Thr Thr Gly Gln Asn Asn Asn Ser Asn Phe Ala Trp Thr Ala Gly
        355                 360                 365

Thr Lys Tyr His Leu Asn Gly Arg Asn Ser Leu Met Asn Pro Gly Pro
    370                 375                 380

Ala Met Ala Ser His Lys Glu Gly Glu Asp Arg Phe Phe Pro Leu Ser
385                 390                 395                 400

Gly Ser Leu Ile Phe Gly Lys Gln Asn Ala Ala Arg Asp Asn Ala Asp
                405                 410                 415

Tyr Ser Asp Val Met Leu Thr Ser Glu Glu Glu Ile Lys Thr Thr Asn
            420                 425                 430

Pro Val Ala Thr Glu Glu Tyr Gly Ile Val Ala Asp Asn Leu Gln Gln
        435                 440                 445

Gln Asn Thr Ala Pro Gln Ile Gly Thr Val Asn Ser Gln Gly Ala Leu
    450                 455                 460

Pro Gly Met Val Trp Gln Asn Arg Asp Val Tyr Leu Gln Gly Pro Ile
465                 470                 475                 480

Trp Ala Lys Ile Pro His Thr Asp Gly Asn Phe His Pro Ser Pro Leu
                485                 490                 495

Met Gly Gly Phe Gly Leu Lys His Pro Pro Pro Gln Ile Leu Ile Lys
            500                 505                 510

Asn Thr Pro Val Pro Ala Asp Pro Pro Thr Thr Phe Asn Gln Ser Lys
        515                 520                 525

Leu Asn Ser Phe Ile Thr Gln Tyr Ser Thr Gly Gln Val Ser Val Glu
    530                 535                 540

Ile Glu Trp Glu Leu Gln Lys Glu Asn Ser Lys Arg Trp Asn Pro Glu
```

545 550 555 560

Ile Gln Tyr Thr Ser Asn Tyr Tyr Lys Ser Thr Ser Val Asp Phe Ala
565 570 575

Val Asn Thr Glu Gly Val Tyr Ser Glu Pro His Pro Ile Gly Thr Arg
580 585 590

Tyr Leu Thr Arg Pro Leu
595

<210> SEQ ID NO 36
<211> LENGTH: 599
<212> TYPE: PRT
<213> ORGANISM: Artificial Sequence
<220> FEATURE:
<223> OTHER INFORMATION: AAV214A VP2

<400> SEQUENCE: 36

Met Ala Pro Gly Lys Lys Arg Pro Val Glu Gln Ser Pro Gln Glu Pro
1 5 10 15

Asp Ser Ser Ser Gly Ile Gly Lys Thr Gly Gln Gln Pro Ala Lys Lys
20 25 30

Arg Leu Asn Phe Gly Gln Thr Gly Asp Ser Glu Ser Val Pro Asp Pro
35 40 45

Gln Pro Leu Gly Glu Pro Pro Ala Thr Pro Ala Ala Val Gly Pro Thr
50 55 60

Thr Met Ala Ser Gly Gly Gly Ala Pro Met Ala Asp Asn Asn Glu Gly
65 70 75 80

Ala Asp Gly Val Gly Asn Ala Ser Gly Asn Trp His Cys Asp Ser Thr
85 90 95

Trp Leu Gly Asp Arg Val Ile Thr Thr Ser Thr Arg Thr Trp Ala Leu
100 105 110

Pro Thr Tyr Asn Asn His Leu Tyr Lys Gln Ile Ser Asn Ser Thr Ser
115 120 125

Gly Gly Ser Ser Asn Asp Asn Ala Tyr Phe Gly Tyr Ser Thr Pro Trp
130 135 140

Gly Tyr Phe Asp Phe Asn Arg Phe His Cys His Phe Ser Pro Arg Asp
145 150 155 160

Trp Gln Arg Leu Ile Asn Asn Asn Trp Gly Phe Arg Pro Lys Arg Leu
165 170 175

Asn Phe Lys Leu Phe Asn Ile Gln Val Lys Glu Val Thr Asp Asn Asn
180 185 190

Gly Val Lys Thr Ile Ala Asn Asn Leu Thr Ser Thr Val Gln Val Phe
195 200 205

Thr Asp Ser Asp Tyr Gln Leu Pro Tyr Val Leu Gly Ser Ala His Gln
210 215 220

Gly Cys Leu Pro Pro Phe Pro Ala Asp Val Phe Met Ile Pro Gln Tyr
225 230 235 240

Gly Tyr Leu Thr Leu Asn Asp Gly Ser Gln Ala Val Gly Arg Ser Ser
245 250 255

Phe Tyr Cys Leu Glu Tyr Phe Pro Ser Gln Met Leu Arg Thr Gly Asn
260 265 270

Asn Phe Thr Phe Ser Tyr Thr Phe Glu Asp Val Pro Phe His Ser Ser
275 280 285

Tyr Ala His Ser Gln Ser Leu Asp Arg Leu Met Asn Pro Leu Ile Asp
290 295 300

Gln Tyr Leu Tyr Tyr Leu Ser Lys Thr Ile Asn Gly Ser Gly Gln Asn 305 310 315 320

Gln Gln Thr Leu Lys Phe Ser Gln Gly Gly Pro Asn Thr Met Ala Asn
325 330 335

Gln Ala Lys Asn Trp Leu Pro Gly Pro Cys Tyr Arg Gln Gln Arg Val
340 345 350

Ser Thr Thr Thr Gly Gln Asn Asn Asn Ser Asn Phe Ala Trp Thr Ala
355 360 365

Gly Thr Lys Tyr His Leu Asn Gly Arg Asn Ser Leu Met Asn Pro Gly
370 375 380

Pro Ala Met Ala Ser His Lys Glu Gly Glu Asp Arg Phe Phe Pro Leu
385 390 395 400

Ser Gly Ser Leu Ile Phe Gly Lys Gln Asn Ala Ala Arg Asp Asn Ala
405 410 415

Asp Tyr Ser Asp Val Met Leu Thr Ser Glu Glu Glu Ile Lys Thr Thr
420 425 430

Asn Pro Val Ala Thr Glu Glu Tyr Gly Ile Val Ala Asp Asn Leu Gln
435 440 445

Gln Gln Asn Thr Ala Pro Gln Ile Gly Thr Val Asn Ser Gln Gly Ala
450 455 460

Leu Pro Gly Met Val Trp Gln Asn Arg Asp Val Tyr Leu Gln Gly Pro
465 470 475 480

Ile Trp Ala Lys Ile Pro His Thr Asp Gly Asn Phe His Pro Ser Pro
485 490 495

Leu Met Gly Gly Phe Gly Leu Lys His Pro Pro Pro Gln Ile Leu Ile
500 505 510

Lys Asn Thr Pro Val Pro Ala Asp Pro Pro Thr Thr Phe Asn Gln Ser
515 520 525

Lys Leu Asn Ser Phe Ile Thr Gln Tyr Ser Thr Gly Gln Val Ser Val
530 535 540

Glu Ile Glu Trp Glu Leu Gln Lys Glu Asn Ser Lys Arg Trp Asn Pro
545 550 555 560

Glu Ile Gln Tyr Thr Ser Asn Tyr Tyr Lys Ser Thr Ser Val Asp Phe
565 570 575

Ala Val Asn Thr Glu Gly Val Tyr Ser Glu Pro His Pro Ile Gly Thr
580 585 590

Arg Tyr Leu Thr Arg Pro Leu
595

<210> SEQ ID NO 37
<211> LENGTH: 599
<212> TYPE: PRT
<213> ORGANISM: Artificial Sequence
<220> FEATURE:
<223> OTHER INFORMATION: AAV214e VP2

<400> SEQUENCE: 37

Met Ala Pro Gly Lys Lys Arg Pro Val Glu Pro Ser Pro Gln Arg Ser
1 5 10 15

Pro Asp Ser Ser Thr Gly Ile Gly Lys Lys Gly Gln Gln Pro Ala Arg
20 25 30

Lys Arg Leu Asn Phe Gly Gln Thr Gly Asp Ser Glu Ser Val Pro Asp
35 40 45

Pro Gln Pro Leu Gly Glu Pro Pro Ala Thr Pro Ala Ala Val Gly Pro
50 55 60

Thr Thr Met Ala Ser Gly Gly Gly Ala Pro Met Ala Asp Asn Asn Glu

-continued

```
65                  70                  75                  80

Gly Ala Asp Gly Val Gly Asn Ala Ser Gly Asn Trp His Cys Asp Ser
                85                  90                  95

Thr Trp Leu Gly Asp Arg Val Ile Thr Thr Ser Thr Arg Thr Trp Ala
            100                 105                 110

Leu Pro Thr Tyr Asn Asn His Leu Tyr Lys Gln Ile Ser Ser Ala Ser
        115                 120                 125

Thr Gly Ala Ser Asn Asp Asn His Tyr Phe Gly Tyr Ser Thr Pro Trp
    130                 135                 140

Gly Tyr Phe Asp Phe Asn Arg Phe His Cys His Phe Ser Pro Arg Asp
145                 150                 155                 160

Trp Gln Arg Leu Ile Asn Asn Asn Trp Gly Phe Arg Pro Lys Arg Leu
                165                 170                 175

Asn Phe Lys Leu Phe Asn Ile Gln Val Lys Glu Val Thr Asp Asn Asn
            180                 185                 190

Gly Val Lys Thr Ile Ala Asn Asn Leu Thr Ser Thr Val Gln Val Phe
        195                 200                 205

Thr Asp Ser Asp Tyr Gln Leu Pro Tyr Val Leu Gly Ser Ala His Gln
    210                 215                 220

Gly Cys Leu Pro Pro Phe Pro Ala Asp Val Phe Met Ile Pro Gln Tyr
225                 230                 235                 240

Gly Tyr Leu Thr Leu Asn Asp Gly Ser Gln Ala Val Gly Arg Ser Ser
                245                 250                 255

Phe Tyr Cys Leu Glu Tyr Phe Pro Ser Gln Met Leu Arg Thr Gly Asn
            260                 265                 270

Asn Phe Thr Phe Ser Tyr Thr Phe Glu Asp Val Pro Phe His Ser Ser
        275                 280                 285

Tyr Ala His Ser Gln Ser Leu Asp Arg Leu Met Asn Pro Leu Ile Asp
    290                 295                 300

Gln Tyr Leu Tyr Tyr Leu Ser Lys Thr Ile Asn Gly Ser Gly Gln Asn
305                 310                 315                 320

Gln Gln Thr Leu Lys Phe Ser Gln Gly Gly Pro Asn Thr Met Ala Asn
                325                 330                 335

Gln Ala Lys Asn Trp Leu Pro Gly Pro Cys Tyr Arg Gln Gln Arg Val
            340                 345                 350

Ser Thr Thr Thr Gly Gln Asn Asn Asn Ser Asn Phe Ala Trp Thr Ala
        355                 360                 365

Gly Thr Lys Tyr His Leu Asn Gly Arg Asn Ser Leu Met Asn Pro Gly
    370                 375                 380

Pro Ala Met Ala Ser His Lys Glu Gly Glu Asp Arg Phe Phe Pro Leu
385                 390                 395                 400

Ser Gly Ser Leu Ile Phe Gly Lys Gln Asn Ala Ala Arg Asp Asn Ala
                405                 410                 415

Asp Tyr Ser Asp Val Met Leu Thr Ser Glu Glu Glu Ile Lys Thr Thr
            420                 425                 430

Asn Pro Val Ala Thr Glu Glu Tyr Gly Ile Val Ala Asp Asn Leu Gln
        435                 440                 445

Gln Gln Asn Thr Ala Pro Gln Ile Gly Thr Val Asn Ser Gln Gly Ala
    450                 455                 460

Leu Pro Gly Met Val Trp Gln Asn Arg Asp Val Tyr Leu Gln Gly Pro
465                 470                 475                 480

Ile Trp Ala Lys Ile Pro His Thr Asp Gly Asn Phe His Pro Ser Pro
                485                 490                 495
```

```
Leu Met Gly Gly Phe Gly Leu Lys His Pro Pro Pro Gln Ile Leu Ile
            500                 505                 510

Lys Asn Thr Pro Val Pro Ala Asp Pro Pro Thr Thr Phe Asn Gln Ser
        515                 520                 525

Lys Leu Asn Ser Phe Ile Thr Gln Tyr Ser Thr Gly Gln Val Ser Val
    530                 535                 540

Glu Ile Glu Trp Glu Leu Gln Lys Glu Asn Ser Lys Arg Trp Asn Pro
545                 550                 555                 560

Glu Ile Gln Tyr Thr Ser Asn Tyr Tyr Lys Ser Thr Ser Val Asp Phe
                565                 570                 575

Ala Val Asn Thr Glu Gly Val Tyr Ser Glu Pro His Pro Ile Gly Thr
            580                 585                 590

Arg Tyr Leu Thr Arg Pro Leu
        595


<210> SEQ ID NO 38
<211> LENGTH: 599
<212> TYPE: PRT
<213> ORGANISM: Artificial Sequence
<220> FEATURE:
<223> OTHER INFORMATION: AAV214e8 VP2

<400> SEQUENCE: 38

Met Ala Pro Gly Lys Lys Arg Pro Val Glu Pro Ser Pro Gln Arg Ser
1               5                   10                  15

Pro Asp Ser Ser Thr Gly Ile Gly Lys Lys Gly Gln Gln Pro Ala Arg
            20                  25                  30

Lys Arg Leu Asn Phe Gly Gln Thr Gly Asp Ser Glu Ser Val Pro Asp
        35                  40                  45

Pro Gln Pro Leu Gly Glu Pro Pro Ala Ala Pro Ser Gly Val Gly Pro
    50                  55                  60

Asn Thr Met Ala Ser Gly Gly Gly Ala Pro Met Ala Asp Asn Asn Glu
65                  70                  75                  80

Gly Ala Asp Gly Val Gly Asn Ala Ser Gly Asn Trp His Cys Asp Ser
                85                  90                  95

Thr Trp Leu Gly Asp Arg Val Ile Thr Thr Ser Thr Arg Thr Trp Ala
            100                 105                 110

Leu Pro Thr Tyr Asn Asn His Leu Tyr Lys Gln Ile Ser Ser Ala Ser
        115                 120                 125

Thr Gly Ala Ser Asn Asp Asn His Tyr Phe Gly Tyr Ser Thr Pro Trp
    130                 135                 140

Gly Tyr Phe Asp Phe Asn Arg Phe His Cys His Phe Ser Pro Arg Asp
145                 150                 155                 160

Trp Gln Arg Leu Ile Asn Asn Asn Trp Gly Phe Arg Pro Lys Arg Leu
                165                 170                 175

Asn Phe Lys Leu Phe Asn Ile Gln Val Lys Glu Val Thr Asp Asn Asn
            180                 185                 190

Gly Val Lys Thr Ile Ala Asn Asn Leu Thr Ser Thr Val Gln Val Phe
        195                 200                 205

Thr Asp Ser Asp Tyr Gln Leu Pro Tyr Val Leu Gly Ser Ala His Gln
    210                 215                 220

Gly Cys Leu Pro Pro Phe Pro Ala Asp Val Phe Met Ile Pro Gln Tyr
225                 230                 235                 240

Gly Tyr Leu Thr Leu Asn Asp Gly Ser Gln Ala Val Gly Arg Ser Ser
                245                 250                 255
```

Phe Tyr Cys Leu Glu Tyr Phe Pro Ser Gln Met Leu Arg Thr Gly Asn
260 265 270

Asn Phe Thr Phe Ser Tyr Thr Phe Glu Asp Val Pro Phe His Ser Ser
275 280 285

Tyr Ala His Ser Gln Ser Leu Asp Arg Leu Met Asn Pro Leu Ile Asp
290 295 300

Gln Tyr Leu Tyr Tyr Leu Ser Lys Thr Ile Asn Gly Ser Gly Gln Asn
305 310 315 320

Gln Gln Thr Leu Lys Phe Ser Gln Gly Gly Pro Asn Thr Met Ala Asn
325 330 335

Gln Ala Lys Asn Trp Leu Pro Gly Pro Cys Tyr Arg Gln Gln Arg Val
340 345 350

Ser Thr Thr Thr Gly Gln Asn Asn Asn Ser Asn Phe Ala Trp Thr Ala
355 360 365

Gly Thr Lys Tyr His Leu Asn Gly Arg Asn Ser Leu Met Asn Pro Gly
370 375 380

Pro Ala Met Ala Ser His Lys Glu Gly Glu Asp Arg Phe Phe Pro Leu
385 390 395 400

Ser Gly Ser Leu Ile Phe Gly Lys Gln Asn Ala Ala Arg Asp Asn Ala
405 410 415

Asp Tyr Ser Asp Val Met Leu Thr Ser Glu Glu Glu Ile Lys Thr Thr
420 425 430

Asn Pro Val Ala Thr Glu Glu Tyr Gly Ile Val Ala Asp Asn Leu Gln
435 440 445

Gln Gln Asn Thr Ala Pro Gln Ile Gly Thr Val Asn Ser Gln Gly Ala
450 455 460

Leu Pro Gly Met Val Trp Gln Asn Arg Asp Val Tyr Leu Gln Gly Pro
465 470 475 480

Ile Trp Ala Lys Ile Pro His Thr Asp Gly Asn Phe His Pro Ser Pro
485 490 495

Leu Met Gly Gly Phe Gly Leu Lys His Pro Pro Pro Gln Ile Leu Ile
500 505 510

Lys Asn Thr Pro Val Pro Ala Asp Pro Pro Thr Thr Phe Asn Gln Ser
515 520 525

Lys Leu Asn Ser Phe Ile Thr Gln Tyr Ser Thr Gly Gln Val Ser Val
530 535 540

Glu Ile Glu Trp Glu Leu Gln Lys Glu Asn Ser Lys Arg Trp Asn Pro
545 550 555 560

Glu Ile Gln Tyr Thr Ser Asn Tyr Tyr Lys Ser Thr Ser Val Asp Phe
565 570 575

Ala Val Asn Thr Glu Gly Val Tyr Ser Glu Pro His Pro Ile Gly Thr
580 585 590

Arg Tyr Leu Thr Arg Pro Leu
595

<210> SEQ ID NO 39
<211> LENGTH: 598
<212> TYPE: PRT
<213> ORGANISM: Artificial Sequence
<220> FEATURE:
<223> OTHER INFORMATION: AAV214e9 VP2

<400> SEQUENCE: 39

Met Ala Pro Gly Lys Lys Arg Pro Val Glu Gln Ser Pro Gln Glu Pro
1 5 10 15

```
Asp Ser Ser Ala Gly Ile Gly Lys Ser Gly Ala Gln Pro Ala Lys Lys
            20                  25                  30

Arg Leu Asn Phe Gly Gln Thr Gly Asp Thr Glu Ser Val Pro Asp Pro
        35                  40                  45

Gln Pro Ile Gly Glu Pro Pro Ala Ala Pro Ser Gly Val Gly Ser Leu
    50                  55                  60

Thr Met Ala Ser Gly Gly Gly Ala Pro Met Ala Asp Asn Asn Glu Gly
65                  70                  75                  80

Ala Asp Gly Val Gly Asn Ala Ser Gly Asn Trp His Cys Asp Ser Thr
                85                  90                  95

Trp Leu Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Ala Ser Thr
        115                 120                 125

Gly Ala Ser Asn Asp Asn His Tyr Phe Gly Tyr Ser Thr Pro Trp Gly
    130                 135                 140

Tyr Phe Asp Phe Asn Arg Phe His Cys His Phe Ser Pro Arg Asp Trp
145                 150                 155                 160

Gln Arg Leu Ile Asn Asn Asn Trp Gly Phe Arg Pro Lys Arg Leu Asn
                165                 170                 175

Phe Lys Leu Phe Asn Ile Gln Val Lys Glu Val Thr Asp Asn Asn Gly
            180                 185                 190

Val Lys Thr Ile Ala Asn Asn Leu Thr Ser Thr Val Gln Val Phe Thr
        195                 200                 205

Asp Ser Asp Tyr Gln Leu Pro Tyr Val Leu Gly Ser Ala His Gln Gly
    210                 215                 220

Cys Leu Pro Pro Phe Pro Ala Asp Val Phe Met Ile Pro Gln Tyr Gly
225                 230                 235                 240

Tyr Leu Thr Leu Asn Asp Gly Ser Gln Ala Val Gly Arg Ser Ser Phe
                245                 250                 255

Tyr Cys Leu Glu Tyr Phe Pro Ser Gln Met Leu Arg Thr Gly Asn Asn
            260                 265                 270

Phe Thr Phe Ser Tyr Thr Phe Glu Asp Val Pro Phe His Ser Ser Tyr
        275                 280                 285

Ala His Ser Gln Ser Leu Asp Arg Leu Met Asn Pro Leu Ile Asp Gln
    290                 295                 300

Tyr Leu Tyr Tyr Leu Ser Lys Thr Ile Asn Gly Ser Gly Gln Asn Gln
305                 310                 315                 320

Gln Thr Leu Lys Phe Ser Gln Gly Gly Pro Asn Thr Met Ala Asn Gln
                325                 330                 335

Ala Lys Asn Trp Leu Pro Gly Pro Cys Tyr Arg Gln Gln Arg Val Ser
            340                 345                 350

Thr Thr Thr Gly Gln Asn Asn Asn Ser Asn Phe Ala Trp Thr Ala Gly
        355                 360                 365

Thr Lys Tyr His Leu Asn Gly Arg Asn Ser Leu Met Asn Pro Gly Pro
    370                 375                 380

Ala Met Ala Ser His Lys Glu Gly Glu Asp Arg Phe Phe Pro Leu Ser
385                 390                 395                 400

Gly Ser Leu Ile Phe Gly Lys Gln Asn Ala Ala Arg Asp Asn Ala Asp
                405                 410                 415

Tyr Ser Asp Val Met Leu Thr Ser Glu Glu Glu Ile Lys Thr Thr Asn
            420                 425                 430
```

Pro Val Ala Thr Glu Glu Tyr Gly Ile Val Ala Asp Asn Leu Gln Gln
435 440 445

Gln Asn Thr Ala Pro Gln Ile Gly Thr Val Asn Ser Gln Gly Ala Leu
450 455 460

Pro Gly Met Val Trp Gln Asn Arg Asp Val Tyr Leu Gln Gly Pro Ile
465 470 475 480

Trp Ala Lys Ile Pro His Thr Asp Gly Asn Phe His Pro Ser Pro Leu
485 490 495

Met Gly Gly Phe Gly Leu Lys His Pro Pro Pro Gln Ile Leu Ile Lys
500 505 510

Asn Thr Pro Val Pro Ala Asp Pro Pro Thr Thr Phe Asn Gln Ser Lys
515 520 525

Leu Asn Ser Phe Ile Thr Gln Tyr Ser Thr Gly Gln Val Ser Val Glu
530 535 540

Ile Glu Trp Glu Leu Gln Lys Glu Asn Ser Lys Arg Trp Asn Pro Glu
545 550 555 560

Ile Gln Tyr Thr Ser Asn Tyr Tyr Lys Ser Thr Ser Val Asp Phe Ala
565 570 575

Val Asn Thr Glu Gly Val Tyr Ser Glu Pro His Pro Ile Gly Thr Arg
580 585 590

Tyr Leu Thr Arg Pro Leu
595

<210> SEQ ID NO 40
<211> LENGTH: 599
<212> TYPE: PRT
<213> ORGANISM: Artificial Sequence
<220> FEATURE:
<223> OTHER INFORMATION: AAV214e10 VP2

<400> SEQUENCE: 40

Met Ala Pro Gly Lys Lys Arg Pro Val Glu Pro Ser Pro Gln Arg Ser
1 5 10 15

Pro Asp Ser Ser Thr Gly Ile Gly Lys Lys Gly Gln Gln Pro Ala Lys
20 25 30

Lys Arg Leu Asn Phe Gly Gln Thr Gly Asp Ser Glu Ser Val Pro Asp
35 40 45

Pro Gln Pro Ile Gly Glu Pro Pro Ala Gly Pro Ser Gly Leu Gly Ser
50 55 60

Gly Thr Met Ala Ser Gly Gly Gly Ala Pro Met Ala Asp Asn Asn Glu
65 70 75 80

Gly Ala Asp Gly Val Gly Asn Ala Ser Gly Asn Trp His Cys Asp Ser
85 90 95

Thr Trp Leu Gly Asp Arg Val Ile Thr Thr Ser Thr Arg Thr Trp Ala
100 105 110

Leu Pro Thr Tyr Asn Asn His Leu Tyr Lys Gln Ile Ser Ser Ala Ser
115 120 125

Thr Gly Ala Ser Asn Asp Asn His Tyr Phe Gly Tyr Ser Thr Pro Trp
130 135 140

Gly Tyr Phe Asp Phe Asn Arg Phe His Cys His Phe Ser Pro Arg Asp
145 150 155 160

Trp Gln Arg Leu Ile Asn Asn Asn Trp Gly Phe Arg Pro Lys Arg Leu
165 170 175

Asn Phe Lys Leu Phe Asn Ile Gln Val Lys Glu Val Thr Asp Asn Asn
180 185 190

```
Gly Val Lys Thr Ile Ala Asn Asn Leu Thr Ser Thr Val Gln Val Phe
        195                 200                 205

Thr Asp Ser Asp Tyr Gln Leu Pro Tyr Val Leu Gly Ser Ala His Gln
    210                 215                 220

Gly Cys Leu Pro Pro Phe Pro Ala Asp Val Phe Met Ile Pro Gln Tyr
225                 230                 235                 240

Gly Tyr Leu Thr Leu Asn Asp Gly Ser Gln Ala Val Gly Arg Ser Ser
                245                 250                 255

Phe Tyr Cys Leu Glu Tyr Phe Pro Ser Gln Met Leu Arg Thr Gly Asn
            260                 265                 270

Asn Phe Thr Phe Ser Tyr Thr Phe Glu Asp Val Pro Phe His Ser Ser
        275                 280                 285

Tyr Ala His Ser Gln Ser Leu Asp Arg Leu Met Asn Pro Leu Ile Asp
    290                 295                 300

Gln Tyr Leu Tyr Tyr Leu Ser Lys Thr Ile Asn Gly Ser Gly Gln Asn
305                 310                 315                 320

Gln Gln Thr Leu Lys Phe Ser Gln Gly Gly Pro Asn Thr Met Ala Asn
                325                 330                 335

Gln Ala Lys Asn Trp Leu Pro Gly Pro Cys Tyr Arg Gln Gln Arg Val
            340                 345                 350

Ser Thr Thr Thr Gly Gln Asn Asn Asn Ser Asn Phe Ala Trp Thr Ala
        355                 360                 365

Gly Thr Lys Tyr His Leu Asn Gly Arg Asn Ser Leu Met Asn Pro Gly
    370                 375                 380

Pro Ala Met Ala Ser His Lys Glu Gly Glu Asp Arg Phe Phe Pro Leu
385                 390                 395                 400

Ser Gly Ser Leu Ile Phe Gly Lys Gln Asn Ala Ala Arg Asp Asn Ala
                405                 410                 415

Asp Tyr Ser Asp Val Met Leu Thr Ser Glu Glu Glu Ile Lys Thr Thr
            420                 425                 430

Asn Pro Val Ala Thr Glu Glu Tyr Gly Ile Val Ala Asp Asn Leu Gln
        435                 440                 445

Gln Gln Asn Thr Ala Pro Gln Ile Gly Thr Val Asn Ser Gln Gly Ala
    450                 455                 460

Leu Pro Gly Met Val Trp Gln Asn Arg Asp Val Tyr Leu Gln Gly Pro
465                 470                 475                 480

Ile Trp Ala Lys Ile Pro His Thr Asp Gly Asn Phe His Pro Ser Pro
                485                 490                 495

Leu Met Gly Gly Phe Gly Leu Lys His Pro Pro Pro Gln Ile Leu Ile
            500                 505                 510

Lys Asn Thr Pro Val Pro Ala Asp Pro Pro Thr Thr Phe Asn Gln Ser
        515                 520                 525

Lys Leu Asn Ser Phe Ile Thr Gln Tyr Ser Thr Gly Gln Val Ser Val
    530                 535                 540

Glu Ile Glu Trp Glu Leu Gln Lys Glu Asn Ser Lys Arg Trp Asn Pro
545                 550                 555                 560

Glu Ile Gln Tyr Thr Ser Asn Tyr Tyr Lys Ser Thr Ser Val Asp Phe
                565                 570                 575

Ala Val Asn Thr Glu Gly Val Tyr Ser Glu Pro His Pro Ile Gly Thr
            580                 585                 590

Arg Tyr Leu Thr Arg Pro Leu
        595
```

<210> SEQ ID NO 41
<211> LENGTH: 533
<212> TYPE: PRT
<213> ORGANISM: Artificial Sequence
<220> FEATURE:
<223> OTHER INFORMATION: AAV214 VP3

<400> SEQUENCE: 41

```
Met Ala Ser Gly Gly Gly Ala Pro Met Ala Asp Asn Asn Glu Gly Ala
1               5                   10                  15

Asp Gly Val Gly Asn Ala Ser Gly Asn Trp His Cys Asp Ser Thr Trp
            20                  25                  30

Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Ala Ser Thr Gly
    50                  55                  60

Ala Ser Asn Asp Asn His Tyr Phe Gly Tyr Ser Thr Pro Trp Gly Tyr
65                  70                  75                  80

Phe Asp Phe Asn Arg Phe His Cys His Phe Ser Pro Arg Asp Trp Gln
                85                  90                  95

Arg Leu Ile Asn Asn Asn Trp Gly Phe Arg Pro Lys Arg Leu Asn Phe
            100                 105                 110

Lys Leu Phe Asn Ile Gln Val Lys Glu Val Thr Asp Asn Asn Gly Val
        115                 120                 125

Lys Thr Ile Ala Asn Asn Leu Thr Ser Thr Val Gln Val Phe Thr Asp
    130                 135                 140

Ser Asp Tyr Gln Leu Pro Tyr Val Leu Gly Ser Ala His Gln Gly Cys
145                 150                 155                 160

Leu Pro Pro Phe Pro Ala Asp Val Phe Met Ile Pro Gln Tyr Gly Tyr
                165                 170                 175

Leu Thr Leu Asn Asp Gly Ser Gln Ala Val Gly Arg Ser Ser Phe Tyr
            180                 185                 190

Cys Leu Glu Tyr Phe Pro Ser Gln Met Leu Arg Thr Gly Asn Asn Phe
        195                 200                 205

Thr Phe Ser Tyr Thr Phe Glu Asp Val Pro Phe His Ser Ser Tyr Ala
    210                 215                 220

His Ser Gln Ser Leu Asp Arg Leu Met Asn Pro Leu Ile Asp Gln Tyr
225                 230                 235                 240

Leu Tyr Tyr Leu Ser Lys Thr Ile Asn Gly Ser Gly Gln Asn Gln Gln
                245                 250                 255

Thr Leu Lys Phe Ser Gln Gly Gly Pro Asn Thr Met Ala Asn Gln Ala
            260                 265                 270

Lys Asn Trp Leu Pro Gly Pro Cys Tyr Arg Gln Gln Arg Val Ser Thr
        275                 280                 285

Thr Thr Gly Gln Asn Asn Asn Ser Asn Phe Ala Trp Thr Ala Gly Thr
    290                 295                 300

Lys Tyr His Leu Asn Gly Arg Asn Ser Leu Met Asn Pro Gly Pro Ala
305                 310                 315                 320

Met Ala Ser His Lys Glu Gly Glu Asp Arg Phe Phe Pro Leu Ser Gly
                325                 330                 335

Ser Leu Ile Phe Gly Lys Gln Asn Ala Ala Arg Asp Asn Ala Asp Tyr
            340                 345                 350

Ser Asp Val Met Leu Thr Ser Glu Glu Glu Ile Lys Thr Thr Asn Pro
        355                 360                 365

Val Ala Thr Glu Glu Tyr Gly Ile Val Ala Asp Asn Leu Gln Gln Gln
```

```
    370                 375                 380

Asn Thr Ala Pro Gln Ile Gly Thr Val Asn Ser Gln Gly Ala Leu Pro
385                 390                 395                 400

Gly Met Val Trp Gln Asn Arg Asp Val Tyr Leu Gln Gly Pro Ile Trp
                405                 410                 415

Ala Lys Ile Pro His Thr Asp Gly Asn Phe His Pro Ser Pro Leu Met
            420                 425                 430

Gly Gly Phe Gly Leu Lys His Pro Pro Pro Gln Ile Leu Ile Lys Asn
        435                 440                 445

Thr Pro Val Pro Ala Asp Pro Pro Thr Thr Phe Asn Gln Ser Lys Leu
    450                 455                 460

Asn Ser Phe Ile Thr Gln Tyr Ser Thr Gly Gln Val Ser Val Glu Ile
465                 470                 475                 480

Glu Trp Glu Leu Gln Lys Glu Asn Ser Lys Arg Trp Asn Pro Glu Ile
                485                 490                 495

Gln Tyr Thr Ser Asn Tyr Tyr Lys Ser Thr Ser Val Asp Phe Ala Val
            500                 505                 510

Asn Thr Glu Gly Val Tyr Ser Glu Pro His Pro Ile Gly Thr Arg Tyr
        515                 520                 525

Leu Thr Arg Pro Leu
    530


<210> SEQ ID NO 42
<211> LENGTH: 534
<212> TYPE: PRT
<213> ORGANISM: Artificial Sequence
<220> FEATURE:
<223> OTHER INFORMATION: AAV214A VP3

<400> SEQUENCE: 42

Met Ala Ser Gly Gly Gly Ala Pro Met Ala Asp Asn Asn Glu Gly Ala
1               5                   10                  15

Asp Gly Val Gly Asn Ala Ser Gly Asn Trp His Cys Asp Ser Thr Trp
            20                  25                  30

Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Asn Ser Thr Ser Gly
    50                  55                  60

Gly Ser Ser Asn Asp Asn Ala Tyr Phe Gly Tyr Ser Thr Pro Trp Gly
65                  70                  75                  80

Tyr Phe Asp Phe Asn Arg Phe His Cys His Phe Ser Pro Arg Asp Trp
                85                  90                  95

Gln Arg Leu Ile Asn Asn Asn Trp Gly Phe Arg Pro Lys Arg Leu Asn
            100                 105                 110

Phe Lys Leu Phe Asn Ile Gln Val Lys Glu Val Thr Asp Asn Asn Gly
        115                 120                 125

Val Lys Thr Ile Ala Asn Asn Leu Thr Ser Thr Val Gln Val Phe Thr
    130                 135                 140

Asp Ser Asp Tyr Gln Leu Pro Tyr Val Leu Gly Ser Ala His Gln Gly
145                 150                 155                 160

Cys Leu Pro Pro Phe Pro Ala Asp Val Phe Met Ile Pro Gln Tyr Gly
                165                 170                 175

Tyr Leu Thr Leu Asn Asp Gly Ser Gln Ala Val Gly Arg Ser Ser Phe
            180                 185                 190

Tyr Cys Leu Glu Tyr Phe Pro Ser Gln Met Leu Arg Thr Gly Asn Asn
```

```
        195                 200                 205

Phe Thr Phe Ser Tyr Thr Phe Glu Asp Val Pro Phe His Ser Ser Tyr
    210                 215                 220

Ala His Ser Gln Ser Leu Asp Arg Leu Met Asn Pro Leu Ile Asp Gln
225                 230                 235                 240

Tyr Leu Tyr Tyr Leu Ser Lys Thr Ile Asn Gly Ser Gly Gln Asn Gln
                245                 250                 255

Gln Thr Leu Lys Phe Ser Gln Gly Gly Pro Asn Thr Met Ala Asn Gln
            260                 265                 270

Ala Lys Asn Trp Leu Pro Gly Pro Cys Tyr Arg Gln Gln Arg Val Ser
        275                 280                 285

Thr Thr Thr Gly Gln Asn Asn Asn Ser Asn Phe Ala Trp Thr Ala Gly
    290                 295                 300

Thr Lys Tyr His Leu Asn Gly Arg Asn Ser Leu Met Asn Pro Gly Pro
305                 310                 315                 320

Ala Met Ala Ser His Lys Glu Gly Glu Asp Arg Phe Phe Pro Leu Ser
                325                 330                 335

Gly Ser Leu Ile Phe Gly Lys Gln Asn Ala Ala Arg Asp Asn Ala Asp
            340                 345                 350

Tyr Ser Asp Val Met Leu Thr Ser Glu Glu Glu Ile Lys Thr Thr Asn
        355                 360                 365

Pro Val Ala Thr Glu Glu Tyr Gly Ile Val Ala Asp Asn Leu Gln Gln
    370                 375                 380

Gln Asn Thr Ala Pro Gln Ile Gly Thr Val Asn Ser Gln Gly Ala Leu
385                 390                 395                 400

Pro Gly Met Val Trp Gln Asn Arg Asp Val Tyr Leu Gln Gly Pro Ile
                405                 410                 415

Trp Ala Lys Ile Pro His Thr Asp Gly Asn Phe His Pro Ser Pro Leu
            420                 425                 430

Met Gly Gly Phe Gly Leu Lys His Pro Pro Pro Gln Ile Leu Ile Lys
        435                 440                 445

Asn Thr Pro Val Pro Ala Asp Pro Pro Thr Thr Phe Asn Gln Ser Lys
    450                 455                 460

Leu Asn Ser Phe Ile Thr Gln Tyr Ser Thr Gly Gln Val Ser Val Glu
465                 470                 475                 480

Ile Glu Trp Glu Leu Gln Lys Glu Asn Ser Lys Arg Trp Asn Pro Glu
                485                 490                 495

Ile Gln Tyr Thr Ser Asn Tyr Tyr Lys Ser Thr Ser Val Asp Phe Ala
            500                 505                 510

Val Asn Thr Glu Gly Val Tyr Ser Glu Pro His Pro Ile Gly Thr Arg
        515                 520                 525

Tyr Leu Thr Arg Pro Leu
    530


<210> SEQ ID NO 43
<211> LENGTH: 533
<212> TYPE: PRT
<213> ORGANISM: Artificial Sequence
<220> FEATURE:
<223> OTHER INFORMATION: AAV214E VP3

<400> SEQUENCE: 43

Met Ala Ser Gly Gly Gly Ala Pro Met Ala Asp Asn Asn Glu Gly Ala
1               5                   10                  15

Asp Gly Val Gly Asn Ala Ser Gly Asn Trp His Cys Asp Ser Thr Trp
```

-continued

```
            20                  25                  30

Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Ala Ser Thr Gly
    50                  55                  60

Ala Ser Asn Asp Asn His Tyr Phe Gly Tyr Ser Thr Pro Trp Gly Tyr
65                  70                  75                  80

Phe Asp Phe Asn Arg Phe His Cys His Phe Ser Pro Arg Asp Trp Gln
                85                  90                  95

Arg Leu Ile Asn Asn Asn Trp Gly Phe Arg Pro Lys Arg Leu Asn Phe
            100                 105                 110

Lys Leu Phe Asn Ile Gln Val Lys Glu Val Thr Asp Asn Asn Gly Val
        115                 120                 125

Lys Thr Ile Ala Asn Asn Leu Thr Ser Thr Val Gln Val Phe Thr Asp
    130                 135                 140

Ser Asp Tyr Gln Leu Pro Tyr Val Leu Gly Ser Ala His Gln Gly Cys
145                 150                 155                 160

Leu Pro Pro Phe Pro Ala Asp Val Phe Met Ile Pro Gln Tyr Gly Tyr
                165                 170                 175

Leu Thr Leu Asn Asp Gly Ser Gln Ala Val Gly Arg Ser Ser Phe Tyr
            180                 185                 190

Cys Leu Glu Tyr Phe Pro Ser Gln Met Leu Arg Thr Gly Asn Asn Phe
        195                 200                 205

Thr Phe Ser Tyr Thr Phe Glu Asp Val Pro Phe His Ser Ser Tyr Ala
    210                 215                 220

His Ser Gln Ser Leu Asp Arg Leu Met Asn Pro Leu Ile Asp Gln Tyr
225                 230                 235                 240

Leu Tyr Tyr Leu Ser Lys Thr Ile Asn Gly Ser Gly Gln Asn Gln Gln
                245                 250                 255

Thr Leu Lys Phe Ser Gln Gly Gly Pro Asn Thr Met Ala Asn Gln Ala
            260                 265                 270

Lys Asn Trp Leu Pro Gly Pro Cys Tyr Arg Gln Gln Arg Val Ser Thr
        275                 280                 285

Thr Thr Gly Gln Asn Asn Asn Ser Asn Phe Ala Trp Thr Ala Gly Thr
    290                 295                 300

Lys Tyr His Leu Asn Gly Arg Asn Ser Leu Met Asn Pro Gly Pro Ala
305                 310                 315                 320

Met Ala Ser His Lys Glu Gly Glu Asp Arg Phe Phe Pro Leu Ser Gly
                325                 330                 335

Ser Leu Ile Phe Gly Lys Gln Asn Ala Ala Arg Asp Asn Ala Asp Tyr
            340                 345                 350

Ser Asp Val Met Leu Thr Ser Glu Glu Glu Ile Lys Thr Thr Asn Pro
        355                 360                 365

Val Ala Thr Glu Glu Tyr Gly Ile Val Ala Asp Asn Leu Gln Gln Gln
    370                 375                 380

Asn Thr Ala Pro Gln Ile Gly Thr Val Asn Ser Gln Gly Ala Leu Pro
385                 390                 395                 400

Gly Met Val Trp Gln Asn Arg Asp Val Tyr Leu Gln Gly Pro Ile Trp
                405                 410                 415

Ala Lys Ile Pro His Thr Asp Gly Asn Phe His Pro Ser Pro Leu Met
            420                 425                 430

Gly Gly Phe Gly Leu Lys His Pro Pro Pro Gln Ile Leu Ile Lys Asn
        435                 440                 445
```

Thr Pro Val Pro Ala Asp Pro Pro Thr Thr Phe Asn Gln Ser Lys Leu
    450                 455                 460

Asn Ser Phe Ile Thr Gln Tyr Ser Thr Gly Gln Val Ser Val Glu Ile
465                 470                 475                 480

Glu Trp Glu Leu Gln Lys Glu Asn Ser Lys Arg Trp Asn Pro Glu Ile
                485                 490                 495

Gln Tyr Thr Ser Asn Tyr Tyr Lys Ser Thr Ser Val Asp Phe Ala Val
            500                 505                 510

Asn Thr Glu Gly Val Tyr Ser Glu Pro His Pro Ile Gly Thr Arg Tyr
        515                 520                 525

Leu Thr Arg Pro Leu
    530

<210> SEQ ID NO 44
<211> LENGTH: 533
<212> TYPE: PRT
<213> ORGANISM: Artificial Sequence
<220> FEATURE:
<223> OTHER INFORMATION: AAV214E8 VP3

<400> SEQUENCE: 44

Met Ala Ser Gly Gly Gly Ala Pro Met Ala Asp Asn Asn Glu Gly Ala
1               5                   10                  15

Asp Gly Val Gly Asn Ala Ser Gly Asn Trp His Cys Asp Ser Thr Trp
            20                  25                  30

Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Ala Ser Thr Gly
    50                  55                  60

Ala Ser Asn Asp Asn His Tyr Phe Gly Tyr Ser Thr Pro Trp Gly Tyr
65                  70                  75                  80

Phe Asp Phe Asn Arg Phe His Cys His Phe Ser Pro Arg Asp Trp Gln
                85                  90                  95

Arg Leu Ile Asn Asn Asn Trp Gly Phe Arg Pro Lys Arg Leu Asn Phe
            100                 105                 110

Lys Leu Phe Asn Ile Gln Val Lys Glu Val Thr Asp Asn Asn Gly Val
        115                 120                 125

Lys Thr Ile Ala Asn Asn Leu Thr Ser Thr Val Gln Val Phe Thr Asp
    130                 135                 140

Ser Asp Tyr Gln Leu Pro Tyr Val Leu Gly Ser Ala His Gln Gly Cys
145                 150                 155                 160

Leu Pro Pro Phe Pro Ala Asp Val Phe Met Ile Pro Gln Tyr Gly Tyr
                165                 170                 175

Leu Thr Leu Asn Asp Gly Ser Gln Ala Val Gly Arg Ser Ser Phe Tyr
            180                 185                 190

Cys Leu Glu Tyr Phe Pro Ser Gln Met Leu Arg Thr Gly Asn Asn Phe
        195                 200                 205

Thr Phe Ser Tyr Thr Phe Glu Asp Val Pro Phe His Ser Ser Tyr Ala
    210                 215                 220

His Ser Gln Ser Leu Asp Arg Leu Met Asn Pro Leu Ile Asp Gln Tyr
225                 230                 235                 240

Leu Tyr Tyr Leu Ser Lys Thr Ile Asn Gly Ser Gly Gln Asn Gln Gln
                245                 250                 255

Thr Leu Lys Phe Ser Gln Gly Gly Pro Asn Thr Met Ala Asn Gln Ala
            260                 265                 270

Lys Asn Trp Leu Pro Gly Pro Cys Tyr Arg Gln Gln Arg Val Ser Thr
275 280 285

Thr Thr Gly Gln Asn Asn Asn Ser Asn Phe Ala Trp Thr Ala Gly Thr
290 295 300

Lys Tyr His Leu Asn Gly Arg Asn Ser Leu Met Asn Pro Gly Pro Ala
305 310 315 320

Met Ala Ser His Lys Glu Gly Glu Asp Arg Phe Phe Pro Leu Ser Gly
325 330 335

Ser Leu Ile Phe Gly Lys Gln Asn Ala Ala Arg Asp Asn Ala Asp Tyr
340 345 350

Ser Asp Val Met Leu Thr Ser Glu Glu Glu Ile Lys Thr Thr Asn Pro
355 360 365

Val Ala Thr Glu Glu Tyr Gly Ile Val Ala Asp Asn Leu Gln Gln Gln
370 375 380

Asn Thr Ala Pro Gln Ile Gly Thr Val Asn Ser Gln Gly Ala Leu Pro
385 390 395 400

Gly Met Val Trp Gln Asn Arg Asp Val Tyr Leu Gln Gly Pro Ile Trp
405 410 415

Ala Lys Ile Pro His Thr Asp Gly Asn Phe His Pro Ser Pro Leu Met
420 425 430

Gly Gly Phe Gly Leu Lys His Pro Pro Pro Gln Ile Leu Ile Lys Asn
435 440 445

Thr Pro Val Pro Ala Asp Pro Pro Thr Thr Phe Asn Gln Ser Lys Leu
450 455 460

Asn Ser Phe Ile Thr Gln Tyr Ser Thr Gly Gln Val Ser Val Glu Ile
465 470 475 480

Glu Trp Glu Leu Gln Lys Glu Asn Ser Lys Arg Trp Asn Pro Glu Ile
485 490 495

Gln Tyr Thr Ser Asn Tyr Tyr Lys Ser Thr Ser Val Asp Phe Ala Val
500 505 510

Asn Thr Glu Gly Val Tyr Ser Glu Pro His Pro Ile Gly Thr Arg Tyr
515 520 525

Leu Thr Arg Pro Leu
530

<210> SEQ ID NO 45
<211> LENGTH: 533
<212> TYPE: PRT
<213> ORGANISM: Artificial Sequence
<220> FEATURE:
<223> OTHER INFORMATION: AAV214E9 VP3

<400> SEQUENCE: 45

Met Ala Ser Gly Gly Gly Ala Pro Met Ala Asp Asn Asn Glu Gly Ala
1 5 10 15

Asp Gly Val Gly Asn Ala Ser Gly Asn Trp His Cys Asp Ser Thr Trp
20 25 30

Leu Gly Asp Arg Val Ile Thr Thr Ser Thr Arg Thr Trp Ala Leu Pro
35 40 45

Thr Tyr Asn Asn His Leu Tyr Lys Gln Ile Ser Ser Ala Ser Thr Gly
50 55 60

Ala Ser Asn Asp Asn His Tyr Phe Gly Tyr Ser Thr Pro Trp Gly Tyr
65 70 75 80

Phe Asp Phe Asn Arg Phe His Cys His Phe Ser Pro Arg Asp Trp Gln
85 90 95

```
Arg Leu Ile Asn Asn Asn Trp Gly Phe Arg Pro Lys Arg Leu Asn Phe
            100                 105                 110

Lys Leu Phe Asn Ile Gln Val Lys Glu Val Thr Asp Asn Asn Gly Val
        115                 120                 125

Lys Thr Ile Ala Asn Asn Leu Thr Ser Thr Val Gln Val Phe Thr Asp
    130                 135                 140

Ser Asp Tyr Gln Leu Pro Tyr Val Leu Gly Ser Ala His Gln Gly Cys
145                 150                 155                 160

Leu Pro Pro Phe Pro Ala Asp Val Phe Met Ile Pro Gln Tyr Gly Tyr
                165                 170                 175

Leu Thr Leu Asn Asp Gly Ser Gln Ala Val Gly Arg Ser Ser Phe Tyr
            180                 185                 190

Cys Leu Glu Tyr Phe Pro Ser Gln Met Leu Arg Thr Gly Asn Asn Phe
        195                 200                 205

Thr Phe Ser Tyr Thr Phe Glu Asp Val Pro Phe His Ser Ser Tyr Ala
    210                 215                 220

His Ser Gln Ser Leu Asp Arg Leu Met Asn Pro Leu Ile Asp Gln Tyr
225                 230                 235                 240

Leu Tyr Tyr Leu Ser Lys Thr Ile Asn Gly Ser Gly Gln Asn Gln Gln
                245                 250                 255

Thr Leu Lys Phe Ser Gln Gly Gly Pro Asn Thr Met Ala Asn Gln Ala
            260                 265                 270

Lys Asn Trp Leu Pro Gly Pro Cys Tyr Arg Gln Gln Arg Val Ser Thr
        275                 280                 285

Thr Thr Gly Gln Asn Asn Asn Ser Asn Phe Ala Trp Thr Ala Gly Thr
    290                 295                 300

Lys Tyr His Leu Asn Gly Arg Asn Ser Leu Met Asn Pro Gly Pro Ala
305                 310                 315                 320

Met Ala Ser His Lys Glu Gly Glu Asp Arg Phe Phe Pro Leu Ser Gly
                325                 330                 335

Ser Leu Ile Phe Gly Lys Gln Asn Ala Ala Arg Asp Asn Ala Asp Tyr
            340                 345                 350

Ser Asp Val Met Leu Thr Ser Glu Glu Glu Ile Lys Thr Thr Asn Pro
        355                 360                 365

Val Ala Thr Glu Glu Tyr Gly Ile Val Ala Asp Asn Leu Gln Gln Gln
    370                 375                 380

Asn Thr Ala Pro Gln Ile Gly Thr Val Asn Ser Gln Gly Ala Leu Pro
385                 390                 395                 400

Gly Met Val Trp Gln Asn Arg Asp Val Tyr Leu Gln Gly Pro Ile Trp
                405                 410                 415

Ala Lys Ile Pro His Thr Asp Gly Asn Phe His Pro Ser Pro Leu Met
            420                 425                 430

Gly Gly Phe Gly Leu Lys His Pro Pro Pro Gln Ile Leu Ile Lys Asn
        435                 440                 445

Thr Pro Val Pro Ala Asp Pro Pro Thr Thr Phe Asn Gln Ser Lys Leu
    450                 455                 460

Asn Ser Phe Ile Thr Gln Tyr Ser Thr Gly Gln Val Ser Val Glu Ile
465                 470                 475                 480

Glu Trp Glu Leu Gln Lys Glu Asn Ser Lys Arg Trp Asn Pro Glu Ile
                485                 490                 495

Gln Tyr Thr Ser Asn Tyr Tyr Lys Ser Thr Ser Val Asp Phe Ala Val
            500                 505                 510
```

Asn Thr Glu Gly Val Tyr Ser Glu Pro His Pro Ile Gly Thr Arg Tyr
515 520 525

Leu Thr Arg Pro Leu
530

<210> SEQ ID NO 46
<211> LENGTH: 533
<212> TYPE: PRT
<213> ORGANISM: Artificial Sequence
<220> FEATURE:
<223> OTHER INFORMATION: AAV214E10 VP3

<400> SEQUENCE: 46

Met Ala Ser Gly Gly Gly Ala Pro Met Ala Asp Asn Asn Glu Gly Ala
1 5 10 15

Asp Gly Val Gly Asn Ala Ser Gly Asn Trp His Cys Asp Ser Thr Trp
20 25 30

Leu Gly Asp Arg Val Ile Thr Thr Ser Thr Arg Thr Trp Ala Leu Pro
35 40 45

Thr Tyr Asn Asn His Leu Tyr Lys Gln Ile Ser Ser Ala Ser Thr Gly
50 55 60

Ala Ser Asn Asp Asn His Tyr Phe Gly Tyr Ser Thr Pro Trp Gly Tyr
65 70 75 80

Phe Asp Phe Asn Arg Phe His Cys His Phe Ser Pro Arg Asp Trp Gln
85 90 95

Arg Leu Ile Asn Asn Asn Trp Gly Phe Arg Pro Lys Arg Leu Asn Phe
100 105 110

Lys Leu Phe Asn Ile Gln Val Lys Glu Val Thr Asp Asn Asn Gly Val
115 120 125

Lys Thr Ile Ala Asn Asn Leu Thr Ser Thr Val Gln Val Phe Thr Asp
130 135 140

Ser Asp Tyr Gln Leu Pro Tyr Val Leu Gly Ser Ala His Gln Gly Cys
145 150 155 160

Leu Pro Pro Phe Pro Ala Asp Val Phe Met Ile Pro Gln Tyr Gly Tyr
165 170 175

Leu Thr Leu Asn Asp Gly Ser Gln Ala Val Gly Arg Ser Ser Phe Tyr
180 185 190

Cys Leu Glu Tyr Phe Pro Ser Gln Met Leu Arg Thr Gly Asn Asn Phe
195 200 205

Thr Phe Ser Tyr Thr Phe Glu Asp Val Pro Phe His Ser Ser Tyr Ala
210 215 220

His Ser Gln Ser Leu Asp Arg Leu Met Asn Pro Leu Ile Asp Gln Tyr
225 230 235 240

Leu Tyr Tyr Leu Ser Lys Thr Ile Asn Gly Ser Gly Gln Asn Gln Gln
245 250 255

Thr Leu Lys Phe Ser Gln Gly Gly Pro Asn Thr Met Ala Asn Gln Ala
260 265 270

Lys Asn Trp Leu Pro Gly Pro Cys Tyr Arg Gln Gln Arg Val Ser Thr
275 280 285

Thr Thr Gly Gln Asn Asn Asn Ser Asn Phe Ala Trp Thr Ala Gly Thr
290 295 300

Lys Tyr His Leu Asn Gly Arg Asn Ser Leu Met Asn Pro Gly Pro Ala
305 310 315 320

Met Ala Ser His Lys Glu Gly Glu Asp Arg Phe Phe Pro Leu Ser Gly
325 330 335

```
Ser Leu Ile Phe Gly Lys Gln Asn Ala Ala Arg Asp Asn Ala Asp Tyr
            340                 345                 350

Ser Asp Val Met Leu Thr Ser Glu Glu Glu Ile Lys Thr Thr Asn Pro
        355                 360                 365

Val Ala Thr Glu Glu Tyr Gly Ile Val Ala Asp Asn Leu Gln Gln Gln
    370                 375                 380

Asn Thr Ala Pro Gln Ile Gly Thr Val Asn Ser Gln Gly Ala Leu Pro
385                 390                 395                 400

Gly Met Val Trp Gln Asn Arg Asp Val Tyr Leu Gln Gly Pro Ile Trp
                405                 410                 415

Ala Lys Ile Pro His Thr Asp Gly Asn Phe His Pro Ser Pro Leu Met
            420                 425                 430

Gly Gly Phe Gly Leu Lys His Pro Pro Pro Gln Ile Leu Ile Lys Asn
        435                 440                 445

Thr Pro Val Pro Ala Asp Pro Pro Thr Thr Phe Asn Gln Ser Lys Leu
    450                 455                 460

Asn Ser Phe Ile Thr Gln Tyr Ser Thr Gly Gln Val Ser Val Glu Ile
465                 470                 475                 480

Glu Trp Glu Leu Gln Lys Glu Asn Ser Lys Arg Trp Asn Pro Glu Ile
                485                 490                 495

Gln Tyr Thr Ser Asn Tyr Tyr Lys Ser Thr Ser Val Asp Phe Ala Val
            500                 505                 510

Asn Thr Glu Gly Val Tyr Ser Glu Pro His Pro Ile Gly Thr Arg Tyr
        515                 520                 525

Leu Thr Arg Pro Leu
    530


<210> SEQ ID NO 47
<211> LENGTH: 2211
<212> TYPE: DNA
<213> ORGANISM: Artificial Sequence
<220> FEATURE:
<223> OTHER INFORMATION: ITB102 45 VP1

<400> SEQUENCE: 47

atggctgccg atggttatct tccagattgg ctcgaggaca acctctctga gggcattcgc      60

gagtggtggg cgctgaaacc tggagccccg aagcccaaag ccaaccagca aaagcaggac     120

gacggccggg gtctggtgct tcctggctac aagtacctcg gacccttcaa cggactcgac     180

aagggggagc ccgtcaacgc ggcggacgca gcggccctcg agcacgacaa ggcctacgac     240

cagcagctca aagcgggtga caatccgtac ctgcggtata accacgccga cgccgagttt     300

caggagcgtc tgcaagaaga tacgtctttt gggggcaacc tcgggcgagc agtcttccag     360

gccaagaagc gggttctcga acctttttggt ctggttgagg aaggtgctaa gacggctcct     420

ggaaagaaac gtccggtaga gcagtcgcca caagagccag actcctcctc gggcatcggc     480

aagacaggcc agcagcccgc taaaaagaga ctcaattttg gtcagactgg cgactcagag     540

tcagtccccg acccacaacc tctcggagaa cctccagcaa cccccgctgc tgtgggacct     600

actacaatgg cttcaggcgg tggcgcacca atggcggaca ataacgaagg cgccgacgga     660

gtgggtaatg cctcaggaaa ttggcattgc gattccacat ggctgggcga cagagtcatc     720

accaccagca cccgcacctg ggccttgccc acctacaata accacctcta caagcaaatc     780

tccagtgctt caacgggggc cagcaacgac aaccactact tcggctacag caccccctgg     840

gggtattttg acttcaacag attccactgc cacttttcac cacgtgactg gcaaagactc     900
```

```
atcaacaaca actggggatt ccgacccaag agactcaact tcaagctctt taacattcaa    960

gtcaaagagg ttacggacaa caatggagtc aagaccatcg ccaataacct taccagcacg   1020

gtccaggtct tcacggactc agactatcag ctcccgtacg tgctcgggtc ggctcacgag   1080

ggctgcctcc cgccgttccc agcggacgtt ttcatgattc ctcagtacgg ctacctaacg   1140

ctcaacaatg gcagccaggc agtgggacgg tcatcctttt actgcctgga atatttccca   1200

tcgcagatgc tgagaacggg caacaacttt accttcagct acacctttga ggacgttcct   1260

ttccacagca gctacgctca cagccagagt ctggaccggc tgatgaatcc tctgattgac   1320

cagtacctgt actacttgtc tcggactcaa acaacaggag gcacggcaaa tacgcagact   1380

ctgggcttca gccaaggtgg gcctaataca atggccaatc aggcaaagaa ctggctgcca   1440

ggaccctgtt accgccaaca acgcgtctca acgacaaccg ggcaaaacaa caatagcaac   1500

tttgcctgga ctgctgggac caaataccat ctgaatggaa gaaattcatt gatgaatcct   1560

ggccccgcta tggcatccca caaagagggc gaggaccgtt tttttcccct gtccgggtcc   1620

ctgatttttg gcaaacaagg cactggcaga gacaatgtgg atgccgacaa agtcatgatc   1680

accaacgagg aagaaatcaa aaccactaac cctgtggcta cagaggaata cggtatcgtg   1740

gcagataact tgcagcagca aaacacggct cctcaaattg gaactgtcaa cagccagggg   1800

gccttacccg gtatggtctg gcagaaccgg gacgtgtacc tgcagggtcc catctgggcc   1860

aagattcctc acacggacgg caacttccac ccgtctccgc tgatgggcgg ctttggcctg   1920

aaacatcctc cgcctcagat cctgatcaag aacacgcctg tacctgcgga tcctccgacc   1980

accttcaacc agtcaaagct gaactctttc atcacgcaat acagcaccgg acaggtcagc   2040

gtggaaattg aatgggagct gcagaaggaa aacagcaagc gctggaaccc cgagatccag   2100

tacacctcca actactacaa atctacaagt gtggactttg ctgttaatac agaaggcgtg   2160

tactctgaac cccaccccat tggcacccgt tacctcaccc gtcccctgta a            2211
```

<210> SEQ ID NO 48
<211> LENGTH: 1605
<212> TYPE: DNA
<213> ORGANISM: Artificial Sequence
<220> FEATURE:
<223> OTHER INFORMATION: ITB102 45 VP3

<400> SEQUENCE: 48

```
atggcttcag gcggtggcgc accaatggcg gacaataacg aaggcgccga cggagtgggt     60

aatgcctcag gaaattggca ttgcgattcc acatggctgg gcgacagagt catcaccacc    120

agcacccgca cctgggcctt gcccacctac aataaccacc tctacaagca aatctccagt    180

gcttcaacgg gggccagcaa cgacaaccac tacttcggct acagcacccc ctgggggtat    240

tttgacttca acagattcca ctgccacttt tcaccacgtg actggcaaag actcatcaac    300

aacaactggg gattccgacc caagagactc aacttcaagc tctttaacat tcaagtcaaa    360

gaggttacgg acaacaatgg agtcaagacc atcgccaata accttaccag cacggtccag    420

gtcttcacgg actcagacta tcagctcccg tacgtgctcg ggtcggctca cgagggctgc    480

ctcccgccgt tcccagcgga cgttttcatg attcctcagt acggctacct aacgctcaac    540

aatggcagcc aggcagtggg acggtcatcc ttttactgcc tggaatattt cccatcgcag    600

atgctgagaa cgggcaacaa ctttaccttc agctacacct ttgaggacgt tcctttccac    660

agcagctacg ctcacagcca gagtctggac cggctgatga atcctctgat tgaccagtac    720

ctgtactact tgtctcggac tcaaacaaca ggaggcacgg caaatacgca gactctgggc    780
```

```
ttcagccaag gtgggcctaa tacaatggcc aatcaggcaa agaactggct gccaggaccc    840

tgttaccgcc aacaacgcgt ctcaacgaca accgggcaaa acaacaatag caactttgcc    900

tggactgctg ggaccaaata ccatctgaat ggaagaaatt cattgatgaa tcctggcccc    960

gctatggcat cccacaaaga gggcgaggac cgtttttttc ccctgtccgg gtccctgatt   1020

tttggcaaac aaggcactgg cagagacaat gtggatgccg acaaagtcat gatcaccaac   1080

gaggaagaaa tcaaaaccac taaccctgtg gctacagagg aatacggtat cgtggcagat   1140

aacttgcagc agcaaaacac ggctcctcaa attggaactg tcaacagcca gggggcctta   1200

cccggtatgg tctggcagaa ccgggacgtg tacctgcagg gtcccatctg ggccaagatt   1260

cctcacacgg acggcaactt ccacccgtct ccgctgatgg gcggctttgg cctgaaacat   1320

cctccgcctc agatcctgat caagaacacg cctgtacctg cggatcctcc gaccaccttc   1380

aaccagtcaa agctgaactc tttcatcacg caatacagca ccggacaggt cagcgtggaa   1440

attgaatggg agctgcagaa ggaaaacagc aagcgctgga accccgagat ccagtacacc   1500

tccaactact acaaatctac aagtgtggac tttgctgtta atacagaagg cgtgtactct   1560

gaaccccacc ccattggcac ccgttacctc acccgtcccc tgtaa                    1605
```

<210> SEQ ID NO 49
<211> LENGTH: 736
<212> TYPE: PRT
<213> ORGANISM: Artificial Sequence
<220> FEATURE:
<223> OTHER INFORMATION: ITB102 45 VP1

<400> SEQUENCE: 49

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
```

```
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Asp Asn Asn Gly Val Lys Thr Ile Ala Asn Asn
                325                 330                 335

Leu Thr Ser Thr Val Gln Val Phe Thr Asp Ser Asp Tyr Gln Leu Pro
            340                 345                 350

Tyr Val Leu Gly Ser Ala His Glu Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Gly Gly Thr Ala Asn Thr Gln Thr Leu Gly Phe Ser
    450                 455                 460

Gln Gly Gly Pro Asn Thr Met Ala Asn Gln Ala Lys Asn Trp Leu Pro
465                 470                 475                 480

Gly Pro Cys Tyr Arg Gln Gln Arg Val Ser Thr Thr Thr Gly Gln Asn
                485                 490                 495

Asn Asn Ser Asn Phe Ala Trp Thr Ala Gly Thr Lys Tyr His Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Glu
                565                 570                 575

Tyr Gly Ile Val Ala Asp Asn Leu Gln Gln Gln Asn Thr Ala Pro Gln
            580                 585                 590

Ile Gly Thr Val Asn Ser Gln Gly Ala Leu Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640
```

```
Lys His Pro Pro Pro Gln Ile Leu Ile Lys Asn Thr Pro Val Pro Ala
                645                 650                 655

Asp Pro Pro Thr Thr Phe Asn Gln Ser Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Ser Val Asp Phe Ala Val Asn Thr Glu Gly Val
705                 710                 715                 720

Tyr Ser Glu Pro His Pro Ile Gly Thr Arg Tyr Leu Thr Arg Pro Leu
                725                 730                 735


<210> SEQ ID NO 50
<211> LENGTH: 599
<212> TYPE: PRT
<213> ORGANISM: Artificial Sequence
<220> FEATURE:
<223> OTHER INFORMATION: ITB102 45 VP2

<400> SEQUENCE: 50

Met Ala Pro Gly Lys Lys Arg Pro Val Glu Gln Ser Pro Gln Glu Pro
1               5                   10                  15

Asp Ser Ser Ser Gly Ile Gly Lys Thr Gly Gln Gln Pro Ala Lys Lys
            20                  25                  30

Arg Leu Asn Phe Gly Gln Thr Gly Asp Ser Glu Ser Val Pro Asp Pro
        35                  40                  45

Gln Pro Leu Gly Glu Pro Pro Ala Thr Pro Ala Ala Val Gly Pro Thr
    50                  55                  60

Thr Met Ala Ser Gly Gly Gly Ala Pro Met Ala Asp Asn Asn Glu Gly
65                  70                  75                  80

Ala Asp Gly Val Gly Asn Ala Ser Gly Asn Trp His Cys Asp Ser Thr
                85                  90                  95

Trp Leu Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Ala Ser Thr
        115                 120                 125

Gly Ala Ser Asn Asp Asn His Tyr Phe Gly Tyr Ser Thr Pro Trp Gly
    130                 135                 140

Tyr Phe Asp Phe Asn Arg Phe His Cys His Phe Ser Pro Arg Asp Trp
145                 150                 155                 160

Gln Arg Leu Ile Asn Asn Asn Trp Gly Phe Arg Pro Lys Arg Leu Asn
                165                 170                 175

Phe Lys Leu Phe Asn Ile Gln Val Lys Glu Val Thr Asp Asn Asn Gly
            180                 185                 190

Val Lys Thr Ile Ala Asn Asn Leu Thr Ser Thr Val Gln Val Phe Thr
        195                 200                 205

Asp Ser Asp Tyr Gln Leu Pro Tyr Val Leu Gly Ser Ala His Glu Gly
    210                 215                 220

Cys Leu Pro Pro Phe Pro Ala Asp Val Phe Met Ile Pro Gln Tyr Gly
225                 230                 235                 240

Tyr Leu Thr Leu Asn Asn Gly Ser Gln Ala Val Gly Arg Ser Ser Phe
                245                 250                 255

Tyr Cys Leu Glu Tyr Phe Pro Ser Gln Met Leu Arg Thr Gly Asn Asn
            260                 265                 270
```

Phe Thr Phe Ser Tyr Thr Phe Glu Asp Val Pro Phe His Ser Ser Tyr
275 280 285

Ala His Ser Gln Ser Leu Asp Arg Leu Met Asn Pro Leu Ile Asp Gln
290 295 300

Tyr Leu Tyr Tyr Leu Ser Arg Thr Gln Thr Thr Gly Gly Thr Ala Asn
305 310 315 320

Thr Gln Thr Leu Gly Phe Ser Gln Gly Gly Pro Asn Thr Met Ala Asn
325 330 335

Gln Ala Lys Asn Trp Leu Pro Gly Pro Cys Tyr Arg Gln Gln Arg Val
340 345 350

Ser Thr Thr Thr Gly Gln Asn Asn Asn Ser Asn Phe Ala Trp Thr Ala
355 360 365

Gly Thr Lys Tyr His Leu Asn Gly Arg Asn Ser Leu Met Asn Pro Gly
370 375 380

Pro Ala Met Ala Ser His Lys Glu Gly Glu Asp Arg Phe Phe Pro Leu
385 390 395 400

Ser Gly Ser Leu Ile Phe Gly Lys Gln Gly Thr Gly Arg Asp Asn Val
405 410 415

Asp Ala Asp Lys Val Met Ile Thr Asn Glu Glu Glu Ile Lys Thr Thr
420 425 430

Asn Pro Val Ala Thr Glu Glu Tyr Gly Ile Val Ala Asp Asn Leu Gln
435 440 445

Gln Gln Asn Thr Ala Pro Gln Ile Gly Thr Val Asn Ser Gln Gly Ala
450 455 460

Leu Pro Gly Met Val Trp Gln Asn Arg Asp Val Tyr Leu Gln Gly Pro
465 470 475 480

Ile Trp Ala Lys Ile Pro His Thr Asp Gly Asn Phe His Pro Ser Pro
485 490 495

Leu Met Gly Gly Phe Gly Leu Lys His Pro Pro Pro Gln Ile Leu Ile
500 505 510

Lys Asn Thr Pro Val Pro Ala Asp Pro Pro Thr Thr Phe Asn Gln Ser
515 520 525

Lys Leu Asn Ser Phe Ile Thr Gln Tyr Ser Thr Gly Gln Val Ser Val
530 535 540

Glu Ile Glu Trp Glu Leu Gln Lys Glu Asn Ser Lys Arg Trp Asn Pro
545 550 555 560

Glu Ile Gln Tyr Thr Ser Asn Tyr Tyr Lys Ser Thr Ser Val Asp Phe
565 570 575

Ala Val Asn Thr Glu Gly Val Tyr Ser Glu Pro His Pro Ile Gly Thr
580 585 590

Arg Tyr Leu Thr Arg Pro Leu
595

<210> SEQ ID NO 51
<211> LENGTH: 534
<212> TYPE: PRT
<213> ORGANISM: Artificial Sequence
<220> FEATURE:
<223> OTHER INFORMATION: ITB102 45 VP3

<400> SEQUENCE: 51

Met Ala Ser Gly Gly Gly Ala Pro Met Ala Asp Asn Asn Glu Gly Ala
1 5 10 15

Asp Gly Val Gly Asn Ala Ser Gly Asn Trp His Cys Asp Ser Thr Trp
20 25 30

```
Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Ala Ser Thr Gly
    50                  55                  60

Ala Ser Asn Asp Asn His Tyr Phe Gly Tyr Ser Thr Pro Trp Gly Tyr
65                  70                  75                  80

Phe Asp Phe Asn Arg Phe His Cys His Phe Ser Pro Arg Asp Trp Gln
                85                  90                  95

Arg Leu Ile Asn Asn Asn Trp Gly Phe Arg Pro Lys Arg Leu Asn Phe
            100                 105                 110

Lys Leu Phe Asn Ile Gln Val Lys Glu Val Thr Asp Asn Asn Gly Val
        115                 120                 125

Lys Thr Ile Ala Asn Asn Leu Thr Ser Thr Val Gln Val Phe Thr Asp
    130                 135                 140

Ser Asp Tyr Gln Leu Pro Tyr Val Leu Gly Ser Ala His Glu Gly Cys
145                 150                 155                 160

Leu Pro Pro Phe Pro Ala Asp Val Phe Met Ile Pro Gln Tyr Gly Tyr
                165                 170                 175

Leu Thr Leu Asn Asn Gly Ser Gln Ala Val Gly Arg Ser Ser Phe Tyr
            180                 185                 190

Cys Leu Glu Tyr Phe Pro Ser Gln Met Leu Arg Thr Gly Asn Asn Phe
        195                 200                 205

Thr Phe Ser Tyr Thr Phe Glu Asp Val Pro Phe His Ser Ser Tyr Ala
    210                 215                 220

His Ser Gln Ser Leu Asp Arg Leu Met Asn Pro Leu Ile Asp Gln Tyr
225                 230                 235                 240

Leu Tyr Tyr Leu Ser Arg Thr Gln Thr Thr Gly Gly Thr Ala Asn Thr
                245                 250                 255

Gln Thr Leu Gly Phe Ser Gln Gly Gly Pro Asn Thr Met Ala Asn Gln
            260                 265                 270

Ala Lys Asn Trp Leu Pro Gly Pro Cys Tyr Arg Gln Gln Arg Val Ser
        275                 280                 285

Thr Thr Thr Gly Gln Asn Asn Asn Ser Asn Phe Ala Trp Thr Ala Gly
    290                 295                 300

Thr Lys Tyr His Leu Asn Gly Arg Asn Ser Leu Met Asn Pro Gly Pro
305                 310                 315                 320

Ala Met Ala Ser His Lys Glu Gly Glu Asp Arg Phe Phe Pro Leu Ser
                325                 330                 335

Gly Ser Leu Ile Phe Gly Lys Gln Gly Thr Gly Arg Asp Asn Val Asp
            340                 345                 350

Ala Asp Lys Val Met Ile Thr Asn Glu Glu Glu Ile Lys Thr Thr Asn
        355                 360                 365

Pro Val Ala Thr Glu Glu Tyr Gly Ile Val Ala Asp Asn Leu Gln Gln
    370                 375                 380

Gln Asn Thr Ala Pro Gln Ile Gly Thr Val Asn Ser Gln Gly Ala Leu
385                 390                 395                 400

Pro Gly Met Val Trp Gln Asn Arg Asp Val Tyr Leu Gln Gly Pro Ile
                405                 410                 415

Trp Ala Lys Ile Pro His Thr Asp Gly Asn Phe His Pro Ser Pro Leu
            420                 425                 430

Met Gly Gly Phe Gly Leu Lys His Pro Pro Pro Gln Ile Leu Ile Lys
        435                 440                 445
```

Asn Thr Pro Val Pro Ala Asp Pro Pro Thr Thr Phe Asn Gln Ser Lys
    450                 455                 460

Leu Asn Ser Phe Ile Thr Gln Tyr Ser Thr Gly Gln Val Ser Val Glu
465                 470                 475                 480

Ile Glu Trp Glu Leu Gln Lys Glu Asn Ser Lys Arg Trp Asn Pro Glu
                485                 490                 495

Ile Gln Tyr Thr Ser Asn Tyr Tyr Lys Ser Thr Ser Val Asp Phe Ala
            500                 505                 510

Val Asn Thr Glu Gly Val Tyr Ser Glu Pro His Pro Ile Gly Thr Arg
        515                 520                 525

Tyr Leu Thr Arg Pro Leu
    530

<210> SEQ ID NO 52
<211> LENGTH: 7
<212> TYPE: PRT
<213> ORGANISM: Artificial Sequence
<220> FEATURE:
<223> OTHER INFORMATION: VR-I

<400> SEQUENCE: 52

Ser Ala Ser Thr Gly Ala Ser
1               5

<210> SEQ ID NO 53
<211> LENGTH: 8
<212> TYPE: PRT
<213> ORGANISM: Artificial Sequence
<220> FEATURE:
<223> OTHER INFORMATION: VR-I

<400> SEQUENCE: 53

Asn Ser Thr Ser Gly Gly Ser Ser
1               5

<210> SEQ ID NO 54
<211> LENGTH: 6
<212> TYPE: PRT
<213> ORGANISM: Artificial Sequence
<220> FEATURE:
<223> OTHER INFORMATION: VR-II

<400> SEQUENCE: 54

Asp Asn Asn Gly Val Lys
1               5

<210> SEQ ID NO 55
<211> LENGTH: 4
<212> TYPE: PRT
<213> ORGANISM: Artificial Sequence
<220> FEATURE:
<223> OTHER INFORMATION: VR-III

<400> SEQUENCE: 55

Asn Asp Gly Ser
1

<210> SEQ ID NO 56
<211> LENGTH: 10
<212> TYPE: PRT
<213> ORGANISM: Artificial Sequence
<220> FEATURE:
<223> OTHER INFORMATION: VR-IV

<400> SEQUENCE: 56

Ile Asn Gly Ser Gly Gln Asn Gln Gln Thr
1 5 10

<210> SEQ ID NO 57
<211> LENGTH: 18
<212> TYPE: PRT
<213> ORGANISM: Artificial Sequence
<220> FEATURE:
<223> OTHER INFORMATION: VR-V

<400> SEQUENCE: 57

Arg Val Ser Thr Thr Thr Gly Gln Asn Asn Asn Ser Asn Phe Ala Trp
1 5 10 15

Thr Ala

<210> SEQ ID NO 58
<211> LENGTH: 13
<212> TYPE: PRT
<213> ORGANISM: Artificial Sequence
<220> FEATURE:
<223> OTHER INFORMATION: VR-VI

<400> SEQUENCE: 58

His Lys Glu Gly Glu Asp Arg Phe Phe Pro Leu Ser Gly
1 5 10

<210> SEQ ID NO 59
<211> LENGTH: 14
<212> TYPE: PRT
<213> ORGANISM: Artificial Sequence
<220> FEATURE:
<223> OTHER INFORMATION: VR-VII

<400> SEQUENCE: 59

Lys Gln Asn Ala Ala Arg Asp Asn Ala Asp Tyr Ser Asp Val
1 5 10

<210> SEQ ID NO 60
<211> LENGTH: 13
<212> TYPE: PRT
<213> ORGANISM: Artificial Sequence
<220> FEATURE:
<223> OTHER INFORMATION: VR-VIII

<400> SEQUENCE: 60

Ala Asp Asn Leu Gln Gln Gln Asn Thr Ala Pro Gln Ile
1 5 10

<210> SEQ ID NO 61
<211> LENGTH: 10
<212> TYPE: PRT
<213> ORGANISM: Artificial Sequence
<220> FEATURE:
<223> OTHER INFORMATION: VR-IX

<400> SEQUENCE: 61

Asn Tyr Tyr Lys Ser Thr Ser Val Asp Phe
1 5 10

<210> SEQ ID NO 62
<211> LENGTH: 2211
<212> TYPE: DNA
<213> ORGANISM: Artificial Sequence
<220> FEATURE:
<223> OTHER INFORMATION: AAV6 VP1

<400> SEQUENCE: 62

```
atggctgccg atggttatct tccagattgg ctcgaggaca acctctctga gggcattcgc     60
gagtggtggg acttgaaacc tggagccccg aaacccaaag ccaaccagca aaagcaggac    120
gacggccggg gtctggtgct tcctggctac aagtacctcg gacccttcaa cggactcgac    180
aagggggagc ccgtcaacgc ggcggatgca gcggccctcg agcacgacaa ggcctacgac    240
cagcagctca aagcgggtga caatccgtac ctgcggtata accacgccga cgccgagttt    300
caggagcgtc tgcaagaaga tacgtctttt gggggcaacc tcgggcgagc agtcttccag    360
gccaagaaga gggttctcga accttttggt ctggttgagg aaggtgctaa gacggctcct    420
ggaaagaaac gtccggtaga gcagtcgcca caagagccag actcctcctc gggcattggc    480
aagacaggcc agcagcccgc taaaaagaga ctcaattttg gtcagactgg cgactcagag    540
tcagtccccg acccacaacc tctcggagaa cctccagcaa cccccgctgc tgtgggacct    600
actacaatgg cttcaggcgg tggcgcacca atggcagaca ataacgaagg cgccgacgga    660
gtgggtaatg cctcaggaaa ttggcattgc gattccacat ggctgggcga cagagtcatc    720
accaccagca cccgaacatg ggccttgccc acctataaca accacctcta caagcaaatc    780
tccagtgctt caacgggggc cagcaacgac aaccactact tcggctacag caccccctgg    840
gggtattttg atttcaacag attccactgc catttctcac cacgtgactg gcagcgactc    900
atcaacaaca attggggatt ccggcccaag agactcaact tcaagctctt caacatccaa    960
gtcaaggagg tcacgacgaa tgatggcgtc acgaccatcg ctaataacct taccagcacg   1020
gttcaagtct tctcggactc ggagtaccag ttgccgtacg tcctcggctc tgcgcaccag   1080
ggctgcctcc ctccgttccc ggcggacgtg ttcatgattc cgcagtacgg ctacctaacg   1140
ctcaacaatg gcagccaggc agtgggacgg tcatcctttt actgcctgga atatttccca   1200
tcgcagatgc tgagaacggg caataacttt accttcagct acaccttcga ggacgtgcct   1260
ttccacagca gctacgcgca cagccagagc ctggaccggc tgatgaatcc tctcatcgac   1320
cagtacctgt attacctgaa cagaactcag aatcagtccg gaagtgccca aaacaaggac   1380
ttgctgttta gccgggggtc tccagctggc atgtctgttc agcccaaaaa ctggctacct   1440
ggaccctgtt accggcagca gcgcgtttct aaaacaaaaa cagacaacaa caacagcaac   1500
tttacctgga ctggtgcttc aaaatataac cttaatgggc gtgaatctat aatcaaccct   1560
ggcactgcta tggcctcaca caaagacgac aaagacaagt tctttcccat gagcggtgtc   1620
atgatttttg gaaaggagag cgccggagct tcaaacactg cattggacaa tgtcatgatc   1680
acagacgaag aggaaatcaa agccactaac cccgtggcca ccgaaagatt tgggactgtg   1740
gcagtcaatc tccagagcag cagcacagac cctgcgaccg gagatgtgca tgttatggga   1800
gccttacctg gaatggtgtg gcaagacaga gacgtatacc tgcagggtcc tatttgggcc   1860
aaaattcctc acacggatgg acactttcac ccgtctcctc tcatgggcgg ctttggactt   1920
aagcacccgc ctcctcagat cctcatcaaa aacacgcctg ttcctgcgaa tcctccggca   1980
gagttttcgg ctacaaagtt tgcttcattc atcacccagt attccacagg acaagtgagc   2040
gtggagattg aatgggagct gcagaaagaa aacagcaaac gctggaatcc cgaagtgcag   2100
tatacatcta actatgcaaa atctgccaac gttgatttca ctgtggacaa caatggactt   2160
tatactgagc ctcgccccat tggcacccgt tacctcaccc gtcccctgta a             2211
```

<210> SEQ ID NO 63
<211> LENGTH: 736

<212> TYPE: PRT
<213> ORGANISM: Artificial Sequence
<220> FEATURE:
<223> OTHER INFORMATION: AAV6 VP1

<400> SEQUENCE: 63

Met Ala Ala Asp Gly Tyr Leu Pro Asp Trp Leu Glu Asp Asn Leu Ser
1 5 10 15

Glu Gly Ile Arg Glu Trp Trp Asp Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Phe Gly Leu Val Glu Glu Gly Ala Lys Thr Ala Pro Gly Lys Lys Arg
130 135 140

Pro Val Glu Gln Ser Pro Gln Glu Pro Asp Ser Ser Ser Gly Ile Gly
145 150 155 160

Lys Thr Gly Gln Gln Pro Ala Lys Lys Arg Leu Asn Phe Gly Gln Thr
165 170 175

Gly Asp Ser Glu Ser Val Pro Asp Pro Gln Pro Leu Gly Glu Pro Pro
180 185 190

Ala Thr Pro Ala Ala Val Gly Pro Thr Thr Met Ala Ser Gly Gly Gly
195 200 205

Ala Pro Met Ala Asp Asn Asn Glu Gly Ala Asp Gly Val Gly Asn Ala
210 215 220

Ser Gly Asn Trp His Cys Asp Ser Thr Trp Leu Gly Asp Arg Val Ile
225 230 235 240

Thr Thr Ser Thr Arg Thr Trp Ala Leu Pro Thr Tyr Asn Asn His Leu
245 250 255

Tyr Lys Gln Ile Ser Ser Ala Ser Thr Gly Ala Ser Asn Asp Asn His
260 265 270

Tyr Phe Gly Tyr Ser Thr Pro Trp Gly Tyr Phe Asp Phe Asn Arg Phe
275 280 285

His Cys His Phe Ser Pro Arg Asp Trp Gln Arg Leu Ile Asn Asn Asn
290 295 300

Trp Gly Phe Arg Pro Lys Arg Leu Asn Phe Lys Leu Phe Asn Ile Gln
305 310 315 320

Val Lys Glu Val Thr Thr Asn Asp Gly Val Thr Thr Ile Ala Asn Asn
325 330 335

Leu Thr Ser Thr Val Gln Val Phe Ser Asp Ser Glu Tyr Gln Leu Pro
340 345 350

Tyr Val Leu Gly Ser Ala His Gln Gly Cys Leu Pro Pro Phe Pro Ala
355 360 365

Asp Val Phe Met Ile Pro Gln Tyr Gly Tyr Leu Thr Leu Asn Asn Gly
370 375 380

```
Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735


<210> SEQ ID NO 64
<211> LENGTH: 599
<212> TYPE: PRT
<213> ORGANISM: Artificial Sequence
<220> FEATURE:
<223> OTHER INFORMATION: AAV6 VP2

<400> SEQUENCE: 64

Thr Ala Pro Gly Lys Lys Arg Pro Val Glu Gln Ser Pro Gln Glu Pro
1               5                   10                  15
```

```
Asp Ser Ser Ser Gly Ile Gly Lys Thr Gly Gln Gln Pro Ala Lys Lys
            20                  25                  30

Arg Leu Asn Phe Gly Gln Thr Gly Asp Ser Glu Ser Val Pro Asp Pro
        35                  40                  45

Gln Pro Leu Gly Glu Pro Pro Ala Thr Pro Ala Ala Val Gly Pro Thr
    50                  55                  60

Thr Met Ala Ser Gly Gly Gly Ala Pro Met Ala Asp Asn Asn Glu Gly
65                  70                  75                  80

Ala Asp Gly Val Gly Asn Ala Ser Gly Asn Trp His Cys Asp Ser Thr
                85                  90                  95

Trp Leu Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Ala Ser Thr
        115                 120                 125

Gly Ala Ser Asn Asp Asn His Tyr Phe Gly Tyr Ser Thr Pro Trp Gly
    130                 135                 140

Tyr Phe Asp Phe Asn Arg Phe His Cys His Phe Ser Pro Arg Asp Trp
145                 150                 155                 160

Gln Arg Leu Ile Asn Asn Asn Trp Gly Phe Arg Pro Lys Arg Leu Asn
                165                 170                 175

Phe Lys Leu Phe Asn Ile Gln Val Lys Glu Val Thr Thr Asn Asp Gly
            180                 185                 190

Val Thr Thr Ile Ala Asn Asn Leu Thr Ser Thr Val Gln Val Phe Ser
        195                 200                 205

Asp Ser Glu Tyr Gln Leu Pro Tyr Val Leu Gly Ser Ala His Gln Gly
    210                 215                 220

Cys Leu Pro Pro Phe Pro Ala Asp Val Phe Met Ile Pro Gln Tyr Gly
225                 230                 235                 240

Tyr Leu Thr Leu Asn Asn Gly Ser Gln Ala Val Gly Arg Ser Ser Phe
                245                 250                 255

Tyr Cys Leu Glu Tyr Phe Pro Ser Gln Met Leu Arg Thr Gly Asn Asn
            260                 265                 270

Phe Thr Phe Ser Tyr Thr Phe Glu Asp Val Pro Phe His Ser Ser Tyr
        275                 280                 285

Ala His Ser Gln Ser Leu Asp Arg Leu Met Asn Pro Leu Ile Asp Gln
    290                 295                 300

Tyr Leu Tyr Tyr Leu Asn Arg Thr Gln Asn Gln Ser Gly Ser Ala Gln
305                 310                 315                 320

Asn Lys Asp Leu Leu Phe Ser Arg Gly Ser Pro Ala Gly Met Ser Val
                325                 330                 335

Gln Pro Lys Asn Trp Leu Pro Gly Pro Cys Tyr Arg Gln Gln Arg Val
            340                 345                 350

Ser Lys Thr Lys Thr Asp Asn Asn Asn Ser Asn Phe Thr Trp Thr Gly
        355                 360                 365

Ala Ser Lys Tyr Asn Leu Asn Gly Arg Glu Ser Ile Ile Asn Pro Gly
    370                 375                 380

Thr Ala Met Ala Ser His Lys Asp Asp Lys Asp Lys Phe Phe Pro Met
385                 390                 395                 400

Ser Gly Val Met Ile Phe Gly Lys Glu Ser Ala Gly Ala Ser Asn Thr
                405                 410                 415

Ala Leu Asp Asn Val Met Ile Thr Asp Glu Glu Glu Ile Lys Ala Thr
            420                 425                 430

Asn Pro Val Ala Thr Glu Arg Phe Gly Thr Val Ala Val Asn Leu Gln
```

```
        435                 440                 445

Ser Ser Ser Thr Asp Pro Ala Thr Gly Asp Val His Val Met Gly Ala
    450                 455                 460

Leu Pro Gly Met Val Trp Gln Asp Arg Asp Val Tyr Leu Gln Gly Pro
465                 470                 475                 480

Ile Trp Ala Lys Ile Pro His Thr Asp Gly His Phe His Pro Ser Pro
                485                 490                 495

Leu Met Gly Gly Phe Gly Leu Lys His Pro Pro Pro Gln Ile Leu Ile
            500                 505                 510

Lys Asn Thr Pro Val Pro Ala Asn Pro Pro Ala Glu Phe Ser Ala Thr
        515                 520                 525

Lys Phe Ala Ser Phe Ile Thr Gln Tyr Ser Thr Gly Gln Val Ser Val
    530                 535                 540

Glu Ile Glu Trp Glu Leu Gln Lys Glu Asn Ser Lys Arg Trp Asn Pro
545                 550                 555                 560

Glu Val Gln Tyr Thr Ser Asn Tyr Ala Lys Ser Ala Asn Val Asp Phe
                565                 570                 575

Thr Val Asp Asn Asn Gly Leu Tyr Thr Glu Pro Arg Pro Ile Gly Thr
            580                 585                 590

Arg Tyr Leu Thr Arg Pro Leu
        595


<210> SEQ ID NO 65
<211> LENGTH: 534
<212> TYPE: PRT
<213> ORGANISM: Artificial Sequence
<220> FEATURE:
<223> OTHER INFORMATION: AAV6 VP3

<400> SEQUENCE: 65

Met Ala Ser Gly Gly Gly Ala Pro Met Ala Asp Asn Asn Glu Gly Ala
1               5                   10                  15

Asp Gly Val Gly Asn Ala Ser Gly Asn Trp His Cys Asp Ser Thr Trp
            20                  25                  30

Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Ala Ser Thr Gly
    50                  55                  60

Ala Ser Asn Asp Asn His Tyr Phe Gly Tyr Ser Thr Pro Trp Gly Tyr
65                  70                  75                  80

Phe Asp Phe Asn Arg Phe His Cys His Phe Ser Pro Arg Asp Trp Gln
                85                  90                  95

Arg Leu Ile Asn Asn Asn Trp Gly Phe Arg Pro Lys Arg Leu Asn Phe
            100                 105                 110

Lys Leu Phe Asn Ile Gln Val Lys Glu Val Thr Thr Asn Asp Gly Val
        115                 120                 125

Thr Thr Ile Ala Asn Asn Leu Thr Ser Thr Val Gln Val Phe Ser Asp
    130                 135                 140

Ser Glu Tyr Gln Leu Pro Tyr Val Leu Gly Ser Ala His Gln Gly Cys
145                 150                 155                 160

Leu Pro Pro Phe Pro Ala Asp Val Phe Met Ile Pro Gln Tyr Gly Tyr
                165                 170                 175

Leu Thr Leu Asn Asn Gly Ser Gln Ala Val Gly Arg Ser Ser Phe Tyr
            180                 185                 190

Cys Leu Glu Tyr Phe Pro Ser Gln Met Leu Arg Thr Gly Asn Asn Phe
```

```
        195                 200                 205

Thr Phe Ser Tyr Thr Phe Glu Asp Val Pro Phe His Ser Ser Tyr Ala
    210                 215                 220

His Ser Gln Ser Leu Asp Arg Leu Met Asn Pro Leu Ile Asp Gln Tyr
225                 230                 235                 240

Leu Tyr Tyr Leu Asn Arg Thr Gln Asn Gln Ser Gly Ser Ala Gln Asn
                245                 250                 255

Lys Asp Leu Leu Phe Ser Arg Gly Ser Pro Ala Gly Met Ser Val Gln
            260                 265                 270

Pro Lys Asn Trp Leu Pro Gly Pro Cys Tyr Arg Gln Gln Arg Val Ser
        275                 280                 285

Lys Thr Lys Thr Asp Asn Asn Asn Ser Asn Phe Thr Trp Thr Gly Ala
    290                 295                 300

Ser Lys Tyr Asn Leu Asn Gly Arg Glu Ser Ile Ile Asn Pro Gly Thr
305                 310                 315                 320

Ala Met Ala Ser His Lys Asp Asp Lys Asp Lys Phe Phe Pro Met Ser
                325                 330                 335

Gly Val Met Ile Phe Gly Lys Glu Ser Ala Gly Ala Ser Asn Thr Ala
            340                 345                 350

Leu Asp Asn Val Met Ile Thr Asp Glu Glu Glu Ile Lys Ala Thr Asn
        355                 360                 365

Pro Val Ala Thr Glu Arg Phe Gly Thr Val Ala Val Asn Leu Gln Ser
    370                 375                 380

Ser Ser Thr Asp Pro Ala Thr Gly Asp Val His Val Met Gly Ala Leu
385                 390                 395                 400

Pro Gly Met Val Trp Gln Asp Arg Asp Val Tyr Leu Gln Gly Pro Ile
                405                 410                 415

Trp Ala Lys Ile Pro His Thr Asp Gly His Phe His Pro Ser Pro Leu
            420                 425                 430

Met Gly Gly Phe Gly Leu Lys His Pro Pro Pro Gln Ile Leu Ile Lys
        435                 440                 445

Asn Thr Pro Val Pro Ala Asn Pro Pro Ala Glu Phe Ser Ala Thr Lys
    450                 455                 460

Phe Ala Ser Phe Ile Thr Gln Tyr Ser Thr Gly Gln Val Ser Val Glu
465                 470                 475                 480

Ile Glu Trp Glu Leu Gln Lys Glu Asn Ser Lys Arg Trp Asn Pro Glu
                485                 490                 495

Val Gln Tyr Thr Ser Asn Tyr Ala Lys Ser Ala Asn Val Asp Phe Thr
            500                 505                 510

Val Asp Asn Asn Gly Leu Tyr Thr Glu Pro Arg Pro Ile Gly Thr Arg
        515                 520                 525

Tyr Leu Thr Arg Pro Leu
    530


<210> SEQ ID NO 66
<211> LENGTH: 2217
<212> TYPE: DNA
<213> ORGANISM: Artificial Sequence
<220> FEATURE:
<223> OTHER INFORMATION: AAV8 VP1

<400> SEQUENCE: 66

atggctgccg atggttatct tccagattgg ctcgaggaca acctctctga gggcattcgc      60

gagtggtggg cgctgaaacc tggagccccg aagcccaaag ccaaccagca aaagcaggac     120
```

```
gacggccggg gtctggtgct tcctggctac aagtacctcg gacccttcaa cggactcgac    180
aagggggagc ccgtcaacgc ggcggacgca gcggccctcg agcacgacaa ggcctacgac    240
cagcagctgc aggcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaga gaccggtaga gccatcaccc cagcgttctc cagactcctc tacgggcatc    480
ggcaagaaag gccaacagcc cgccagaaaa agactcaatt ttggtcagac tggcgactca    540
gagtcagttc cagaccctca acctctcgga gaacctccag cagcgccctc tggtgtggga    600
cctaatacaa tggctgcagg cggtggcgca ccaatggcag acaataacga aggcgccgac    660
ggagtgggta gttcctcggg aaattggcat tgcgattcca catggctggg cgacagagtc    720
atcaccacca gcacccgaac ctgggccctg cccacctaca acaaccacct ctacaagcaa    780
atctccaacg ggacatcggg aggagccacc aacgacaaca cctacttcgg ctacagcacc    840
ccctgggggt attttgactt taacagattc cactgccact tttcaccacg tgactggcag    900
cgactcatca acaacaactg gggattccgg cccaagagac tcagcttcaa gctcttcaac    960
atccaggtca aggaggtcac gcagaatgaa ggcaccaaga ccatcgccaa taacctcacc   1020
agcaccatcc aggtgtttac ggactcggag taccagctgc cgtacgttct cggctctgcc   1080
caccagggct gcctgcctcc gttcccggcg gacgtgttca tgattcccca gtacggctac   1140
ctaacactca acaacggtag tcaggccgtg ggacgctcct ccttctactg cctggaatac   1200
tttccttcgc agatgctgag aaccggcaac aacttccagt ttacttacac cttcgaggac   1260
gtgcctttcc acagcagcta cgcccacagc cagagcttgg accggctgat gaatcctctg   1320
attgaccagt acctgtacta cttgtctcgg actcaaacaa caggaggcac ggcaaatacg   1380
cagactctgg gcttcagcca aggtgggcct aatacaatgg ccaatcaggc aaagaactgg   1440
ctgccaggac cctgttaccg ccaacaacgc gtctcaacga caaccgggca aaacaacaat   1500
agcaactttg cctggactgc tgggaccaaa taccatctga atggaagaaa ttcattggct   1560
aatcctggca tcgctatggc aacacacaaa gacgacgagg agcgtttttt tcccagtaac   1620
gggatcctga tttttggcaa acaaaatgct gccagagaca atgcggatta cagcgatgtc   1680
atgctcacca gcgaggaaga aatcaaaacc actaaccctg tggctacaga ggaatacggt   1740
atcgtggcag ataacttgca gcagcaaaac acggctcctc aaattggaac tgtcaacagc   1800
caggggggcct tacccggtat ggtctggcag aaccgggacg tgtacctgca gggtcccatc   1860
tgggccaaga ttcctcacac ggacggcaac ttccacccgt ctccgctgat gggcggcttt   1920
ggcctgaaac atcctccgcc tcagatcctg atcaagaaca cgcctgtacc tgcggatcct   1980
ccgaccacct tcaaccagtc aaagctgaac tctttcatca cgcaatacag caccggacag   2040
gtcagcgtgg aaattgaatg ggagctgcag aaggaaaaca gcaagcgctg gaaccccgag   2100
atccagtaca cctccaacta ctacaaatct acaagtgtgg actttgctgt taatacagaa   2160
ggcgtgtact ctgaaccccg ccccattggc acccgttacc tcacccgtaa tctgtaa      2217
```

<210> SEQ ID NO 67
<211> LENGTH: 738
<212> TYPE: PRT
<213> ORGANISM: Artificial Sequence
<220> FEATURE:
<223> OTHER INFORMATION: AAV8 VP1

<400> SEQUENCE: 67

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415
```

Thr Phe Glu Asp Val Pro Phe His Ser Ser Tyr Ala His Ser Gln Ser
420 425 430

Leu Asp Arg Leu Met Asn Pro Leu Ile Asp Gln Tyr Leu Tyr Tyr Leu
435 440 445

Ser Arg Thr Gln Thr Thr Gly Gly Thr Ala Asn Thr Gln Thr Leu Gly
450 455 460

Phe Ser Gln Gly Gly Pro Asn Thr Met Ala Asn Gln Ala Lys Asn Trp
465 470 475 480

Leu Pro Gly Pro Cys Tyr Arg Gln Gln Arg Val Ser Thr Thr Thr Gly
485 490 495

Gln Asn Asn Asn Ser Asn Phe Ala Trp Thr Ala Gly Thr Lys Tyr His
500 505 510

Leu Asn Gly Arg Asn Ser Leu Ala Asn Pro Gly Ile Ala Met Ala Thr
515 520 525

His Lys Asp Asp Glu Glu Arg Phe Phe Pro Ser Asn Gly Ile Leu Ile
530 535 540

Phe Gly Lys Gln Asn Ala Ala Arg Asp Asn Ala Asp Tyr Ser Asp Val
545 550 555 560

Met Leu Thr Ser Glu Glu Glu Ile Lys Thr Thr Asn Pro Val Ala Thr
565 570 575

Glu Glu Tyr Gly Ile Val Ala Asp Asn Leu Gln Gln Gln Asn Thr Ala
580 585 590

Pro Gln Ile Gly Thr Val Asn Ser Gln Gly Ala Leu Pro Gly Met Val
595 600 605

Trp Gln Asn Arg Asp Val Tyr Leu Gln Gly Pro Ile Trp Ala Lys Ile
610 615 620

Pro His Thr Asp Gly Asn Phe His Pro Ser Pro Leu Met Gly Gly Phe
625 630 635 640

Gly Leu Lys His Pro Pro Pro Gln Ile Leu Ile Lys Asn Thr Pro Val
645 650 655

Pro Ala Asp Pro Pro Thr Thr Phe Asn Gln Ser Lys Leu Asn Ser Phe
660 665 670

Ile Thr Gln Tyr Ser Thr Gly Gln Val Ser Val Glu Ile Glu Trp Glu
675 680 685

Leu Gln Lys Glu Asn Ser Lys Arg Trp Asn Pro Glu Ile Gln Tyr Thr
690 695 700

Ser Asn Tyr Tyr Lys Ser Thr Ser Val Asp Phe Ala Val Asn Thr Glu
705 710 715 720

Gly Val Tyr Ser Glu Pro Arg Pro Ile Gly Thr Arg Tyr Leu Thr Arg
725 730 735

Asn Leu

<210> SEQ ID NO 68
<211> LENGTH: 601
<212> TYPE: PRT
<213> ORGANISM: Artificial Sequence
<220> FEATURE:
<223> OTHER INFORMATION: AAV8 VP2

<400> SEQUENCE: 68

Met Ala Pro Gly Lys Lys Arg Pro Val Glu Pro Ser Pro Gln Arg Ser
1 5 10 15

Pro Asp Ser Ser Thr Gly Ile Gly Lys Lys Gly Gln Gln Pro Ala Arg
20 25 30

Lys Arg Leu Asn Phe Gly Gln Thr Gly Asp Ser Glu Ser Val Pro Asp

```
        35                  40                  45

Pro Gln Pro Leu Gly Glu Pro Pro Ala Ala Pro Ser Gly Val Gly Pro
    50                  55                  60

Asn Thr Met Ala Ala Gly Gly Gly Ala Pro Met Ala Asp Asn Asn Glu
65                  70                  75                  80

Gly Ala Asp Gly Val Gly Ser Ser Ser Gly Asn Trp His Cys Asp Ser
                85                  90                  95

Thr Trp Leu Gly Asp Arg Val Ile Thr Thr Ser Thr Arg Thr Trp Ala
            100                 105                 110

Leu Pro Thr Tyr Asn Asn His Leu Tyr Lys Gln Ile Ser Asn Gly Thr
        115                 120                 125

Ser Gly Gly Ala Thr Asn Asp Asn Thr Tyr Phe Gly Tyr Ser Thr Pro
    130                 135                 140

Trp Gly Tyr Phe Asp Phe Asn Arg Phe His Cys His Phe Ser Pro Arg
145                 150                 155                 160

Asp Trp Gln Arg Leu Ile Asn Asn Asn Trp Gly Phe Arg Pro Lys Arg
                165                 170                 175

Leu Ser Phe Lys Leu Phe Asn Ile Gln Val Lys Glu Val Thr Gln Asn
            180                 185                 190

Glu Gly Thr Lys Thr Ile Ala Asn Asn Leu Thr Ser Thr Ile Gln Val
        195                 200                 205

Phe Thr Asp Ser Glu Tyr Gln Leu Pro Tyr Val Leu Gly Ser Ala His
    210                 215                 220

Gln Gly Cys Leu Pro Pro Phe Pro Ala Asp Val Phe Met Ile Pro Gln
225                 230                 235                 240

Tyr Gly Tyr Leu Thr Leu Asn Asn Gly Ser Gln Ala Val Gly Arg Ser
                245                 250                 255

Ser Phe Tyr Cys Leu Glu Tyr Phe Pro Ser Gln Met Leu Arg Thr Gly
            260                 265                 270

Asn Asn Phe Gln Phe Thr Tyr Thr Phe Glu Asp Val Pro Phe His Ser
        275                 280                 285

Ser Tyr Ala His Ser Gln Ser Leu Asp Arg Leu Met Asn Pro Leu Ile
    290                 295                 300

Asp Gln Tyr Leu Tyr Tyr Leu Ser Arg Thr Gln Thr Thr Gly Gly Thr
305                 310                 315                 320

Ala Asn Thr Gln Thr Leu Gly Phe Ser Gln Gly Gly Pro Asn Thr Met
                325                 330                 335

Ala Asn Gln Ala Lys Asn Trp Leu Pro Gly Pro Cys Tyr Arg Gln Gln
            340                 345                 350

Arg Val Ser Thr Thr Thr Gly Gln Asn Asn Asn Ser Asn Phe Ala Trp
        355                 360                 365

Thr Ala Gly Thr Lys Tyr His Leu Asn Gly Arg Asn Ser Leu Ala Asn
    370                 375                 380

Pro Gly Ile Ala Met Ala Thr His Lys Asp Asp Glu Glu Arg Phe Phe
385                 390                 395                 400

Pro Ser Asn Gly Ile Leu Ile Phe Gly Lys Gln Asn Ala Ala Arg Asp
                405                 410                 415

Asn Ala Asp Tyr Ser Asp Val Met Leu Thr Ser Glu Glu Glu Ile Lys
            420                 425                 430

Thr Thr Asn Pro Val Ala Thr Glu Glu Tyr Gly Ile Val Ala Asp Asn
        435                 440                 445

Leu Gln Gln Gln Asn Thr Ala Pro Gln Ile Gly Thr Val Asn Ser Gln
    450                 455                 460
```

```
Gly Ala Leu Pro Gly Met Val Trp Gln Asn Arg Asp Val Tyr Leu Gln
465                 470                 475                 480

Gly Pro Ile Trp Ala Lys Ile Pro His Thr Asp Gly Asn Phe His Pro
                485                 490                 495

Ser Pro Leu Met Gly Gly Phe Gly Leu Lys His Pro Pro Pro Gln Ile
            500                 505                 510

Leu Ile Lys Asn Thr Pro Val Pro Ala Asp Pro Pro Thr Thr Phe Asn
        515                 520                 525

Gln Ser Lys Leu Asn Ser Phe Ile Thr Gln Tyr Ser Thr Gly Gln Val
    530                 535                 540

Ser Val Glu Ile Glu Trp Glu Leu Gln Lys Glu Asn Ser Lys Arg Trp
545                 550                 555                 560

Asn Pro Glu Ile Gln Tyr Thr Ser Asn Tyr Tyr Lys Ser Thr Ser Val
                565                 570                 575

Asp Phe Ala Val Asn Thr Glu Gly Val Tyr Ser Glu Pro Arg Pro Ile
            580                 585                 590

Gly Thr Arg Tyr Leu Thr Arg Asn Leu
        595                 600
```

<210> SEQ ID NO 69
<211> LENGTH: 535
<212> TYPE: PRT
<213> ORGANISM: Artificial Sequence
<220> FEATURE:
<223> OTHER INFORMATION: AAV8 VP3

<400> SEQUENCE: 69

```
Met Ala Ala Gly Gly Gly Ala Pro Met Ala Asp Asn Asn Glu Gly Ala
1               5                   10                  15

Asp Gly Val Gly Ser Ser Ser Gly Asn Trp His Cys Asp Ser Thr Trp
            20                  25                  30

Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Asn Gly Thr Ser Gly
    50                  55                  60

Gly Ala Thr Asn Asp Asn Thr Tyr Phe Gly Tyr Ser Thr Pro Trp Gly
65                  70                  75                  80

Tyr Phe Asp Phe Asn Arg Phe His Cys His Phe Ser Pro Arg Asp Trp
                85                  90                  95

Gln Arg Leu Ile Asn Asn Asn Trp Gly Phe Arg Pro Lys Arg Leu Ser
            100                 105                 110

Phe Lys Leu Phe Asn Ile Gln Val Lys Glu Val Thr Gln Asn Glu Gly
        115                 120                 125

Thr Lys Thr Ile Ala Asn Asn Leu Thr Ser Thr Ile Gln Val Phe Thr
    130                 135                 140

Asp Ser Glu Tyr Gln Leu Pro Tyr Val Leu Gly Ser Ala His Gln Gly
145                 150                 155                 160

Cys Leu Pro Pro Phe Pro Ala Asp Val Phe Met Ile Pro Gln Tyr Gly
                165                 170                 175

Tyr Leu Thr Leu Asn Asn Gly Ser Gln Ala Val Gly Arg Ser Ser Phe
            180                 185                 190

Tyr Cys Leu Glu Tyr Phe Pro Ser Gln Met Leu Arg Thr Gly Asn Asn
        195                 200                 205

Phe Gln Phe Thr Tyr Thr Phe Glu Asp Val Pro Phe His Ser Ser Tyr
    210                 215                 220
```

```
Ala His Ser Gln Ser Leu Asp Arg Leu Met Asn Pro Leu Ile Asp Gln
225                 230                 235                 240

Tyr Leu Tyr Tyr Leu Ser Arg Thr Gln Thr Thr Gly Gly Thr Ala Asn
                245                 250                 255

Thr Gln Thr Leu Gly Phe Ser Gln Gly Gly Pro Asn Thr Met Ala Asn
            260                 265                 270

Gln Ala Lys Asn Trp Leu Pro Gly Pro Cys Tyr Arg Gln Gln Arg Val
        275                 280                 285

Ser Thr Thr Thr Gly Gln Asn Asn Asn Ser Asn Phe Ala Trp Thr Ala
    290                 295                 300

Gly Thr Lys Tyr His Leu Asn Gly Arg Asn Ser Leu Ala Asn Pro Gly
305                 310                 315                 320

Ile Ala Met Ala Thr His Lys Asp Asp Glu Glu Arg Phe Phe Pro Ser
                325                 330                 335

Asn Gly Ile Leu Ile Phe Gly Lys Gln Asn Ala Ala Arg Asp Asn Ala
            340                 345                 350

Asp Tyr Ser Asp Val Met Leu Thr Ser Glu Glu Glu Ile Lys Thr Thr
        355                 360                 365

Asn Pro Val Ala Thr Glu Glu Tyr Gly Ile Val Ala Asp Asn Leu Gln
    370                 375                 380

Gln Gln Asn Thr Ala Pro Gln Ile Gly Thr Val Asn Ser Gln Gly Ala
385                 390                 395                 400

Leu Pro Gly Met Val Trp Gln Asn Arg Asp Val Tyr Leu Gln Gly Pro
                405                 410                 415

Ile Trp Ala Lys Ile Pro His Thr Asp Gly Asn Phe His Pro Ser Pro
            420                 425                 430

Leu Met Gly Gly Phe Gly Leu Lys His Pro Pro Pro Gln Ile Leu Ile
        435                 440                 445

Lys Asn Thr Pro Val Pro Ala Asp Pro Pro Thr Thr Phe Asn Gln Ser
    450                 455                 460

Lys Leu Asn Ser Phe Ile Thr Gln Tyr Ser Thr Gly Gln Val Ser Val
465                 470                 475                 480

Glu Ile Glu Trp Glu Leu Gln Lys Glu Asn Ser Lys Arg Trp Asn Pro
                485                 490                 495

Glu Ile Gln Tyr Thr Ser Asn Tyr Tyr Lys Ser Thr Ser Val Asp Phe
            500                 505                 510

Ala Val Asn Thr Glu Gly Val Tyr Ser Glu Pro Arg Pro Ile Gly Thr
        515                 520                 525

Arg Tyr Leu Thr Arg Asn Leu
    530                 535
```

<210> SEQ ID NO 70
<211> LENGTH: 2214
<212> TYPE: DNA
<213> ORGANISM: Artificial Sequence
<220> FEATURE:
<223> OTHER INFORMATION: AAV9 VP1

<400> SEQUENCE: 70

```
atggctgccg atggttatct tccagattgg ctcgaggaca acctctctga gggcattcgc     60

gagtggtggg cgctgaaacc tggagccccg aagcccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacggcaa ggcctacgac    240
```

```
cagcagctgc aggcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaga gaccggtaga gccatcaccc cagcgttctc cagactcctc tacgggcatc    480
ggcaagaaag gccaacagcc cgccagaaaa agactcaatt ttggtcagac tggcgactca    540
gagtcagttc cagaccctca acctctcgga gaacctccag cagcgccctc tggtgtggga    600
cctaatacaa tggctgcagg cggtggcgca ccaatggcag acaataacga aggcgccgac    660
ggagtgggta attcctcggg aaattggcat tgcgattcca catggctggg ggacagagtc    720
atcaccacca gcacccgaac ctgggcattg cccacctaca acaaccacct ctacaagcaa    780
atctccaatg gaacatcggg aggaagcacc aacgacaaca cctactttgg ctacagcacc    840
ccctgggggt attttgactt caacagattc cactgccact tctcaccacg tgactggcag    900
cgactcatca acaacaactg gggattccgg ccaaagagac tcaacttcaa gctgttcaac    960
atccaggtca aggaggttac gacgaacgaa ggcaccaaga ccatcgccaa taaccttacc   1020
agcaccgtcc aggtctttac ggactcggag taccagctac cgtacgtcct aggctctgcc   1080
caccaaggat gcctgccacc gtttcctgca gacgtcttca tggttcctca gtacggctac   1140
ctgacgctca acaatggaag tcaagcgtta ggacgttctt ctttctactg tctggaatac   1200
ttcccttctc agatgctgag aaccggcaac aactttcagt tcagctacac tttcgaggac   1260
gtgcctttcc acagcagcta cgcacacagc cagagtctag atcgactgat gaacccccctc   1320
atcgaccagt acctatacta cctggtcaga acacagacaa ctggaactgg gggaactcaa   1380
actttggcat tcagccaagc aggccctagc tcaatggcca atcaggctag aaactgggta   1440
cccgggcctt gctaccgtca gcagcgcgtc tccacaacca ccaaccaaaa taacaacagc   1500
aactttgcgt ggacgggagc tgctaaattc aagctgaacg ggagagactc gctaatgaat   1560
cctggcgtgg ctatggcatc gcacaaagac gacgaggacc gcttctttcc atcaagtggc   1620
gttctcatat ttggcaagca aggagccggg aacgatggag tcgactacag ccaggtgctg   1680
attacagatg aggaagaaat taaagccacc aaccctgtag ccacagagga atacggagca   1740
gtggccatca acaaccaggc cgctaacacg caggcgcaaa ctggacttgt gcataaccag   1800
ggagttattc ctggtatggt ctggcagaac cgggacgtgt acctgcaggg ccctatttgg   1860
gctaaaatac ctcacacaga tggcaacttt cacccgtctc ctctgatggg tggatttgga   1920
ctgaaacacc cacctccaca gattctaatt aaaaatacac cagtgccggc agatcctcct   1980
cttaccttca atcaagccaa gctgaactct ttcatcacgc agtacagcac gggacaagtc   2040
agcgtggaaa tcgagtggga gctgcagaaa gaaaacagca agcgctggaa tccagagatc   2100
cagtatactt caaactacta caaatctaca aatgtggact ttgctgtcaa taccaaaggt   2160
gtttactctg agcctcgccc cattggtact cgttacctca cccgtaattt gtaa         2214
```

```
<210> SEQ ID NO 71
<211> LENGTH: 736
<212> TYPE: PRT
<213> ORGANISM: Artificial Sequence
<220> FEATURE:
<223> OTHER INFORMATION: AAV9 VP1

<400> SEQUENCE: 71

Met Ala Ala Asp Gly Tyr Leu Pro Asp Trp Leu Glu Asp Asn Leu Ser
1               5                   10                  15
```

-continued

```
Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
```

```
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 72
<211> LENGTH: 599
<212> TYPE: PRT
<213> ORGANISM: Artificial Sequence
<220> FEATURE:
<223> OTHER INFORMATION: AAV9 VP2

<400> SEQUENCE: 72

Met Ala Pro Gly Lys Lys Arg Pro Val Glu Gln Ser Pro Gln Glu Pro
1               5                   10                  15

Asp Ser Ser Ala Gly Ile Gly Lys Ser Gly Ala Gln Pro Ala Lys Lys
            20                  25                  30

Arg Leu Asn Phe Gly Gln Thr Gly Asp Thr Glu Ser Val Pro Asp Pro
        35                  40                  45

Gln Pro Ile Gly Glu Pro Pro Ala Ala Pro Ser Gly Val Gly Ser Leu
    50                  55                  60

Thr Met Ala Ser Gly Gly Gly Ala Pro Val Ala Asp Asn Asn Glu Gly
```

```
65                  70                  75                  80

Ala Asp Gly Val Gly Ser Ser Ser Gly Asn Trp His Cys Asp Ser Gln
                85                  90                  95

Trp Leu Gly Asp Arg Val Ile Thr Thr Ser Thr Arg Thr Trp Ala Leu
            100                 105                 110

Pro Thr Tyr Asn Asn His Leu Tyr Lys Gln Ile Ser Asn Ser Thr Ser
        115                 120                 125

Gly Gly Ser Ser Asn Asp Asn Ala Tyr Phe Gly Tyr Ser Thr Pro Trp
    130                 135                 140

Gly Tyr Phe Asp Phe Asn Arg Phe His Cys His Phe Ser Pro Arg Asp
145                 150                 155                 160

Trp Gln Arg Leu Ile Asn Asn Asn Trp Gly Phe Arg Pro Lys Arg Leu
                165                 170                 175

Asn Phe Lys Leu Phe Asn Ile Gln Val Lys Glu Val Thr Asp Asn Asn
            180                 185                 190

Gly Val Lys Thr Ile Ala Asn Asn Leu Thr Ser Thr Val Gln Val Phe
        195                 200                 205

Thr Asp Ser Asp Tyr Gln Leu Pro Tyr Val Leu Gly Ser Ala His Glu
    210                 215                 220

Gly Cys Leu Pro Pro Phe Pro Ala Asp Val Phe Met Ile Pro Gln Tyr
225                 230                 235                 240

Gly Tyr Leu Thr Leu Asn Asp Gly Ser Gln Ala Val Gly Arg Ser Ser
                245                 250                 255

Phe Tyr Cys Leu Glu Tyr Phe Pro Ser Gln Met Leu Arg Thr Gly Asn
            260                 265                 270

Asn Phe Gln Phe Ser Tyr Glu Phe Glu Asn Val Pro Phe His Ser Ser
        275                 280                 285

Tyr Ala His Ser Gln Ser Leu Asp Arg Leu Met Asn Pro Leu Ile Asp
    290                 295                 300

Gln Tyr Leu Tyr Tyr Leu Ser Lys Thr Ile Asn Gly Ser Gly Gln Asn
305                 310                 315                 320

Gln Gln Thr Leu Lys Phe Ser Val Ala Gly Pro Ser Asn Met Ala Val
                325                 330                 335

Gln Gly Arg Asn Tyr Ile Pro Gly Pro Ser Tyr Arg Gln Gln Arg Val
            340                 345                 350

Ser Thr Thr Val Thr Gln Asn Asn Asn Ser Glu Phe Ala Trp Pro Gly
        355                 360                 365

Ala Ser Ser Trp Ala Leu Asn Gly Arg Asn Ser Leu Met Asn Pro Gly
    370                 375                 380

Pro Ala Met Ala Ser His Lys Glu Gly Glu Asp Arg Phe Phe Pro Leu
385                 390                 395                 400

Ser Gly Ser Leu Ile Phe Gly Lys Gln Gly Thr Gly Arg Asp Asn Val
                405                 410                 415

Asp Ala Asp Lys Val Met Ile Thr Asn Glu Glu Glu Ile Lys Thr Thr
            420                 425                 430

Asn Pro Val Ala Thr Glu Ser Tyr Gly Gln Val Ala Thr Asn His Gln
        435                 440                 445

Ser Ala Gln Ala Gln Ala Gln Thr Gly Trp Val Gln Asn Gln Gly Ile
    450                 455                 460

Leu Pro Gly Met Val Trp Gln Asp Arg Asp Val Tyr Leu Gln Gly Pro
465                 470                 475                 480

Ile Trp Ala Lys Ile Pro His Thr Asp Gly Asn Phe His Pro Ser Pro
                485                 490                 495
```

Leu Met Gly Gly Phe Gly Met Lys His Pro Pro Pro Gln Ile Leu Ile
500 505 510

Lys Asn Thr Pro Val Pro Ala Asp Pro Pro Thr Ala Phe Asn Lys Asp
515 520 525

Lys Leu Asn Ser Phe Ile Thr Gln Tyr Ser Thr Gly Gln Val Ser Val
530 535 540

Glu Ile Glu Trp Glu Leu Gln Lys Glu Asn Ser Lys Arg Trp Asn Pro
545 550 555 560

Glu Ile Gln Tyr Thr Ser Asn Tyr Tyr Lys Ser Asn Asn Val Glu Phe
565 570 575

Ala Val Asn Thr Glu Gly Val Tyr Ser Glu Pro Arg Pro Ile Gly Thr
580 585 590

Arg Tyr Leu Thr Arg Asn Leu
595

<210> SEQ ID NO 73
<211> LENGTH: 534
<212> TYPE: PRT
<213> ORGANISM: Artificial Sequence
<220> FEATURE:
<223> OTHER INFORMATION: AAV9 VP3

<400> SEQUENCE: 73

Met Ala Ser Gly Gly Gly Ala Pro Val Ala Asp Asn Asn Glu Gly Ala
1 5 10 15

Asp Gly Val Gly Ser Ser Ser Gly Asn Trp His Cys Asp Ser Gln Trp
20 25 30

Leu Gly Asp Arg Val Ile Thr Thr Ser Thr Arg Thr Trp Ala Leu Pro
35 40 45

Thr Tyr Asn Asn His Leu Tyr Lys Gln Ile Ser Asn Ser Thr Ser Gly
50 55 60

Gly Ser Ser Asn Asp Asn Ala Tyr Phe Gly Tyr Ser Thr Pro Trp Gly
65 70 75 80

Tyr Phe Asp Phe Asn Arg Phe His Cys His Phe Ser Pro Arg Asp Trp
85 90 95

Gln Arg Leu Ile Asn Asn Asn Trp Gly Phe Arg Pro Lys Arg Leu Asn
100 105 110

Phe Lys Leu Phe Asn Ile Gln Val Lys Glu Val Thr Asp Asn Asn Gly
115 120 125

Val Lys Thr Ile Ala Asn Asn Leu Thr Ser Thr Val Gln Val Phe Thr
130 135 140

Asp Ser Asp Tyr Gln Leu Pro Tyr Val Leu Gly Ser Ala His Glu Gly
145 150 155 160

Cys Leu Pro Pro Phe Pro Ala Asp Val Phe Met Ile Pro Gln Tyr Gly
165 170 175

Tyr Leu Thr Leu Asn Asp Gly Ser Gln Ala Val Gly Arg Ser Ser Phe
180 185 190

Tyr Cys Leu Glu Tyr Phe Pro Ser Gln Met Leu Arg Thr Gly Asn Asn
195 200 205

Phe Gln Phe Ser Tyr Glu Phe Glu Asn Val Pro Phe His Ser Ser Tyr
210 215 220

Ala His Ser Gln Ser Leu Asp Arg Leu Met Asn Pro Leu Ile Asp Gln
225 230 235 240

Tyr Leu Tyr Tyr Leu Ser Lys Thr Ile Asn Gly Ser Gly Gln Asn Gln
245 250 255

Gln Thr Leu Lys Phe Ser Val Ala Gly Pro Ser Asn Met Ala Val Gln
260 265 270

Gly Arg Asn Tyr Ile Pro Gly Pro Ser Tyr Arg Gln Gln Arg Val Ser
275 280 285

Thr Thr Val Thr Gln Asn Asn Asn Ser Glu Phe Ala Trp Pro Gly Ala
290 295 300

Ser Ser Trp Ala Leu Asn Gly Arg Asn Ser Leu Met Asn Pro Gly Pro
305 310 315 320

Ala Met Ala Ser His Lys Glu Gly Glu Asp Arg Phe Phe Pro Leu Ser
325 330 335

Gly Ser Leu Ile Phe Gly Lys Gln Gly Thr Gly Arg Asp Asn Val Asp
340 345 350

Ala Asp Lys Val Met Ile Thr Asn Glu Glu Glu Ile Lys Thr Thr Asn
355 360 365

Pro Val Ala Thr Glu Ser Tyr Gly Gln Val Ala Thr Asn His Gln Ser
370 375 380

Ala Gln Ala Gln Ala Gln Thr Gly Trp Val Gln Asn Gln Gly Ile Leu
385 390 395 400

Pro Gly Met Val Trp Gln Asp Arg Asp Val Tyr Leu Gln Gly Pro Ile
405 410 415

Trp Ala Lys Ile Pro His Thr Asp Gly Asn Phe His Pro Ser Pro Leu
420 425 430

Met Gly Gly Phe Gly Met Lys His Pro Pro Pro Gln Ile Leu Ile Lys
435 440 445

Asn Thr Pro Val Pro Ala Asp Pro Pro Thr Ala Phe Asn Lys Asp Lys
450 455 460

Leu Asn Ser Phe Ile Thr Gln Tyr Ser Thr Gly Gln Val Ser Val Glu
465 470 475 480

Ile Glu Trp Glu Leu Gln Lys Glu Asn Ser Lys Arg Trp Asn Pro Glu
485 490 495

Ile Gln Tyr Thr Ser Asn Tyr Tyr Lys Ser Asn Asn Val Glu Phe Ala
500 505 510

Val Asn Thr Glu Gly Val Tyr Ser Glu Pro Arg Pro Ile Gly Thr Arg
515 520 525

Tyr Leu Thr Arg Asn Leu
530

<210> SEQ ID NO 74
<211> LENGTH: 6
<212> TYPE: PRT
<213> ORGANISM: Artificial Sequence
<220> FEATURE:
<223> OTHER INFORMATION: VRII-204/AAV6

<400> SEQUENCE: 74

Thr Asn Asp Gly Val Lys
1 5

<210> SEQ ID NO 75
<211> LENGTH: 4
<212> TYPE: PRT
<213> ORGANISM: Artificial Sequence
<220> FEATURE:
<223> OTHER INFORMATION: VRIII-204/AAV6

<400> SEQUENCE: 75

Asn Asn Gly Ser

1

<210> SEQ ID NO 76
<211> LENGTH: 11
<212> TYPE: PRT
<213> ORGANISM: Artificial Sequence
<220> FEATURE:
<223> OTHER INFORMATION: VRIV-204/AAV6

<400> SEQUENCE: 76

Gln Asn Gln Ser Gly Ser Ala Gln Asn Lys Asp
1               5                   10

<210> SEQ ID NO 77
<211> LENGTH: 18
<212> TYPE: PRT
<213> ORGANISM: Artificial Sequence
<220> FEATURE:
<223> OTHER INFORMATION: VRV-204/AAV6

<400> SEQUENCE: 77

Arg Val Ser Lys Thr Lys Thr Asp Asn Asn Asn Ser Asn Phe Thr Trp
1               5                   10                  15

Thr Gly

<210> SEQ ID NO 78
<211> LENGTH: 13
<212> TYPE: PRT
<213> ORGANISM: Artificial Sequence
<220> FEATURE:
<223> OTHER INFORMATION: VRVI-204/AAV6

<400> SEQUENCE: 78

His Lys Asp Asp Lys Asp Lys Phe Phe Pro Met Ser Gly
1               5                   10

<210> SEQ ID NO 79
<211> LENGTH: 14
<212> TYPE: PRT
<213> ORGANISM: Artificial Sequence
<220> FEATURE:
<223> OTHER INFORMATION: VRVII-204/AAV6

<400> SEQUENCE: 79

Lys Glu Ser Ala Gly Ala Ser Asn Thr Ala Leu Asp Asn Val
1               5                   10

<210> SEQ ID NO 80
<211> LENGTH: 13
<212> TYPE: PRT
<213> ORGANISM: Artificial Sequence
<220> FEATURE:
<223> OTHER INFORMATION: VRVIII-204/AAV6

<400> SEQUENCE: 80

Ala Val Asn Leu Gln Asn Ser Ser Thr Asp Pro Ala Thr
1               5                   10

<210> SEQ ID NO 81
<211> LENGTH: 10
<212> TYPE: PRT
<213> ORGANISM: Artificial Sequence
<220> FEATURE:
<223> OTHER INFORMATION: VRIX-204/AAV6

<400> SEQUENCE: 81

```
Asn Tyr Ala Lys Ser Ala Asn Val Asp Phe
1               5                   10
```

<210> SEQ ID NO 82
<211> LENGTH: 2211
<212> TYPE: DNA
<213> ORGANISM: Artificial Sequence
<220> FEATURE:
<223> OTHER INFORMATION: AAV214-AB VP1

<400> SEQUENCE: 82

```
atggctgccg atggttatct tccagattgg ctcgaggaca acctctctga gggcattcgc     60
gagtggtggg cgctgaaacc tggagccccg aagcccaaag ccaaccagca aaagcaggac    120
gacggccggg gtctggtgct tcctggctac aagtacctcg gacccttcaa cggactcgac    180
aagggggagc ccgtcaacgc ggcggacgca gcggccctcg agcacgacaa ggcctacgac    240
cagcagctca aagcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga accttttggt ctggttgagg aaggtgctaa gacggctcct    420
ggaaagaaac gtccggtaga gcagtcgcca caagagccag actcctcctc gggcatcggc    480
aagacaggcc agcagcccgc taaaaagaga ctcaattttg gtcagactgg cgactcagag    540
tcagtccccg acccacaacc tctcggagaa cctccagcaa cccccgctgc tgtgggacct    600
actacaatgg cttcaggcgg tggcgcacca atggcggaca ataacgaagg cgccgacgga    660
gtgggtaatg cctcaggaaa ttggcattgc gattccacat ggctgggcga cagagtcatc    720
accaccagca cccgcacctg ggccttgccc acctacaata accacctcta caagcaaatc    780
tccagcagca catctggagg atcttcaaat gacaacgcct acttcggcta cagcaccccc    840
tgggggtatt ttgacttcaa cagattccac tgccactttt caccacgtga ctggcaaaga    900
ctcatcaaca acaactgggg attccgaccc aagagactca acttcaagct ctttaacatt    960
caagtcaaag aggttacgga caacaatgga gtcaagacca tcgccaataa ccttaccagc   1020
acggtccagg tcttcacgga ctcagactat cagctcccgt acgtcctcgg ctctgcgcac   1080
cagggctgcc tccctccgtt cccggcggac gtgttcatga ttccgcagta cggctaccta   1140
acgctcaacg acggcagcca ggcagtggga cggtcatcct ttactgcct ggaatatttc   1200
ccatcgcaga tgctgagaac gggcaacaac tttaccttca gctacacctt tgaggacgtt   1260
cctttccaca gcagctacgc tcacagccag agtctggacc gtctcatgaa tcctctgatt   1320
gaccagtacc tgtactactt gtctaagact atcaacggat ccggccagaa tcagcagact   1380
ctgaagttca gccaaggtgg gcctaataca atggccaatc aggcaaagaa ctggctgcca   1440
ggaccctgtt accgccaaca acgcgtctca acgacaaccg ggcaaaacaa caatagcaac   1500
tttgcctgga ctgctgggac caaataccat ctgaatggaa gaaattcatt gatgaatcct   1560
ggccccgcta tggcatccca caaagagggc gaggaccgtt tttttcccct gtccgggtcc   1620
ctgatttttg gcaaacaaaa tgctgccaga gacaatgcgg attacagcga tgtcatgctc   1680
accagcgagg aagaaatcaa aaccactaac cctgtggcta cagaggaata cggtatcgtg   1740
gcagataact tgcagcagca aaacacggct cctcaaattg gaactgtcaa cagccagggg   1800
gccttacccg gtatggtctg gcagaaccgg gacgtgtacc tgcagggtcc catctgggcc   1860
aagattcctc acacggacgg caacttccac ccgtctccgc tgatgggcgg ctttggcctg   1920
aaacatcctc cgcctcagat cctgatcaag aacacgcctg tacctgcgga tcctccgacc   1980
```

accttcaacc agtcaaagct gaactctttc atcacgcaat acagcaccgg acaggtcagc 2040
gtggaaattg aatgggagct gcagaaggaa aacagcaagc gctggaaccc cgagatccag 2100
tacacctcca actactacaa atctacaagt gtggactttg ctgttaatac agaaggcgtg 2160
tactctgaac cccaccccat tggcacccgt tacctcaccc gtcccctgta a 2211

<210> SEQ ID NO 83
<211> LENGTH: 1605
<212> TYPE: DNA
<213> ORGANISM: Artificial Sequence
<220> FEATURE:
<223> OTHER INFORMATION: AAV214-AB VP3

<400> SEQUENCE: 83
atggcttcag gcggtggcgc accaatggcg gacaataacg aaggcgccga cggagtgggt 60
aatgcctcag gaaattggca ttgcgattcc acatggctgg gcgacagagt catcaccacc 120
agcacccgca cctgggcctt gcccacctac aataaccacc tctacaagca aatctccagc 180
agcacatctg gaggatcttc aaatgacaac gcctacttcg gctacagcac cccctggggg 240
tattttgact tcaacagatt ccactgccac ttttcaccac gtgactggca aagactcatc 300
aacaacaact ggggattccg acccaagaga ctcaacttca agctctttaa cattcaagtc 360
aaagaggtta cggacaacaa tggagtcaag accatcgcca ataaccttac cagcacggtc 420
caggtcttca cggactcaga ctatcagctc ccgtacgtcc tcggctctgc gcaccagggc 480
tgcctccctc cgttcccggc ggacgtgttc atgattccgc agtacggcta cctaacgctc 540
aacgacggca gccaggcagt gggacggtca tccttttact gcctggaata tttcccatcg 600
cagatgctga gaacgggcaa caactttacc ttcagctaca cctttgagga cgttcctttc 660
cacagcagct acgctcacag ccagagtctg gaccgtctca tgaatcctct gattgaccag 720
tacctgtact acttgtctaa gactatcaac ggatccggcc agaatcagca gactctgaag 780
ttcagccaag gtgggcctaa tacaatggcc aatcaggcaa agaactggct gccaggaccc 840
tgttaccgcc aacaacgcgt ctcaacgaca accgggcaaa acaacaatag caactttgcc 900
tggactgctg ggaccaaata ccatctgaat ggaagaaatt cattgatgaa tcctggcccc 960
gctatggcat cccacaaaga gggcgaggac cgtttttttc ccctgtccgg gtccctgatt 1020
tttggcaaac aaaatgctgc cagagacaat gcggattaca gcgatgtcat gctcaccagc 1080
gaggaagaaa tcaaaaccac taaccctgtg gctacagagg aatacggtat cgtggcagat 1140
aacttgcagc agcaaaacac ggctcctcaa attggaactg tcaacagcca gggggcctta 1200
cccggtatgg tctggcagaa ccgggacgtg tacctgcagg gtcccatctg ggccaagatt 1260
cctcacacgg acggcaactt ccacccgtct ccgctgatgg gcggctttgg cctgaaacat 1320
cctccgcctc agatcctgat caagaacacg cctgtacctg cggatcctcc gaccaccttc 1380
aaccagtcaa agctgaactc tttcatcacg caatacagca ccggacaggt cagcgtggaa 1440
attgaatggg agctgcagaa ggaaaacagc aagcgctgga accccgagat ccagtacacc 1500
tccaactact acaaatctac aagtgtggac tttgctgtta atacagaagg cgtgtactct 1560
gaaccccacc ccattggcac ccgttacctc acccgtcccc tgtaa 1605

<210> SEQ ID NO 84
<211> LENGTH: 736
<212> TYPE: PRT
<213> ORGANISM: Artificial Sequence
<220> FEATURE:
<223> OTHER INFORMATION: AAV214AB VP1

<400> SEQUENCE: 84

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr 405 410 415

Phe Glu Asp Val Pro Phe His Ser Ser Tyr Ala His Ser Gln Ser Leu
420 425 430

Asp Arg Leu Met Asn Pro Leu Ile Asp Gln Tyr Leu Tyr Tyr Leu Ser
435 440 445

Lys Thr Ile Asn Gly Ser Gly Gln Asn Gln Gln Thr Leu Lys Phe Ser
450 455 460

Gln Gly Gly Pro Asn Thr Met Ala Asn Gln Ala Lys Asn Trp Leu Pro
465 470 475 480

Gly Pro Cys Tyr Arg Gln Gln Arg Val Ser Thr Thr Thr Gly Gln Asn
485 490 495

Asn Asn Ser Asn Phe Ala Trp Thr Ala Gly Thr Lys Tyr His Leu Asn
500 505 510

Gly Arg Asn Ser Leu Met Asn Pro Gly Pro Ala Met Ala Ser His Lys
515 520 525

Glu Gly Glu Asp Arg Phe Phe Pro Leu Ser Gly Ser Leu Ile Phe Gly
530 535 540

Lys Gln Asn Ala Ala Arg Asp Asn Ala Asp Tyr Ser Asp Val Met Leu
545 550 555 560

Thr Ser Glu Glu Glu Ile Lys Thr Thr Asn Pro Val Ala Thr Glu Glu
565 570 575

Tyr Gly Ile Val Ala Asp Asn Leu Gln Gln Gln Asn Thr Ala Pro Gln
580 585 590

Ile Gly Thr Val Asn Ser Gln Gly Ala Leu Pro Gly Met Val Trp Gln
595 600 605

Asn Arg Asp Val Tyr Leu Gln Gly Pro Ile Trp Ala Lys Ile Pro His
610 615 620

Thr Asp Gly Asn Phe His Pro Ser Pro Leu Met Gly Gly Phe Gly Leu
625 630 635 640

Lys His Pro Pro Pro Gln Ile Leu Ile Lys Asn Thr Pro Val Pro Ala
645 650 655

Asp Pro Pro Thr Thr Phe Asn Gln Ser Lys Leu Asn Ser Phe Ile Thr
660 665 670

Gln Tyr Ser Thr Gly Gln Val Ser Val Glu Ile Glu Trp Glu Leu Gln
675 680 685

Lys Glu Asn Ser Lys Arg Trp Asn Pro Glu Ile Gln Tyr Thr Ser Asn
690 695 700

Tyr Tyr Lys Ser Thr Ser Val Asp Phe Ala Val Asn Thr Glu Gly Val
705 710 715 720

Tyr Ser Glu Pro His Pro Ile Gly Thr Arg Tyr Leu Thr Arg Pro Leu
725 730 735

<210> SEQ ID NO 85
<211> LENGTH: 599
<212> TYPE: PRT
<213> ORGANISM: Artificial Sequence
<220> FEATURE:
<223> OTHER INFORMATION: AAV214AB VP2

<400> SEQUENCE: 85

Met Ala Pro Gly Lys Lys Arg Pro Val Glu Gln Ser Pro Gln Glu Pro
1 5 10 15

Asp Ser Ser Ser Gly Ile Gly Lys Thr Gly Gln Gln Pro Ala Lys Lys
20 25 30

Arg Leu Asn Phe Gly Gln Thr Gly Asp Ser Glu Ser Val Pro Asp Pro

```
        35                  40                  45

Gln Pro Leu Gly Glu Pro Pro Ala Thr Pro Ala Ala Val Gly Pro Thr
    50                  55                  60

Thr Met Ala Ser Gly Gly Gly Ala Pro Met Ala Asp Asn Asn Glu Gly
65                  70                  75                  80

Ala Asp Gly Val Gly Asn Ala Ser Gly Asn Trp His Cys Asp Ser Thr
                85                  90                  95

Trp Leu Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Ser Thr Ser
        115                 120                 125

Gly Gly Ser Ser Asn Asp Asn Ala Tyr Phe Gly Tyr Ser Thr Pro Trp
    130                 135                 140

Gly Tyr Phe Asp Phe Asn Arg Phe His Cys His Phe Ser Pro Arg Asp
145                 150                 155                 160

Trp Gln Arg Leu Ile Asn Asn Asn Trp Gly Phe Arg Pro Lys Arg Leu
                165                 170                 175

Asn Phe Lys Leu Phe Asn Ile Gln Val Lys Glu Val Thr Asp Asn Asn
            180                 185                 190

Gly Val Lys Thr Ile Ala Asn Asn Leu Thr Ser Thr Val Gln Val Phe
        195                 200                 205

Thr Asp Ser Asp Tyr Gln Leu Pro Tyr Val Leu Gly Ser Ala His Gln
    210                 215                 220

Gly Cys Leu Pro Pro Phe Pro Ala Asp Val Phe Met Ile Pro Gln Tyr
225                 230                 235                 240

Gly Tyr Leu Thr Leu Asn Asp Gly Ser Gln Ala Val Gly Arg Ser Ser
                245                 250                 255

Phe Tyr Cys Leu Glu Tyr Phe Pro Ser Gln Met Leu Arg Thr Gly Asn
            260                 265                 270

Asn Phe Thr Phe Ser Tyr Thr Phe Glu Asp Val Pro Phe His Ser Ser
        275                 280                 285

Tyr Ala His Ser Gln Ser Leu Asp Arg Leu Met Asn Pro Leu Ile Asp
    290                 295                 300

Gln Tyr Leu Tyr Tyr Leu Ser Lys Thr Ile Asn Gly Ser Gly Gln Asn
305                 310                 315                 320

Gln Gln Thr Leu Lys Phe Ser Gln Gly Gly Pro Asn Thr Met Ala Asn
                325                 330                 335

Gln Ala Lys Asn Trp Leu Pro Gly Pro Cys Tyr Arg Gln Gln Arg Val
            340                 345                 350

Ser Thr Thr Thr Gly Gln Asn Asn Asn Ser Asn Phe Ala Trp Thr Ala
        355                 360                 365

Gly Thr Lys Tyr His Leu Asn Gly Arg Asn Ser Leu Met Asn Pro Gly
    370                 375                 380

Pro Ala Met Ala Ser His Lys Glu Gly Glu Asp Arg Phe Phe Pro Leu
385                 390                 395                 400

Ser Gly Ser Leu Ile Phe Gly Lys Gln Asn Ala Ala Arg Asp Asn Ala
                405                 410                 415

Asp Tyr Ser Asp Val Met Leu Thr Ser Glu Glu Glu Ile Lys Thr Thr
            420                 425                 430

Asn Pro Val Ala Thr Glu Glu Tyr Gly Ile Val Ala Asp Asn Leu Gln
        435                 440                 445

Gln Gln Asn Thr Ala Pro Gln Ile Gly Thr Val Asn Ser Gln Gly Ala
    450                 455                 460
```

Leu Pro Gly Met Val Trp Gln Asn Arg Asp Val Tyr Leu Gln Gly Pro
465 470 475 480

Ile Trp Ala Lys Ile Pro His Thr Asp Gly Asn Phe His Pro Ser Pro
485 490 495

Leu Met Gly Gly Phe Gly Leu Lys His Pro Pro Pro Gln Ile Leu Ile
500 505 510

Lys Asn Thr Pro Val Pro Ala Asp Pro Pro Thr Thr Phe Asn Gln Ser
515 520 525

Lys Leu Asn Ser Phe Ile Thr Gln Tyr Ser Thr Gly Gln Val Ser Val
530 535 540

Glu Ile Glu Trp Glu Leu Gln Lys Glu Asn Ser Lys Arg Trp Asn Pro
545 550 555 560

Glu Ile Gln Tyr Thr Ser Asn Tyr Tyr Lys Ser Thr Ser Val Asp Phe
565 570 575

Ala Val Asn Thr Glu Gly Val Tyr Ser Glu Pro His Pro Ile Gly Thr
580 585 590

Arg Tyr Leu Thr Arg Pro Leu
595

<210> SEQ ID NO 86
<211> LENGTH: 534
<212> TYPE: PRT
<213> ORGANISM: Artificial Sequence
<220> FEATURE:
<223> OTHER INFORMATION: AAV214AB VP3

<400> SEQUENCE: 86

Met Ala Ser Gly Gly Gly Ala Pro Met Ala Asp Asn Asn Glu Gly Ala
1 5 10 15

Asp Gly Val Gly Asn Ala Ser Gly Asn Trp His Cys Asp Ser Thr Trp
20 25 30

Leu Gly Asp Arg Val Ile Thr Thr Ser Thr Arg Thr Trp Ala Leu Pro
35 40 45

Thr Tyr Asn Asn His Leu Tyr Lys Gln Ile Ser Ser Ser Thr Ser Gly
50 55 60

Gly Ser Ser Asn Asp Asn Ala Tyr Phe Gly Tyr Ser Thr Pro Trp Gly
65 70 75 80

Tyr Phe Asp Phe Asn Arg Phe His Cys His Phe Ser Pro Arg Asp Trp
85 90 95

Gln Arg Leu Ile Asn Asn Asn Trp Gly Phe Arg Pro Lys Arg Leu Asn
100 105 110

Phe Lys Leu Phe Asn Ile Gln Val Lys Glu Val Thr Asp Asn Asn Gly
115 120 125

Val Lys Thr Ile Ala Asn Asn Leu Thr Ser Thr Val Gln Val Phe Thr
130 135 140

Asp Ser Asp Tyr Gln Leu Pro Tyr Val Leu Gly Ser Ala His Gln Gly
145 150 155 160

Cys Leu Pro Pro Phe Pro Ala Asp Val Phe Met Ile Pro Gln Tyr Gly
165 170 175

Tyr Leu Thr Leu Asn Asp Gly Ser Gln Ala Val Gly Arg Ser Ser Phe
180 185 190

Tyr Cys Leu Glu Tyr Phe Pro Ser Gln Met Leu Arg Thr Gly Asn Asn
195 200 205

Phe Thr Phe Ser Tyr Thr Phe Glu Asp Val Pro Phe His Ser Ser Tyr
210 215 220

Ala His Ser Gln Ser Leu Asp Arg Leu Met Asn Pro Leu Ile Asp Gln
225 230 235 240

Tyr Leu Tyr Tyr Leu Ser Lys Thr Ile Asn Gly Ser Gly Gln Asn Gln
245 250 255

Gln Thr Leu Lys Phe Ser Gln Gly Gly Pro Asn Thr Met Ala Asn Gln
260 265 270

Ala Lys Asn Trp Leu Pro Gly Pro Cys Tyr Arg Gln Gln Arg Val Ser
275 280 285

Thr Thr Thr Gly Gln Asn Asn Asn Ser Asn Phe Ala Trp Thr Ala Gly
290 295 300

Thr Lys Tyr His Leu Asn Gly Arg Asn Ser Leu Met Asn Pro Gly Pro
305 310 315 320

Ala Met Ala Ser His Lys Glu Gly Glu Asp Arg Phe Phe Pro Leu Ser
325 330 335

Gly Ser Leu Ile Phe Gly Lys Gln Asn Ala Ala Arg Asp Asn Ala Asp
340 345 350

Tyr Ser Asp Val Met Leu Thr Ser Glu Glu Glu Ile Lys Thr Thr Asn
355 360 365

Pro Val Ala Thr Glu Glu Tyr Gly Ile Val Ala Asp Asn Leu Gln Gln
370 375 380

Gln Asn Thr Ala Pro Gln Ile Gly Thr Val Asn Ser Gln Gly Ala Leu
385 390 395 400

Pro Gly Met Val Trp Gln Asn Arg Asp Val Tyr Leu Gln Gly Pro Ile
405 410 415

Trp Ala Lys Ile Pro His Thr Asp Gly Asn Phe His Pro Ser Pro Leu
420 425 430

Met Gly Gly Phe Gly Leu Lys His Pro Pro Pro Gln Ile Leu Ile Lys
435 440 445

Asn Thr Pro Val Pro Ala Asp Pro Pro Thr Thr Phe Asn Gln Ser Lys
450 455 460

Leu Asn Ser Phe Ile Thr Gln Tyr Ser Thr Gly Gln Val Ser Val Glu
465 470 475 480

Ile Glu Trp Glu Leu Gln Lys Glu Asn Ser Lys Arg Trp Asn Pro Glu
485 490 495

Ile Gln Tyr Thr Ser Asn Tyr Tyr Lys Ser Thr Ser Val Asp Phe Ala
500 505 510

Val Asn Thr Glu Gly Val Tyr Ser Glu Pro His Pro Ile Gly Thr Arg
515 520 525

Tyr Leu Thr Arg Pro Leu
530

<210> SEQ ID NO 87
<211> LENGTH: 8
<212> TYPE: PRT
<213> ORGANISM: Artificial Sequence
<220> FEATURE:
<223> OTHER INFORMATION: AAV214AB VR-1 amino acid

<400> SEQUENCE: 87

Ser Ser Thr Ser Gly Gly Ser Ser
1 5

<210> SEQ ID NO 88
<211> LENGTH: 6719
<212> TYPE: DNA
<213> ORGANISM: Artificial Sequence
<220> FEATURE:
<223> OTHER INFORMATION: pA-CF1

<400> SEQUENCE: 88

```
tcctgcaggc agctgcgcgc tcgctcgctc actgaggccg cccgggcaaa gcccgggcgt     60
cgggcgacct ttggtcgccc ggcctcagtg agcgagcgag cgcgcagaga gggagtggcc    120
aactccatca ctaggggttc ctgcggccgc atggaggcgg tactatgtag atgagaattc    180
aggagcaaac tgggaaaagc aactgcttcc aaatatttgt gatttttaca gtgtagtttt    240
ggaaaaactc ttagcctacc aattcttcta agtgttttaa aatgtgggag ccagtacaca    300
tgaagttata gagtgtttta atgaggctta aatatttacc gtaactatga aatgctacgc    360
atatcatgct gttcaggctc cgtggccacg caactcatac cggtagtact cgccaccatg    420
cagagaagcc ccctggagaa ggcctctgtg gtgagcaagc tgttcttcag ctggaccaga    480
cccatcctga gaaagggcta cagacagaga ctggagctgt ctgacatcta ccagatcccc    540
tctgtggact ctgctgacaa cctgtctgag aagctggaga gagagtggga cagagagctg    600
gccagcaaga agaaccccaa gctgatcaat gccctgagaa gatgcttctt ctggagattc    660
atgttctatg gcatcttcct gtacctgggg gaggtgacca aggctgtgca gcccctgctg    720
ctgggcagaa tcattgccag ctatgaccct gacaacaagg aggagagaag cattgccatc    780
tacctgggca ttggcctgtg cctgctgttc attgtgagaa ccctgctgct gcaccctgcc    840
atctttggcc tgcaccacat tggcatgcag atgagaattg ccatgttcag cctgatctac    900
aagaagaccc tgaagctgag cagcagagtg ctggacaaga tcagcattgg ccagctggtg    960
agcctgctga gcaacaacct gaacaagttt gatgagggcc tggccctggc ccactttgtg   1020
tggattgccc ccctgcaggt ggccctgctg atgggcctga tctgggagct gctgcaggcc   1080
tctgccttct gtggcctggg cttcctgatt gtgctggccc tgttccaggc tggcctgggc   1140
agaatgatga tgaagtacag agaccagaga gctggcaaga tctctgagag actggtgatc   1200
acctctgaga tgattgagaa catccagtct gtgaaggcct actgctggga ggaggccatg   1260
gagaagatga ttgagaacct gagacagaca gagctgaagc tgaccagaaa ggctgcctat   1320
gtgagatact tcaacagctc tgccttcttc ttctctggct tctttgtggt gttcctgtct   1380
gtgctgccct atgccctgat caagggcatc atcctgagaa agatcttcac caccatcagc   1440
ttctgcattg tgctgagaat ggctgtgacc agacagttcc cctgggctgt gcagacctgg   1500
tatgacagcc tgggggccat caacaagatc caggacttcc tgcagaagca ggagtacaag   1560
accctggagt acaacctgac caccacagag gtggtgatgg agaatgtgac agccttctgg   1620
gaggagggct ttggggagct gtttgagaag gccaagcaga acaacaacaa cagaaagacc   1680
agcaatgggg atgacagcct gttcttcagc aacttcagcc tgctgggcac ccctgtgctg   1740
aaggacatca acttcaagat tgagagaggc cagctgctgg ctgtggctgg cagcacaggg   1800
gctggcaaga ccagcctgct gatgatgatc atgggggagc tggagccctc tgagggcaag   1860
atcaagcact ctggcagaat cagcttctgc agccagttca gctggatcat gcctggcacc   1920
atcaaggaga acatcatctt tggggtgagc tatgatgagt acagatacag atctgtgatc   1980
aaggcctgcc agctggagga ggacatcagc aagtttgctg agaaggacaa cattgtgctg   2040
ggggaggggg gcatcaccct gtctgggggc cagagagcca gaatcagcct ggccagagct   2100
gtgtacaagg atgctgacct gtacctgctg gacagcccct ttggctacct ggatgtgctg   2160
acagagaagg agatctttga gagctgtgtg tgcaagctga tggccaacaa gaccagaatc   2220
```

ctggtgacca gcaagatgga gcacctgaag aaggctgaca agatcctgat cctgcatgag 2280
ggcagcagct acttctatgg caccttctct gagctgcaga acctgcagcc tgacttcagc 2340
agcaagctga tgggctgtga cagctttgac cagttctctg ctgagagaag aaacagcatc 2400
ctgacagaga ccctgcacag attcagcctg gagggggatg cccctgtgag ctggacagag 2460
accaagaagc agagcttcaa gcagacaggg gagtttgggg agaagagaaa gaacagcatc 2520
ctgaacccca tcaacagcac cctgcaggcc agaagaagac agtctgtgct gaacctgatg 2580
acccactctg tgaaccaggg ccagaacatc cacagaaaga ccacagccag caccagaaag 2640
gtgagcctgg ccccccaggc caacctgaca gagctggaca tctacagcag aagactgagc 2700
caggagacag gcctggagat ctctgaggag atcaatgagg aggacctgaa ggagtgcttc 2760
tttgatgaca tggagagcat ccctgctgtg accacctgga acacctacct gagatacatc 2820
acagtgcaca agagcctgat ctttgtgctg atctggtgcc tggtgatctt cctggctgag 2880
gtggctgcca gcctggtggt gctgtggctg ctgggcaaca ccccccctgca ggacaagggc 2940 aacagcaccc acagcagaaa caacagctat gctgtgatca tcaccagcac cagcagctac 3000
tatgtgttct acatctatgt gggggtggct gacaccctgc tggccatggg cttcttcaga 3060
ggcctgcccc tggtgcacac cctgatcaca gtgagcaaga tcctgcacca caagatgctg 3120
cactctgtgc tgcaggcccc catgagcacc ctgaacaccc tgaaggctgg gggcatcctg 3180
aacagattca gcaaggacat tgccatcctg gatgacctgc tgcccctgac catctttgac 3240
ttcatccagc tgctgctgat tgtgattggg gccattgctg tggtggctgt gctgcagccc 3300
tacatctttg tggccacagt gcctgtgatt gtggccttca tcatgctgag agcctacttc 3360
ctgcagacca gccagcagct gaagcagctg gagtctgagg gcagaagccc catcttcacc 3420
cacctggtga ccagcctgaa gggcctgtgg accctgagag cctttggcag acagccctac 3480
tttgagaccc tgttccacaa ggccctgaac ctgcacacag ccaactggtt cctgtacctg 3540
agcaccctga gatggttcca gatgagaatt gagatgatct ttgtgatctt cttcattgct 3600
gtgaccttca tcagcatcct gaccacaggg gagggggagg gcagagtggg catcatcctg 3660
accctggcca tgaacatcat gagcaccctg cagtgggctg tgaacagcag cattgatgtg 3720
gacagcctga tgagatctgt gagcagagtg ttcaagttca ttgacatgcc cacagagggc 3780
aagcccacca agagcaccaa gccctacaag aatggccagc tgagcaaggt gatgatcatt 3840
gagaacagcc atgtgaagaa ggatgacatc tggccctctg ggggccagat gacagtgaag 3900
gacctgacag ccaagtacac agaggggggc aatgccatcc tggagaacat cagcttcagc 3960
atcagccctg gccagagagt gggcctgctg ggcagaacag gctctggcaa gagcaccctg 4020
ctgtctgcct tcctgagact gctgaacaca gagggggaga tccagattga tggggtgagc 4080
tgggacagca tcaccctgca gcagtggaga aaggcctttg gggtgatccc ccagaaggtg 4140
ttcatcttct ctggcacctt cagaaagaac ctggacccct atgagcagtg gtctgaccag 4200
gagatctgga aggtggctga tgaggtgggc ctgagatctg tgattgagca gttccctggc 4260
aagctggact ttgtgctggt ggatgggggc tgtgtgctga gccatggcca caagcagctg 4320
atgtgcctgg ccagatctgt gctgagcaag gccaagatcc tgctgctgga tgagccctct 4380
gcccacctgg accctgtgac ctaccagatc atcagaagaa ccctgaagca ggcctttgct 4440
gactgcacag tgatcctgtg tgagcacaga attgaggcca tgctggagtg ccagcagttc 4500
ctggtgattg aggagaacaa ggtgagacag tatgacagca tccagaagct gctgaatgag 4560
agaagcctgt tcagacaggc catcagcccc tctgacagag tgaagctgtt ccccccacaga 4620 aacagcagca agtgcaagag caagccccag attgctgccc tgaaggagga gaccgaggag 4680
gaggtgcagg acaccagact gtaaataaaa tacgaaatgg atctgaggaa cccctagtga 4740
tggagttggc cactccctct ctgcgcgctc gctcgctcac tgaggccggg cgaccaaagg 4800
tcgcccgacg cccgggcttt gcccgggcgg cctcagtgag cgagcgagcg cgcagagagg 4860
gagtggccaa ttaattaagg cgatgaacgg taatcgtaaa actagcatgt caatcatatg 4920
taccccggtt gataatcaga aaagccccaa aaacaggaag attgtataag cattaattaa 4980
tttaaataca tggacatgtc agaattggtt aattggttgt aacactgacc cctatttgtt 5040
tatttttcta aatacattca aatatgtatc cgctcatgag acaataaccc tgataaatgc 5100
ttcaataata ttgaaaaagg aagaatatga gccatattca acgggaaacg tcgaggccgc 5160
gattaaattc caacatggat gctgatttat atgggtataa atgggctcgc gataatgtcg 5220
ggcaatcagg tgcgacaatc tatcgcttgt atgggaagcc cgatgcgcca gagttgtttc 5280
tgaaacatgg caaaggtagc gttgccaatg atgttacaga tgagatggtc agactaaact 5340
ggctgacgga atttatgcca cttccgacca tcaagcattt tatccgtact cctgatgatg 5400
catggttact caccactgcg atccccggaa aaacagcgtt ccaggtatta gaagaatatc 5460
ctgattcagg tgaaaatatt gttgatgcgc tggcagtgtt cctgcgccgg ttgcactcga 5520
ttcctgtttg taattgtcct tttaacagcg atcgcgtatt tcgcctcgct caggcgcaat 5580
cacgaatgaa taacggtttg gttgatgcga gtgattttga tgacgagcgt aatggctggc 5640
ctgttgaaca agtctggaaa gaaatgcata aacttttgcc attctcaccg gattcagtcg 5700
tcactcatgg tgatttctca cttgataacc ttatttttga cgaggggaaa ttaataggtt 5760
gtattgatgt tggacgagtc ggaatcgcag accgatacca ggatcttgcc atcctatgga 5820
actgcctcgg tgagttttct ccttcattac agaaacggct ttttcaaaaa tatggtattg 5880
ataatcctga tatgaataaa ttgcagtttc atttgatgct cgatgagttt ttctaaaagc 5940
agagcattac gctgacttga cgggacggcg caagctcatg accaaaatcc cttaacgtga 6000
gttacgcgcg cgtcgttcca ctgagcgtca gaccccgtag aaaagatcaa aggatcttct 6060
tgagatcctt tttttctgcg cgtaatctgc tgcttgcaaa caaaaaaacc accgctacca 6120
gcggtggttt gtttgccgga tcaagagcta ccaactcttt ttccgaaggt aactggcttc 6180
agcagagcgc agataccaaa tactgttctt ctagtgtagc cgtagttagc ccaccacttc 6240
aagaactctg tagcaccgcc tacatacctc gctctgctaa tcctgttacc agtggctgct 6300
gccagtggcg ataagtcgtg tcttaccggg ttggactcaa gacgatagtt accggataag 6360
gcgcagcggt cgggctgaac ggggggttcg tgcacacagc ccagcttgga gcgaacgacc 6420
tacaccgaac tgagatacct acagcgtgag ctatgagaaa gcgccacgct tcccgaaggg 6480
agaaaggcgg acaggtatcc ggtaagcggc agggtcggaa caggagagcg cacgagggag 6540
cttccagggg gaaacgcctg gtatctttat agtcctgtcg ggtttcgcca cctctgactt 6600
gagcgtcgat ttttgtgatg ctcgtcaggg gggcggagcc tatggaaaaa cgccagcaac 6660
gcggcctttt tacggttcct ggccttttgc tggccttttg ctcacatgtt taaaccatg 6719

<210> SEQ ID NO 89
<211> LENGTH: 6751
<212> TYPE: DNA
<213> ORGANISM: Artificial Sequence
<220> FEATURE:
<223> OTHER INFORMATION: pA-CF3

<400> SEQUENCE: 89

```
tcctgcaggc agctgcgcgc tcgctcgctc actgaggccg cccgggcaaa gcccgggcgt     60
cgggcgacct ttggtcgccc ggcctcagtg agcgagcgag cgcgcagaga gggagtggcc    120
aactccatca ctaggggttc ctgcggccgc atggaggcgg tactatgtag atgagaattc    180
aggagcaaac tgggaaaagc aactgcttcc aaatatttgt gatttttaca gtgtagtttt    240
ggaaaaactc ttagcctacc aattcttcta agtgttttaa aatgtgggag ccagtacaca    300
tgaagttata gagtgtttta atgaggctta aatatttacc gtaactatga aatgctacgc    360
atatcatgct gttcaggctc cgtggccacg caactcatac cggtagtact cgccaccatg    420
cagagaagcc ccctggagaa ggcctctgtg gtgagcaagc tgttcttcag ctggaccaga    480
cccatcctga gaaagggcta cagacagaga ctggagctgt ctgacatcta ccagatcccc    540
tctgtggact ctgctgacaa cctgtctgag aagctggaga gagagtggga cagagagctg    600
gccagcaaga agaaccccaa gctgatcaat gccctgagaa gatgcttctt ctggagattc    660
atgttctatg gcatcttcct gtacctgggg gaggtgacca aggctgtgca gcccctgctg    720
ctgggcagaa tcattgccag ctatgaccct gacaacaagg aggagagaag cattgccatc    780
tacctgggca ttggcctgtg cctgctgttc attgtgagaa ccctgctgct gcaccctgcc    840
atctttggcc tgcaccacat tggcatgcag atgagaattg ccatgttcag cctgatctac    900
aagaagaccc tgaagctgag cagcagagtg ctggacaaga tcagcattgg ccagctggtg    960
agcctgctga gcaacaacct gaacaagttt gatgagggcc tggccctggc ccactttgtg   1020
tggattgccc ccctgcaggt ggccctgctg atgggcctga tctgggagct gctgcaggcc   1080
tctgccttct gtggcctggg cttcctgatt gtgctggccc tgttccaggc tggcctgggc   1140
agaatgatga tgaagtacag agaccagaga gctggcaaga tctctgagag actggtgatc   1200
acctctgaga tgattgagaa catccagtct gtgaaggcct actgctggga ggaggccatg   1260
gagaagatga ttgagaacct gagacagaca gagctgaagc tgaccagaaa ggctgcctat   1320
gtgagatact tcaacagctc tgccttcttc ttctctggct tctttgtggt gttcctgtct   1380
gtgctgccct atgccctgat caagggcatc atcctgagaa agatcttcac caccatcagc   1440
ttctgcattg tgctgagaat ggctgtgacc agacagttcc cctgggctgt gcagacctgg   1500
tatgacagcc tgggggccat caacaagatc caggacttcc tgcagaagca ggagtacaag   1560
accctggagt acaacctgac caccacagag gtggtgatgg agaatgtgac agccttctgg   1620
gaggagggct ttggggagct gtttgagaag gccaagcaga acaacaacaa cagaaagacc   1680
agcaatgggg atgacagcct gttcttcagc aacttcagcc tgctgggcac ccctgtgctg   1740
aaggacatca acttcaagat tgagagaggc cagctgctgg ctgtggctgg cagcacaggg   1800
gctggcaaga ccagcctgct gatgatgatc atgggggagc tggagccctc tgagggcaag   1860
atcaagcact ctggcagaat cagcttctgc agccagttca gctggatcat gcctggcacc   1920
atcaaggaga acatcatctt tggggtgagc tatgatgagt acagatacag atctgtgatc   1980
aaggcctgcc agctggagga ggacatcagc aagtttgctg agaaggacaa cattgtgctg   2040
ggggaggggg gcatcaccct gtctgggggc cagagagcca gaatcagcct ggccagagct   2100
gtgtacaagg atgctgacct gtacctgctg gacagcccct ttggctacct ggatgtgctg   2160
acagagaagg agatctttga gagctgtgtg tgcaagctga tggccaacaa gaccagaatc   2220
ctggtgacca gcaagatgga gcacctgaag aaggctgaca agatcctgat cctgcatgag   2280
ggcagcagct acttctatgg caccttctct gagctgcaga acctgcagcc tgacttcagc   2340
```

agcaagctga tgggctgtga cagctttgac cagttctctg ctgagagaag aaacagcatc 2400
ctgacagaga ccctgcacag attcagcctg gagggggatg cccctgtgag ctggacagag 2460
accaagaagc agagcttcaa gcagacaggg gagtttgggg agaagagaaa gaacagcatc 2520
ctgaacccca tcaacagcac cctgcaggcc agaagaagac agtctgtgct gaacctgatg 2580
acccactctg tgaaccaggg ccagaacatc cacagaaaga ccacagccag caccagaaag 2640
gtgagcctgg ccccccaggc caacctgaca gagctggaca tctacagcag aagactgagc 2700
caggagacag gcctggagat ctctgaggag atcaatgagg aggacctgaa ggagtgcttc 2760
tttgatgaca tggagagcat ccctgctgtg accacctgga acacctacct gagatacatc 2820
acagtgcaca agagcctgat ctttgtgctg atctggtgcc tggtgatctt cctggctgag 2880
gtggctgcca gcctggtggt gctgtggctg ctgggcaaca ccccccctgca ggacaagggc 2940
aacagcaccc acagcagaaa caacagctat gctgtgatca tcaccagcac cagcagctac 3000
tatgtgttct acatctatgt gggggtggct gacaccctgc tggccatggg cttcttcaga 3060
ggcctgcccc tggtgcacac cctgatcaca gtgagcaaga tcctgcacca caagatgctg 3120
cactctgtgc tgcaggcccc catgagcacc ctgaacaccc tgaaggctgg gggcatcctg 3180
aacagattca gcaaggacat tgccatcctg gatgacctgc tgcccctgac catctttgac 3240
ttcatccagc tgctgctgat tgtgattggg gccattgctg tggtggctgt gctgcagccc 3300
tacatctttg tggccacagt gcctgtgatt gtggccttca tcatgctgag agcctacttc 3360
ctgcagacca gccagcagct gaagcagctg gagtctgagg gcagaagccc catcttcacc 3420
cacctggtga ccagcctgaa gggcctgtgg accctgagag cctttggcag acagccctac 3480
tttgagaccc tgttccacaa ggccctgaac ctgcacacag ccaactggtt cctgtacctg 3540
agcaccctga gatggttcca gatgagaatt gagatgatct ttgtgatctt cttcattgct 3600
gtgaccttca tcagcatcct gaccacaggg gagggggagg gcagagtggg catcatcctg 3660
accctggcca tgaacatcat gagcaccctg cagtgggctg tgaacagcag cattgatgtg 3720
gacagcctga tgagatctgt gagcagagtg ttcaagttca ttgacatgcc cacagagggc 3780
aagcccacca agagcaccaa gccctacaag aatggccagc tgagcaaggt gatgatcatt 3840
gagaacagcc atgtgaagaa ggatgacatc tggccctctg gggggccagat gacagtgaag 3900
gacctgacag ccaagtacac agaggggggc aatgccatcc tggagaacat cagcttcagc 3960
atcagccctg gccagagagt gggcctgctg ggcagaacag gctctggcaa gagcaccctg 4020
ctgtctgcct tcctgagact gctgaacaca gagggggaga tccagattga tggggtgagc 4080
tgggacagca tcaccctgca gcagtggaga aaggcctttg gggtgatccc ccagaaggtg 4140
ttcatcttct ctggcacctt cagaaagaac ctggacccct atgagcagtg gtctgaccag 4200
gagatctgga aggtggctga tgaggtgggc ctgagatctg tgattgagca gttccctggc 4260
aagctggact ttgtgctggt ggatgggggc tgtgtgctga gccatggcca caagcagctg 4320
atgtgcctgg ccagatctgt gctgagcaag gccaagatcc tgctgctgga tgagccctct 4380
gcccacctgg accctgtgac ctaccagatc atcagaagaa ccctgaagca ggcctttgct 4440
gactgcacag tgatcctgtg tgagcacaga attgaggcca tgctggagtg ccagcagttc 4500
ctggtgattg aggagaacaa ggtgagacag tatgacagca tccagaagct gctgaatgag 4560
agaagcctgt tcagacaggc catcagcccc tctgacagag tgaagctgtt cccccacaga 4620
aacagcagca agtgcaagag caagccccag attgctgccc tgaaggagga gaccgaggag 4680

```
gaggtgcagg acaccagact gtaaataaat atctttattt tcattacatc tgtgtgttgg   4740
tttttgtgt ggatctgagg aacccctagt gatggagttg gccactccct ctctgcgcgc   4800
tcgctcgctc actgaggccg ggcgaccaaa ggtcgcccga cgcccgggct ttgcccgggc   4860
ggcctcagtg agcgagcgag cgcgcagaga gggagtggcc aattaattaa ggcgatgaac   4920
ggtaatcgta aaactagcat gtcaatcata tgtaccccgg ttgataatca gaaaagcccc   4980
aaaaacagga agattgtata agcattaatt aatttaaata catggacatg tcagaattgg   5040
ttaattggtt gtaacactga cccctatttg tttatttttc taaatacatt caaatatgta   5100
tccgctcatg agacaataac cctgataaat gcttcaataa tattgaaaaa ggaagaatat   5160
gagccatatt caacgggaaa cgtcgaggcc gcgattaaat tccaacatgg atgctgattt   5220
atatgggtat aaatgggctc gcgataatgt cgggcaatca ggtgcgacaa tctatcgctt   5280
gtatgggaag cccgatgcgc cagagttgtt tctgaaacat ggcaaaggta gcgttgccaa   5340
tgatgttaca gatgagatgg tcagactaaa ctggctgacg gaatttatgc cacttccgac   5400
catcaagcat tttatccgta ctcctgatga tgcatggtta ctcaccactg cgatccccgg   5460
aaaaacagcg ttccaggtat tagaagaata tcctgattca ggtgaaaata ttgttgatgc   5520
gctggcagtg ttcctgcgcc ggttgcactc gattcctgtt tgtaattgtc cttttaacag   5580
cgatcgcgta tttcgcctcg ctcaggcgca atcacgaatg aataacggtt tggttgatgc   5640
gagtgatttt gatgacgagc gtaatggctg gcctgttgaa caagtctgga aagaaatgca   5700
taaacttttg ccattctcac cggattcagt cgtcactcat ggtgatttct cacttgataa   5760
ccttattttt gacgagggga aattaatagg ttgtattgat gttggacgag tcggaatcgc   5820
agaccgatac caggatcttg ccatcctatg gaactgcctc ggtgagtttt ctccttcatt   5880
acagaaacgg ctttttcaaa aatatggtat tgataatcct gatatgaata aattgcagtt   5940
tcatttgatg ctcgatgagt ttttctaaaa gcagagcatt acgctgactt gacgggacgg   6000
cgcaagctca tgaccaaaat cccttaacgt gagttacgcg cgcgtcgttc cactgagcgt   6060
cagaccccgt agaaaagatc aaaggatctt cttgagatcc ttttttctg cgcgtaatct   6120
gctgcttgca aacaaaaaaa ccaccgctac cagcggtggt ttgtttgccg gatcaagagc   6180
taccaactct ttttccgaag gtaactggct tcagcagagc gcagatacca aatactgttc   6240
ttctagtgta gccgtagtta gcccaccact tcaagaactc tgtagcaccg cctacatacc   6300
tcgctctgct aatcctgtta ccagtggctg ctgccagtgg cgataagtcg tgtcttaccg   6360
ggttggactc aagacgatag ttaccggata aggcgcagcg gtcgggctga acggggggtt   6420
cgtgcacaca gcccagcttg gagcgaacga cctacaccga actgagatac ctacagcgtg   6480
agctatgaga aagcgccacg cttcccgaag ggagaaaggc ggacaggtat ccggtaagcg   6540
gcagggtcgg aacaggagag cgcacgaggg agcttccagg gggaaacgcc tggtatcttt   6600
atagtcctgt cgggtttcgc cacctctgac ttgagcgtcg atttttgtga tgctcgtcag   6660
gggggcggag cctatggaaa aacgccagca acgcggcctt tttacggttc ctggcctttt   6720
gctggccttt tgctcacatg tttaaaccat g                                  6751
```

```
<210> SEQ ID NO 90
<211> LENGTH: 6603
<212> TYPE: DNA
<213> ORGANISM: Artificial Sequence
<220> FEATURE:
<223> OTHER INFORMATION: pA-CF5

<400> SEQUENCE: 90
```

```
tcctgcaggc agctgcgcgc tcgctcgctc actgaggccg cccgggcaaa gcccgggcgt     60
cgggcgacct ttggtcgccc ggcctcagtg agcgagcgag cgcgcagaga gggagtggcc    120
aactccatca ctaggggttc ctgcggccgc aatatttgca tgtcgctatg tgttctggga    180
aatcaccata aacgtgaaat gtctttggat ttgggaatct tcgaagttct gtatgagacc    240
acagatctcc accggtagta ctcgccacca tgcagagaag ccccctggag aaggcctctg    300
tggtgagcaa gctgttcttc agctggacca gacccatcct gagaaagggc tacagacaga    360
gactggagct gtctgacatc taccagatcc cctctgtgga ctctgctgac aacctgtctg    420
agaagctgga gagagagtgg gacagagagc tggccagcaa gaagaacccc aagctgatca    480
atgccctgag aagatgcttc ttctggagat tcatgttcta tggcatcttc ctgtacctgg    540
gggaggtgac caaggctgtg cagcccctgc tgctgggcag aatcattgcc agctatgacc    600
ctgacaacaa ggaggagaga agcattgcca tctacctggg cattggcctg tgcctgctgt    660
tcattgtgag aaccctgctg ctgcaccctg ccatctttgg cctgcaccac attggcatgc    720
agatgagaat tgccatgttc agcctgatct acaagaagac cctgaagctg agcagcagag    780
tgctggacaa gatcagcatt ggccagctgg tgagcctgct gagcaacaac ctgaacaagt    840
ttgatgaggg cctggccctg gcccactttg tgtggattgc ccccctgcag gtggccctgc    900
tgatgggcct gatctgggag ctgctgcagg cctctgcctt ctgtggcctg ggcttcctga    960
ttgtgctggc cctgttccag gctggcctgg gcagaatgat gatgaagtac agagaccaga   1020
gagctggcaa gatctctgag agactggtga tcacctctga gatgattgag aacatccagt   1080
ctgtgaaggc ctactgctgg gaggaggcca tggagaagat gattgagaac ctgagacaga   1140
cagagctgaa gctgaccaga aaggctgcct atgtgagata cttcaacagc tctgccttct   1200
tcttctctgg cttctttgtg gtgttcctgt ctgtgctgcc ctatgccctg atcaagggca   1260
tcatcctgag aaagatcttc accaccatca gcttctgcat tgtgctgaga atggctgtga   1320
ccagacagtt cccctgggct gtgcagacct ggtatgacag cctgggggcc atcaacaaga   1380
tccaggactt cctgcagaag caggagtaca agaccctgga gtacaacctg accaccacag   1440
aggtggtgat ggagaatgtg acagccttct gggaggaggg ctttggggag ctgtttgaga   1500
aggccaagca gaacaacaac aacagaaaga ccagcaatgg ggatgacagc ctgttcttca   1560
gcaacttcag cctgctgggc acccctgtgc tgaaggacat caacttcaag attgagagag   1620
gccagctgct ggctgtggct ggcagcacag ggctggcaa gaccagcctg ctgatgatga   1680
tcatggggga gctggagccc tctgagggca agatcaagca ctctggcaga atcagcttct   1740
gcagccagtt cagctggatc atgcctggca ccatcaagga gaacatcatc tttggggtga   1800
gctatgatga gtacagatac agatctgtga tcaaggcctg ccagctggag gaggacatca   1860
gcaagtttgc tgagaaggac aacattgtgc tgggggaggg gggcatcacc ctgtctgggg   1920
gccagagagc cagaatcagc ctggccagag ctgtgtacaa ggatgctgac ctgtacctgc   1980
tggacagccc ctttggctac ctggatgtgc tgacagagaa ggagatcttt gagagctgtg   2040
tgtgcaagct gatggccaac aagaccagaa tcctggtgac cagcaagatg gagcacctga   2100
agaaggctga caagatcctg atcctgcatg agggcagcag ctacttctat ggcaccttct   2160
ctgagctgca gaacctgcag cctgacttca gcagcaagct gatgggctgt gacagctttg   2220
accagttctc tgctgagaga agaaacagca tcctgacaga gaccctgcac agattcagcc   2280
tggaggggga tgcccctgtg agctggacag agaccaagaa gcagagcttc aagcagacag   2340
```

-continued

```
gggagtttgg ggagaagaga aagaacagca tcctgaaccc catcaacagc accctgcagg   2400
ccagaagaag acagtctgtg ctgaacctga tgacccactc tgtgaaccag ggccagaaca   2460
tccacagaaa gaccacagcc agcaccagaa aggtgagcct ggccccccag gccaacctga   2520
cagagctgga catctacagc agaagactga gccaggagac aggcctggag atctctgagg   2580
agatcaatga ggaggacctg aaggagtgct tctttgatga catggagagc atccctgctg   2640
tgaccacctg gaacacctac ctgagataca tcacagtgca caagagcctg atctttgtgc   2700
tgatctggtg cctggtgatc ttcctggctg aggtggctgc cagcctggtg gtgctgtggc   2760
tgctgggcaa caccccccctg caggacaagg gcaacagcac ccacagcaga aacaacagct   2820
atgctgtgat catcaccagc accagcagct actatgtgtt ctacatctat gtgggggtgg   2880
ctgacaccct gctggccatg ggcttcttca gaggcctgcc cctggtgcac accctgatca   2940
cagtgagcaa gatcctgcac cacaagatgc tgcactctgt gctgcaggcc cccatgagca   3000
ccctgaacac cctgaaggct gggggcatcc tgaacagatt cagcaaggac attgccatcc   3060
tggatgacct gctgcccctg accatctttg acttcatcca gctgctgctg attgtgattg   3120
gggccattgc tgtggtggct gtgctgcagc cctacatctt tgtggccaca gtgcctgtga   3180
ttgtggcctt catcatgctg agagcctact tcctgcagac cagccagcag ctgaagcagc   3240
tggagtctga gggcagaagc cccatcttca cccacctggt gaccagcctg aagggcctgt   3300
ggaccctgag agcctttggc agacagccct actttgagac cctgttccac aaggccctga   3360
acctgcacac agccaactgg ttcctgtacc tgagcaccct gagatggttc cagatgagaa   3420
ttgagatgat ctttgtgatc ttcttcattg ctgtgacctt catcagcatc ctgaccacag   3480
gggaggggga gggcagagtg ggcatcatcc tgaccctggc catgaacatc atgagcaccc   3540
tgcagtgggc tgtgaacagc agcattgatg tggacagcct gatgagatct gtgagcagag   3600
tgttcaagtt cattgacatg cccacagagg gcaagcccac caagagcacc aagccctaca   3660
agaatggcca gctgagcaag gtgatgatca ttgagaacag ccatgtgaag aaggatgaca   3720
tctggccctc tgggggccag atgacagtga aggacctgac agccaagtac acagaggggg   3780
gcaatgccat cctggagaac atcagcttca gcatcagccc tggccagaga gtgggcctgc   3840
tgggcagaac aggctctggc aagagcaccc tgctgtctgc cttcctgaga ctgctgaaca   3900
cagaggggga gatccagatt gatggggtga gctgggacag catcaccctg cagcagtgga   3960
gaaaggcctt tggggtgatc cccagaaggg tgttcatctt ctctggcacc ttcagaaaga   4020
acctggaccc ctatgagcag tggtctgacc aggagatctg gaaggtggct gatgaggtgg   4080
gcctgagatc tgtgattgag cagttccctg gcaagctgga ctttgtgctg gtggatgggg   4140
gctgtgtgct gagccatggc cacaagcagc tgatgtgcct ggccagatct gtgctgagca   4200
aggccaagat cctgctgctg gatgagccct ctgcccacct ggaccctgtg acctaccaga   4260
tcatcagaag aaccctgaag caggcctttg ctgactgcac agtgatcctg tgtgagcaca   4320
gaattgaggc catgctggag tgccagcagt tcctggtgat tgaggagaac aaggtgagac   4380
agtatgacag catccagaag ctgctgaatg agagaagcct gttcagacag gccatcagcc   4440
cctctgacag agtgaagctg ttcccccaca gaaacagcag caagtgcaag agcaagcccc   4500
agattgctgc cctgaaggag gagaccgagg aggaggtgca ggacaccaga ctgtaaataa   4560
atatctttat tttcattaca tctgtgtgtt ggttttttgt gtggatctga ggaaccccta   4620
gtgatggagt tggccactcc ctctctgcgc gctcgctcgc tcactgaggc cgggcgacca   4680
aaggtcgccc gacgcccggg ctttgcccgg gcggcctcag tgagcgagcg agcgcgcaga   4740
```

gagggagtgg ccaattaatt aaggcgatga acggtaatcg taaaactagc atgtcaatca 4800
tatgtacccc ggttgataat cagaaaagcc ccaaaaacag gaagattgta taagcattaa 4860
ttaatttaaa tacatggaca tgtcagaatt ggttaattgg ttgtaacact gacccctatt 4920
tgtttatttt tctaaataca ttcaaatatg tatccgctca tgagacaata accctgataa 4980
atgcttcaat aatattgaaa aaggaagaat atgagccata ttcaacggga aacgtcgagg 5040
ccgcgattaa attccaacat ggatgctgat ttatatgggt ataaatgggc tcgcgataat 5100
gtcgggcaat caggtgcgac aatctatcgc ttgtatggga agcccgatgc gccagagttg 5160
tttctgaaac atggcaaagg tagcgttgcc aatgatgtta cagatgagat ggtcagacta 5220
aactggctga cggaatttat gccacttccg accatcaagc attttatccg tactcctgat 5280
gatgcatggt tactcaccac tgcgatcccc ggaaaaacag cgttccaggt attagaagaa 5340
tatcctgatt caggtgaaaa tattgttgat gcgctggcag tgttcctgcg ccggttgcac 5400
tcgattcctg tttgtaattg tccttttaac agcgatcgcg tatttcgcct cgctcaggcg 5460
caatcacgaa tgaataacgg tttggttgat gcgagtgatt ttgatgacga gcgtaatggc 5520
tggcctgttg aacaagtctg gaaagaaatg cataaacttt tgccattctc accggattca 5580
gtcgtcactc atggtgattt ctcacttgat aaccttattt ttgacgaggg gaaattaata 5640
ggttgtattg atgttggacg agtcggaatc gcagaccgat accaggatct tgccatccta 5700
tggaactgcc tcggtgagtt ttctccttca ttacagaaac ggctttttca aaaatatggt 5760
attgataatc ctgatatgaa taaattgcag tttcatttga tgctcgatga gtttttctaa 5820
aagcagagca ttacgctgac ttgacgggac ggcgcaagct catgaccaaa atcccttaac 5880
gtgagttacg cgcgcgtcgt tccactgagc gtcagacccc gtagaaaaga tcaaaggatc 5940
ttcttgagat cctttttttc tgcgcgtaat ctgctgcttg caaacaaaaa aaccaccgct 6000
accagcggtg gtttgtttgc cggatcaaga gctaccaact ctttttccga aggtaactgg 6060
cttcagcaga gcgcagatac caaatactgt tcttctagtg tagccgtagt tagcccacca 6120
cttcaagaac tctgtagcac cgcctacata cctcgctctg ctaatcctgt taccagtggc 6180
tgctgccagt ggcgataagt cgtgtcttac cgggttggac tcaagacgat agttaccgga 6240
taaggcgcag cggtcgggct gaacgggggg ttcgtgcaca cagcccagct tggagcgaac 6300
gacctacacc gaactgagat acctacagcg tgagctatga gaaagcgcca cgcttcccga 6360
agggagaaag gcggacaggt atccggtaag cggcagggtc ggaacaggag agcgcacgag 6420
ggagcttcca gggggaaacg cctggtatct ttatagtcct gtcgggtttc gccacctctg 6480
acttgagcgt cgatttttgt gatgctcgtc aggggggcgg agcctatgga aaaacgccag 6540
caacgcggcc tttttacggt tcctggcctt ttgctggcct tttgctcaca tgtttaaacc 6600
atg 6603

<210> SEQ ID NO 91
<211> LENGTH: 7519
<212> TYPE: DNA
<213> ORGANISM: Artificial Sequence
<220> FEATURE:
<223> OTHER INFORMATION: pA-CF7

<400> SEQUENCE: 91
tcctgcaggc agctgcgcgc tcgctcgctc actgaggccg cccgggcaaa gcccgggcgt 60
cgggcgacct ttggtcgccc ggcctcagtg agcgagcgag cgcgcagaga gggagtggcc 120

```
aactccatca ctaggggttc ctgcggccgc aatatttgca tgtcgctatg tgttctggga    180
aatcaccata aacgtgaaat gtctttggat ttgggaatct tcgaagttct gtatgagacc    240
acagatctcc accggtagta ctcgccacca tgcagagaag ccccctggag aaggcctctg    300
tggtgagcaa gctgttcttc ccccctggag aaggcctctg tggtgagcaa gctgttcttc    360
agctggacca gacccatcct gagaaagggc tacagacaga gactggagct gtctgacatc    420
taccagatcc cctctgtgga ctctgctgac aacctgtctg agaagctgga gagagagtgg    480
gacagagagc tggccagcaa gaagaacccc aagctgatca atgccctgag aagatgcttc    540
ttctggagat tcatgttcta tggcatcttc ctgtacctgg gggaggtgac caaggctgtg    600
cagcccctgc tgctgggcag aatcattgcc agctatgacc cagcccctgc tgctgggcag    660
aatcattgcc agctatgacc ctgacaacaa ggaggagaga agcattgcca tctacctggg    720
cattggcctg tgcctgctgt tcattgtgag aaccctgctg ctgcaccctg ccatctttgg    780
cctgcaccac attggcatgc agatgagaat tgccatgttc agcctgatct acaagaagac    840
cctgaagctg agcagcagag tgctggacaa gatcagcatt ggccagctgg tgagcctgct    900
gagcaacaac ctgaacaagt ttgatgaggg cctggccctg gcccactttg tgtggattgc    960
ttgatgaggg cctggccctg gcccactttg tgtggattgc cccctgcag gtggccctgc    1020
tgatgggcct gatctgggag ctgctgcagg cctctgcctt ctgtggcctg ggcttcctga   1080
ttgtgctggc cctgttccag gctggcctgg gcagaatgat gatgaagtac agagaccaga   1140
gagctggcaa gatctctgag agactggtga tcacctctga gatgattgag aacatccagt   1200
ctgtgaaggc ctactgctgg gaggaggcca tggagaagat gattgagaac ctgagacaga   1260
cagagctgaa gctgaccaga aaggctgcct atgtgagata cttcaacagc tctgccttct   1320
tcttctctgg cttctttgtg gtgttcctgt ctgtgctgcc tctgccttct tcttctctgg   1380
cttctttgtg gtgttcctgt ctgtgctgcc ctatgccctg atcaagggca tcatcctgag   1440
aaagatcttc accaccatca gcttctgcat tgtgctgaga atggctgtga ccagacagtt   1500
cccctgggct gtgcagacct ggtatgacag cctgggggcc atcaacaaga tccaggactt   1560
cctgcagaag caggagtaca agaccctgga gtacaacctg accaccacag aggtggtgat   1620
ggagaatgtg acagccttct gggaggaggg ctttggggag ctgtttgaga aggccaagca   1680
gaacaacaac aacagaaaga ccagcaatgg ggatgacagc ctgttcttca gcaacttcag   1740
cctgctgggc acccctgtgc ggatgacagc ctgttcttca gcaacttcag cctgctgggc   1800
acccctgtgc tgaaggacat caacttcaag attgagagag gccagctgct ggctgtggct   1860
ggcagcacag ggctggcaa gaccagcctg ctgatgatga tcatgggga gctggagccc     1920
tctgagggca agatcaagca ctctggcaga atcagcttct gcagccagtt cagctggatc   1980
atgcctggca ccatcaagga gaacatcatc tttggggtga gctatgatga gtacagatac   2040
agatctgtga tcaaggcctg ccagctggag gaggacatca agatctgtga tcaaggcctg   2100
ccagctggag gaggacatca gcaagtttgc tgagaaggac aacattgtgc tgggggaggg   2160
gggcatcacc ctgtctgggg gccagagagc cagaatcagc ctggccagag ctgtgtacaa   2220
ggatgctgac ctgtacctgc tggacagccc ctttggctac ctggatgtgc tgacagagaa   2280
ggagatcttt gagagctgtg tgtgcaagct gatggccaac aagaccagaa tcctggtgac   2340
cagcaagatg gagcacctga agaaggctga caagatcctg atcctgcatg agggcagcag   2400
agaaggctga caagatcctg atcctgcatg agggcagcag ctacttctat ggcaccttct   2460
ctgagctgca gaacctgcag cctgacttca gcagcaagct gatgggctgt gacagctttg   2520
```

accagttctc tgctgagaga agaaacagca tcctgacaga gaccctgcac agattcagcc 2580
tggaggggga tgcccctgtg agctggacag agaccaagaa gcagagcttc aagcagacag 2640
gggagtttgg ggagaagaga aagaacagca tcctgaaccc catcaacagc atcagaaagt 2700
tcagcattgt gcagaagacc catcaacagc atcagaaagt tcagcattgt gcagaagacc 2760
cccctgcaga tgaatggcat tgaggaggac tctgatgagc cctggagag aagactgagc 2820
ctggtgcctg actctgagca gggggaggcc atcctgccca gaatctctgt gatcagcaca 2880
ggccccaccc tgcaggccag aagaagacag tctgtgctga acctgatgac ccactctgtg 2940
aaccagggcc agaacatcca ccactctgtg aaccagggcc agaacatcca cagaaagacc 3000
acagccagca ccagaaaggt gagcctggcc ccccaggcca acctgacaga gctggacatc 3060
tacagcagaa gactgagcca ggagacaggc ctggagatct ctgaggagat caatgaggag 3120
gacctgaagg agtgcttctt tgatgacatg gagagcatcc ctgctgtgac cacctggaac 3180
acctacctga gatacatcac agtgcacaag agcctgatct ttgtgctgat ctggtgcctg 3240
gtgatcttcc tggctgaggt ggctgccagc ctggtggtgc gtgatcttcc tggctgaggt 3300
ggctgccagc ctggtggtgc tgtggctgct gggcaacacc cccctgcagg acaagggcaa 3360
cagcacccac agcagaaaca acagctatgc tgtgatcatc accagcacca gcagctacta 3420
tgtgttctac atctatgtgg gggtggctga caccctgctg gccatgggct tcttcagagg 3480
cctgcccctg gtgcacaccc tgatcacagt gagcaagatc ctgcaccaca agatgctgca 3540
ctctgtgctg caggccccca tgagcaccct gaacaccctg aaggctgggg gcatcctgaa 3600
tgagcaccct gaacaccctg aaggctgggg gcatcctgaa cagattcagc aaggacattg 3660
ccatcctgga tgacctgctg cccctgacca tctttgactt catccagctg ctgctgattg 3720
tgattggggc cattgctgtg gtggctgtgc tgcagcccta catctttgtg gccacagtgc 3780
ctgtgattgt ggccttcatc atgctgagag cctacttcct gcagaccagc cagcagctga 3840
agcagctgga gtctgagggc agaagcccca tcttcaccca cctggtgacc agcctgaagg 3900
gcctgtggac cctgagagcc cctggtgacc agcctgaagg gcctgtggac cctgagagcc 3960
tttggcagac agccctactt tgagaccctg ttccacaagg ccctgaacct gcacacagcc 4020
aactggttcc tgtacctgag caccctgaga tggttccaga tgagaattga gatgatcttt 4080
gtgatcttct tcattgctgt gaccttcatc agcatcctga ccacagggga gggggagggc 4140
agagtgggca tcatcctgac cctggccatg aacatcatga gcaccctgca gtgggctgtg 4200
aacagcagca ttgatgtgga cagcctgatg agatctgtga gcagagtgtt caagttcatt 4260
gacatgccca cagagggcaa gcccaccaag agcaccaagc cctacaagaa tggccagctg 4320
cagagggcaa gcccaccaag agcaccaagc cctacaagaa tggccagctg agcaaggtga 4380
tgatcattga gaacagccat gtgaagaagg atgacatctg gccctctggg ggccagatga 4440
cagtgaagga cctgacagcc aagtacacag agggggggcaa tgccatcctg gagaacatca 4500
gcttcagcat cagccctggc cagagagtgg gcctgctggg cagaacaggc tctggcaaga 4560
gcaccctgct gtctgccttc ctgagactgc tgaacacaga gggggagatc cagattgatg 4620
gggtgagctg ggacagcatc accctgcagc agtggagaaa ggcctttggg gtgatccccc 4680
agaaggtgtt catcttctct ggcaccttca gaaagaacct gtgatccccc agaaggtgtt 4740
catcttctct ggcaccttca gaaagaacct ggacccctat gagcagtggt ctgaccagga 4800
gatctggaag gtggctgatg aggtgggcct gagatctgtg attgagcagt tccctggcaa 4860

```
gctggacttt gtgctggtgg atgggggctg tgtgctgagc catggccaca agcagctgat   4920
gtgcctggcc agatctgtgc tgagcaaggc caagatcctg ctgctggatg agccctctgc   4980
ccacctggac cctgtgacct accagatcat cagaagaacc ctgaagcagg cctttgctga   5040
accagatcat cagaagaacc ctgaagcagg cctttgctga ctgcacagtg atcctgtgtg   5100
agcacagaat tgaggccatg ctggagtgcc agcagttcct ggtgattgag gagaacaagg   5160
tgagacagta tgacagcatc cagaagctgc tgaatgagag aagcctgttc agacaggcca   5220
tcagcccctc tgacagagtg aagctgttcc cccacagaaa cagcagcaag tgcaagagca   5280
agccccagat tgctgccctg aaggaggaga ccgaggagga ggtgcaggac accagactgt   5340
aaataaatat ctttattttc attacatctg tgtgttggtt ttttgtgtgg atctgaggaa   5400
cccctagtga tggagttggc cactccctct ctgcgcgctc atctgaggaa cccctagtga   5460
tggagttggc cactccctct ctgcgcgctc gctcgctcac tgaggccggg cgaccaaagg   5520
tcgcccgacg cccgggcttt gcccgggcgg cctcagtgag cgagcgagcg cgcagagagg   5580
gagtggccaa ttaattaagg cgatgaacgg taatcgtaaa actagcatgt caatcatatg   5640
taccccggtt gataatcaga aaagccccaa aaacaggaag attgtataag cattaattaa   5700
tttaaataca tggacatgtc agaattggtt aattggttgt aacactgacc cctatttgtt   5760
tatttttcta aatacattca aatatgtatc cgctcatgag acaataaccc tgataaatgc   5820
ttcaataata ttgaaaaagg aagaatatga gccatattca acgggaaacg tcgaggccgc   5880
gattaaattc caacatggat gctgatttat atgggtataa atgggctcgc gataatgtcg   5940
ggcaatcagg tgcgacaatc tatcgcttgt atgggaagcc cgatgcgcca gagttgtttc   6000
gataatgtcg ggcaatcagg tgcgacaatc tatcgcttgt atgggaagcc cgatgcgcca   6060
gagttgtttc tgaaacatgg caaaggtagc gttgccaatg atgttacaga tgagatggtc   6120
agactaaact ggctgacgga atttatgcca cttccgacca tcaagcattt tatccgtact   6180
cctgatgatg catggttact caccactgcg atccccggaa aaacagcgtt ccaggtatta   6240
gaagaatatc ctgattcagg tgaaaatatt gttgatgcgc tggcagtgtt cctgcgccgg   6300
ttgcactcga ttcctgtttg taattgtcct tttaacagcg atcgcgtatt tcgcctcgct   6360
caggcgcaat cacgaatgaa taacggtttg gttgatgcga gtgattttga tgacgagcgt   6420
aatggctggc ctgttgaaca agtctggaaa gaaatgcata aacttttgcc attctcaccg   6480
gattcagtcg tcactcatgg tgatttctca cttgataacc ttatttttga cgaggggaaa   6540
ttaataggtt gtattgatgt tggacgagtc ggaatcgcag accgatacca ggatcttgcc   6600
atcctatgga actgcctcgg tgagttttct ccttcattac agaaacggct ttttcaaaaa   6660
tatggtattg ataatcctga tatgaataaa ttgcagtttc atttgatgct cgatgagttt   6720
ttctaaaagc agagcattac gctgacttga cgggacggcg caagctcatg accaaaatcc   6780
cttaacgtga gttacgcgcg cgtcgttcca ctgagcgtca gaccccgtag aaaagatcaa   6840
aggatcttct tgagatcctt tttttctgcg cgtaatctgc tgcttgcaaa caaaaaaacc   6900
accgctacca gcggtggttt gtttgccgga tcaagagcta ccaactcttt ttccgaaggt   6960
aactggcttc agcagagcgc agataccaaa tactgttctt ctagtgtagc cgtagttagc   7020
ccaccacttc aagaactctg tagcaccgcc tacatacctc gctctgctaa tcctgttacc   7080
agtggctgct gccagtggcg ataagtcgtg tcttaccggg ttggactcaa gacgatagtt   7140
accggataag gcgcagcggt cgggctgaac ggggggttcg tgcacacagc ccagcttgga   7200
ccagcttgga gcgaacgacc tacaccgaac tgagatacct acagcgtgag ctatgagaaa   7260
```

```
gcgccacgct tcccgaaggg agaaaggcgg acaggtatcc ggtaagcggc agggtcggaa   7320

caggagagcg cacgagggag cttccagggg gaaacgcctg gtatctttat agtcctgtcg   7380

ggtttcgcca cctctgactt gagcgtcgat ttttgtgatg ctcgtcaggg gggcggagcc   7440

tatggaaaaa cgccagcaac gcggcctttt tacggttcct ggccttttgc tggccttttg   7500

ctcacatgtt taaaccatg                                                7519
```

```
<210> SEQ ID NO 92
<211> LENGTH: 11577
<212> TYPE: DNA
<213> ORGANISM: Artificial Sequence
<220> FEATURE:
<223> OTHER INFORMATION: pHELPK plasmid DNA

<400> SEQUENCE: 92

ggtacccaac tccatgctta acagtcccca ggtacagccc accctgcgtc gcaaccagga     60

acagctctac agcttcctgg agcgccactc gccctacttc cgcagccaca gtgcgcagat    120

taggagcgcc acttcttttt gtcacttgaa aaacatgtaa aaataatgta ctaggagaca    180

ctttcaataa aggcaaatgt ttttatttgt acactctcgg gtgattattt accccccacc    240

cttgccgtct gcgccgttta aaaatcaaag ggttctgccg gcgcatcgct atgcgccact    300

ggcagggaca cgttgcgata ctggtgttta gtgctccact taaactcagg cacaaccatc    360

cgcggcagct cggtgaagtt ttcactccac aggctgcgca ccatcaccaa cgcgtttagc    420

aggtcgggcg ccgatatctt gaagtcgcag ttggggcctc cgccctgcgc gcgcgagttg    480

cgatacacag ggttgcagca ctggaacact atcagcgccg ggtggtgcac gctggccagc    540

acgctcttgt cggagatcag atccgcgtcc aggtcctccg cgttgctcag ggcgaacgga    600

gtcaactttg gtagctgcct tcccaaaaag ggtgcatgcc caggctttga gttgcactcg    660

caccgtagtg gcatcagaag gtgaccgtgc ccggtctggg cgttaggata cagcgcctgc    720

atgaaagcct tgatctgctt aaaagccacc tgagcctttg cgccttcaga gaagaacatg    780

ccgcaagact tgccggaaaa ctgattggcc ggacaggccg cgtcatgcac gcagcacctt    840

gcgtcggtgt tggagatctg caccacattt cggccccacc ggttcttcac gatcttggcc    900

ttgctagact gctccttcag cgcgcgctgc ccgttttcgc tcgtcacatc catttcaatc    960

acgtgctcct tatttatcat aatgctcccg tgtagacact taagctcgcc ttcgatctca   1020

gcgcagcggt gcagccacaa cgcgcagccc gtgggctcgt ggtgcttgta ggttacctct   1080

gcaaacgact gcaggtacgc ctgcaggaat cgccccatca tcgtcacaaa ggtcttgttg   1140

ctggtgaagg tcagctgcaa cccgcggtgc tcctcgttta gccaggtctt gcatacggcc   1200

gccagagctt ccacttggtc aggcagtagc ttgaagtttg cctttagatc gttatccacg   1260

tggtacttgt ccatcaacgc gcgcgcagcc tccatgccct tctcccacgc agacacgatc   1320

ggcaggctca gcgggtttat caccgtgctt tcactttccg cttcactgga ctcttccttt   1380

tcctcttgcg tccgcatacc ccgcgccact gggtcgtctt cattcagccg ccgcaccgtg   1440

cgcttacctc ccttgccgtg cttgattagc accggtgggt tgctgaaacc caccatttgt   1500

agcgccacat cttctctttc ttcctcgctg tccacgatca cctctgggga tggcgggcgc   1560

tcgggcttgg gagaggggcg cttctttttc tttttggacg caatggccaa atccgccgtc   1620

gaggtcgatg gccgcgggct gggtgtgcgc ggcaccagcg catcttgtga cgagtcttct   1680

tcgtcctcgg actcgagacg ccgcctcagc cgcttttttg ggggcgcgcg gggaggcggc   1740
```

```
ggcgacggcg acggggacga cacgtcctcc atggttggtg gacgtcgcgc cgcaccgcgt   1800
ccgcgctcgg gggtggtttc gcgctgctcc tcttcccgac tggccatttc cttctcctat   1860
aggcagaaaa agatcatgga gtcagtcgag aaggaggaca gcctaaccgc cccctttgag   1920
ttcgccacca ccgcctccac cgatgccgcc aacgcgccta ccaccttccc cgtcgaggca   1980
cccccgcttg aggaggagga agtgattatc gagcaggacc caggttttgt aagcgaagac   2040
gacgaggatc gctcagtacc aacagaggat aaaaagcaag accaggacga cgcagaggca   2100
aacgaggaac aagtcgggcg gggggaccaa aggcatggcg actacctaga tgtgggagac   2160
gacgtgctgt tgaagcatct gcagcgccag tgcgccatta tctgcgacgc gttgcaagag   2220
cgcagcgatg tgcccctcgc catagcggat gtcagccttg cctacgaacg ccacctgttc   2280
tcaccgcgcg taccccccaa acgccaagaa aacggcacat gcgagcccaa cccgcgcctc   2340
aacttctacc ccgtatttgc cgtgccagag gtgcttgcca cctatcacat ctttttccaa   2400
aactgcaaga taccccctatc ctgccgtgcc aaccgcagcc gagcggacaa gcagctggcc   2460
ttgcggcagg gcgctgtcat acctgatatc gcctcgctcg acgaagtgcc aaaaatcttt   2520
gagggtcttg gacgcgacga gaaacgcgcg gcaaacgctc tgcaacaaga aaacagcgaa   2580
aatgaaagtc actgtggagt gctggtggaa cttgagggtg acaacgcgcg cctagccgtg   2640
ctgaaacgca gcatcgaggt cacccacttt gcctacccgg cacttaacct accccccaag   2700
gttatgagca cagtcatgag cgagctgatc gtgcgccgtg cacgacccct ggagagggat   2760
gcaaacttgc aagaacaaac cgaggagggc ctacccgcag ttggcgatga gcagctggcg   2820
cgctggcttg agacgcgcga gcctgccgac ttggaggagc gacgcaagct aatgatggcc   2880
gcagtgcttg ttaccgtgga gcttgagtgc atgcagcggt tctttgctga cccggagatg   2940
cagcgcaagc tagaggaaac gttgcactac acctttcgcc agggctacgt gcgccaggcc   3000
tgcaaaattt ccaacgtgga gctctgcaac ctggtctcct accttggaat tttgcacgaa   3060
aaccgcctcg ggcaaaacgt gcttcattcc acgctcaagg gcgaggcgcg ccgcgactac   3120
gtccgcgact gcgtttactt atttctgtgc tacacctggc aaacggccat gggcgtgtgg   3180
cagcaatgcc tggaggagcg caacctaaag gagctgcaga agctgctaaa gcaaaacttg   3240
aaggacctat ggacggcctt caacgagcgc tccgtggccg cgcacctggc ggacattatc   3300
ttccccgaac gcctgcttaa aaccctgcaa cagggtctgc cagacttcac cagtcaaagc   3360
atgttgcaaa actttaggaa ctttatccta gagcgttcag gaattctgcc cgccacctgc   3420
tgtgcgcttc ctagcgactt tgtgcccatt aagtaccgtg aatgccctcc gccgctttgg   3480
ggtcactgct accttctgca gctagccaac taccttgcct accactccga catcatggaa   3540
gacgtgagcg gtgacggcct actggagtgt cactgtcgct gcaacctatg caccccgcac   3600
cgctccctgg tctgcaattc gcaactgctt agcgaaagtc aaattatcgg tacctttgag   3660
ctgcagggtc cctcgcctga cgaaaagtcc gcggctccgg ggttgaaact cactccgggg   3720
ctgtggacgt cggcttacct tcgcaaattt gtacctgagg actaccacgc ccacgagatt   3780
aggttctacg aagaccaatc ccgcccgcca aatgcggagc ttaccgcctg cgtcattacc   3840
cagggccaca tccttggcca attgcaagcc atcaacaaag cccgccaaga gtttctgcta   3900
cgaaagggac ggggggttta cctggacccc cagtccggcg aggagctcaa cccaatcccc   3960
ccgccgccgc agccctatca gcagccgcgg gcccttgctt cccaggatgg cacccaaaaa   4020
gaagctgcag ctgccgccgc cgccacccac ggacgaggag gaatactggg acagtcaggc   4080
agaggaggtt ttggacgagg aggaggagat gatggaagac tgggacagcc tagacgaagc   4140
```

```
ttccgaggcc gaagaggtgt cagacgaaac accgtcaccc tcggtcgcat tcccctcgcc   4200
ggcgccccag aaattggcaa ccgttcccag catcgctaca acctccgctc ctcaggcgcc   4260
gccggcactg cctgttcgcc gacccaaccg tagatgggac accactggaa ccagggccgg   4320
taagtctaag cagccgccgc cgttagccca agagcaacaa cagcgccaag gctaccgctc   4380
gtggcgcggg cacaagaacg ccatagttgc ttgcttgcaa gactgtgggg gcaacatctc   4440
cttcgcccgc cgctttcttc tctaccatca cggcgtggcc ttcccccgta acatcctgca   4500
ttactaccgt catctctaca gcccctactg caccggcggc agcggcagcg gcagcaacag   4560
cagcggtcac acagaagcaa aggcgaccgg atagcaagac tctgacaaag cccaagaaat   4620
ccacagcggc ggcagcagca ggaggaggag cgctgcgtct ggcgcccaac gaacccgtat   4680
cgacccgcga gcttagaaat aggatttttc ccactctgta tgctatattt caacaaagca   4740
ggggccaaga acaagagctg aaaataaaaa acaggtctct gcgctccctc acccgcagct   4800
gcctgtatca caaaagcgaa gatcagcttc ggcgcacgct ggaagacgcg gaggctctct   4860
tcagcaaata ctgcgcgctg actcttaagg actagtttcg cgccctttct caaatttaag   4920
cgcgaaaact acgtcatctc cagcggccac acccggcgcc agcacctgtc gtcagcgcca   4980
ttatgagcaa ggaaattccc acgccctaca tgtggagtta ccagccacaa atgggacttg   5040
cggctggagc tgcccaagac tactcaaccc gaataaacta catgagcgcg ggaccccaca   5100
tgatatcccg ggtcaacgga atccgcgccc accgaaaccg aattctcctc gaacaggcgg   5160
ctattaccac cacacctcgt aataacctta atccccgtag ttggcccgct gccctggtgt   5220
accaggaaag tcccgctccc accactgtgg tacttcccag agacgcccag gccgaagttc   5280
agatgactaa ctcaggggcg cagcttgcgg gcggctttcg tcacagggtg cggtcgcccg   5340
ggcgttttag ggcggagtaa cttgcatgta ttgggaattg tagttttttt aaaatgggaa   5400
gtgacgtatc gtgggaaaac ggaagtgaag atttgaggaa gttgtgggtt ttttggcttt   5460
cgtttctggg cgtaggttcg cgtgcggttt tctgggtgtt ttttgtggac tttaaccgtt   5520
acgtcatttt ttagtcctat atatactcgc tctgtacttg gccctttta cactgtgact   5580
gattgagctg gtgccgtgtc gagtggtgtt ttttaatagg tttttttact ggtaaggctg   5640
actgttatgg ctgccgctgt ggaagcgctg tatgttgttc tggagcggga gggtgctatt   5700
ttgcctaggc aggagggttt ttcaggtgtt tatgtgtttt tctctcctat taattttgtt   5760
atacctccta tgggggctgt aatgttgtct ctacgcctgc gggtatgtat tcccccgggc   5820
tatttcggtc gctttttagc actgaccgat gttaaccaac ctgatgtgtt taccgagtct   5880
tacattatga ctccggacat gaccgaggaa ctgtcggtgg tgctttttaa tcacggtgac   5940
cagttttttt acggtcacgc cggcatggcc gtagtccgtc ttatgcttat aagggttgtt   6000
tttcctgttg taagacaggc ttctaatgtt taaatgtttt tttttttgtt attttatttt   6060
gtgtttaatg caggaacccg cagacatgtt tgagagaaaa atggtgtctt tttctgtggt   6120
ggttccggaa cttacctgcc tttatctgca tgagcatgac tacgatgtgc ttgctttttt   6180
gcgcgaggct ttgcctgatt ttttgagcag caccttgcat tttatatcgc cgcccatgca   6240
acaagcttac ataggggcta cgctggttag catagctccg agtatgcgtg tcataatcag   6300
tgtgggttct tttgtcatgg ttcctggcgg ggaagtggcc gcgctggtcc gtgcagacct   6360
gcacgattat gttcagctgg ccctgcgaag ggacctacgg gatcgcggta tttttgttaa   6420
tgttccgctt ttgaatctta tacaggtctg tgaggaacct gaatttttgc aatcatgatt   6480
```

```
cgctgcttga ggctgaaggt ggagggcgct ctggagcaga tttttacaat ggccggactt   6540
aatattcggg atttgcttag agacatattg ataaggtggc gagatgaaaa ttatttgggc   6600
atggttgaag gtgctggaat gtttatagag gagattcacc ctgaagggtt tagcctttac   6660
gtccacttgg acgtgagggc agtttgcctt ttggaagcca ttgtgcaaca tcttacaaat   6720
gccattatct gttctttggc tgtagagttt gaccacgcca ccggagggga gcgcgttcac   6780
ttaatagatc ttcattttga ggttttggat aatcttttgg aataaaaaaa aaaaaacatg   6840
gttcttccag ctcttcccgc tcctcccgtg tgtgactcgc agaacgaatg tgtaggttgg   6900
ctgggtgtgg cttattctgc ggtggtggat gttatcaggg cagcggcgca tgaaggagtt   6960
tacatagaac ccgaagccag gggcgcctg gatgctttga gagagtggat atactacaac   7020
tactacacag agcgagctaa gcgacgagac cggagacgca gatctgtttg tcacgcccgc   7080
acctggtttt gcttcaggaa atatgactac gtccggcgtt ccatttggca tgacactacg   7140
accaacacga tctcggttgt ctcggcgcac tccgtacagt agggatcgcc tacctccttt   7200
tgagacagag acccgcgcta ccatactgga ggatcatccg ctgctgcccg aatgtaacac   7260
tttgacaatg cacaacgtga gttacgtgcg aggtcttccc tgcagtgtgg gatttacgct   7320
gattcaggaa tgggttgttc cctgggatat ggttctgacg cgggaggagc ttgtaatcct   7380
gaggaagtgt atgcacgtgt gcctgtgttg tgccaacatt gatatcatga cgagcatgat   7440
gatccatggt tacgagtcct gggctctcca ctgtcattgt tccagtcccg gttccctgca   7500
gtgcatagcc ggcgggcagg ttttggccag ctggtttagg atggtggtgg atggcgccat   7560
gtttaatcag aggtttatat ggtaccggga ggtggtgaat tacaacatgc caaaagaggt   7620
aatgtttatg tccagcgtgt ttatgagggg tcgccactta atctacctgc gcttgtggta   7680
tgatggccac gtgggttctg tggtccccgc catgagcttt ggatacagcg ccttgcactg   7740
tgggattttg aacaatattg tggtgctgtg ctgcagttac tgtgctgatt taagtgagat   7800
cagggtgcgc tgctgtgccc ggaggacaag gcgtctcatg ctgcgggcgg tgcgaatcat   7860
cgctgaggag accactgcca tgttgtattc ctgcaggacg gagcggcggc ggcagcagtt   7920
tattcgcgcg ctgctgcagc accaccgccc tatcctgatg cacgattatg actctacccc   7980
catgtaggcg tggacttccc cttcgccgcc cgttgagcaa ccgcaagttg gacagcagcc   8040
tgtggctcag cagctggaca gcgacatgaa cttaagcgag ctgcccgggg agtttattaa   8100
tatcactgat gagcgtttgg ctcgacagga aaccgtgtgg aatataacac ctaagaatat   8160
gtctgttacc catgatatga tgctttttaa ggccagccgg ggagaaagga ctgtgtactc   8220
tgtgtgttgg gagggaggtg gcaggttgaa tactagggtt ctgtgagttt gattaaggta   8280
cggtgatcaa tataagctat gtggtggtgg ggctatacta ctgaatgaaa aatgacttga   8340
aattttctgc aattgaaaaa taaacacgtt gaaacataac atgcaacagg ttcacgattc   8400
tttattcctg ggcaatgtag gagaaggtgt aagagttggt agcaaaagtt tcagtggtgt   8460
attttccact ttcccaggac catgtaaaag acatagagta agtgcttacc tcgctagttt   8520
ctgtggattc actagaatcg atgtaggatg ttgcccctcc tgacgcggta ggagaagggg   8580
agggtgccct gcatgtctgc cgctgctctt gctcttgccg ctgctgagga ggggggcgca   8640
tctgccgcag caccggatgc atctgggaaa agcaaaaaag gggctcgtcc ctgtttccgg   8700
aggaatttgc aagcggggtc ttgcatgacg gggaggcaaa cccccgttcg ccgcagtccg   8760
gccggcccga gactcgaacc gggggtcctg cgactcaacc cttggaaaat aaccctccgg   8820
ctacagggag cgagccactt aatgctttcg ctttccagcc taaccgctta cgccgcgcgc   8880
```

```
ggccagtggc caaaaaagct agcgcagcag ccgccgcgcc tggaaggaag ccaaaaggag   8940
cgctccccccg ttgtctgacg tcgcacacct gggttcgaca cgcgggcggt aaccgcatgg   9000
atcacggcgg acggccggat ccggggttcg aaccccggtc gtccgccatg ataccccttgc   9060
gaatttatcc accagaccac ggaagagtgc ccgcttacag gctctccttt tgcacggtct   9120
agagcgtcaa cgactgcgca cgcctcaccg gccagagcgt cccgaccatg gagcactttt   9180
tgccgctgcg caacatctgg aaccgcgtcc gcgactttcc gcgcgcctcc accaccgccg   9240
ccggcatcac ctggatgtcc aggtacatct acggattacg tcgacgttta aaccatatga   9300
tcagctcact caaaggcggt aatacggtta tccacagaat caggggataa cgcaggaaag   9360
aacatgtgag caaaaggcca gcaaaaggcc aggaaccgta aaaaggccgc gttgctggcg   9420
tttttccata ggctccgccc ccctgacgag catcacaaaa atcgacgctc aagtcagagg   9480
tggcgaaacc cgacaggact ataaagatac caggcgtttc cccctggaag ctccctcgtg   9540
cgctctcctg ttccgaccct gccgcttacc ggatacctgt ccgcctttct cccttcggga   9600
agcgtggcgc tttctcatag ctcacgctgt aggtatctca gttcggtgta ggtcgttcgc   9660
tccaagctgg gctgtgtgca cgaacccccc gttcagcccg accgctgcgc cttatccggt   9720
aactatcgtc ttgagtccaa cccggtaaga cacgacttat cgccactggc agcagccact   9780
ggtaacagga ttagcagagc gaggtatgta ggcggtgcta cagagttctt gaagtggtgg   9840
cctaactacg gctacactag aagaacagta tttggtatct gcgctctgct gaagccagtt   9900
accttcggaa aaagagttgg tagctcttga tccggcaaac aaaccaccgc tggtagcggt   9960
ggtttttttg tttgcaagca gcagattacg cgcagaaaaa aaggatctca agaagatcct  10020
ttgatctttt ctacggggtc tgacgctcag tggaacgaaa actcacgtta agggattttg  10080
gtcatgagat tatcaaaaag gatcttcacc tagatccttt taaattaaaa atgaagtttt  10140
aaatcaatct aaagtatata tgagtaaact tggtctgaca gttagaaaaa ctcatcgagc  10200
atcaaatgaa actgcaattt attcatatca ggattatcaa taccatattt ttgaaaaagc  10260
cgtttctgta atgaaggaga aaactcaccg aggcagttcc ataggatggc aagatcctgg  10320
tatcggtctg cgattccgac tcgtccaaca tcaatacaac ctattaattt cccctcgtca  10380
aaaataaggt tatcaagtga gaaatcacca tgagtgacga ctgaatccgg tgagaatggc  10440
aaaagtttat gcatttcttt ccagacttgt tcaacaggcc agccattacg ctcgtcatca  10500
aaatcactcg catcaaccaa accgttattc attcgtgatt gcgcctgagc gagacgaaat  10560
acgcgatcgc tgttaaaagg acaattacaa acaggaatcg aatgcaaccg gcgcaggaac  10620
actgccagcg catcaacaat attttcacct gaatcaggat attcttctaa tacctggaat  10680
gctgttttcc cagggatcgc agtggtgagt aaccatgcat catcaggagt acggataaaa  10740
tgcttgatgg tcggaagagg cataaattcc gtcagccagt ttagtctgac catctcatct  10800
gtaacatcat tggcaacgct acctttgcca tgtttcagaa acaactctgg cgcatcgggc  10860
ttcccataca atcgatagat tgtcgcacct gattgcccga cattatcgcg agcccattta  10920
tacccatata aatcagcatc catgttggaa tttaatcgcg gcctagagca agacgtttcc  10980
cgttgaatat ggctcatact cttccttttt caatattatt gaagcattta tcagggttat  11040
tgtctcatga gcggatacat atttgaatgt atttagaaaa ataaacaaat aggggttccg  11100
cgcacatttc cccgaaaagt gccacctgac gtctaagaaa ccattattat catgacatta  11160
acctataaaa ataggcgtat cacgaggccc tttcgtctcg cgcgtttcgg tgatgacggt  11220
```

gaaaacctct gacacatgca gctcccggag acggtcacag cttgtctgta agcggatgcc 11280
gggagcagac aacaacgtca aagggcgaaa aaccgtctat cagggcgatg gcccactacg 11340
tgaaccatca ccctaatcaa gtttttttggg gtcgaggtgc cgtaaagcac taaatcggaa 11400
ccctaaaggg agcccccgat ttagagcttg acggggaaag ccggcgaacg tggcgagaaa 11460
ggaagggaag aaagcgaaag gagcgggcgc tagggcgctg gcaagtgtag cggtcacgct 11520
gcgcgtaacc accacacccg ccgcgcttaa tgcgccgcta cagggcgcga tggatcc 11577

<210> SEQ ID NO 93
<211> LENGTH: 4443
<212> TYPE: DNA
<213> ORGANISM: Artificial Sequence
<220> FEATURE:
<223> OTHER INFORMATION: CFTR

<400> SEQUENCE: 93
atgcagagaa gccccctgga gaaggcctct gtggtgagca agctgttctt cagctggacc 60
agacccatcc tgagaaaggg ctacagacag agactggagc tgtctgacat ctaccagatc 120
ccctctgtgg actctgctga caacctgtct gagaagctgg agagagagtg ggacagagag 180
ctggccagca agaagaaccc caagctgatc aatgccctga gaagatgctt cttctggaga 240
ttcatgttct atggcatctt cctgtacctg gggggaggtga ccaaggctgt gcagcccctg 300
ctgctgggca gaatcattgc cagctatgac cctgacaaca aggaggagag aagcattgcc 360
atctacctgg gcattggcct gtgcctgctg ttcattgtga gaaccctgct gctgcaccct 420
gccatctttg gcctgcacca cattggcatg cagatgagaa ttgccatgtt cagcctgatc 480
tacaagaaga ccctgaagct gagcagcaga gtgctggaca agatcagcat tggccagctg 540
gtgagcctgc tgagcaacaa cctgaacaag tttgatgagg gcctggccct ggcccacttt 600
gtgtggattg ccccccctgca ggtggccctg ctgatgggcc tgatctggga gctgctgcag 660
gcctctgcct tctgtggcct gggcttcctg attgtgctgg ccctgttcca ggctggcctg 720
ggcagaatga tgatgaagta cagagaccag agagctggca agatctctga gagactggtg 780
atcacctctg agatgattga gaacatccag tctgtgaagg cctactgctg ggaggaggcc 840
atggagaaga tgattgagaa cctgagacag acagagctga agctgaccag aaaggctgcc 900
tatgtgagat acttcaacag ctctgccttc ttcttctctg gcttctttgt ggtgttcctg 960
tctgtgctgc cctatgccct gatcaagggc atcatcctga gaaagatctt caccaccatc 1020
agcttctgca ttgtgctgag aatggctgtg accagacagt tcccctgggc tgtgcagacc 1080
tggtatgaca gcctgggggc catcaacaag atccaggact tcctgcagaa gcaggagtac 1140
aagaccctgg agtacaacct gaccaccaca gaggtggtga tggagaatgt gacagccttc 1200
tgggaggagg gctttgggga gctgtttgag aaggccaagc agaacaacaa caacagaaag 1260
accagcaatg gggatgacag cctgttcttc agcaacttca gcctgctggg cacccctgtg 1320
ctgaaggaca tcaacttcaa gattgagaga ggccagctgc tggctgtggc tggcagcaca 1380
ggggctggca agaccagcct gctgatgatg atcatggggg agctggagcc ctctgagggc 1440
aagatcaagc actctggcag aatcagcttc tgcagccagt tcagctggat catgcctggc 1500
accatcaagg agaacatcat ctttggggtg agctatgatg agtacagata cagatctgtg 1560
atcaaggcct gccagctgga ggaggacatc agcaagtttg ctgagaagga caacattgtg 1620
ctgggggagg ggggcatcac cctgtctggg ggccagagag ccagaatcag cctggccaga 1680
gctgtgtaca aggatgctga cctgtacctg ctggacagcc cctttggcta cctggatgtg 1740

```
ctgacagaga aggagatctt tgagagctgt gtgtgcaagc tgatggccaa caagaccaga   1800
atcctggtga ccagcaagat ggagcacctg aagaaggctg acaagatcct gatcctgcat   1860
gagggcagca gctacttcta tggcaccttc tctgagctgc agaacctgca gcctgacttc   1920
agcagcaagc tgatgggctg tgacagcttt gaccagttct ctgctgagag aagaaacagc   1980
atcctgacag agaccctgca cagattcagc ctggaggggg atgcccctgt gagctggaca   2040
gagaccaaga agcagagctt caagcagaca ggggagtttg gggagaagag aaagaacagc   2100
atcctgaacc ccatcaacag catcagaaag ttcagcattg tgcagaagac ccccctgcag   2160
atgaatggca ttgaggagga ctctgatgag cccctggaga gaagactgag cctggtgcct   2220
gactctgagc agggggaggc catcctgccc agaatctctg tgatcagcac aggccccacc   2280
ctgcaggcca gaagaagaca gtctgtgctg aacctgatga cccactctgt gaaccagggc   2340
cagaacatcc acagaaagac cacagccagc accagaaagg tgagcctggc cccccaggcc   2400
aacctgacag agctggacat ctacagcaga agactgagcc aggagacagg cctggagatc   2460
tctgaggaga tcaatgagga ggacctgaag gagtgcttct ttgatgacat ggagagcatc   2520
cctgctgtga ccacctggaa cacctacctg agatacatca cagtgcacaa gagcctgatc   2580
tttgtgctga tctggtgcct ggtgatcttc ctggctgagg tggctgccag cctggtggtg   2640
ctgtggctgc tgggcaacac cccccctgcag gacaagggca acagcaccca cagcagaaac   2700
aacagctatg ctgtgatcat caccagcacc agcagctact atgtgttcta catctatgtg   2760
ggggtggctg acaccctgct ggccatgggc ttcttcagag gcctgcccct ggtgcacacc   2820
ctgatcacag tgagcaagat cctgcaccac aagatgctgc actctgtgct gcaggccccc   2880
atgagcaccc tgaacaccct gaaggctggg ggcatcctga acagattcag caaggacatt   2940
gccatcctgg atgacctgct gcccctgacc atctttgact tcatccagct gctgctgatt   3000
gtgattgggg ccattgctgt ggtggctgtg ctgcagccct acatctttgt ggccacagtg   3060
cctgtgattg tggccttcat catgctgaga gcctacttcc tgcagaccag ccagcagctg   3120
aagcagctgg agtctgaggg cagaagcccc atcttcaccc acctggtgac cagcctgaag   3180
ggcctgtgga ccctgagagc ctttggcaga cagccctact ttgagaccct gttccacaag   3240
gccctgaacc tgcacacagc caactggttc ctgtacctga gcaccctgag atggttccag   3300
atgagaattg agatgatctt tgtgatcttc ttcattgctg tgaccttcat cagcatcctg   3360
accacagggg agggggaggg cagagtgggc atcatcctga ccctggccat gaacatcatg   3420
agcaccctgc agtgggctgt gaacagcagc attgatgtgg acagcctgat gagatctgtg   3480
agcagagtgt tcaagttcat tgacatgccc acagagggca agcccaccaa gagcaccaag   3540
ccctacaaga atggccagct gagcaaggtg atgatcattg agaacagcca tgtgaagaag   3600
gatgacatct ggccctctgg gggccagatg acagtgaagg acctgacagc caagtacaca   3660
gagggggggca atgccatcct ggagaacatc agcttcagca tcagccctgg ccagagagtg   3720
ggcctgctgg gcagaacagg ctctggcaag agcaccctgc tgtctgcctt cctgagactg   3780
ctgaacacag agggggagat ccagattgat ggggtgagct gggacagcat caccctgcag   3840
cagtggagaa aggcctttgg ggtgatcccc cagaaggtgt tcatcttctc tggcaccttc   3900
agaaagaacc tggaccccta tgagcagtgg tctgaccagg agatctggaa ggtggctgat   3960
gaggtgggcc tgagatctgt gattgagcag ttccctggca agctggactt tgtgctggtg   4020
gatgggggct gtgtgctgag ccatggccac aagcagctga tgtgcctggc cagatctgtg   4080
```

ctgagcaagg ccaagatcct gctgctggat gagccctctg cccacctgga ccctgtgacc 4140
taccagatca tcagaagaac cctgaagcag gcctttgctg actgcacagt gatcctgtgt 4200
gagcacagaa ttgaggccat gctggagtgc cagcagttcc tggtgattga ggagaacaag 4260
gtgagacagt atgacagcat ccagaagctg ctgaatgaga gaagcctgtt cagacaggcc 4320
atcagcccct ctgacagagt gaagctgttc ccccacagaa acagcagcaa gtgcaagagc 4380
aagccccaga ttgctgccct gaaggaggag accgaggagg aggtgcagga caccagactg 4440
taa 4443

<210> SEQ ID NO 94
<211> LENGTH: 1480
<212> TYPE: PRT
<213> ORGANISM: Artificial Sequence
<220> FEATURE:
<223> OTHER INFORMATION: CFTR protein

<400> SEQUENCE: 94

```
Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
```

```
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
    690                 695                 700

Ile Asn Ser Ile Arg Lys Phe Ser Ile Val Gln Lys Thr Pro Leu Gln
705                 710                 715                 720
```

```
Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
    770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Phe Phe Asp Asp Met Glu Ser Ile Pro Ala Val Thr Thr Trp Asn Thr
        835                 840                 845

Tyr Leu Arg Tyr Ile Thr Val His Lys Ser Leu Ile Phe Val Leu Ile
    850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
    930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile  Val Ile Gly Ala Ile  Ala Val Val
        995                 1000                 1005

Ala Val  Leu Gln Pro Tyr Ile  Phe Val Ala Thr Val  Pro Val Ile
    1010                 1015                 1020

Val Ala  Phe Ile Met Leu Arg  Ala Tyr Phe Leu Gln  Thr Ser Gln
    1025                 1030                 1035

Gln Leu  Lys Gln Leu Glu Ser  Glu Gly Arg Ser Pro  Ile Phe Thr
    1040                 1045                 1050

His Leu  Val Thr Ser Leu Lys  Gly Leu Trp Thr Leu  Arg Ala Phe
    1055                 1060                 1065

Gly Arg  Gln Pro Tyr Phe Glu  Thr Leu Phe His Lys  Ala Leu Asn
    1070                 1075                 1080

Leu His  Thr Ala Asn Trp Phe  Leu Tyr Leu Ser Thr  Leu Arg Trp
    1085                 1090                 1095

Phe Gln  Met Arg Ile Glu Met  Ile Phe Val Ile Phe  Phe Ile Ala
    1100                 1105                 1110

Val Thr  Phe Ile Ser Ile Leu  Thr Thr Gly Glu Gly  Glu Gly Arg
    1115                 1120                 1125
```

```
Val Gly  Ile Ile Leu Thr Leu  Ala Met Asn Ile Met  Ser Thr Leu
    1130                 1135                 1140

Gln Trp  Ala Val Asn Ser Ser  Ile Asp Val Asp Ser  Leu Met Arg
    1145                 1150                 1155

Ser Val  Ser Arg Val Phe Lys  Phe Ile Asp Met Pro  Thr Glu Gly
    1160                 1165                 1170

Lys Pro  Thr Lys Ser Thr Lys  Pro Tyr Lys Asn Gly  Gln Leu Ser
    1175                 1180                 1185

Lys Val  Met Ile Ile Glu Asn  Ser His Val Lys Lys  Asp Asp Ile
    1190                 1195                 1200

Trp Pro  Ser Gly Gly Gln Met  Thr Val Lys Asp Leu  Thr Ala Lys
    1205                 1210                 1215

Tyr Thr  Glu Gly Gly Asn Ala  Ile Leu Glu Asn Ile  Ser Phe Ser
    1220                 1225                 1230

Ile Ser  Pro Gly Gln Arg Val  Gly Leu Leu Gly Arg  Thr Gly Ser
    1235                 1240                 1245

Gly Lys  Ser Thr Leu Leu Ser  Ala Phe Leu Arg Leu  Leu Asn Thr
    1250                 1255                 1260

Glu Gly  Glu Ile Gln Ile Asp  Gly Val Ser Trp Asp  Ser Ile Thr
    1265                 1270                 1275

Leu Gln  Gln Trp Arg Lys Ala  Phe Gly Val Ile Pro  Gln Lys Val
    1280                 1285                 1290

Phe Ile  Phe Ser Gly Thr Phe  Arg Lys Asn Leu Asp  Pro Tyr Glu
    1295                 1300                 1305

Gln Trp  Ser Asp Gln Glu Ile  Trp Lys Val Ala Asp  Glu Val Gly
    1310                 1315                 1320

Leu Arg  Ser Val Ile Glu Gln  Phe Pro Gly Lys Leu  Asp Phe Val
    1325                 1330                 1335

Leu Val  Asp Gly Gly Cys Val  Leu Ser His Gly His  Lys Gln Leu
    1340                 1345                 1350

Met Cys  Leu Ala Arg Ser Val  Leu Ser Lys Ala Lys  Ile Leu Leu
    1355                 1360                 1365

Leu Asp  Glu Pro Ser Ala His  Leu Asp Pro Val Thr  Tyr Gln Ile
    1370                 1375                 1380

Ile Arg  Arg Thr Leu Lys Gln  Ala Phe Ala Asp Cys  Thr Val Ile
    1385                 1390                 1395

Leu Cys  Glu His Arg Ile Glu  Ala Met Leu Glu Cys  Gln Gln Phe
    1400                 1405                 1410

Leu Val  Ile Glu Glu Asn Lys  Val Arg Gln Tyr Asp  Ser Ile Gln
    1415                 1420                 1425

Lys Leu  Leu Asn Glu Arg Ser  Leu Phe Arg Gln Ala  Ile Ser Pro
    1430                 1435                 1440

Ser Asp  Arg Val Lys Leu Phe  Pro His Arg Asn Ser  Ser Lys Cys
    1445                 1450                 1455

Lys Ser  Lys Pro Gln Ile Ala  Ala Leu Lys Glu Glu  Thr Glu Glu
    1460                 1465                 1470

Glu Val  Gln Asp Thr Arg Leu
    1475                 1480
```

<210> SEQ ID NO 95
<211> LENGTH: 1428
<212> TYPE: PRT
<213> ORGANISM: Artificial Sequence
<220> FEATURE:
<223> OTHER INFORMATION: CFTRdeltaR protein

<400> SEQUENCE: 95

Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn

```
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
    690                 695                 700

Ile Asn Ser Thr Leu Gln Ala Arg Arg Arg Gln Ser Val Leu Asn Leu
705                 710                 715                 720

Met Thr His Ser Val Asn Gln Gly Gln Asn Ile His Arg Lys Thr Thr
                725                 730                 735

Ala Ser Thr Arg Lys Val Ser Leu Ala Pro Gln Ala Asn Leu Thr Glu
            740                 745                 750

Leu Asp Ile Tyr Ser Arg Arg Leu Ser Gln Glu Thr Gly Leu Glu Ile
        755                 760                 765

Ser Glu Glu Ile Asn Glu Glu Asp Leu Lys Glu Cys Phe Phe Asp Asp
    770                 775                 780

Met Glu Ser Ile Pro Ala Val Thr Thr Trp Asn Thr Tyr Leu Arg Tyr
785                 790                 795                 800

Ile Thr Val His Lys Ser Leu Ile Phe Val Leu Ile Trp Cys Leu Val
                805                 810                 815

Ile Phe Leu Ala Glu Val Ala Ala Ser Leu Val Val Leu Trp Leu Leu
            820                 825                 830
```

-continued

```
Gly Asn Thr Pro Leu Gln Asp Lys Gly Asn Ser Thr His Ser Arg Asn
        835                 840                 845

Asn Ser Tyr Ala Val Ile Ile Thr Ser Thr Ser Ser Tyr Tyr Val Phe
    850                 855                 860

Tyr Ile Tyr Val Gly Val Ala Asp Thr Leu Leu Ala Met Gly Phe Phe
865                 870                 875                 880

Arg Gly Leu Pro Leu Val His Thr Leu Ile Thr Val Ser Lys Ile Leu
                885                 890                 895

His His Lys Met Leu His Ser Val Leu Gln Ala Pro Met Ser Thr Leu
            900                 905                 910

Asn Thr Leu Lys Ala Gly Gly Ile Leu Asn Arg Phe Ser Lys Asp Ile
        915                 920                 925

Ala Ile Leu Asp Asp Leu Leu Pro Leu Thr Ile Phe Asp Phe Ile Gln
    930                 935                 940

Leu Leu Leu Ile Val Ile Gly Ala Ile Ala Val Val Ala Val Leu Gln
945                 950                 955                 960

Pro Tyr Ile Phe Val Ala Thr Val Pro Val Ile Val Ala Phe Ile Met
                965                 970                 975

Leu Arg Ala Tyr Phe Leu Gln Thr Ser Gln Gln Leu Lys Gln Leu Glu
            980                 985                 990

Ser Glu Gly Arg Ser Pro Ile Phe  Thr His Leu Val Thr  Ser Leu Lys
        995                 1000                1005

Gly Leu  Trp Thr Leu Arg Ala  Phe Gly Arg Gln Pro  Tyr Phe Glu
    1010                1015                1020

Thr Leu  Phe His Lys Ala Leu  Asn Leu His Thr Ala  Asn Trp Phe
    1025                1030                1035

Leu Tyr  Leu Ser Thr Leu Arg  Trp Phe Gln Met Arg  Ile Glu Met
    1040                1045                1050

Ile Phe  Val Ile Phe Phe Ile  Ala Val Thr Phe Ile  Ser Ile Leu
    1055                1060                1065

Thr Thr  Gly Glu Gly Glu Gly  Arg Val Gly Ile Ile  Leu Thr Leu
    1070                1075                1080

Ala Met  Asn Ile Met Ser Thr  Leu Gln Trp Ala Val  Asn Ser Ser
    1085                1090                1095

Ile Asp  Val Asp Ser Leu Met  Arg Ser Val Ser Arg  Val Phe Lys
    1100                1105                1110

Phe Ile  Asp Met Pro Thr Glu  Gly Lys Pro Thr Lys  Ser Thr Lys
    1115                1120                1125

Pro Tyr  Lys Asn Gly Gln Leu  Ser Lys Val Met Ile  Ile Glu Asn
    1130                1135                1140

Ser His  Val Lys Lys Asp Asp  Ile Trp Pro Ser Gly  Gly Gln Met
    1145                1150                1155

Thr Val  Lys Asp Leu Thr Ala  Lys Tyr Thr Glu Gly  Gly Asn Ala
    1160                1165                1170

Ile Leu  Glu Asn Ile Ser Phe  Ser Ile Ser Pro Gly  Gln Arg Val
    1175                1180                1185

Gly Leu  Leu Gly Arg Thr Gly  Ser Gly Lys Ser Thr  Leu Leu Ser
    1190                1195                1200

Ala Phe  Leu Arg Leu Leu Asn  Thr Glu Gly Glu Ile  Gln Ile Asp
    1205                1210                1215

Gly Val  Ser Trp Asp Ser Ile  Thr Leu Gln Gln Trp  Arg Lys Ala
    1220                1225                1230
```

```
Phe Gly  Val Ile Pro Gln Lys  Val Phe Ile Phe Ser  Gly Thr Phe
    1235                 1240                 1245

Arg Lys  Asn Leu Asp Pro Tyr  Glu Gln Trp Ser Asp  Gln Glu Ile
    1250                 1255                 1260

Trp Lys  Val Ala Asp Glu Val  Gly Leu Arg Ser Val  Ile Glu Gln
    1265                 1270                 1275

Phe Pro  Gly Lys Leu Asp Phe  Val Leu Val Asp Gly  Gly Cys Val
    1280                 1285                 1290

Leu Ser  His Gly His Lys Gln  Leu Met Cys Leu Ala  Arg Ser Val
    1295                 1300                 1305

Leu Ser  Lys Ala Lys Ile Leu  Leu Leu Asp Glu Pro  Ser Ala His
    1310                 1315                 1320

Leu Asp  Pro Val Thr Tyr Gln  Ile Ile Arg Arg Thr  Leu Lys Gln
    1325                 1330                 1335

Ala Phe  Ala Asp Cys Thr Val  Ile Leu Cys Glu His  Arg Ile Glu
    1340                 1345                 1350

Ala Met  Leu Glu Cys Gln Gln  Phe Leu Val Ile Glu  Glu Asn Lys
    1355                 1360                 1365

Val Arg  Gln Tyr Asp Ser Ile  Gln Lys Leu Leu Asn  Glu Arg Ser
    1370                 1375                 1380

Leu Phe  Arg Gln Ala Ile Ser  Pro Ser Asp Arg Val  Lys Leu Phe
    1385                 1390                 1395

Pro His  Arg Asn Ser Ser Lys  Cys Lys Ser Lys Pro  Gln Ile Ala
    1400                 1405                 1410

Ala Leu  Lys Glu Glu Thr Glu  Glu Glu Val Gln Asp  Thr Arg Leu
    1415                 1420                 1425
```

```
<210> SEQ ID NO 96
<211> LENGTH: 250
<212> TYPE: DNA
<213> ORGANISM: Artificial Sequence
<220> FEATURE:
<223> OTHER INFORMATION: Mouse U1a promoter sequence

<400> SEQUENCE: 96

atggaggcgg tactatgtag atgagaattc aggagcaaac tgggaaaagc aactgcttcc     60

aaatatttgt gatttttaca gtgtagtttt ggaaaaactc ttagcctacc aattcttcta    120

agtgttttaa aatgtgggag ccagtacaca tgaagttata gagtgtttta atgaggctta    180

aatatttacc gtaactatga aatgctacgc atatcatgct gttcaggctc cgtggccacg    240

caactcatac                                                            250


<210> SEQ ID NO 97
<211> LENGTH: 101
<212> TYPE: DNA
<213> ORGANISM: Artificial Sequence
<220> FEATURE:
<223> OTHER INFORMATION: Polymerase III H1 mutant promoter sequence

<400> SEQUENCE: 97

aatatttgca tgtcgctatg tgttctggga aatcaccata aacgtgaaat gtctttggat     60

ttgggaatct tcgaagttct gtatgagacc acagatctcc a                         101


<210> SEQ ID NO 98
<211> LENGTH: 2214
<212> TYPE: DNA
<213> ORGANISM: Artificial Sequence
<220> FEATURE:
```

<223> OTHER INFORMATION: AAV110 DNA

<400> SEQUENCE: 98
atggctgccg atggttatct tccagattgg ctcgaggaca acctctctga gggcattcgc 60
gagtggtggg acttgaaacc tggagccccg aaacccaaag ccaaccagca aaagcaggac 120
gacggccggg gtctggtgct tcctggctac aagtacctcg gacccttcaa cggactcgac 180
aagggggagc ccgtcaacgc ggcggatgca gcggccctcg agcacgacaa ggcctacgac 240
cagcagctca aagcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540
gagtcagtcc ccgacccaca acctctcgga gaacctccag caacccccgc tgctgtggga 600
cctactacaa tggcttcagg cggtggcgca ccaatggcag acaataacga aggcgccgac 660
ggagtgggta atgcctcagg aaattggcat tgcgattcca catggctggg cgacagagtc 720
atcaccacca gcacccgaac atgggccttg cccacctata acaaccacct ctacaagcaa 780
atctccagtg cttcaacggg ggccagcaac gacaaccact acttcggcta cagcaccccc 840
tgggggtatt ttgatttcaa cagattccac tgccatttct caccacgtga ctggcagcga 900
ctcatcaaca acaattgggg attccggccc aagagactca acttcaagct cttcaacatc 960
caagtcaagg aggtcacgac gaatgatggc gtcacgacca tcgctaataa ccttaccagc 1020
acggttcaag tcttctcgga ctcggagtac cagttgccgt acgtcctcgg ctctgcgcac 1080
cagggctgcc tccctccgtt cccggcggac gtgttcatga ttccgcagta cggctaccta 1140
acgctcaaca atggcagcca ggcagtggga cggtcatcct tttactgcct ggaatatttc 1200
ccatcgcaga tgctgagaac gggcaataac tttaccttca gctacacctt cgaggacgtg 1260
cctttccaca gcagctacgc gcacagccag agcctggacc ggctgatgaa tcctctcatc 1320
gaccagtacc tgtattacct gaacagaact cagaatcagt ccggaagtgc ccaaaacaag 1380
gacttgctgt ttagccgggg gtctccagct ggcatgtctg ttcagcccaa aaactggcta 1440
cctggaccct gttaccggca gcagcgcgtt tctaaaacaa aaacagacaa caacaacagc 1500
aactttacct ggactggtgc ttcaaaatat aaccttaatg ggcgtgaatc tataatcaac 1560
cctggcactg ctatggcctc acacaaagac gacaaagaca agttctttcc catgagcggt 1620
gtcatgattt ttggaaagga gagcgccgga gcttcaaaca ctgcattgga caatgtcatg 1680
atcacagacg aagaggaaat caaagccact aaccccgtgg ccaccgaaag atttgggact 1740
gtggcagtca atctccagag cagcagcaca gaccctgcga ccggagatgt gcatgttatg 1800
ggagccttac ctggaatggt gtggcaagac agagacgtat acctgcaggg tcctatttgg 1860
gccaaaattc ctcacacgga tggacacttt cacccgtctc ctctcatggg cggctttgga 1920
cttaagcacc cgcctcctca gatcctcatc aaaaacacgc ctgttcctgc gaatcctccg 1980
gcagagtttt cggctacaaa gtttgcttca ttcatcaccc agtattccac aggacaagtg 2040
agcgtggaga ttgaatggga gctgcagaaa gaaaacagca aacgctggaa tcccgaagtg 2100
cagtatacat ctaactatgc aaaatctgcc aacgttgatt tcactgtgga caacaatgga 2160
ctttatactg agcctcgccc cattggcacc cgttacctca cccgtcccct gtaa 2214

<210> SEQ ID NO 99
<211> LENGTH: 1509
<212> TYPE: DNA
<213> ORGANISM: Homo sapiens
<220> FEATURE:
<221> NAME/KEY: misc_feature
<222> LOCATION: (1)..(1509)
<223> OTHER INFORMATION: Sulfoglucosamine sulfohydrolase (SGSH)

<400> SEQUENCE: 99

```
atgagctgcc ccgtgcccgc ctgctgcgcg ctgctgctag tcctggggct ctgccgggcg     60
cgtccccgga acgcactgct gctcctcgcg gatgacggag gctttgagag tggcgcgtac    120
aacaacagcg ccatcgccac cccgcacctg gacgccttgg cccgccgcag cctcctcttt    180
cgcaatgcct tcacctcggt cagcagctgc tctcccagcc gcgccagcct cctcactggc    240
ctgccccagc atcagaatgg gatgtacggg ctgcaccagg acgtgcacca cttcaactcc    300
ttcgacaagg tgcggagcct gccgctgctg ctcagccaag ctggtgtgcg cacaggcatc    360
atcgggaaga agcacgtggg gccggagacc gtgtacccgt ttgactttgc gtacacggag    420
gagaatggct ccgtcctcca ggtggggcgg aacatcacta gaattaagct gctcgtccgg    480
aaattcctgc agactcagga tgaccagcct ttcttcctct acgtcgcctt ccacgacccc    540
caccgctgtg ggcactccca gccccagtac ggaaccttct gtgagaagtt tggcaacgga    600
gagagcggca tgggtcgtat cccagactgg acccccccagg cctacgaccc actggacgtg    660
ctggtgcctt acttcgtccc caacaccccg gcagcccgag ccgacctggc cgctcagtac    720
accaccgtcg gccgcatgga ccaaggagtt ggactggtgc tccaggagct gcgtgacgcc    780
ggtgtcctga acgacacact ggtgatcttc acgtccgaca acgggatccc cttccccagc    840
ggcaggacca acctgtactg gccgggcact gctgaaccct tactggtgtc atccccggag    900
cacccaaaac gctggggcca agtcagcgag gcctacgtga gcctcctaga cctcacgccc    960
accatcttgg attggttctc gatcccgtac cccagctacg ccatctttgg ctcgaagacc   1020
atccacctca ctggccggtc cctcctgccg gcgctggagg ccgagcccct ctgggccacc   1080
gtctttggca gccagagcca ccacgaggtc accatgtcct accccatgcg ctccgtgcag   1140
caccggcact tccgcctcgt gcacaacctc aacttcaaga tgccctttcc catcgaccag   1200
gacttctacg tctcacccac cttccaggac ctcctgaacc gcaccacagc tggtcagccc   1260
acgggctggt acaaggacct ccgtcattac tactaccggg cgcgctggga gctctacgac   1320
cggagccggg acccccacga gacccagaac ctggccaccg acccgcgctt tgctcagctt   1380
ctggagatgc ttcgggacca gctggccaag tggcagtggg agacccacga cccctgggtg   1440
tgcgcccccg acggcgtcct ggaggagaag ctctctcccc agtgccagcc cctccacaat   1500
gagctgtga                                                           1509
```

<210> SEQ ID NO 100
<211> LENGTH: 1509
<212> TYPE: DNA
<213> ORGANISM: Artificial Sequence
<220> FEATURE:
<223> OTHER INFORMATION: Codon optimized CO1-SGSH

<400> SEQUENCE: 100

```
atgagctgtc ctgttccagc ctgttgtgcc ctgctgctgg ttctgggact gtgcagagcc     60
agacctagga acgctctgct gctgctcgct gacgatggcg gatttgagag cggcgcctac    120
aacaacagcg ccattgccac acctcacctg gatgccctgg ccagaagaag cctgctgttc    180
```

agaaacgcct tcaccagcgt gtccagctgc agcccttcta gagctagcct gctgacagga 240
ctgccccagc accagaatgg gatgtatggc ctgcaccagg acgtgcacca cttcaacagc 300
ttcgacaaag tgcggagcct gcctctgctt ctgtctcaag ccggcgtcag aacaggcatc 360
atcggcaaga aacacgtggg ccccgagaca gtgtacccct tcgatttcgc ctacaccgaa 420
gagaacggca gcgtgctgca agtgggcaga aacatcaccc ggatcaagct gctcgtgcgg 480
aagttcctgc agacccagga cgaccagcct ttcttcctgt acgtggcctt ccacgatcct 540
cacagatgcg gccatagcca gcctcagtac ggcaccttct gcgagaagtt tggcaacggc 600
gagagcggca tgggcagaat ccctgattgg acccctcagg cctacgatcc cctggatgtg 660
ctggtgcctt acttcgtgcc taacacacca gccgccagag ccgatctggc cgctcagtat 720
acaaccgtgg gaagaatgga ccaaggcgtc ggcctggttc tgcaagagct tagagatgcc 780
ggcgtgctga acgacaccct ggtcatcttt accagcgaca acggcatccc ctttccatct 840
ggccggacca atctgtactg gcctggaaca gctgagcccc tgctggtgtc tagccctgag 900
caccctaaga gatggggcca agtgtctgag gcctacgtgt ccctgctgga tctgacccct 960
accatcctgg actggttcag catcccctat cctagctacg ccatcttcgg cagcaagacc 1020
atccacctga ccggcagatc tctgctgcca gctctggaag ctgaacctct gtgggccaca 1080
gtgtttggca gccagtctca ccacgaagtg acaatgagct accccatgcg gagcgtgcag 1140
cacagacact tcagactggt gcacaacctg aacttcaaga tgccctttcc aatcgaccag 1200
gacttctatg tgtccccaac cttccaggac ctgctgaaca gaaccacagc cggccaacct 1260
accggctggt acaaggacct gcggcactac tactatagag ccagatggga gctgtacgac 1320
cggtccagag atccccacga gacacagaac ctggccaccg atcctagatt cgcccagctg 1380
ctggaaatgc tgagagatca gctggccaag tggcagtggg agacacacga tccttgggtc 1440
tgcgctcctg atggcgtgct ggaagagaag ctgtcccctc agtgtcagcc cctgcacaac 1500
gagctttaa 1509

<210> SEQ ID NO 101
<211> LENGTH: 1596
<212> TYPE: DNA
<213> ORGANISM: Artificial Sequence
<220> FEATURE:
<223> OTHER INFORMATION: Codon optimized + GET CO1-SGSH-GET

<400> SEQUENCE: 101
atgagctgtc ctgttccagc ctgttgtgcc ctgctgctgg ttctgggact gtgcagagcc 60
agacctagga acgctctgct gctgctcgct gacgatggcg gatttgagag cggcgcctac 120
aacaacagcg ccattgccac acctcacctg gatgccctgg ccagaagaag cctgctgttc 180
agaaacgcct tcaccagcgt gtccagctgc agcccttcta gagctagcct gctgacagga 240
ctgccccagc accagaatgg gatgtatggc ctgcaccagg acgtgcacca cttcaacagc 300
ttcgacaaag tgcggagcct gcctctgctt ctgtctcaag ccggcgtcag aacaggcatc 360
atcggcaaga aacacgtggg ccccgagaca gtgtacccct tcgatttcgc ctacaccgaa 420
gagaacggca gcgtgctgca agtgggcaga aacatcaccc ggatcaagct gctcgtgcgg 480
aagttcctgc agacccagga cgaccagcct ttcttcctgt acgtggcctt ccacgatcct 540
cacagatgcg gccatagcca gcctcagtac ggcaccttct gcgagaagtt tggcaacggc 600
gagagcggca tgggcagaat ccctgattgg acccctcagg cctacgatcc cctggatgtg 660
ctggtgcctt acttcgtgcc taacacacca gccgccagag ccgatctggc cgctcagtat 720

```
acaaccgtgg gaagaatgga ccaaggcgtc ggcctggttc tgcaagagct tagagatgcc    780

ggcgtgctga acgacaccct ggtcatcttt accagcgaca acggcatccc ctttccatct    840

ggccggacca atctgtactg gcctggaaca gctgagcccc tgctggtgtc tagccctgag    900

caccctaaga gatggggcca agtgtctgag gcctacgtgt ccctgctgga tctgacccct    960

accatcctgg actggttcag catcccctat cctagctacg ccatcttcgg cagcaagacc   1020

atccacctga ccggcagatc tctgctgcca gctctggaag ctgaacctct gtgggccaca   1080

gtgtttggca gccagtctca ccacgaagtg acaatgagct accccatgcg gagcgtgcag   1140

cacagacact tcagactggt gcacaacctg aacttcaaga tgccctttcc aatcgaccag   1200

gacttctatg tgtccccaac cttccaggac ctgctgaaca gaaccacagc cggccaacct   1260

accggctggt acaaggacct gcggcactac tactatagag ccagatggga gctgtacgac   1320

cggtccagag atccccacga gacacagaac ctggccaccg atcctagatt cgcccagctg   1380

ctggaaatgc tgagagatca gctggccaag tggcagtggg agacacacga tccttgggtc   1440

tgcgctcctg atggcgtgct ggaagagaag ctgtcccctc agtgtcagcc cctgcacaac   1500

gagctgcggc gtcgtcggcg aagaagaaga aagcgcaaga aaaaaggcaa aggcctgggc   1560

aagaagcggg acccctgtct gagaaagtac aaataa                             1596
```

<210> SEQ ID NO 102
<211> LENGTH: 1509
<212> TYPE: DNA
<213> ORGANISM: Artificial Sequence
<220> FEATURE:
<223> OTHER INFORMATION: Codon optimized CO2-SGSH

<400> SEQUENCE: 102

```
atgagctgcc ctgtgcctgc ctgctgtgcc ctgctgctgg tgctgggcct gtgcagagcc     60

agacctagga atgccctgct gctgctggct gatgatgggg gctttgagag tggggcctac    120

aacaacagtg ccattgccac cccccacctg gatgccctgg ccagaagaag cctgctgttc    180

agaaatgcct tcaccagtgt gagcagctgc agccccagca gagccagcct gctgacaggc    240

ctgccccagc accagaatgg catgtatggc ctgcaccagg atgtgcacca cttcaacagc    300

tttgacaagg tgagaagcct gcccctgctg ctgagccagg ctggggtgag aacaggcatc    360

attggcaaga agcatgtggg ccctgagaca gtgtacccct ttgactttgc ctacacagag    420

gagaatggca gtgtgctgca ggtgggcaga aacatcacca gaatcaagct gctggtgaga    480

aagttcctgc agacccagga tgaccagccc ttcttcctgt atgtggcctt ccatgacccc    540

cacagatgtg gccacagcca gccccagtat ggcaccttct gtgagaagtt tggcaatggg    600

gagagtggca tgggcagaat ccctgactgg accccccagg cctatgaccc cctggatgtg    660

ctggtgccct actttgtgcc caacacccct gctgccagag ctgacctggc tgcccagtac    720

accacagtgg gcagaatgga ccagggggtg ggcctggtgc tgcaggagct gagagatgct    780

ggggtgctga atgacaccct ggtgatcttc accagtgaca atggcatccc cttccccagt    840

ggcagaacca acctgtactg gcctggcaca gctgagcccc tgctggtgag cagccctgag    900

caccccaaga gatggggcca ggtgagtgag gcctatgtga gcctgctgga cctgaccccc    960

accatcctgg actggttcag catcccctac cccagctatg ccatctttgg cagcaagacc   1020

atccacctga caggcagaag cctgctgcct gccctggagg ctgagcccct gtgggccaca   1080

gtgtttggca gccagagcca ccatgaggtg accatgagct accccatgag aagtgtgcag   1140
```

```
cacagacact tcagactggt gcacaacctg aacttcaaga tgcccttccc cattgaccag   1200

gacttctatg tgagccccac cttccaggac ctgctgaaca gaaccacagc tggccagccc   1260

acaggctggt acaaggacct gagacactac tactacagag ccagatggga gctgtatgac   1320

agaagcagag acccccatga gacccagaac ctggccacag accccagatt tgcccagctg   1380

ctggagatgc tgagagacca gctggccaag tggcagtggg agacccatga cccctgggtg   1440

tgtgcccctg atggggtgct ggaggagaag ctgagccccc agtgccagcc cctgcacaat   1500

gagctgtga                                                           1509
```

<210> SEQ ID NO 103
<211> LENGTH: 921
<212> TYPE: DNA
<213> ORGANISM: Artificial Sequence
<220> FEATURE:
<223> OTHER INFORMATION: Codon optimized Ceroid Lipofuscinosis, Neuronal, 1 (CLN1)

<400> SEQUENCE: 103

```
atggcttctc cggggtgtct gtggctgctg gcagtggcac tccttccctg gacttgcgcc     60

agccgggctc tgcagcacct cgaccctcca gcccctcttc cactggtgat ttggcacgga    120

atgggtgatt cctgctgtaa tcccctgtca atgggagcca tcaagaagat ggtggagaag    180

aagatccctg gaatctacgt gctgtcactg gagattggaa agaccctgat ggaggacgtc    240

gagaactcct tcttcctcaa tgtcaactct caagtgacca ccgtctgcca ggccctggcc    300

aaggacccga agctgcagca ggggtataat gctatggggt tcagccaggg aggacagttc    360

cttcgggctg tggcccaacg ctgccctagc ccacccatga tcaacctgat ctcagtgggt    420

ggccagcatc agggcgtgtt cggacttccc cggtgtcccg gggaatcctc tcatatctgc    480

gacttcatcc gcaaaactct caatgcaggc gcttattcaa aggtcgtcca agagaggctg    540

gtgcaagccg agtactggca cgatcccatt aaggaggacg tgtacagaaa tcactcaatc    600

tttctggccg acattaacca ggagaggggga attaacgaat catataagaa gaatctcatg    660

gccctcaaaa agttcgtcat ggtgaagttc cttaacgata gcattgtgga cccagtggac    720

agcgaatggt tcggatttta ccgctcaggc caggcaaaag aaaccatccc tctccaagag    780

acttctcttt acacccaaga cagacttggg cttaaggaaa tggataacgc tggtcagctg    840

gtgttcctcg ccaccgaagg tgaccatctg cagctcagcg aagagtggtt ctacgctcat    900

atcatcccgt ttcttggttg a                                              921
```

<210> SEQ ID NO 104
<211> LENGTH: 885
<212> TYPE: DNA
<213> ORGANISM: Homo sapiens
<220> FEATURE:
<221> NAME/KEY: misc_feature
<222> LOCATION: (1)..(885)
<223> OTHER INFORMATION: Survival Motor Neuron 1 (SMN1)

<400> SEQUENCE: 104

```
atggcgatga gcagcggcgg cagtggtggc ggcgtcccgg agcaggagga ttccgtgctg     60

ttccggcgcg gcacaggcca gagcgatgat tctgacattt gggatgatac agcactgata    120

aaagcatatg ataaagctgt ggcttcattt aagcatgctc taaagaatgg tgacatttgt    180

gaaacttcgg gtaaaccaaa aaccacacct aaaagaaaac ctgctaagaa gaataaaagc    240

caaaagaaga atactgcagc ttccttacaa cagtggaaag ttggggacaa atgttctgcc    300
```

atttggtcag aagacggttg catttaccca gctaccattg cttcaattga ttttaagaga 360
gaaacctgtg ttgtggttta cactggatat ggaaatagag aggagcaaaa tctgtccgat 420
ctactttccc caatctgtga agtagctaat aatatagaac agaatgctca agagaatgaa 480
aatgaaagcc aagtttcaac agatgaaagt gagaactcca ggtctcctgg aaataaatca 540
gataacatca agcccaaatc tgctccatgg aactcttttc tccctccacc accccccatg 600
ccagggccaa gactgggacc aggaaagcca ggtctaaaat tcaatggccc accaccgcca 660
ccgccaccac caccacccca cttactatca tgctggctgc ctccatttcc ttctggacca 720
ccaataattc ccccaccacc tcccatatgt ccagattctc ttgatgatgc tgatgctttg 780
ggaagtatgt taatttcatg gtacatgagt ggctatcata ctggctatta tatgggtttt 840
agacaaaatc aaaaagaagg aaggtgctca cattccttaa attaa 885

<210> SEQ ID NO 105
<211> LENGTH: 885
<212> TYPE: DNA
<213> ORGANISM: Artificial Sequence
<220> FEATURE:
<223> OTHER INFORMATION: Codon optimized CO1-SMN1

<400> SEQUENCE: 105
atggcgatgt ctagtggtgg atctggtggc ggcgtgcccg agcaagaaga tagcgtcctg 60
ttcagaagag gcaccggcca gagcgacgac agcgacatct gggatgatac agccctgatc 120
aaggcctacg acaaggccgt ggccagcttt aagcacgccc tgaagaacgg cgatatctgc 180
gagacaagcg gcaagcccaa gaccacacct aagagaaagc ccgccaagaa gaacaagagc 240
cagaagaaga ataccgccgc cagcctgcag cagtggaaag tgggcgataa gtgcagcgcc 300
atttggagcg aggacggctg tatctaccct gccacaatcg ccagcatcga cttcaagcgg 360
gaaacctgcg tggtggtgta cacaggctac ggcaacagag aggaacagaa cctgagcgac 420
ctgctgtccc caatttgcga ggtggccaac aacatcgagc agaacgccca agagaacgag 480
aacgagtccc aggtgtccac cgacgagagc gagaatagca gaagccccgg caacaagagc 540
gacaacatca agcctaagag cgccccttgg aacagcttcc tgcctcctcc tccaccaatg 600
cctggaccta gactcggacc tggaaagccc ggcctgaagt tcaatggacc tccaccaccg 660
ccaccacctc cgcctccaca tcttctgtct tgttggctgc ctccatttcc tagcggccct 720
ccaatcatcc cgccacctcc acctatctgc cccgacagtc tggatgatgc tgatgccctg 780
ggctccatgc tgatctcttg gtacatgagc ggctaccaca ccggctacta catgggcttc 840
agacagaacc agaaagaggg ccgttgcagc cacagcctga actga 885

<210> SEQ ID NO 106
<211> LENGTH: 885
<212> TYPE: DNA
<213> ORGANISM: Artificial Sequence
<220> FEATURE:
<223> OTHER INFORMATION: Codon optimized CO2-SMN1

<400> SEQUENCE: 106
atggccatga gcagtggggg cagtggagga ggggtgcctg agcaggagga cagtgtgctg 60
ttcagaagag gcacaggcca gagtgatgac agtgacatct gggatgacac agccctgatc 120
aaggcctatg acaaggctgt ggccagcttc aagcatgccc tgaagaatgg ggacatctgt 180
gagaccagtg gcaagcccaa gaccaccccc aagagaaagc ctgccaagaa gaacaagagc 240
cagaagaaga acacagctgc cagcctgcag cagtggaagg tgggagacaa gtgcagtgcc 300
atctggagtg aggatggctg catctaccct gccaccattg ccagcattga cttcaagaga 360
gagacctgtg tggtggtgta cacaggctat ggcaacagag aggagcagaa cctgagtgac 420
ctgctgagcc ccatctgtga ggtggccaac aacattgagc agaatgccca ggagaatgag 480
aatgagagcc aggtgagcac agatgagagt gagaacagca gaagccctgg caacaagagt 540
gacaacatca agcccaagag tgccccttgg aacagcttcc tgccaccccc accacccatg 600
cctggcccca gactgggccc tggcaagcct ggcctgaagt tcaatggccc accacccccct 660 cctccaccac cccctcccca cctgctgagc tgctggctgc ccccttccc cagtggccca 720 cccatcatcc cacctccccc acccatctgc cctgacagcc tggatgatgc tgatgccctg 780
ggcagcatgc tgatcagctg gtacatgagt ggctaccaca caggctacta catgggcttc 840
agacagaacc agaaggaggg cagatgcagc cacagcctga actga 885

<210> SEQ ID NO 107
<211> LENGTH: 1548
<212> TYPE: DNA
<213> ORGANISM: Homo sapiens
<220> FEATURE:
<221> NAME/KEY: misc_feature
<222> LOCATION: (1)..(1548)
<223> OTHER INFORMATION: Tissue Non-specific Alkaline Phosphatase
(TNALP)

<400> SEQUENCE: 107
atgatttcac cattcttagt actggccatt ggcacctgcc ttactaactc actagtgcca 60
gagaaagaga aagaccccaa gtactggcga gaccaagcgc aagagacact gaaatatgcc 120
ctggagcttc agaagctcaa caccaacgtg gctaagaatg tcatcatgtt cctgggagat 180
gggatgggtg tctccacagt gacggctgcc cgcatcctca agggtcagct ccaccacaac 240
cctggggagg agaccaggct ggagatggac aagttcccct tcgtggccct ctccaagacg 300
tacaacacca atgcccaggt ccctgacagc gccggcaccg ccaccgccta cctgtgtggg 360
gtgaaggcca atgagggcac cgtgggggta agcgcagcca ctgagcgttc ccggtgcaac 420
accacccagg ggaacgaggt cacctccatc ctgcgctggg ccaaggacgc tgggaaatct 480
gtgggcattg tgaccaccac gagagtgaac catgccaccc ccagcgccgc ctacgcccac 540
tcggctgacc gggactggta ctcagacaac gagatgcccc ctgaggcctt gagccagggc 600
tgtaaggaca tcgcctacca gctcatgcat aacatcaggg acattgacgt gatcatgggg 660
ggtggccgga aatacatgta ccccaagaat aaaactgatg tggagtatga gagtgacgag 720
aaagccaggg gcacgaggct ggacggcctg gacctcgttg acacctggaa gagcttcaaa 780
ccgagataca agcactccca cttcatctgg aaccgcacgg aactcctgac ccttgacccc 840
cacaatgtgg actacctatt gggtctcttc gagccagggg acatgcagta cgagctgaac 900
aggaacaacg tgacggaccc gtcactctcc gagatggtgg tggtggccat ccagatcctg 960
cggaagaacc ccaaaggctt cttcttgctg gtggaaggag gcagaattga ccacgggcac 1020
catgaaggaa aagccaagca ggccctgcat gaggcggtgg agatggaccg ggccatcggg 1080
caggcaggca gcttgacctc ctcggaagac actctgaccg tggtcactgc ggaccattcc 1140
cacgtcttca catttggtgg atacaccccc cgtggcaact ctatctttgg tctggccccc 1200
atgctgagtg acacagacaa gaagcccttc actgccatcc tgtatggcaa tgggcctggc 1260
tacaaggtgg tgggcggtga acgagagaat gtctccatgg tggactatgc tcacaacaac 1320
taccaggcgc agtctgctgt gcccctgcgc cacgagaccc acggcgggga ggacgtggcc 1380

```
gtcttctcca agggccccat ggcgcacctg ctgcacggcg tccacgagca gaactacgtc   1440

ccccacgtga tggcgtatgc agcctgcatc ggggccaacc tcggccactg tgctcctgcc   1500

agctcggcag gatccgatga tgacgacgac gatgacgatg atgattga                1548
```

<210> SEQ ID NO 108
<211> LENGTH: 1548
<212> TYPE: DNA
<213> ORGANISM: Artificial Sequence
<220> FEATURE:
<223> OTHER INFORMATION: Codon optimized, CO1-TNALP contains D10 tag at C end

<400> SEQUENCE: 108

```
atgatctctc catttctggt gctggccatc ggcacctgtc tgaccaactc actagtgccc     60

gagaaagaga aggaccccaa gtactggcgc gatcaggccc aagagacact gaagtacgcc    120

ctggaactgc agaaactgaa caccaacgtg gccaagaacg tgatcatgtt cctcggcgac    180

ggcatgggcg tgtccacagt tacagccgcc agaatcctga agggccagct gcaccataat    240

cctggcgaag agacacggct ggaaatggac aagttcccat tcgtggccct gagcaagacc    300

tacaacacca atgctcaggt gcccgattct gccggaacag ccacagctta tctgtgcggc    360

gtgaaggcca atgagggcac cgttggagtg tctgccgcca ccgaaagatc ccggtgcaat    420

accacacagg gcaacgaagt gaccagcatc ctgagatggg ccaaagacgc cggcaagtct    480

gtgggcatcg tgaccaccac cagagtgaac cacgccacac ctagcgccgc ctatgctcac    540

tctgccgaca gagactggta cagcgacaac gagatgcctc ctgaggctct gtctcagggc    600

tgcaaggata tcgcctacca gctgatgcac aacatccggg acattgatgt gatcatgggc    660

ggaggccgga agtacatgta tcccaagaac aagaccgacg tcgagtacga gagcgacgag    720

aaggccagag gcacaagact ggatggcctg gacctggtgg atacctggaa gtccttcaag    780

ccccggtaca agcacagcca cttcatctgg aaccggaccg agctgctgac actggaccct    840

cacaatgtgg actacctgct gggcctgttc gagcccggcg atatgcagta cgagctgaac    900

cggaacaacg tgacagaccc cagcctgagc gagatggtgg ttgtggccat tcagatcctg    960

cggaagaacc ccaagggatt cttcctgctg gtggaaggcg gcaggatcga tcacggacac   1020

catgagggaa aagccaagca ggccctgcac gaggccgtcg aaatggatag agccattggc   1080

caggccggca gcctgacaag ctctgaggat acactgaccg tggtcaccgc cgatcacagc   1140

cacgtgttca cattcggcgg ctacacccct agaggcaaca gcatctttgg actggcccct   1200

atgctgagcg acaccgacaa gaagcctttc accgccatcc tgtacggcaa cggccctggc   1260

tataaggttg tcggaggcga gagggaaaac gtgtccatgg tggattacgc ccacaacaac   1320

taccaggctc agagcgccgt gcctctgaga cacgaaacac acggcggaga agatgtggcc   1380

gtgttcagca agggccccat ggctcatctg ctgcatggcg tgcacgagca gaattacgtg   1440

ccacacgtga tggcctacgc cgcctgtatt ggagccaatc tgggacattg tgcccctgcc   1500

agtagcgccg gatccgacga tgatgacgac gacgatgacg atgactga                1548
```

<210> SEQ ID NO 109
<211> LENGTH: 1548
<212> TYPE: DNA
<213> ORGANISM: Artificial Sequence
<220> FEATURE:
<223> OTHER INFORMATION: Codon optimized, CO2-TNALP contains D10 tag at C end

<400> SEQUENCE: 109
atgatcagcc ccttcctggt gctggccatt ggcacctgcc tgaccaacag cctggtgcct 60
gagaaggaga aggaccccaa gtactggaga gaccaggccc aggagaccct gaagtatgcc 120
ctggagctgc agaagctgaa caccaatgtg gccaagaatg tgatcatgtt cctgggggat 180
ggcatggggg tgagcacagt gacagctgcc agaatcctga agggccagct gcaccacaac 240
cctggggagg agaccagact ggagatggac aagttcccct ttgtggccct gagcaagacc 300
tacaacacca atgcccaggt gcctgacagt gctggcacag ccacagccta cctgtgtggg 360
gtgaaggcca atgagggcac agtgggggtg agtgctgcca cagagagaag cagatgcaac 420
accacccagg gcaatgaggt gaccagcatc ctgagatggg ccaaggatgc tggcaagagt 480
gtgggcattg tgaccaccac cagagtgaac catgccaccc ccagtgctgc ctatgcccac 540
agtgctgaca gagactggta cagtgacaat gagatgcccc ctgaggccct gagccagggc 600
tgcaaggaca ttgcctacca gctgatgcac aacatcagag acattgatgt gatcatgggg 660
gggggcagaa agtacatgta ccccaagaac aagacagatg tggagtatga gagtgatgag 720
aaggccagag gcaccagact ggatggcctg gacctggtgg acacctggaa gagcttcaag 780
cccagataca agcacagcca cttcatctgg aacagaacag agctgctgac cctggacccc 840
cacaatgtgg actacctgct gggcctgttt gagcctgggg acatgcagta tgagctgaac 900
agaaacaatg tgacagaccc cagcctgagt gagatggtgg tggtggccat ccagatcctg 960
agaaagaacc ccaagggctt cttcctgctg gtggaggggg gcagaattga ccatggccac 1020
catgagggca aggccaagca ggccctgcat gaggctgtgg agatggacag agccattggc 1080
caggctggca gcctgaccag cagtgaggac accctgacag tggtgacagc tgaccacagc 1140
catgtgttca cctttggggg ctacaccccc agaggcaaca gcatctttgg cctggccccc 1200
atgctgagtg acacagacaa gaagcccttc acagccatcc tgtatggcaa tggccctggc 1260
tacaaggtgg tgggggggga gagagagaat gtgagcatgg tggactatgc ccacaacaac 1320
taccaggccc agagtgctgt gccccctgaga catgagaccc atgggggga ggatgtggct 1380 gtgttcagca agggccccat ggcccacctg ctgcatgggg tgcatgagca gaactatgtg 1440
ccccatgtga tggcctatgc tgcctgcatt ggggccaacc tgggccactg tgcccctgcc 1500
agcagtgctg gatccgatga tgatgatgat gatgatgatg atgactga 1548

<210> SEQ ID NO 110
<211> LENGTH: 636
<212> TYPE: DNA
<213> ORGANISM: Homo sapiens
<220> FEATURE:
<221> NAME/KEY: misc_feature
<222> LOCATION: (1)..(636)
<223> OTHER INFORMATION: Glial Cell Derived Neurotrophic Factor (GDNF)

<400> SEQUENCE: 110
atgaagttat gggatgtcgt ggctgtctgc ctggtgctgc tccacaccgc gtccgccttc 60
ccgctgcccg ccggcaagag gcctcccgag gcgcccgccg aagaccgctc cctcggccgc 120
cgccgcgcgc ccttcgcgct gagcagtgac tcaaatatgc cagaggatta tcctgatcag 180
ttcgatgatg tcatggattt tattcaagcc accattaaaa gactgaaaag gtcaccagat 240
aaacaaatgg cagtgcttcc tagaagagag cggaatcggc aggctgcagc tgccaaccca 300
gagaattcca gaggaaaagg tcggagaggc cagaggggca aaaaccgggg ttgtgtctta 360
actgcaatac atttaaatgt cactgacttg ggtctgggct atgaaaccaa ggaggaactg 420
atttttaggt actgcagcgg ctcttgcgat gcagctgaga caacgtacga caaaatattg 480
aaaaacttat ccagaaatag aaggctggtg agtgacaaag tagggcaggc atgttgcaga 540
cccatcgcct ttgatgatga cctgtcgttt ttagatgata acctggttta ccatattcta 600
agaaagcatt ccgctaaaag gtgtggatgt atctaa 636

<210> SEQ ID NO 111
<211> LENGTH: 1611
<212> TYPE: DNA
<213> ORGANISM: Homo sapiens
<220> FEATURE:
<221> NAME/KEY: misc_feature
<222> LOCATION: (1)..(1611)
<223> OTHER INFORMATION: Tissue Glucosyl Ceramidase beta (GBA1)

<400> SEQUENCE: 111
atggagtttt caagtccttc cagagaggaa tgtcccaagc ctttgagtag ggtaagcatc 60
atggctggca gcctcacagg attgcttcta cttcaggcag tgtcgtgggc atcaggtgcc 120
cgcccctgca tccctaaaag cttcggctac agctcggtgg tgtgtgtctg caatgccaca 180
tactgtgact cctttgaccc cccgaccttt cctgcccttg gtaccttcag ccgctatgag 240
agtacacgca gtgggcgacg gatggagctg agtatggggc ccatccaggc taatcacacg 300
ggcacaggcc tgctactgac cctgcagcca gaacagaagt tccagaaagt gaagggattt 360
ggaggggcca tgacagatgc tgctgctctc aacatccttg ccctgtcacc ccctgcccaa 420
aatttgctac ttaaatcgta cttctctgaa gaaggaatcg gatataacat catccgggta 480
ccaatggcca gctgtgactt ctccatccgc acctacacct atgcagacac ccctgatgat 540
ttccagttgc acaacttcag cctcccagag gaagatacca agctcaagat acccctgatt 600
caccgagccc tgcagttggc ccagcgtccc gtttcactcc ttgccagccc ctggacatca 660
cccacttggc tcaagaccaa tggagcggtg aatgggaagg ggtcactcaa gggacagccc 720
ggagacatct accaccagac ctgggccaga tactttgtga agttcctgga tgcctatgct 780
gagcacaagt tacagttctg ggcagtgaca gctgaaaatg agccttctgc tgggctgttg 840
agtggatacc ccttccagtg cctgggcttc acccctgaac atcagcgaga cttcattgcc 900
cgtgacctag gtcctaccct cgccaacagt actcaccaca atgtccgcct actcatgctg 960
gatgaccaac gcttgctgct gccccactgg gcaaaggtgg tactgacaga cccagaagca 1020
gctaaatatg ttcatggcat tgctgtacat tggtacctgg actttctggc tccagccaaa 1080
gccaccctag gggagacaca ccgcctgttc cccaacacca tgctctttgc ctcagaggcc 1140
tgtgtgggct ccaagttctg ggagcagagt gtgcggctag gctcctggga tcgagggatg 1200
cagtacagcc acagcatcat cacgaacctc ctgtaccatg tggtcggctg gaccgactgg 1260
aaccttgccc tgaaccccga aggaggaccc aattgggtgc gtaactttgt cgacagtccc 1320
atcattgtag acatcaccaa ggacacgttt tacaaacagc ccatgttcta ccaccttggc 1380
cacttcagca agttcattcc tgagggctcc cagagagtgg ggctggttgc cagtcagaag 1440
aacgacctgg acgcagtggc actgatgcat cccgatggct ctgctgttgt ggtcgtgcta 1500
aaccgctcct ctaaggatgt gcctcttacc atcaaggatc ctgctgtggg cttcctggag 1560
acaatctcac ctggctactc cattcacacc tacctgtggc gtcgccagtg a 1611

<210> SEQ ID NO 112
<211> LENGTH: 1611
<212> TYPE: DNA

<213> ORGANISM: Artificial Sequence
<220> FEATURE:
<223> OTHER INFORMATION: Codon optimized CO1-GBA1

<400> SEQUENCE: 112
atggagttca gcagccccag cagagaggag tgccccaagc ccctgagcag agtgagcatc 60
atggctggca gcctgacagg cctgctgctg ctgcaggctg tgagctgggc cagtggggcc 120
agaccctgca tccccaagag ctttggctac agcagtgtgg tgtgtgtgtg caatgccacc 180
tactgtgaca gctttgaccc ccccaccttc cctgccctgg gcaccttcag cagatatgag 240
agcaccagaa gtggcagaag aatggagctg agcatgggcc ccatccaggc caaccacaca 300
ggcacaggcc tgctgctgac cctgcagcct gagcagaagt tccagaaggt gaagggcttt 360 ggggggggcca tgacagatgc tgctgccctg aacatcctgg ccctgagccc ccctgcccag 420
aacctgctgc tgaagagcta cttcagtgag gagggcattg gctacaacat catcagagtg 480
ccaatggcca gctgtgactt cagcatcaga acctacacct atgctgacac ccctgatgac 540
ttccagctgc acaacttcag cctgcctgag gaggacacca agctgaagat ccccctgatc 600
cacagagccc tgcagctggc ccagagacct gtgagcctgc tggccagccc ctggaccagc 660
cccacctggc tgaagaccaa tggggctgtg aatggcaagg gcagcctgaa gggccagcct 720
ggggacatct accaccagac ctgggccaga tactttgtga agttcctgga tgcctatgct 780
gagcacaagc tgcagttctg ggctgtgaca gctgagaatg agcccagtgc tggcctgctg 840
agtggctacc ccttccagtg cctgggcttc accccctgagc accagagaga cttcattgcc 900
agagacctgg gccccaccct ggccaacagc acccaccaca atgtgagact gctgatgctg 960
gatgaccaga gactgctgct gccccactgg gccaaggtgg tgctgacaga ccctgaggct 1020
gccaagtatg tgcatggcat tgctgtgcac tggtacctgg acttcctggc ccctgccaag 1080
gccaccctgg gggagaccca cagactgttc cccaacacca tgctgtttgc cagtgaggcc 1140
tgtgtgggca gcaagttctg ggagcagagt gtgagactgg gcagctggga cagaggcatg 1200
cagtacagcc acagcatcat caccaacctg ctgtaccatg tggtgggctg gacagactgg 1260
aacctggccc tgaaccctga gggggggcccc aactgggtga gaaactttgt ggacagcccc 1320
atcattgtgg acatcaccaa ggacaccttc tacaagcagc ccatgttcta ccacctgggc 1380
cacttcagca agttcatccc tgagggcagc cagagagtgg gcctggtggc cagccagaag 1440
aatgacctgg atgctgtggc cctgatgcac cctgatggca gtgctgtggt ggtggtgctg 1500
aacagaagca gcaaggatgt gcccctgacc atcaaggacc ctgctgtggg cttcctggag 1560
accatcagcc ctggctacag catccacacc tacctgtgga gaagacagtg a 1611

<210> SEQ ID NO 113
<211> LENGTH: 1611
<212> TYPE: DNA
<213> ORGANISM: Artificial Sequence
<220> FEATURE:
<223> OTHER INFORMATION: Codon optimized CO2-GBA1

<400> SEQUENCE: 113
atggagttta gcagccctag cagagaggaa tgccccaagc ctctgagccg ggtgtcaatc 60
atggccggat ctctgacagg actgctgctg cttcaggccg tgtcttgggc ttctggcgct 120
agaccttgca tccccaagag cttcggctac agcagcgtcg tgtgcgtgtg caatgccacc 180
tactgcgaca gcttcgaccc tcctaccttt cctgctctgg gcaccttcag cagatacgag 240
agcaccagat ccggcagacg gatggaactg agcatgggac ccatccaggc caatcacaca 300

```
ggcactggcc tgctgctgac actgcagcct gagcagaaat tccagaaagt gaaaggcttc    360
ggcggagcca tgacagatgc cgccgctctg aatatcctgg ctctgtctcc accagctcag    420
aacctgctgc tcaagagcta cttcagcgag gaaggcatcg gctacaacat catccgggtg    480
ccaatggcca gctgcgactt cagcatccgg acctacacct acgccgacac acccgacgat    540
ttccagctgc acaacttcag cctgcctgaa gaggacacca agctgaagat ccctctgatc    600
cacagagccc tgcagctggc acaaagaccc gtttctctgc tggctagccc ctggacatct    660
cccacctggc tgaaaacaaa tggcgccgtg aatggcaagg gcagcctgaa aggccaacct    720
ggcgatatct accaccagac ctgggccaga tacttcgtga agttcctgga cgcctatgcc    780
gagcacaagc tgcagttttg ggccgtgaca gccgagaacg aaccttctgc tggactgctg    840
agcggctacc cctttcagtg cctgggcttt acacccgagc accagcggga ctttatcgcc    900
agagatctgg gacccacact ggccaatagc acccaccata atgtgcggct gctgatgctg    960
gacgaccaga gactgcttct gccccactgg gctaaagtgg tgctgacaga tcctgaggcc   1020
gccaaatacg tgcacggaat cgccgtgcac tggtatctgg actttctggc ccctgccaag   1080
gccacactgg gagagacaca cagactgttc cccaacacca tgctgttcgc cagcgaagcc   1140
tgtgtgggca gcaagttttg ggaacagagc gtgcggctcg gcagctggga tagaggcatg   1200
cagtacagcc acagcatcat caccaacctg ctgtaccacg tcgtcggctg gaccgactgg   1260
aatctggccc tgaatcctga aggcggccct aactgggtcc gaaacttcgt ggacagcccc   1320
atcatcgtgg acatcaccaa ggacaccttc tacaagcagc ccatgttcta ccacctggga   1380
cacttcagca agttcatccc cgagggctct cagcgcgttg gactggtggc cagccagaag   1440
aatgatctgg acgccgtggc tctgatgcac cctgatggat ctgctgtggt ggtggtcctg   1500
aaccgcagca gcaaagatgt gcccctgacc atcaaggatc ccgccgtggg attcctggaa   1560
acaatcagcc ctggctactc catccacacc tacctgtggc ggagacagtg a            1611
```

<210> SEQ ID NO 114
<211> LENGTH: 1962
<212> TYPE: DNA
<213> ORGANISM: Homo sapiens
<220> FEATURE:
<221> NAME/KEY: misc_feature
<222> LOCATION: (1)..(1962)
<223> OTHER INFORMATION: Iduronidase alpha-L- (IDUA)

<400> SEQUENCE: 114

```
atgcgtcccc tgcgcccccg cgccgcgctg ctggcgctcc tggcctcgct cctggccgcg     60
cccccggtgg ccccggccga ggccccgcac ctggtgcatg tggacgcggc ccgcgcgctg    120
tggcccctgc ggcgcttctg gaggagcaca ggcttctgcc ccccgctgcc acacagccag    180
gctgaccagt acgtcctcag ctgggaccag cagctcaacc tcgcctatgt gggcgccgtc    240
cctcaccgcg gcatcaagca ggtccggacc cactggctgc tggagcttgt caccaccagg    300
gggtccactg gacggggcct gagctacaac ttcacccacc tggacgggta cctggacctt    360
ctcagggaga accagctcct cccagggttt gagctgatgg gcagcgcctc gggccacttc    420
actgactttg aggacaagca gcaggtgttt gagtggaagg acttggtctc cagcctggcc    480
aggagataca tcggtaggta cggactggcg catgtttcca agtggaactt cgagacgtgg    540
aatgagccag accaccacga ctttgacaac gtctccatga ccatgcaagg cttcctgaac    600
tactacgatg cctgctcgga gggtctgcgc gccgccagcc ccgccctgcg gctgggaggc    660
```

cccggcgact ccttccacac cccaccgcga tccccgctga gctggggcct cctgcgccac 720
tgccacgacg gtaccaactt cttcactggg gaggcgggcg tgcggctgga ctacatctcc 780
ctccacagga agggtgcgcg cagctccatc tccatcctgg agcaggagaa ggtcgtcgcg 840
cagcagatcc ggcagctctt ccccaagttc gcggacaccc ccatttacaa cgacgaggcg 900
gacccgctgg tgggctggtc cctgccacag ccgtggaggg cggacgtgac ctacgcggcc 960
atggtggtga aggtcatcgc gcagcatcag aacctgctac tggccaacac cacctccgcc 1020
ttcccctacg cgctcctgag caacgacaat gccttcctga gctaccaccc gcaccccttc 1080
gcgcagcgca cgctcaccgc gcgcttccag gtcaacaaca cccgcccgcc gcacgtgcag 1140
ctgttgcgca agccggtgct cacggccatg ggctgctgg cgctgctgga tgaggagcag 1200
ctctgggccg aagtgtcgca ggccgggacc gtcctggaca gcaaccacac ggtgggcgtc 1260
ctggccagcg cccaccgccc ccagggcccg gccgacgcct ggcgcgccgc ggtgctgatc 1320
tacgcgagcg acgacacccg cgcccacccc aaccgcagcg tcgcggtgac cctgcggctg 1380
cgcggggtgc cccccggccc gggcctggtc tacgtcacgc gctacctgga caacgggctc 1440
tgcagccccg acggcgagtg gcggcgcctg ggccggcccg tcttccccac ggcagagcag 1500
ttccggcgca tgcgcgcggc tgaggacccg gtggccgcgg cgccccgccc cttacccgcc 1560
ggcggccgcc tgaccctgcg ccccgcgctg cggctgccgt cgcttttgct ggtgcacgtg 1620
tgtgcgcgcc ccgagaagcc gcccgggcag gtcacgcggc tccgcgccct gcccctgacc 1680
caagggcagc tggttctggt ctggtcggat gaacacgtgg gctccaagtg cctgtggaca 1740
tacgagatcc agttctctca ggacggtaag gcgtacaccc cggtcagcag gaagccatcg 1800
accttcaacc tctttgtgtt cagcccagac acaggtgctg tctctggctc ctaccgagtt 1860
cgagccctgg actactgggc ccgaccaggc cccttctcgg accctgtgcc gtacctggag 1920
gtccctgtgc caagagggcc cccatccccg ggcaatccat ga 1962

<210> SEQ ID NO 115
<211> LENGTH: 1962
<212> TYPE: DNA
<213> ORGANISM: Artificial Sequence
<220> FEATURE:
<223> OTHER INFORMATION: Codon optimized CO1-IDUA

<400> SEQUENCE: 115
atgagacccc tgagacccag agctgccctg ctggccctgc tggccagcct gctggctgcc 60
ccccctgtgg cccctgctga ggccccccac cttgtacatg tggatgctgc cagagccctg 120
tggcccctga gaagattctg gagaagcaca ggcttctgcc ccccccctgcc ccacagccag 180 gctgaccagt atgtgctgag ctgggaccag cagctgaacc tggcctatgt gggggctgtg 240
ccccacagag gcatcaagca ggtgagaacc cactggctgc tggagctggt gaccaccaga 300
ggcagcacag gcagaggcct gagctacaac ttcacccacc tggatggcta cctggacctg 360
ctgagagaga accagctgct gcctggcttt gagctgatgg gcagtgccag tggccacttc 420
acagactttg aggacaagca gcaggtgttt gagtggaagg acctggtgag cagcctggcc 480
agaagataca ttggcagata tggcctggcc catgtgagca agtggaactt tgagacctgg 540
aatgagcctg accaccatga ctttgacaat gtgagcatga ccatgcaggg cttcctgaac 600
tactatgatg cctgcagtga gggcctgaga gctgccagcc ctgccctgag actgggggc 660 cctggggaca gcttccacac ccccccccaga agcccccctga gctggggcct gctgagacac 720
tgccatgatg gcaccaactt cttcacaggg gaggctgggg tgagactgga ctacatcagc 780

```
ctgcacagaa agggggccag aagcagcatc agcatcctgg agcaggagaa ggtggtggcc    840

cagcagatca gacagctgtt ccccaagttt gctgacaccc ccatctacaa tgatgaggct    900

gaccccctgg tgggctggag cctgccccag ccctggagag ctgatgtgac ctatgctgcc    960

atggtggtga aggtgattgc ccagcaccag aacctgctgc tggccaacac caccagtgcc   1020

ttcccctatg ccctgctgag caatgacaat gccttcctga gctaccaccc ccaccccttt   1080

gcccagagaa ccctgacagc cagattccag gtgaacaaca ccagaccccc ccatgtgcag   1140

ctgctgagaa agcctgtgct gacagccatg ggcctgctgg ccctgctgga tgaggagcag   1200

ctgtgggctg aggtgagcca ggctggcaca gtgctggaca gcaaccacac agtgggggtg   1260

ctggccagtg cccacagacc ccagggccct gctgatgcct ggagagctgc tgtgctgatc   1320

tatgccagtg atgacaccag agcccacccc aacagaagtg tggctgtgac cctgagactg   1380

agaggggtgc cccctggccc tggcctggtg tatgtgacca gatacctgga caatggcctg   1440

tgcagccctg atggggagtg gagaagactg ggcagacctg tgttccccac agctgagcag   1500

ttcagaagaa tgagagctgc tgaggaccct gtggctgctg cccccagacc cctgcctgct   1560

gggggcagac tgaccctgag acctgccctg agactgccca gcctgctgct ggtgcatgtg   1620

tgtgccagac ctgagaagcc ccctggccag gtgaccagac tgagagccct gcccctgacc   1680

cagggccagc tggtgctggt gtggagtgat gagcatgtgg gcagcaagtg cctgtggacc   1740

tatgagatcc agttcagcca ggatggcaag gcctacaccc ctgtgagcag aaagcccagc   1800

accttcaacc tgtttgtgtt cagccctgac acaggggctg tgagtggcag ctacagagtg   1860

agagccctgg actactgggc cagacctggc cccttcagtg accctgtgcc ctacctggag   1920

gtgcctgtgc ccagaggccc ccccagccct ggcaacccct ga                      1962
```

<210> SEQ ID NO 116
<211> LENGTH: 1578
<212> TYPE: DNA
<213> ORGANISM: Homo sapiens
<220> FEATURE:
<221> NAME/KEY: misc_feature
<222> LOCATION: (1)..(1578)
<223> OTHER INFORMATION: Cytochrome P450 family 4 subfamily V member 2 (CYP4V2)

<400> SEQUENCE: 116

```
atggcggggc tctggctggg gctcgtgtgg cagaagctgc tgctgtgggg cgcggcgagt     60

gccctttccc tggccggcgc cagtctggtc ctgagcctgc tgcagagggt ggcgagctac    120

gcgcggaaat ggcagcagat gcggcccatc cccacggtgg cccgcgccta cccactggtg    180

ggccacgcgc tgctgatgaa gccggacggg cgagaatttt ttcagcagat cattgagtac    240

acagaggaat accgccacat gccgctgctg aagctctggg tcgggccagt gcccatggtg    300

gccctttata atgcagaaaa tgtggaggta attttaacta gttcaaagca aattgacaaa    360

tcctctatgt acaagttttt agaaccatgg cttggcctag gacttcttac aagtactgga    420

aacaaatggc gctccaggag aaagatgtta acacccactt tccattttac cattctggaa    480

gatttcttag atatcatgaa tgaacaagca aatatattgg ttaagaaact tgaaaaacac    540

attaaccaag aagcatttaa ctgctttttt tacatcactc tttgtgcctt agatatcatc    600

tgtgaaacag ctatggggaa gaatattggt gctcaaagta atgatgattc cgagtatgtc    660

cgtgcagttt atagaatgag tgagatgata tttcgaagaa taaagatgcc ctggctttgg    720

cttgatctct ggtatcttat gtttaaagaa ggatgggaac acaaaaagag ccttcagatc    780
```

```
ctacatactt ttaccaacag tgtcatcgct gaacgggcca atgaaatgaa cgccaatgaa    840

gactgtagag gtgatggcag gggctctgcc ccctccaaaa ataaacgcag ggcctttctt    900

gacttgcttt taagtgtgac tgatgacgaa gggaacaggc taagtcatga agatattcga    960

gaagaagttg acaccttcat gtttgagggg cacgatacaa ctgcagctgc aataaactgg   1020

tccttatacc tgttgggttc taacccagaa gtccagaaaa aagtggatca tgaattggat   1080

gacgtgtttg ggaagtctga ccgtcccgct acagtagaag acctgaagaa acttcggtat   1140

ctggaatgtg ttattaagga gacccttcgc ctttttcctt ctgttccttt atttgcccgt   1200

agtgttagtg aagattgtga agtggcaggt tacagagttc taaaaggcac tgaagccgtc   1260

atcattccct atgcattgca cagagatccg agatacttcc ccaaccccga ggagttccag   1320

cctgagcggt tcttccccga gaatgcacaa gggcgccatc catatgccta cgtgcccttc   1380

tctgctggcc ccaggaactg tataggtcaa aagtttgctg tgatggaaga aaagaccatt   1440

ctttcgtgca tcctgaggca cttttggata gaatccaacc agaaaagaga agagcttggt   1500

ctagaaggac agttgattct tcgtccaagt aatggcatct ggatcaagtt gaagaggaga   1560

aatgcagatg aacgctaa                                                 1578
```

```
<210> SEQ ID NO 117
<211> LENGTH: 711
<212> TYPE: DNA
<213> ORGANISM: Homo sapiens
<220> FEATURE:
<221> NAME/KEY: misc_feature
<222> LOCATION: (1)..(711)
<223> OTHER INFORMATION: Retinoschisin 1 (RS1)

<400> SEQUENCE: 117

atgagccgca agatagaagg ctttttgtta ttacttctct ttggctatga agccacattg     60

ggattatcgt ctaccgagga tgaaggcgag gacccctggt atcaaaaagc atgcgatgaa    120

ggcgaggacc cctggtatca aaaagcatgc aagtgcgatt gccaaggagg acccaatgct    180

ctgtggtctg caggtgccac ctccttggac tgtataccag aatgcccata tcacaagcct    240

ctgggtttcg agtcagggga ggtcacaccg gaccagatca cctgctctaa cccggagcag    300

tatgtgggct ggtattcttc gtggactgca aacaaggccc ggctcaacag tcaaggcttt    360

gggtgtgcct ggctctccaa gttccaggac agtagccagt ggttacagat agatctgaag    420

gagatcaaag tgatttcagg gatcctcacc caggggcgct gtgacatcga tgagtggatg    480

accaagtaca gcgtgcagta caggaccgat gagcgcctga actggattta ctacaaggac    540

cagactggaa acaaccgggt cttctatggc aactcggacc gcacctccac ggttcagaac    600

ctgctgcggc cccccatcat ctcccgcttc atccgcctca tcccgctggg ctggcacgtc    660

cgcattgcca tccggatgga gctgctggag tgcgtcagca agtgtgcctg a            711
```

```
<210> SEQ ID NO 118
<211> LENGTH: 2565
<212> TYPE: DNA
<213> ORGANISM: Homo sapiens
<220> FEATURE:
<221> NAME/KEY: misc_feature
<222> LOCATION: (1)..(2565)
<223> OTHER INFORMATION: Phosphodiesterase 6B (PDE6B)

<400> SEQUENCE: 118

atgagcctca gtgaggagca ggcccggagc tttctggacc agaaccccga ttttgcccgc     60
```

```
cagtactttg ggaagaaact gagccctgag aatgtggccg cggcctgcga ggacgggtgc    120
ccgccggact gcgacagcct ccgggacctc tgccaggtgg aggagagcac ggcgctgctg    180
gagctggtgc aggatatgca ggagagcatc aacatggagc gcgtggtctt caaggtcctg    240
cggcgcctct gcaccctgct gcaggccgac cgctgcagcc tcttcatgta ccgccagcgc    300
aacggcgtgg ccgagctggc caccaggctt ttcagcgtgc agccggacag cgtcctggag    360
gactgcctgg tgccccccga ctccgagatc gtcttcccac tggacatcgg ggtcgtgggc    420
cacgtggctc agaccaaaaa gatggtgaac gtcgaggacg tggccgagtg ccctcacttc    480
agctcatttg ctgacgagct cactgactac aagacaaaga atatgctggc cacacccatc    540
atgaatggca aagacgtcgt ggcggtgatc atggcagtga acaagctcaa cggcccattc    600
ttcaccagcg aagacgaaga tgtgttcttg aagtacctga attttgccac gttgtacctg    660
aaaatctatc acctgagcta cctccacaac tgcgagacgc gccgcggcca ggtgctgctg    720
tggtcggcca acaaggtgtt tgaggagctg acggacatcg agaggcagtt ccacaaggcc    780
ttctacacgg tgcgggccta cctcaactgc gagcggtact ccgtgggcct cctggacatg    840
accaaggaga aggaattttt tgacgtgtgg tctgtgctga tgggagagtc ccagccgtac    900
tcgggcccac gcacgcctga tggccgggaa attgtcttct acaaagtgat cgactacatc    960
ctccacggca aggaggagat caaggtcatt cccacaccct cagccgatca ctgggccctg   1020
gccagcggcc ttccaagcta cgtggcagaa agcggcttta tttgtaacat catgaatgct   1080
tccgctgacg aaatgttcaa atttcaggaa ggggccctgg acgactccgg gtggctcatc   1140
aagaatgtgc tgtccatgcc catcgtcaac aagaaggagg agattgtggg agtcgccaca   1200
ttttacaaca ggaaagacgg gaagcccttt gacgaacagg acgaggttct catggagtcc   1260
ctgacacagt tcctgggctg gtcagtgatg aacaccgaca cctacgacaa gatgaacaag   1320
ctggagaacc gcaaggacat cgcacaggac atggtccttt accacgtgaa gtgcgacagg   1380
gacgagatcc agctcatcct gccaaccaga gcgcgcctgg ggaaggagcc tgctgactgc   1440
gatgaggacg agctgggcga aatcctgaag gaggagctgc cagggcccac cacatttgac   1500
atctacgaat tccacttctc tgacctggag tgcaccgaac tggacctggt caaatgtggc   1560
atccagatgt actacgagct gggcgtggtc cgaaagttcc agatccccca ggaggtcctg   1620
gtgcggttcc tgttctccat cagcaaaggc taccggagaa tcacctacca caactggcgc   1680
cacggcttca acgtggccca gacgatgttc acgctgctca tgaccggcaa actgaagagc   1740
tactacacgg acctggaggc cttcgccatg gtgacagccg gcctgtgcca tgacatcgac   1800
caccgcggca ccaacaacct gtaccagatg aagtcccaga accccttggc taaactccac   1860
ggctcctcga ttttggagcg gcaccacctg gagtttggga agttcctgct ctcggaggag   1920
accctgaaca tctaccagaa cctgaaccgg cggcagcacg agcacgtgat ccacctgatg   1980
gacatcgcca tcatcgccac ggacctggcc ctgtacttca agaagagagc gatgtttcag   2040
aagatcgtgg atgagtccaa gaactaccag gacaagaaga gctgggtgga gtacctgtcc   2100
ctggagacga cccggaagga gatcgtcatg gccatgatga tgacagcctg cgacctgtct   2160
gccatcacca agccctggga agtccagagc aaggtcgcac ttctcgtggc tgctgagttc   2220
tgggagcaag gtgacttgga aaggacagtc ttggatcagc agcccattcc tatgatggac   2280
cggaacaagg cggccgagct ccccaagctg caagtgggct tcatcgactt cgtgtgcaca   2340
ttcgtgtaca aggagttctc tcgtttccac gaagagatcc tgcccatgtt cgaccgactg   2400
cagaacaata ggaaagagtg gaaggcgctg gctgatgagt atgaggccaa agtgaaggct   2460
```

ctggaggaga aggaggagga ggagagggtg gcagccaaga aagtaggcac agaaatttgc 2520
aatggcggcc cagcacccaa gtcttcaacc tgctgtatcc tgtga 2565

<210> SEQ ID NO 119
<211> LENGTH: 1497
<212> TYPE: DNA
<213> ORGANISM: Homo sapiens
<220> FEATURE:
<221> NAME/KEY: misc_feature
<222> LOCATION: (1)..(1497)
<223> OTHER INFORMATION: Methyl-CpG Binding Protein (MeCP2)

<400> SEQUENCE: 119
atggccgccg ccgccgccgc cgcgccgagc ggaggaggag gaggaggcga ggaggagaga 60
ctggaagaaa agtcagaaga ccaggacctc cagggcctca aggacaaacc cctcaagttt 120
aaaaaggtga agaaagataa gaaagaagag aaagagggca agcatgagcc cgtgcagcca 180
tcagcccacc actctgctga gcccgcagag gcaggcaaag cagagacatc agaagggtca 240
ggctccgccc cggctgtgcc ggaagcttct gcctccccca aacagcggcg ctccatcatc 300
cgtgaccggg gacccatgta tgatgacccc accctgcctg aaggctggac acggaagctt 360
aagcaaagga aatctggccg ctctgctggg aagtatgatg tgtatttgat caatccccag 420
ggaaaagcct ttcgctctaa agtggagttg attgcgtact tcgaaaaggt aggcgacaca 480
tccctggacc ctaatgattt tgacttcacg gtaactggga gagggagccc ctcccggcga 540
gagcagaaac cacctaagaa gcccaaatct cccaaagctc caggaactgg cagaggccgg 600
ggacgcccca aagggagcgg caccacgaga cccaaggcgg ccacgtcaga gggtgtgcag 660
gtgaaaaggg tcctggagaa aagtcctggg aagctccttg tcaagatgcc ttttcaaact 720
tcgccagggg gcaaggctga ggggggtggg gccaccacat ccacccaggt catggtgatc 780
aaacgccccg gcaggaagcg aaaagctgag gccgaccctc aggccattcc caagaaacgg 840
ggccgaaagc cggggagtgt ggtggcagcc gctgccgccg aggccaaaaa gaaagccgtg 900
aaggagtctt ctatccgatc tgtgcaggag accgtactcc ccatcaagaa gcgcaagacc 960
cgggagacgg tcagcatcga ggtcaaggaa gtggtgaagc ccctgctggt gtccaccctc 1020
ggtgagaaga gcgggaaagg actgaagacc tgtaagagcc ctgggcggaa aagcaaggag 1080
agcagcccca aggggcgcag cagcagcgcc tcctcacccc ccaagaagga gcaccaccac 1140
catcaccacc actcagagtc cccaaaggcc cccgtgccac tgctcccacc cctgccccca 1200
cctccacctg agcccgagag ctccgaggac cccaccagcc cccctgagcc ccaggacttg 1260
agcagcagcg tctgcaaaga ggagaagatg cccagaggag gctcactgga gagcgacggc 1320
tgccccaagg agccagctaa gactcagccc gcggttgcca ccgccgccac ggccgcagaa 1380
aagtacaaac accgagggga gggagagcgc aaagacattg tttcatcctc catgccaagg 1440
ccaaacagag aggagcctgt ggacagccgg acgcccgtga ccgagagagt tagctag 1497

<210> SEQ ID NO 120
<211> LENGTH: 2232
<212> TYPE: DNA
<213> ORGANISM: Homo sapiens
<220> FEATURE:
<221> NAME/KEY: misc_feature
<222> LOCATION: (1)..(2232)
<223> OTHER INFORMATION: N-acetyl-alpha-glucosaminidase (NAGLU)

<400> SEQUENCE: 120

```
atggaggcgg tggcggtggc cgcggcggtg ggggtccttc tcctggccgg ggccgggggc     60
gcggcaggcg acgaggcccg ggaggcggcg gccgtgcggg cgctcgtggc ccggctgctg    120
gggccaggcc ccgcggccga cttctccgtg tcggtggagc gcgctctggc tgccaagccg    180
ggcttggaca cctacagcct gggcggcggc ggcgcggcgc gcgtgcgggt gcgcggctcc    240
acgggcgtgg cggccgccgc ggggctgcac cgctacctgc gcgacttctg tggctgccac    300
gtggcctggt ccggctctca gctgcgcctg ccgcggccac tgccagccgt gccgggggag    360
ctgaccgagg ccacgcccaa caggtaccgc tattaccaga atgtgtgcac gcaaagctac    420
tccttcgtgt ggtgggactg ggcccgctgg gagcgagaga tagactggat ggcgctgaat    480
ggcatcaacc tggcactggc ctggagcggc caggaggcca tctggcagcg ggtgtacctg    540
gccttgggcc tgacccaggc agagatcaat gagttcttta ctggtcctgc cttcctggcc    600
tgggggcgaa tgggcaacct gcacacctgg gatggccccc tgccccccctc ctggcacatc    660
aagcagcttt acctgcagca ccgggtcctg gaccagatgc gctccttcgg catgacccca    720
gtgctgcctg cattcgcggg gcatgttccc gaggctgtca ccagggtgtt ccctcaggtc    780
aatgtcacga agatgggcag ttggggccac tttaactgtt cctactcctg ctccttcctt    840
ctggctccgg aagaccccat attccccatc atcgggagcc tcttcctgcg agagctgatc    900
aaagagtttg gcacagacca catctatggg gccgacactt tcaatgagat gcagccacct    960
tcctcagagc cctcctacct tgccgcagcc accactgccg tctatgaggc catgactgca   1020
gtggatactg aggctgtgtg gctgctccaa ggctggctct tccagcacca gccgcagttc   1080
tgggggcccg cccagatcag ggctgtgctg ggagctgtgc cccgtggccg cctcctggtt   1140
ctggacctgt ttgctgagag ccagcctgtg tatacccgca ctgcctcctt ccagggccag   1200
cccttcatct ggtgcatgct gcacaacttt gggggaaacc atggtctttt tggagcccta   1260
gaggctgtga acggaggccc agaagctgcc cgcctcttcc ccaactccac catggtaggc   1320
acgggcatgg cccccgaggg catcagccag aacgaagtgg tctattccct catggctgag   1380
ctgggctggc gaaaggaccc agtgccagat ttggcagcct gggtgaccag ctttgccgcc   1440
cggcggtatg gggtctccca cccggacgca ggggcagcgt ggaggctact gctccggagt   1500
gtgtacaact gctccgggga ggcctgcagg ggccacaatc gtagcccgct ggtcaggcgg   1560
ccgtccctac agatgaatac cagcatctgg tacaaccgat ctgatgtgtt tgaggcctgg   1620
cggctgctgc tcacatctgc tccctccctg gccaccagcc ccgccttccg ctacgacctg   1680
ctggacctca ctcggcaggc agtgcaggag ctggtcagct tgtactatga ggaggcaaga   1740
agcgcctacc tgagcaagga gctggcctcc ctgttgaggg ctggaggcgt cctggcctat   1800
gagctgctgc cggcactgga cgaggtgctg gctagtgaca gccgcttctt gctgggcagc   1860
tggctagagc aggcccgagc agcggcagtc agtgaggccg aggccgattt ctacgagcag   1920
aacagccgct accagctgac cttgtggggg ccagaaggca acatcctgga ctatgccaac   1980
aagcagctgg cggggttggt ggccaactac tacacccctc gctggcggct tttcctggag   2040
gcgctggttg acagtgtggc ccagggcatc cctttccaac agcaccagtt tgacaaaaat   2100
gtcttccaac tggagcaggc cttcgttctc agcaagcaga ggtaccccag ccagccgcga   2160
ggagacactg tggacctggc caagaagatc ttcctcaaat attaccccgg ctgggtggcc   2220
ggctcttggt ga                                                       2232
```

<210> SEQ ID NO 121
<211> LENGTH: 1317

<212> TYPE: DNA
<213> ORGANISM: Homo sapiens
<220> FEATURE:
<221> NAME/KEY: misc_feature
<222> LOCATION: (1)..(1317)
<223> OTHER INFORMATION: Ceroid Lipofuscinosis, Neuronal 3 (CLN3)

<400> SEQUENCE: 121
atgggaggct gtgcaggctc gcggcggcgc ttttcggatt ccgaggggga ggagaccgtc 60
ccggagcccc ggctccctct gttggaccat cagggcgcgc attggaagaa cgcggtgggc 120
ttctggctgc tgggcctttg caacaacttc tcttatgtgg tgatgctgag tgccgcccac 180
gacatcctta gccacaagag gacatcggga aaccagagcc atgtggaccc aggcccaacg 240
ccgatccccc acaacagctc atcacgattt gactgcaact ctgtctctac ggctgctgtg 300
ctcctggcgg acatcctccc cacactcgtc atcaaattgt tggctcctct tggccttcac 360
ctgctgccct acagccccccg ggttctcgtc agtgggattt gtgctgctgg aagcttcgtc 420
ctggttgcct tttctcattc tgtggggacc agcctgtgtg gtgtggtctt cgctagcatc 480
tcatcaggcc ttggggaggt caccttcctc tccctcactg ccttctaccc cagggccgtg 540
atctcctggt ggtcctcagg gactggggga gctgggctgc tgggggccct gtcctacctg 600
ggcctcaccc aggccggcct ctcccctcag cagaccctgc tgtccatgct gggtatccct 660
gccctgctgc tggccagcta tttcttgttg ctcacatctc ctgaggccca ggaccctgga 720
ggggaagaag aagcagagag cgcagcccgg cagcccctca taagaaccga ggccccggag 780
tcgaagccag gctccagctc cagcctctcc cttcgggaaa ggtggacagt gttcaagggt 840
ctgctgtggt acattgttcc cttggtcgta gtttactttg ccgagtattt cattaaccag 900
ggactttttg aactcctctt tttctggaac acttccctga gtcacgctca gcaataccgc 960
tggtaccaga tgctgtacca ggctggcgtc tttgcctccc gctcttctct ccgctgctgt 1020
cgcatccgtt tcacctgggc cctggccctg ctgcagtgcc tcaacctggt gttcctgctg 1080
gcagacgtgt ggttcggctt tctgccaagc atctacctcg tcttcctgat cattctgtat 1140
gaggggctcc tgggaggcgc agcctacgtg aacaccttcc acaacatcgc cctggagacc 1200
agtgatgagc accgggagtt tgcaatggcg gccacctgca tctctgacac actggggatc 1260
tccctgtcgg ggctcctggc tttgcctctg catgacttcc tctgccagct ctcctga 1317

<210> SEQ ID NO 122
<211> LENGTH: 1317
<212> TYPE: DNA
<213> ORGANISM: Artificial Sequence
<220> FEATURE:
<223> OTHER INFORMATION: Codon optimized CO1-CLN3

<400> SEQUENCE: 122
atgggaggat gtgctgggtc aagaagacgg tttagcgatt ccgaaggaga ggagactgtg 60
cctgagccaa gactgcccct gctggatcac cagggagcac actggaagaa cgcagtggga 120
ttctggctgc tgggcctgtg caacaacttc agctacgtgg tcatgctgtc cgccgcccac 180
gacatcctgt cccacaagcg gacctccggc aatcagtctc acgtggaccc cggccctaca 240
ccaatccccc acaacagcag cagccggttc gactgtaatt ccgtgtctac cgcagccgtg 300
ctgctggcag acatcctgcc caccctggtc atcaagctgc tggcaccact gggcctgcac 360
ctgctgcctt attctccaag ggtgctggtg agcggcatct gcgcagcagg cagcttcgtg 420
ctggtggcct ttagccactc cgtgggcacc tctctgtgcg gagtggtgtt tgcaagcatc 480
agctccggcc tgggagaggt gaccttcctg agcctgacag ccttttaccc tcgcgccgtg 540
atctcctggt ggtctagcgg cacaggagga gcaggcctgc tgggcgccct gtcctatctg 600
ggcctgaccc aggcaggcct gtccccacag cagacactgc tgtctatgct gggcatccct 660
gccctgctgc tggcaagcta cttcctgctg ctgacctccc cagaggcaca ggaccccgga 720
ggagaggagg aggccgagag cgccgcaagg cagccactga tcaggaccga ggcaccagag 780
tccaagcctg gctcctctag ctccctgtct ctgcgggaga gatggacagt gttcaagggc 840
ctgctgtggt acatcgtgcc cctggtggtg gtgtacttcg ccgagtactt catcaaccag 900
ggcctgtttg agctgctgtt cttttggaat acctctctga gccacgccca gcagtaccgg 960
tggtatcaga tgctgtatca ggcaggcgtg ttcgcctccc ggtctagcct gagatgctgt 1020
cggatcagat tcacctgggc actggccctg ctgcagtgcc tgaacctggt gttcctgctg 1080
gccgacgtgt ggttcggctt tctgccctct atctacctgg tgtttctgat catcctgtat 1140
gagggcctgc tgggaggagc agcctatgtg aacaccttcc acaatatcgc cctggagaca 1200
tctgacgagc acagagagtt tgctatggcc gccacctgta tcagcgatac actgggcatc 1260
tctctgagcg gactgctggc tctgcctctg catgactttc tgtgccagct gagttaa 1317

<210> SEQ ID NO 123
<211> LENGTH: 2859
<212> TYPE: DNA
<213> ORGANISM: Homo sapiens
<220> FEATURE:
<221> NAME/KEY: misc_feature
<222> LOCATION: (1)..(2859)
<223> OTHER INFORMATION: Acid Alpha-Glucosidase (GAA)

<400> SEQUENCE: 123
atgggagtga ggcacccgcc ctgctcccac cggctcctgg ccgtctgcgc cctcgtgtcc 60
ttggcaaccg ctgcactcct ggggcacatc ctactccatg atttcctgct ggttccccga 120
gagctgagtg gctcctcccc agtcctggag gagactcacc cagctcacca gcagggagcc 180
agcagaccag ggccccggga tgcccaggca caccccggcc gtcccagagc agtgcccaca 240
cagtgcgacg tcccccccaa cagccgcttc gattgcgccc ctgacaaggc catcacccag 300
gaacagtgcg aggcccgcgg ctgttgctac atccctgcaa agcaggggct gcagggagcc 360
cagatggggc agccctggtg cttcttccca cccagctacc ccagctacaa gctggagaac 420
ctgagctcct ctgaaatggg ctacacggcc accctgaccc gtaccacccc caccttcttc 480
cccaaggaca tcctgaccct gcggctggac gtgatgatgg agactgagaa ccgcctccac 540
ttcacgatca aagatccagc taacaggcgc tacgaggtgc ccttggagac cccgcatgtc 600
cacagccggg caccgtcccc actctacagc gtggagttct ccgaggagcc cttcggggtg 660
atcgtgcgcc ggcagctgga cggccgcgtg ctgctgaaca cgacggtggc gccccctgttc 720 tttgcggacc agttccttca gctgtccacc tcgctgccct cgcagtatat cacaggcctc 780
gccgagcacc tcagtcccct gatgctcagc accagctgga ccaggatcac cctgtggaac 840
cgggaccttg cgcccacgcc cggtgcgaac ctctacgggt ctcacccttt ctacctggcg 900
ctggaggacg gcgggtcggc acacggggtg ttcctgctaa acagcaatgc catggatgtg 960
gtcctgcagc cgagccctgc ccttagctgg aggtcgacag gtgggatcct ggatgtctac 1020
atcttcctgg gcccagagcc caagagcgtg gtgcagcagt acctggacgt tgtgggatac 1080
ccgttcatgc cgccatactg gggcctgggc ttccacctgt gccgctgggg ctactcctcc 1140
accgctatca cccgccaggt ggtggagaac atgaccaggg cccacttccc cctggacgtc 1200

```
cagtggaacg acctggacta catggactcc cggagggact tcacgttcaa caaggatggc   1260

ttccgggact tcccggccat ggtgcaggag ctgcaccagg gcggccggcg ctacatgatg   1320

atcgtggatc ctgccatcag cagctcgggc cctgccggga gctacaggcc ctacgacgag   1380

ggtctgcgga ggggggtttt catcaccaac gagaccggcc agccgctgat tgggaaggta   1440

tggcccgggt ccactgcctt ccccgacttc accaacccca cagccctggc ctggtgggag   1500

gacatggtgg ctgagttcca tgaccaggtg cccttcgacg gcatgtggat tgacatgaac   1560

gagccttcca acttcatcag ggctctgag gacggctgcc ccaacaatga gctggagaac   1620

ccaccctacg tgcctggggt ggttgggggg accctccagg cggccaccat ctgtgcctcc   1680

agccaccagt ttctctccac acactacaac ctgcacaacc tctacggcct gaccgaagcc   1740

atcgcctccc acagggcgct ggtgaaggct cgggggacac gcccatttgt gatctcccgc   1800

tcgacctttg ctggccacgg ccgatacgcc ggccactgga cgggggacgt gtggagctcc   1860

tgggagcagc tcgcctcctc cgtgccagaa atcctgcagt ttaacctgct gggggtgcct   1920

ctggtcgggg ccgacgtctg cggcttcctg ggcaacacct cagaggagct gtgtgtgcgc   1980

tggacccagc tgggggcctt ctaccccttc atgcggaacc acaacagcct gctcagtctg   2040

ccccaggagc cgtacagctt cagcgagccg gcccagcagg ccatgaggaa ggccctcacc   2100

ctgcgctacg cactcctccc ccacctctac acactgttcc accaggccca cgtcgcgggg   2160

gagaccgtgg cccggcccct cttcctggag ttccccaagg actctagcac ctggactgtg   2220

gaccaccagc tcctgtgggg ggaggccctg ctcatcaccc cagtgctcca ggccgggaag   2280

gccgaagtga ctggctactt ccccttgggc acatggtacg acctgcagac ggtgccagta   2340

gaggcccttg gcagcctccc acccccacct gcagctcccc gtgagccagc catccacagc   2400

gaggggcagt gggtgacgct gccggccccc ctggacacca tcaacgtcca cctccgggct   2460

gggtacatca tcccccctgca gggccctggc ctcacaacca cagagtcccg ccagcagccc   2520

atggccctgg ctgtggccct gaccaagggt ggggaggccc gaggggagct gttctgggac   2580

gatggagaga gcctggaagt gctggagcga ggggcctaca cacaggtcat cttcctggcc   2640

aggaataaca cgatcgtgaa tgagctggta cgtgtgacca gtgagggagc tggcctgcag   2700

ctgcagaagg tgactgtcct gggcgtggcc acggcgcccc agcaggtcct ctccaacggt   2760

gtccctgtct ccaacttcac ctacagcccc gacaccaagg tcctggacat ctgtgtctcg   2820

ctgttgatgg gagagcagtt tctcgtcagc tggtgttag                          2859
```

<210> SEQ ID NO 124
<211> LENGTH: 2859
<212> TYPE: DNA
<213> ORGANISM: Artificial Sequence
<220> FEATURE:
<223> OTHER INFORMATION: Codon optimized CO1-GAA

<400> SEQUENCE: 124

```
atgggagtcc gccacccgcc ctgctcacat cgcctgcttg ctgtctgtgc cctcgtgtca     60

cttgctaccg ccgcgctgct tggtcacatt ctgctgcacg actttttact agttccgagg    120

gaactgtcgg gatccagccc cgtgctcgag gaaactcacc ccgcgcacca acagggggcg    180

tccaggccgg gaccgcgcga cgcccaggcc cacccgggcc ggcctcgggc cgtgccaact    240

cagtgcgatg tgccgccgaa ctcccgcttc gactgtgcgc ctgacaaggc cataacccag    300

gaacagtgcg aagcacgcgg ctgctgctat attccggcga agcagggctt gcagggtgcc    360
```

caaatgggtc agccttggtg cttctttccc ccgtcgtacc cctcgtacaa gctggagaac 420
ctgagcagca gcgaaatggg gtacaccgcc actctgaccc ggacgacccc gaccttcttc 480
ccgaaagaca tcctgaccct gcggctggat gtgatgatgg aaactgagaa cagactgcac 540
ttcactatca aggaccccgc gaaccgcaga tatgaggtgc cactggaaac cccctcatgtg 600
cattcccggg ccccatcccc tctgtactcg gtggaattct ccgaagaacc cttcggggtc 660
attgtgcgcc ggcagcttga tggccgggtc ctgctcaaca ccaccgtggc accccttttc 720
ttcgctgacc agttcctcca gctgagcacc tcgctgccga gccagtacat caccggactg 780
gccgagcacc tctcccctct gatgctgtcc actagctgga ctaggatcac tctgtggaac 840
cgggatctgg cccctacccc gggcgcgaac ctgtacggat cgcacccctt ctacctggcc 900
ctcgaggacg gaggctccgc ccacggagtg ttcctgctga actccaacgc tatggacgtg 960
gtgctccagc cgtcccctgc actgtcctgg cggagcacag gggtattct ggatgtctac 1020
atcttcctcg gcccggagcc aaagtccgtg gtgcaacagt atctggatgt cgtgggttac 1080
ccattcatgc cgccatactg ggccttggc ttccacctgt gccgctgggg atacagctcc 1140
accgccatca ctagacaggt cgtggaaaac atgactagag cccacttccc cctcgatgtc 1200
cagtggaatg acctggacta catggattcc agacgcgact tcactttcaa caaggatgga 1260
ttcagagatt tccccgctat ggtccaagaa ctgcaccagg gtggccggcg gtacatgatg 1320
attgtggacc ccgccatttc aagctccgga ccagcgggct cgtaccggcc ctacgacgaa 1380
ggtttgcgcc gcggcgtgtt catcactaac gaaaccggcc agccactgat tgggaaggtc 1440
tggcctggaa gcaccgcgtt cccggacttc actaacccaa cggccttggc gtggtgggag 1500
gacatggtgg ccgaattcca cgaccaagtc ccattcgacg gaatgtggat cgacatgaac 1560
gagcccagca acttcatccg aggctccgag gacggctgcc ctaacaacga acttgagaac 1620
cctccgtacg tgcctggcgt cgtcggcgga acactgcagg ccgctacgat ctgtgcctca 1680
tcgcatcagt tcctgtcaac ccactacaac ctccataatc tgtacggcct caccgaagcc 1740
atcgcctccc accgggccct ggtcaaggcc cgggggacta ggcccttcgt gattagccgg 1800
agcactttcg ccggacacgg aagatacgcc ggacattgga ccggcgacgt gtggtcatcg 1860
tgggagcagc tcgcctcctc cgtccccgaa atcctgcagt tcaatctcct gggagtcccc 1920
ctcgtgggcg cggacgtgtg cggattcctg ggcaatacct ctgaggagct gtgcgtgaga 1980
tggacccagc tgggggcgtt ctaccccttc atgcggaacc acaactcact gctgtccctg 2040
cctcaagagc cgtactcatt ctccgagccg gcacaacagg ccatgcgaaa ggctctgacc 2100
ctccgctatg cgctcttgcc ccacctctac actctgtttc accaagccca tgtcgcgggc 2160
gaaacagtgg ccagaccact ctttctggaa ttcccaaagg actcctcaac ctggactgtg 2220
gatcatcagc tgctctgggg agaggcactg ctgatcaccc cggtgctcca agccggaaag 2280
gcggaagtga ccggatactt ccctctcggt acttggtacg acctccaaac cgtgccggtc 2340
gaggccctgg gcagcttgcc tccgccgccg gctgccccgc gggagcctgc aatccactcc 2400
gaggggcaat gggtgaccct ccctgcacca ctggacacca tcaacgtgca cctccgggcc 2460
ggctacatca tcccgctgca aggaccgggt ctgactacca ccgaatcccg gcagcagccc 2520
atggcactgg ccgtggccct gaccaaggga ggggaagcac ggggagaact cttttgggac 2580
gatggagaat ccctggaagt gctcgagcgg ggagcctaca ctcaagtcat ctttcttgcc 2640
cgcaacaaca ccatcgtgaa cgaattggtc cgcgtgacct ccgagggggc cggactccag 2700
ctgcaaaaag tgaccgtgct gggggtggca accgccccgc aacaagtgtt gtctaacgga 2760
gtgccggtgt ccaacttcac ctactcccct gataccaaag ttctagatat ttgcgtgagc 2820
ctgctgatgg gagaacagtt cctggtgtcc tggtgctga 2859

<210> SEQ ID NO 125
<211> LENGTH: 2859
<212> TYPE: DNA
<213> ORGANISM: Artificial Sequence
<220> FEATURE:
<223> OTHER INFORMATION: Codon optimized CO2-GAA

<400> SEQUENCE: 125
atgggagtta gacaccctcc atgtagccac agactgctgg ccgtgtgtgc tctggtgtct 60
ctggctacag ctgccctgct gggacatatc ctgctgcacg acttcttact agttcccaga 120
gagctgtccg gcagcagccc tgtgctggaa gaaacacacc ctgcacatca gcagggcgcc 180
tctagacctg gacctagaga tgctcaggcc catcctggca gacctagagc tgtgcccaca 240
cagtgtgacg tgccacctaa cagcagattc gactgcgccc ctgacaaggc catcacacaa 300
gagcagtgtg aagccagagg ctgctgctac atccctgcca aacaaggact gcagggcgct 360
cagatgggac agccctggtg cttcttccca ccatcttacc ccagctacaa gctggaaaac 420
ctgagcagca gcgagatggg ctacaccgcc acactgacca gaaccacacc tacattcttc 480
ccgaaggaca tcctgacact gcggctggac gtgatgatgg aaaccgagaa ccggctgcac 540
ttcaccatca aggaccccgc caatcggaga tacgaggtgc cactggaaac ccctcacgtg 600
cactctagag ccccatctcc actgtacagc gtggaattca gcgaggaacc cttcggcgtg 660
atcgtgcgga gacagctgga tggaagagtg ctgctgaaca ccacagtggc ccctctgttc 720
ttcgccgacc agtttctgca gctgtccacc agcctgccta gccagtatat cacaggcctg 780
gccgagcacc tgtctccact gatgctgtct accagctgga cccggatcac cctgtggaac 840
agggatcttg ctcctacacc tggcgccaac ctgtacggct ctcacccttt ttatctggcc 900
ctggaagatg gcggatctgc ccacggtgtc tttctgctga actccaacgc catggacgtg 960
gtgctgcagc catctcctgc tctgtcttgg agaagcacag gcggcatcct ggacgtgtac 1020
atctttctgg gccccgagcc taagagcgtg gtgcagcagt atctggacgt cgtgggctac 1080
cccttcatgc ctccttattg gggcctgggc ttccacctgt gcagatgggg atacagcagc 1140
accgccatca ccagacaggt ggtggaaaac atgacccggg ctcacttccc actggatgtg 1200
cagtggaacg acctggacta catggacagc agacgggact tcaccttcaa caaggacggc 1260
ttcagagact tccccgccat ggtgcaagaa ctgcaccaag gcggcagacg gtacatgatg 1320
atcgtggatc cagccatcag ctctagcggc cctgccggct cttacagacc ttacgatgag 1380
ggcctgagaa gaggcgtgtt catcaccaac gagacaggcc agcctctgat cggcaaagtg 1440
tggcctggca gcacagcctt tccagacttc acaaacccca ccgctctggc ttggtgggaa 1500
gatatggtgg ccgagtttca cgatcaggtg cccttcgacg gcatgtggat cgacatgaac 1560
gagcccagca acttcatccg ggcagcgag gatggctgcc ccaacaacga actggaaaat 1620
cctccttacg tgcccggcgt tgtcggcgga acacttcagg ccgctacaat ctgtgccagc 1680
agccaccagt tcctcagcac ccactacaac ctgcacaatc tgtatggcct gaccgaggcc 1740
attgccagcc atagagccct ggttaaggcc aggggcacca gacctttcgt gatcagcaga 1800
agcaccttcg ccggccacgg cagatatgcc ggacattgga caggcgacgt gtggtctagt 1860
tgggagcagc tggctagcag cgtgccagag atcctgcagt tcaatctgct gggcgtgcca 1920

```
ctcgtgggag ccgatgtttg tggcttcctg ggcaacacct ccgaggaact gtgtgtgcgt   1980
tggacacagc tgggcgcctt ctatcccttc atgagaaacc acaacagcct tctcagcctg   2040
ccacaagagc cctacagctt ctctgagcct gcacagcagg ccatgagaaa ggccctgact   2100
ctgagatacg ctctgctgcc ccacctgtac accctgtttc accaggctca tgtggccggg   2160
gagacagtgg ctagacctct gttcctggaa ttccccaagg acagctccac ctggaccgtg   2220
gatcatcagc tgctgtgggg agaagccctg ctcatcacac ctgttctgca ggccggaaag   2280
gccgaagtga ccggctattt tcctctcggc acttggtacg acctgcagac cgtgcctgtt   2340
gaggctctgg gatctcttcc tccacctcct gccgctccta gagagcctgc cattcactct   2400
gaaggccagt gggttaccct gcctgctcct ctggacacca tcaacgtgca cctgagagct   2460
ggctacatca tccctctgca aggccctggc ctgacaacca ccgaatctag acagcagccc   2520
atggctctgg ccgtggcttt gacaaaaggc ggagaggcta gaggcgagct gttctgggat   2580
gatggcgaga gcctggaagt gctggaacgg ggcgcttata cccaagtgat cttcctggcc   2640
agaaacaaca ccatcgtgaa cgaactcgtg cgcgtgacca gtgaaggtgc tggactgcaa   2700
ctgcagaaag tgaccgtgct cggagtggcc acagcacctc agcaggttct gtctaatggc   2760
gtgcccgtgt ccaacttcac atacagcccc gacaccaagg tcctggacat ctgtgtgtca   2820
ctgctgatgg gcgagcagtt cctggtgtcc tggtgttga                         2859
```

<210> SEQ ID NO 126
<211> LENGTH: 2859
<212> TYPE: DNA
<213> ORGANISM: Artificial Sequence
<220> FEATURE:
<223> OTHER INFORMATION: Codon optimized CO3-GAA

<400> SEQUENCE: 126

```
atgggggtga gacacccccc ctgcagccac agactgctgg ctgtgtgtgc cctggtgagc     60
ctggccacag ctgccctgct gggccacatc ctgctgcatg acttcctact agtgcccaga    120
gagctgagtg gcagcagccc tgtgctggag gagacccacc ctgcccacca gcagggggcc    180
agcagacctg gccccagaga tgcccaggcc caccctggca gacccagagc tgtgcccacc    240
cagtgtgatg tgccccccaa cagcagattt gactgtgccc ctgacaaggc catcacccag    300
gagcagtgtg aggccagagg ctgctgctac atccctgcca agcagggcct gcagggggcc    360
cagatgggcc agccctggtg cttcttcccc cccagctacc ccagctacaa gctggagaac    420
ctgagcagca gtgagatggg ctacacagcc accctgacca gaaccacccc caccttcttc    480
cccaaggaca tcctgaccct gagactggat gtgatgatgg agacagagaa cagactgcac    540
ttcaccatca aggaccctgc caacagaaga tatgaggtgc ccctggagac cccccatgtg    600
cacagcagag cccccagccc cctgtacagt gtggagttca gtgaggagcc ctttggggtg    660
attgtgagaa gacagctgga tggcagagtg ctgctgaaca ccacagtggc ccccctgttc    720
tttgctgacc agttcctgca gctgagcacc agcctgccca gccagtacat cacaggcctg    780
gctgagcacc tgagcccccct gatgctgagc accagctgga ccagaatcac cctgtggaac    840
agagacctgg cccccacccc tggggccaac ctgtatggca gccacccctt ctacctggcc    900
ctggaggatg gggcagtgc  ccatggggtg ttcctgctga acagcaatgc catggatgtg    960
gtgctgcagc ccagccctgc cctgagctgg agaagcacag gggggcatcct ggatgtgtac   1020
atcttcctgg gccctgagcc caagagtgtg gtgcagcagt acctggatgt ggtgggctac   1080
cccttcatgc cccccctactg gggcctgggc ttccacctgt gcagatgggg ctacagcagc   1140
```

```
acagccatca ccagacaggt ggtggagaac atgaccagag cccacttccc cctggatgtg   1200

cagtggaatg acctggacta catggacagc agaagagact tcaccttcaa caaggatggc   1260

ttcagagact tccctgccat ggtgcaggag ctgcaccagg ggggcagaag atacatgatg   1320

attgtggacc ctgccatcag cagcagtggc cctgctggca gctacagacc ctatgatgag   1380

ggcctgagaa gaggggtgtt catcaccaat gagacaggcc agcccctgat tggcaaggtg   1440

tggcctggca gcacagcctt ccctgacttc accaacccca cagccctggc ctggtgggag   1500

gacatggtgg ctgagttcca tgaccaggtg ccctttgatg gcatgtggat tgacatgaat   1560

gagcccagca acttcatcag aggcagtgag gatggctgcc ccaacaatga gctggagaac   1620

ccccccctatg tgcctggggt ggtgggggc accctgcagg ctgccaccat ctgtgccagc   1680

agccaccagt tcctgagcac ccactacaac ctgcacaacc tgtatggcct gacagaggcc   1740

attgccagcc acagagccct ggtgaaggcc agaggcacca gaccctttgt gatcagcaga   1800

agcacctttg ctggccatgg cagatatgct ggccactgga caggggatgt gtggagcagc   1860

tgggagcagc tggccagcag tgtgcctgag atcctgcagt tcaacctgct gggggtgccc   1920

ctggtggggg ctgatgtgtg tggcttcctg ggcaacacca gtgaggagct gtgtgtgaga   1980

tggacccagc tgggggcctt ctaccccttc atgagaaacc acaacagcct gctgagcctg   2040

ccccaggagc cctacagctt cagtgagcct gcccagcagg ccatgagaaa ggccctgacc   2100

ctgagatatg ccctgctgcc ccacctgtac accctgttcc accaggccca tgtggctggg   2160

gagacagtgg ccagacccct gttcctggag ttccccaagg acagcagcac ctggacagtg   2220

gaccaccagc tgctgtgggg ggaggccctg ctgatcaccc ctgtgctgca ggctggcaag   2280

gctgaggtga caggctactt ccccctgggc acctggtatg acctgcagac agtgcctgtg   2340

gaggccctgg gcagcctgcc cccccccct gctgcccccca gagagcctgc catccacagt   2400

gagggccagt gggtgaccct gcctgccccc ctggacacca tcaatgtgca cctgagagct   2460

ggctacatca tcccccctgca gggccctggc ctgaccacca cagagagcag acagcagccc   2520

atggccctgg ctgtggccct gaccaagggg ggggaggcca gaggggagct gttctgggat   2580

gatggggaga gcctggaggt gctggagaga ggggcctaca cccaggtgat cttcctggcc   2640

agaaacaaca ccattgtgaa tgagctggtg agagtgacca gtgagggggc tggcctgcag   2700

ctgcagaagg tgacagtgct gggggtggcc acagcccccc agcaggtgct gagcaatggg   2760

gtgcctgtga gcaacttcac ctacagccct gacaccaagg tgctggacat ctgtgtgagc   2820

ctgctgatgg gggagcagtt cctggtgagc tggtgctga                         2859
```

```
<210> SEQ ID NO 127
<211> LENGTH: 1290
<212> TYPE: DNA
<213> ORGANISM: Homo sapiens
<220> FEATURE:
<221> NAME/KEY: misc_feature
<222> LOCATION: (1)..(1290)
<223> OTHER INFORMATION: Alpha-Galactosidase A (GLA)

<400> SEQUENCE: 127
```

```
atgcagctga ggaacccaga actacatctg ggctgcgcgc ttgcgcttcg cttcctggcc     60

ctcgtttcct gggacatccc tggggctaga gcactggaca atggattggc aaggacgcct    120

accatgggct ggctgcactg ggagcgcttc atgtgcaacc ttgactgcca ggaagagcca    180

gattcctgca tcagtgagaa gctcttcatg gagatggcag agctcatggt ctcagaaggc    240
```

```
tggaaggatg caggttatga gtacctctgc attgatgact gttggatggc tccccaaaga    300

gattcagaag gcagacttca ggcagaccct cagcgctttc ctcatgggat tcgccagcta    360

gctaattatg ttcacagcaa aggactgaag ctagggattt atgcagatgt tggaaataaa    420

acctgcgcag gcttccctgg gagttttgga tactacgaca ttgatgccca gacctttgct    480

gactggggag tagatctgct aaaatttgat ggttgttact gtgacagttt ggaaaatttg    540

gcagatggtt ataagcacat gtccttggcc ctgaatagga ctggcagaag cattgtgtac    600

tcctgtgagt ggcctcttta tatgtggccc tttcaaaagc ccaattatac agaaatccga    660

cagtactgca atcactggcg aaattttgct gacattgatg attcctggaa aagtataaag    720

agtatcttgg actggacatc ttttaaccag gagagaattg ttgatgttgc tggaccaggg    780

ggttggaatg acccagatat gttagtgatt ggcaactttg gcctcagctg gaatcagcaa    840

gtaactcaga tggccctctg ggctatcatg gctgctcctt tattcatgtc taatgacctc    900

cgacacatca gccctcaagc caaagctctc cttcaggata aggacgtaat tgccatcaat    960

caggacccct tgggcaagca agggtaccag cttagacagg gagacaactt tgaagtgtgg   1020

gaacgacctc tctcaggctt agcctgggct gtagctatga taaaccggca ggagattggt   1080

ggacctcgct cttataccat cgcagttgct tccctgggta aaggagtggc ctgtaatcct   1140

gcctgcttca tcacacagct cctccctgtg aaaaggaagc tagggttcta tgaatggact   1200

tcaaggttaa gaagtcacat aaatcccaca ggcactgttt tgcttcagct agaaaataca   1260

atgcagatgt cattaaaaga cttactttaa                                    1290
```

<210> SEQ ID NO 128
<211> LENGTH: 1290
<212> TYPE: DNA
<213> ORGANISM: Artificial Sequence
<220> FEATURE:
<223> OTHER INFORMATION: Codon optimized CO1-GLA

<400> SEQUENCE: 128

```
atgcagctga gaaatcctga actgcacctg ggctgtgccc tggctctgag atttctggct     60

ctggtgtcct gggacattcc tggcgctaga gccctggata atggcctggc cagaacacct    120

acaatgggct ggctgcactg ggagagattc atgtgcaacc tggactgcca agaggaaccc    180

gacagctgca tcagcgagaa gctgttcatg gaaatggccg agctgatggt gtccgaaggc    240

tggaaggatg ccggctacga gtacctgtgc atcgacgatt gctggatggc ccctcagaga    300

gattctgagg gcagactgca ggccgatcct cagagatttc ctcacggaat ccggcagctg    360

gccaactacg tgcactctaa gggactgaag ctgggcatct acgccgacgt gggcaacaag    420

acatgtgccg gctttccagg cagcttcggc tactacgata tcgacgccca gacctttgcc    480

gattggggcg tcgacctgct gaagttcgat ggctgctact gcgacagcct ggaaaacctg    540

gccgacggct acaaacacat gtctctggcc ctgaaccgga ccggcagatc tatcgtgtac    600

tcttgcgagt ggcccctgta catgtggccc ttccagaagc ctaactacac cgagatcaga    660

cagtactgca accactggcg gaacttcgcc gacatcgatg acagctggaa gtccatcaag    720

agcatcctgg actggaccag cttcaatcaa gagcggatcg tggatgtggc tggcccaggc    780

ggatggaacg atcctgatat gctggtcatc ggcaacttcg gcctgagctg gaatcagcaa    840

gtgacccaga tggccctgtg ggccattatg gccgctcctc tgttcatgag caacgacctg    900

agacacatca gccctcaggc caaggctctg ctgcaggata aggacgtgat cgccatcaac    960

caggatcctc tgggcaagca gggctatcag ctgagacagg gcgacaattt cgaagtgtgg   1020
```

```
gaaagacctc tgagcggcct ggcttgggcc gtcgccatga tcaatagaca agagatcggc   1080
ggaccccggt cctatacaat tgccgtggct tctctcggaa aaggcgtggc ctgcaatcct   1140
gcctgcttta tcacacagct gctccccgtg aagagaaagc tgggctttta cgagtggacc   1200
agcagactga gatcccacat caaccccaca ggcactgttc tgctgcaact ggaaaacaca   1260
atgcagatga gcctgaagga cctgctgtag                                    1290
```

<210> SEQ ID NO 129
<211> LENGTH: 1377
<212> TYPE: DNA
<213> ORGANISM: Artificial Sequence
<220> FEATURE:
<223> OTHER INFORMATION: Codon optimized + GET, CO1-GLA-GET

<400> SEQUENCE: 129

```
atgcagctga gaaatcctga actgcacctg ggctgtgccc tggctctgag atttctggct     60
ctggtgtcct gggacattcc tggcgctaga gccctggata atggcctggc cagaacacct    120
acaatgggct ggctgcactg ggagagattc atgtgcaacc tggactgcca agaggaaccc    180
gacagctgca tcagcgagaa gctgttcatg gaaatggccg agctgatggt gtccgaaggc    240
tggaaggatg ccggctacga gtacctgtgc atcgacgatt gctggatggc ccctcagaga    300
gattctgagg gcagactgca ggccgatcct cagagatttc ctcacggaat ccggcagctg    360
gccaactacg tgcactctaa gggactgaag ctgggcatct acgccgacgt gggcaacaag    420
acatgtgccg gctttccagg cagcttcggc tactacgata tcgacgccca gacctttgcc    480
gattggggcg tcgacctgct gaagttcgat ggctgctact gcgacagcct ggaaaacctg    540
gccgacggct acaaacacat gtctctggcc ctgaaccgga ccggcagatc tatcgtgtac    600
tcttgcgagt ggcccctgta catgtggccc ttccagaagc ctaactacac cgagatcaga    660
cagtactgca accactggcg gaacttcgcc gacatcgatg acagctggaa gtccatcaag    720
agcatcctgg actggaccag cttcaatcaa gagcggatcg tggatgtggc tggcccaggc    780
ggatggaacg atcctgatat gctggtcatc ggcaacttcg gcctgagctg gaatcagcaa    840
gtgacccaga tggccctgtg ggccattatg gccgctcctc tgttcatgag caacgacctg    900
agacacatca gccctcaggc caaggctctg ctgcaggata aggacgtgat cgccatcaac    960
caggatcctc tgggcaagca gggctatcag ctgagacagg gcgacaattt cgaagtgtgg   1020
gaaagacctc tgagcggcct ggcttgggcc gtcgccatga tcaatagaca agagatcggc   1080
ggaccccggt cctatacaat tgccgtggct tctctcggaa aaggcgtggc ctgcaatcct   1140
gcctgcttta tcacacagct gctccccgtg aagagaaagc tgggctttta cgagtggacc   1200
agcagactga gatcccacat caaccccaca ggcactgttc tgctgcaact ggaaaacaca   1260
atgcagatga gcctgaagga cctgctgcgg agaagaagaa ggcgcagacg caagcgcaag   1320
aagaaaggca aaggcctcgg caagaagcgg gacccctgtc tgagaaagta caagtaa      1377
```

<210> SEQ ID NO 130
<211> LENGTH: 1290
<212> TYPE: DNA
<213> ORGANISM: Artificial Sequence
<220> FEATURE:
<223> OTHER INFORMATION: Codon optimized CO2-GLA

<400> SEQUENCE: 130

```
atgcagctga gaaaccctga gctgcacctg ggctgtgccc tggccctgag attcctggcc     60
```

```
ctggtgagct gggacatccc tggggccaga gccctggaca atgggctagc cagaaccccc    120
accatgggct ggctgcactg ggagagattc atgtgcaacc tggactgcca ggaggagcct    180
gacagctgca tcagtgagaa gctgttcatg gagatggctg agctgatggt gagtgagggc    240
tggaaggatg ctggctatga gtacctgtgc attgatgact gctggatggc cccccagaga    300
gacagtgagg gcagactgca ggctgacccc cagagattcc cccatggcat cagacagctg    360
gccaactatg tgcacagcaa gggcctgaag ctgggcatct atgctgatgt gggcaacaag    420
acctgtgctg gcttccctgg cagctttggc tactatgaca ttgatgccca gacctttgct    480
gactgggggg tggacctgct gaagtttgat ggctgctact gtgacagcct ggagaacctg    540
gctgatggct acaagcacat gagcctggcc ctgaacagaa caggcagaag cattgtgtac    600
agctgtgagt ggcccctgta catgtggccc ttccagaagc ccaactacac agagatcaga    660
cagtactgca accactggag aaactttgct gacattgatg acagctggaa gagcatcaag    720
agcatcctgg actggaccag cttcaaccag gagagaattg tggatgtggc tggccctggg    780
ggctggaatg accctgacat gctggtgatt ggcaactttg gcctgagctg gaaccagcag    840
gtgacccaga tggccctgtg ggccatcatg gctgcccccc tgttcatgag caatgacctg    900
agacacatca gcccccaggc caaggccctg ctgcaggaca aggatgtgat tgccatcaac    960
caggaccccc tgggcaagca gggctaccag ctgagacagg gggacaactt tgaggtgtgg   1020
gagagacccc tgagtggcct ggcctgggct gtggccatga tcaacagaca ggagattggg   1080
ggccccagaa gctacaccat tgctgtggcc agcctgggca agggggtggc ctgcaaccct   1140
gcctgcttca tcacccagct gctgcctgtg aagagaaagc tgggcttcta tgagtggacc   1200
agcagactga gaagccacat caaccccaca ggcacagtgc tgctgcagct ggagaacacc   1260
atgcagatga gcctgaagga cctgctgtga                                    1290
```

<210> SEQ ID NO 131
<211> LENGTH: 1290
<212> TYPE: DNA
<213> ORGANISM: Artificial Sequence
<220> FEATURE:
<223> OTHER INFORMATION: Codon optimized CO3-GLA

<400> SEQUENCE: 131

```
atgcagctga gaaaccctga gctgcacctg ggctgtgccc tggccctgag attcctggcc     60
ctggtgagct gggacatccc tggggccaga gccctggaca atgggctagc cagaaccccc    120
accatgggct ggctgcactg ggagagattc atgtgcaacc tggactgcca ggaggagcct    180
gacagctgca tcagtgagaa gctgttcatg gagatggctg agctgatggt gagtgagggc    240
tggaaggatg ctggctatga gtacctgtgc attgatgact gctggatggc cccccagaga    300
gacagtgagg gcagactgca ggctgacccc cagagattcc cccatggcat cagacagctg    360
gccaactatg tgcacagcaa gggcctgaag ctgggcatct atgctgatgt gggcaacaag    420
acctgtgctg gcttccctgg cagctttggc tactatgaca ttgatgccca gacctttgct    480
gactgggggg tggacctgct gaagtttgat ggctgctact gtgacagcct ggagaacctg    540
gctgatggct acaagcacat gagcctggcc ctgaacagaa caggcagaag cattgtgtac    600
agctgtgagt ggcccctgta catgtggccc ttccagaagc ccaactacac agagatcaga    660
cagtactgca accactggag aaactttgct gacattgatg acagctggaa gagcatcaag    720
agcatcctgg actggaccag cttcaaccag gagagaattg tggatgtggc tggccctggg    780
ggctggaatg accctgacat gctggtgatt ggcaactttg gcctgagctg gaaccagcag    840
```

gtgacccaga tggccctgtg ggccatcatg gctgcccccc tgttcatgag caatgacctg 900
agacacatca gcccccaggc caaggccctg ctgcaggaca aggatgtgat tgccatcaac 960
caggaccccc tgggcaagca gggctaccag ctgagacagg gggacaactt tgaggtgtgg 1020
gagagacccc tgagtggcct ggcctgggct gtggccatga tcaacagaca ggagattggg 1080
ggccccagaa gctacaccat tgctgtggct tccctgggta aaggagtggc ctgtaatcct 1140
gcctgcttca tcacacagct cctccctgtg aaaaggaagc tagggttcta tgaatggact 1200
tcaaggttaa gaagtcacat aaatcccaca ggcactgttt tgcttcagct agaaaataca 1260
atgcagatgt cattaaaaga cttactttaa 1290

<210> SEQ ID NO 132
<211> LENGTH: 4287
<212> TYPE: DNA
<213> ORGANISM: Artificial Sequence
<220> FEATURE:
<223> OTHER INFORMATION: Codon optimized, Cystic Fibrosis Transmembrane Regulator deltaR (CFTRdeltaR) contains R domain deletion

<400> SEQUENCE: 132
atgcagagaa gcccccctgga gaaggcctct gtggtgagca agctgttctt cagctggacc 60
agacccatcc tgagaaaggg ctacagacag agactggagc tgtctgacat ctaccagatc 120
ccctctgtgg actctgctga caacctgtct gagaagctgg agagagagtg ggacagagag 180
ctggccagca agaagaaccc caagctgatc aatgccctga gaagatgctt cttctggaga 240
ttcatgttct atggcatctt cctgtacctg gggggaggtga ccaaggctgt gcagcccctg 300
ctgctgggca gaatcattgc cagctatgac cctgacaaca aggaggagag aagcattgcc 360
atctacctgg gcattggcct gtgcctgctg ttcattgtga gaaccctgct gctgcaccct 420
gccatctttg gcctgcacca cattggcatg cagatgagaa ttgccatgtt cagcctgatc 480
tacaagaaga ccctgaagct gagcagcaga gtgctggaca agatcagcat tggccagctg 540
gtgagcctgc tgagcaacaa cctgaacaag tttgatgagg gcctggccct ggcccacttt 600
gtgtggattg cccccctgca ggtggccctg ctgatgggcc tgatctggga gctgctgcag 660
gcctctgcct tctgtggcct gggcttcctg attgtgctgg ccctgttcca ggctggcctg 720
ggcagaatga tgatgaagta cagagaccag agagctggca agatctctga gagactggtg 780
atcacctctg agatgattga gaacatccag tctgtgaagg cctactgctg ggaggaggcc 840
atggagaaga tgattgagaa cctgagacag acagagctga agctgaccag aaaggctgcc 900
tatgtgagat acttcaacag ctctgccttc ttcttctctg gcttctttgt ggtgttcctg 960
tctgtgctgc cctatgccct gatcaagggc atcatcctga gaaagatctt caccaccatc 1020
agcttctgca ttgtgctgag aatggctgtg accagacagt tcccctgggc tgtgcagacc 1080
tggtatgaca gcctgggggc catcaacaag atccaggact tcctgcagaa gcaggagtac 1140
aagaccctgg agtacaacct gaccaccaca gaggtggtga tggagaatgt gacagccttc 1200
tgggaggagg gctttgggga gctgtttgag aaggccaagc agaacaacaa caacagaaag 1260
accagcaatg gggatgacag cctgttcttc agcaacttca gcctgctggg cacccctgtg 1320
ctgaaggaca tcaacttcaa gattgagaga ggccagctgc tggctgtggc tggcagcaca 1380
ggggctggca agaccagcct gctgatgatg atcatggggg agctggagcc ctctgagggc 1440
aagatcaagc actctggcag aatcagcttc tgcagccagt tcagctggat catgcctggc 1500
accatcaagg agaacatcat ctttggggtg agctatgatg agtacagata cagatctgtg 1560

```
atcaaggcct gccagctgga ggaggacatc agcaagtttg ctgagaagga caacattgtg   1620
ctgggggagg ggggcatcac cctgtctggg ggccagagag ccagaatcag cctggccaga   1680
gctgtgtaca aggatgctga cctgtacctg ctggacagcc cctttggcta cctggatgtg   1740
ctgacagaga aggagatctt tgagagctgt gtgtgcaagc tgatggccaa caagaccaga   1800
atcctggtga ccagcaagat ggagcacctg aagaaggctg acaagatcct gatcctgcat   1860
gagggcagca gctacttcta tggcaccttc tctgagctgc agaacctgca gcctgacttc   1920
agcagcaagc tgatgggctg tgacagcttt gaccagttct ctgctgagag aagaaacagc   1980
atcctgacag agaccctgca cagattcagc ctggaggggg atgcccctgt gagctggaca   2040
gagaccaaga agcagagctt caagcagaca ggggagtttg ggagaagag aaagaacagc   2100
atcctgaacc ccatcaacag caccctgcag gccagaagaa gacagtctgt gctgaacctg   2160
atgacccact ctgtgaacca gggccagaac atccacagaa agaccacagc cagcaccaga   2220
aaggtgagcc tggcccccca ggccaacctg acagagctgg acatctacag cagaagactg   2280
agccaggaga caggcctgga gatctctgag gagatcaatg aggaggacct gaaggagtgc   2340
ttctttgatg acatggagag catccctgct gtgaccacct ggaacaccta cctgagatac   2400
atcacagtgc acaagagcct gatctttgtg ctgatctggt gcctggtgat cttcctggct   2460
gaggtggctg ccagcctggt ggtgctgtgg ctgctgggca acacccccct gcaggacaag   2520
ggcaacagca cccacagcag aaacaacagc tatgctgtga tcatcaccag caccagcagc   2580
tactatgtgt tctacatcta tgtgggggtg gctgacaccc tgctggccat gggcttcttc   2640
agaggcctgc ccctggtgca caccctgatc acagtgagca agatcctgca ccacaagatg   2700
ctgcactctg tgctgcaggc ccccatgagc accctgaaca ccctgaaggc tgggggcatc   2760
ctgaacagat tcagcaagga cattgccatc ctggatgacc tgctgcccct gaccatcttt   2820
gacttcatcc agctgctgct gattgtgatt ggggccattg ctgtggtggc tgtgctgcag   2880
ccctacatct ttgtggccac agtgcctgtg attgtggcct tcatcatgct gagagcctac   2940
ttcctgcaga ccagccagca gctgaagcag ctggagtctg agggcagaag ccccatcttc   3000
acccacctgg tgaccagcct gaagggcctg tggaccctga gagcctttgg cagacagccc   3060
tactttgaga ccctgttcca caaggccctg aacctgcaca cagccaactg gttcctgtac   3120
ctgagcaccc tgagatggtt ccagatgaga attgagatga tctttgtgat cttcttcatt   3180
gctgtgacct tcatcagcat cctgaccaca ggggaggggg agggcagagt gggcatcatc   3240
ctgaccctgg ccatgaacat catgagcacc ctgcagtggg ctgtgaacag cagcattgat   3300
gtggacagcc tgatgagatc tgtgagcaga gtgttcaagt tcattgacat gcccacagag   3360
ggcaagccca ccaagagcac caagccctac aagaatggcc agctgagcaa ggtgatgatc   3420
attgagaaca gccatgtgaa gaaggatgac atctggccct ctgggggcca gatgacagtg   3480
aaggacctga cagccaagta cacagagggg ggcaatgcca tcctggagaa catcagcttc   3540
agcatcagcc ctggccagag agtgggcctg ctgggcagaa caggctctgg caagagcacc   3600
ctgctgtctg ccttcctgag actgctgaac acagaggggg agatccagat tgatggggtg   3660
agctgggaca gcatcaccct gcagcagtgg agaaaggcct ttggggtgat cccccagaag   3720
gtgttcatct tctctggcac cttcagaaag aacctggacc cctatgagca gtggtctgac   3780
caggagatct ggaaggtggc tgatgaggtg ggcctgagat ctgtgattga gcagttccct   3840
ggcaagctgg actttgtgct ggtggatggg ggctgtgtgc tgagccatgg ccacaagcag   3900
```

```
ctgatgtgcc tggccagatc tgtgctgagc aaggccaaga tcctgctgct ggatgagccc   3960

tctgcccacc tggaccctgt gacctaccag atcatcagaa gaaccctgaa gcaggccttt   4020

gctgactgca cagtgatcct gtgtgagcac agaattgagg ccatgctgga gtgccagcag   4080

ttcctggtga ttgaggagaa caaggtgaga cagtatgaca gcatccagaa gctgctgaat   4140

gagagaagcc tgttcagaca ggccatcagc ccctctgaca gagtgaagct gttcccccac   4200

agaaacagca gcaagtgcaa gagcaagccc cagattgctg ccctgaagga ggagaccgag   4260

gaggaggtgc aggacaccag actgtaa                                       4287
```

<210> SEQ ID NO 133
<211> LENGTH: 4443
<212> TYPE: DNA
<213> ORGANISM: Artificial Sequence
<220> FEATURE:
<223> OTHER INFORMATION: Codon optimized, full length Cystic Fibrosis Transmembrane Regulator (CFTR)

<400> SEQUENCE: 133

```
atgcagagaa gccccctgga gaaggcctct gtggtgagca agctgttctt cagctggacc     60

agacccatcc tgagaaaggg ctacagacag agactggagc tgtctgacat ctaccagatc    120

ccctctgtgg actctgctga caacctgtct gagaagctgg agagagagtg ggacagagag    180

ctggccagca agaagaaccc caagctgatc aatgccctga gaagatgctt cttctggaga    240

ttcatgttct atggcatctt cctgtacctg ggggaggtga ccaaggctgt gcagcccctg    300

ctgctgggca gaatcattgc cagctatgac cctgacaaca aggaggagag aagcattgcc    360

atctacctgg gcattggcct gtgcctgctg ttcattgtga gaaccctgct gctgcaccct    420

gccatctttg gcctgcacca cattggcatg cagatgagaa ttgccatgtt cagcctgatc    480

tacaagaaga ccctgaagct gagcagcaga gtgctggaca agatcagcat tggccagctg    540

gtgagcctgc tgagcaacaa cctgaacaag tttgatgagg gcctggccct ggcccacttt    600

gtgtggattg ccccccctgca ggtggccctg ctgatgggcc tgatctggga gctgctgcag    660

gcctctgcct tctgtggcct gggcttcctg attgtgctgg ccctgttcca ggctggcctg    720

ggcagaatga tgatgaagta cagagaccag agagctggca agatctctga gagactggtg    780

atcacctctg agatgattga gaacatccag tctgtgaagg cctactgctg ggaggaggcc    840

atggagaaga tgattgagaa cctgagacag acagagctga agctgaccag aaaggctgcc    900

tatgtgagat acttcaacag ctctgccttc ttcttctctg gcttctttgt ggtgttcctg    960

tctgtgctgc cctatgccct gatcaagggc atcatcctga gaaagatctt caccaccatc   1020

agcttctgca ttgtgctgag aatggctgtg accagacagt tcccctgggc tgtgcagacc   1080

tggtatgaca gcctgggggc catcaacaag atccaggact tcctgcagaa gcaggagtac   1140

aagaccctgg agtacaacct gaccaccaca gaggtggtga tggagaatgt gacagccttc   1200

tgggaggagg gctttgggga gctgtttgag aaggccaagc agaacaacaa caacagaaag   1260

accagcaatg gggatgacag cctgttcttc agcaacttca gcctgctggg caccccctgtg   1320

ctgaaggaca tcaacttcaa gattgagaga ggccagctgc tggctgtggc tggcagcaca   1380

ggggctggca agaccagcct gctgatgatg atcatggggg agctggagcc ctctgagggc   1440

aagatcaagc actctggcag aatcagcttc tgcagccagt tcagctggat catgcctggc   1500

accatcaagg agaacatcat ctttggggtg agctatgatg agtacagata cagatctgtg   1560

atcaaggcct gccagctgga ggaggacatc agcaagtttg ctgagaagga caacattgtg   1620
```

ctgggggagg ggggcatcac cctgtctggg ggccagagag ccagaatcag cctggccaga 1680
gctgtgtaca aggatgctga cctgtacctg ctggacagcc cctttggcta cctggatgtg 1740
ctgacagaga aggagatctt tgagagctgt gtgtgcaagc tgatggccaa caagaccaga 1800
atcctggtga ccagcaagat ggagcacctg aagaaggctg acaagatcct gatcctgcat 1860
gagggcagca gctacttcta tggcaccttc tctgagctgc agaacctgca gcctgacttc 1920
agcagcaagc tgatgggctg tgacagcttt gaccagttct ctgctgagag aagaaacagc 1980
atcctgacag agaccctgca cagattcagc ctggaggggg atgcccctgt gagctggaca 2040
gagaccaaga agcagagctt caagcagaca ggggagtttg ggggagaagag aaagaacagc 2100
atcctgaacc ccatcaacag catcagaaag ttcagcattg tgcagaagac cccccctgcag 2160
atgaatggca ttgaggagga ctctgatgag cccctggaga gaagactgag cctggtgcct 2220
gactctgagc agggggaggc catcctgccc agaatctctg tgatcagcac aggcccccacc 2280
ctgcaggcca gaagaagaca gtctgtgctg aacctgatga cccactctgt gaaccagggc 2340
cagaacatcc acagaaagac cacagccagc accagaaagg tgagcctggc cccccaggcc 2400
aacctgacag agctggacat ctacagcaga agactgagcc aggagacagg cctggagatc 2460
tctgaggaga tcaatgagga ggacctgaag gagtgcttct ttgatgacat ggagagcatc 2520
cctgctgtga ccacctggaa cacctacctg agatacatca cagtgcacaa gagcctgatc 2580
tttgtgctga tctggtgcct ggtgatcttc ctggctgagg tggctgccag cctggtggtg 2640
ctgtggctgc tgggcaacac ccccctgcag gacaagggca acagcaccca cagcagaaac 2700
aacagctatg ctgtgatcat caccagcacc agcagctact atgtgttcta catctatgtg 2760
ggggtggctg acaccctgct ggccatgggc ttcttcagag gcctgcccct ggtgcacacc 2820
ctgatcacag tgagcaagat cctgcaccac aagatgctgc actctgtgct gcaggccccc 2880
atgagcaccc tgaacaccct gaaggctggg ggcatcctga acagattcag caaggacatt 2940
gccatcctgg atgacctgct gcccctgacc atctttgact tcatccagct gctgctgatt 3000
gtgattgggg ccattgctgt ggtggctgtg ctgcagccct acatctttgt ggccacagtg 3060
cctgtgattg tggccttcat catgctgaga gcctacttcc tgcagaccag ccagcagctg 3120
aagcagctgg agtctgaggg cagaagcccc atcttcaccc acctggtgac cagcctgaag 3180
ggcctgtgga ccctgagagc ctttggcaga cagccctact ttgagaccct gttccacaag 3240
gccctgaacc tgcacacagc caactggttc ctgtacctga gcaccctgag atggttccag 3300
atgagaattg agatgatctt tgtgatcttc ttcattgctg tgaccttcat cagcatcctg 3360
accacagggg agggggaggg cagagtgggc atcatcctga ccctggccat gaacatcatg 3420
agcaccctgc agtgggctgt gaacagcagc attgatgtgg acagcctgat gagatctgtg 3480
agcagagtgt tcaagttcat tgacatgccc acagagggca agcccaccaa gagcaccaag 3540
ccctacaaga atggccagct gagcaaggtg atgatcattg agaacagcca tgtgaagaag 3600
gatgacatct ggccctctgg gggccagatg acagtgaagg acctgacagc caagtacaca 3660
gagggggggca atgccatcct ggagaacatc agcttcagca tcagccctgg ccagagagtg 3720
ggcctgctgg gcagaacagg ctctggcaag agcaccctgc tgtctgcctt cctgagactg 3780
ctgaacacag agggggagat ccagattgat ggggtgagct gggacagcat caccctgcag 3840
cagtggagaa aggcctttgg ggtgatcccc cagaaggtgt tcatcttctc tggcaccttc 3900
agaaagaacc tggaccccta tgagcagtgg tctgaccagg agatctggaa ggtggctgat 3960
gaggtgggcc tgagatctgt gattgagcag ttccctggca agctggactt tgtgctggtg 4020

```
gatgggggct gtgtgctgag ccatggccac aagcagctga tgtgcctggc cagatctgtg   4080

ctgagcaagg ccaagatcct gctgctggat gagccctctg cccacctgga ccctgtgacc   4140

taccagatca tcagaagaac cctgaagcag gcctttgctg actgcacagt gatcctgtgt   4200

gagcacagaa ttgaggccat gctggagtgc cagcagttcc tggtgattga ggagaacaag   4260

gtgagacagt atgacagcat ccagaagctg ctgaatgaga gaagcctgtt cagacaggcc   4320

atcagcccct ctgacagagt gaagctgttc ccccacagaa acagcagcaa gtgcaagagc   4380

aagccccaga ttgctgccct gaaggaggag accgaggagg aggtgcagga caccagactg   4440

taa                                                                 4443
```

```
<210> SEQ ID NO 134
<211> LENGTH: 502
<212> TYPE: PRT
<213> ORGANISM: Homo sapiens
<220> FEATURE:
<221> NAME/KEY: MISC_FEATURE
<222> LOCATION: (1)..(502)
<223> OTHER INFORMATION: Sulfoglucosamine sulfohydrolase (SGSH)

<400> SEQUENCE: 134

Met Ser Cys Pro Val Pro Ala Cys Cys Ala Leu Leu Leu Val Leu Gly
1               5                   10                  15

Leu Cys Arg Ala Arg Pro Arg Asn Ala Leu Leu Leu Leu Ala Asp Asp
            20                  25                  30

Gly Gly Phe Glu Ser Gly Ala Tyr Asn Asn Ser Ala Ile Ala Thr Pro
        35                  40                  45

His Leu Asp Ala Leu Ala Arg Arg Ser Leu Leu Phe Arg Asn Ala Phe
    50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
            100                 105                 110

Gln Ala Gly Val Arg Thr Gly Ile Ile Gly Lys Lys His Val Gly Pro
        115                 120                 125

Glu Thr Val Tyr Pro Phe Asp Phe Ala Tyr Thr Glu Glu Asn Gly Ser
    130                 135                 140

Val Leu Gln Val Gly Arg Asn Ile Thr Arg Ile Lys Leu Leu Val Arg
145                 150                 155                 160

Lys Phe Leu Gln Thr Gln Asp Asp Gln Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
        195                 200                 205

Asp Trp Thr Pro Gln Ala Tyr Asp Pro Leu Asp Val Leu Val Pro Tyr
    210                 215                 220

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
                245                 250                 255

Leu Arg Asp Ala Gly Val Leu Asn Asp Thr Leu Val Ile Phe Thr Ser
            260                 265                 270
```

Asp Asn Gly Ile Pro Phe Pro Ser Gly Arg Thr Asn Leu Tyr Trp Pro
275 280 285

Gly Thr Ala Glu Pro Leu Leu Val Ser Ser Pro Glu His Pro Lys Arg
290 295 300

Trp Gly Gln Val Ser Glu Ala Tyr Val Ser Leu Leu Asp Leu Thr Pro
305 310 315 320

Thr Ile Leu Asp Trp Phe Ser Ile Pro Tyr Pro Ser Tyr Ala Ile Phe
325 330 335

Gly Ser Lys Thr Ile His Leu Thr Gly Arg Ser Leu Leu Pro Ala Leu
340 345 350

Glu Ala Glu Pro Leu Trp Ala Thr Val Phe Gly Ser Gln Ser His His
355 360 365

Glu Val Thr Met Ser Tyr Pro Met Arg Ser Val Gln His Arg His Phe
370 375 380

Arg Leu Val His Asn Leu Asn Phe Lys Met Pro Phe Pro Ile Asp Gln
385 390 395 400

Asp Phe Tyr Val Ser Pro Thr Phe Gln Asp Leu Leu Asn Arg Thr Thr
405 410 415

Ala Gly Gln Pro Thr Gly Trp Tyr Lys Asp Leu Arg His Tyr Tyr Tyr
420 425 430

Arg Ala Arg Trp Glu Leu Tyr Asp Arg Ser Arg Asp Pro His Glu Thr
435 440 445

Gln Asn Leu Ala Thr Asp Pro Arg Phe Ala Gln Leu Leu Glu Met Leu
450 455 460

Arg Asp Gln Leu Ala Lys Trp Gln Trp Glu Thr His Asp Pro Trp Val
465 470 475 480

Cys Ala Pro Asp Gly Val Leu Glu Glu Lys Leu Ser Pro Gln Cys Gln
485 490 495

Pro Leu His Asn Glu Leu
500

<210> SEQ ID NO 135
<211> LENGTH: 531
<212> TYPE: PRT
<213> ORGANISM: Artificial Sequence
<220> FEATURE:
<223> OTHER INFORMATION: Codon optimized + GET CO1-SGSH-GET

<400> SEQUENCE: 135

Met Ser Cys Pro Val Pro Ala Cys Cys Ala Leu Leu Leu Val Leu Gly
1 5 10 15

Leu Cys Arg Ala Arg Pro Arg Asn Ala Leu Leu Leu Leu Ala Asp Asp
20 25 30

Gly Gly Phe Glu Ser Gly Ala Tyr Asn Asn Ser Ala Ile Ala Thr Pro
35 40 45

His Leu Asp Ala Leu Ala Arg Arg Ser Leu Leu Phe Arg Asn Ala Phe
50 55 60

Thr Ser Val Ser Ser Cys Ser Pro Ser Arg Ala Ser Leu Leu Thr Gly
65 70 75 80

Leu Pro Gln His Gln Asn Gly Met Tyr Gly Leu His Gln Asp Val His
85 90 95

His Phe Asn Ser Phe Asp Lys Val Arg Ser Leu Pro Leu Leu Leu Ser
100 105 110

Gln Ala Gly Val Arg Thr Gly Ile Ile Gly Lys Lys His Val Gly Pro
115 120 125

```
Glu Thr Val Tyr Pro Phe Asp Phe Ala Tyr Thr Glu Glu Asn Gly Ser
    130                 135                 140

Val Leu Gln Val Gly Arg Asn Ile Thr Arg Ile Lys Leu Leu Val Arg
145                 150                 155                 160

Lys Phe Leu Gln Thr Gln Asp Asp Gln Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
        195                 200                 205

Asp Trp Thr Pro Gln Ala Tyr Asp Pro Leu Asp Val Leu Val Pro Tyr
    210                 215                 220

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
                245                 250                 255

Leu Arg Asp Ala Gly Val Leu Asn Asp Thr Leu Val Ile Phe Thr Ser
            260                 265                 270

Asp Asn Gly Ile Pro Phe Pro Ser Gly Arg Thr Asn Leu Tyr Trp Pro
        275                 280                 285

Gly Thr Ala Glu Pro Leu Leu Val Ser Ser Pro Glu His Pro Lys Arg
    290                 295                 300

Trp Gly Gln Val Ser Glu Ala Tyr Val Ser Leu Leu Asp Leu Thr Pro
305                 310                 315                 320

Thr Ile Leu Asp Trp Phe Ser Ile Pro Tyr Pro Ser Tyr Ala Ile Phe
                325                 330                 335

Gly Ser Lys Thr Ile His Leu Thr Gly Arg Ser Leu Leu Pro Ala Leu
            340                 345                 350

Glu Ala Glu Pro Leu Trp Ala Thr Val Phe Gly Ser Gln Ser His His
        355                 360                 365

Glu Val Thr Met Ser Tyr Pro Met Arg Ser Val Gln His Arg His Phe
    370                 375                 380

Arg Leu Val His Asn Leu Asn Phe Lys Met Pro Phe Pro Ile Asp Gln
385                 390                 395                 400

Asp Phe Tyr Val Ser Pro Thr Phe Gln Asp Leu Leu Asn Arg Thr Thr
                405                 410                 415

Ala Gly Gln Pro Thr Gly Trp Tyr Lys Asp Leu Arg His Tyr Tyr Tyr
            420                 425                 430

Arg Ala Arg Trp Glu Leu Tyr Asp Arg Ser Arg Asp Pro His Glu Thr
        435                 440                 445

Gln Asn Leu Ala Thr Asp Pro Arg Phe Ala Gln Leu Leu Glu Met Leu
    450                 455                 460

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
                485                 490                 495

Pro Leu His Asn Glu Leu Arg Arg Arg Arg Arg Arg Arg Arg Lys Arg
            500                 505                 510

Lys Lys Lys Gly Lys Gly Leu Gly Lys Lys Arg Asp Pro Cys Leu Arg
        515                 520                 525

Lys Tyr Lys
    530
```

<210> SEQ ID NO 136
<211> LENGTH: 306
<212> TYPE: PRT
<213> ORGANISM: Artificial Sequence
<220> FEATURE:
<223> OTHER INFORMATION: Codon optimized Ceroid Lipofuscinosis, Neuronal, 1 (CLN1)

<400> SEQUENCE: 136

Met Ala Ser Pro Gly Cys Leu Trp Leu Leu Ala Val Ala Leu Leu Pro
1               5                   10                  15

Trp Thr Cys Ala Ser Arg Ala Leu Gln His Leu Asp Pro Pro Ala Pro
            20                  25                  30

Leu Pro Leu Val Ile Trp His Gly Met Gly Asp Ser Cys Cys Asn Pro
        35                  40                  45

Leu Ser Met Gly Ala Ile Lys Lys Met Val Glu Lys Lys Ile Pro Gly
    50                  55                  60

Ile Tyr Val Leu Ser Leu Glu Ile Gly Lys Thr Leu Met Glu Asp Val
65                  70                  75                  80

Glu Asn Ser Phe Phe Leu Asn Val Asn Ser Gln Val Thr Thr Val Cys
                85                  90                  95

Gln Ala Leu Ala Lys Asp Pro Lys Leu Gln Gln Gly Tyr Asn Ala Met
            100                 105                 110

Gly Phe Ser Gln Gly Gly Gln Phe Leu Arg Ala Val Ala Gln Arg Cys
        115                 120                 125

Pro Ser Pro Pro Met Ile Asn Leu Ile Ser Val Gly Gly Gln His Gln
    130                 135                 140

Gly Val Phe Gly Leu Pro Arg Cys Pro Gly Glu Ser Ser His Ile Cys
145                 150                 155                 160

Asp Phe Ile Arg Lys Thr Leu Asn Ala Gly Ala Tyr Ser Lys Val Val
                165                 170                 175

Gln Glu Arg Leu Val Gln Ala Glu Tyr Trp His Asp Pro Ile Lys Glu
            180                 185                 190

Asp Val Tyr Arg Asn His Ser Ile Phe Leu Ala Asp Ile Asn Gln Glu
        195                 200                 205

Arg Gly Ile Asn Glu Ser Tyr Lys Lys Asn Leu Met Ala Leu Lys Lys
    210                 215                 220

Phe Val Met Val Lys Phe Leu Asn Asp Ser Ile Val Asp Pro Val Asp
225                 230                 235                 240

Ser Glu Trp Phe Gly Phe Tyr Arg Ser Gly Gln Ala Lys Glu Thr Ile
                245                 250                 255

Pro Leu Gln Glu Thr Ser Leu Tyr Thr Gln Asp Arg Leu Gly Leu Lys
            260                 265                 270

Glu Met Asp Asn Ala Gly Gln Leu Val Phe Leu Ala Thr Glu Gly Asp
        275                 280                 285

His Leu Gln Leu Ser Glu Glu Trp Phe Tyr Ala His Ile Ile Pro Phe
    290                 295                 300

Leu Gly
305

<210> SEQ ID NO 137
<211> LENGTH: 294
<212> TYPE: PRT
<213> ORGANISM: Homo sapiens
<220> FEATURE:
<221> NAME/KEY: MISC_FEATURE
<222> LOCATION: (1)..(294)

<223> OTHER INFORMATION: Survival Motor Neuron 1 (SMN1)

<400> SEQUENCE: 137

Met Ala Met Ser Ser Gly Gly Ser Gly Gly Gly Val Pro Glu Gln Glu
1 5 10 15

Asp Ser Val Leu Phe Arg Arg Gly Thr Gly Gln Ser Asp Asp Ser Asp
20 25 30

Ile Trp Asp Asp Thr Ala Leu Ile Lys Ala Tyr Asp Lys Ala Val Ala
35 40 45

Ser Phe Lys His Ala Leu Lys Asn Gly Asp Ile Cys Glu Thr Ser Gly
50 55 60

Lys Pro Lys Thr Thr Pro Lys Arg Lys Pro Ala Lys Lys Asn Lys Ser
65 70 75 80

Gln Lys Lys Asn Thr Ala Ala Ser Leu Gln Gln Trp Lys Val Gly Asp
85 90 95

Lys Cys Ser Ala Ile Trp Ser Glu Asp Gly Cys Ile Tyr Pro Ala Thr
100 105 110

Ile Ala Ser Ile Asp Phe Lys Arg Glu Thr Cys Val Val Val Tyr Thr
115 120 125

Gly Tyr Gly Asn Arg Glu Glu Gln Asn Leu Ser Asp Leu Leu Ser Pro
130 135 140

Ile Cys Glu Val Ala Asn Asn Ile Glu Gln Asn Ala Gln Glu Asn Glu
145 150 155 160

Asn Glu Ser Gln Val Ser Thr Asp Glu Ser Glu Asn Ser Arg Ser Pro
165 170 175

Gly Asn Lys Ser Asp Asn Ile Lys Pro Lys Ser Ala Pro Trp Asn Ser
180 185 190

Phe Leu Pro Pro Pro Pro Pro Met Pro Gly Pro Arg Leu Gly Pro Gly
195 200 205

Lys Pro Gly Leu Lys Phe Asn Gly Pro Pro Pro Pro Pro Pro Pro Pro
210 215 220

Pro Pro His Leu Leu Ser Cys Trp Leu Pro Pro Phe Pro Ser Gly Pro
225 230 235 240

Pro Ile Ile Pro Pro Pro Pro Pro Ile Cys Pro Asp Ser Leu Asp Asp
245 250 255

Ala Asp Ala Leu Gly Ser Met Leu Ile Ser Trp Tyr Met Ser Gly Tyr
260 265 270

His Thr Gly Tyr Tyr Met Gly Phe Arg Gln Asn Gln Lys Glu Gly Arg
275 280 285

Cys Ser His Ser Leu Asn
290

<210> SEQ ID NO 138
<211> LENGTH: 515
<212> TYPE: PRT
<213> ORGANISM: Homo sapiens
<220> FEATURE:
<221> NAME/KEY: MISC_FEATURE
<222> LOCATION: (1)..(515)
<223> OTHER INFORMATION: Tissue Non-specific Alkaline Phosphatase (TNALP)

<400> SEQUENCE: 138

Met Ile Ser Pro Phe Leu Val Leu Ala Ile Gly Thr Cys Leu Thr Asn
1 5 10 15

Ser Leu Val Pro Glu Lys Glu Lys Asp Pro Lys Tyr Trp Arg Asp Gln
20 25 30

```
Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300

Thr Asp Pro Ser Leu Ser Glu Met Val Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
        435                 440                 445
```

Leu Arg His Glu Thr His Gly Gly Glu Asp Val Ala Val Phe Ser Lys
450 455 460

Gly Pro Met Ala His Leu Leu His Gly Val His Glu Gln Asn Tyr Val
465 470 475 480

Pro His Val Met Ala Tyr Ala Ala Cys Ile Gly Ala Asn Leu Gly His
485 490 495

Cys Ala Pro Ala Ser Ser Ala Gly Ser Asp Asp Asp Asp Asp Asp Asp
500 505 510

Asp Asp Asp
515

<210> SEQ ID NO 139
<211> LENGTH: 211
<212> TYPE: PRT
<213> ORGANISM: Homo sapiens
<220> FEATURE:
<221> NAME/KEY: MISC_FEATURE
<222> LOCATION: (1)..(211)
<223> OTHER INFORMATION: Glial Cell Derived Neurotrophic Factor (GDNF)

<400> SEQUENCE: 139

Met Lys Leu Trp Asp Val Val Ala Val Cys Leu Val Leu Leu His Thr
1 5 10 15

Ala Ser Ala Phe Pro Leu Pro Ala Gly Lys Arg Pro Pro Glu Ala Pro
20 25 30

Ala Glu Asp Arg Ser Leu Gly Arg Arg Arg Ala Pro Phe Ala Leu Ser
35 40 45

Ser Asp Ser Asn Met Pro Glu Asp Tyr Pro Asp Gln Phe Asp Asp Val
50 55 60

Met Asp Phe Ile Gln Ala Thr Ile Lys Arg Leu Lys Arg Ser Pro Asp
65 70 75 80

Lys Gln Met Ala Val Leu Pro Arg Arg Glu Arg Asn Arg Gln Ala Ala
85 90 95

Ala Ala Asn Pro Glu Asn Ser Arg Gly Lys Gly Arg Arg Gly Gln Arg
100 105 110

Gly Lys Asn Arg Gly Cys Val Leu Thr Ala Ile His Leu Asn Val Thr
115 120 125

Asp Leu Gly Leu Gly Tyr Glu Thr Lys Glu Glu Leu Ile Phe Arg Tyr
130 135 140

Cys Ser Gly Ser Cys Asp Ala Ala Glu Thr Thr Tyr Asp Lys Ile Leu
145 150 155 160

Lys Asn Leu Ser Arg Asn Arg Arg Leu Val Ser Asp Lys Val Gly Gln
165 170 175

Ala Cys Cys Arg Pro Ile Ala Phe Asp Asp Asp Leu Ser Phe Leu Asp
180 185 190

Asp Asn Leu Val Tyr His Ile Leu Arg Lys His Ser Ala Lys Arg Cys
195 200 205

Gly Cys Ile
210

<210> SEQ ID NO 140
<211> LENGTH: 536
<212> TYPE: PRT
<213> ORGANISM: Homo sapiens
<220> FEATURE:
<221> NAME/KEY: MISC_FEATURE
<222> LOCATION: (1)..(536)
<223> OTHER INFORMATION: Tissue Glucosyl Ceramidase beta (GBA1)

<400> SEQUENCE: 140

```
Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
    290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
        355                 360                 365

Leu Phe Pro Asn Thr Met Leu Phe Ala Ser Glu Ala Cys Val Gly Ser
    370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415
```

```
Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
        435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
        515                 520                 525

His Thr Tyr Leu Trp Arg Arg Gln
    530                 535


<210> SEQ ID NO 141
<211> LENGTH: 653
<212> TYPE: PRT
<213> ORGANISM: Homo sapiens
<220> FEATURE:
<221> NAME/KEY: MISC_FEATURE
<222> LOCATION: (1)..(653)
<223> OTHER INFORMATION: Iduronidase alpha-L- (IDUA)

<400> SEQUENCE: 141

Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
            20                  25                  30

His Val Asp Ala Ala Arg Ala Leu Trp Pro Leu Arg Arg Phe Trp Arg
        35                  40                  45

Ser Thr Gly Phe Cys Pro Pro Leu Pro His Ser Gln Ala Asp Gln Tyr
    50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
            100                 105                 110

His Leu Asp Gly Tyr Leu Asp Leu Leu Arg Glu Asn Gln Leu Leu Pro
        115                 120                 125

Gly Phe Glu Leu Met Gly Ser Ala Ser Gly His Phe Thr Asp Phe Glu
    130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
        195                 200                 205

Leu Arg Ala Ala Ser Pro Ala Leu Arg Leu Gly Gly Pro Gly Asp Ser
    210                 215                 220
```

```
Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
            260                 265                 270

Leu Glu Gln Glu Lys Val Val Ala Gln Gln Ile Arg Gln Leu Phe Pro
        275                 280                 285

Lys Phe Ala Asp Thr Pro Ile Tyr Asn Asp Glu Ala Asp Pro Leu Val
    290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
        355                 360                 365

Phe Gln Val Asn Asn Thr Arg Pro Pro His Val Gln Leu Leu Arg Lys
    370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
        435                 440                 445

His Pro Asn Arg Ser Val Ala Val Thr Leu Arg Leu Arg Gly Val Pro
    450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
        515                 520                 525

Ala Leu Arg Leu Pro Ser Leu Leu Leu Val His Val Cys Ala Arg Pro
    530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
            580                 585                 590

Thr Pro Val Ser Arg Lys Pro Ser Thr Phe Asn Leu Phe Val Phe Ser
        595                 600                 605

Pro Asp Thr Gly Ala Val Ser Gly Ser Tyr Arg Val Arg Ala Leu Asp
    610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
```

645 650

<210> SEQ ID NO 142
<211> LENGTH: 525
<212> TYPE: PRT
<213> ORGANISM: Homo sapiens
<220> FEATURE:
<221> NAME/KEY: MISC_FEATURE
<222> LOCATION: (1)..(525)
<223> OTHER INFORMATION: Cytochrome P450 family 4 subfamily V member 2
(CYP4V2)

<400> SEQUENCE: 142

Met Ala Gly Leu Trp Leu Gly Leu Val Trp Gln Lys Leu Leu Leu Trp
1 5 10 15

Gly Ala Ala Ser Ala Leu Ser Leu Ala Gly Ala Ser Leu Val Leu Ser
20 25 30

Leu Leu Gln Arg Val Ala Ser Tyr Ala Arg Lys Trp Gln Gln Met Arg
35 40 45

Pro Ile Pro Thr Val Ala Arg Ala Tyr Pro Leu Val Gly His Ala Leu
50 55 60

Leu Met Lys Pro Asp Gly Arg Glu Phe Phe Gln Gln Ile Ile Glu Tyr
65 70 75 80

Thr Glu Glu Tyr Arg His Met Pro Leu Leu Lys Leu Trp Val Gly Pro
85 90 95

Val Pro Met Val Ala Leu Tyr Asn Ala Glu Asn Val Glu Val Ile Leu
100 105 110

Thr Ser Ser Lys Gln Ile Asp Lys Ser Ser Met Tyr Lys Phe Leu Glu
115 120 125

Pro Trp Leu Gly Leu Gly Leu Leu Thr Ser Thr Gly Asn Lys Trp Arg
130 135 140

Ser Arg Arg Lys Met Leu Thr Pro Thr Phe His Phe Thr Ile Leu Glu
145 150 155 160

Asp Phe Leu Asp Ile Met Asn Glu Gln Ala Asn Ile Leu Val Lys Lys
165 170 175

Leu Glu Lys His Ile Asn Gln Glu Ala Phe Asn Cys Phe Phe Tyr Ile
180 185 190

Thr Leu Cys Ala Leu Asp Ile Ile Cys Glu Thr Ala Met Gly Lys Asn
195 200 205

Ile Gly Ala Gln Ser Asn Asp Asp Ser Glu Tyr Val Arg Ala Val Tyr
210 215 220

Arg Met Ser Glu Met Ile Phe Arg Arg Ile Lys Met Pro Trp Leu Trp
225 230 235 240

Leu Asp Leu Trp Tyr Leu Met Phe Lys Glu Gly Trp Glu His Lys Lys
245 250 255

Ser Leu Gln Ile Leu His Thr Phe Thr Asn Ser Val Ile Ala Glu Arg
260 265 270

Ala Asn Glu Met Asn Ala Asn Glu Asp Cys Arg Gly Asp Gly Arg Gly
275 280 285

Ser Ala Pro Ser Lys Asn Lys Arg Arg Ala Phe Leu Asp Leu Leu Leu
290 295 300

Ser Val Thr Asp Asp Glu Gly Asn Arg Leu Ser His Glu Asp Ile Arg
305 310 315 320

Glu Glu Val Asp Thr Phe Met Phe Glu Gly His Asp Thr Thr Ala Ala
325 330 335

Ala Ile Asn Trp Ser Leu Tyr Leu Leu Gly Ser Asn Pro Glu Val Gln

```
            340                 345                 350

Lys Lys Val Asp His Glu Leu Asp Asp Val Phe Gly Lys Ser Asp Arg
        355                 360                 365

Pro Ala Thr Val Glu Asp Leu Lys Lys Leu Arg Tyr Leu Glu Cys Val
    370                 375                 380

Ile Lys Glu Thr Leu Arg Leu Phe Pro Ser Val Pro Leu Phe Ala Arg
385                 390                 395                 400

Ser Val Ser Glu Asp Cys Glu Val Ala Gly Tyr Arg Val Leu Lys Gly
                405                 410                 415

Thr Glu Ala Val Ile Ile Pro Tyr Ala Leu His Arg Asp Pro Arg Tyr
            420                 425                 430

Phe Pro Asn Pro Glu Glu Phe Gln Pro Glu Arg Phe Phe Pro Glu Asn
        435                 440                 445

Ala Gln Gly Arg His Pro Tyr Ala Tyr Val Pro Phe Ser Ala Gly Pro
    450                 455                 460

Arg Asn Cys Ile Gly Gln Lys Phe Ala Val Met Glu Glu Lys Thr Ile
465                 470                 475                 480

Leu Ser Cys Ile Leu Arg His Phe Trp Ile Glu Ser Asn Gln Lys Arg
                485                 490                 495

Glu Glu Leu Gly Leu Glu Gly Gln Leu Ile Leu Arg Pro Ser Asn Gly
            500                 505                 510

Ile Trp Ile Lys Leu Lys Arg Arg Asn Ala Asp Glu Arg
        515                 520                 525


<210> SEQ ID NO 143
<211> LENGTH: 236
<212> TYPE: PRT
<213> ORGANISM: Homo sapiens
<220> FEATURE:
<221> NAME/KEY: MISC_FEATURE
<222> LOCATION: (1)..(236)
<223> OTHER INFORMATION: Retinoschisin 1 (RS1)

<400> SEQUENCE: 143

Met Ser Arg Lys Ile Glu Gly Phe Leu Leu Leu Leu Leu Phe Gly Tyr
1               5                   10                  15

Glu Ala Thr Leu Gly Leu Ser Ser Thr Glu Asp Glu Gly Glu Asp Pro
            20                  25                  30

Trp Tyr Gln Lys Ala Cys Asp Glu Gly Glu Asp Pro Trp Tyr Gln Lys
        35                  40                  45

Ala Cys Lys Cys Asp Cys Gln Gly Gly Pro Asn Ala Leu Trp Ser Ala
    50                  55                  60

Gly Ala Thr Ser Leu Asp Cys Ile Pro Glu Cys Pro Tyr His Lys Pro
65                  70                  75                  80

Leu Gly Phe Glu Ser Gly Glu Val Thr Pro Asp Gln Ile Thr Cys Ser
                85                  90                  95

Asn Pro Glu Gln Tyr Val Gly Trp Tyr Ser Ser Trp Thr Ala Asn Lys
            100                 105                 110

Ala Arg Leu Asn Ser Gln Gly Phe Gly Cys Ala Trp Leu Ser Lys Phe
        115                 120                 125

Gln Asp Ser Ser Gln Trp Leu Gln Ile Asp Leu Lys Glu Ile Lys Val
    130                 135                 140

Ile Ser Gly Ile Leu Thr Gln Gly Arg Cys Asp Ile Asp Glu Trp Met
145                 150                 155                 160

Thr Lys Tyr Ser Val Gln Tyr Arg Thr Asp Glu Arg Leu Asn Trp Ile
                165                 170                 175
```

```
Tyr Tyr Lys Asp Gln Thr Gly Asn Asn Arg Val Phe Tyr Gly Asn Ser
            180                 185                 190

Asp Arg Thr Ser Thr Val Gln Asn Leu Leu Arg Pro Pro Ile Ile Ser
        195                 200                 205

Arg Phe Ile Arg Leu Ile Pro Leu Gly Trp His Val Arg Ile Ala Ile
    210                 215                 220

Arg Met Glu Leu Leu Glu Cys Val Ser Lys Cys Ala
225                 230                 235


<210> SEQ ID NO 144
<211> LENGTH: 854
<212> TYPE: PRT
<213> ORGANISM: Homo sapiens
<220> FEATURE:
<221> NAME/KEY: MISC_FEATURE
<222> LOCATION: (1)..(854)
<223> OTHER INFORMATION: Phosphodiesterase 6B (PDE6B)

<400> SEQUENCE: 144

Met Ser Leu Ser Glu Glu Gln Ala Arg Ser Phe Leu Asp Gln Asn Pro
1               5                   10                  15

Asp Phe Ala Arg Gln Tyr Phe Gly Lys Lys Leu Ser Pro Glu Asn Val
            20                  25                  30

Ala Ala Ala Cys Glu Asp Gly Cys Pro Pro Asp Cys Asp Ser Leu Arg
        35                  40                  45

Asp Leu Cys Gln Val Glu Glu Ser Thr Ala Leu Leu Glu Leu Val Gln
    50                  55                  60

Asp Met Gln Glu Ser Ile Asn Met Glu Arg Val Val Phe Lys Val Leu
65                  70                  75                  80

Arg Arg Leu Cys Thr Leu Leu Gln Ala Asp Arg Cys Ser Leu Phe Met
                85                  90                  95

Tyr Arg Gln Arg Asn Gly Val Ala Glu Leu Ala Thr Arg Leu Phe Ser
            100                 105                 110

Val Gln Pro Asp Ser Val Leu Glu Asp Cys Leu Val Pro Pro Asp Ser
        115                 120                 125

Glu Ile Val Phe Pro Leu Asp Ile Gly Val Val Gly His Val Ala Gln
    130                 135                 140

Thr Lys Lys Met Val Asn Val Glu Asp Val Ala Glu Cys Pro His Phe
145                 150                 155                 160

Ser Ser Phe Ala Asp Glu Leu Thr Asp Tyr Lys Thr Lys Asn Met Leu
                165                 170                 175

Ala Thr Pro Ile Met Asn Gly Lys Asp Val Val Ala Val Ile Met Ala
            180                 185                 190

Val Asn Lys Leu Asn Gly Pro Phe Phe Thr Ser Glu Asp Glu Asp Val
        195                 200                 205

Phe Leu Lys Tyr Leu Asn Phe Ala Thr Leu Tyr Leu Lys Ile Tyr His
    210                 215                 220

Leu Ser Tyr Leu His Asn Cys Glu Thr Arg Arg Gly Gln Val Leu Leu
225                 230                 235                 240

Trp Ser Ala Asn Lys Val Phe Glu Glu Leu Thr Asp Ile Glu Arg Gln
                245                 250                 255

Phe His Lys Ala Phe Tyr Thr Val Arg Ala Tyr Leu Asn Cys Glu Arg
            260                 265                 270

Tyr Ser Val Gly Leu Leu Asp Met Thr Lys Glu Lys Glu Phe Phe Asp
        275                 280                 285
```

```
Val Trp Ser Val Leu Met Gly Glu Ser Gln Pro Tyr Ser Gly Pro Arg
    290                 295                 300

Thr Pro Asp Gly Arg Glu Ile Val Phe Tyr Lys Val Ile Asp Tyr Ile
305                 310                 315                 320

Leu His Gly Lys Glu Glu Ile Lys Val Ile Pro Thr Pro Ser Ala Asp
                325                 330                 335

His Trp Ala Leu Ala Ser Gly Leu Pro Ser Tyr Val Ala Glu Ser Gly
            340                 345                 350

Phe Ile Cys Asn Ile Met Asn Ala Ser Ala Asp Glu Met Phe Lys Phe
        355                 360                 365

Gln Glu Gly Ala Leu Asp Asp Ser Gly Trp Leu Ile Lys Asn Val Leu
    370                 375                 380

Ser Met Pro Ile Val Asn Lys Lys Glu Glu Ile Val Gly Val Ala Thr
385                 390                 395                 400

Phe Tyr Asn Arg Lys Asp Gly Lys Pro Phe Asp Glu Gln Asp Glu Val
                405                 410                 415

Leu Met Glu Ser Leu Thr Gln Phe Leu Gly Trp Ser Val Met Asn Thr
            420                 425                 430

Asp Thr Tyr Asp Lys Met Asn Lys Leu Glu Asn Arg Lys Asp Ile Ala
        435                 440                 445

Gln Asp Met Val Leu Tyr His Val Lys Cys Asp Arg Asp Glu Ile Gln
    450                 455                 460

Leu Ile Leu Pro Thr Arg Ala Arg Leu Gly Lys Glu Pro Ala Asp Cys
465                 470                 475                 480

Asp Glu Asp Glu Leu Gly Glu Ile Leu Lys Glu Glu Leu Pro Gly Pro
                485                 490                 495

Thr Thr Phe Asp Ile Tyr Glu Phe His Phe Ser Asp Leu Glu Cys Thr
            500                 505                 510

Glu Leu Asp Leu Val Lys Cys Gly Ile Gln Met Tyr Tyr Glu Leu Gly
        515                 520                 525

Val Val Arg Lys Phe Gln Ile Pro Gln Glu Val Leu Val Arg Phe Leu
    530                 535                 540

Phe Ser Ile Ser Lys Gly Tyr Arg Arg Ile Thr Tyr His Asn Trp Arg
545                 550                 555                 560

His Gly Phe Asn Val Ala Gln Thr Met Phe Thr Leu Leu Met Thr Gly
                565                 570                 575

Lys Leu Lys Ser Tyr Tyr Thr Asp Leu Glu Ala Phe Ala Met Val Thr
            580                 585                 590

Ala Gly Leu Cys His Asp Ile Asp His Arg Gly Thr Asn Asn Leu Tyr
        595                 600                 605

Gln Met Lys Ser Gln Asn Pro Leu Ala Lys Leu His Gly Ser Ser Ile
    610                 615                 620

Leu Glu Arg His His Leu Glu Phe Gly Lys Phe Leu Leu Ser Glu Glu
625                 630                 635                 640

Thr Leu Asn Ile Tyr Gln Asn Leu Asn Arg Arg Gln His Glu His Val
                645                 650                 655

Ile His Leu Met Asp Ile Ala Ile Ile Ala Thr Asp Leu Ala Leu Tyr
            660                 665                 670

Phe Lys Lys Arg Ala Met Phe Gln Lys Ile Val Asp Glu Ser Lys Asn
        675                 680                 685

Tyr Gln Asp Lys Lys Ser Trp Val Glu Tyr Leu Ser Leu Glu Thr Thr
    690                 695                 700

Arg Lys Glu Ile Val Met Ala Met Met Met Thr Ala Cys Asp Leu Ser
```

705 710 715 720

Ala Ile Thr Lys Pro Trp Glu Val Gln Ser Lys Val Ala Leu Leu Val
725 730 735

Ala Ala Glu Phe Trp Glu Gln Gly Asp Leu Glu Arg Thr Val Leu Asp
740 745 750

Gln Gln Pro Ile Pro Met Met Asp Arg Asn Lys Ala Ala Glu Leu Pro
755 760 765

Lys Leu Gln Val Gly Phe Ile Asp Phe Val Cys Thr Phe Val Tyr Lys
770 775 780

Glu Phe Ser Arg Phe His Glu Glu Ile Leu Pro Met Phe Asp Arg Leu
785 790 795 800

Gln Asn Asn Arg Lys Glu Trp Lys Ala Leu Ala Asp Glu Tyr Glu Ala
805 810 815

Lys Val Lys Ala Leu Glu Glu Lys Glu Glu Glu Glu Arg Val Ala Ala
820 825 830

Lys Lys Val Gly Thr Glu Ile Cys Asn Gly Gly Pro Ala Pro Lys Ser
835 840 845

Ser Thr Cys Cys Ile Leu
850

<210> SEQ ID NO 145
<211> LENGTH: 498
<212> TYPE: PRT
<213> ORGANISM: Homo sapiens
<220> FEATURE:
<221> NAME/KEY: MISC_FEATURE
<222> LOCATION: (1)..(498)
<223> OTHER INFORMATION: Methyl-CpG Binding Protein (MeCP2)

<400> SEQUENCE: 145

Met Ala Ala Ala Ala Ala Ala Ala Pro Ser Gly Gly Gly Gly Gly Gly
1 5 10 15

Glu Glu Glu Arg Leu Glu Glu Lys Ser Glu Asp Gln Asp Leu Gln Gly
20 25 30

Leu Lys Asp Lys Pro Leu Lys Phe Lys Lys Val Lys Lys Asp Lys Lys
35 40 45

Glu Glu Lys Glu Gly Lys His Glu Pro Val Gln Pro Ser Ala His His
50 55 60

Ser Ala Glu Pro Ala Glu Ala Gly Lys Ala Glu Thr Ser Glu Gly Ser
65 70 75 80

Gly Ser Ala Pro Ala Val Pro Glu Ala Ser Ala Ser Pro Lys Gln Arg
85 90 95

Arg Ser Ile Ile Arg Asp Arg Gly Pro Met Tyr Asp Asp Pro Thr Leu
100 105 110

Pro Glu Gly Trp Thr Arg Lys Leu Lys Gln Arg Lys Ser Gly Arg Ser
115 120 125

Ala Gly Lys Tyr Asp Val Tyr Leu Ile Asn Pro Gln Gly Lys Ala Phe
130 135 140

Arg Ser Lys Val Glu Leu Ile Ala Tyr Phe Glu Lys Val Gly Asp Thr
145 150 155 160

Ser Leu Asp Pro Asn Asp Phe Asp Phe Thr Val Thr Gly Arg Gly Ser
165 170 175

Pro Ser Arg Arg Glu Gln Lys Pro Pro Lys Lys Pro Lys Ser Pro Lys
180 185 190

Ala Pro Gly Thr Gly Arg Gly Arg Gly Arg Pro Lys Gly Ser Gly Thr
195 200 205

Thr Arg Pro Lys Ala Ala Thr Ser Glu Gly Val Gln Val Lys Arg Val
    210                 215                 220

Leu Glu Lys Ser Pro Gly Lys Leu Leu Val Lys Met Pro Phe Gln Thr
225                 230                 235                 240

Ser Pro Gly Gly Lys Ala Glu Gly Gly Gly Ala Thr Thr Ser Thr Gln
                245                 250                 255

Val Met Val Ile Lys Arg Pro Gly Arg Lys Arg Lys Ala Glu Ala Asp
            260                 265                 270

Pro Gln Ala Ile Pro Lys Lys Arg Gly Arg Lys Pro Gly Ser Val Val
        275                 280                 285

Ala Ala Ala Ala Ala Glu Ala Lys Lys Lys Ala Val Lys Glu Ser Ser
    290                 295                 300

Ile Arg Ser Val Gln Glu Thr Val Leu Pro Ile Lys Lys Arg Lys Thr
305                 310                 315                 320

Arg Glu Thr Val Ser Ile Glu Val Lys Glu Val Val Lys Pro Leu Leu
                325                 330                 335

Val Ser Thr Leu Gly Glu Lys Ser Gly Lys Gly Leu Lys Thr Cys Lys
            340                 345                 350

Ser Pro Gly Arg Lys Ser Lys Glu Ser Ser Pro Lys Gly Arg Ser Ser
        355                 360                 365

Ser Ala Ser Ser Pro Pro Lys Lys Glu His His His His His His His
    370                 375                 380

Ser Glu Ser Pro Lys Ala Pro Val Pro Leu Leu Pro Pro Leu Pro Pro
385                 390                 395                 400

Pro Pro Pro Glu Pro Glu Ser Ser Glu Asp Pro Thr Ser Pro Pro Glu
                405                 410                 415

Pro Gln Asp Leu Ser Ser Ser Val Cys Lys Glu Glu Lys Met Pro Arg
            420                 425                 430

Gly Gly Ser Leu Glu Ser Asp Gly Cys Pro Lys Glu Pro Ala Lys Thr
        435                 440                 445

Gln Pro Ala Val Ala Thr Ala Ala Thr Ala Ala Glu Lys Tyr Lys His
    450                 455                 460

Arg Gly Glu Gly Glu Arg Lys Asp Ile Val Ser Ser Ser Met Pro Arg
465                 470                 475                 480

Pro Asn Arg Glu Glu Pro Val Asp Ser Arg Thr Pro Val Thr Glu Arg
                485                 490                 495

Val Ser

<210> SEQ ID NO 146
<211> LENGTH: 743
<212> TYPE: PRT
<213> ORGANISM: Homo sapiens
<220> FEATURE:
<221> NAME/KEY: MISC_FEATURE
<222> LOCATION: (1)..(743)
<223> OTHER INFORMATION: N-acetyl-alpha-glucosaminidase (NAGLU)

<400> SEQUENCE: 146

Met Glu Ala Val Ala Val Ala Ala Ala Val Gly Val Leu Leu Leu Ala
1               5                   10                  15

Gly Ala Gly Gly Ala Ala Gly Asp Glu Ala Arg Glu Ala Ala Ala Val
            20                  25                  30

Arg Ala Leu Val Ala Arg Leu Leu Gly Pro Gly Pro Ala Ala Asp Phe
        35                  40                  45

Ser Val Ser Val Glu Arg Ala Leu Ala Ala Lys Pro Gly Leu Asp Thr

```
    50                  55                  60

Tyr Ser Leu Gly Gly Gly Gly Ala Ala Arg Val Arg Val Arg Gly Ser
65                  70                  75                  80

Thr Gly Val Ala Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
            100                 105                 110

Pro Leu Pro Ala Val Pro Gly Glu Leu Thr Glu Ala Thr Pro Asn Arg
        115                 120                 125

Tyr Arg Tyr Tyr Gln Asn Val Cys Thr Gln Ser Tyr Ser Phe Val Trp
    130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
            180                 185                 190

Phe Thr Gly Pro Ala Phe Leu Ala Trp Gly Arg Met Gly Asn Leu His
        195                 200                 205

Thr Trp Asp Gly Pro Leu Pro Pro Ser Trp His Ile Lys Gln Leu Tyr
    210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
            260                 265                 270

Cys Ser Tyr Ser Cys Ser Phe Leu Leu Ala Pro Glu Asp Pro Ile Phe
        275                 280                 285

Pro Ile Ile Gly Ser Leu Phe Leu Arg Glu Leu Ile Lys Glu Phe Gly
    290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Ala Thr Thr Ala Val Tyr Glu
                325                 330                 335

Ala Met Thr Ala Val Asp Thr Glu Ala Val Trp Leu Leu Gln Gly Trp
            340                 345                 350

Leu Phe Gln His Gln Pro Gln Phe Trp Gly Pro Ala Gln Ile Arg Ala
        355                 360                 365

Val Leu Gly Ala Val Pro Arg Gly Arg Leu Leu Val Leu Asp Leu Phe
    370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
        435                 440                 445

Ser Gln Asn Glu Val Val Tyr Ser Leu Met Ala Glu Leu Gly Trp Arg
    450                 455                 460

Lys Asp Pro Val Pro Asp Leu Ala Ala Trp Val Thr Ser Phe Ala Ala
465                 470                 475                 480
```

```
Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
        515                 520                 525

Ile Trp Tyr Asn Arg Ser Asp Val Phe Glu Ala Trp Arg Leu Leu Leu
    530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
        595                 600                 605

Val Leu Ala Ser Asp Ser Arg Phe Leu Leu Gly Ser Trp Leu Glu Gln
    610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
    690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Gly Trp Val Ala Gly Ser Trp
            740


<210> SEQ ID NO 147

<400> SEQUENCE: 147

000


<210> SEQ ID NO 148
<211> LENGTH: 429
<212> TYPE: PRT
<213> ORGANISM: Homo sapiens
<220> FEATURE:
<221> NAME/KEY: MISC_FEATURE
<222> LOCATION: (1)..(429)
<223> OTHER INFORMATION: Alpha-Galactosidase A (GLA)

<400> SEQUENCE: 148

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45
```

```
Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
            420                 425
```

<210> SEQ ID NO 149
<211> LENGTH: 458
<212> TYPE: PRT
<213> ORGANISM: Artificial Sequence
<220> FEATURE:

<223> OTHER INFORMATION: Codon optimized + GET, CO1-GLA-GET

<400> SEQUENCE: 149

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
405 410 415

Leu Glu Asn Thr Met Gln Met Ser Leu Lys Asp Leu Leu Arg Arg Arg
420 425 430

Arg Arg Arg Arg Arg Lys Arg Lys Lys Lys Gly Lys Gly Leu Gly Lys
435 440 445

Lys Arg Asp Pro Cys Leu Arg Lys Tyr Lys
450 455

<210> SEQ ID NO 150
<211> LENGTH: 1428
<212> TYPE: PRT
<213> ORGANISM: Artificial Sequence
<220> FEATURE:
<223> OTHER INFORMATION: Codon optimized, Cystic Fibrosis Transmembrane
Regulator deltaR (CFTRdeltaR) contains R domain deletion

<400> SEQUENCE: 150

Met Gln Arg Ser Pro Leu Glu Lys Ala Ser Val Val Ser Lys Leu Phe
1 5 10 15

Phe Ser Trp Thr Arg Pro Ile Leu Arg Lys Gly Tyr Arg Gln Arg Leu
20 25 30

Glu Leu Ser Asp Ile Tyr Gln Ile Pro Ser Val Asp Ser Ala Asp Asn
35 40 45

Leu Ser Glu Lys Leu Glu Arg Glu Trp Asp Arg Glu Leu Ala Ser Lys
50 55 60

Lys Asn Pro Lys Leu Ile Asn Ala Leu Arg Arg Cys Phe Phe Trp Arg
65 70 75 80

Phe Met Phe Tyr Gly Ile Phe Leu Tyr Leu Gly Glu Val Thr Lys Ala
85 90 95

Val Gln Pro Leu Leu Leu Gly Arg Ile Ile Ala Ser Tyr Asp Pro Asp
100 105 110

Asn Lys Glu Glu Arg Ser Ile Ala Ile Tyr Leu Gly Ile Gly Leu Cys
115 120 125

Leu Leu Phe Ile Val Arg Thr Leu Leu Leu His Pro Ala Ile Phe Gly
130 135 140

Leu His His Ile Gly Met Gln Met Arg Ile Ala Met Phe Ser Leu Ile
145 150 155 160

Tyr Lys Lys Thr Leu Lys Leu Ser Ser Arg Val Leu Asp Lys Ile Ser
165 170 175

Ile Gly Gln Leu Val Ser Leu Leu Ser Asn Asn Leu Asn Lys Phe Asp
180 185 190

Glu Gly Leu Ala Leu Ala His Phe Val Trp Ile Ala Pro Leu Gln Val
195 200 205

Ala Leu Leu Met Gly Leu Ile Trp Glu Leu Leu Gln Ala Ser Ala Phe
210 215 220

Cys Gly Leu Gly Phe Leu Ile Val Leu Ala Leu Phe Gln Ala Gly Leu
225 230 235 240

Gly Arg Met Met Met Lys Tyr Arg Asp Gln Arg Ala Gly Lys Ile Ser
245 250 255

Glu Arg Leu Val Ile Thr Ser Glu Met Ile Glu Asn Ile Gln Ser Val
260 265 270

Lys Ala Tyr Cys Trp Glu Glu Ala Met Glu Lys Met Ile Glu Asn Leu
275 280 285

Arg Gln Thr Glu Leu Lys Leu Thr Arg Lys Ala Ala Tyr Val Arg Tyr
290 295 300

```
Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
    690                 695                 700

Ile Asn Ser Thr Leu Gln Ala Arg Arg Arg Gln Ser Val Leu Asn Leu
705                 710                 715                 720
```

```
Met Thr His Ser Val Asn Gln Gly Gln Asn Ile His Arg Lys Thr Thr
                725                 730                 735

Ala Ser Thr Arg Lys Val Ser Leu Ala Pro Gln Ala Asn Leu Thr Glu
            740                 745                 750

Leu Asp Ile Tyr Ser Arg Arg Leu Ser Gln Glu Thr Gly Leu Glu Ile
        755                 760                 765

Ser Glu Glu Ile Asn Glu Glu Asp Leu Lys Glu Cys Phe Phe Asp Asp
    770                 775                 780

Met Glu Ser Ile Pro Ala Val Thr Thr Trp Asn Thr Tyr Leu Arg Tyr
785                 790                 795                 800

Ile Thr Val His Lys Ser Leu Ile Phe Val Leu Ile Trp Cys Leu Val
                805                 810                 815

Ile Phe Leu Ala Glu Val Ala Ala Ser Leu Val Val Leu Trp Leu Leu
            820                 825                 830

Gly Asn Thr Pro Leu Gln Asp Lys Gly Asn Ser Thr His Ser Arg Asn
        835                 840                 845

Asn Ser Tyr Ala Val Ile Ile Thr Ser Thr Ser Ser Tyr Tyr Val Phe
    850                 855                 860

Tyr Ile Tyr Val Gly Val Ala Asp Thr Leu Leu Ala Met Gly Phe Phe
865                 870                 875                 880

Arg Gly Leu Pro Leu Val His Thr Leu Ile Thr Val Ser Lys Ile Leu
                885                 890                 895

His His Lys Met Leu His Ser Val Leu Gln Ala Pro Met Ser Thr Leu
            900                 905                 910

Asn Thr Leu Lys Ala Gly Gly Ile Leu Asn Arg Phe Ser Lys Asp Ile
        915                 920                 925

Ala Ile Leu Asp Asp Leu Leu Pro Leu Thr Ile Phe Asp Phe Ile Gln
    930                 935                 940

Leu Leu Leu Ile Val Ile Gly Ala Ile Ala Val Val Ala Val Leu Gln
945                 950                 955                 960

Pro Tyr Ile Phe Val Ala Thr Val Pro Val Ile Val Ala Phe Ile Met
                965                 970                 975

Leu Arg Ala Tyr Phe Leu Gln Thr Ser Gln Gln Leu Lys Gln Leu Glu
            980                 985                 990

Ser Glu Gly Arg Ser Pro Ile Phe  Thr His Leu Val Thr  Ser Leu Lys
        995                 1000                1005

Gly Leu  Trp Thr Leu Arg Ala  Phe Gly Arg Gln Pro  Tyr Phe Glu
    1010                1015                1020

Thr Leu  Phe His Lys Ala Leu  Asn Leu His Thr Ala  Asn Trp Phe
    1025                1030                1035

Leu Tyr  Leu Ser Thr Leu Arg  Trp Phe Gln Met Arg  Ile Glu Met
    1040                1045                1050

Ile Phe  Val Ile Phe Phe Ile  Ala Val Thr Phe Ile  Ser Ile Leu
    1055                1060                1065

Thr Thr  Gly Glu Gly Glu Gly  Arg Val Gly Ile Ile  Leu Thr Leu
    1070                1075                1080

Ala Met  Asn Ile Met Ser Thr  Leu Gln Trp Ala Val  Asn Ser Ser
    1085                1090                1095

Ile Asp  Val Asp Ser Leu Met  Arg Ser Val Ser Arg  Val Phe Lys
    1100                1105                1110

Phe Ile  Asp Met Pro Thr Glu  Gly Lys Pro Thr Lys  Ser Thr Lys
    1115                1120                1125

Pro Tyr  Lys Asn Gly Gln Leu  Ser Lys Val Met Ile  Ile Glu Asn
```

1130 1135 1140

Ser His Val Lys Lys Asp Asp Ile Trp Pro Ser Gly Gly Gln Met
1145 1150 1155

Thr Val Lys Asp Leu Thr Ala Lys Tyr Thr Glu Gly Gly Asn Ala
1160 1165 1170

Ile Leu Glu Asn Ile Ser Phe Ser Ile Ser Pro Gly Gln Arg Val
1175 1180 1185

Gly Leu Leu Gly Arg Thr Gly Ser Gly Lys Ser Thr Leu Leu Ser
1190 1195 1200

Ala Phe Leu Arg Leu Leu Asn Thr Glu Gly Glu Ile Gln Ile Asp
1205 1210 1215

Gly Val Ser Trp Asp Ser Ile Thr Leu Gln Gln Trp Arg Lys Ala
1220 1225 1230

Phe Gly Val Ile Pro Gln Lys Val Phe Ile Phe Ser Gly Thr Phe
1235 1240 1245

Arg Lys Asn Leu Asp Pro Tyr Glu Gln Trp Ser Asp Gln Glu Ile
1250 1255 1260

Trp Lys Val Ala Asp Glu Val Gly Leu Arg Ser Val Ile Glu Gln
1265 1270 1275

Phe Pro Gly Lys Leu Asp Phe Val Leu Val Asp Gly Gly Cys Val
1280 1285 1290

Leu Ser His Gly His Lys Gln Leu Met Cys Leu Ala Arg Ser Val
1295 1300 1305

Leu Ser Lys Ala Lys Ile Leu Leu Leu Asp Glu Pro Ser Ala His
1310 1315 1320

Leu Asp Pro Val Thr Tyr Gln Ile Ile Arg Arg Thr Leu Lys Gln
1325 1330 1335

Ala Phe Ala Asp Cys Thr Val Ile Leu Cys Glu His Arg Ile Glu
1340 1345 1350

Ala Met Leu Glu Cys Gln Gln Phe Leu Val Ile Glu Glu Asn Lys
1355 1360 1365

Val Arg Gln Tyr Asp Ser Ile Gln Lys Leu Leu Asn Glu Arg Ser
1370 1375 1380

Leu Phe Arg Gln Ala Ile Ser Pro Ser Asp Arg Val Lys Leu Phe
1385 1390 1395

Pro His Arg Asn Ser Ser Lys Cys Lys Ser Lys Pro Gln Ile Ala
1400 1405 1410

Ala Leu Lys Glu Glu Thr Glu Glu Glu Val Gln Asp Thr Arg Leu
1415 1420 1425

<210> SEQ ID NO 151
<211> LENGTH: 1480
<212> TYPE: PRT
<213> ORGANISM: Artificial Sequence
<220> FEATURE:
<223> OTHER INFORMATION: Codon optimized, full length Cystic Fibrosis Transmembrane Regulator (CFTR)

<400> SEQUENCE: 151

Met Gln Arg Ser Pro Leu Glu Lys Ala Ser Val Val Ser Lys Leu Phe
1 5 10 15

Phe Ser Trp Thr Arg Pro Ile Leu Arg Lys Gly Tyr Arg Gln Arg Leu
20 25 30

Glu Leu Ser Asp Ile Tyr Gln Ile Pro Ser Val Asp Ser Ala Asp Asn
35 40 45

```
Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Met Ile Met Gly Glu Leu Glu Pro Ser Glu Gly
```

```
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
    690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
    770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Phe Phe Asp Asp Met Glu Ser Ile Pro Ala Val Thr Thr Trp Asn Thr
        835                 840                 845

Tyr Leu Arg Tyr Ile Thr Val His Lys Ser Leu Ile Phe Val Leu Ile
    850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895
```

His Ser Arg Asn Asn Ser Tyr Ala Val Ile Ile Thr Ser Thr Ser Ser
900 905 910

Tyr Tyr Val Phe Tyr Ile Tyr Val Gly Val Ala Asp Thr Leu Leu Ala
915 920 925

Met Gly Phe Phe Arg Gly Leu Pro Leu Val His Thr Leu Ile Thr Val
930 935 940

Ser Lys Ile Leu His His Lys Met Leu His Ser Val Leu Gln Ala Pro
945 950 955 960

Met Ser Thr Leu Asn Thr Leu Lys Ala Gly Gly Ile Leu Asn Arg Phe
965 970 975

Ser Lys Asp Ile Ala Ile Leu Asp Asp Leu Leu Pro Leu Thr Ile Phe
980 985 990

Asp Phe Ile Gln Leu Leu Leu Ile Val Ile Gly Ala Ile Ala Val Val
995 1000 1005

Ala Val Leu Gln Pro Tyr Ile Phe Val Ala Thr Val Pro Val Ile
1010 1015 1020

Val Ala Phe Ile Met Leu Arg Ala Tyr Phe Leu Gln Thr Ser Gln
1025 1030 1035

Gln Leu Lys Gln Leu Glu Ser Glu Gly Arg Ser Pro Ile Phe Thr
1040 1045 1050

His Leu Val Thr Ser Leu Lys Gly Leu Trp Thr Leu Arg Ala Phe
1055 1060 1065

Gly Arg Gln Pro Tyr Phe Glu Thr Leu Phe His Lys Ala Leu Asn
1070 1075 1080

Leu His Thr Ala Asn Trp Phe Leu Tyr Leu Ser Thr Leu Arg Trp
1085 1090 1095

Phe Gln Met Arg Ile Glu Met Ile Phe Val Ile Phe Phe Ile Ala
1100 1105 1110

Val Thr Phe Ile Ser Ile Leu Thr Thr Gly Glu Gly Glu Gly Arg
1115 1120 1125

Val Gly Ile Ile Leu Thr Leu Ala Met Asn Ile Met Ser Thr Leu
1130 1135 1140

Gln Trp Ala Val Asn Ser Ser Ile Asp Val Asp Ser Leu Met Arg
1145 1150 1155

Ser Val Ser Arg Val Phe Lys Phe Ile Asp Met Pro Thr Glu Gly
1160 1165 1170

Lys Pro Thr Lys Ser Thr Lys Pro Tyr Lys Asn Gly Gln Leu Ser
1175 1180 1185

Lys Val Met Ile Ile Glu Asn Ser His Val Lys Lys Asp Asp Ile
1190 1195 1200

Trp Pro Ser Gly Gly Gln Met Thr Val Lys Asp Leu Thr Ala Lys
1205 1210 1215

Tyr Thr Glu Gly Gly Asn Ala Ile Leu Glu Asn Ile Ser Phe Ser
1220 1225 1230

Ile Ser Pro Gly Gln Arg Val Gly Leu Leu Gly Arg Thr Gly Ser
1235 1240 1245

Gly Lys Ser Thr Leu Leu Ser Ala Phe Leu Arg Leu Leu Asn Thr
1250 1255 1260

Glu Gly Glu Ile Gln Ile Asp Gly Val Ser Trp Asp Ser Ile Thr
1265 1270 1275

Leu Gln Gln Trp Arg Lys Ala Phe Gly Val Ile Pro Gln Lys Val
1280 1285 1290

```
Phe Ile  Phe Ser Gly Thr Phe  Arg Lys Asn Leu Asp  Pro Tyr Glu
    1295                 1300                 1305

Gln Trp  Ser Asp Gln Glu Ile  Trp Lys Val Ala Asp  Glu Val Gly
    1310                 1315                 1320

Leu Arg  Ser Val Ile Glu Gln  Phe Pro Gly Lys Leu  Asp Phe Val
    1325                 1330                 1335

Leu Val  Asp Gly Gly Cys Val  Leu Ser His Gly His  Lys Gln Leu
    1340                 1345                 1350

Met Cys  Leu Ala Arg Ser Val  Leu Ser Lys Ala Lys  Ile Leu Leu
    1355                 1360                 1365

Leu Asp  Glu Pro Ser Ala His  Leu Asp Pro Val Thr  Tyr Gln Ile
    1370                 1375                 1380

Ile Arg  Arg Thr Leu Lys Gln  Ala Phe Ala Asp Cys  Thr Val Ile
    1385                 1390                 1395

Leu Cys  Glu His Arg Ile Glu  Ala Met Leu Glu Cys  Gln Gln Phe
    1400                 1405                 1410

Leu Val  Ile Glu Glu Asn Lys  Val Arg Gln Tyr Asp  Ser Ile Gln
    1415                 1420                 1425

Lys Leu  Leu Asn Glu Arg Ser  Leu Phe Arg Gln Ala  Ile Ser Pro
    1430                 1435                 1440

Ser Asp  Arg Val Lys Leu Phe  Pro His Arg Asn Ser  Ser Lys Cys
    1445                 1450                 1455

Lys Ser  Lys Pro Gln Ile Ala  Ala Leu Lys Glu Glu  Thr Glu Glu
    1460                 1465                 1470

Glu Val  Gln Asp Thr Arg Leu
    1475                 1480
```

<210> SEQ ID NO 152
<211> LENGTH: 250
<212> TYPE: DNA
<213> ORGANISM: Artificial Sequence
<220> FEATURE:
<223> OTHER INFORMATION: Mouse U1a promoter

<400> SEQUENCE: 152

```
atggaggcgg tactatgtag atgagaattc aggagcaaac tgggaaaagc aactgcttcc     60

aaatatttgt gatttttaca gtgtagtttt ggaaaaactc ttagcctacc aattcttcta    120

agtgttttaa aatgtgggag ccagtacaca tgaagttata gagtgtttta atgaggctta    180

aatatttacc gtaactatga aatgctacgc atatcatgct gttcaggctc cgtggccacg    240

caactcatac                                                          250
```

<210> SEQ ID NO 153
<211> LENGTH: 101
<212> TYPE: DNA
<213> ORGANISM: Artificial Sequence
<220> FEATURE:
<223> OTHER INFORMATION: Polymerase III H1 mutant promoter

<400> SEQUENCE: 153

```
aatatttgca tgtcgctatg tgttctggga aatcaccata aacgtgaaat gtctttggat     60

ttgggaatct tcgaagttct gtatgagacc acagatctcc a                        101
```

<210> SEQ ID NO 154
<211> LENGTH: 701
<212> TYPE: DNA
<213> ORGANISM: Artificial Sequence
<220> FEATURE:

<223> OTHER INFORMATION: Chicken beta-actin hybrid promoter CBh (CBh promoter consists of CMV enhancer, CBA promoter, first CBA exon and partial intron)

<400> SEQUENCE: 154

```
cgttacataa cttacggtaa atggcccgcc tggctgaccg cccaacgacc cccgcccatt     60
gacgtcaata gtaacgccaa tagggacttt ccattgacgt caatgggtgg agtatttacg    120
gtaaactgcc cacttggcag tacatcaagt gtatcatatg ccaagtacgc cccctattga    180
cgtcaatgac ggtaaatggc ccgcctggca ttgtgcccag tacatgacct tatgggactt    240
tcctacttgg cagtacatct acgtattagt catcgctatt accatggtcg aggtgagccc    300
cacgttctgc ttcactctcc ccatctcccc cccctcccca cccccaattt tgtatttatt    360
tattttttaa ttattttgtg cagcgatggg ggcggggggg gggggggggc gcgcgccagg    420
cggggcgggg cggggcgagg ggcggggcgg ggcgaggcgg agaggtgcgg cggcagccaa    480
tcagagcggc gcgctccgaa agtttccttt tatggcgagg cggcggcggc ggcggcccta    540
taaaaagcga agcgcgcggc gggcgggagt cgctgcgcgc tgccttcgcc ccgtgccccg    600
ctccgccgcc gcctcgcgcc gcccgccccg gctctgactg accgcgttac tcccacaggt    660
gagcgggcgg gacggccctt ctcctccggg ctgtaattag c                        701
```

<210> SEQ ID NO 155
<211> LENGTH: 229
<212> TYPE: DNA
<213> ORGANISM: Artificial Sequence
<220> FEATURE:
<223> OTHER INFORMATION: MeCP2 min promoter sequence

<400> SEQUENCE: 155

```
agctgaatgg ggtccgcctc ttttccctgc ctaaacagac aggaactcct gccaattgag     60
ggcgtcaccg ctaaggctcc gccccagcct gggctccaca accaatgaag ggtaatctcg    120
acaaagagca aggggtgggg cgcgggcgcg caggtgcagc agcacacagg ctggtcggga    180
gggcggggcg cgacgtctgc cgtgcggggt cccggcatcg gttgcgcgc                229
```

<210> SEQ ID NO 156
<211> LENGTH: 737
<212> TYPE: DNA
<213> ORGANISM: Artificial Sequence
<220> FEATURE:
<223> OTHER INFORMATION: MeCP2 promoter sequence

<400> SEQUENCE: 156

```
tcaaaccatc tgattcaaca atgcacgacc gatctcttat gggcttggca cacaccatct     60
gcccattata aacgtctgca aagaccaagg tttgatatgt tgattttact gtcagcctta    120
agagtgcgac atctgctaat ttagtgtaat aatacaatca gtagaccctt taaaacaagt    180
cccttggctt ggaacaacgc caggctcctc aacaggcaac tttgctactt ctacagaaaa    240
tgataataaa gaaatgctgg tgaagtcaaa tgcttatcac aatggtgaac tactcagcag    300
ggaggctcta ataggcgcca agagcctaga cttccttaag cgccagagtc cacaagggcc    360
cagttaatcc tcaacattca aatgctgccc acaaaaccag cccctctgtg ccctagccgc    420
ctcttttttc caagtgacag tagaactcca ccaatccgca gctgaatggg gtccgcctct    480
tttccctgcc taaacagaca ggaactcctg ccaattgagg gcgtcaccgc taaggctccg    540
ccccagcctg ggctccacaa ccaatgaagg gtaatctcga caaagagcaa ggggtggggc    600
gcgggcgcgc aggtgcagca gcacacaggc tggtcgggag ggcggggcgc gacgtctgcc    660
```

gtgcggggtc ccggcatcgg ttgcgcgcgc gctccctcct ctcggagaga gggctgtggt 720
aaaacccgtc cggaaaa 737

<210> SEQ ID NO 157
<211> LENGTH: 418
<212> TYPE: DNA
<213> ORGANISM: Artificial Sequence
<220> FEATURE:
<223> OTHER INFORMATION: MeCP418 promoter sequence

<400> SEQUENCE: 157
ataggcgcca agagcctaga cttccttaag cgccagagtc cacaagggcc cagttaatcc 60
tcaacattca aatgctgccc acaaaaccag cccctctgtg ccctagccgc ctcttttttc 120
caagtgacag tagaactcca ccaatccgca gctgaatggg gtccgcctct tttccctgcc 180
taaacagaca ggaactcctg ccaattgagg gcgtcaccgc taaggctccg ccccagcctg 240
ggctccacaa ccaatgaagg gtaatctcga caaagagcaa ggggtggggc gcgggcgcgc 300
aggtgcagca gcacacaggc tggtcgggag ggcggggcgc gacgtctgcc gtgcggggtc 360
ccggcatcgg ttgcgcgcgc gctccctcct ctcggagaga gggctgtggt aaaacccg 418

<210> SEQ ID NO 158
<211> LENGTH: 426
<212> TYPE: DNA
<213> ORGANISM: Artificial Sequence
<220> FEATURE:
<223> OTHER INFORMATION: MeCP426 promoter sequence

<400> SEQUENCE: 158
ataggcgcca agagcctaga cttccttaag cgccagagtc cacaagggcc cagttaatcc 60
tcaacattca aatgctgccc acaaaaccag cccctctgtg ccctagccgc ctcttttttc 120
caagtgacag tagaactcca ccaatccgca gctgaatggg gtccgcctct tttccctgcc 180
taaacagaca ggaactcctg ccaattgagg gcgtcaccgc taaggctccg ccccagcctg 240
ggctccacaa ccaatgaagg gtaatctcga caaagagcaa ggggtggggc gcgggcgcgc 300
aggtgcagca gcacacaggc tggtcgggag ggcggggcgc gacgtctgcc gtgcggggtc 360
ccggcatcgg ttgcgcgcgc gctccctcct ctcggagaga gggctgtggt aaaacccgtc 420
cggaaa 426

<210> SEQ ID NO 159
<211> LENGTH: 400
<212> TYPE: DNA
<213> ORGANISM: Artificial Sequence
<220> FEATURE:
<223> OTHER INFORMATION: VMD2 promoter

<400> SEQUENCE: 159
aattctgtca ttttactagg gtgatgaaat tcccaagcaa caccatcctt ttcagataag 60
ggcactgagg ctgagagagg agctgaaacc tacccggggt caccacacac aggtggcaag 120
gctgggacca gaaaccagga ctgttgactc tggattttag ggccatggta gagggggtgt 180
tgccctaaat tccagccctg gtctcagccc aacaccctcc aagaagaaat tagaggggcc 240
atggccaggc tgtgctagcc gttgcttctg agcagattac aagaagggac taagacaagg 300
actcctttgt ggaggtcctg gcttagggag tcaagtgacg gcggctcagc actcacgtgg 360
gcagtgccag cctctaagag tgggcagggg cactggccac 400

<210> SEQ ID NO 160
<211> LENGTH: 136
<212> TYPE: DNA
<213> ORGANISM: Artificial Sequence
<220> FEATURE:
<223> OTHER INFORMATION: PDE6b promoter

<400> SEQUENCE: 160
cccatttgta ggagtgagtc agctgacccg cccccggggt tcctaatctc actaagaaag 60
actttgctga tgacagggtt tcctgggagt ccatgcgtgc ctggagcagc agcgtctcca 120
gggacaggca gccacc 136

<210> SEQ ID NO 161
<211> LENGTH: 2035
<212> TYPE: DNA
<213> ORGANISM: Artificial Sequence
<220> FEATURE:
<223> OTHER INFORMATION: mRho promoter

<400> SEQUENCE: 161
gcgccaatca gccgatgact tctaacaata ctcttaactc acacagagct tgtctcactg 60
agccaacacc ctgtaccctc agctcagtga cggctttcaa cctgtggggc tgcctctgtt 120
acccaagtga gagagggcca gtgctcccag aggtgacctt gtttgcccat tctctccctg 180
ggtcagccag tgtttatctg ttgtataccc agtccaccct gcaggctcac atcagagcct 240
aggagatggc tagtgtcccc gcggagacca cgatgaagct tcccagctgt ctcaagcaca 300
agctggctgc agaggctgct gaggcactgc tagctgggga tgggggcagg gtagatctgg 360
ggctgaccac cagggtcaga atcagaacct ccaccttgac ctcattaacg ctggtcttaa 420
tcaccaagcc aagctcctta aactgctagt ggccaactcc caggccctga cacacatacc 480
tgccctgtgt tcccaaacaa gacacctgca tggaaggaag gggttgctt ttctaagcaa 540 acatctagga atcccgggtg cagtgtgagg agactaggcg agggagtact ttaagggcct 600
caaggctcag agaggaatac ttcttccctg gttagcctcg tgcctaggct ccagggtctt 660
tgtcctgcct ggatacctat gtggcaaggg gcatagcatt tcccccacca tcagctctta 720
gctcaacctt atcttctcgg aaagactgcg cagtgtaaca acacagcaga gacttttctt 780
ttgtcccctg tctacccctg taactgctac tcagaagcat ctttctcaca gggtactggc 840
ttcttgcatc cagagttttt tgtctccctc gggcccccag aatcaaattc ttcctctggg 900
actcagtgga tgtttcacac acgtatcggc ctgacagtca tcctggagca tcctacacag 960
gggccatcac agctgcatgt cagaaatgct ggcctcacat cctcagacac caggcctagt 1020
gctggtcttc ctcagactgg cgtccccagc aggccagtag gatcatcttt tagcctacag 1080
agttctgaag cctcagagcc ccaggtccct ggtcatcttc tctgcccctg agatttttcc 1140
aagttgtatg ccttctaggt aaggcaaaac ttcttacgcc cctcctcgtg gcctccaggc 1200
cccacatgct cacctgaata acctggcagc ctgctccctc atgcagggac cacgtcctgc 1260
tgcacccagc aggccatccc gtctccatag cccatggtca tccctccctg gacaggaatg 1320
tgtctcctcc ccgggctgag tcttgctcaa gctagaagca ctccgaacag ggttatgggc 1380
gcctcctcca tctcccaagt ggctggctta tgaatgttta atgtacatgt gagtgaacaa 1440
attccaattg aacgcaacaa atagttatcg agccgctgag ccgggggcg gggggtgtga 1500 gactggaggc gatggacgga gctgacggca cacacagctc agatctgtca agtgagccat 1560
tgtcagggct tggggactgg ataagtcagg gggtctcctg ggaagagatg ggataggtga 1620

-continued

```
gttcaggagg agacattgtc aactggagcc atgtggagaa gtgaatttag ggcccaaagg   1680

ttccagtcgc agcctgaggc caccagactg acatggggag gaattcccag aggactctgg   1740

ggcagacaag atgagacacc ctttcctttc tttacctaag ggcctccacc cgatgtcacc   1800

ttggcccctc tgcaagccaa ttaggccccg gtggcagcag tgggattagc gttagtatga   1860

tatctcgcgg atgctgaatc agcctctggc ttagggagag aaggtcactt tataagggtc   1920

tgggggggt cagtgcctgg agttgcgctg tgggagccgt cagtggctga gctcgccaag   1980

cagccttggt ctctgtctac gaagagcccg tggggcagcc tcgagagccg cagcc        2035


<210> SEQ ID NO 162
<211> LENGTH: 511
<212> TYPE: DNA
<213> ORGANISM: Artificial Sequence
<220> FEATURE:
<223> OTHER INFORMATION: CMV promoter

<400> SEQUENCE: 162

ccgttacata acttacggta aatggcccgc ctggctgacc gcccaacgac ccccgcccat     60

tgacgtcaat agtaacgcca atagggactt tccattgacg tcaatgggtg gagtatttac    120

ggtaaactgc ccacttggca gtacatcaag tgtatcatat gccaagtacg ccccctattg    180

acgtcaatga cggtaaatgg cccgcctggc attgtgccca gtacatgacc ttatgggact    240

ttcctacttg gcagtacatc tacgtattag tcatcgctat taccatggtg atgcggtttt    300

ggcagtacat caatgggcgt ggatagcggt ttgactcacg gggatttcca agtctccacc    360

ccattgacgt caatgggagt ttgttttggc accaaaatca acgggacttt ccaaaatgtc    420

gtaacaactc cgccccattg acgcaaatgg gcggtaggcg tgtacggtgg gaggtctata    480

taagcagagc tcgtttagtg aaccgtcaga t                                   511


<210> SEQ ID NO 163
<211> LENGTH: 334
<212> TYPE: DNA
<213> ORGANISM: Artificial Sequence
<220> FEATURE:
<223> OTHER INFORMATION: UbC promoter

<400> SEQUENCE: 163

ggcctccgcg ccgggttttg gcgcctcccg cgggcgcccc cctcctcacg gcgagcgctg     60

ccacgtcaga cgaagggcgc agcgagcgtc ctgatccttc cgcccggacg ctcaggacag    120

cggcccgctg ctcataagac tcggccttag aaccccagta tcagcagaag gacattttag    180

gacgggactt gggtgactct agggcactgg ttttctttcc agagagcgga acaggcgagg    240

aaaagtagtc ccttctcggc gattctgcgg agggatctcc gtggggcggt gaacgccgat    300

gattatataa ggacgcgccg ggtgtggcac agct                                334
```